US006605432B1

(12) United States Patent
Huang

(10) Patent No.: US 6,605,432 B1
(45) Date of Patent: Aug. 12, 2003

(54) HIGH-THROUGHPUT METHODS FOR DETECTING DNA METHYLATION

(75) Inventor: Tim Hui-Ming Huang, Columbia, MO (US)

(73) Assignee: Curators of the University of Missouri, Columbia, MO (US)

(*) Notice: Subject to any disclaimer, the term of this patent is extended or adjusted under 35 U.S.C. 154(b) by 0 days.

(21) Appl. No.: 09/497,855

(22) Filed: Feb. 4, 2000

Related U.S. Application Data

(60) Provisional application No. 60/120,592, filed on Feb. 18, 1999, and provisional application No. 60/118,760, filed on Feb. 5, 1999.

(51) Int. Cl.[7] .............................. C07H 21/04; C12Q 1/68
(52) U.S. Cl. ..................... 435/6; 435/91.2; 435/287.2; 536/23.1
(58) Field of Search .................. 435/6, 91.2, 287.2; 536/23.1

(56) References Cited

U.S. PATENT DOCUMENTS

| | | | | |
|---|---|---|---|---|
| 4,683,202 A | | 7/1987 | Mullis ........................... | 435/91 |
| 4,800,159 A | | 1/1989 | Mullis et al. ............. | 435/172.3 |
| 5,143,854 A | * | 9/1992 | Pirrung et al. ............... | 436/518 |
| 5,589,339 A | | 12/1996 | Hampson et al. ............... | 435/6 |
| 5,591,575 A | | 1/1997 | Hampson et al. ............... | 435/6 |
| 5,786,146 A | | 7/1998 | Herman et al. ............... | 435/6 |
| 5,858,659 A | * | 1/1999 | Sapolsky et al. ............... | 435/6 |
| 5,871,917 A | | 2/1999 | Duffy ........................... | 435/6 |
| 6,045,994 A | * | 4/2000 | Zabeau et al. ................. | 435/6 |
| 6,300,071 B1 | * | 10/2001 | Vuylsteke et al. ............. | 435/6 |

OTHER PUBLICATIONS

Donini et al. "AFLP fingerprinting reveals pattern differences between template DNA extracted form different plant organs" Genome, 1997 40: 521–526.*

Akopyants et al., "PCR–based Subtractive Hybridization and Differences in Gene Content Among Strains of *Helicobacter pylori*", Proc. Natl. Acad. Sci. USA, vol. 95, pp. 13108–13113 (1998).

Antequera, F., et al., "High Levels of De Novo Methylation and Altered Chromatin Structure at CpG Islands in Cell Lines", Cell, vol. 62, pp. 503–514 (1990).

Baylin et al., "Alterations in DNA Methylation: A Fundamental Aspect of Neoplasia", Advances in Cancer Research, pp. 140–196 (1998).

Baylin, Stephen B., "Tying it all Together: Epigenetics, Genetics, Cell Cycle, and Cancer", Science, vol. 277, pp. 1948–1949, (1997).

Belinsky et al., "Aberrant Methylation of p16$^{INK4a}$ is an Early Event in Lung Cancer and a Potential Biomarker for Early Diagnosis", Proc. Natl. Acad. Sci. USA, vol. 95, pp. 11891–11896 (1998).

Belinsky et al., "Increased Cytosine DNA–methyltransferase Activity is Target–cell–specific and an Early Event in Lung Cancer", Proc. Natl. Acad. Sci. USA, vol. 93, pp. 4045–4050 (1996).

(List continued on next page.)

Primary Examiner—Gary Benzion
Assistant Examiner—Jeanine Goldberg
(74) Attorney, Agent, or Firm—Barry L. Davison; Davis Wright Tremaine LLP

(57) ABSTRACT

The present invention provides a method of hybridization, differential methylation hybridization (DMH) for high throughput methylation analysis of multiple CpG island loci. DMH utilizes nucleic acid probes prepared from a cell sample to screen numerous CpG dinucleotide rich fragments affixed on a screening array. Positive hybridization signals indicate the presence of methylated sites. Methods of preparing the hybridization probes and screening array are also provided.

22 Claims, 11 Drawing Sheets

OTHER PUBLICATIONS

Bloom, H.J.G. and Richardson, W.W., "Histological Grading and Prognosis in Breast Cancer", British Journal of Cancer, vol. 11, pp. 359–377 (1957).

Brandeis, M. et al., "Sp1 Elements Protect a CpG Island from de novo Methylation", Nature, vol. 371, pp. 435–438 (1994).

Carotti et al., "Influence of Pre–existing Methylation on the de Novo Activity of Eukaryotic DNA Methyltransferase", Biochem. J., vol. 37, pp. 1101–1108 (1998).

Christman et al., "5–Methyl–2'–deoxycytidine in Single–Stranded DNA can act in cis to Signal de novo DNA Methylation", Proc. Natl. Acad. Sci USA, vol. 92, pp. 7347–7351 (1995).

Chuang et al., "Human DNA–(Cytosine–5) Methyltransferase–PCNA Complex as a Target for $p21^{WAF1}$", Science, vol. 277, pp. 1996–2000 (1997).

Craig et al., "Removal of Repetitive Sequences from FISH Probes Using PCR–Assisted Affinity Chromatography", Hum. Genet., vol. 100, No. 472–476 (1997).

Cross et al., "Purification of CpG Islands Using a Methylated DNA Binding Column", Nature Genet., vol. 6, pp. 236–244 (1994).

Frommer, M. et al., "A Genomic Sequencing Protocol that Yields a Positive Display of 5–Methylcytosine Residues in Individual DNA strands", Proc. Natl. Acad. Sci. USA, vol. 89, pp. 1827–1831 (1992).

Graff et al., "Mapping Patterns of CpG Island Methylation in Normal and Neoplastic Cells Implicates Both Upstream and Downstream Regions in de Novo Methylation", J. Biol. Chem., vol. 272, No. 35, pp. 22322–22329 (1997).

Herman et al., "Methylation–specific PCR: A Novel PCR Assay for Methylation Status of CpG Islands", Proc. Natl. Acad. Sci. USA, vol. 93, pp. 9821–9826 (1996).

Huang, T.H., et al., "Methylation Profiling of CpG Islands in Human Breast Cancer Cells", Human Molecular Genetics, vol. 8, No. 3, pp. 459–470 (1999).

Jones, P.A. "DNA Methylation Errors and Cancer[1]", Cancer Res., vol. 56, pp. 2463–2467 (1996).

Laird et al., "DNA Methylation and Cancer", Hum. Mol. Genet., vol. 3, pp. 1487–1495 (1994).

Lee J.H. and Welch D.R., "Identification of Highly Expressed Genes in Metastasis–Suppressed Chromosome 6/Human Malignant Melanoma Hybrid Cells Using Subtractive Hybridization and Differential Display", Int. J. Cancer, vol. 71, pp. 1035–1044 (1997).

Li et al., "Role for DNA Methylation in Genomic Imprinting", Nature, vol. 366, pp. 362–365 (1993).

Mummaneni, P. et al., "Epigenetic Gene Inactivation Induced by a Cis–acting Methylation Center", J. Biol. Chem., vol. 270, No. 2, pp. 788–792 (1995).

Pfeifer, G.P., et al., "Polymerase Chain Reaction–Aided Genomic Sequencing of an X Chromosome–linked CpG Island: Methylation Patterns Suggest Clonal Inheritance, CpG Site Autonomy, and an Explanation of Activity State Stability", Proc. Natl. Acad. Sci. USA, vol. 87, pp. 8252–8256 (1990).

Saiki et al., "Primer–Directed Enzymatic Amplification of DNA with a Thermostable DNA Polymerase", Science, vol. 239, pp. 487–491 (1988).

Schena et al., "Quantitative Monitoring of Gene Expression Patterns with a Complementary DNA Microarray", Science, vol. 270, pp. 467–470 (1995).

Singer–Sam, J. and Riggs, A.D., "X Chromosone Inactivation and DNA Methylation", DNA Methylation: Molecular Biology and Biological Significance, pp. 358–384 (1993).

Vertino et al., "De Novo Methylation of CpG Island Sequences in Human Fibroblasts Overexpressing DNA (Cytosine–5–)–Methyltransferase", Mol. Cell Biol., vol. 16, pp. 4555–4565 (1996).

Wu et al., "Expression of Prokaryotic HhaI DNA Methyltransferase Is Transforming and Lethal to NIH 3T3 Cells", Cancer Res., vol. 56, pp. 616–622 (1996).

Frudakis et al. GenCore; Geneseq, clone V 49815, WO97/25426, published Jul. 17, 1997.*

Lafranchi et al. , GenCore; EST, clone F16311, Genome Researach, 1996, 6(1): 35–42.*

Frudakis et al. GenCore; Geneseq, clone VX83369, WO97/25426, published Jul. 17, 1997.*

Pan, GenCore, Genseq, clone X22302, WO99/06426, published Feb. 11, 1999.*

Adams et al. GeneCore; EST clone AA313068, Nature, 1995, 377 (6547, Supplement): 3–174.*

Cross et al. GeneCore; GenEmbl, clone HS13F7R, Nature Genetics, 1994, 6(3): 236–244.*

Tubby, GeneCore; Geneseq, clone HS29K1, Dec. 18, 1997.*

* cited by examiner

HIGH-THROUGHPUT METHODS FOR DETECTING DNA METHYLATION

This application claims priority to copending U.S. provisional patent application Ser. No. 60/120,592, filed Feb. 18, 1999 and to copending U.S. provisional patent application Ser. No. 60/118,760, filed Feb. 5, 1999, both incorporated herein by reference.

This invention was made with Government support under National Institute of Health grant No. DHHS 5 R29 CA 69065 and U.S. Army Medical Research and Material Command grant No. DAMD 17-98-1-8214. The Government has certain rights in the invention.

FIELD OF INVENTION

The present invention relates to methods for detecting the presence or absence of methylated CpG islands within a genome utilizing a microarray based technology, Differential Methylation Hybridization (DMH). The invention is also used for identifying methylation patterns in a cell sample which may be indicative of a disease state. Also provided are methods for preparing nucleic acid fragments and nucleic acid probes to be used in said DMH methods.

BACKGROUND OF INVENTION

Epigenetic events are heritable alterations in gene function which are mediated by factors other than changes in primary DNA sequence. DNA methylation is one of the most widely studied epigenetic mechanisms and numerous studies have been conducted to determine its role in oncogenesis. DNA methylation usually occurs at cytosines located 5' of guanines, known as CpG dinucleotides, in the human genome. DNA (cytosine-5)-methyltransferase (DNA-MTase) catalyzes this reaction by adding a methyl group from S-adenosyl-L-methionine to the fifth carbon position of the cytosines. While DNA-MTase favors hemimethylated substrates for its normal maintenance activity in the cell, the enzyme also exhibits an ability to methylate CpG dinucleotides de novo. Most cytosines within the CpG dinucleotides are methylated in the human genome, but some remain unmethylated in specific CpG dinucleotide rich genomic regions, known as CpG islands. See Antequera, F. et al., *Cell* 62: 503–514 (1990).

Methylation of CpG islands is known to play a critical role in regulating gene expression. This effect is exerted via altering local chromatin structure and limiting the access of protein factors to initiate gene transcription. In normal cells, this epigenetic modification is associated with transcriptional silencing of imprinted genes, some repetitive elements and genes on the inactive X chromosome. See Li et al., *Nature* 366: 362–365 (1993); Singer-Sam, J. and Riggs A. D., (1993) In Jost, J. P., and Saluz, H. P. (eds), "DNA Methylation: Molecular Biology and Biological Significance," p.358–384. In neoplastic cells, it has been observed that the normally unmethylated CpG islands can become aberrently methylated, or hypermethylated. See Jones, P. A., *Cancer Res.* 56: 2463–2467 (1996); Baylin et al., *Advances in Cancer Research*, In Vande Woude, G. F.: and Klein, G. (eds) 72: 141–196 (1997).

In addition to classic genetic mutations, hypermethylation of CpG islands is an alternative mechanism for inactivation of tumor suppressor genes and there is growing evidence that altered cytosine methylation patterns play important roles in cancer development. See e.g., Belinsky et al., 95 *Proc. Natl. Acad. Sci. USA* 11891–11896 (1998); Baylin et al., *Advances in Cancer Research*, In Vande Woude, G. F. and Klein, G. (eds.) 72: 141–196 (1997). The methylation patterns of DNA from cancer tumor cells are generally different than those of normal cells. See Laird et al., *Hum. Mol. Genet.* 3: 1487–1495 (1994). Tumor cell DNA is generally undermethylated relative to normal cell DNA, but selected regions of the tumor cell genome may be more methylated than the same regions of a normal cell genome. Hence, detection of altered methylation patterns in a tumor cell genome is an indication that the cell is cancerous.

Recently, the molecular mechanisms underlying CpG island hypermethylation in cancer have been explored and evidence suggests that increased DNA-MTase levels can contribute to tumorigenesis by promoting de novo methylation of CpG island sequences. See Vertino et al., *Mol. Cell Biol.*, 16: 4555–4565 (1996); Wu et al., *Cancer Res.*, 56: 616–622 (1996). For instance, if hypermethylation occurs in the CpG islands of genes related to growth-inhibitory activities, it may lead to associated transcriptional silencing and promote neoplastic cell proliferation. Further, recent data has shown:that dysregulation of p21, a cell cycle regulator that normally modulates DNA-MTase action may also promote de novo methylation. See Chuang et al., *Science* 277: 1996–2000 (1997). Studies have suggested that local cis-acting signals and trans-acting factors capable of preventing specific CpG islands from de novo methylation can be disrupted in tumor cells. See Brandeis, M. et al., *Nature*, 371: 435–438 (1995); Mummaneni, P. et al.,*J. Biol. Chem.*, 270: 788–792 (1995); Graff et al., *J. Biol. Chem.*, 272: 22322–22329 (1997).

Presently, there is no direct evidence that disturbances of such local factors results in de novo methylation of specific CpG islands. Rather, de novo methylation is commonly thought to be a generalized phenomenon associated with a stochastic process in tumor cells possessing aberrant DNA-MTase activities. See Jones, P. A., *Cancer Res.*, 56, 2463–2467 (1996); Pfeifer et al.,*Proc. Natl. Acad. Sci. USA*, 87: 8252–8256. (1990). This random methylation process can occur at CpG dinucleotide sites located within the regulatory regions of tumor suppressor genes. The progressive silencing of their transcripts may provide tumor cells with a growth advantage, and the specific hypermethylated sites observed in particular cancer types could be the result of clonal selection during tumor development.

Thus, identification of genetic changes in tumorigenesis is a major focus in molecular cancer research. However, the differences in CpG island methylation patterns between normal and cancer cells remain poorly understood.

Traditionally, methylation analysis has been carried out by Southern hybridization which assesses a few methylation-sensitive restriction sites within CpG islands of known genes. More sensitive assays for mapping DNA methylation patterns such as bisulfite DNA sequencing and methylation-specific PCR, have allowed a detailed analysis of multiple CpG dinucleotides across a single CpG island of interest. Bisulfite DNA sequencing utilizes bisulfite-induced modification of genomic DNA under conditions whereby unmethylated cytosine is converted to uracil. The bisulfite-modified sequence is then amplified by PCR with two sets of strand-specific primers to yield a pair of fragments, one from each strand, in which all uracil and thymine residues are amplified as thymine and only 5-methylcytosine residues are amplified as cytosine. The PCR products can be sequenced or can be cloned and sequenced to provide methylation maps of single DNA molecules. See Frommer, M. et al., *Proc. Natl. Acad. Sci.* 89: 1827–1831 (1992).

Similarly, methylation-specific PCR, another widely used assay, can assess the methylation status of CpG dinucleotide sites within a CpG island, independent of the use of methylation-sensitive restriction enzymes. This assay entails the initial modification of DNA by sodium bisulfite or another comparable agent thus converting all unmethylated, but not methylated, cytosines to uracil. Subsequent amplification with primers specific for methylated DNA results in the amplification of DNA consisting of methylated CpG dinucleotides. See U.S. Pat. No. 5,786,146; Herman et al., Proc. Natl. Acad. Sci. USA 93: 9821–9826 (1996).

These approaches have yielded important information regarding the local methylation control of individual genes. However, current methods have been restricted to analyzing one gene at a time and have not been used to conduct a genome-wide study. As a further step toward a more comprehensive understanding of the underlying mechanisms, it is necessary to perform large-scale or a genome-wide analysis of methylation patterns of DNA in cancer cells.

Accordingly, a need presently exists for technology designed to detect methylation of DNA on a large scale, to identify previously uncharacterized CpG islands associated with gene silencing and to shed light on other, as yet unidentified factors governing aberrant methylation of CpG island loci. Each cancer type may have its own unique methylation pattern that defines its growth rate, tendency to spread, and responsiveness to therapies. By examining a large number of loci in a series of cancers, global methylation profiles can be constructed. Cataloging these molecular patterns could lead to early detection, more accurate diagnosis, and development of better treatment therapies of cancer.

SUMMARY OF THE INVENTION

Accordingly, among the objects of the present invention may be noted the provision of a novel DNA array-based method, differential methylation hybridization (DMH) to detect the presence or absence of hypermethylated nucleic acid sequences in a cell sample. DMH utilizes a set of CpG dinucleotide rich fragments prepared from tumor cells or normal cells to simultaneously screen numerous genomic nucleic acid fragments. The use of DMH provides an accurate and efficient method for the identification of DNA methylation patterns in cancer and thus, DMH has wide-ranging applications in clinical diagnosis and genetic typing of cancer.

An object of the present invention is to provide a process for detecting the presence or absence of methylation of a CpG dinucleotide rich region of a nucleic acid sequence within a genome. A nucleic acid sequence is digested with a enzyme which digests nucleic acid sequences into fragments in which CpG islands are preserved. These fragments containing the CpG islands are then digested with a methylation-sensitive enzyme resulting in a digestion product comprising methylated CpG island loci. The digestion product is amplified and labeled to form amplicons which are used to screen a plurality of nucleic acid fragments affixed to a solid support. The presence or absence of labeled amplicons bound to the plurality of nucleic acid fragments of the screening array is then determined.

It is another object of the present invention to provide a process for identifying methylation patterns in a cancer cell using amplicons generated from cancer and non-cancer cells to screen an array containing genomic fragments.

Another object of the present invention is to provide a screening array comprising a solid support and a plurality of CpG dinucleotide rich fragments affixed to the solid support. The CpG dinucleotide rich fragments are at least about 200 nucleotides in length and contain at least 50% guanine and cytosine.

Yet another object of the present invention is to provide a process for generating a screening array comprising a plurality of nucleic acid fragments containing expressed sequences which includes contacting a nucleic acid sequence with an enzyme which digests the nucleic acid sequences into fragments in which CpG islands are preserved; amplifying and screening the fragments to identify sequences which include expressed sequences and affixing the fragments containing expressed sequences to a solid support. It is another object of the present invention to provide a set of amplicons to be used to probe the nucleic acid fragments affixed on a solid support of the screening array. The amplicons are CpG dinucleotide rich fragments which are derived from digesting a nucleic acid sequence with a restriction enzyme which digests the sequence into fragments in which CpG dinucleotide fragments are preserved. The resulting digestion products are then amplified and used to probe nucleic acid fragments of the screening array.

Other objects and features of the present invention will be in part apparent and in part pointed out hereinafter.

BRIEF DESCRIPTION OF THE DRAWINGS

Corresponding reference characters indicate corresponding parts throughout the several views of the drawings.

FIG. 9A is the initial screening and FIG. 9B is the corresponding subarray. Both FIGS. 9A and 9B are shown with some of the hypermethylated clones later dotted on the subarray dotted with their x- and y-coordinates. PCR products of CpG island tags were dotted onto membranes hybridized first with radiolabeled normal amplicons. The same membranes, or duplicate membranes, were later hybridized with tumor amplicons. Each CpG island tag is represented with two parallel dots in order to differentiate specific hybridization signals from non-specific background signals, which generally appear as scattered single dots. Five to six sets of positive controls were dotted on the four corners of the arrays to serve as orientation markers and for comparison of hybridization signal intensities.

DEFINITIONS AND ABBREVIATIONS

Figure 1:
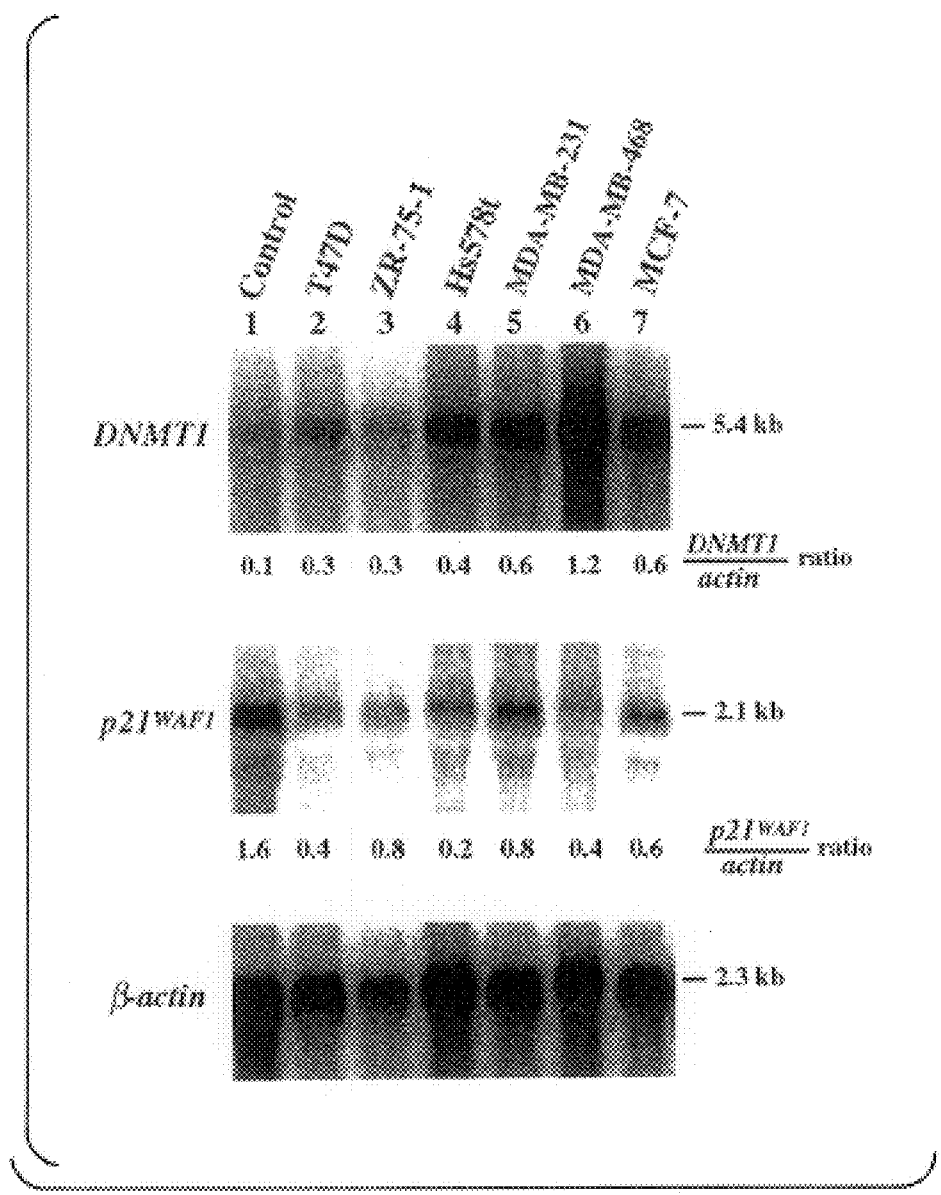
FIG. 1 is a Northern hybridization analysis of DNMT1 and $p21^{WAF1}$ gene expression in breast cancer cell lines. Total RNA (20 $\mu$g) isolated from normal fibroblast (lane 1) and breast cancer cell lines—T47D (lane 2), ZR-75-1 (lane 3), Hs578t (lane 4), MDA-MB-231 (lane 5), MDA-MB-468 (lane 6), and MCF-7 (lane 7) was subjected to Northern analysis. The membrane was probed with DNMT1 (top panel), $p21^{WAF1}$ (middle panel), and b-actin (bottom panel), respectively. The predicted sizes (kb) of the indicated transcripts were calculated using the RNA MW I ladder (Boehringer Mannheim) as a standard. Band intensities were quantified with ImageQuant Software (Molecular Dynamics) and the relative levels of DNMT1 and $p21^{WAF1}$ mRNAs were normalized with the expression level of b-actin in each sample lane.

To facilitate understanding of the invention, a number of terms are defined below:

The nucleotide bases are abbreviated herein as follows: A represents adenine; C represents cytosine; G represents guanine; T represents thymine; U represents uracil.

As used herein, the terms "GC dinucleotide" and "CpG dinucleotide" are used interchangeably.

As used herein, the terms "GC-rich" and "CpG dinucleotide rich" are used interchangeably.

As used herein, the terms "screening" and "probing" are used interchangeably.

A "CpG dinucleotide" is a dinucleotide sequence containing an adjacent guanine and cytosine where the cytosine is located 5' of guanine.

A "CpG dinucleotide rich" nucleic acid fragment may be any nucleic acid fragment in which CpG dinucleotides comprise at least 50% of the nucleic sequence and which have a length of at least 200 base pairs.

A "CpG island" is a CpG dinucleotide rich region where CpG dinucleotides comprise at least 50% of the DNA sequence.

"DMH" is the abbreviation for differential methylation hybridization.

"ECIST" is the abbreviation for Expressed CpG Island Sequence Tags.

"HBC" is the abbreviation for "hypermethylation in breast cancer."

The procedures disclosed herein which involve the molecular manipulation of nucleic acids are known to those skilled in the art. See generally Fredrick M. Ausubel et al.

(1995), "Short Protocols in Molecular Biology," John Wiley and Sons, and Joseph Sambrook et al. (1989), "Molecular Cloning, A Laboratory Manual," second ed., Cold Spring Harbor Laboratory Press as incorporated herein by reference.

DETAILED DESCRIPTION

The present invention provides differential methylation hybridization (DMH) for a high-throughput analysis of DNA methylation. Unlike presently existing methylation analysis methods such as Southern hybridization, bisulfite DNA sequencing and methylation-specific PCR which are restricted to analyzing one gene at a time, DMH utilizes numerous CpG dinucleotide rich genomic fragments specifically designed to allow simultaneous analysis of multiple, preferably hundreds and more preferably, thousands of methylation-associated genes in the genome. As such, the use of DMH provides an accurate and efficient means for the identification of DNA methylation patterns in cells and thus, DMH has wide-ranging applications in clinical diagnosis and genetic typing of cancer.

DMH integrates a high-density, microarray-based screening strategy to detect the presence or absence of methylated CpG dinucleotide genomic fragments. See Schena et al., Science 270: 467–470 (1995). In a preferred embodiment, CpG dinucleotide nucleic acid fragments from a genomic library are generated, amplified and affixed on a solid support to create a CpG dinucleotide rich screening array. Amplicons are generated by digesting DNA from a sample with restriction endonucleases which digest the DNA into fragments but leaves the methylated CpG islands intact. These amplicons are used to probe the CpG dinucleotide rich fragments affixed on the screening array to identify methylation patterns in the CpG dinucleotide rich regions of the DNA sample. Accordingly, DMH may be used to identify hypermethylated sequences in cancer cells by the simultaneous screening of numerous amplified ECIST DNA fragments. Using such technology, it is possible to generate an index set of genes which are commonly methylated in various types of cancer and an index set of genes which are specifically methylated for a particular type of cancer. Thus, DMH can be a useful diagnostic tool for a large scale or a genome-wide screening of methylation of DNA in cancer and may be directly applied in a clinical setting for patient analysis.

The Screening Array

The screening array of the present invention comprises multiple CpG dinucleotide rich fragments affixed to a solid support. These CpG dinucleotide rich fragments affixed to the solid support of the screening array are employed to identify the presence or absence of methylated sites in cells. Further, these CpG dinucleotide fragments may be any nucleic acid fragment in which CpG dinucleotides comprise at least 50% of the nucleic sequence and which have a length of at least 200 base pairs. In a preferred embodiment, the CpG dinucleotide fragments affixed to the solid support of the screening array are selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45 and SEQ ID NO: 46.

Preferably, the CpG dinucleotide fragments are derived from DNA clones selected from a genomic library, and more preferably from a genomic library in which the concentration of CpG dinucleotides has been enriched. Examples of such CpG dinucleotide rich genomic libraries are the CGI library, the avian CGI library and the mouse CGI library, each of which is available from the United Kingdom Human Genome Center. In a preferred embodiment, the nucleic acid fragments are derived from DNA clones of the CGI library and are, themselves, CpG islands.

If the nucleic acid fragments are derived from DNA clones of a pre-existing library such as the CGI library, the library is preferably pre-screened with an enzyme to eliminate repetitive sequences. Repetitive sequences are short stretches of DNA dispersed throughout the genome in thousands of copies with no apparent known function which could potentially interfere with the hybridization process. A preferred method utilizes Cot-1 which hybridizes with repetitive sequences such as AluI and KpnI families. DNA clones negative or weakly positive for the Cot-1 hybridization signals are then selected for amplification, i.e., clones positive for Cot-1 DNA are not selected.

The selected CpG dinucleotide nucleic acid fragments are amplified using methods of amplification known in the art. Any nucleic acid specimen can be utilized as the starting nucleic acid template, provided that it contains the specific nucleic acid sequence containing the target DNA sequence i.e., the CpG island. Thus, the amplification process may employ DNA or RNA, wherein DNA or RNA may be double or single stranded. In the event that RNA is to be used as a template, enzymes, and/or conditions optimal for reverse transcribing the template to DNA known to those in the art would be utilized.

Suitable in vitro amplification techniques include but are not limited to, the polymerase chain reaction (PCR) method, transcription-based amplification system (TAS), self-sustained sequence replication system (3SR), ligation amplification reaction (LAR), Qβ RNA replication system and run-off transcription. A preferred method of amplification is PCR amplification which involves an enzymatic chain reaction in which exponential quantities of the target locus (i.e., CpG islands) are produced relative to the number of reaction steps performed. PCR amplification techniques and many variations of PCR are known and well documented. See e.g., Saiki et al., Science 239: 487–491 (1988); U.S. Pat. Nos. 4,682,195, 4,683,202 and 4,800,159, which are incorporated herein by reference.

Typically, the selected DNA clone is denatured, thus forming single strands which are used as templates. One oligonucleotide primer is substantially complementary to the negative (−) strand and another primer is substantially complementary to the positive (+) strand. DNA primers are DNA sequences capable of initiating synthesis of a primer extension product. Primers "substantially complementary" to each strand of the target nucleic acid sequence will hybridize to their respective nucleic acid strands under favorable conditions known to one skilled in the art e.g., pH, salt, cation, temperature. In a preferred embodiment, the primers used in the amplification step are HGMP 3558: 5' CGG CGG CCT GCA GGT CTG ACC TTA A (SEQ ID NO: 47) and HGMP 3559: 5' AAC GCG TTG GGA GCT CTC CCT TAA (SEQ ID NO: 48).

Annealing the primers to the denatured DNA templates is followed by extension with an enzyme to result in newly synthesized + and − strands containing the target DNA sequence containing the CpG islands. This annealing process consists of the hybridization of the primer to complementary nucleotides of the DNA sequence template in a buffered aqueous solution. The buffer mixture containing the DNA templates and the primers is then heated to a temperature sufficient to separate the two complementary strands of DNA. In a preferred embodiment, the mixture containing the DNA templates and the primers is heated to about 90 to 100° C. from about 1 to 10 minutes, even more preferably from 1 to 4 minutes to allow the DNA templates to denature and form single strands. The mix is next cooled to a temperature sufficient to allow the primers to specifically anneal to sequences flanking the gene or sequence of interest. Preferably, the mixture is cooled to 50 to 60° C., for approximately 1 to 5 minutes. It is understood that the nucleotide sequence of the primer need not be completely complementary to the portion of the DNA template in order to effectively anneal to the DNA template.

A primer extension enzyme is then added which will initiate the primer extension reaction to produce newly synthesized DNA strands. Heat stable enzymes such as pwo, *Thermus aquaticus* or *Thermococcus litoralis* DNA polymerases which eliminate the need to add enzyme after each denaturation cycle may be used as the primer extension enzyme. Other preferred amplification enzymes which may be used include but are not limited to, *Escherichia coli* DNA polymerase I, Klenow fragment of *E. coli* DNA polymerase I, T4 DNA polymerase, T7 DNA polymerase Thermus aquaticus (Taq) DNA polymerase, SP6 RNA polymerase, T7 RNA polymerase, T3 RNA polymerase, T4 polynucleotide kinase, Avian Myeloblastosis Virus reverse transcriptase, Moloney Murine Leukemia Virus reverse transcriptase, T4 DNA ligase, *E. coli* DNA ligase or Qβ replicase. The temperature of the reaction mixture is then set to the optimum for the DNA polymerase to allow DNA extension to proceed.

These newly synthesized strands are used as templates in repeated cycles of amplification. Thus, PCR consists of multiple cycles of DNA melting, annealing and extension resulting in an exponential production of the target DNA sequence containing the target CpG islands.

After amplification, methylation-sensitive sites of the amplified products are preferably identified by digestion with a methylation-sensitive restriction enzyme. Examples of such methylation-sensitive enzymes are BstU I, SmaI, SacII, EagI, MspI, HpaII, HhaI and BssHII which digest non-methylated CpG dinucleotide regions. In a preferred embodiment, BstU I is used. Positive CpG dinucleotide nucleic acid fragments containing the methylation-sensitive sites are used for DMH analysis.

The amplified CpG dinucleotide rich fragments are denatured, transferred to a solid support and immobilized on the solid support using methods known in the art. Such methods that may be used to crosslink the CpG dinucleotide rich fragments to the solid support include but are not limited to UV light, poly-L-lysine treatment and heat. In a preferred embodiment, the CpG dinucleotide rich fragments are denatured, transferred and immobilized using an UV light to crosslink the CpG dinucleotide rich fragments to the solid support. Depending upon the assay, at least 20, preferably at least 100, more preferably at least 500, or even most preferably at least 1,000 amplified CpG dinucleotide rich fragments are transferred to and immobilized on the solid support.

In a preferred embodiment of the invention, the CpG dinucleotide rich fragments affixed to the solid support of the screening array, are CpG islands containing expressed sequences. CpG island fragments which contain expressed sequences are referred to, herein as Expressed CpG Island Sequence Tags (ECIST). In a preferred embodiment, ECIST fragments contain part of the promoter and the first exon of a gene. Typically, the length of each ECIST fragment is at least 0.3 kb, preferably 0.4 to 0.5 kb, and most preferably 0.4 kb. In a preferred embodiment, the ECIST fragments affixed to the solid support of the screening array are CpG island fragments selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45 and SEQ ID NO: 46.

ECIST fragments may be identified after the DNA clone is selected from a genomic library and amplified as described above. ECIST fragments are identified by transferring the amplified CpG dinucleotide rich fragments to membranes and screening the CpG dinucleotide rich fragments with a nucleic acid probe to detect the CpG dinucleotide rich fragments which contain sequences expressed in the sample to be evaluated. The nucleic acid probe used for detection of ECIST fragments may be from any source including breast, colon, ovarian, lung and prostate tissue and may be extracted using a variety of methods known in the art. Further, the nucleic acid probe may be DNA, cDNA, or RNA of the gene, or a fragment of the gene, having at least one of the target sequences described above, or an RNA fragment corresponding to such a cDNA fragment. In a preferred embodiment, the nucleic acid probe used to screen for ECIST fragments is a cDNA probe. A positive hybridization signal of the nucleic acid probe to the amplified CpG dinucleotide rich fragment is indicative of a ECIST fragment.

After screening to identify ECIST fragments, methylation-sensitive sites of the amplified products are preferably identified by digestion with a methylation-sensitive restriction enzyme. Examples of such methylation-sensitive enzymes are BstU I, SmaI, SacII, EagI, MspI, HpaII, HhaI and BssHII which digest non-methylated CpG dinucleotide regions. In a preferred embodiment, BstU I is used. Positive CpG dinucleotide nucleic acid fragments containing the methylation-sensitive sites are ECIST fragments which are used for DMH analysis. Where the CpG dinucleotide fragments are ECIST fragments, the undigested nucleic acid fragment contains part of the promoter and first exon of the expressed genes.

The ECIST fragments are denatured, transferred to a solid support and immobilized on the solid support using methods known in the art. Such methods that may be used to crosslink the ECIST fragments to the solid support include but are not limited to UV light, poly-L-lysine treatment and heat. In a preferred embodiment, the ECIST fragments are denatured, transferred and immobilized using an UV light to crosslink the ECIST fragments to the solid support. Depending upon the assay, at least 20, preferably at least 100, more preferably at least 500, or even most preferably at least 1,000 amplified ECIST fragments are transferred to and immobilized on the solid support.

The ECIST fragments affixed to the solid support are used to identify the presence or absence of methylated CpG dinucleotide sites in a cell sample. Further, the exon-containing portions of ECIST sequences may be used for measuring levels of the corresponding gene expression in the cell sample being tested.

Accordingly, the present invention is directed to a process for generating a screening array containing expressed gene sequences including:

a. contacting a nucleic acid sequence with an enzyme which digests the nucleic acid sequence into fragments in which CpG islands are preserved;

b. amplifying the fragments to form a plurality of CpG island fragments;

c. screening the plurality of CpG island fragments with a nucleic acid probe to identify CpG island fragments which contain expressed sequences; and d. affixing the CpG island fragments which contain expressed sequences onto a solid support of the screening array.

In addition to the CpG dinucleotide fragments, other known DNA sequences may be placed on the solid support to serve as orientation marks and for normalization of hybridization signal intensities. For example, CpG dinucleotide fragments for ER, WT1, Rb and p16 may be used.

Any solid support to which the CpG dinucleotide rich fragments may be attached may be employed in the present invention. Examples of suitable solid support materials include, but are not limited to, silicates such as glass and silica gel, cellulose and nitrocellulose papers, and nylon membranes. The solid support material may be used in a wide variety of shapes including, but not limited to slides and membranes. Slides provide several functional advantages and thus are a preferred form of solid support. Due to their flat surface, probe and hybridization reagents can be minimized using glass slides. Slides also enable the targeted application of reagents, are easy to keep at a constant temperature, are easy to wash and facilitate the direct visualization of RNA and/or DNA immobilized on the solid support.

A universal or generic DNA array containing these CpG dinucleotide rich fragments can be developed to use as a hybridization template for methylation screening of various types of cancer. Such cancers include but are not limited to breast, prostate, colon, lung, liver and ovarian cancer. However, those skilled in the art will be able to develop screening arrays containing CpG dinucleotide rich fragments specific for particular cancer types.

Preparation of Amplicons

The amplicons of the present invention are amplified nucleic acid fragments derived from a cell sample which are used to probe the CpG dinucleotide rich fragments of the screening array. Generally, amplicons are single or double-stranded amplification products which contain a copy of the target nucleic acid sequence. Amplicons are prepared by isolating and purifying a nucleotide sequence, preferably DNA, from a sample and digesting the isolated and purified nucleotide sequence with a restriction endonuclease which cuts the sequence into fragments but leaves CpG dinucleotide rich regions, i.e., CpG islands intact.

The sample of genomic DNA may be obtained from normal (control) cells, an individual's primary tumors or from clinical specimens containing tumor cells. Cancerous cell types which may be used to prepare the amplicons include but are not limited to breast cancer, ovarian cancer, colon cancer, leukemia, kidney cell cancer, liver cell cancer and lung cancer. Genomic DNA samples can be obtained from any mammalian body fluid, secretion, cell-type or tissue, as well as any cultured cell or tissue. In a preferred embodiment, two sets of amplicons containing methylated CpG dinucleotide sequences are prepared. One set of amplicons is prepared from DNA from non-tumor (control) cells to be used as a reference and a second set of amplicons is prepared from tumor cells.

It is preferred that the restriction enzyme used is an enzyme which has a recognition sequence in regions other than the CpG dinucleotide rich regions of the nucleotide sequence. In a preferred embodiment, the restriction enzyme digests the portions of the nucleotide sequence not containing CpG dinucleotides into fragments having a length of less than 200 base pairs which are then discarded. Examples of appropriate restriction enzymes include but are not limited to MseI, Tsp509, NlaIII and BfaI. In a more preferred embodiment, the restriction enzyme MseI, whose recognition sequence, TTAA rarely occurs in CpG dinucleotide sites, is used to digest the nucleic acid sequence. Preferably, the endonuclease-restricted, intact CpG islands are nucleotide fragments in which CpG dinucleotides comprise at least 50% of the nucleic acids and are typically between 200 to 2,000 base pairs in length.

The cleaved ends of the endonuclease-restricted, intact CpG islands are then ligated to linker primers and amplified. The endonuclease-restricted CpG islands are preferably amplified according to the procedure outlined above. In a preferred embodiment, unphosphorylated linker primers such as H24 5' AGG CAA CTG TGC TAT CCG AGG GAT (SEQ ID NO:49) and H12 5' TAA TCC CTC GGA (SEQ ID NO:50) are employed in the extension step of PCR amplification.

Because repetitive DNA sequences in the amplified CpG islands may later interfere with the hybridization process, such sequences may optionally be depleted from the ligated DNA using a subtractive hybridization approach. Examples of repetitive sequences are the Alu I and Kpn I families. Various subtractive hybridization techniques are known and well documented in the art. See e.g., Akopyants et al., *Proc. Natl. Acad. Sci. USA* 95:13108–13 (1998); Lee J. H. and Welch D. R., *Int. J. Cancer* 71: 1035–44 (1997); U.S. Pat. Nos. 5,591,575 and 5,589,339. In a preferred embodiment, a subtractive hybridization approach is carried out using Cot-1 in which human Cot-1 DNA containing enriched repetitive sequences is preferably nick translated, biotin-labeled and added to the treated genomic DNA. See Craig et al., *Hum. Genet.*, 100: 472–476 (1997) as incorporated herein by reference. The resulting DNA mixture is then purified and denatured, and the biotin labeled repetitive sequences are allowed to hybridize to the complementary repetitive sequences on the genomic DNA. Biotin has a high affinity for avidin; therefore, when streptavidin-magnetic particles are added to the DNA mixture, the repetitive sequence hybrids will attach to the magnetic particles via biotin-streptavidin interaction. The repetitive sequence hybrids are then separated from the CpG islands using a magnetic particle separator. The supernatant containing the CpG islands is removed and purified using methods known in the art.

The resulting amplicons containing methylated and unmethylated CpG islands are purified and digested with appropriate methylation-sensitive restriction enzymes. The methylation-sensitive restriction enzymes will cut their DNA recognition sites when those sites are not methylated but do not cut the DNA site if it is methylated. Thus, unmethylated CpG islands are degraded and methylated CpG islands survive the endonuclease treatment. Examples of such methylation-sensitive enzymes are BstU I, SmaI, SacII, EagI, MspI, HpaII, HhaI and BssHIII. In a preferred embodiment, BstU I, whose recognition sequence, CGCG, occurs frequently within CpG islands is used. This methylation-sensitive enzyme is particularly preferred if the CpG dinucleotide fragments immobilized on the screening array are derived from DNA clones selected from the CGI genomic library because approximately 80% of the CGI inserts contain BstU I sites. See Cross et al., *Nature Genet.*, 6: 236–244 (1994).

In a preferred embodiment, only a fraction of the methylated and unmethylated CpG islands are digested with a methylation-sensitive restriction enzyme. The remaining fraction is not digested with a methylation-sensitive enzyme. As a result, two sets of amplicons are generated to probe the CpG dinucleotide rich screening array: one set of amplicons containing methylated and unmethylated amplicons (e.g., amplicons treated with Mse I, but not BstU I) and a second set of amplicons containing methylated amplicons (e.g., amplicons treated with Mse I and BstU I). The set of amplicons containing methylated and unmethylated CpG islands are preferably used a control in hybridization to determine whether the CpG dinucleotide rich nucleic fragments of the screening array are representative of the repertoire of CpG dinucleotide fragments. The second set of amplicons containing methylated CpG islands are then used to identify methylated CpG island sequences in the cell sample.

The endonuclease restricted amplicons are then amplified, preferably using PCR as is generally described above in connection with the preparation of CpG dinucleotide rich fragments. A relatively low number of amplification cycles is preferably used to prevent the overabundance of remaining repetitive sequences generated by PCR. In a particularly preferred embodiment, the amplicons are subjected to least fifteen and no more than about thirty amplification cycles. In a more preferred embodiment, the amplicons are subjected to approximately fifteen amplification cycles.

The amplicons are then preferably purified and labeled. The term "labeled" is herein used to indicate that there is some method to visualize the CpG dinucleotide fragments hybridized to the amplicons. There are many different labels and methods of labeling known to those of ordinary skill in the art. Moreover, a wide variety of direct and/or indirect means are available to enable visualization of the subject nucleic sequences that have hybridized to the prepared DNA array. Suitable visualizing means include radioisotope labels and non-radioisotope labels such as fluorescence-based detection technologies. Examples of radioisotope labels that can be used include $^{32}p$ and $^{33}P$-dCTP and examples of non-radioisotope labels that can be used include Cy3-dUTP and Cy5-dUTP. Further, any labeling techniques known to those in the art could be useful to label the subject nucleic acid sequence in of this invention. Several factors may govern the choice of labeling means, including the effect of the label on the rate of hybridization and binding of the methylated amplicons to the CpG dinucleotide rich screening array, the nature and intensity of the signal generated by the label and the expense and ease in which the label is applied.

In particular, the present invention provides a process for isolating a set of amplicons to identify methylation patterns from a cell sample which includes:
 a. contacting nucleic acid sequences with an enzyme which digests the nucleic acid sequences into fragments in which CpG islands are preserved;
 b. attaching the cleaved ends of the fragments to linker primers to form linker primer products;
 c. contacting the linker primer product with a methylation-sensitive enzyme which digests the linker primer products having unmethylated CpG dinucleotide sequences but not methylated CpG dinucleotide sequences to form a digestion product comprising methylated CpG island loci; and
 d. amplifying the digestion product to form amplicons.

Screening

The labeled amplicons are used to screen the CpG dinucleotide fragments of the screening array produced using the above methods. Labeled amplicons having a complementary sequence to that of a CpG dinucleotide fragment affixed on the solid support of the screening array will result in a positive hybridization signal. Preferably, the CpG dinucleotide fragments affixed to the screening array are ECIST fragments. If amplicons are used to probe ECIST fragments, positive hybridization signals will also indicate the presence of DNA sequences which are expressed in the cell sample.

In a preferred embodiment, methylated (e.g., MseI/BstU I-pretreated amplicons) amplicons are used to screen the CpG dinucleotide rich fragments of the screening array. Positive hybridization signals indicate the presence of methylated DNA in the cell sample.

In particular, the present invention is directed to a process for determining the presence or absence of methylation of a CpG dinucleotide rich region of a nucleic acid sequence within a genome, the process comprising:
 (a) contacting the nucleic acid sequence with an enzyme which digests the nucleic acid sequences into fragments in which CpG islands are preserved;
 (b) attaching the fragments to linker primers to form linker primer products;
 (c) contacting the linker primer products with a methylation-sensitive enzyme which digests the linker primer products having unmethylated CpG dinucleotide sequences but not methylated CpG dinucleotide sequences to form a digestion product comprising methylated CpG island loci;
 (d) amplifying the digestion product to form amplicons;
 (e) labeling the amplicons;
 (f) contacting the labeled amplicons with a screening array comprising a plurality of nucleic acid fragments affixed to a solid support; and
 (g) determining the presence or absence of labeled amplicons bound to the plurality of nucleic acid fragments of the screening array.

In a preferred embodiment, the CpG dinucleotide fragments of the screening array are screened using two sets of endonuclease treated amplicons: one set of amplicons which contain methylated and unmethylated CpG islands (e.g., amplicons treated with Mse I, but not BstU I) and a second set of amplicons which contain methylated CpG islands (e.g., amplicons treated with MseI and BstU I). This first set of amplicons containing methylated and unmethylated CpG islands is preferably used as a control in hybridization to determine whether the amplified products are representative of the repertoire of CpG dinucleotide rich fragments. Preferably, the first set of amplicons containing methylated and unmethylated amplicons are amplicons treated with Mse I. The first set of amplicons is completely removed and the screening array is then rehybridized using the second set of amplicons containing methylated CpG islands. Alternatively, the second set of amplicons containing methylated CpG islands is used to screen a second screening array containing CpG dinucleotide fragments which are identical to the CpG dinucleotide fragments of the screening array probed with the first set of amplicons. In a preferred embodiment, the second set of amplicons contain Mse I/BstU I-pretreated amplicons. Positive hybridization signals resulting from the second hybridization using amplicons containing methylated CpG islands indicate the presence of methylated CpG island sequences in the cell sample being tested. Further, positive hybridization signals using both sets of amplicons (e.g., Mse I treated amplicons and Mse I/BstU I amplicons) indicate the presence of aberrently methylated DNA in the cell sample.

Accordingly, the present invention provides a process for determining the presence or absence of aberrently methylated DNA in a cell sample, said process comprising:

a) preparing a first set of amplicons comprising (i) contacting a nucleic acid sequence with an enzyme which digests the nucleic acid sequences fragments in which CpG islands are preserved to form a digestion product comprising methylated and unmethylated CpG island loci; (ii) attaching the digestion product to linker primers to form linker primer products; (iii) amplifying the linker primer products to form amplicons; (iv) labeling the amplicons;

b) preparing a second set of amplicons comprising (i) contacting nucleic acid sequences with an enzyme which digests the nucleic acid sequences into fragments in which CpG islands are preserved; (ii) attaching the fragments to linker primers to form linker primer products; (iii) contacting the linker primer products with a methylation-sensitive enzyme which. digests the linker primer products having unmethylated CpG dinucleotide sequences but not methylated CpG dinucleotide sequences to form a second digestion product comprising methylated CpG island loci; (iv) amplifying the second digestion product to form amplicons; (v) labeling the amplicons;

c) contacting the first set of amplicons with a first screening array comprising a plurality of nucleic acid fragments affixed to a solid support and determining the presence or absence of labeled amplicons bound to the plurality of nucleic acid fragments of the first screening array;

d) contacting the second set of amplicons with a second screening array which comprises a plurality of nucleic acid fragments affixed to a solid support wherein the plurality of nucleic acid fragments of the second screening array are identical to the plurality of nucleic acid fragments of the first screening array and determining the presence or absence of labeled amplicons bound to the plurality of nucleic acid fragments of the second screening array; and e) observing whether the presence or absence of the first set of amplicons bound to the nucleic acid fragments of the first screening array is the same as the presence or absence of the second set of amplicons bound to the nucleic acid fragments of the second screening array.

In another preferred embodiment, the screening array is probed using two sets of methylated amplicons. The first set of methylated amplicons is prepared from a non-cancer (control) cell to be used as a reference and the second set of methylated amplicons is prepared from a cancer cell. The CpG dinucleotide fragments of the screening array are first screened using amplicons containing methylated CpG islands prepared from a non-cancer cell. Preferably, Mse I/BstU I treated amplicons from a non-cancer cell will be used in this first hybridization. The first set of methylated amplicons is completely removed and the screening array is then rehybridized using the second set of amplicons containing methylated CpG islands prepared from a cancer cell. Preferably, Mse I/BstU I treated amplicons from a tumor cell will be employed in this second screening. Alternatively, the second set of amplicons are used to screen a second screening array containing CpG dinucleotide fragments which are identical to the CpG dinucleotide fragments of the screening array screened with the first set of methylated amplicons prepared from non-tumor cells. The difference in the hybridization signal intensities using the second set of methylated amplicons from a cancer cell as compared to the intensities of the hybridization signals obtained using the first set of methylated amplicons from a non-cancer (control) cell reflects the aberrant methylation patterns of the corresponding sequences in the cancer cell DNA.

In particular, the present invention is directed to a process for identifying methylation patterns in DNA from a cancer cell including:

a. isolating a first set of amplicons comprising (i) contacting nucleic acid sequences derived from a cancer cell with an enzyme which digests the nucleic acid sequences into fragments in which CpG islands are preserved; (ii) attaching the fragments to linker primers to form linker primer products; (iii) contacting the fragments with a methylation-sensitive enzyme which digests the fragments having unmethylated CpG dinucleotide sequences but not methylated CpG dinucleotide sequences to form a digestion product comprising methylated CpG island loci; (iv) amplifying the digestion product to form amplicons; and (v) labeling the amplicons;

b. isolating a second set of amplicons comprising repeating (i) through (v) of step (a) wherein the nucleic acid sequences of (i) are nucleic acid sequences derived from a non-cancer cell;

c. contacting the first set of amplicons with a first screening array comprising a plurality of nucleic acid fragments affixed to a solid support and determining the presence or absence of labeled amplicons bound to the plurality of nucleic acid fragments of the screening array;

d. contacting the second set of amplicons with a second screening array comprising a plurality of nucleic acid fragments affixed to a solid support wherein said plurality of nucleic acid fragments of the second screening array are identical to the plurality of nucleic acid fragments of the first screening array and determining the presence or absence of labeled amplicons bound to the plurality of nucleic acid fragments of the second screening array; and e. observing whether the presence or absence of the first set of amplicons bound to the plurality of nucleic acid fragments of the first screening array is the same as the presence or absence of the second set of amplicons bound to the plurality of the nucleic acid fragments of the second screening array.

Preferably, gene silencing associated with DNA methylation can be confirmed by rescreening the same screening array with cDNA derived from the cancer samples using methods known in the art.

A Experimental results utilizing the present DMH methods suggest that alterations of cell methylation patterns is related to tumor growth in cancer development. Specifically, the present DMH methods have been used to identify hypermethylated CpG island sites which may act as markers indicating whether a patient has cancer. These sites were identified using tumor cells from breast cancer patients. The alteration of the methylation pattern in CpG dinucleotides may be a key, and a common event, in the development of neoplasia. Aside from effect of DNA-MTase on methylation, the present experiments suggest that additional factors such as pre-existing methylation of CpG dinucleotides may account for de novo methylation in cancer cell lines.

Without being bound by any theory, a mechanism may exist whereby methylated CpG islands could progressively accumulate during tumor development; therefore, pre-existing methylation within a CpG island locus may promote subsequent de novo methylation in cancer cells. As a result of CpG island hypermethylation, critical tumor suppressor genes may become silenced, leading to some cells with growth advantage. The results of the experiments discussed in the following examples offer an alternative explanation for the underlying mechanisms in direct contrast to the random nature of the de novo DNA methylase activities previously proposed in transformed cells.

Further, differential methylation patterns in various clinical specimens may reflect different stages or types of cancer. Thus, a determination of the methylation patterns in tumor cells would allow for the identification of gene markers indicative of cancer. Hence, the present DMH methods have broad utility for identifying differentially methylated CpG island sites in a genome; for mapping hypermethylated DNA sites which are related to disease development; for understanding the role of DNA methylation in normal cell genomic DNA imprinting, differentiation, and development; for understanding the role of DNA methylation in tumorigenesis; and for diagnosing and monitoring the prognosis of disease.

The following examples illustrate the invention, but are not to be taken as limiting the various aspects of the invention so illustrated.

EXAMPLE 1

Materials and Methods

Cell culture and tissue sample preparations. The T47D, ZR-75-1, Hs578t, and MDA-MB-468 breast cancer cell lines were acquired from the American Type Culture Collection (Rockville, Md.). The MDA-MB-231 and MCF-7 cell lines were obtained from Dr. Wade V. Welshons at the University of Missouri School of Veterinary Medicine (Columbia, Mo.). T47D and ZR-75-1 were maintained in RPMI 1640 media with 10% fetal bovine serum, while the remaining cell lines were maintained in Earle's Modified Eagle's Medium with 10% fetal bovine serum. Breast tumor and adjacent, non-neoplastic tissue (used as a normal control) were obtained from patients undergoing mastectomies at the Ellis Fischel Cancer Center (Columbia, Mo.). Total RNA and genomic DNA from samples were isolated using the RNeasy Total RNA Kit™ (Qiagen) and QIAamp Tissue Kit™, respectively.

Northern hybridization. Twenty mg of total RNA from breast cancer cell lines and a normal control fibroblast sample were electrophoresed on a 1.4% agarose gel in the presence of 2.2 mM formaldehyde and transferred to a nylon membrane. cDNA probes were prepared from cells known to express DNMT1 and p21$^{WAF1}$ by reverse transcription-PCR. A 192-bp product was generated for DNMT1 using primers 5' ATC TAG CTG CCA AAC GGA G (SEQ ID NO: 51) (sense strand) and 5' CAC TGA ATG CAC TTG GGA GG (SEQ ID NO: 52) (antisense strand). A 206-bp product was generated for p21$^{WAF1}$ using primers 5' AAC TAG GCG GTT GAA TGA GAG GTT (SEQ ID NO: 53) (sense strand) and 5' GTG ACA GCG ATG GGA AGG AG (SEQ ID NO: 54) (antisense strand). The resulting PCR products were isolated and $^{32}$P-labeled using the Multiprime DNA labeling system (Amersham). The Northern membrane was hybridized with radiolabeled DNMT1 and p21$^{WAF1}$ cDNA probes, respectively. Hybridization was performed in 8 ml Hybrisol I (Oncor) at 42° C. overnight. Washing was performed once for 20 min in 0.1% SDS-0.5×SSC (1×SSC is 0.15 M NaCl plus 0.015 M sodium citrate, pH 7.0) and twice for 20 min each in 0.1% SDS-0.2×SSC at 65° C. The same membrane was also hybridized with a $^{32}$P-labeled b-actin cDNA (1.1-kb) probe to determine the amount of RNA loaded. The hybridized membrane was subjected to phosphorimage analysis with a Molecular Dynamics PhosphorImager, and band intensities were quantified with ImageQuant Software (Molecular Dynamics). The levels of DNMT1 and p21$^{WAF1}$ mRNAs were normalized with the level of b-actin mRNA in the respective sample lanes.

Amplicon generation. Approximately 2 mg of genomic DNA from breast cancer cell lines or normal breast tissue were restricted to completion with 10 units of Mse I per mg DNA following the conditions recommended by the supplier (New England Biolabs). The digests were purified, and mixed with 0.5 nmol of unphosphorylated linkers H-24 and H-12 in a DNA ligase buffer (New England Biolabs). The oligonucleotide sequences were as follows: H-24: 5' AGG CAA CTG TGC TAT CCG AGG GAT (SEQ ID NO: 49) and H-12: 5' TAA TCC CTC GGA (SEQ ID NO: 50). Oligonucleotides were annealed by cooling the mixture gradually from 50° to 25° C. and then ligated to the cleaved ends of the DNA fragments by incubation with 400 units of T4 DNA ligase (New England Biolabs) at 16° C. Repetitive DNA sequences were depleted from the ligated DNA using a subtraction hybridization protocol described by Craig et al. Briefly, human Cot-1 DNA (20 mg; Gibco/BRL) containing enriched repetitive sequences was biotin-labeled using the Nick Translation Kit (Gibco/BRL) and added to the treated genomic DNA. The DNA mixture was purified and dried under vacuum. The dried mixture was redissolved in 10 ml of 6×SSC and 0.1% SDS, denatured by boiling for 10 min, and hybridized at 65° C. overnight. One hundred ml (1 mg) of streptavidin-magnetic particles were added to the hybridization mixture and incubated at room temperature for 30 min. Streptavidin-magnetic particles were prepared according to the manufacturer's instructions (Boehringer Mannheim). Tubes were applied to a magnetic particle separator (Boehringer Mannheim) and the supernatant was aspirated. This supernatant was incubated again at room temperature for 30 min with freshly prepared streptavidin-magnetic particle solution. After the incubation, the second supernatant was removed and DNA was purified using a QIAquick kit (Qiagen). Half of the resulting DNA was digested with the methylation-sensitive endonuclease BstU I (New England Biolabs) following the conditions recommended by the supplier. PCR reactions were performed with the pretreated DNAs (Mse I or Mse I/BstU I) (500 ng) in a 100 ml volume, containing 0.4 mM T-24 primer, 2 units Deep Vent (exo-) DNA polymerase (New England Biolabs), 5% (v/v) dimethyl sulfoxide, and 200 mM dNTPs in a buffer provided by the supplier. The tubes were incubated for 3 min at 72° C. to fill in 5' protruding ends of ligated linkers and subjected to 15 cycles of amplification consisting of 1 min denaturation at 95° C. and 3 min annealing and extension at 72° C. in a PTC-100 thermocycler (MJ Research). The final extension was lengthened to 10 min. The use of low amplification cycles is essential to prevent overabundance of leftover repetitive sequences generated by PCR. The amplified products, designated as "Mse I-pretreated amplicons" or "Mse I/BstU I-pretreated amplicons," were purified using the QIAquick kit, and 50 ng of the DNA were $^{32}$P-labeled using the random primer labeling system as described above.

Differential methylation hybridization. Approximately 3,000 clones derived from the CGI genomic library were prescreened with $^{32}$P-labeled Cot-1 DNA. Clones negative or weakly positive for the Cot-1 hybridization signals were picked and placed into 96-well PCR microplates. A fraction of each colony was transferred to a well of separate 96-well culture chambers for later use. Insert from each clone was amplified in a total volume of 20 ml per tube following the conditions described earlier. Thirty cycles of amplification were performed with denaturing for 1 min at 94° C., annealing for 1 min at 55° C., and extension for 3 min at 72° C. The primers used for amplification were HGMP 3558: 5' CGG CCG CCT GCA GGT CTG ACC TTA A (SEQ ID NO: 47) and HGMP 3559: 5' AAC GCG TTG GGA GCT CTC CCT TAA (SEQ ID NO: 48). After PCR, 1 ml of the amplified products was digested with the methylation-sensitive BstU I, and the digests were size fractionated on 1% agarose gels. Inserts (0.2 to 1.5-kb) of the tested CGI clones containing multiple BstU I sites (based on the digestion patterns) were selected for further analysis. The remaining DNA was denatured at 95° C. for 5 min, 2 ml of tracking dye (bromophenol blue) was added to each tube and the DNA was transferred to nylon membranes using a 96-pin MULTI-PRINT™ replicator (V & P Scientific). Each PCR sample was dotted in duplicate, and the position of each dot in the array was marked by the tracking dye. Each pin transfers an approximately 0.4 ml-hanging drop (about 40 ng DNA) onto a membrane. An alignment device (LIBRARY COPIER™; V&P Scientific) was used in conjunction with the replicator to convert three 96-well PCR samples in duplicate into one recipient of 276 dots on a 10×12-cm nylon membrane. Additionally, 3 positive controls were dotted in quadruplicate on the corners (the top and bottom three rows of the first and last columns) of array to serve as orientation marks and for normalization of hybridization signal intensities of dotted genomic fragments. Membranes were first hybridized with $^{32}$P-labeled Mse I-pretreated amplicons overnight at 65° C. in 10 ml of High Efficiency Hybridization solution (Molecular Research, Inc.). Washing was performed once for 20 min in 0.1% SDS-0.5×SSC (1×SSC is 0.15 M NaCl plus 0.015 M sodium citrate, pH 7.0) and twice for 20 min each in 0.1% SDS-0.2×SSC at 65° to 75° C. Autoradiography and analysis were completed using the Molecular Dynamics PhosphorImager and the ImageQuant Software as described earlier. Probes were completely stripped, and the same membranes were rehybridized with $^{32}$P-labeled Mse I/BstU I-pretreated amplicons. Each hybridization experiment was independently performed twice using duplicate membranes.

DNA Sequencing. Plasmid DNA was prepared from positive CGI clones and sequenced using the DyeDeoxy Terminator Cycle Sequencing kit and the automated ABI PRISM 377 sequencer. The nucleotide sequence data were compared to GenBank using the BLAST program.

Methylation Analysis by Southern Hybridization. Genomic DNA (10 mg) from breast cancer cell lines or breast specimens was digested to completion with Mse I or Mse I/BstU I. The restriction products were separated on 1.0% agarose gels and transferred to nylon membranes. Portions of CGI clone inserts were PCR-amplified as probes for Southern hybridization. Amplified products were designed to be ~200 to 300-bp in length and contain no BstU I sites. Hybridization was conducted in 8 to 10 ml of High Efficiency Hybridization solution for overnight at 65–70° C. Post-hybridization washing was carried out as described above. Southern blots were subjected to phosphorimage analysis, and band intensities were quantified with the ImageQuant software.

EXAMPLE 2

Expression of DNMT1 and p21$^{WAF1}$ Genes in Breast Cancer Cells

Human cancer cells have increased DNA-MTase activities known to promote CpG island hypermethylation during tumor progression. See Vertino et al., *Mol. Cell Biol.*, 16:4555–4565 (1996); Wu et al., *Cancer Res.*, 56: 616–622 (1996); Belinsky et al., *Proc. Natl. Acad. Sci. USA*, 93: 4045–4050 (1996). Since DNMT1 is primarily responsible for DNA-MTase synthesis, we determined its mRNA levels in breast cancer cell lines T47D, ZR-75-1, Hs578t, MDA-MB-231, MDA-MB-468, and MCF-7.

RNA from breast cancer cell lines T47D, ZR-75-1, Hs578t, MDA-MB-231, MDA-MB-468, and MCF-7 were isolated and prepared for Northern analysis using the methods and materials provided in Example 1. cDNA probes for DNMT1 and p21$^{WAF1}$ were also prepared using the methods and materials described in Example 1. Northern analysis showed 3- to 12-fold higher levels of the 5.4-kb DNMT1 mRNA in these cell lines compared with a normal control sample (FIG. 1, upper panel). These results are consistent with a previous study that showed both increases of DNMT1 mRNA levels and the resulting elevation of DNA-MTase enzyme activities in the same cell lines.

It has also been recently shown that the p21 protein negatively regulates targeting of DNA-MTase to the replication-associated protein PCNA. It has been proposed that the presence of p21 prevents DNA-MTase access to replicating DNA, thereby impeding hypermethylation in normal cells, while loss or decreased expression of p21 in tumor cells may facilitate aberrant methylation. Therefore, the expression of the 2.1-kb p21$^{WAF1}$ transcript, the gene encoding p21 in these breast cancer cells, was detected in the cell lines with levels 2- to 8-fold lower than the normal control sample (FIG. 1, middle panel). This result, together with the DNMT1 finding, suggests that these breast cancer cell lines possess an increased capacity to aberrently methylate their genomes.

EXAMPLE 3

Methylation Profiling of CpG Islands in Human Breast Cancer Cells by Differential Methylation Hybridization (DMH)

Figure 2:
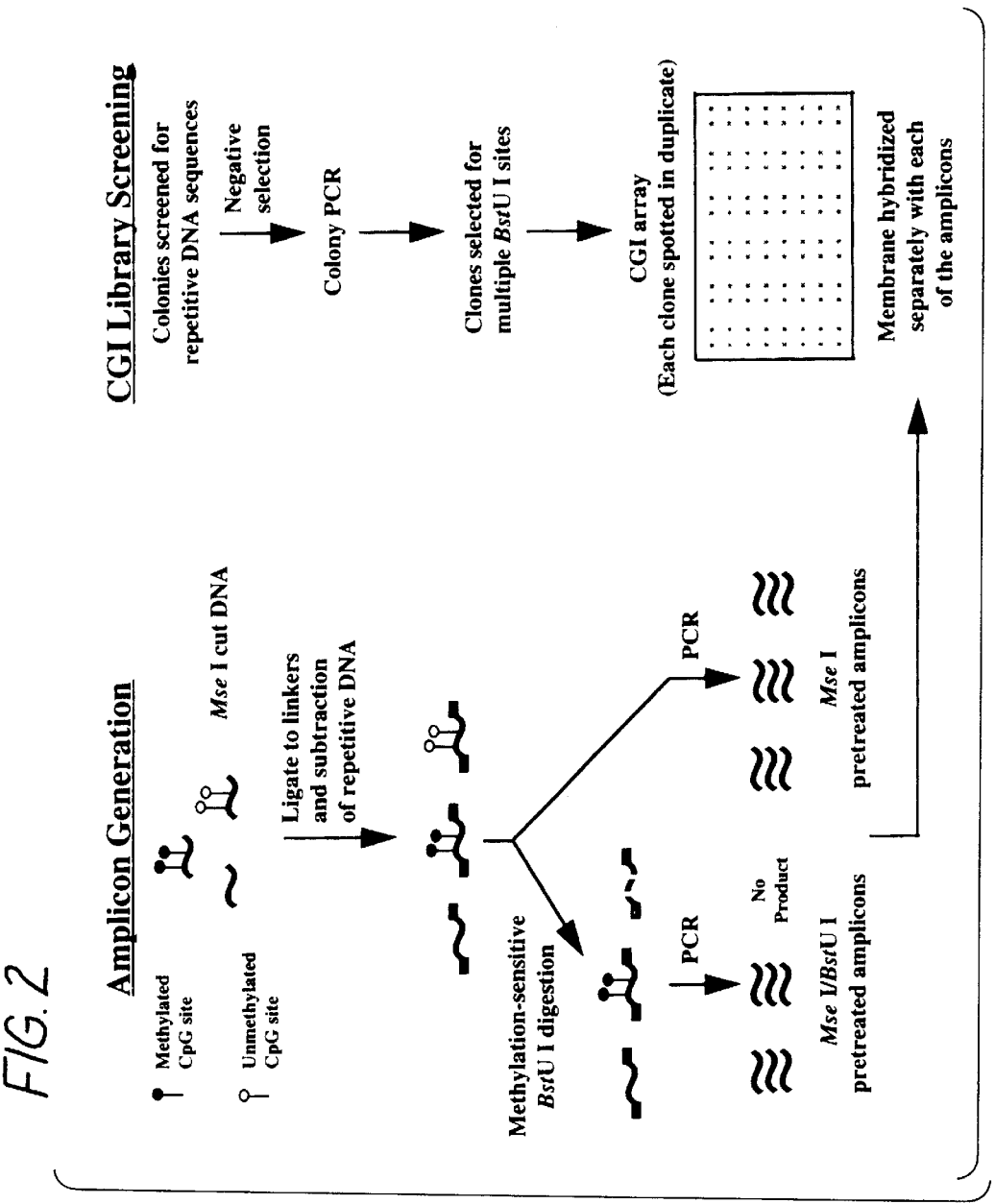
FIG. 2 is a schematic flowchart for differential methylation hybridization. The diagram illustrates the preparation of amplicons used as hybridization probes and selection of CpG island genomic clones gridded on high-density arrays.

DMH was utilized to determine the extent of CpG island sequences undergoing de novo methylation in the 6 cancer cell lines described above in Example 2 (FIG. 2). Genomic DNA from breast cancer cells (T47D, ZR-75-1, Hs578t and MDA-MB-468) was used to prepare amplicons as described above in the Materials and Methods provided in Example 1. DNA from normal breast tissue was similarly digested and used as a control. The cleaved ends of the CpG dinucleotide rich fragments were ligated to linkers and repetitive sequences such as the Alu I and Kpn I families were removed from the digests using a Cot-1 subtractive hybridization approach (see Materials and Methods).

Figure 3:
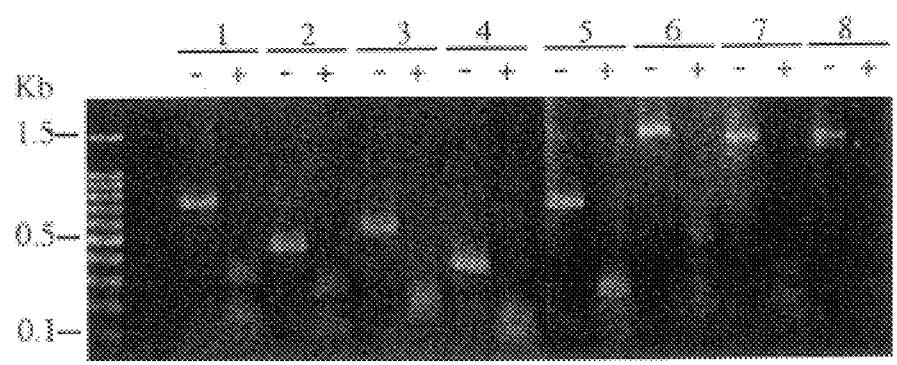
FIG. 3 is BstU I analysis of CpG island clones. Inserts from each clone was amplified by colony PCR and digested with BstU I. The digested (+) and undigested (−) insert DNA samples were separated on 1.5% agarose gels and stained with ethidium bromide. Based on the sizes of the digested fragments, clones containing more than or equal to two BstU I sites were further selected for analysis by differential methylation hybridization. Molecular weight markers (100-bp ladder; Promega) are shown at left.

Half of the subtracted DNA was further treated with methylation-sensitive endonuclease BstU I and both BstU I-digested and undigested, control DNAs were used as templates for linker-PCR (see Material and Methods). Genomic fragments containing unmethylated BstU I sites were cut and could not be amplified in the treated samples, whereas the same fragments were amplified in the undigested, control samples. Some fragments containing methylated BstU I sites in the cells were protected from the digestion and were amplified bylinker-PCR. The PCR products designated as "Mse I-pretreated amplicons" or "Mse I/BstU I-pretreated amplicons" were used as probes for screening hypermethylated sequences. CpG island clones were preselected from the CGI library to contain multiple BstU I sites (FIG. 3), and their amplified insert DNA (0.2 to 1.5-kb) was gridded on high-density arrays as described in the Materials and Methods of Example 1.

Results of DMH Analysis

Figure 4:
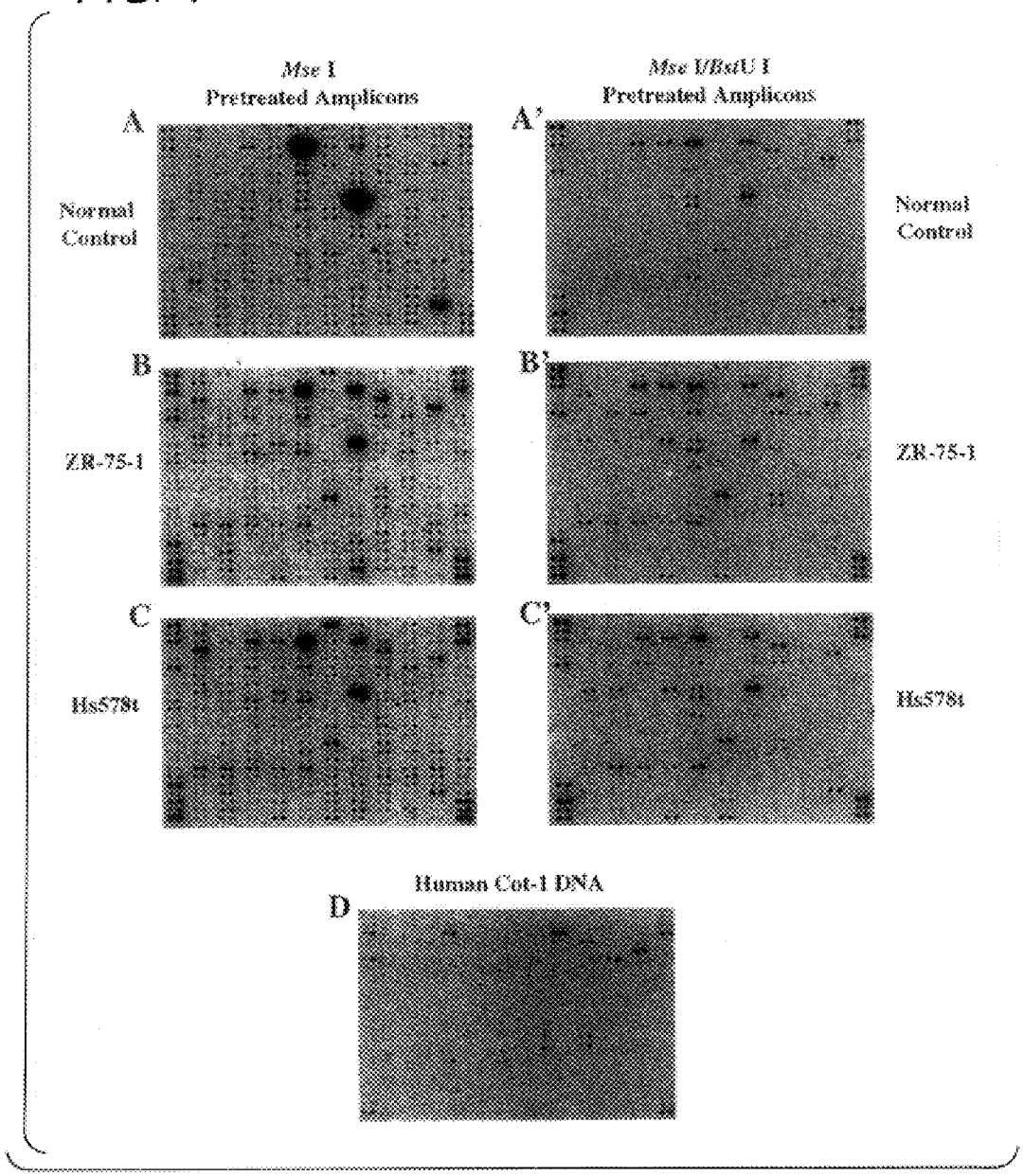
FIG. 4 show representative results of differential methylation hybridization. PCR products of CpG island clones were dotted onto membranes in duplicate and hybridized first with $^{32}$P-labeled Mse I-pretreated amplicons as shown here for a normal breast sample (control), ZR-75-1, and Hs578t breast cancer cell lines (panels A, B, and C). The same membranes were later hybridized with $^{32}$P-labeled Mse I/BstU I-pretreated amplicons (panels A', B' and C'). Panel D: the membrane was hybridized with a repetitive DNA probe, human Cot-1 DNA (Gibco/BRL). Three positive control DNA samples were dotted in quadruplicate on the four corners of array to serve as orientation marks and for comparison of hybridization signal intensities.

FIG. 4 shows the representative results of 276 CpG island loci analyzed by DMH. Various degrees of hybridization signals observed could be attributed to different sizes of amplified products. Mse I-pretreated amplicons were expected to hybridize the matching Mse I-restricted CpG island sequences on the membranes; the hybridization signals, however, were detected in approximately 86% of these island loci (panels A, B, and C). The unhybridized loci could be derived from the Y chromosome due to the fact that this CGI library was originally constructed using male DNA, whereas the amplicons were prepared from female cells. Excluding the unhybridized loci (panel A) and the 14 Cot-1 positive loci (panel D), the Mse I/BstU I-pretreated amplicons derived from a normal breast tissue sample detected positive hybridization signals in 9.7% (23 of 237 loci) of the tested CpG island sequences (panel A'). The positive signals represent methylated BstU I sites located within these CpG island loci, some of which could be derived from the transcriptionally inactivated X chromosome or "imprinted genes." This low percentage is consistent with the notion that the majority of CpG islands are ummethylated in normal cells. A few prominent hybridization signals were observed on the filter hybridized with Mse I-pretreated amplicons (panel A); the intensity of these signals, however, was decreased on the filter hybridized with Mse I/BstU I-pretreated amplicons (panel A'). This may be attributed to the presence of some abundant sequences (e.g., ribosomal DNA or Cot-1 related sequences) known to be methylated in the normal genome.

Figure 5:
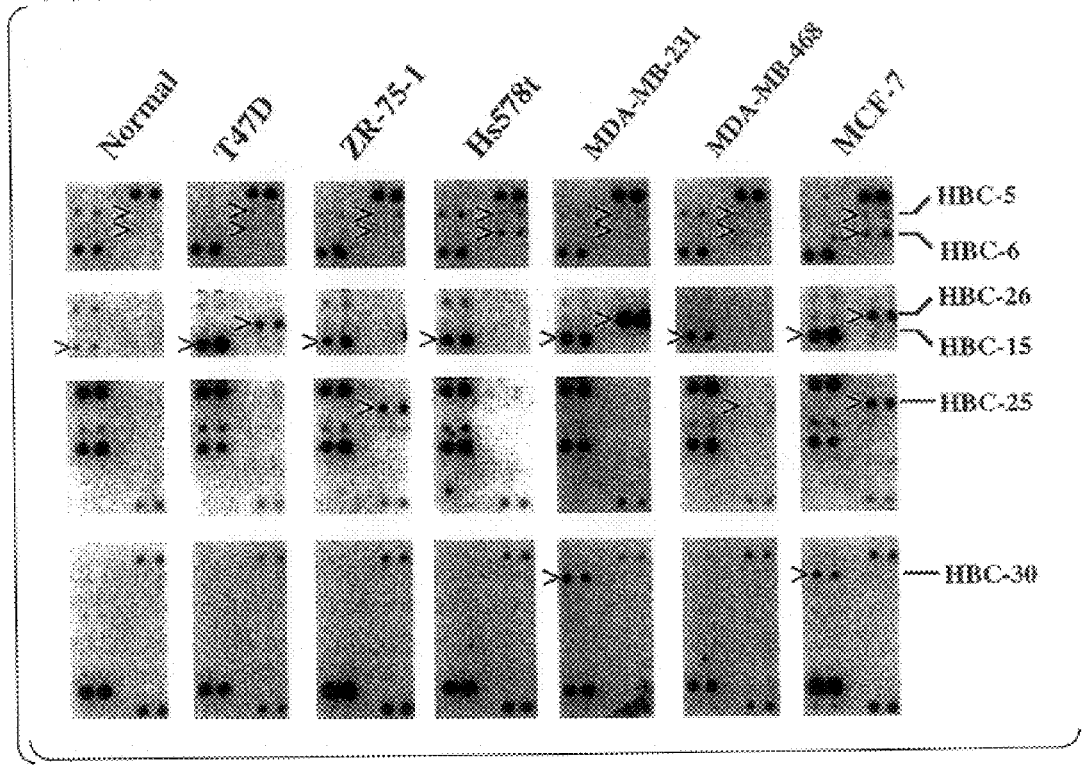
FIG. 5 represents identification of hypermethylated CpG island loci by differential methylation hybridization. PCR products of CpG island clones were dotted onto membranes in duplicate and probed with the Mse I/BstU I-pretreated amplicons for the normal control and breast cancer cell lines as indicated. Probes were prepared as described in the text. Clones shown at right (also marked by >) containing hypermethylated BstU I sites were identified on the autoradiogram showing greater hybridization signal intensities of dots hybridized with probes prepared from the breast cancer cell lines than the same dots probed with the normal breast control.

An increased number of hybridization signals were detected in the CpG island arrays hybridized with the Mse I/BstU I amplicons derived from the 6 breast cancer cell lines. Representative results were shown for cell lines ZR-75-1 and Hs578t (panels B, B', C, and C'). Methylated BstU I sites were observed in 15.0% of these tested loci in Hs578t, 15.6% in T47D, 18.0% in MDA-MB-468, 19.4% in ZR-75-1, 22.7% in MDA-MB-231, and 23.6% in MCF-7 cells, respectively. Although hypermethylation was extensive relative to the normal breast sample, the overall levels varied among these cell lines. Methylation pattern analysis led to the identification of hypermethylated CpG island loci present in these cell lines relative to the normal control; some loci appeared to be methylated in all 6 cell lines, whereas others were sporadically methylated in only a few cell lines (FIG. 5).

Nucleotide Sequencing of Hypermethylated CTG Island Loci

Thirty-four positive CpG island loci selected from the 276 CpG island array and from other DMH screenings were further characterized by nucleotide sequencing. Inserts of these CGI clones were sequenced and internal BstU I sites were verified. The sequence data were used to search for known sequences in the GenBank database. Thirty of these loci are listed in Table 1. (Four other loci not listed here were false-positive findings; their hypermethylation status in breast cancer cells was not confirmed by subsequent Southern analysis.) Nine of the 30 clones contained sequences identical to the known expressed sequences of HPK1, DCIS1, Potassium channel protein, PAX2, PAX7, GALNR2, EST03867, ESTAA827755, and EST88248. Six clones matched existing CpG island sequence tags.

EXAMPLE 4

Figure 6:
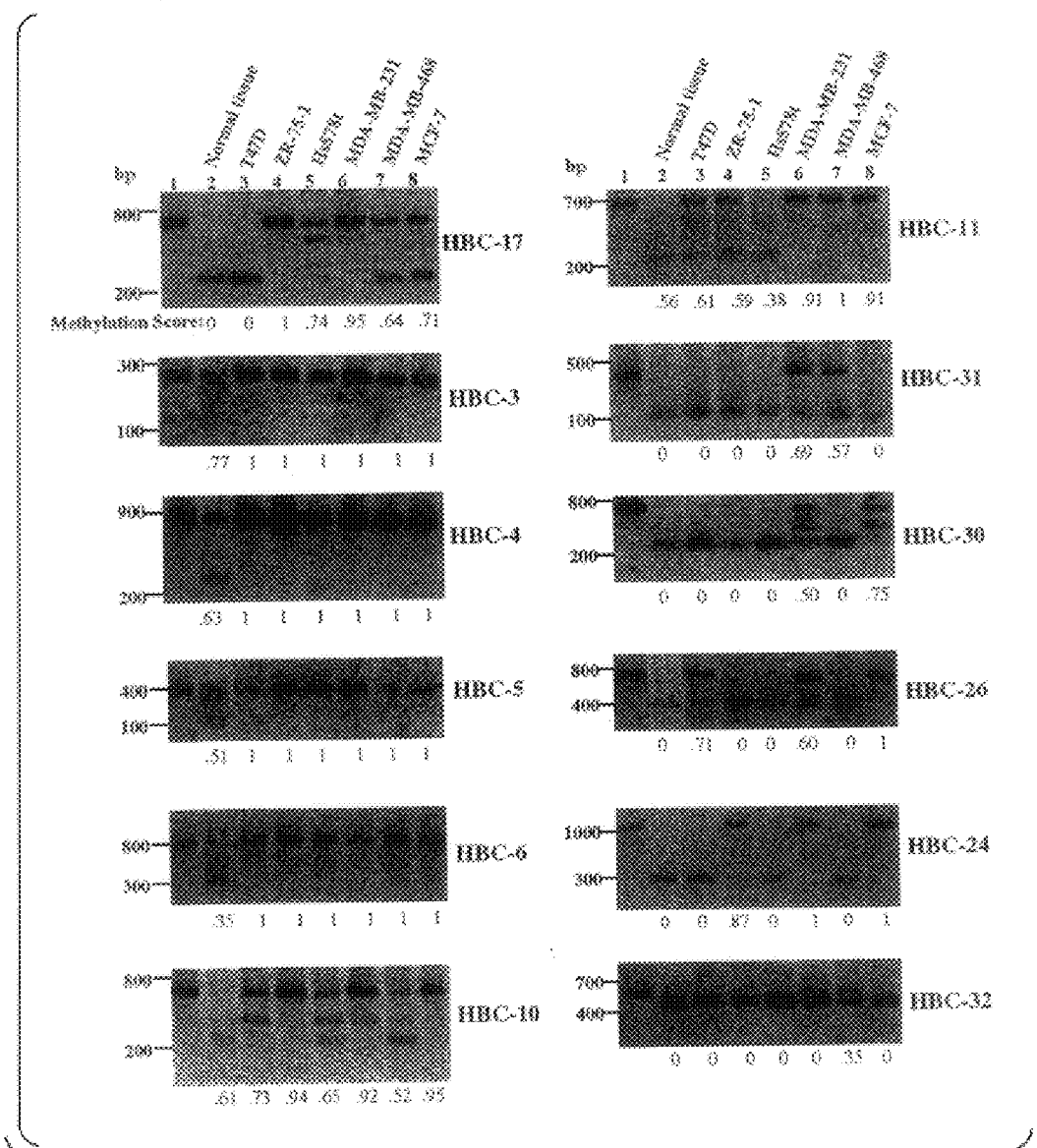
FIG. 6 show representative results of methylation analysis by Southern hybridization. Genomic DNA (10 mg) from a normal breast tissue sample (lane 2) and breast cancer cell lines—T46D (lane 3), ZR-75-1 (lane 4), Hs578t (lane 5), MDA-MB231 (lane 6), MDA-MB-468 (lane 7), and MCF-7 (lane 8) were treated consecutively with Mse I and methylation sensitive BstU I, and subjected to Southern hybridization. Lane 1 contains control DNA digested with Mse I only. The digests were hybridized with genomic fragments (200–300-bp) derived from CpG island clones shown at right. Molecular weight markers (100-bp ladder; Promega) are shown at left. Percent of methylation was calculated as the intensity of the methylation band relative to the combined intensities of all bands. Percent of incomplete methylation was similarly calculated. The methylation score shown at the bottom of each lane was the sum total of the percent of complete methylation multiplied by 0.5.

Profiling Methylation Patterns of CpG Island Loci in Breast Cancer Cells by Southern Hybridization The methylation status of CpG island loci detected in the cancer cell lines was independently confirmed by Southern analysis (FIG. 6). Hybridization probes were generated from the cloned inserts by PCR. Amplified products were designed to be ~200 to 300-bp in length and contain no BstU I sites. For example, the probe for HBC ("hypermethylation in breast cancer")-17 SEQ ID NO: 15 detected a 750-bp fragment in the Mse I-digested, control DNA lane (top left panel, lane 1). The same or similar-sized fragments were detected in the Mse I/BstU I double-digested DNA samples of ZR-75-1, Hs578t, MDA-MB-231, MDA-MB-468, and MCF-7 (lanes 4–8). The presence of this fragment was a result of all the BstU I sites within HBC-17 SEQ ID NO: 15 being insensitive to restriction and, therefore, methylated in these cells. A 300-bp fragment was present in the T47D DNA sample (lane 3). This band was shown in the digested normal, control DNA (lane 2), suggesting all the tested sites were unmethylated in the cells and digested by BstU I to give a 300-bp fragment. The unmethylated fragment was also present in MDA-MB-468 and MCF-7 cells (lanes 7 and 8). Partially methylated fragments (400 and 600-bp) were identified in Hs578t or MDA-MB-231 cells, which can be attributed to a portion of the tested BstU I sites being methylated in HBC-17 SEQ ID NO: 15.

Because it was not possible to measure the degrees of methylation at each tested site based on this Southern analysis, a semiquantitative approach was developed for these samples. First, percent of complete methylation was calculated as the densitometric intensity of the 750-bp fragment relative to the combined intensities of all fragments from each lane. Percent of incomplete methylation (i.e., the 400 and 600-bp fragments) and unmethylation (i.e., the 300-bp fragment) was similarly calculated. Each fraction was further assigned a value, with complete methylation being 1, incomplete methylation 0.5, and unmethylation 0. The methylation score for each sample was the sum total of the percent of complete methylation multiplied by 1 plus the percent of incomplete methylation multiplied by 0.5. The scores derived using this method were in agreement with the results based on a visual comparison of band intensities for each sample lane. This approach was applied for the rest of the CpG island loci. Additional examples of Southern hybridization and the resulting methylation scores are shown in FIG. 6. To ensure a complete methylation-sensitive restriction of the cell line DNA samples, membranes were rehybridized with a negative control probe, 7–120, whose corresponding BstU I sites were known to be unmethylated in the cell line DNA as well as in a few normal breast DNA samples (data not shown).

Figure 7:
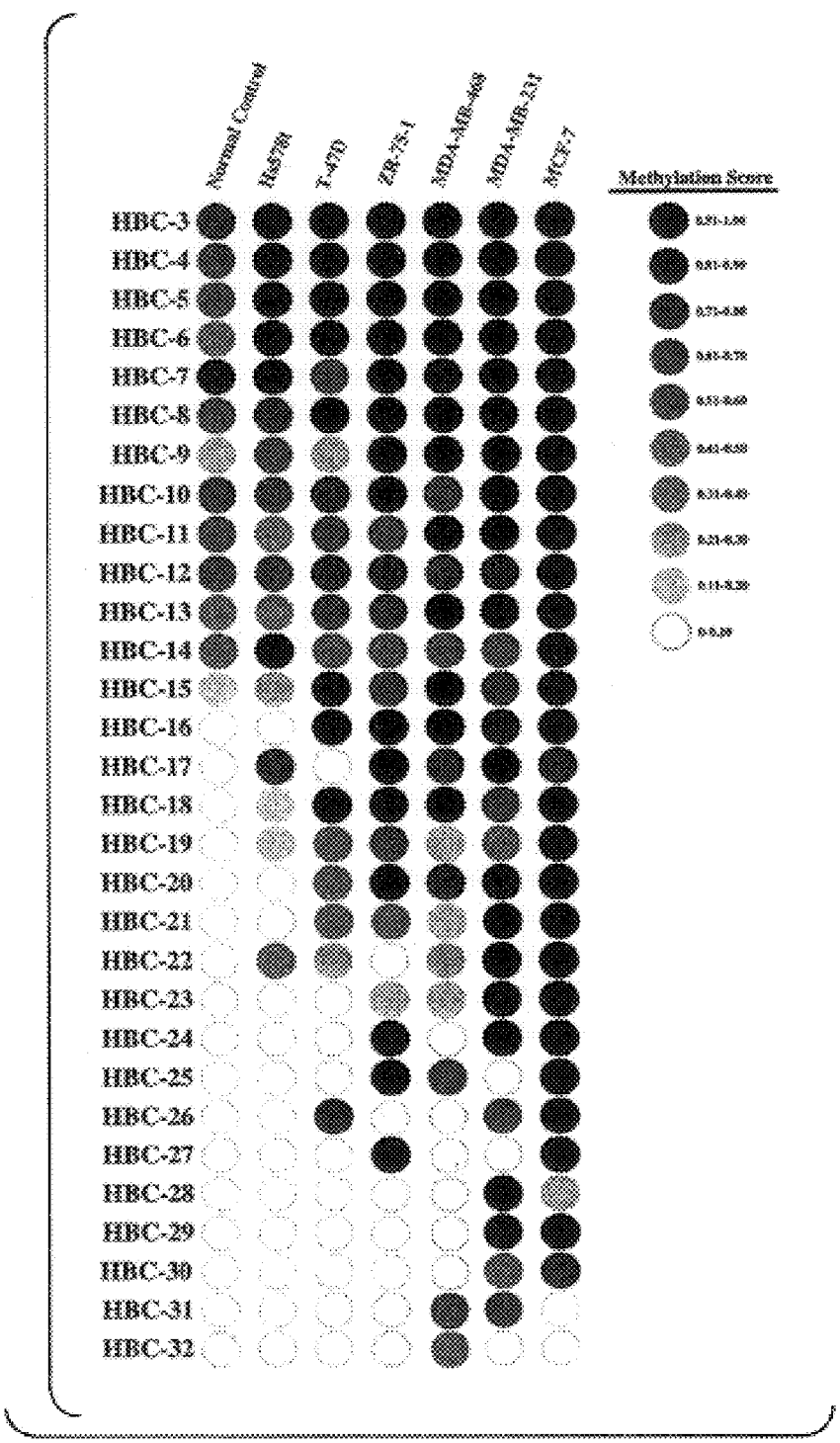
FIG. 7 is the methylation pattern analysis of 30 CpG island loci in breast cancer cell lines. Gray scales shown at right represent methylation scores of the 30 CpG island loci analyzed by Southern analysis (see examples in FIG. 5). The breast cancer cell lines indicated were arranged from left to right according to their increased methylation abilities (i.e., % of hypermethylated loci). The normal control was shown at the far left. Thirty CpG island loci (HBC-3 to -32) SEQ ID NO: 1 through SEQ ID NO: 30 were listed from top to bottom according to their increased methylation scores derived from these cell lines.

Methylation scores of the 30 CpG island loci analyzed in the breast cancer cell lines and 1 normal control sample are summarized in FIG. 7. These cell lines are arranged from left to right according to their increased methylation abilities (i.e., % of hypermethylated loci), and the CpG island loci are listed from top to bottom according to their increased methylation scores derived from these cell lines. Methylation pattern analysis indicated that CpG islands might differ in their susceptibility to hypermethylation in these breast cancer cells. In loci HBC-3 to -15 SEQ ID NO: 1 to SEQ ID NO: 13, various degrees of methylation at the tested BstU I sites were seen in the normal control sample. This pre-existing methylation condition was also observed in additional normal breast samples tested (data not shown). Hypermethylation of these loci appeared to be present and extensive in all the 6 cell lines examined. In A contrast, hypermethylation in other loci (HBC-16 to -32 SEQ ID NO: 14 to SEQ ID NO: 30) not displaying detectable pre-existing methylation in the normal control appeared to be less frequent in these cell lines. In some cases (e.g., HBC-23 to -32 SEQ ID NO: 21 through SEQ ID NO: 30), hypermethylation was observed only in a few cell lines. This observation suggests that a trend exists in which CpG island loci associated with the pre-existing condition are inclined to de novo methylation in cancer cells. Pattern analysis also revealed that the overall methylation frequencies were varied among these cell lines. Methylation (methylation score greater than 0.1) was observed in 57% of these 30 loci in Hs578t, 67% in T47D, 77% in ZR-75-1, 80% in MDA-MB-468, 90% in MDA-MB-231, and 93% in MCF-7 cells, respectively. These differences were more obvious by comparing methylation patterns among the loci (HBC-16 to 32 SEQ ID NO: 14 to SEQ ID NO: 30) not exhibiting the detectable pre-existing condition. In the two extreme cases, for example, only 4 of these 17 loci showed detectable methylation in Hs578t cells, whereas 15 of these loci had extensive methylation in MCF-7 cells. The results suggest that these cell lines differ in their intrinsic abilities to methylate CpG island sequences.

EXAMPLE 5

Methylation Analysis of Primary Breast Tumors by Southern Hybridization

Figure 8:
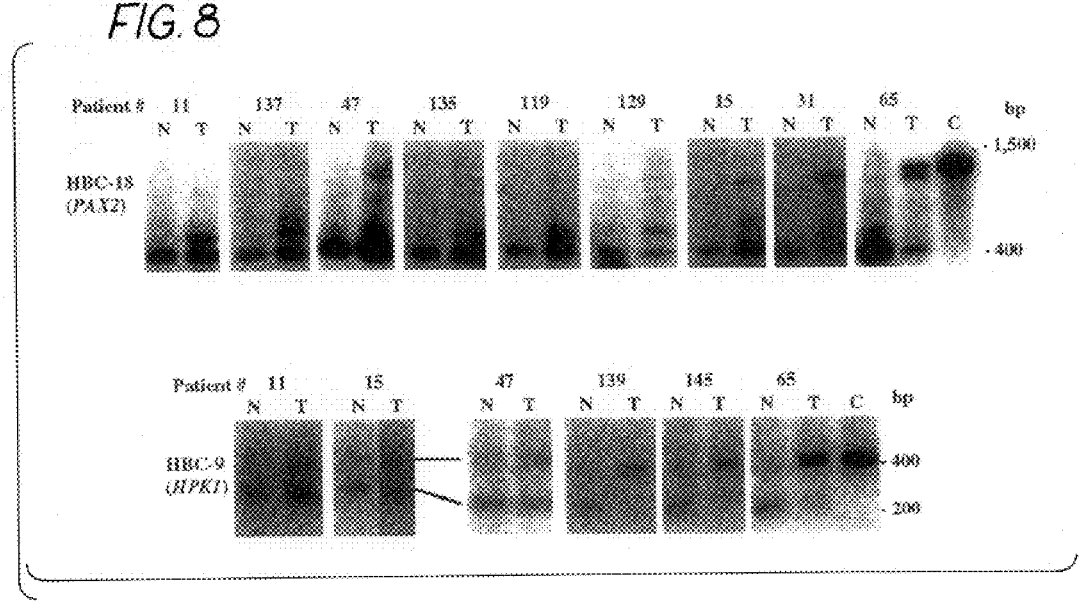
FIG. 8 is the methylation analysis of HBC-18 SEQ ID NO: 16 and -9 SEQ ID NO: 7 by Southern blot hybridization. Genomic DNA (10 mg) of breast tumor and the matching normal tissue was treated consecutively with Mse I and methylation-sensitive BstU I and subjected to Southern hybridization using the cloned genomic fragments as probes. These CpG island clones (HBC-18 SEQ ID NO: 16 and -19SEQ ID NO: 17) contained sequences identical to the 5' end of PAX2 (paired box-containing gene 2) and the promoter and exon 1 of HPK1 (hematopoietic progenitor kinase gene 1), respectively. C: control DNA digested with Mse I only, T: breast tumor, and N: normal breast tissue. Patient numbers are shown at the top of lanes. Molecular weight markers (100 bp ladder; Promega) are shown at right.

It has been demonstrated that CpG islands associated with nonessential genes might become methylated over time in immortalized cells that have been in culture for many years. See Antequera et al., *Cell* 62: 503–514 (1990). We, therefore, determined whether our in vitro findings could represent bona-fide de novo methylation in primary breast tumors. We validated the methylation status of 9 CpG island loci (HBC-6 SEQ ID NO: 4, -8 SEQ ID NO: 6, -9 SEQ ID NO: 7, -12 SEQ ID NO: 10, -15 SEQ ID NO: 13, -18 SEQ ID NO: 16, -20 SEQ ID NO: 18, -22 SEQ ID NO: 20, and -23 SEQ ID NO: 21) in primary breast tumors by Southern hybridization. As shown in FIG. 8, upper panel, HBC-18 SEQ ID NO: 16 was hypermethylated in the tumor DNA samples of patients 47, 135, 119, 129, 15, 31, and 65 relative to their paired normal breast tissue. Incomplete methylation of HBC-18 SEQ ID NO: 16 loci was detected in tumors of patients 11 and 137. In FIG. 8, lower panel, pre-existing methylation of HBC-9 SEQ ID NO: 7 was observed in the normal breast tissue of these patients consistent with the previous observation (FIG. 7). Hypermethylation of HBC-9 SEQ ID NO: 7 was observed in the tumor lanes of patients 47, 139, 145, and 65, showing increased band intensity of the 440-bp fragment relative to that of the same band in normal lanes. On preliminary observation, de novo methylation of two loci, HBC-16 SEQ ID NO: 14 and 26 SEQ ID NO: 24 was not present in 2 primary breast tumors (data not shown).

Comparisons of methylation patterns among the cell lines and a normal control indicate that the 30 CpG island loci might differ in their propensity for de novo methylation. This inherent condition may be at least in part influenced by a pre-existing methylation condition in local genomic sequences. As described in Example 4, loci HBC-3 to -15 SEQ ID NO: 15 seemed to be more susceptible to de novo methylation as compared to other loci (FIG. 7). Normal breast samples had detectable methylation in this group of CpG islands; methylation of these loci appeared to be extensive to complete in the cancer cell lines examined. In contrast, other loci without this pre-existing condition were less inclined to de novo methylation in breast cancer cells. This observation suggests that pre-existing methylation within a CpG island locus may promote subsequent de novo methylation in cancer cells.

This observation is further supported by several previous in vitro findings, showing that the activity of DNA-MTase could be positively influenced by a partial pre-methylation condition. See Christman et al., *Proc. Natl. Acad. Sci. USA,* 92: 7347–7351,(1995); Carotti et al., *Biochem. J.,* 37: 1101–1108 (1998). These studies found that single- or double-stranded synthetic polymers were poor substrates of the eukaryotic DNA-MTase, yet were efficiently methylated by the enzyme following the introduction of a small number of 5-methylcytosines by a prokaryotic methylase. Carotti et al. showed that the presence of 5-methylcytosines in double-stranded DNA substrates, either of natural or synthetic origins, stimulated in vitro methylation of neighboring CpG dinucleotides by DNA-MTase. Carotti et al., supra. The extent of stimulation depended both on the number and the distributions of the 5-methylcytosine residues, which could not be spaced too closely to exert the effect. This phenomenon has also been observed in human fibroblast cells transfected with a DNA-MTase cDNA. See Vertino et al., *Mol. Cell Biol.,* 16: 4555–4565 (1996). CpG island loci that were subject to de novo methylation in the transfected clones overexpressing DNA-MTase had low, but detectable levels of methylation in the parental lines. In contrast, CpG island loci found to be resistant to methylation in these transfected clones were devoid of methylation in the parental line.

This methylation-spreading phenomenon can account for the extensive methylation in CpG island loci with the pre-existing condition. It has been suggested that during tumorigenesis, pre-existing methylated repetitive elements may act as de novo methylation centers (i.e., cis-acting signals) from which methylation spreads into adjacent CpG island sequences. The results of these experiments indicate that methylation spread may actually occur from within a CpG-island sequence in tumor cells. The existing 5-methylcytosine residues in the sequence may stimulate the de novo methylation function of DNA-MTase. Although DNA-MTase prefers hemimethylated substrates for its maintenance activity in normal cells, the enzyme may have a second regulatory domain "sensing" the presence of 5-methylcytosines within CpG island sequences, allowing for de novo methylation. The "sensing" function could become more operative due to aberrantly high DNA-MTase levels in tumor cells. This may in turn lead to de novo methylation of cytosines located near sequences already containing methylated CpG dinucleotides. The newly methylated sites may acquire the ability to stimulate the subsequent methylation of adjacent sequences via DNA-MTase. This "domino" effect of methylation could progress with time to include the entire CpG island region, leading to the associated transcriptional silencing.

Differential Methylation Abilities in Breast Cancer Cell Lines

A second characteristic of our findings was that these breast cancer cell lines exhibited differential methylation potentials. In the two extreme cases, Hs578t and MCF-7 cells, the former showed a lack of ability to methylate the CpG island group (HBC-16 to -32 SEQ ID NO: 14 to SEQ ID NO: 30) without the pre-existing condition described above whereas the latter was proficient in methylating these CpG island loci. This suggests that the observed differences among these cell lines could not be solely due to the aberrant DNA-MTase action. The degrees of methylation appeared not to be correlated with the increased levels of DNMT1 expression or with the decreased levels of p21$^{WAF1}$ expression observed in these cells (FIGS. 1 and 7).

Thus, these results suggest that additional cellular factors may govern CpG island hypermethylation. One possibility may be an as yet unidentified or uncharacterized gene encoding a de novo methylase. Another possibility is that the various degrees of de novo methylation observed in these cancer cells might simply result from fixation of a hypermethylator phenotype that affords a greater proliferation potential. Finally, differential methylation abilities could be related to deficiencies in DNA repair in these cell lines.

EXAMPLE 6

DMH Screening of Breast Cancer Tumors

We have demonstrated the likelihood of potential mechanisms governing methylation in breast cancer cells by pattern analysis. DMH was then applied to determine whether patterns of specific epigenetic alterations correlate with pathological parameters in the patients analyzed.

Isolation of Amplicons from Breast Tumor DNA

DHM was used to analyze breast tumor specimens obtained from 28 female patients undergoing mastectomies at the Ellis Fischel Cancer Center (Columbia, Mo.) between 1992 and 1998. Adjacent, normal parenchyma was obtained from the same patient to serve as a normal control. All tumors used in this study were classified as infiltrating ductal carcinomas and were graded based on the Nottingham modified criteria of Bloom and Richardson. See Bloom, H. J. G. and Richardson, W. W., *Br. J. Cancer* 9: 359–377 (1957). This tumor-grading method was based on histological features of tubule formation, nuclear pleomorphism, and mitotic activity, and points were assigned for each category accordingly. The overall tumor grade was the sum total of scores between 3–9. Tumors with poorly differentiated phenotypes (8–9 points) are likely to have less or no tubular structures, irregular and large nuclei, and high mitotic counts. Tumors with moderately (6–7 points) or well differentiated (3–5 points) phenotypes may have definite tubule formation, moderate outlines of epithelial cell shapes and uniformity of nuclear chromatin, and low mitotic indexes. High-molecular-weight DNA was isolated from these specimens using QIAamp Tissue KitJ (Qiagen).

DMH was performed as provided in the materials and methods of Example 1. Genomic DNA (0.5–1 mg) from breast tumor or normal samples was utilized to prepare the amplicons as described in Example 1. The amplified products, labeled as normal or tumor amplicons, were purified and $^{32}$P-labeled for array hybridization. BstUI-positive, Cot-I-negative or -weakly positive CpG island clones were prepared from the CGI genomic library and used for 96-well format PCR as described in Example 1. Membranes were first hybridized with normal amplicons, and autoradiography was conducted using the Molecular Dynamics PhosphorImager. Probes were stripped and the same membranes, or duplicate membranes, were hybridized with tumor amplicons and scanned with the PhosphorImager.

Data Analysis

Dot intensities for positive CpG island tags were measured using the volume review protocol of ImageQuant software (Molecular Dynamics). The raw volume data from tumor and normal samples were normalized prior to comparison. This was achieved by ratio determination of the internal control tags. Briefly, two internal control tags with close volume ratios were selected to estimate hybridization differences between paired amplicons. One of these two control tags from each amplicon was further used to calculate a factor for normalization:

$$\text{Normalization factor} = \frac{\text{Normal internal control tag volume}}{\text{Tumor internal control tag volume}}$$

This factor was applied to normalize tumor tag volumes. For tags with preexisting methylation in normal tissue, the normal tag volume was subtracted from the normalized tumor volume. For tags without preexisting methylation in the normal tags, the normalized tumor volume was used directly. Statistical analyses were performed using the SigmaStat software (version 2.0). The hypermethylation differences among different groups of tumor grades were determined by the unpaired t-test and by the Mann-Whitney rank sum test when the data failed the normality test. The difference was considered significant when the P value was less than 0.05.

Results and Discussion

Figure 9A:
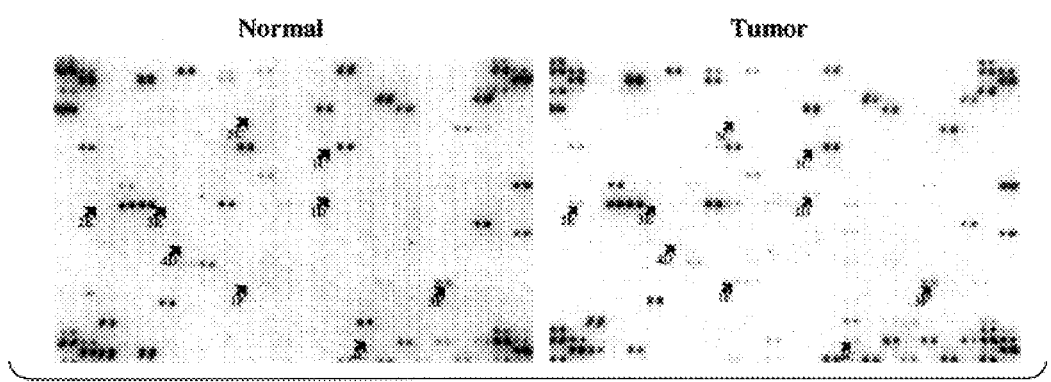
FIGS. 9A and 9B are representative results of differential methylation hybridization from one breast cancer patient.
Figure 9B:
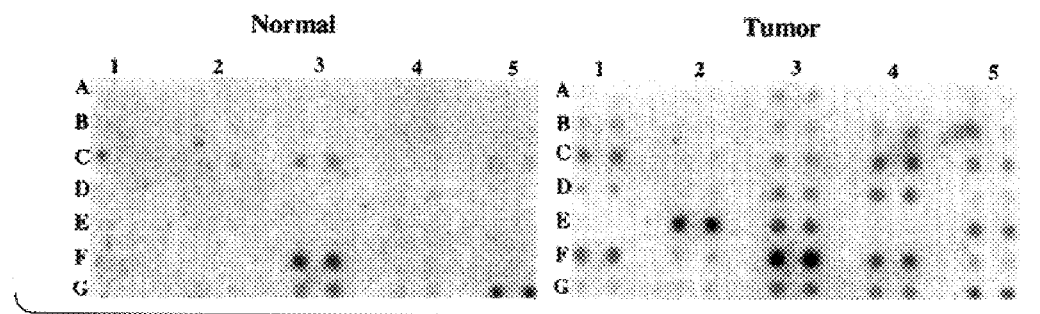

DMH was initially applied to 28 paired breast tumor and normal samples using an array panel containing more than 1,000 CpG island tags. FIG. 9A shows representative results of DMH screening in paired normal and tumor samples of patient 103. Based on visual inspection, hypermethylated sequences were identified in breast tumors, showing detectable hybridization signals in CpG island tags probed with tumor amplicons, but not in the same tags probed with normal amplicons (see examples indicated by arrows). This is because methylated BstUI sites in tumor DNA were protected from restriction within CpG island sequences, which were then amplified by linker-PCR and hybridized to the corresponding tags. The same sites, however, were unmethylated or partially methylated in normal DNA and were restricted by BstUI; therefore, no hybridization signals were detected in the arrays. Some of these hypermethylated CGI island tags were confirmed in the subsequent secondary screening (FIG. 9B).

A few CpG island tags were detected by normal amplicons (i.e., preexisting methylation) but showed greater signal intensities when probed with tumor amplicons (e.g., CpG island tags on the lower right hand corner in FIG. 9A). These sequences usually exhibited more prominent hybridization signals among all of the tags, likely representing abundant copies of CpG dinucleotide rich ribosomal DNA as previously described in the cell line study. Methylation of ribosomal DNA has previously been observed in normal cells, but shown to increase to a greater extent in breast tumors. Another possibility is the increased copy numbers of normally methylated CpG island loci in tumors due to aneuploidy. Excluding this preexisting condition, the extent of hypermethylation in unmethylated CpG islands was quite variable among patients in this group; close to 9% of the tested BstUI sites exhibited complete methylation in some breast tumors examined while others had little or no detectable change in the tested sites.

Sequence Characterization of CpG Island Tags. Thirty CpG island tags positive for hypermethylation in the primary screening were selected for further characterization. DNA sequencing results showed that 9 of these tags contained sequences identical to known cDNAs, PAX7 (5' end), Caveolin-1 (exon2), GATA-3 (exon 1), and COL9A1 (exon 1), and 5 ESTs (AI928953, AA604922, AA313564, AI500696, and AI381934) as shown in Table 1.

This finding is consistent with that of Lisanti and coworkers where they also observed CpG island methylation in the Caveolin-1 gene in breast cancer cell lines. Five CpG island tags, HBC-17 SEQ ID NO: 16, 19 SEQ ID NO: 17, 24 SEQ ID NO: 22, 25 SEQ ID NO: 23, and 27 SEQ ID NO: 25, found to be hypermethylated in breast cancer cell lines as discussed in Example 5 were also identified in this study. The remainder twenty-five tags were numerically assigned as HBC-33 to -57 SEQ ID NO: 31 to SEQ ID NO: 46.

Figure 10:
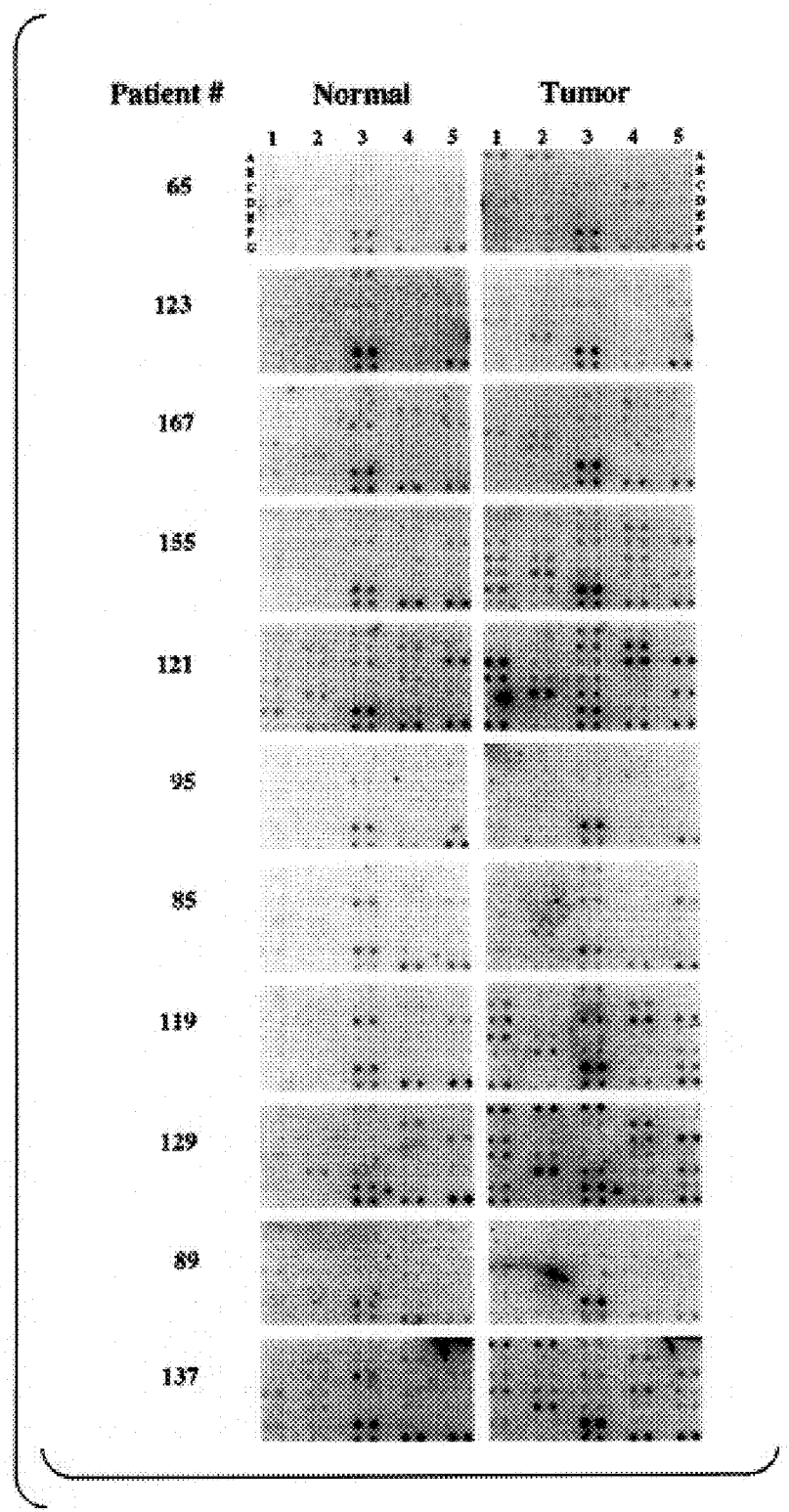
FIG. 10 represents the identification of hypermethylated CpG island loci by differential methylation hybridization. The 30 CpG island tags shown in this subarray panel were selected from an initial DMH screening of >1,000 tags. Five additional tags—coordinates on the x- and y-axes are 3C, 3F, 3G, 4G and 5G—were included as internal controls. CpG island tags were dotted onto membranes in duplicate and probed with radiolabeled amplicons for the normal and breast tumors as indicated. DMH screening from 11 of 28 patients were represented here, and experiments were performed independently at least twice.

Secondary Screening of DMH in Breast Tumors. As shown earlier in FIG. 9B, the 30 CpG island tags were rearrayed for secondary DMH screening in the patient group to confirm their hypermethylation status (see representative results in FIG. 10). Five additional tags—coordinates on the x- and y-axes are 3C, 3F, 3G, 4G, and 5G—showing no hybridization intensity differences among a few of the breast tumors tested in the primary screening were chosen as internal controls. Again, most normal controls showed few or no detectable hybridization signals at the tested loci, whereas the corresponding breast tumors exhibited various degrees of hybridization intensities, reflecting the differences in CpG island hypermethylation.

To semiquantify the methylation differences, hybridization signal intensity for each CpG island tag was measured using the volume review protocol of ImageQuant software as described in Materials and Methods. From FIG. 10, it is clear that dot intensities of the internal controls sometimes varied among patients or between a patient's paired tumor and normal samples, likely due to tissue heterogeneity or tumor aneuploidy. Therefore, internal control volume ratios were tested and two with close volume ratios were selected for normalization. The adjusted tumor volumes were used for clinical correlation in this patient group.

Figure 11:
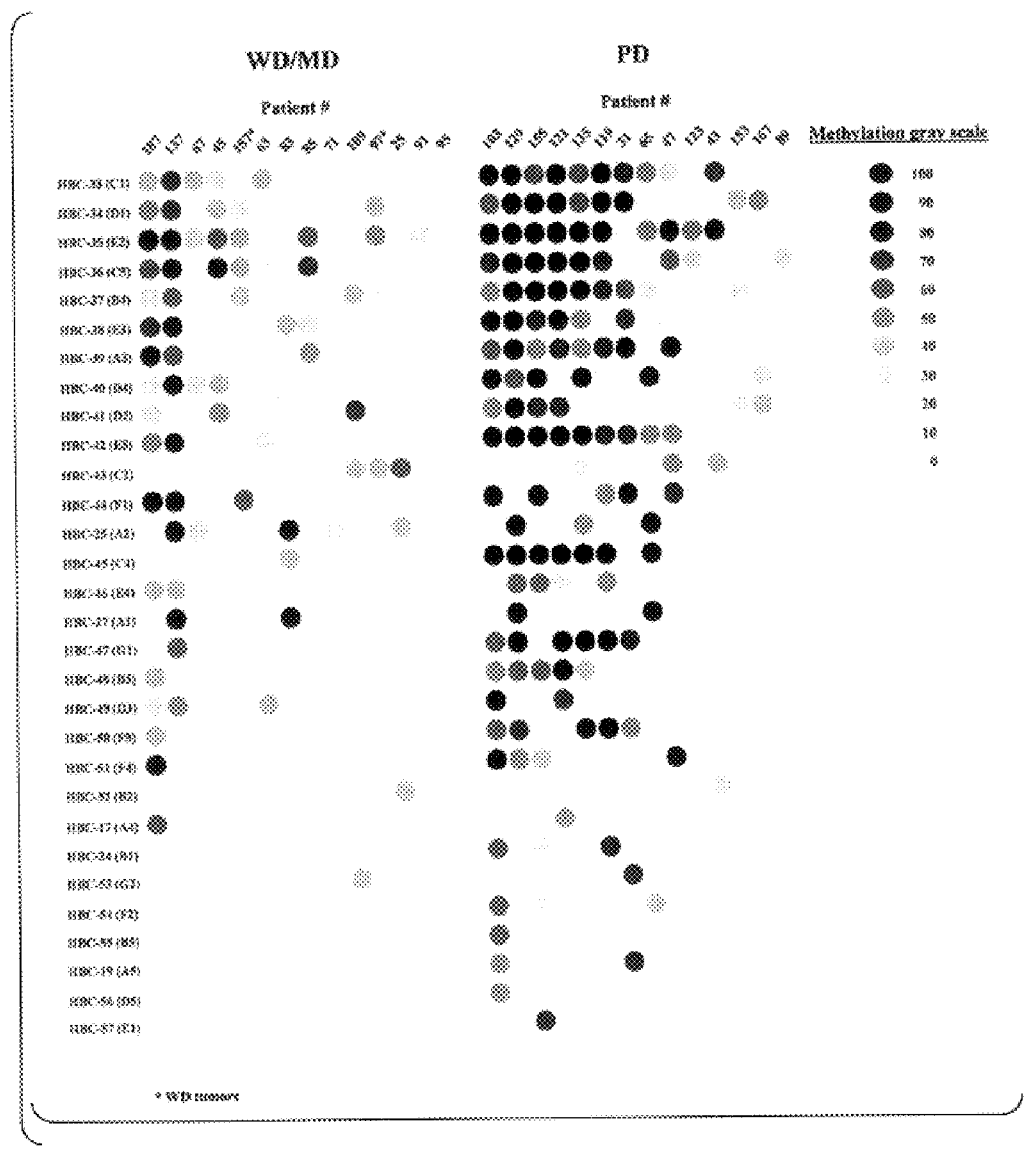
FIG. 11 represents the hypermethylation pattern analysis of 30 CpG island loci in 28 primary breast tumors. Methylation gray scale shown at the right represents volume. percentile generated by ranking hybridization signal intensities of these tested loci. Data from primary tumors were presented according to their tumor grades: well-/moderately differentiated (WD/MD), and poorly differentiated (PD). Within[ ]each group, patients were arranged from left to right according to their increased methylation propensities. Thirty CpG island loci (on the left of the panel with their secondary screening coordinates shown in parenthesis) were listed from top to bottom according to their increased methylation scales derived from the primary tumors. Five CpG island loci (HBC-17 SEQ ID NO: 15, 19 SEQ ID NO: 17, 24 SEQ ID NO: 22, 25 SEQ ID NO: 23, and 27SEQ ID NO: 25) were found to be hypermethylated in breast cancer cell lines.

CpG Island Hypermethylation and Tumor Grades. Statistical analysis revealed that CpG island hypermethylation was associated with histological grades of breast tumors (P—0.041). To aid in visualizing differences in CpG island hypermethylation among different tumor grades, we devised a gray scale by categorizing tumor methylation volumes into percentiles as depicted in FIG. 11. The $PD^3$ group exhibited more frequent and extensive hypermethylation at the loci tested than their $MD/WD^3$ counterparts did; half of the 14 PD tumors showed extensive hypermethylation at multiple loci (>10), while only two of the 14 MD/WD tumors showed hypermethylation at these loci. Moreover, the greatest degrees of differences were seen at loci HBC-42 SEQ ID NO: 36, -45 SEQ ID NO: 38, and -47 that were frequently hypermethylated in PD tumors, but not in MD/WD. This result suggests that patients with more advanced disease status are prone to methylation alterations. It should be noted that some of the patients showed little or no changes of methylation at the loci tested. This indicates that progression of some tumors may be independent of this epigenetic event or the alteration could occur in later stages of tumor development in such patients. No association of hypermethylation with other clinical parameters was found in this study.

The results of these experiments indicate that differential methylation patterns observed in various clinical specimens may reflect different stages or types of cancer. In this case, the most common methylation of CpG island loci (e.g., HBC-33, -34 SEQ ID NO: 31, -35, and -36) observed among different tumor grades likely occurs early during tumor development, while methylation groups (e.g., HBC-42 SEQ ID NO: 36, -45 SEQ ID NO: 38, and -47) observed preferentially in PD, but not in WD/MD groups, occur in later stages.

In view of the above, it will be seen that the several objects of the invention are achieved.

Other features, objects and advantages of the present invention will be apparent to those skilled in the art. The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

TABLE 1

A list of positive CpG Island clones isolated by differential methylation hybridization

| CpG Island Clone | Insert Size (kb) | GenBank Match | ATCC Accession Number | SEQ ID NO |
|---|---|---|---|---|
| HBC-3 | 0.25 | | | 1 |
| HBC-4 | 0.90 | | | 2 |
| HBC-5 | 0.40 | DCIS1 | L27636 | 3 |
| HBC-6 | 0.80 | CGI Clone 28f11 | Z60565 | 4 |
| HBC-7 | 0.60 | CGI Clone 178c6 | Z59859 | 5 |
| HBC-8 | 0.38 | CGI Clone 200b9 | Z55140 | 6 |
| HBC-9 | 0.44 | HPK1 | U66464 | 7 |
| HBC-10 | 0.75 | K + Channel Protein | Z93016 | 8 |
| HBC-11 | 0.70 | | | 9 |
| HBC-12 | 0.50 | CGI Clone 86e9 | Z63556 | 10 |
| HBC-13 | 1.00 | CGI Clone 31g5 | Z60696 | 11 |
| HBC-14 | 0.70 | | | 12 |
| HBC-15 | 1.50 | CGI Clone 7c5 | Z66179 | 13 |
| HBC-16 | 1.00 | EST AA827755 | ESTAA827 | 14 |
| HBC-17 | 0.75 | | | 15 |
| HBC-18 | 1.30 | PAX2 | M89470 | 16 |
| HBC-19 | 0.90 | PAX7 | AL021528 | 17 |
| HBC-20 | 0.45 | CGI clone 67g9 | Z62363 | 18 |
| HBC-21 | 0.90 | | | 19 |
| HBC-22 | 0.45 | | | 20 |
| HBC-23 | 0.90 | | | 21 |
| HBC-24 | 1.10 | IMAGE:2518953 5'mRNA | AI928953 | 22 |
| HBC-25 | 0.70 | | | 23 |
| HBC-26 | 0.70 | GALNR2 | AF058762 | 24 |
| HBC-27 | 0.70 | | | 25 |
| HBC-28 | 0.60 | | | 26 |
| HBC-29 | 0.70 | | | 27 |
| HBC-30 | 0.80 | | | 28 |
| HBC-31 | 0.50 | EST 03867 | T05978 | 29 |
| HBC032 | 0.60 | EST88248 | T35610 | 30 |
| HBC-34 | 0.95 | IMAGE:1113203 3'mRNA | AA604922 | 31 |
| HBC-37 | 1.00 | PAC 163M9 | AL021920 | 32 |
| HBC-38 | 0.50 | CGI 40c10 | Z58446 | 33 |
| HBC-39 | 0.60 | EST185442 | AA313564 | 34 |
| HBC-41 | 0.60 | CGI 29h6 | Z58110 | 35 |
| HBC-42 | 0.50 | CGI 13f7 | Z56764 | 36 |
| HBC-43 | 0.80 | Genomic Clone NH0444B04 | AC007392 | 37 |
| HBC-45 | 0.50 | PAC 29K1 | Z98745 | 38 |
| HBC-46 | 0.65 | IMAGE:2177671 3'mRNA | AI500696 | 39 |
| HBC-48 | 1.50 | BAC CLONE RG300E22 | AC004774 | 40 |
| HBC-49 | 0.50 | CGI 40c10 | Z58447 | 41 |
| HBC-51 | 0.70 | COL9A1 (alt exon1) | M32133 | 42 |

TABLE 1-continued

A list of positive CpG Island clones isolated by differential methylation hybridization

| CpG Island Clone | Insert Size (kb) | GenBank Match | ATCC Accession Number | SEQ ID NO |
|---|---|---|---|---|
| HBC-52 | 0.60 | IMAGE:2092259 3'mRNA | AI381934 | 43 |
| HBC-53 | 0.80 | Genomic Clone NH0444B04 | AC007392 | 44 |
| HBC-55 | 0.80 | CAVEOLIN-1 (exon2) | AF095592 | 45 |
| HBC-57 | 0.90 | GATA-3(exon1) | X55122 | 46 |

```
2341  ttcaaacatt ttattttctg tgcatagcett atagcactgt attataggaa tcagagtgta
2401  taagcaaaaa aatgaaataa aacttcttga agaccatttc cattatttat gattaaatca
2461  atgaaactat acaatttcca cattaaatac aaattagtaa aagaattcct ccaagtagta
2521  ttgcatataa gctacaactt taccccaact attttaatca ctatgattcg agatttccta
2581  ggatttaaca gcccaagatt gggctgttac tacctcagca agaacaatca ccagtaaata
2641  catgaactgg ggtatagct gaattttag aaactctcca gacaaaccac gtgttagagg
2701  aggtaagtag aaaaactaat gttgagctg tgctattcct accaggaact atgtcaaata
2761  tgcaaagttc aaacattctt agtaaaataa tatgaaagga tctatatata ctgtaaattt
2821  agcaaaaaca cttttatgta cagaagccta aatatcttag gaggtttaga ataccaatga
2881  agagaattgt taattcttca aggctggttt cttatgagga ttaaaaacca gcccttagtc
2941  tcagatgcat tccacctaga tgtgttcacg aactccatag agtaagaaat ataaaccatg
3001  aatatgtact cttaatttcc attcttcaac ttaatgttct atagtacttc agattttaa
3061  atccagagtt tggtgtacac ttaggaaatt atagtaagag tagattagag aagatttgct
3121  tgttttcctt ttgaagccat gtgaaggttt attaccctgt gtatttcat cactgaaaag
3181  ttccccggtg actaataaaa taaaagtgtc acaagctaca tgatggatct cttcttttaa
3241  tgttgcatac agtttcagtt tggctagtga gggctaacta gctcagccct agtttgcattt
3301  tattagagtt gaccactaaa aactaaataa ggaagttacc agtaaagcta attcccaata
3361  caagcaaaaa acaaaaacaa aaacaaaaa caaaaccatt cgcataataa aatatatcct
3421  taacacaaaa taagggtata acatattctg cagcatgaca ttttatttta tttctcagct
3481  gtagcttttt cattcagaaa ttggagacca tcttttcact gagttgttat tccttcctct
3541  tcccttagct tagggatatg ttgaaaaagg cttttcaaca agtattttat tttttacaag
3601  ttgctatgaa attaaaattt atatatatat cttaagtgtt tataaagcac tcaaaattgt
3661  agcttacatg tatatgactt ctgaaaataa aaatcacact tctaacataa tcttctgct
3721  ctgcaaaaat attctacata catgcatatg atcaaaacaa tcttttcatg tttggggtat
3781  ttcttacaca tagtaaaaga aaagtcaaca attatatcag tacttcccct gttaagataa
3841  ctgagtgcca cctagtgttc aatttctgca actactaagc ttacaaattc aatactgcta
3901  ttaaaaccca ggtctgaaa acggcatttt ggaaatcttt ttttttttt tttatgttta
3961  cggtggcaaa atacgactat gaaaagaaca tgatatcaaa atcagtataa aaatagccac
4021  aggctactta aatatgacaa acagacttat tttttttctt caaatgcaga cttctgcctc
4081  cctcaaattg tatcaaaatc tcaagggaat atctaggtaa ctggaatata cacaatgact
4141  ctatacaatc aagaggccag ggcttaatca gattccgtga ggacaaggca aatgatttct
4201  tcaaaacacc cattttctta ctggaagtgg taggaaaagc agcaatgcat ggttttttt
4261  tttttttttt ttgtaattag tagacatggt cttctaccca taagctccat tacattaaaa
4321  gaacaaagtg ggcttaacat ctcacttaag ataattcagc attattatca gtttttaaaaa
4381  aaccaaaaat atcttagaaa caaatcagtc tgctttaaca aattgcattc atgctaatga
4441  aattttaatc ttctttgtca tgatcaaaat ccaaattgta ggacaatctt cagaaaagat
4501  ggaatgtaaa atgttgagtt caatttagat gtcatcaata tcttcatcat catctccaat
4561  gtcatcaaac tgaattcat catcatctcc aggaccaaat gtatcagttt cattgatttt
4621  agcatgctct ggaagctcgc cgtatgcctg cagacttcta gcttcgtctg cattgtattt
4681  taaaattaca tcagcttttgt tatcctggta gtctcggaga ccaaccaaaa taatgtccga
4741  ggtatttatc caaacctttt ttctcaattt tcctctgatg tgcataacc tctttacacc
4801  atcgaaacac attgcttcta gccgtccatt tcccaacatt ttgattacct gagcatactc
4861  ctgaccatcc tctttgaata ccagttctct tttttcagat tcattctcat tcttacccct
4921  gcgtctattt ttacctcctt taccttcatt cttgggcatg gcggtggcgg cgacctcgcg
4981  gcgtctctga cttcttccg ggtagcggcg accgcggcgg ctgctgctcc gaggggcgac
5041  acgagggagc gcgcgggacc aagtaggtgc tggaggccag gcaacgtgcg cgggagaggc
5101  tggcgaccca gctcttcgga gatccgcctg cgtccacgct cggcggcagc aaaatgctct
5161  tctggttttc aatgtggtgg gtgccctat ggttgtagtc cttttataat gcaaaacaaa
5221  attatttta acttacggtt tgcatgtttc caaaacctca tgtggtctct aagtaggcct
5281  tagtatttct ataataatca gttggctaga acttatatt attattatta ttattattat
5341  tattattatt attagcagtg tgccacaaac taattgtaga aattcaaact tatacgcagc
5401  ctcattttgg gtaagagttc tcctattaac ctcctgtcct cctcttcccc actacttgtc
5461  aggtgtggaa ttggccaaca gcacccaaat gtgatagctg actccaggga gggaaggtga
5521  gccccacacc ctgtgctctt accgggactg gtggttcct cctgttcagc ctcattcttg
5581  ctttggccac aagtctcata gcccaggtcc tggaggtcca cctggacctg tttactgtcc
```

-continued

```
5641   tgcttcagca agggttcacc tgcgtgggaa gagacagcag gtgttacaga atgtctgaat
5701   ttcccacata tgccctcagc ctcaatggca cataccctaa ccttgtgggg cagggagggc
5761   agatccacag tgcgagagaa gcttctttga actggtggga gaagagacca ccagctccag
5821   gaagcagaat ttctttccac aggaggagcc tgcatttgcc attgataatc tcccttcag
5881   ataacctagg ccttagttgg gacaaggtat ctgtaagtca gggattgtgt actctcatct
5941   ctagcagccc cattgaagct ggcaagtgct ttatcagcag gggttcaata aatgttgaat
6001   ggagctgaac taatttagag tcccaagaca cctagacctg cactgtccaa taaggtagtt
6061   agtagccaca tatggccact ttatactaaa ttaactaaaa ttaaataaaa ccaaatgtcc
6121   aagttgcact agccacactt catgtgctca ataccacgt tatgtctgta tagaacatac
6181   agagcttata agacgtacag gctagttctt tactagtaag tcatagttac ctactaagta
6241   taactctgta tttctccagc tcgttcgcct gagcaaagac agtggcttct gatagcagca
6301   gcttctcctg gagatcttga tagcgttgtt tgcattgtga cagctgggag cgcaggtgct
6361   gggtggaccc tggtgggcta aacgctgatt gggcccagtg tcacaaggct gggactggtt
6421   ctccaactgt gaaaggggcc aagacaagga tcaggacagt ccgaggccac ccccatgcag
6481   tgatgaccac ggcccgttgt gaaccccgtg gactttactc aagtctgtca cagcacttct
6541   catgccattt ggcagtgact tgctttccag atggagctcc tggagtgctg ggataatgtt
6601   ttcttcatat ctgtatccac agcacacagc acagcgccaa tcaagtctac agaggagctc
6661   ttaggaaacg ttttctcagt ggtcaaaaag agaagggtg gaaccctcca ctcatctccc
6721   ctcacattct gtgccatcga ttctctcaga atcccctgta ttccccattt tactgaatct
6781   tcagcatggc tcctcccta aacaggatcc caataaccca tctgaggtcc aggaacagac
6841   acctgtgatg agctgtgacc aaaaaaaaaa aaaaaaatgg cattgataag gaagggatgt
6901   cattacatac tacttgtctg ggctgcctca taacctgatg catccctatg ttacagcagt
6961   tacccctcc tattaaaatt acctgtttat gtgccatctt tccttaccat attaagtatc
7021   tcaagggcag ccattggttt tattgcccca tgccaatgcc tagtgtgtta tctgaaaaat
7081   taagtactca agaatatttt atatttgtaaa aggctttcta aaggctgaat gtaggctgaa
7141   tattattact gttgtttgtg gtacaaagag accttctct tggtacctct tgattcacat
7201   gggagaacgt tttaaagtaa acactgtcat ctccagcct ctccagtgg ttttcattc
7261   catctaagcc tacattgact tggtgggcat ccactgtgaa ggtagcccca aggtcaagc
7321   tctgggtct ggggcaaggc ctcacagtca cattccctc ctcttggtgt tggtgcttcc
7381   caggagaacc aaccagttct gtgtttattc tgtcgatggt gctggtcaga tgcacaagga
7441   gctctggagt aagtttacta ttccttctt tgctactcag cacaagttgt tcttgaggag
7501   gttgatgata ttgtgggcat tcttcagttt tccctggagc tttctgaact cagcctgaag
7561   actactctca ctcagacccct ctttggcaac cacagtctca accaccacct tgcccttctc
7621   cttgtcttcc tcaatctccc atccctcaga catttctgct ctttcagctc tgcattctca
7681   aggcaaagat gggttctggg tctccacagt tgccagactt ttctccaaag ccacctgag
7741   gaactaaaag aaaatcatgc tttgaagaag ttaggccatt aaagagggcc caagagaac
7801   atgagattgc aaaggtagtt tttgatgaga acaaaaacaa acaaaaaaag cagatctaaa
7861   atgaactccc tacccagaac ctccttagtc aggcaataag agcaataaga tctcaagact
7921   aagttttatt attattatta ttattattat tattattat attattattt gagacagggt
7981   ctcgctctgt tgccggggtg gagcgcagtg gtgagatcat ggctcactgc agccacgacc
8041   tcctgggctc acgtaatcct cccacctcag cctcccaagt agctggaacc acaggtgtgt
8101   gccactacac ccagctaatt tttttttttt taatcgagac ggagtctcgc tctgtcaccc
8161   aggctggagt gcagtggcac gatccggctc cactgcaacc tctgcctccc aggttcaagc
8221   gattttcctg cctcagcctt ctgagtagct gggattatag gagcgtgcca ccatgcccag
8281   ctaatttttg tattttagt agagacgggg tttcaccatg ttggtcaggc tggtcttgaa
8341   ctcctgacct caggtgatca ttctgcctca gcctcccaaa gtgctgggat tacaggcgtg
8401   agccactgag cccggcccac ccagctaatt tttttttttt tgaaatggag tctcactctg
8461   ttgcccaggc tggagtacaa aatggcgtga tcccggctaa ctgcaacctc cgcttcccag
8521   attcaagtga ttctcctgcc tcagcctccc gagtagctgg gattacaggc atgtgccatc
8581   acacccacct aattttttata tttttagtag agacggggt tcaccatgtt ggccaggctg
8641   gtcttgaact cctgacctca ggtgatctac cgcgcttcagc ctcccaaagt gctgggatta
8701   caggtatgat ccactgtgtg cagccccgtg cagctaatta aaaaaaattt tttttcgtag
8761   gcctggtgtg aaggctcatg cctgtaatcc cagcactttg ggaggctgag gcgggtggat
8821   cacctgaggt caggagttcg agaccagcat gaccaacatg gcaaaacccg gcctctacta
8881   aaaatacaaa aattagccag gcgtggtggc aggcgcctgt aatcccaact acctgggagg
8941   ctgaggcagg agaatcactt gaacccagga ggtagaggtt gcagtgagcc aagattgtgc
9001   cattgcactc cagcctgggc aacaagagca aaactctgtc tcaaaaaaaa aaaaaaaaag
9061   gccaggcttg atggctcatg cctataatcc cacaacttg ggaggccgag gcgggtggat
9121   cacttcaggt caggagtttg agaccagttt ggccaacatg tgaaaccca tctctactaa
9181   aaatacaaaa ttagctgggt gcggtggcac atgcttgtaa tcccagctac ttgggaggct
9241   gaggcaggag aatcacttga acccaggagg cagaggttgc atgagcccag atcgccactg
9301   cactccagac tgggtgacaa gagtgaaacc ccatctcaaa aaaagaaaaa aaaattttt
9361   tttttttttc agaatgaggt ctcactgcat tgcccaggct ggtctcaaac ttctggactc
9421   aagtggtccc cctgccttgg cctctcaaag tgctgggatt acatgtgtaa gccaccatgc
9481   ctggccaaag acttactttt acaggaggag tataaaacat ctcattagta attttcataa
9541   ttgattatgt gtcgaaataa tatttttgat attttgtgtc aagtaacact actaaaatta
9601   agctcaccta tatccttcta cattttcact gtggctacta gaaaatttta aattacatct
9661   gtggctctca ttacattct attggacagc actgggctgg gtgagatgac taggggcaga
9721   aagtacattc tgagggccag acaatcaagg tgattgatac tggggttagg ttaactgaag
9781   ggtagaaaag gccaggttaa taggaggcag ggactgagta accgggaaca aagttatcag
9841   agcatgagag agagattctg gggtcagcc gtctgggata ttatagggag gaaggaggct
9901   gtgctacaag ggccaagaga caggaggatg cactcaagtt ggcctggatg aagggacgac
9961   cctctgcgac ttgggtgggg gtaagggtgg caggctgggg ccagccctgc actcactgct
10021  tctgcttcct agaaggagaa acagtgtcac ttggtacctc cacctcaggg gcgcagtcaa
10081  gacccgctgc caggccagcc tctgcctgac cgccggctca cctctcttct tccagcttct
10141  tccgcaggag gtccacctc caggcgggca tgctggccag ccggcctcc tcctcctcct
10201  gaaacacaac cacaaagctt cagagcctgc aggggctggg agataggggg caccctcaac
10261  ctggggacct gaaggagtca gggtcacagg aagtgaccct ttgatgcat ttctgtggga
10321  caagtggatg gaggtgcctg gtcacacccc ctcagagctg gcctcctttc tcctagtaac
```

-continued

```
10381  ccagacccttt gtgtcctaca ggaggcacca gagagatcag agctgagtgg gacagaagca
10441  gagaaaaagt agccgggacc cagaggtcct gagcctgatt ccccacaggg gcaggtggcc
10501  aatggccaca ggtccaagat ctctgggcag acgcagatgc gggccccac ccagcctctt
10561  ggctcaggga gattcaggct gccctggct ccctgagaa ggaccttcag cccatggttg
10621  ccctcttccc aacagagtgg atacgtgctc tacaatcgtg gggctgcaat gacatcaggg
10681  gcaggtgtgg tgtccaacat aggcagttta cagcaaacag ttttatttcc tgaatattac
10741  agaggagaaa gggtctgtac accgcacact tcacacagaa cactgcacac gtggctccct
10801  tgacctcagc caaggaggta gctgtgaact ccagtggaaa accagagagc aggccacact
10861  gccccaggga ggagccgcag ccctcactc agagggctt cttctgctgc ctggctccac
10921  acagagctca gcaagaccac ggggccagag ggggacacct ggtttgttct gtgcctgccc
10981  tgcctatccg accaacgccc cacacaacct gctcacgatg ggacctcaga ggctgaggca
11041  gcctggtcct gggccctccg ggctgctcaa ggccacagtc ctgggttctt cccgctgctt
11101  cacgcctctg gagggcgtca gacaggcgtc caggcccacg ttaagacgct cgagggtgaa
11161  ctgcgaattc cgaattccgc tgctcagatg tcaaacagct ctgcctcctt ctccttccag
11221  aaggagaagc tgcggtcgat gtagcggcag atgtcctcgt tgctgaattc gcccatctca
11281  gacactagtt ccaaagggtc ttcggcgggg gcttcggaac ccggagagtc tgagatccgg
11341  ggaggcgcgg cggggaggcg cggcgggccg gcgggcgggc gggcggtggc ggcggctgcg
11401  gcacaggggc cagggcctcg cgctgccct tgggcgggtc cccttctga accggagcgg
11461  cctcttcggt ccgctcctgt tcttcccct tctcttcctt tttcttcgcc tgttcttcgg
11521  gggccggccc agcctccagg ccgtttccga agaacctgtg cctgaggtcc tcgaagccgt
11581  cgctccagcc gcgccggccg gcctccacct cctccagcac cacgcggtgg aagaggcgga
11641  tgcgctccca cgggtggctg tccagccggt ggaacatctc gtagcacagt aggtggcgga
11701  acttgcgatc ctcgcggctc aggcccatct ccggtagctg gaagtagccg agcatgaaga
11761  ggtcgagcgt gaggctttcg tagcgcgggg gtgcgccgcc gtctaggggc gacaggaagt
11821  gctggggcca gtacacgccg tgcgccaggc ccgggcttgg cggcacgtgc cgccgcaggc
11881  tccgccagtg gtgcagcagc ttgcccactg cctgccgctg cctcagcagc tgccgcagcc
11941  gttcgttggg gctgtgggcc tcgcccttgc tcaccgcag ccgggggcg tccgtggcct
12001  ccagctccgg ccagcacggg cggccgtcac gccagggagc agtctgccta ggcgcgcctg
12061  gtccgcggaa ggccgggtcc gaggaaggcc cagaggcgcc agtgctccag gaagaggtaa
12121  acgatgcgct ccttgcgcag gtcgaggtag tcctggacgc cgcgcagttc cgtgcagagg
12181  ggcggccggc gcgccagctg ctcgggctca agtagcgccg cctggcaatc ctgtgcctca
12241  ggcggggccca gggtgtccag gggctcccag tcggccagcg ggccgtgggc ggcggcggcg
12301  ctgggctggc cagagccggc cgccacgtag tcctcctaca ggatgggctc gcggaccggg
12361  gcgccagcgg actgcggggg cttgcggcgc ggacacgcgc ggggcgccgc gtcagtgcg
12421  cgcagctcgt aggtggcgcg gtgatgctgc acggagacgc cgcactcgag gatctcgcgc
12481  gccacagcct cgcggcacca gttgagccag tgcgagcggc ccaggcaaag cggccccggc
12541  agtcagggcg cctcaggcag cggcgccagc ggctggcccg tgtcagcggt cggcagctcc
12601  gccaggtgcg caggccggcc gcccagccgcg gctagcagcg tggcatgct cttgagcagc
12661  gtggagatct tgctgcacca ggcgggcagg ctggcggcgc ggcatgcat tcgcgcgggg
12721  tcgacggtga agcgcggctc cacagggcga cggagatggg cagcagctgc tcagctccag
12781  ttgctccagg cgcgcctcca gcttcgtgcg cttgtgcagc acctgcaggt tctcgattgc
12841  tgctcgatgc ggaggatgtc ggcctcggtc atgagctcgc caaagggcca gaggatggcg
12901  ttgtgctcgc gggagtacct ccagccctcg cggggtacc tccagccctc gcggggtag
12961  cagcacgagc tggcggccgt cagctaaggc ggggaagaca agagagggga gggaggcgcg
13021  tctccctctg gcccagctcc cgccgtggcg ccaggaacct tttgcatgtc ctgggtggtg
13081  taatggctcc gcggggctgc gtctgcaggg agggaccgcg tctggccggc gggggggtgac
13141  gctggggtga ggctccggcc tgagccgccg ctccaggctc tgggcagtgt ccactttggt
13201  cgctggcggg gggcacggcc ggttgctgct cgctgctgcg gcggcaagaa caggccagca
13261  gacgggggtct ccatgcctgg cttgttcgct cattacacca cccaaggaac ttgccaaagg
13321  ccttgaagct gagaggcgcg gtggcccgcc ccaacccatc cgagggcggc tattgtgagg
13381  cctctcctcc cagactcatg accccttctc cagctcccct gtggcccaag ccttccgctc
13441  cctgtggtca atgtttatg tgcagaatga gaggccactc ctctcttaaa gaggctgcag
13501  ctgcagcttc cactgagctg cccaccctc cctccttc gtcgtgctgg acagctgggc
13561  accgtaatat tctcatttgc tcacttttct ccacctctga tgtccagttt ccccctgg
13621  ggcctgccatc gcctccacag aggtccctga ttcatcttgg ccctatggga tccactcccc
13681  acatacaaat aggaagcagc ctcttccctg cttaacactc cccgcacccg gctccccagt
13741  gctccaggag aaagtccgtt ctcttctggg cctctggcca ggtcttggta acctggcccc
13801  cactgaggtc tctccagctc agcgaccccc ttcctccagg acagtcaggg ccacatccac
13861  tctcacttcc agactgccct gtcccacctg cggctcttca gcccctctc tgcctggcca
13921  ccccctcactc gtcttccaag tgttacctta gacatcacct cctccttccc taacacaccc
13981  cccagcccac gtataaggtg gccggttagg gctgccccag tccctgcgt tccccattgc
14041  agctggctgt gttgcatcag cccaggtact tctctccact gccaccact ctctcacact
14101  gccccatttt gtgtgcttgg tgactcgcac acatgtccgc agccaccta gagcaggcct
14161  tgatatgttc accatgaatc cccagaggct acaagcgtgt ggggcacata aatggcactc
14221  gggggccagg cgtggtggct cacgcctgta atcccagcac tttgggaggc cgaggcgggc
14281  agatcacttg aggccaggag ttcaagacca gcctgccaa catggtgaaa ccccatctct
14341  actaagaata caaaaattag ccgggcatgg ttggcgggca tctgtagtcc cagctactcg
14401  ggaggctgag gcgggagaat cacttgaacc caggaggtgg aggttgcagt gagtcaagat
14461  cgcaccactg tactccagcc tcagtgacag agtgagaccc tgtctcaaaa aataaaaaa
14521  taataaaaat aaatggcatt cggggaatag tttttggatg aatggaaagc aactcatcct
14581  gccagctggt gctgatcagc tcaccttaca gagaaggaaa ctgaggctgg atgaggctca
14641  gtatcggcag ctggaaggcg gcagcgcagc aatggagacc aggtccctaa gactgagacc
14701  aaagctctct tggctactca gtgtggtcct tggaccagtg tcatcagcag cctcacccag
14761  gagctggcta gaaatgcaga acctcagccc tgccagacc tcctgaatcc gaacaggcct
14821  tttaaccaga tcccaggtgc tgggcaggtg aaggagagtc tgagaaaggc tgctgtctca
14881  ctccaaggac aagctgctgg gggtgtgtgt ggagactggg acaagcccca aacggggtcg
14941  tgccaccctg atttccctaa agaagatggc cgggcacagt ggctcatgcc tgtaatccca
15001  gccctggcca acatggtgaa acccgtctc taataaaaat acaaaaaat tagctgggcg
15061  tggtggcatg cgcctgtaat cccagctacc tgagaggctg aggcaggaga atcatttgaa
```

```
15121  cccaggagac aaaggttgca gtgagccgag atcgcgccac tgcactccag cctgggcgac
15181  agagcaagcc tctgtctcac gaaaaagaaa aaaagaaaaa gaaagaaaga aagaaaatag
15241  gaggtcccga ggttggtgtt gggggtggcg tgggggatgg gctgtgcatc cagatgcaga
15301  ccccagggct ccctgggcac cccgccccac ccactttcca cctctgctcc tcctcctcct
15361  ccatcttcag ctgcatcttg cccaccatca cctggcgctt ccactcgggc ttgggacggc
15421  cctgctcatc gtgcgtgggg atgagcgcct ccacgtccag ctgcacccc ggcgcaggag
15481  tagtgggcgg caccggaacc aagcttccgt tgagcagcgg ctgaaacccc gcagctggcg
15541  gtgtggggct ccggactggt aacagtgcag gtgacacaga cggcagcggc caatcgggct
15601  gcagggagaa gcgtgggc tgagcgcctg gtggcctagg gccagggaag ccgggtcgca
15661  ggctcctgct gggcccgcct acctggaagg ccggctgcct gctgcctgag aacactgtgg
15721  tcagcccctt gctctgtggc gtcggcttca ggctcttgcc tgccttaatc tcagccagta
15781  gctccgagtt gtcgcccatc gggaacatca cgttgaaaga cttggtgcct atgcagaggc
15841  aggagatgag gcactggcca gggtggggct gcatccctgc caccctcac ccgcccctct
15901  gcagccccct tcccaactcc agattggatg ggtgcccatc ctcggggcca gcgggcagct
15961  ctccagatcc caggtcctgc aagcagcttt caggccccc agaggcaggc ccttggttcc
16021  ccgactgtgg caaccccacc atcctccccc accctactca cgggatggag ggcccctgcc
16081  tggagacccc tgggagttca tggtggctct tgggcatata ttcctgccca gccactgact
16141  gcccagcccc aaaacactac ctggaatcag ccaccggacc tttgtcccag gtttcctggc
16201  tcagcccggc tgggtggagc ctccctctgg ccctctccct acatcagcaa agcctcagtg
16261  acccttgagc tgagtcaatt ggggcctcca tggacatgca gagtccagac cccagagtgc
16321  cagtaccacc tgctcccctc cctcgccacc acacccacag acagacgcac aagcagacac
16381  attggttgca agccgggagc acatttatgg caaagcacgg ctcagctcta ggggaaagca
16441  gagcccttac taaggccaca ggaggcaccc aggaagaagg gcagcaggta atatgcaaac
16501  acccagggca gagggtgcat tttctggctt agccggagga ggcgaatgga gatttggaga
16561  gataggtctc ttgagtcccg atgaaggggt caggtctggg agggaggaat aaaatgggcc
16621  gacagctctt ggattccgag gctggggatc ccagagtgca gtcaccggga ggagaagagt
16681  aggagaaagg gaaaatcggt gtggcttact catttattta ggcaaaacca tcagccaggc
16741  gcagaatgct tgggtgcata tgtgggtatg agggtaggta tgaggtgcaa ggccccaccc
16801  atgcatcgag gttctctcgc ctgccagccc ctgcccctgc cctttcctca aggctgggcc
16861  cctcctcccg tgcttttcct gcctcttccc cccacccgc gcctcagcct cagccaggag
16921  ccgcgcacgc agctactcac tcttcctgtg cctcaggact ctcacttcta gggaccaaga
16981  ggagagaagt gacagcggag ttaggaggga aaggggggcca ggatgagact gggatagcag
17041  gggacaggga gcgggccagg gagagcagga gggggggaagt ggagaagaga ggaggagcat
17101  ttctgcccat ctgaccctgg ctcaggctgc tctggggccc catgaggggtg gtccatcgag
17161  ttcctggttt ggctggtgcc cctgagggct gggcagggca gggccaccag tggctctagc
17221  ccccagcaag ggcctccacc ttggcactgg gttggggtag ggcacccagc cctggctgtg
17281  ctgggtgggg gtgtctgggg aagcccagag tatattttc tctgcccta gcttcagccc
17341  tgctgcagac tgtggaggga aggagaagga ggctcggcag gtgctggaca tgcttccatg
17401  ggctctggtc tgcaggggct ggggctccat aggaaccata gggggacaag ctctgctctg
17461  cactcctagt cagggagatg aagcttttgag gggtgccact aagcagatc tctgccctga
17521  gtggctgggt gatgaaggca ccccagccag gctgggatgg gagcaccaca tctaggcacc
17581  ctgtcctggg cctctaggt gtcctgcag ggggacactg tcccaccta cagaaaagaa
17641  gcccaggaat cctgcgccag tctagctctt aaaaaggatg cctagggaag tcaccgggga
17701  gggaggggga aacatggtgg gtcacagctt tgccccata gccaggctct ggctggccca
17761  gggcccctgg caggaactgg ctaggaaagg ttcctggcat atctaagaag gcttcaggtc
17821  tgtgctgctt ggaaagacaa gagaaagacg tggagagagg aagagaggct caggatagac
17881  aggggcaggg ggaagggtgg ccagctgcgg ggcctctctg aagctggttc gacttcaagt
17941  gtccctccag taccagctca tcagaaaacac cagcaccagc tcatgggaaa caccagcgcc
18001  agagctggaa ggccctttct agcccgtggg aggcaggccc agagagggga ggggacttgt
18061  ccaggccaca cagctagagg gtgggaggca ggcccagact ggggaaggga cttgccccag
18121  gctgtgcagc ccggtcctgc tttggcagga cctcaagcaa cccagagccc tctcttaggg
18181  tcaagtactc aatgcggtag gggtggccgg aagaccatgt agaagaggaa ggacccgggc
18241  agtgacagct gggggagggg tggtgtctag atttccctcc ccttttcaggg ctagcgccgc
18301  cccccacccc tcaacctgcc cctactcact gccggtgggc gaggaggagc ggcgctgccc
18361  gcagccaggg ccagcgccct cagggggcag aggcgggacc ggcggcgcg aactcgcggc
18421  ctcgggcagg ggcggcggcg gcgcgggcgg cggcagctgc tgctccctgg acgccttggg
18481  gtccgcggcg cagccgttag gcacgtggtt cccagggagt tccgcctgcg gggatgaagg
18541  tggggggctca cctccagct tagggagagg ctgagggtc tgggtcacat ctggccgggg
18601  gcgcgtgcag agccgcggtc aggtgtggca gagcagttgg ggcccacgta gcatccgcga
18661  cggctgcgcc ggctgcgggg gagcggaggg gccttcgagc gagccgcgg cggcagggcc
18721  gaggcgcggg cagccggcgg gcgcgggctg gcgggcacgc acctcctcgc ggtgcgccat
18781  ccgccgggcgt gcgaccagcg tctcgccggg gcagcgcc agctgccgt agtagtcccc
18841  cgtgctgggc tgcttgctga aagcgcgggg cttgcggctg gagtcctgcc tccgtagccc
18901  gtcgtggccg tcgcaggagc tcggctgcgg gaagacagtg accggtgggg ctcgggcaag
18961  tgcccggtag gcgccccca cgcctcccca cccagctctt cacctcctgg gaactcgcgg
19021  ccagcggccg tcggggggtg cagcagccga cttcctagac cccctgttct cacggtgggc
19081  agcgggcgag gttcatgggg gcctcggtgg aagggcaggc tccgccgcc ttacagggag
19141  gggttctggg caccggccaa ggggcacagg gtccccact gaggccagaa ggggcgggcc
19201  caggggcggg ccggcccagc cccgacgcca ggggagcta gagaagggc acctccagc
19261  ttagccttca ctaggccctc ggccgcactc cgctctcggc tgtcagaagg actgcgggtg
19321  cccagggctc cgcggagccc tgtctttcgg gggtcccggg ccggagggag ccccctccag
19381  agcctgtgct ctccgaggct ccggcttgcc ccggaccccg cttgtccgtc taggggctgc
19441  tccaacctgc cacggtgctg gtggtcctgc tgtgcacctg gcggcggggg cggcaggacc
19501  cgacacctgc tttacgtgat acttcctctc aggttacaga cgcccgcgca cggccagcct
19561  atgggctccg acggcctgac atcacccggg gcccgccaat cccaggccga accccccca
19621  gccgtcgcgg atgccacggg ggcgccaact actctgccac acctggccgc ggctctgcac
19681  ccgcccccggg ccagatgtga ccccgccccc tgccctctc cctaagctgg gagctgagcc
19741  cccaccttca tccccgcccg agaggagaga gggctgaccg tggcagagg gggcctctca
19801  tatttggctg ccggctccgg gtcgcgtccc caccgtttcc ctcctgcatc tggaaaccat
```

-continued

```
19861  cgccatccac gaaagcgaca ccgacacccg cgctcaagcc tcggatttca ggggccgtaa
19921  ggcggggtcg ggtgacagcg cggcttcccg ccccgtcgca gctgccccca actaggccca
19981  gctcagtgag ggagagtgag gcggccgggc caaagactga gtgaccgggt gggggctgtc
20041  ccctgcccca ctctccagcc catgcgtccc tgcggtggcc tcagacccct caccccgccc
20101  gacctggctc acgttgcagg aaacgcgaca ccgcaggatt cgtttctgg gccagccccgc
20161  cggctccgcg ccccctgcag cccggaggct ccgacgccac gaccctgctc ccacctgcgg
20221  tcaggcaccc gcgcgggagg cgccgcggcg acacaaagag cccttgtag agcttcccgg
20281  cccggggccct ggcgtctgcg gcccagcacg cacacagccg ggagggacgc acacagccgg
20341  gagggggctc gcacagccag gaggtgacct cacagacctg gcacttgggc tcagcggtgg
20401  agaggggggca ctggctgggc cacctgtcct gtggattgg gcggggccca cagtctgcgc
20461  cgggagctca acgattccag ggccccctgca gccctacccg cccggccccc tctgcctccc
20521  agagatgaaa gggggaaagcc actgtgggag cttggtctaa ggtggcgtga agagggcagc
20581  tactggagct ggcctgcagg tttgtgtcc ctcccatgcc tcccttgccc actggccttg
20641  tgacctgagt caccttgtat gaattggccc tggggtggct ttgccttggg cttaagagag
20701  aactgcaagg tcccaggctc cagcaggacc ccagggagct gccacaccac atctggccac
20761  ctgtgacctc aggctgtccc ctcacctctt agaccatcct tgctctgttc ctgtggccag
20821  aacgccagtg ttcccaggg cacctgccg aggatacccg caattgctca gaccagacct
20881  ctgccccaat ccctgctcca gagcctcagc caggcgcctg caggccccag acatccctag
20941  gcacctcaca cttcacctac ccacccctgcc ctcatcctct ccacacagcc tcgcttccct
21001  ccagggctcc cagctcaggc ctggccctt ccccccaggag ctcaagccct aaactggaac
21061  cagccacagc ttcacttcct cccagccccct actgccggtg ggcgcccagc cctgctagtg
21121  cctgctcacc ttcctccctc cctccttcca gcccttacct ctacagccat gccactggca
21181  ccttccacct ggcagccacc tccctggggt gacactctcc gactgagcct ggggctgtgg
21241  gggtggggggg gcatgcttgg ggaggggcag tctccatgca ttctctgtca actccatgac
21301  aaccccggcca ctcctgtgca agaggtggca caggccccagt tcctggtgag aacagctgt
21361  ctggacctgc gtccttcacc ccccagctcc catggagggc agtgacctgc tcttactctc
21421  ctcccagtcc agtgtccagc cctgacccct cgtgggactc gccaggagct ttgactcttg
21481  aatatgccat ggacccaggg acccccaccc tgtgcccact agtgaggcca ggcctttggc
21541  ctgactggcc cccatcagcc cagtacccct gctggaggc aggcagtggg tgaggggctca
21601  ctacctcctt cttgagggcc tctgtctcca cgtggcggag tttgttcttg gtctgcatgt
21661  agatgtcagc tgcctgtggt cccacaggag gcttgggaga tgggtagcta ggtgggggtg
21721  ggggcagttg ggtgcctggg ggcggggggtg gcggggggaa gctgggtggg ggtgggtgggg
21781  gtatgggcttt cccaatcgtg ccccaaggca ggccccagctc tggggttcagc atgtccatgt
21841  agctctgtat gtctgcagct ctagtgctgg aaagccctgg ggaggcagaa ggaagggcca
21901  gatttggaag catgcagaca gcctttcccc caagaatgag actctccacc acctggaaac
21961  aacttgccga gggccaaggt gggctccggg caccacttgg tacacctgtt gtggcccctg
22021  gcgttgctgg gcttcctctc cctggccctg ccctgcccca gcccagcact tattggggga
22081  agaccaggca ctccggtttg gaggggaagc actgaggct ttggtgtgtc tagagggcag
22141  ggtcacctgg aaggggaggg tctactcctt gggagtacag atggccacat ccaatctttg
22201  cagggcaccc tgccaggtct ggaggccacc atctggtggc gtgaagcagg cattgcaagt
22261  ggatggacgc ccatgctcag ggcacggtca gggtgtgtgt acacacaagc ctgcagtctg
22321  ccgaggcgat tgtgaatttg tgtatgttg agtgtgtacg catttgtgca catgcttctt
22381  tgtattgatg aatgtgtgtg cattgctctg tggacatggt gtgtgtgt gtgcatatct
22441  gtagtatgga aatagagcat tgtgtgcttg tgtgtaaggt gggtgtgtgc agatattagc
22501  atggctctgt atgtgtgttc atatctgtat gctgtgtgta cacatgtaca agtgtgtgct
22561  tttgtgtgtg agtagctaag aataatgaat ggtgggtggc acacgtggat tttgtgggtg
22621  gggagagtac atgtggatgt acatgtatgt ctgtgatgag cacacacaag tatgagtgac
22681  atctgtctct caccagaaag gggtgtcgcct ccccatgttt aaaagcaagt gataagagta
22741  gtctccgata ttggctgtgg caggctggcc canggccaac cctcacagcc cagcagtctg
22801  gcttcagtct gctctccctc cccctcttcc tcctgggcac actccaccac tggagggtgc
22861  tggcccttga tgctggagtg gctggaggag caggagtcgt agttggagag ggtgctggtg
22921  ggcgagctga ggtcaaagtt cagaggctgg accgacaccg tggtgttggg tgaggacatg
22981  cctgaatccg gctgcttcgc ctccagctcc acggatggat cccgggagag cacgcagtgc
23041  tccatgctct gaagggggagg cagggaggcc atgaaggcaa ctgcaccca agatgcgttg
23101  ctctccagcc caggggtccta ctcagccatg cctttgccgt gggatcttgg ccaagccaca
23161  ccctctctg gggtctcttc cccatcgcta gagggtcttt caggttcctc cgggttaaga
23221  ttcaagccca gccccgccag gcagaggacc caggttcctg ggaaactccc tccctggct
23281  cctccctgat taggaggggtg gagagatcga cgaggagggg gccttgagct gcacccccagg
23341  gggagaactg ccaggagatc ggccttctcc ctcacagatc ggcacaggct ccatgggggaa
23401  gggcacagca caggcccatc cctagtgacc tggctggcaa gccagctctc cttgccagac
23461  ctgggacctg gagcagactc ccaacaccag cccgccctgt ctcctgatgg ggcccttggg
23521  gtaagggtag ggcctggatg gccagctgag cagtgatggg cagccagagc tcaggctgcc
23581  aggcctgcca ttcccccgcc ctgcccggtc tgtgcgtctg accacaggcc tgtcccctcc
23641  cggtgcagag ggggctgtgg taggggcct gcttacattg cccatgctgc ccctgctgcc
23701  ggcaagcccg cttgctccgc tgcctcctgc ccaggcctgc tcctccttgc cccgtgcccc
23761  ctccctacct aagaagtgtc acaggcaccc tgggagagag aggcaggcct ggcaccaggt
23821  aacggctcag cggccgcgct cattggcccc gtaattaggg gctctgctgg agtgtttgcc
23881  ttttctgggc cagcgtcttc tgtggcttgg gtctgtccct gcctcagctg ggcctgcttg
23941  agtgagggga ccagggcaca cacacccccac ccattccagg ggaccaggcc ctgttaccta
24001  ccgcaggagt caggggagcc ataggaggtg gcatgggcag cacccaaagg tgctctttac
24061  ctgggcaaca gcagtgggtg ctgagggcac caagccctga ccctgtagg cagcagataa
24121  gaggctgggc cacacagcagt gtactgcgcc tggcctgagc cacccagctc tgcagtctgg
24181  gactgtggct tcaaactttc cctccccgac ttactagcta tttcaggcga gtcacctgtg
24241  cttttttgtgc ctatgtttct ttatctgcaa atggggggtaa cagcactact tgctctgctg
24301  agctccagga catggcgccc agtaaatgcc atactgtcaa atttttttt tttttttt
24361  agacggagtt ttgttcttgt tgccaggct ggagtacagt ggcgcgtgtc tggctcagtg
24421  caacctccac ctcctgagtt caagcaattc tcctgcctca gcctcccaag tagttggaat
24481  taaaggcacc cgccaccaca cccagctaat ttttgtatat ttagtagaga tgggggttca
24541  tcatgttgac caggctggtc tcgaaccctg acttcaggtg atccaccccgc ctcagcttct
```

-continued

```
24601   caaagtgcag gcatgagcca ccacacccgg cctgtcaact tttttatttt attttatttt
24661   atttttagac ggagtcttgc tctgtcacca ggctggagtg cagtggcgcg gtcttggctt
24721   actgcaacct ccgcctcctg ggttcaagcg attctcctgc ctcagcctcc cgagtagctg
24781   ggactacagg cgtgtgctac cacaccctgac taatttttt tttttttgt agttttagta
24841   gatacggggt ttcaccatgt tggccaggat ggtcttgatc tactgacctc gtgatctgcc
24901   cgcctcggcc tcccaaagtg ctgggattac aggcatgagc caccgcgcct ggcctgagcc
24961   actgcaccca gccaactatt tttttaatgt actgtgaaga gtaactgaga ttacaccttt
25021   aaggcactcg gcagggtacc tgcctaagtc agaatccaat gaatagtgtt tgctgtccta
25081   tgaccactag cagctgcatc cagacaggcc ctcaggtgcc ctgggctctg gtgccacccc
25141   ccatggtccc tcgacagagt cacaggctct cttaactgat ggggacccac cactgatgca
25201   gaaatgtcct tccctgtgtc catcccggct tatataccct agtgacagag tgctgactac
25261   ctgctgggcc attcattctc ttccagagac tctttctcgg ggggaagttc accctcaggc
25321   ccacctgcag cctctggcct ctgggccttg ctgtgttctg cagccccag agccaggacc
25381   atcccctgt gctggcaggg acgacagatg gacagacggt gctcagggca cagaccatct
25441   gccttcttcc ctccgggcct catttcacag ccactccatg gccaggctgc cccatggagt
25501   tggtccgcat ccttttgggg ttggctgtga ggcccactct cttccctgcc tattgcctca
25561   aagcaggcat tgtaccagat ggtgcagagc cctcacttgg agacatccac agctgagttc
25621   aagtcccagt aggtcacttc gtggctgtct caccataaaa acataattta aaaagagtag
25681   catgggtttc cagttatgac ccagccatga agtcagctaa tatatggtgc aggggcagag
25741   aggtggctcc tggtcaggcc atcaaggtag gttctccact ctaccactta ctggtgatgc
25801   gatcctggtg ccccgcagac tcccttacc catatgtgga acgggacact tacactctct
25861   tctgcagagg gtggctgtga gttatacccca agctaatgtc tatgggtagg tgaatgagcc
25921   tgcctgttcc caatggggcc tgtcttgtga tttctccagc cttaccccttt ggggtgaccc
25981   tgttcttccc tgtcctcttt ccgttaacct ttgtgcctct actccctcag tccccagcag
26041   gcagtggttc tgggctgaca ggtcgtgtgg ggtagcgggc ttcacgtctc tgaacctcag
26101   cttcctcctt ggtaaaaggg gtgacgacac ccaccactgg ggtggagggg cgagaagaga
26161   gaatgcaaca ggagcagcgc agggatcgta ccaggttctc caccgtgcgc aggcagtggg
26221   tgcagtggct gtggccgttg aagtccgaca ggtcagccggc cgcgtacccg tcgcggtcgc
26281   ggacttccag ctccgcgccg ttcactacca ggatctggca gcactgtggg ggcacgcagt
26341   gaggacccgg ccgcggccac gagctgggac ccccgcgccc gggcagggcc gtgcggagag
26401   cgcggtgcca gcagagggcg cgcgccccca ccccgggccc gcgctgacct ctagctcccc
26461   gttctcggcg gcgtcgtaca gcgcggtccc gccccacagg tcagccgaga tctccccgcc
26521   gtgcagcagc agccagctga gcaccttgct gtggccgcgg ctcgccgcga agtgcgtggc
26581   ggtggcgccg tctttgtcct gctccgacag gctcacgtcg gtgcagctca cctgggcggg
26641   aggggcgggg agagagggcc gggggatggg ggccaggccc ctgcaggccc cgcccacggt
26701   cctccgcccc actcctgatg gccccgctcc ctccactccc cgccctgccg gctccgcccc
26761   gtctccctc cgcaccgccc gggcccggag ctccaccaac acacgatgac cgggctgtgg
26821   cccatctgcg ccgcggcgtg cagtgggtc atgccgtcgt gggcgcgcgc gtgcgggtcc
26881   gcgccgcatt cctgcaccag gtactgcgtc acctccaggt ggccctcctg gcacgccagg
26941   tacaggggcg tggcaccgtt ctttggtttgg gcattcactc ccctgcgagg acacagcgcc
27001   caccgtgggc tttcagcgcc tcacccctc cgaggcctcc ttaccgcc ccctcccctc
27061   ccggggagcc ctggacggca gggagagtgg gcgggagagg gccctgtcac cggcccgctg
27121   ccgcccgggg ggctccgcct ggactgagtc ctgagccacc ctccctcaga ggccctgag
27181   ggcgtcccac ccagcactgc cctgccctca ctcccacttt tttttttttt tttttttt
27241   tgagaagaag tctagctctg tcgcccaggc tggagtgcag tggctggatc ttggctcact
27301   gcaatctctg cctcccgggt tcaagcgatt cttctgcttc agcctcctga gtagctggga
27361   ttacaggcat gcgccaccac gccccgctaa tcttttgtat ttttagtaga gacggggttt
27421   caccatgttg accaggctgg tctcgaactt ctgacctgt gatccgcccg cctcggcctc
27481   ccaaagtgct gggattacag agccaccgcg cccagcctca gtcccacttt ttaaccgagt
27541   tctacaaaga tgtggtgagc tggccttctc tccccctctcg cccactgtca ccatgagtcc
27601   ccacaactgc tgtgtctgac ctctatccct ttcatcgtgt gcccccctcca tctggaatgt
27661   ccttccatcc tcctccctct tgaagactca gtacccatcc ctcctccatg agggccaccc
27721   tgatttattt ccccccttgct ggcctccgcc ccacactgcc cagggccact atgagcatga
27781   cctgtcatgc ttggttgacc ataactgatt ttgaccttttg cctccccccag aagactgagt
27841   tcccagccgg caggctggta aggggttgcca gacaaaatgc agttcacaca gttcaaccgg
27901   aatttcggat gaacggataa tgctttagta ttctatatcc caaatatttgc atgggacata
27961   cttatactaa aatacaactt ttttatctga gattcaaagc tagtcaaaca tccccgggttt
28021   tgttgttgct gttttgtta atctggcagc cctcgggatg tccactatgt actgaatgct
28081   tctgctgtgc tagctctggg ctacggcact ggcaagcagg ttcttcttt tttttttta
28141   tttttgagac ggagtctttc tctgtcatcc aggctggaat gcaatggcgc aatctcagct
28201   cactgcaccc tctgcctcct gggttcaagc cattctcctg cctgagcctc ccaaacagct
28261   gggactacag gcatgtgcca ccacgcctgg ctaattttcg tattttagc agaaacccag
28321   ttttgccatc ttggccaggc tggtctcaaa ctcctgagct caagtgatcc gcctgtctcg
28381   gcctcccaaa gtgctgggat tacaggtgtg agccactgcg cccggccatc aactattact
28441   gtgaccatca actgagatta caccggtaag gcacctagca ggggacctgc cagaatcaga
28501   attcagtcaa tggtgcagct acagctgggg aggctcacag gtggggctgg gactctgtgc
28561   catcacccat agtcccacaa cagaggcaca gactcagctc tctcctcggt cacacagttg
28621   gtaagtggca cttgaacacc catctgtctg tgcatgcagg gcctggctgg caatatgggc
28681   atgcaggagt gaagagatg gaatgtgtct caggggctcc tcctagggcc tagttttcgg
28741   ctgtcactgt cccttatcct tgctctgcca gcccagaggg ggcctaccta gggaacagca
28801   gggctgtcct ggctgctgag ctgttgggtg tgaacagccc agggtgcagt tgccaccaaa
28861   ggacactagg tggagccaca acctaccccc agacccagga gaagtccag gttgggggcc
28921   acgacctatt gggttccagt tcaccttttg tgcctaggag gccaattcct cacaggactt
28981   gacatcctgc ccatctacct cccccagtct ttcacccccgt agataacca catgctccac
29041   cctgcattca tccctcgttc acccatccaa ctgcccatcc acttgttgcc tgcccatcaa
29101   cgtgcaccag gctaccccccc tttgcccacc cacccctcttg ttccaacac gactcagccc
29161   ctcttctgac ccctgtcacg tgtgccctct ccctccctct cacacacatc ctgagcccct
29221   cccagctggc atctccctgt ccctaaagcc ctggttctct gtccacttcc ctgactctg
29281   agaccccaag gctgactctg actgagaccc ctgactctgc agccccatg gaccccact
```

-continued

```
29341  cactgatttc tcctccctcc ccactcccta gacacagggc tgccatttgc tggggctgat
29401  gctgagccgg gcacttcatg atggtgcggg gagcaggcac catgcctggt gatccagagg
29461  gggtcccgtc aacacagatg agggagacag aagacccagc tacgtatcta tcttcagaaa
29521  catgctggct cgtggctgcc agcctccaca ccccagcgcc agcgtcaccc ccacacacac
29581  tcacatactg ctgcatcaga acaggctgtt gaatatttca tgaccgacgc tcagcggcct
29641  aaattattca ccccgtaacc aaggcacagt gagtgccggg gtctttggga tcaggggctg
29701  gtgggggccc actgggttct ttctgcagag gcccacggcg gtgtacacag cgggtggggg
29761  gccagacctg cagtgagctc tgctctctca gcactcccta cttggcagag atccatgacc
29821  caggggtgcc cagccagcca gagaaggtct gagaagctgg catcaagcag gatctgagca
29881  gcagggggaa gtggtaccca cggcctcctg cagggccgct ggctggcact cccagcccaa
29941  gttcctggca cggaatgagc cctcagtaag tgctggagct catcaccatt ctcattagta
30001  ttccaccatc tgcactcatg cgccccatta tggagtcaga gcctccagct tggaatacccc
30061  cagaacatga ggcagatatg ctgttgggct gggtgggaag gggtcctggc tcaacatccc
30121  cttccacctt ggcctgagga caagaagaac aatgggcact ctcacagtca ctggggagta
30181  ttacaaagat atggatgagc ataaggacca aaatgaaatt cccatcacac acctggaatc
30241  caagcacctc gggaggccaa agcaggagga ctgcctgagc ctaggagttc gagaccagcc
30301  tgggcaacat agagagacct ccgtctctac aaacaataca aaaatgagcc aggtgtgttg
30361  gtgcacacct gtagtcccag ccactcagga ggctgaggag ggaggatcac ttgagtccaa
30421  gaagttgagg ctgcagggaa ctatgatcat accgctgcac tccagcctgg gtgtcagagc
30481  aagagcctat ctctaaaata aataaataaa tgagaaaata aacaaaattc ccatcactag
30541  agagaggaat taataaaagt aataatagta aataataata atagtgatag cagccaccat
30601  ttactgaatg attactctgt ctcaagcact gtgatgagta caacacacac gttctctcag
30661  ctggtctttg taacaacccc acaggacagg tgttagcatt gttcttctgg tacagatgag
30721  gaaactgagg cacagagagc taagatcact ctgtgagaaa gaggcagagc cccgatttga
30781  ggctgtgtct gatgcagagc ctgcttctga ctccaaatgt gccacgtcta caccccttct
30841  gctcttggtc ggtctgtccc tctgcctccc tccctccctc ccactgcaca gaccactgcc
30901  cttccccaca gacctcactg ctgggaactc aggaacactc tttgacagct gctggggcac
30961  agccccgcag gaggacctgg ctcgagtccc gtgcctttga gctgtgccac agtctgctt
31021  cttgtctctt tgtgttccca aacccatcca tgaatgggg gcaacagttg tcatcctgac
31081  ctcgtcaga gtgcctgaga agtgcctgca gagccctgag cacaggcctg gtgcctggcg
31141  cacagccatt gctgaacttt aggatccttc cctgtgcctg ggaggaccag ccaccagggg
31201  ggtctatggc tggcctggcc tgtccgggtc ctgccaagta cgggccaggc tgggcatcat
31261  ttctgctgtg gggaacacta cctagagggg agaggatggg tcttgggga gacctctgac
31321  tcccagaccc ttgccagctc tagccctgac cacagtgaca gctgcagaaa agtgctccca
31381  gaccaagccc ttgcccttg ccccggcttt gacccaaacc ctctttgtag gtcagaggcg
31441  ccctggcgat gatcgtataa atcatgattt gttttctttc tcctgggaac aaagatgcta
31501  tggatgaact gtaactattc atcaagtcac ctctgattac acaaaagaaa catgggtccc
31561  ccgtgtgggc tgtgggaatc tctgcggag actggtgcca gctgactgcc agcaccgccg
31621  cagggagtga gctgcccatg gagccagagt cgggctgcag aatgattccc gcagcccgcc
31681  ccactgccag tcacgcctcc ccagagggag gccaggaaga ggctgtccct ccgaggatca
31741  gtctggttgt ggcccgtgac tgctttcaat tgaaattcac ggagcttg gtggatctac
31801  ggctctcggt gtcctccagt caaacttccc ggcctatgtt aaaagattcc caagtaggcc
31861  tggcccaggg aagaaatgca gccccgattt gagaaaggtt ctacacccca gcccatcagc
31921  tagcatggaa tagttccaga agcctacagt tgcctgcaac tctcccagcc tcccaggtct
31981  tcctcctggc ccgtaattag gccaaatttg accccccctg aggcctctac acctccccac
32041  atcactgcca gttccaccat ggcagggct cgaggccgac cctctttca ttaggttctc
32101  agctctcctc ccctcaaaga tgcctggctt ccctgacccc tcaacttaaa gaaccatccc
32161  catcgcttcc taccaaactc ctcatttcac tatatagcac ttgccactcc tgaattatct
32221  tgttctccta ttcctccagac ccatacatgc gtggatagaa gaatgtgtgg ctgacgtgat
32281  gacaggccgg gcagttgagt gcacccactt gctgtttgtt gaatgaataa atatgagaag
32341  ggacatccag gccaggagta ggggatgtct cttcactcat ggccgcagcc tggtagagca
32401  ggttagatcc acttgccaga taggctcgga aatgcccaga ggggagtttt gtctagggtc
32461  acatgcaatg agctgtaggc agagtggaca agtccctggg attccatgcc ccactcattc
32521  agcagatgtt tactggagtc aggctctggg catacagagc cgggaagaca aagcccctgg
32581  cctattagt cacggacaga cgggatgaaa acacacatct gtctgtgtga tgcagggccc
32641  agccagaaat ccgggcatgc agggagtgaa gagatggaat gtgtctcagg ggcttctcct
32701  aggggttagc ttccggctgt cacgcaggat gcacacagaa cgcaaagcca ggcaaccata
32761  gggcggctgg gaggccaggt gcagtggctc atgcctgtaa tcccagcact tgggaggcc
32821  gaggtgggcg gatcacctga gttcaggagt tcgagaccag cctggccaac atgtgaaac
32881  cccatctcta ctaataatac aaaaattagc caggtgtggt gccatatgca cctataatcc
32941  tggctactca ggaggctaag gcaggagaat cacctgaacc tgggaggtgg aggttacaga
33001  gagctgtgcc actgcactca agcctgggca atagagcaag agtcgagtct caaggaaaag
33061  ggcagcaggg aacaaggtca gcgggaaagt gagtgggcat catgggcgcg ggtgacaatt
33121  tcagcgaggc tcagggttgg ccttgctgag gtgaggtctg ggcaaagact tgcaggaagg
33181  cagggagcag gcggggatct ctgatccctg cagagggatc agcctctgtg aaggcagggg
33241  tgctggcctg ttggaggga ccacagcccg gaggagggac agcctctggg ccattgtaag
33301  gaagtgagca gcattccctg tcagtggcca gaagcctgtg acgggaggtg ctcttttttt
33361  tttgtgaaac ggagtcttgc tctgttgccc aggctggaat gcagtggcac aatctcagct
33421  cactgtaacc gctgcctccc aggttcaagt gattcttatg cctcagcctc ccaagcagct
33481  gggactacag gcgggagcca ccacacccgg ctaactattt ttccccctga gatggagtct
33541  tgctctgtcg cccaggcttg agtgcagtgg cgcaatcttg gttcactgca acctccgcct
33601  tccgggttca gcaattctc tgcctcagc ctctgagta gcgggattac agcacccac
33661  caccatgccc agctaatttt tgtattttt agtagagacg gggtttcacc gtattggcca
33721  agctggtctc aagttcctga ccttgtgatc cgcccgcctc agcttcccaa agtgctggga
33781  ttacaggcat gaaccactgc accagaccag gacttgcatt gtcttttctt ttcttttctt
33841  tttcttttt gagacggagt cttgctctgt cgcccaggct ggagtacagt ggctcgatct
33901  tggctcactg caagctccgc ctcccgggtt ccagcaattc tcctgcctca gcctccgag
33961  ttgctgggac tacaggcacg tgccaccaca cccgcgctaat ttttgtattt tttagtagag
34021  acggggtttc tccatgttgg ccaggctggt ctcgaactcc tgacctcgtg ttccgcccgc
```

```
34081  ctcagcctcc caaagtgctg ggattacagg tgtgagccac cacacccagc aggacttgtg
34141  ttttcaaagg ctgcgggtgg acatggacgg gtgaaggcca gggccttttca ggcttactga
34201  ggacttcccc ttttccgttc tgtagtgcac agcctcacag agccttgggc ccagctgagc
34261  ccaaggggtt caggtagccc ccacgtgagg cagaaagggg gtttctcaga agccctggga
34321  tgcccagca gcgtgctgct tacagagccc cagggtccaa ggctcagctc tcccccttag
34381  aagggtaggg caggagcact agccccggtt agatgacagc tgggaccagg agctgctggt
34441  ggagacacga gatggtctcc tgctgtgagg ggcttccccg gactccacca ggcccttcct
34501  ttcccagagc ctccacgtgg gtcagggagt caaggacggc agccacctcc tcagtgtgga
34561  cacaggcccc gcccccacgc cctgcagcca ggtgaactga cagacaccag gggtagatct
34621  ggggctgctg ataaaaagga atgagccccc acggcctgtg gcagaatcag ggaccacccc
34681  aggcagagcc tccagccttc taagggggag agttgagccc tgggccctgg ggctctctaa
34741  gctgagagtt gctagggggct tcccaacaaa ctcccttttct gtcccaggtg ggggctgcct
34801  gaacccctgg ccgtgggag cagccagact ccgtgaagct ttgcacaaag gaagggaaaa
34861  ggggaagtct gcagtggact tgaaaggccc tgagtgatta ggacctggac caggagtggg
34921  agagagaccc agagaggagg tacagcctgc tcaaggccac acagcaagcc agtgatgacc
34981  acagctggtg aatcagcctc tctaaaacac catttctgta cctgtcagct ccaccaggca
35041  gggacgcttg tctggttcac cagcatatca ctggcattta gaatattgcc tggcacatag
35101  aagatgctca ataaacatta gttgaatgag tccatctgta aaatgggctg attacatagc
35161  tactgctcgg ggtggttgtg tgactcagat gacactgggt ggtgccagac ccctagaaga
35221  tactcagcac caggtctttt ttttctttct tttctttct ttccttcctt tctttcattc
35281  gttcctttt tttttttt ttttttgga cagatgtcttg ctctgttgcc caggctggaa
35341  tgcaatagca tgatctgggc tcactgcaac ctccgcctcc ctggttcaag cgattctcct
35401  gcctcagcct ccctagtagc tgggattaca agcatgtgcc acctgtacag gcatagccca
35461  gccacacacc cagctaattt tgtattttt ggtagagacg gggtttcacc atgttggtca
35521  ggctgtcttc gaactcttga cctcaggtga tccacctgcc tcagcctccc aaagtgctgg
35581  gattacaggc gtgagccacc atacccagcc ccaggtactt tccaatccca ttccagtcta
35641  gtctggtcag gggtaggga ggctttgggg gaaggaggca cctgctgaag ttgataacat
35701  ctctgggcta actggttttc cagcttgctg tgactggcag caccccacgag cccaggggaa
35761  gagactggag cctcctcact ccccagcctg gaagctcaag cctcagggtc ccagctgatc
35821  cccagctccc cgacccacac agccctgtcc agctgctcag gccctgggac agccagaagc
35881  aggtgtgagg ggggcagagt gagctcctgg gccccaggac cctcctggga gggtggccac
35941  tggccttggg gccacctgct cttcgccccct cctcactctg ccctgaatgg gggtctggac
36001  cccttgttcc cctccatcag ccactggagc tcctgctggg agggccaacc ctcccaactc
36061  aatctccctg agaccccagag cctgggactt gcccagccca gctcctgcca gccccgtacc
36121  tcccaactga gaggtccttt ttctttttct ttttttccc cacctggaga tggagtttca
36181  ctcttgttgc ccaggttgta gtgcaatggc gcgatcttgg ctcactgcaa cctccgtctg
36241  ccgggttcaa gcgattctcc tgcctcagcc tcctgagtgg ctgggattac aggcacgcgc
36301  caccacaccc ggctaatttt gtatgagaga tcccttttct acaagggctc agagggaggg
36361  tcccacgtgg cagcagcccc gaggtcactg tgacaagtcc tctgcttctg ggaagacttg
36421  gccccatgaa cgggatagac agggaggtgt ggggggatgtg caggacattc ctgcaatctc
36481  aagcactttc tattataaca ccccaaggtg tagccctgga attagctgag cctccccgag
36541  gctgtccagc cttccagctc ctctgcagcg tgtcacttcc atgtctcatg gccacccaca
36601  gccctcct gggcaggatc gagtttccca ccagcaggtc cgggagccct tcctccctca
36661  gcactcaccc acgcgccagc gagagagctg agccttgtga ataattcaca gcaattcaca
36721  gcaggcccca gaggctcgca agatcatgaa gctgggccac ctgggtgccc tgattgggcc
36781  ctgtgcctg gggcagctca agcctctgcc ctaccagct cccagccttc atatccacag
36841  cctcggtgag caggaatccc tacccgcaag ataggaggtt aagtgggtac cccagccccc
36901  aacccccaatt cccagctgct cttcctgcat aagcccagcc tggcaaccac agaaagacac
36961  cttcttatca gtcgagtcac atgctgctgt ggggaacgga gcccaagccc tctgtccgca
37021  tccctgagat tcatgctgac tcctggggg ctggcagctc atcagtccag gccatctggc
37081  cactgggtcg gcaccagcgc ccaatcacac acagcacctg gcatggcctg ggagggggtc
37141  agggttcccc agccccggag ccctggaggg cgttccacag cacagccagt cttcctaaca
37201  cctgggatcc agcccacgga gggatcgtgg cttctcagtg aggaaggctt aggggccggc
37261  ggtccccacc agcacttgca taaggcgggc tcagcgtctt ccagttcaca cttgggccat
37321  attggtcccg ccatcagggg cacctgcccc tctcaagacc tgtccttctc ctctgcttga
37381  agtgaggggg tgggacaggt gcatcagaat caccgccatg aggggtgggga catgtcccag
37441  gtgtggctcc caggccccaa cctggagagt ctaactcagg aatctgggac agcctccaag
37501  aggtgttgac aggagccagt tggaaccctc tactcaaggg tccctgggtc cctcctagtc
37561  taaatcccac tgacttttgac atgatccaaa ccctagttttg ttttggaagta gtgaattcat
37621  accaaagcag ccaccaagaa ggcctggcag ggctggttgt gaagcacccc ttcctccggg
37681  tgctgctgt tgggtctccc actaaccaaa ccagggagcc ccttcttagc aaggatggaa
37741  ccaggcccag ctcccttgtc ctgggctgag gggaccactg gagcccggcc tggtgggtcc
37801  tagggcacc ctacatccac gccagtgtgc ctgggcccaa gaggctgcag ctgtggctac
37861  cttgccacat ggccatatgg ccagaactgg cctccagctt gctccctggt ggccagggc
37921  cctgcaggca cacccagaaa ctgaccagtg gtggggacag gccagaccct ctacctcgt
37981  agctgctctc gtcctgaggc tgggtccaca ttcacatttc catctcaggc tcccacttag
38041  actaacgagg gtcacccatc agagtaaccc actccccgct cagaccctg tggcatctgg
38101  caccctaccc tctcagacag ggcctgggca gcttttccca ggatccctgc ctccccaggc
38161  gcacctaaga cctgagtctc ttcctccctc cccaagactc acacatgcca cctgctctgt
38221  tcgacccacc accccacccg ggggagctcc cagaccactc cccaggaggt ttgggatccc
38281  catgcttccc ttgatagtgg gaatgggctg aggggccaca ggagataaca agttgctttc
38341  tggatggcct ccagccaggg gctctggggt caggaggtgg ggtggggtt ggggaggggc
38401  ctttctccct taactgcttg gtaactaatg gggttcccctt tctgcctgtt tgactagggc
38461  ctaggaggcg ctcctgccct tgctgcccc aactccattc tgaacagtct tgcaaatgag
38521  cacagcctga gccagagaga gcccctgcgg cagaagcagc ccaaggggaa caggtgacct
38581  tggcctgtgt gccagcctc ccaggtccag ctgcgtgcgg ccggcagct gaggatgttg
38641  ggagcacctg cttgcagggc tctgggggca gcccagaag gggttttcca ggaggggaag
38701  atttcatgtt gagtgggagc catttctctg gcctggccct ctggcccag gatggcactt
38761  ggagggatca ttgccctgga gtgccagaga agtgtggaaa atccaggca tccccaaag
```

```
38821  ccctggcccg gcccacccag aggacccctt aagaggagtg atcttactca gggtagtgcc
38881  tgacgagaag cctcagggag gggaagtctc ctttggctgc agcgtagtgg ataggcaggg
38941  cgcccatgtc tgtggccgcg gtgggatccc caccgccatg atgcaagagc cagttcacca
39001  ccttggggtg gccaaagcgg cagtcagat gcaagactgt gggaccagaa ttgtctttgt
39061  cctgtgggag gagagcgggt tcaagtccta aagcctgttg ctgccccgcc cctggcttgg
39121  gccgctccca gactcccaca ggcctggaag gtagctctgt gctctctgtc ttccctggaa
39181  gaattggcca ggcctcactc agcagtggtt tttttgggtc aagcggatcc tgggtttgaa
39241  tcctgcttct gtccttgggc aactaattgg ccctctctga accgtacgta gccaataggc
39301  agcaccgtgc agggttttca gaggctgcag gtcctgactg cgagctgcct acacgacagg
39361  cacctggttg tcatggcagg agactggctc caggcccagg gccacagccc tgactcccag
39421  gggctcaggg aatgcctgaa ggagtgacac agggttactg ggctgagcag ggccaggaag
39481  ggtggctgtg gggctgtacc aagctagcat caggattggg gggcagcccc tgcatccaac
39541  acttgccccc tctctctcca cccttcctag gtgtcacgtg ggaacagaga cctccacctt
39601  ggtgcgcctc cagcaaccca acctcagtgc cttagtcagg caataagggc cctggggact
39661  ggtttgggta ggaaggacac accaaatgag caggaggaat ttccccatag aggcgaagag
39721  aatccagaga tggtgaggga gaaaagcaca taagaaatta aaaacaaatg caaacaaaca
39781  aggttgaaac agggctggag ggtgtgaatg tggtgattct tctcttcctg aggagacagg
39841  gtcctgcgag ttttgtcaca agtcaggaag ctccatcagc tctgcaacac ctgagtcctg
39901  gatggcggga gatgatggct taagatatct gggcgcaaag cctgaggccc tgcctgtaac
39961  tccgactccc tcaagggcag ctgagaggga ggactcaggg cactggggaa agtcagcaga
40021  cccagtcaca gaattagaat aaggtggagc tacgcaggga agacaacacc aactatttcc
40081  tttttcttat tttattttat tttatttatt tattttttt gagatggagt ctcgctctgt
40141  cgcccaggct ggagtgaagt ggtgcgatct cggctcactg caagctccac ctcctgggtt
40201  cacgccttc tcctgcctca gcctcccgag tggctgggac tacaggcacc tgccaccgcg
40261  cctggataat tttttattt ttgtatttt agtagagacg gggtttcacc atgttagcca
40321  ggatggtctc gatctcctga cctcatgatc tgcccacctc agcctcccaa agtgctgaga
40381  tcacaggcgt gagccaccgt gccctgccaa caccaactat ttcattggca gtagaagaat
40441  cacactctgc agctactgag aggtggaggt gaagccaccc tgccgagcag ccaacctcac
40501  ttttttggtta ttatccttgt gccgatgctg ccggacaaac tctctctaca aatctcagca
40561  tgtggaagaa acagaggcag gaacaattgc ccagcacctt tctatttctc gaggacactc
40621  ttgaagttat tcatcaatgt tttaattaaa gcagatctta tcgcttttcc tcaaatggga
40681  acttgttcac ttttagactt tgttattgtt cattttgggc ttatctttgg tctttttcctg
40741  tgctcttaaa agggtgcaaa tcaaaatctg agttatgata atccacttat catatgacta
40801  attacttcag tacaaggagt tcctgcctgt ctgtccaata tgaatcttac tacgtcccaa
40861  tgtcacattg gcttctttc cttctcggtg gcagcatttg gagcttttac ttaacttagg
40921  gtcaatttcg acctctgaat tttccacccc tccccacag ctgttgctgg gtcatgctgt
40981  tttcttttat ctctataaat attgtgactt gtaattgtca cttataat cattctggct
41041  atactgaatc attccccat tatccaagtc atccaaatat tcgatgtgca tttccacaaa
41101  tcatgtagtg gccccctgat tggggatgat ttgtagaatt aattatagc tttagatctc
41161  cattcaggtc ttcaggtcac caatacatta agcagagcag ggccctgaac agcttatatg
41221  gatcaacgat tgacagagct gtcggggtg ctgcaaagcc actgactttt tgctgttccc
41281  cgtaacaaag tatgttcaaa tctaggtcac aggtttgtgg tagggtcgat tcacagtata
41341  catgtgcaac ggcgttcagt agcatagcag ttgaggttgt gaagacatgt gcacccaggt
41401  caaagaagaa agatccttag acaaagccgc tcaattccca ggcacccaat cttccttggg
41461  ctttgtgaac ctgagatttg acaggctctt gggaatgtct gtctctaaga ctctgttgtc
41521  aggcttaatc aggctggtgg ccatctccat atgtgccccc ccagcattg tgacaaaata
41581  agggaagggg gacccaataa agctactct gaaagcttat gatcccaccc ctcatttaaa
41641  ctatgtgatg ttgtcattct atataaactc tttccaagta acttaactaa aacacacttt
41701  gccattagtc ttgagtgtgg gcacagcatt attcttttct aggccttaag ggttccttct
41761  gctaaaaat aatgtctaac tttcatgaag tttacccat attaaagtgc cttctgaata
41821  tatattatct tgttctattg gtttcaatat acctatttc tttaaaaga aaaaatgat
41881  gaaccatgag tgttaacacc agaaaaacct taaggtacat ctgatctaat ttcccacttt
41941  aaagtgagaa aatcaaacag tgcctagggg tttgattttt ccccaggcta attcgggttt
42001  tcatatttcc atctcaaagt ggactttctt tggctaactt taagttttaa acgtaaaggc
42061  ctgaaaagta actccaggat cagcttttc attagttttg atcgtgtatc aaagcaaata
42121  tttctttccc ccaaatgaaa ccccagggct tccagtattt gtagtgatag tgtgaatcca
42181  ttaggtctat ttttaattat atctctctta ttggttattt ttttcacatt tcctaactca
42241  tttgtgatat tgcttccata taattcaact ttttgtgcgc tgggttccca tttgccccac
42301  aaaggcctat gtgcaaatct gatatcctgt ttgaatgaca ttgtttttgtt tttaccttat
42361  tgcttcctat ctttcacaac aatgttgtca gttctcaaca ttaaggcatt aaaaattagc
42421  ttttctcaaa tgctcagcat cattaatcat tagggaaatg caaattaaaa ccataatgaa
42481  tatcatctca cacctgttag agtggcattt gtcaaaaagg tgaatgatgt gttagacata
42541  atgcagagaa aagggaacac acacattgtg aataggtatg taaattagta cagctggtgt
42601  ggaaaacagt atggagtttc ctcaaaaaac taaaaataga atctaccccta tgatccagga
42661  acccctatttc tgggtacata tccaagagaa gcttcagaga gtgctttgtt gggttttctg
42721  gaacccggca gggctcaggt gtgtggggat gcgctctgtg agcctgtgtt tcctccgccg
42781  tgagggctcc tcccgctcct gtaggaaaag gcagtgcccca tttgtcttg tccatgtggg
42841  actccaaagg gtccagacgc gacagaaagg cggcgaatcc tctcagagtg ggcaggggag
42901  gagatgatag aatatgggga gggagatagaa tatgggaatg gggcagtaga ggggtgggat
42961  ttcatgaaat ttcctgattc aaggctatca tgaagtaggc ctctttggga gctcggcccct
43021  ccagtcgctg gtgagggtaa catcccacca gtctctggtg aggtccagtc gcctccgccg
43081  actgcattga aagccaaaag cagaactagg ccagcaccgc ggcctggcgt ccagtgaccc
43141  agcggtctgc atattcccca gggtggaagc actcggactt caggtttgaa ggcaatgcgg
43201  tcaccactgc aataagaaaa gcaactaggg aaaatggcac cttcttctcc aaactttga
43261  gacactcttg ctctgtcgtc caggctggag tgcagtggca cgatctcggc tcactgcgac
43321  ctctgcctcc cgggttcaag cgattctcct gcctcggcct cccaagaagc taatttttgg
43381  catagagaga gagagggggg aagggggggg gagagagatt gattttaatg tcttcaagca
43441  aaaagagact ctttctgcct gttggccatc tgctgccagg tgaacgtgaa aatccatcga
43501  gacgctttct gtgaaaaccg cctttatctc tttgtccctc ttaggttaaa atccgcactc
```

-continued

```
43561  caaaaccta  ttgaacagaa  aaattacaaa  aagcacatat  aagacgtttc  agttttgtaa
43621  agggtaaaat  gaaactgccc  ttcaggaaga  atcagaagac  cgacgaggga  gagaggagcg
43681  atcgtgaaat  ctaagtgggc  tgcccccggg  tcttccaggg  ttttgtactc  ggtggcttgg
43741  cctgagttga  tgtgcccata  ttttcaaaca  gccaagtgcc  ctgagacaca  gcctttgcta
43801  cggtacctgc  tgaaatctgg  aagtgtgatt  aactattact  taaattgagt  ggggcagact
43861  aagagacagc  agcagtgaag  gatgccctt   gggagaaaga  cgtcgaggcg  ctgaggccaa
43921  agggtccgtg  aggaaagagc  ccgcagctcg  cgccccctcgg cctgcggaag  ggagggcaag
43981  gagggtccta  cggttcctgg  gaggacgcga  agagccaaga  gctctgacag  ctggcgccgg
44041  ggaaaaggcc  ccgaggcggg  gtccgcatcc  ctggaagggc  ggcgtccaca  ctcctgcgag
44101  gcacggggcg  cccgggggct  ggaagctcaa  agcccgccgg  cttctgcagc  ttctggagct
44161  tctgggagcc  aagagtgtca  gccggaagga  tcccgcacac  ggcgcttagt  tctggaactg
44221  gatacccggg  ggaggatgcg  ggatcccgaa  gcccgggtgt  gggtccccgt  ggtcttcgtg
44281  ttgggggtag  gtgcggaacg  ctaagcctgg  gcctactggg  agccatagtc  ttcttgatgg
44341  ctggtgctta  ttgggctttt  ttcagtcgaa  tttcaaaatg  cagttgaatt  tcttactttg
44401  gaaacgataa  tagaaatggc  tgacctcaga  ttttcatgat  tatgttttgc  cttttccagt
44461  gtatgtgcag  tttctgtagt  atagtggtta  tcatgtttgc  ctcacatgtg  aaagacctt
44521  ggctcgagac  tgagggggaaa catggttttt  tggttttct   ttttgtccct  aaatttagtg
44581  agtttaatcg  aggtttgggaa acaaacagaa  aagtagttga  acctgtggct  cactttaga
44641  cctcctcaat  ctagacagat  tgttgaccag  gctacagttt  ccactggtct  gccagcaaga
44701  ggcctgctta  atgttagctt  tggttccaga  aattccttaa  gattctcttc  attctcttct
44761  gtcgcctgaa  ttttcatagg  ctgacactga  aagtggatga  catctttaatg catttcctaa
44821  gtgtcccgct  gggcttcgct  ttactctgat  aagttgcaga  tctggctgat  ttgcgagaca
44881  aaaacaaaat  attttttaa   aagattctaa  atctgcatct  ggaactgta   gagtcaataa
44941  tctgaaacca  cacgaattat  ctacatacaa  aagattttga  atgcataccc  cttcccaaa
45001  taatcctcag  aaaaccggtt  aagttttagc  atctatgact  ctgagatgca  tatgaggcct
45061  ttgtaaattt  agaagttgag  agtagaaagt  acaggtttgt  attttagaag  gagatttggg
45121  aataaatata  gctctggtgg  atatagatca  tatgttaagg  tttgttggcc  agagctggtg
45181  tgtgtcttgg  gtgttgggca  aagaacagag  aacagccaaa  gctctgcgag  gtcaatgtga
45241  agggtgattt  ccttggtggg  ctcaagttta  tgacgcagcc  tggacctagc  ttggcttctc
45301  agctagagaa  gaagcatgat  tccatgtcac  agctcctgtc  tttgaaaaag  tcataatgac
45361  tcccagaccc  aacatgtggg  gaaaactctg  gatttgtctc  ttcagttgaa  tgtctccgtt
45421  gaaaattgag  gaaagaaatc  tctctactat  ttgaacttca  tcaaaagact  aatatgttaa
45481  tattttgacc  gtcaatattt  cctaaaacta  gtctatcct   ttcatagcta  atacatcaaa
45541  gcatattaac  ttaggaaatg  ggattctccc  aaacaaggaa  acattgacgg  caagggttct
45601  taatcttttc  acaccacatt  tccttcaaat  gctttataca  tcttcaagca  gacaaataat
45661  agtattataa  tgattacgag  accgatcatt  actcttttgc  caaaaaaacc  agcgacaaaa
45721  gactaactta  gtggaccaac  ctttgtttct  tcattatctg  tacattgatt  ctgtcctttt
45781  atttcgtctt  tcttctaatt  ctgcttctgc  ttcttgtttc  ctccctggat  ttgaacttta
45841  tttacctaaa  ctaccagtta  ggttaccttc  tcagaacctc  taaggcagca  gtttgagatt
45901  gacaatggaa  gatttaagat  tagaaaaaag  aaacatgaat  gaatttctga  tgttttatta
45961  taggggttta  taatgcaggt  agaaagacct  ttttcagact  taagagtttg  atccaccaaa
46021  tgagctattt  tgatatttat  aactttgtct  agtaaaagtt  tcctataaaa  acatttggtt
46081  tggatatgtt  tgttagcttt  tagtcgacac  ttgaaaaagg  cggttggaag  gttctaagtc
46141  tttttggata  ctctttctc   ttatccccca  ggccgtgggt  gtgtagaggc  cttggtggtg
46201  cagtggtaga  attctcgcct  cccacgtggg  agacccgggt  tcaattcccg  gccaatgcag
46261  caggtacttc  ttcatttcat  tatggccttt  tacccgtctt  ttacgctgca  aaattatact
46321  gcataaccta  atagtgcatt  taggggcttg  gccaccacaa  ggtaaagtga  caacattact
46381  cacgagagta  gcggcaagag  acattcagga  cactaaccca  ggacccatgc  aattgttgga
46441  ctcaaacagc  ttagcaaagt  ggcaagcacg  aagtctttcc  ggtgagtcac  tgcagttttg
46501  atattggtac  ctgttacttt  catctattca  cggggcggat  ccctgcaaac  ccgaagaatc
46561  atcaggttcc  tgattcgcgt  gctggaccct  gggcttactg  ctgagccact  gtagagagga
46621  tcaagaaatg  acgctcttgg  aaggagagaa  gctgcgggca  ggacagtcac  gtcagaggtc
46681  caagaggctt  cagcggccca  aagaaaggga  aggtgtgtgg  ggaagaatct  gcgtggagat
46741  gaggggagcg  gcggggactg  gtccttgcgc  agaggtggcc  agtggaccct  cagggctgta
46801  ccccagacac  cgtgaaccga  atttgctcac  atcgtcagcg  gccgcggcct  ccgcgtgctt
46861  tgtgggccca  tcggtgttct  gcgagggatt  ccgtgtgtct  ggcaatgtct  gtcaacaggt
46921  gttggcctga  aatttggccg  ggcacgttgg  ctcatgcctg  taatcccagc  actgtgtgag
46981  gccgaggcgg  atggatcgct  tgaggtcaag  agttcaagac  cagcctggct  aacatggaaa
47041  aatcccgtct  ctactaaaaa  tacaaaaatt  agccgaatgt  ggtggcatgc  acctgctatt
47101  ccggctactt  gggaggctga  ggcaggagaa  tcgcttgaac  ccaggaggca  gaggttgcag
47161  tgagccaaga  ttgcgctact  gcactccacc  tgggcgacag  agcgagactg  cgtcaaaaaa
47221  aaaaaaaaaa  agcagcgaaa  gaaggcagag  atgtcaatgg  gacaaagaga  cctcccagga
47281  ggcttgttgt  agaggcagtg  ggtggatcct  gggagatgag  atttttttaa  aattatgtag
47341  cagaatgggg  agagaaacgg  agaagcgcat  gaaagagaga  aaagcacgaa  aatcggcggc
47401  gtccaagaat  aaagcagata  aaatagtgtg  agtgttttta  cattcaaaaa  atagaagaag
47461  tgcaatgctt  gtcagcaggc  tttgtggtcg  tgtagtgttc  aatacttgta  gttgtggttg
47521  ccacaacctg  ggttctaatc  tgagtcacag  tagtgttttc  tagcctgcga  ttgtggctaa
47581  tagacctgtc  gtttgctttg  cctttaatcc  tagcagcctc  cagagagcag  agtaaacctc
47641  tggccccgaa  gggcgccagc  ttctggagtt  tagccacacag cgcagaaact  agggggcggc
47701  ctggccgata  ggaaaacttg  gacatgctct  ttgtctcaca  attgagcagg  aaaaattccc
47761  gtaggtgaag  atgccgcctc  tcaagggccc  tttgtctgta  gcttccactg  gtgaaaataat
47821  gcggttatag  tcttttttcgg tagagaaaac  ggctgtatca  gtgaatttt   ttaaaaacac
47881  aaaacgagaa  cgagtttta   atgagctgac  aataaaatct  aaactagttg  tcatggtctg
47941  cacaggcttg  cctccattcc  ccatctgcta  atttttatga  gaacagtaaa  ttattactat
48001  tatcattatt  tttgagacgt  agtcttgttc  tgtcacccag  gctggagtgc  cgtggctcaa
48061  tctcggctca  ctgcaacctg  tgtctccgag  gttcaagcaa  tgagaacagt  aagaagcta
48121  cagttcacat  aaagtgcaca  aatctttagt  gcaatttagt  tagttttgat  caatgttatc
48181  accacccagc  tcaagttata  gaaaattgcc  atcatctgag  aaaggcctgt  tagagccct
48241  gtccaggtga  ttcccaccct  gtgtcctctt  agttatcact  attctgatgt  ctattcccac
```

-continued

```
48301  aggttacaat tgcctgttct taaagttcac atgagtgaat gtacatatgt tttgtgtctg
48361  gccttttct ccagttacat tcattatact catgagatat atccacgtag tttcatagat
48421  cacttctcaa ttttgggtt attgatttct tgtgctgaat attcttataa cagtctttgt
48481  gtgcacttga gattcatgga agtccttcaa ttgctgggtc atgacctgag tataagttta
48541  acatcagtat aaattgccag tcttctagaa tgcttttcg ccagcgatga cagttgaagt
48601  ggcaccaaat tcttgtcagc atttggtgta ctaactttgt taaatgtagc tatgctctca
48661  gaccaggctg gccaacatgg caaaaccctg tctctactca aaatacaaaa attagctggg
48721  catggtggca tgcacctgta gtcccagcta ctccggaggg ggatgttgca gtgagtcaag
48781  atcgcaccat tgcactccag cttgcgtgac agaatgagac cctgtctcag aaaaaaaaaa
48841  aaagtagcca tacactggtg agtggttagt gctatctcag tgtggaatta atttgtattt
48901  gcctaatgag caatcctatg aagcatattt tcttatggct tccagcatat aagaaactct
48961  cctttgcaaa ggcctattcg aatatttgc cctattttat ttggcttagc tctatattac
49021  tgacttacaa aagtctctct atatattcaa gaattgagtc ttgttttgac gtttttaaa
49081  ttatacttta agttttaagg tacatgtgca caacgtgcag gtttgttaca tatgtataca
49141  tgtgccatgt tggtgtgctg cacccattaa ctcgtcattt acattaggta tatctcctga
49201  tgctatccct cccctcccc ccacccccaca acagtccccg gtgtgtgatg ttcccctttcc
49261  tgtgtccaag tgttctcatt gttgaattcc cacctatgag tgagaacatg cggtgtttgg
49321  tttttttgtcc ttgcgatagt ttgctgagaa tgatggtttc cagcttcatc cctgtccta
49381  caaaggacat gaactcatca ttttttatgg ttgcatagta ttccatggtg tatatgtgcc
49441  acattttctt aatccagtct atcattgtgg gacatttggg ttggttccaa gtctatgcta
49501  ttgtgaatag tgccgcaata aacatacgtg tgcatgtgtc tttatagcag cctgatttat
49561  aatcctttga gtatataccc agtaatggga tggctgggtc aaatggtatt tctagttcta
49621  gatccctgag gaatcaccat actgacttcc acaatggttg aactagttta cagtcccacc
49681  aacagtgtaa aagtgttcct atttctccac atcctcccca acacctgttg cttcctgact
49741  ttttaatgat caccattcta acaggtgtga gatgdtatct cactgtcggtt ttgatttgca
49801  tttccctgat ggccactgat gatgaggatt ttttcatgta tctttttggct gcataaatgt
49861  cttcttttga gaagtgtctg ttcatacect tcgcccactt gttgatgggg ttgtttgttc
49921  ttttctgtga aatttgtttg agttctttgt agattctgat gaaactacag atgagtagat
49981  tgcaaaaatt ttctcccatt ctgtaggttg cctgttcact ctaatgacag tttctttttgc
50041  tgtgcagaag cccttaagtt taattagatc ccatttgtca attttggctt ttgttgccat
50101  tgctttcggt gttttagaca tgaagtactt gcccatgcct atgtcctgaa tggtattgcc
50161  taggtttttct tctaggcttt ttatggtttt aggtctgaca tttaagtctt taatccatct
50221  tgaattaatt tttgtataag gtgtaaggaa aggatccagt ttcagcttc aacatatggc
50281  tagccagttt tcccagcacc atttattaaa tagggaatcc tttcccccatt tcttgttttt
50341  gtcaggtttg tcaaagatca gatagttgta gatgtgtggc attatttctg agggctctgt
50401  tctcctccat tggtctatat ctctgttttg gtaccagtac catgctgttt tggttactgt
50461  agccttgtag tatagttttga agtcaggttag cgtgatgcct ccagctttgt tctttggct
50521  taggattgac atggcaatgc gggctctttt ttggttccat atgaacttta aagtagtttt
50581  ttccaattct gtgaagaaag tcattggtag cttgatgggg atggcatgga atctataaat
50641  taccttgggc agtatgacca ttttcccgat agtgattctt cctacccatg agcgtggaat
50701  gttcttccat ttgtttgtat cctgttttat tttgttgagc agtgttttgt agttctccett
50761  gaagaggtcc ttcacatccc ttgtaagttg gattcctagg tattttattc tctttgaagc
50821  aattgtgaat gggagttccc tcatgatttg gctctctgtt tgtctgttat tggtgtataa
50881  gaatgcttgt gatctttgca caagaattct gtatgctgag gagtcattt taaaataaat
50941  atattgcaaa tgactttcc cagtcagtga aaagtctgac tgaaagctgt caactgaaaa
51001  atcacacaat ttataaattt agaagggaga ttttatttt tataaatggt tacagcctgc
51061  aaggtggcca ttctgacaga caggaaggca taccctcttg ctgctgaaac ctgaaaagta
51121  cgtttccagg gaggggaggg gggaacaggg attttatgttg atgtggtggg ccacatatac
51181  atattcaaca gggaataggga ggagctctga atattcatga agggatcctg ctgcatgcat
51241  gctgagtaaa catgcctgtt acatgcaacc catgttcatt ttggggtgga gacaacattt
51301  aaatacatta taattaggcc ctatgcttca aaaggggaag cagggacaca aaggcagtca
51361  agtgcacagc ctctgtaaac cgtccagaac ccgtccacag ccagtgctct cttatcaagg
51421  ggaagttact gaaatcagtc tcttgtccaa tcaaagctgt agttatggct tgtgtaggga
51481  gggctcagtc agtttatggt aatgggtgag ctgcaagtgc ttcagcattg cttatctcaa
51541  ggccagtgct tgtttagcta gagaaaaaaa ggaagaagaa aaaacctgt ggcaattgga
51601  acatagttta ttctttaagt tgaggggcgc atgactccac cttgcctggc gtggccttag
51661  gtctcgttta tcataccata tcttactact gcaaggagtc tgttctgtca gtcttaggat
51721  ctctattta acaataatgc tggtcagttg tgtctaaacc acaaagggag agagtataag
51781  gagaggtgtc tgagattcca actactgggc aggaactcag tagttaagac ttctctggg
51841  tctccttggc caagaaacag tctgtccagt tggttgagtg gctttggatt ttaattttag
51901  ttctcaaagc atttaatttg atgaaatttt gccatatttt ttctttattt ttaaagcctg
51961  ttatgttcta taagaaatct ttctactcag gatagtgaat gtattctctt aattttatct
52021  ctctatgagt tccagcgttt tagttttaat ttttaaattg atgacatcta aaattctact
52081  cctaaccaaa acattcctgg gggtgaccaa ggacaactcc aaaaatcttc cataaatgga
52141  agtaagactt actccttgaa gaacttactg ggatctgggc ctgcagggca cagtggctt
52201  agtgcacctc tgctcttacg actattcaga aattgtcttt gtgaacccat caggctgttt
52261  caaaatcagc aatttagggc ttgcttgcaa catgcagtta tgcagcagct gttttgtgga
52321  tctggtgagt gcctgcacgc atagttcccc gggaattttc tgaatttgaa ttctcatggt
52381  atttcaagtg gctcagttgt ctctttcttt tcttttcttt tcttttcttt tcttttttt
52441  tttttgagtc agagtcttgc tctgtcaccc aggctggagt gcagtgctg gagtgcagtg
52501  gcgcgatctc agatcactgc aagctccgcc tcccgggttc acgccattct cctgcctctg
52561  cctccccagt agctgggact acaggcaccc gccaccacgc ccggctactt tttgtattt
52621  ttagtagaga cgaggtttta ccgtggtctt catctgacct cgtgatccgc ccgcctcggt
52681  ctcccaaagt gttgggatta caggcgtgag ccaccgcgcc cggccagttg tctcttttctt
52741  ttgcctactg ccacacacgt accaccaaat cctgcactcc aagctgcttc tacaccctgg
52801  actcccaacc tccagttaga caatccacat cttcccacac ctgcctcagg ctccatcagg
52861  ctactgtgcc tcctgcagca accaggccag gggaatctg gattcctatt acacttctga
52921  ggaaggtggt cagggagtgt ggaggatgtg ggtgggaggg ggtgaggttg aggcaggag
52981  tacactgtgg tcttctgtct tctacctcat tggcccaggt gctgctctcc ctccggttgt
```

-continued

| | |
|---|---|
| 53041 | ctgctttcag ccctgcctgg gaaatcaggc cggcgccctg atcttcctga ctctcatttt |
| 53101 | gtgaggaacc tgaacggatg agccatcgct cttgtcccac acgttctgtc caaaggtgc |
| 53161 | cctcctctct gcttgctcgg gggcctgccc tctgagctct ggcactcagg ctgggatgcc |
| 53221 | gcccagtaca gaggctctgc agccctgcag gggtctgact gttccacacc agcaggataa |
| 53281 | aggccacagg gcatgctgtg gtggaaaagc attcagaggt gtgggctgaa ggcctctctt |
| 53341 | tccacagtcc ctttgaagac accatggaag taggcaccc cttgacagac aaggtggccc |
| 53401 | aaggcctggc ttcacatgca ggctcttggg tcccagcggg tcctctctgt gcctggtata |
| 53461 | gccaactgct tcacgcatct tacccggttt cctctcctcc acaacccaag ctcctcctcg |
| 53521 | acccccttgc tcagctgtcc tcaggacagc aagatcccca gcccttggaa aagcccatct |
| 53581 | ctagtgcttg gggagggagt tgggttcagg tggtctaacc acagaagaac agagaacctg |
| 53641 | aggcaggagg aaatccctc ccttgctggg tctcttggca cagcccatcc aggggtctgg |
| 53701 | gtcagggtcc aggtatactc tacctcctct gaggacctgg gttttcaggc ccccgaggtt |
| 53761 | ggtcaatgtg gagtctttcc cactgttcat ctgggaactg aaggaatatc ccatggggcc |
| 53821 | ctctcttact cattagagac acccagaaaa tactccatcc agcagaaact gggtgcagtg |
| 53881 | taccagacca ctataattat aattgcagga tgtggaggtc agatacgttt tgtgggtatt |
| 53941 | ttctctctgt ctgtggcttg cttgcctttt cgctttctta gtggtatctt ttgatgagaa |
| 54001 | ggtgtggcta atgttgatga agtctcattt atcatgtctt tcttatatat gtatttttc |
| 54061 | tgtgtcctgc ttgttggtag gctaatcttt gcctgccaac aagtcacaaa gtatccttga |
| 54121 | aatgctttat atctttaact tttaagtttt ggtgtgtaat gcggctgaaa ttactttgt |
| 54181 | gtgtaacgtg agggagaata acattgttgg tctccccaca tccatataga agttcattaa |
| 54241 | ttgaaatgat ttatttttctt ttattgaact gcttttactg aaaacccatt tattgaccgt |
| 54301 | atagctgtgg atcaatttca ggttttctaa ctcaggctgt ttatccgttt gtcactcttg |
| 54361 | atgccttgtg tctaatagct tatagtaaac cttaaagtca gatagtacaa gtccttgttc |
| 54421 | ttttccacac attgcaataa attttgaaat agataataac tcatgaaacc atcacacaca |
| 54481 | tcaggatatg ctgtcacttc atcccttcct gacatggttt ggccgtgccc tcacccaaat |
| 54541 | ctcaacttga attgtatctc ccagaattcc catgtgttgt gggagggact taggaggagg |
| 54601 | taattgaatc atggggggcgg gtctttcctg tgctattctc ctgatagcca gtaagtctca |
| 54661 | ctatctgatg ggtttctcag gggttttctgc tttggcttct tcctcatttt ctcttgctgc |
| 54721 | tgccttgtaa gaagtgcctt ttgcctcccg ccatgattcc gaggcctccc cagtcatatg |
| 54781 | gaaatgtaag tccaattaaa cctctttttg gtcctggact ctgttatgta tttgtcagca |
| 54841 | gcatgaaaac ggactaatac actctcattt ctgagtggga cacatgctgt cactcacata |
| 54901 | tgctggttgc tgacttgtga cggaagattc tctattgtac cctctgggga caatacatct |
| 54961 | ccagttgcct gcggggagga tgaaccctca agagtcaatg tgttgactga ctctaaatat |
| 55021 | gggttcctgg tgctccatgc tcatgcagcc atagggaagg aaaggggact atcaagagcc |
| 55081 | aagggatccc ccatacgact ttactcagat cttggaactt ttagatgctg tccaactccc |
| 55141 | aaagaaataa caattactca ctgcagggga caccagaagg gagacacttt tattattaga |
| 55201 | ggaaattccc tggtggaaag agcagctaag gccacaacta aggaaaccct ggtatttcaa |
| 55261 | gctgctgcgc tactaccagg tactgcatcc gtgtcagtga caccatacta taccctaag |
| 55321 | gaaattaaag ggactgagta aaaggcttcc agggagaccc tctggatgg ttgctacaaa |
| 55381 | agaacaaact ctattcctga ggctgacaga tgggaaataa ttaaacattt tcatgattcc |
| 55441 | tcacatttgg gacgggattt tccattcaaa ttagtttcct aaatattctt cgggaaggga |
| 55501 | ctgttctaaa ctataaaaag ggtaccact caggaagcca ccccatacccc cgatccctgc |
| 55561 | ttaaacctgt acaacaccaa ggaacatacc atggtgaaga ctggcagaca gacttaaccc |
| 55621 | agatgccacc ttacagggaa ctacaagatt tgctagtatt tatagacact ttcaccaggt |
| 55681 | ggatagaagc tttccccaca aggacaggaa aagtactgga agtgtctaaa ttcttaaaga |
| 55741 | aatcattcca agatttggat taccaaaagg tttgcaaggt gacaactgac ctcacttcac |
| 55801 | agctaaggtg acccagtgag gtcatgccctc agccttaggc attacctgtc ttcattcctc |
| 55861 | atggagatct cagtcttcaa ataacataga aagccaatcg cgacattagc aaaactcttt |
| 55921 | cagtttgggg gcttgcctgc cctgcgtcac tatcattgtt tccttgggtt tcccaggaat |
| 55981 | gtacatgtgt gagactgccg ccctgcttat agatctgttt ccctgcaagg aaacaggaat |
| 56041 | atgttgcctg tggcttccag agttggagat acatgtagtt gcaccactga gggctaacat |
| 56101 | ttaattttgg aatcaagtga tgcattcaga ctggttgcta tcattctgtg gtatatattt |
| 56161 | agtgaacaca ttcatgattg agtttcttgc ttttagctgg agcaagaaag ttttataatt |
| 56221 | gtgatttgta tgaaaaaatc ataggcaagg gaatggatgt aaaataaact ttattgtcag |
| 56281 | aggtttctaa aggctcatcc ttcaaggaaa atggacatat gctgaagagc tgataaactg |
| 56341 | tctacagcag tgttattcta acctaatctt gattccaagt tcttgccatt ttcctccagc |
| 56401 | tactgttgac tccagttata tataggatgg gggaaagggg attatctacg aatgtaggca |
| 56461 | tcactttctc ttgggcagtt atcacattgg cagactgaag ggaagtgatt tctacaatca |
| 56521 | aactatccat ttggagtaca aatctggagt ggctgtaaaa ttcggttctc agagatgaac |
| 56581 | ttgcagattc ggacttttcaa ttgttctgtt gttttagttt ttctcatcaa ctggggaact |
| 56641 | gttttgtgact aagctttgtt aaaagtagag aagagctttt cataattcca acattagttg |
| 56701 | ttacctgaaa caaacaaaaa cacacacaga gacaattaaa cagtaatctt tggtgaggtc |
| 56761 | ttgctgatac ctgaggctgg agtgagagct gagtggtgat acagctcatg tgcgtgatcc |
| 56821 | agattgcgca ctcctatga gactgtaact gatgcctgat gacctgaagt ggaacagttt |
| 56881 | catatggaaa acatccacca cccccttcca tggaaaaatt gtcttccatg aaaccagtct |
| 56941 | ctggtgacaa aaaggttgag gacagccaaa aaggctgctt taaatgataa ccttcccccaa |
| 57001 | aactaaatta ccccctgtaaa atgaatgaaa ggccaccaag ttagaaggat gaaagggggcc |
| 57061 | tgatttctac taagatgtat gcctcgtaa ataattacca gccattattc cagagtcac |
| 57121 | aagattggca gcttccccaa ttactgctgt gaagaacatc actattgtag aacctaagat |
| 57181 | tggcctcttg agatgtcttt tcaggctttt gcatttctga ctgctggaag gcaccatcctg |
| 57241 | gcccgaaaat caaccagtcc cttagccccc acccagaagc tgacctccatg caggagggcc |
| 57301 | attttccacg ccctgtgat ttcatccca acaatcagca ccacgcaagc cctagcccc |
| 57361 | tccccaccaa actatcttg aaaaccccct tacctccaag ccttcagtga gattgctttg |
| 57421 | agtaataact ctgtctccca catgtcgtgg ctggcctgtg tcaatgaaac cgtttcctgc |
| 57481 | agtgccatgg tctccatgaa ttgagttttt gtgtacattg gtcaggaaga acccatcagg |
| 57541 | cggttacatc tgcaggatgg tgccaggttct ttcacaaag gctggtcaga taccccagaaa |
| 57601 | acatttctcc actactacct ggacaatgtg tctccctgtc aatctccagg gaatggggcc |
| 57661 | tggatcaagt atttagtatt cagcagttac tacactgtca cctaatccct cattttcaat |
| 57721 | attttgccat gcttccagtg gcctaactgg ccaccatgcc acagaatctt tactttatga |

```
57781  tctccaagga gaactctcca ctcgatgttt tgtgatttga gcaatggaat agaatctgat
57841  actggtgggc tggggagggt ccctggacac tggtgggatc tcgaccccag ccgtggtgtc
57901  caggctcttg acaccatcgt gagaacaaag tcaaagatga gtcagcagat agtgaaagaa
57961  gagatttatt gcaaagcaaa aagtacacac tcaagaaagg ggagcttggg catcccaag
58021  agagaataat gggttctggg gtttcatctt gatgggtttc tttaaccaag aattggaata
58081  ttcacgaaaa ttcctgggta aaggtggaga tttcttggaa ctgtggtgcc atttttacat
58141  caaacactgg tctcagaact gtcatggcac tggcgggtgt gtgatttagt atgttaatga
58201  gcatataatg agggcctagg taaaacctcc atccaatcca gcaccacgtt gggtccactc
58261  agccttagcc agcttggtcc cacccctggt ttttcagcgt cttaacagcc cacagcctca
58321  agtcatgtaa atctgctgcc tagaatttgt tatcctgtga ccaccctgta gtattcctgt
58381  ctgaaatcta cttgtaaata ttcaaatggt ctttcacttg ggcattccaa ctttgcttac
58441  ttcacagtgt ttcctgcgta atatataaga aaagatgatc cagacatttg ttaaacatct
58501  caaataagat gtagcccagg tatttgtgtc aaatttggat tattttggtt tcgtctttgc
58561  agaatataaa aaactaacat gaggtaagca ctaaggtgtg gagatggctg tgcaagagat
58621  gacaaagtcc agcaccacgc ttgagagtgt ccaatcatct cttctgggac agcatatttt
58681  tctacaatac ggattttga aaaaaaaaac aacatcaaaa aaaaaaaaac ctacaagatt
58741  catgaaactg gacacctgtc tttataacat taccagtgat aaaaccagta aggacggctg
58801  gtttgcagtc atctaagcag cctctttact ttcataaata tggtttctct ctgatattaa
58861  acggcttcca attgcaagcg gaatgctgca tcacaaggat aaggatgtga agagaaccgg
58921  ttctttttgt aatccgaaac attctagtct gcgaattaaa agccattatt tgaagaagga
58981  tgccccggct ccatctggcc accgaaaggt tgctccttaa cacaggctaa ggaccagctt
59041  ctttgggaga gaacagacgc aggggcggga gggaaaaagg gagaggcaga cgtcacttcc
59101  ccttggcggc tctggcagca gattggtcgg ttgagtggca gaaaggcaga cggggactgg
59161  gcaaggcact gtcggtgaca tcacggacag ggcgacttct atgtagatga ggcagccgcag
59221  aggctgctgc ttcgccactt gctgcttcgc cacgaaggag ttcccgtgcc ctgggagcgg
59281  gttcaggacc gcggatcgga agtgagaatc ccagctgtgt gtcagggctg gaaagggctc
59341  gggagtgcgc ggggcaagtg accgtgtgtg taaagagtga ggcgtatgag gctgtgtcgg
59401  ggcagagccc gaagatctca tacttacctg gcagggggaga taccatgatc acgaaggtgg
59461  ttttcccagg gcgaggctta tccattgcac tccggatgtg ctgaccctg cgatttccc
59521  aaatgtggga aactcgactg cataatttgt ggtagtgggg gactgcgttc gcgctttccc
59581  ctgactttct ggagtttcaa aaacagaccg tacgccaagg gtcatgtctt ttttcgtatt
59641  ggtttgtgtc ttagttgtta atcctacagt ggaggcctgg ggaataagaa gtaacatgtg
59701  gcctgcacgc cataggagaa aaagcgagca tcagccgtat cggctttgta acacaaatta
59761  gctatcgtga agtccgctca gctcttccat ttctaccctg gctgcttttt gcagggattg
59821  gtccgtggtc tccagtctct tgggttctca ccctgtgtga aaatcttcgt gtttttccct
59881  accccccaag tcacctctta cacagcctct gcttccaagc gcagccccca caggagtttg
59941  taggatttct gtgctagcgg ggagtgtgtt ctcacctcat agagccaggt agaaattatg
60001  cagatgggcg ctgttctctg ggaagaaagc agggccttg ggctctcag tgtccccgtt
60061  gggttgtaga cataacactc ttactttgcg taggggaacg gctctgccgg cccccaggtg
60121  ccctagcgca tatgcatgga ggcccgcagg tcagaaccgc agtctcacct gtcttggcgg
60181  aaatgccctg cgatcctccc ggagatagaa ggcgggaagt tttatgagga gccggtccag
60241  tttccctact atctcctgca gttcatatat ctagtgtttc tttagacttt aagcgactgc
60301  ttcatgtttg atgtctcact cccacatcct acatccactg ccagccaact ttatagatag
60361  caccgtgacc catccttccc accccccaaga agcccttttc tatttctggt gccagtgtcc
60421  tccccagtcc ctctttcttc aggccctcgc ttatcacctt catggacaga aaatacttag
60481  ctctctctca acctgaggtt tacacctgac acgcatcagt gccctggcaa attccttaat
60541  acccccttctc aaatggcact gtaaatcatc tctttttaac tcccagaact atctaattgg
60601  ttttgtccct gcactacatg aacactagta ttccactaca gaggaaaacc ccaggcctag
60661  cgatagcggt tctgggcatt gtgccagcct ctcccagggt atgttttctg acctcaccta
60721  cttttgatca gctgaggtca ggagttcaag accagcctga ccaacatggc aaaactccgt
60781  ctctactaaa aacacataca cacgcacaat aataataata atgataataa taataattgc
60841  cgggcgcagt ggtgtgtgtc tgtaatccca actactcggg aggctgaggc aggagaatcg
60901  cttgaacccg ggaggtggag gttactgtga gccgagatcg cgccattgca ccgcagcctg
60961  ggcaacagag taagactctg tctcaaaaag agaaaaaaaa ttagtgcatc tgagacatat
61021  tattggagac agtagaatcc tgcgtccaac aggcacttgg tgcagatctg aacccattga
61081  gctattggct catgttccct atgttctatt aagtatcatg agcagaaatt gagctctttg
61141  gcttttaccc actgagtatg gctataggac aggtctctct ctctctctct ctctctctct
61201  ctctctctct ttctctctca ttctttgcat cattattttt tgccatcagt gtgggttttt
61261  ggttttgagg ttatgaagtg aatttctggg gacaatctct gttgggtcgt gttaacaagg
61321  atccagtccc tgtttggtga tacatgacag ctaatctggt ctgtgagtct tctttattgt
61381  ctatttattg tcctgagaat aatggcattt cctgatattt gagactgcag caatgataag
61441  ttgttcagat cttgtctttc caatgtttgg taaacatttt ataggcccaa tttttgtcaa
61501  tatctgcaag agtggcatct ctgttacaag agtgatctta ctactcgatg tcccccctcc
61561  cacccaactt catttcctag gggctcttgg ctttaacgaa tttactgtat ctaaaagaca
61621  tcttagtaca ggaagaaaac taaatctgta gcatgtaagg agcagtttta tttgttggt
61681  atattcaggt ttctaaccag ctgaaaaatt caaatacatg cccttaagg attaagttta
61741  aaccacacta cagaaagaga aagatttat atgatcacat ataagcaatg gaatcagcaa
61801  tatgagtact tttcacaact atacaaatca aatttaataa tctccagaac attaaggaag
61861  ttcagcccctt aatggaaatg aatgaaaaga aattattcac ccactgttac atgccctgga
61921  aagagaatgt cctgccagac tcaaaagagt atcacaatat tactcagatt ttcagcaatg
61981  aaggccctcc gaggatctaa tgatgttcat attttcagtt tatttccttc actgataaac
62041  attgttaata gataccattg cctctgtttg cactttaagt gatgttactt agaacaattc
62101  gtttctttag catgcaccct agtttggtgg aaggaattttt ccttcttttc aaatatagga
62161  tattttctca tgaaacaaat tggcatactc tttcagtgaa gtgaatagac aaattagatc
62221  tctacaattg taaggagtc actgccccaa ttatctttag aacaataata atcacttata
62281  taaattaaaa ataagaaaat taagccaggt atggtggctc atagctacag tcccagcact
62341  ttaagagttg gagaccagcc tgggcaacac agtgaaaccc ctgtctctac aaatttttaa
62401  gtattagcta attttttaaa gttggccggg catgataatg catgctgta atctcaggct
62461  gcagtgaact atgattgtgc cactgccctc cagcctgagt gacagaatga gactcccaac
```

-continued

```
62521  tcaaaaaaaa aaaaaaggaa agaaaattaa gaatttgttg aaaattgttt tactacaatg
62581  ctaggctgca tgtcttgcac ctgtactccc agcaactcaa caggctgagg cggaaggatt
62641  gctttaggcc agcagttgga gaccagcctg gggaacaggg catgacatca tctctaaaaa
62701  aatacaaggc aagctgagcc aggaggattg cctgagccca gaagttccaa gttggtcagc
62761  tatgattgcc ccactgcact ctagcctgga taacagagca agaccctgtg ccttatttt
62821  aaatttatgt tatttttta ctacttatgc ttatttatct atttatttat ttttgagaca
62881  gagtcttgct ctgtagccca ggctagagtg cagtggtgcc atctcagctc actgcaagct
62941  ctgcctccca ggttgaagct atttccctgc ctcagcctcc agagtagctg ggattatagg
63001  cacacgccac cacgcccagc taattttat atgtttagta gagacagggt ttcatcatgt
63061  ttgccaggct agtctcaaac tcctgacctc aagtgataca cctgtctcgg cctcccaaag
63121  tgctgggatt acaggtgtga gccaactcgc ccaggctcct tatgcttgaa atgtgaggtt
63181  tcattaggga aaaattttct tgttgaattt ctaacatgaa aaaataatag atttagctgt
63241  agattaaatt aatggtcctg gtagtttggt acaataaaat aaatgaagtt gatagcagag
63301  aggaatcttt gatgcttttg aacaatttaa ataatgtaat atttttata taaagacatg
63361  aaaaagttca ttacattatt attatattta tttatttatt tatttatttt gagatgtagt
63421  ctcactctgt cgcctaagct agagtgcagt ggtgcaatct cggctcactg caaccactgc
63481  ttcccgggtt caagcaattc tcctgtctca gcctcctgag tagctgggat tacaggcaca
63541  caccaccaca cttggctaat ttttgtattt ttagtagaca cggggtttca ccatgttggt
63601  caggctgtct tgaactcctg acctcatgat cctcctgcta tggcttccca aagcgctggg
63661  gttacaggca taggccactg cacctggccc attacattat tttttaaaaa tcagtgtgac
63721  tctttgaca aattagaatg gtttaataat cttggttagg ctgggcatgg tggctcatgc
63781  ctgtagtcca agcactttgg gagcccgagg tcaggagttt gagaccagcc tggccaacat
63841  ggtgaaaccc tgtctctact aaaaatacaa aaattagccg ggcatggtgg ggggctcctg
63901  taatcccagc tactcagaag gctgaggcag gagaattgct tgaactcagg aggcagaggt
63961  cgcagtgagc caagatcacg ccattgcact ccagcctggg ggggcaacag agtgagactc
64021  tgtctcaaaa aatcataaa taatttaaaaa taaagtataa aaaattaaaa ttacgtgttc
64081  aaatacatta aatatatggc aatgaaaagg aggcctagca tgactgactg cattttgctc
64141  ctaacccttc ctaccgtgtg gtgacatctt ccaggctaac tgcttttttct tatttctgca
64201  cataggccaa gctatctatg ggagggattt agcttacagt ttaactttaa agcacagatg
64261  ataataatcc cttccccaaa ctaactcctg agaagataga gaggttgtat acacaagtaa
64321  cagtgttatg ctgaagattt ataagagaag tgtgacctga caaaggacca acaattttca
64381  ccatccccctt gggctctcac tgcagcccat gtctgtcatt gtcagacctc ttcacctcaa
64441  tcgcctcctt cttcctccct tcccctaatgt acaaggagcc ggaaaatagt attaatttaa
64501  gatggttctt caggatgtta cttccaccatc tgttcagttt ggtggctctc tggaataaag
64561  tcaccttccc tgccccttaca cctcaactct cgacttattg gctgtcatgc agcaagtggt
64621  gagtgcagta agccgagatc acaccactgc actccagtct gggtgacct gtctcaaaaa
64681  aaaaaaaaaa aaaaaaacag agagagagag agaaattttgg ttttgaacc agacaaatta
64741  aataggagac ttaattccaa tgagacctag aaatgtctaa atttctaaaa tttctaaaag
64801  aactgagaaa attgcctcca ttgaggaagt aagctgaagg aggtagactg tcatgttttc
64861  tgatttgaga aatattgagg aggctttgtc tctttcacct ccaactgctc cttctcctcc
64921  tgcccctgca cctgcatagt cttcttacc tgagccttcc tgtcctgcct tgcctcttct
64981  tccatcacca tcacctaagg aaagtcccca gggatctggt ccttcctg aaactctgt
65041  tctgacagcc cctttcaagg taaaacccaa acccacagga agaggggagc ctaccgttgt
65101  gtataccact tcaccaaaac gtgaattaag aatattataa aggacttccc tgatctaaac
65161  ttaaatacat ttcactcttc tgtttctaaa gcaggctcca agatcctgta ggctttggca
65221  gaaaatttga cttaactgtt gaaaccttgtg agcccaaata ttctgatctt tatcaattaa
65281  ctcacatgct ggtgaagaag ggaaggccac taactggttg caaaaggtaa attggaagga
65341  ttttcaaaaa gggactgaag cagaacatga aaggttcaca ttt1caccaa atatctccaa
65401  gttgccattc cccaggtcct tcctaaaaat atagattgga ggataattca gcattgtact
65461  aaaaagccag acaaatctgt cttttgcttaa ctaaaatggt ttgagagcca ggtgtggtag
65521  ttcatgcctg taatcccagc acttttggag gctgaggcgg gtgaatcact tgaggtcagg
65581  agattgagac cagcctgcca acatggtgaa accctgtctc cactaaaaat acaaaaatta
65641  gccaggtggc tactcaggag gctgaagcaa aagaattgct tgaacccagg aggtggaggt
65701  tgcagtgagc tgagatcctg ctactgcaat acagcctggg agacagagcg agactctgtc
65761  tcacaaagaa aaaaataaaa agaaaaaaga aaatagaaa aaaaaatagc agggtagtag
65821  aaatataatg cacacaagaa tgataatcat gaagacaatc tgattctaca agagtaaggg
65881  aacctattcc attagagagc caactgaaaa catcaaatcc cagttcacac cccagggtgt
65941  ggggtcacgt gcctgtaatc ccagctactc gggaggatta gtaaggaggt ttgcttgaat
66001  tcatgaggtc aaggcaggag taaaccctga tcatgccact gcactccagc ctggtgtgaca
66061  gtgagacctt gtctcaaaaa caaacaaaca aacaaacaaa caaaaaccca caaaaccaaa
66121  caacaacaaa ttgccacctc actctgaaat cacagtggca aacatcactt tgctattgac
66181  aaattaaaag aaaaacactc cctcttgcta tcaacctggc ctcttgctct aacatgtctg
66241  acccatggtt taaaatgccc aaaagctgat gtcctcaaat tataatacac ttacctattc
66301  tgcaccagca tttattttttg tctggaggag atcaccatcc atggtcctgt aaatgtctaa
66361  cagcatggaa tgatgaaggg cagtgtcttt taggatattt ggttatatct atatatatgg
66421  ctctgaagaa acccaacact gggcgagttc cctcaaactt ttcactaggc atgaccactg
66481  ctgtatttta gatagagatt ctgtcggggca aaacctgaga attatctgcc tggctatcta
66541  gaagatagct ccttgcattt tttgggggag aacacttttg cttcaaggga gtgtttcctc
66601  ccaggattag aaatctttct gtaacctcag gaaacattgc tgatgaaaac caggcatggt
66661  gtgctgtaca acttgtagta ataaggcaga agttaaaagg aaaagacagg ttccctgtac
66721  ttggctgact ccaagacctg ccatagatag agcccctagca gatcctcggt aacacgatct
66781  gaaaagtcag agccgcgagg agtgagttcc ggagactctc tcaacacagt aagccccaac
66841  aaagataaga ggaaaaaaca acaaatgcct ttactacctt ctctttcccc cttcccattt
66901  ctaattattc aagttttgtt aagttcttga tttcccttca gtgcagctgc aaggtcacca
66961  gctatacttg cattgcaaga cctgtgacag tttgattagc tgcctttgtt ctgcttctat
67021  aagccctctt gcctgccccc gagtttcatg ccatcaaatt cccgccgcgc cattcaaact
67081  agccgacccc ctttcagaag tgtctataaa gttaagccct gtctttgttc ggggctcagc
67141  ctttggattt tcatctgctg ggcctcagtg cagtcaataa atcctcctgt tccacccatt
67201  ggtctctctg ttcctgat tcccacaaca gtagtagggg actgcgttcc cactttcccc
```

-continued

```
67261  tggtctttca tggtatgaat aatggacagc atttttttt ttcacctata gtcgcaggct
67321  cggtctcagt gattgtatgc tgtggtcagc tgtttttgtt tttgtgagac cttgctttct
67381  tgtttactgt cctgggacag atgtctgtag tcacttgttt cctcgggagg caaatttcag
67441  tctctgtggg ggaggtctcc catgttagct gtggtggtac ttggcaggca gagctcaggg
67501  atctaggctt ccgtgctttg tagattgctc aatggtcccc aaggcctagt ggcttttaac
67561  accacttgaa aacctagtg tttttccact gtccccagag tcacctctta cacagcctct
67621  ttttttgttt gtttgactt ttctctgaga gacagtctca ctgtatcttg gttgaatcga
67681  tcctcccacc tcagcctctg gagtagcaga ggcacgagtc accacagccg gctatatct
67741  gttcttgttt ttgttgttgt ggtggctgtc ttgttttt aagagttgaa gtttctccat
67801  gttgcccagg cgacgtgctc ccggcgaagg aggccgcctg cctgggggcg ggctggagcc
67861  acgtccagg gctggggggcg ctgtgggcac tgtgggtgcc gcacccaccg ctgcccggca
67921  ctggaggcca agagagcgtt cccgacgggc tccgcggatg ccccgccgcg tcctgctgcc
67981  catcctgccc gggttgtcgc gggccggggg cacgacaaga ggccggggtc tgcccggacg
68041  cagcggcctg cagggcgcag ctgtccctcc accagccggg gtccctcgc tcagcccatg
68101  agacaaataa atgaatacat aaataaataa ataaataaaa gatggagtct tgctctgtcg
68161  cccagggtgg agtgcagtgg tgcgatctcg gctcacttca acctctgcct cccaggttca
68221  agtgattctc ctgcctcagc ctcctgagta actgggatta caggtgcatg ccaccacacc
68281  cggctaattt ttcgattttt agtagagacg ggatttcatc acgttggcca ggctggtctc
68341  gaaccctga cttcaagtga tccacccgcc ttgacctccc gaagtgctgg gattacaggc
68401  atgagccact gcacccagcc agaagtgggc attaatatgc aggcgccgta tagggcaaca
68461  tctgtgtgca cctcttacaa atcttaatgc tgtgtatatg aggggagtcc ttcgtgtccc
68521  cctggggatg tttgaggttg cctgtatgtg ttatgtgtgt gcatattttt aagctcagat
68581  atgcataggc ggattgacac ctctgtttga atgtattccc atgagctcat gccattaatt
68641  caccatcaca agaaatattt actgagcgtg agccatgcca ttccacagac accattatag
68701  cactaagata caatgaggaa caaaaaatcc aggctttctg agctcacact ggggtggggg
68761  catggtggga agacacaggc atcaatgtaa taaacagaaa ccacgacagg gctaagtgtt
68821  ctggaggaga ggcgcatggt gtactgaggc ccctgacgta gaccccaggt gcacctttga
68881  gctttgcttg catggtttgg gtttgtgggc tcacctgcat gtgtccatgc atgccccatc
68941  tgcgtgcccg tgcatggcctg catcacccca tgcacacgtg cactgcccct gggcttgccc
69001  acatgtgctg ctccccaggg cgccaggcta tcagcctaca aggcattgtg ggtctgggcc
69061  cagcctgcca cccctacag aggcctgagc ctgccttccc aggaggccca ggactctcac
69121  ccaggggccct tccctgcagc tggagcaggc tctgtggctg caatctggtg agctggagac
69181  gcaagagccc aggggggctgg tactccagag cgtggagttg cggaggcagc tgcaggagga
69241  gcaggcctcc tagtggcgca agctgcaggc ctacctggag ggccagcagc ggcaggccca
69301  gcttgtgcag cggctgcagg gcaaggtcag ggccacccat tcctgctctt tccctcccac
69361  gtgttcactt tgccctgccc ccacccctgg ggctcaccat cagctcccaa tccccagatt
69421  ctccagtaca agaagaggtt ctcggagctg gagcagctgt tggagagatc cggagagctg
69481  gagcagcagc agctgagggt gggtgccagg gtggggcaga ggcaggccct gccctccacc
69541  tgcccagcct gatgctttaa cctctctgcc acccaggacg cagagcacag ccaagacctg
69601  gagagtgccc tcatctggct ggaggaggag cagcagggag ggccagggct ggcagcatgg
69661  ccccctgggc gagcgcctac tgatcccctg tgccccattc aggagtgcca gcctggccca
69721  ggtgaatgcc atgctctgag aacagctgga ccaggcaggt ttggccaacc aggctctgag
69781  tgaggagata cgaaaggtga ccagtgactg gactcgcagc tgcaaggagc tggagcagtg
69841  ggaggcggca tggaggcgcg aggaggaggt gggcatgggg gtgcagggag gccggcgata
69901  taagaggaag ataatgcaca attatgctag tgagctctc ttttccaata atgttttgcac
69961  ttctcaatac tacatttaaa aaggaaatag gagcacttga acggttaagt aagaagatga
70021  acaaaattga acagaggaaa aataactgtc tgaagacatg ttgaaaatac atttaaagac
70081  agtctgtctg agacaggagc tgagctggcc aatccatctt ttaaatcatt gaacatcatt
70141  caggtgtcaa gtatttgacc tggagcctag aagggagga gagagtccaa aaaaaagtca
70201  aaatataaag aaaaaaaatt aaagaacttg tcccacaaat caggcaacca aggtctaaac
70261  ttataccctc tgcctgggta aattgttgtt gcttctttct gtgactctta aaagatgtac
70321  catatacctc atttaatgac tttgctttat tcatgaaaac tctatcccca tgggaaaagc
70381  tgtttaaatga aaaagattt cttttaagta gaaaaattat gaaaggattc cttccaaccc
70441  tccatacccca aaatatctca aatgaattat gtatctatca attatcaata tatatcaaaa
70501  tataccaatt aaaaaatatca gttaaacaat acgtcaattg aactatgaaa gcaagcttat
70561  ttaagtagca aagaataacg tgaaggttag taagtatagc ttatacttaa aatacaatga
70621  attgaaagct catggcactt catagagtag gaagaagaaa cttaatagaa agtggtagtt
70681  gggcgagaag gactgcaagg gagttatttg gaaaatgcat ttttttattc tgcatcattt
70741  tgttcacaaa ttattcctaa tcttttgtga atttgtggat ttcttgaact caaaccagac
70801  ttaaaaatac agttatagca cagaaaaaaa tctttaatgg caaaataaaa gctaagcaag
70861  agagccttc aaaacacatg aaaataacac acacatacaa aaaaaaaaga ataaagagat
70921  gtacaagtga caccttcctca accttctcac ttggtgtaca tatgcacagt aaattatttt
70981  gggctcagcc aagcatggga gcaattcaaa tagatccata tgatattctc tgattagaaa
71041  ctcttgtgga gtaagttggt gagtgtatct ttgcctaaaa cagtcatgtc aaaatatagc
71101  ttcctatagc atattttattt agtatcattt tggtgaaaaa gtggttatac agaatagaaa
71161  agagttgtcc aaaactaagt ggttgacctt tccagagcca ttacctgcag aattgttatg
71221  taagtctgtt ccatactcat aaaggaatac tcagctgacc caactgattt tctcgtgttt
71281  tttccttcaa gggctagtag aagtctatat gttgtggtgg aaaacaacct cagcccata
71341  gtccaacatt tgcctatcaa aacttgtcct atgatttata aaactagaac ctcactggta
71401  agtcacattc ctagagtctc ccccatccct aaccccagtc acggaaaata aatcaaatca
71461  ttgcactctt ttcttaacaa agagcataca tttaaaactt gagtaaaatt acaggtaccg
71521  tctgggtcct tcaaggggga acttgaagtc tcaataccgc agttgtccaa tcagaggatc
71581  caagatgaat atactcaagg acttttatgct tggcatcctc tggagacagt acataaccac
71641  cagcttggtt taactggaga ttcatttggg ttaggagaaa ttatgtaggc aatgtactta
71701  gtcaatggag gcctcatccc tgaagactta caagaatctg aattcgtatg ttacttttcc
71761  ttttaatggag tggaattcca aatgaaaata atcaaacagc atgtgcataa acattagata
71821  taatacccac atttacaaag cctttataga tatgcaagtg ttattcgtc tgtccctagc
71881  ttctgtacag aattttaatgg gtagctgtta ctatttttatt gctgtataaa aatgaggaaa
71941  ctgataagtt gtctaaaggt gcacaatcaa aacacatcaa agccattgtg aaatacaggt
```

-continued

```
72001  ccccggattt caaaaacaga tcttctgctt ataaattcag tcttttcat actgccataa
72061  actccagaat gggaaaacaa agttactatc agaaaagctt cttttagctg ggcgtggtgg
72121  ctcatgcctg taatcgcagc atattgggag gccaagacag gcggatcact tgaggtcggg
72181  agttcgagac cagcctggcc aacatggtga tctctactaca aaatacaaaa attagctggg
72241  catggtggcg gacacctgta attccagcta cttgggaggc tgaggcagta aatcgcttg
72301  agctggggag gccgagatgg cgtagtgatc cgagatggcg ccactgcact ccagcctggg
72361  tgacagagtg agccgacatc gcgccactgc actccagcct gggtgacaga gtgagactcc
72421  atctcaaaag aaaaaagaaa gcttatttt tcccctaatc accataatat tcactattaa
72481  gtgagggaaa tagaaataat ttatttagca aatcctttct agttcaaata atttgtatac
72541  aggctgtgca aacataataa tgagattctt tttagtcatc ttgctttata tcactaatta
72601  cactcttatt taatgatatt ttaaagaaaa acgtgtttat tttcaagtag aaaactcata
72661  tctgtccacc aaggaaagct gtaacaaatg taaaatacat aaaaaagata actgctaaat
72721  ttctaaagca ttccagaaaa agacaaatag aagggtgtca gattaggaaa gtatgtcttg
72781  taaggtgtaa cggacagact gatgagctta gagatgtgga tctcaaagtg gttctcagag
72841  caacacagatc aggtcacct gggaacgtgt tagaaatgca gattctcagg taccatccca
72901  catttaatga atcagaagct cagagtagag accagcaatt tgttttaaca agtccttcag
72961  ggattctgat acagctgatg tttgagaaac actagcttta ggtaaacgta agagggtcac
73021  gttagtattt ttaaatcatt ggaagttggt ttgttttgtt ttttcttaag tgggactcat
73081  ttatacttca atacacagaa tggatattta gaggaagtcg ttttgacct aacacggatg
73141  agcatttcca attgaatagc gctttctgat aatggggctg cccactacaa gtgaataact
73201  gggttctct aggctggagc tgcagacagg tcactatgtg tatggaggat tgtattaata
73261  tgatcgtggc tcttatagc tctgcattac taatattctg ttttaaagtc tctcctcaat
73321  atccaatgtc tctgtgtgaa tgatggtaag gagtgggtaa cagtaacaat catcctgttg
73381  ttgacaacag atgataagag aaagcccaac tttcacactct gtataacctt acaccaatgc
73441  cccattcctc gtctaattt ttttacatgt taacacatga ccttggcatt actaaataag
73501  aagccctctc acttagaacc cgatgcagta tgataaaaat tatttttgaga acaatcagga
73561  gctctagttt tcaattctgc ttctcttctc aagtagttct gtgccttagt ttcttctttg
73621  taaatttaaa tggttggaac agaggatctg ttaagtgtga ttcaagctga aattgtatgt
73681  agcccacact gagtttctct gctataccccc taacccattc aacaatcaca ccaccagttt
73741  tcaggactca cagtaggata gccgtctatc atttgttaat aggtgtgctc tttcatccaa
73801  acaagaaact catgattct gcagtttttt attctagcca ggttctaggt gctggcctgg
73861  aactataaaa cgaacatttc acaaaaagtt atgacaatat acaaaggaaa gacaatttct
73921  ttgaatatcc ataatctcaa tatgcagtct ggctgtggat ggccaagaga tagtttcctt
73981  aactggaaaa agcttttaaa tgaggcttgg tggaagatat atctttgcat cattacaaag
74041  aagaaaaaag agaaatctca caactgaaga aagtgaaatc cactttactt aatgcggacc
74101  tctgtctctg gtgtgcaggt cctctgtgtc caaagataat tagcacttta taatgctaat
74161  tattataatt aggtctgaga aaaaaatcat taggggggtag gcccgttcac tgattttcaa
74221  ctgccccctc tatttaaaaa taaggtcatt tttctatgaa atacctttag gagctcaaag
74281  cagaaagagg gttataaa atcctgtgta ggtataagcc tgagttttta atattcttat
74341  aattctgtga tgtgtctgga aactgaaccg ggaggaaaac agtgaaccta tttagtccag
74401  gagactagaa atcaggactc agaaggtaa acatttctgt aatagttagt cctcaaatag
74461  tcattcattg accttccact ggggtgtctgg caatgtgcaa gctgcttcta gatgctacct
74521  catgtaacaa ccatcacagt tgcacagagc aagtactagt actccacttt catagataaa
74581  gaagtaaaat cttagaaatt agctgcccaa tgtcatgtat gtaggaaagg aaagctggat
74641  tctgattcat atttgctggc tccaaagcac ttgttgtaaa tacttcacta tcctgtgctt
74701  acatgtaaat gtaccatttc tcttaggggt cttgaaatac tgaaccaaag aatggtgtag
74761  gggaagggca gtttagaaat acctggaaat ttggttgtt gaaggaagcc cactctcaga
74821  tggtaggaga tcaagctaac agaatagctg agaatatttt ctgaggcccc agaagtataa
74881  aaacggtcta ggggggaaaa tttgggacac agagtgaaaa tagcctgcct ctgaagacca
74941  gcttcatttc ttccccctctg ggtgttaatg aaagagcctt taactttgcc aggcctcagt
75001  tactaatttc taaacaact gctgctacta ttactacgga tcttactgct actatgacca
75061  ccaccaccac cacatcagtt actgagaact gaactagatg ccaagcaaaa atggtaaaca
75121  cttcatatac attatctttt taaacacaaa atgtactatt aatccagttt tacatataag
75181  aaaactgagg ctcaaagagg ctaagtaatt tgtatgtgaa catgctttac acatgtaaa
75241  acaccttatt agtagaatc actattatta agaacctatc agccggagag gaagaattgg
75301  ccttttatct ttctaagatg cacagttgtc tttctgttta atggttttt aaaaatccccc
75361  ctgtgacaag ctccagagga caaataattt gtttcttgtg gtgtatggct ctctaaatga
75421  attaattgat aggcatccca ttgtcagtct cagggatgtg gaaataaaac agacatgaga
75481  tgttttttac caaactaatt tgtgctttaa acacataaat aataaatata tatatattaa
75541  agtaaatgtg tatttaccgt ctctcctgct ccactttgaa ttcaagaacc cgtgtctttg
75601  ttgggtcact gcactgtcaa ttgagaagtt tggttttgtt tctttgagtg ttagtaagtg
75661  gcattaaatg gtaaatattg ccggggggaaa gaaaggagaa aaacagctct tccaatccat
75721  ccctgtttcc attcaattaa aggagggtag aaagaatact taagataatt gtaataagtc
75781  taatagaata gcaggagcca ctcttttcct ttcagtaggc cattagctca gaactatttt
75841  cagagtaata ctaagatgat atttgccttt tcactgtgtt ggcacttgta ttgataaggc
75901  aaaaacagtg gagtcttagc aaaaattaag accatgaaca caaactgcac taggaataat
75961  tctcttcttc attactgttt acttgcaggg ggaaaaacca ttttcgttta agaaagtcct
76021  tggtgaagta gtaaaaatat taatttttatt aaatctcaac cttgagtaca agtcttgtcc
76081  ttgactgtac ttacaagttt tgtcctcccc aaagcatatg gcgtcaaggc tgggcctaac
76141  ccagtctcat gaccttgtga atccagtcca caaacacaga gacacgcgtg aagacggctg
76201  gccagcgcga ccttgtgcat actcggttgg ggattctaat tcctttcagg acccagcagt
76261  tgtgggtaaa gcaggcaagt gggccccgt agtcaccctg gcaggtagga gaactgatga
76321  gggcccgggg ccacagcaat gactagcctg cttcatgata aaatagttca tttctagccc
76381  cccataccct tccagggctg gcccagggcc ctgccaccaa cctcacaggc cccacaggg
76441  gccaacagtc cctcagtgca catctcgctc tcccgcacat gtcctcggtg cttgatgtta
76501  cactcctggt tggagatgac gttcagcaag gccacattta ggactgtgtc attacccgta
76561  cctgcagtga gggaatgggg gagaaggaga cggtcctgga ggaagatcca gggctgggcc
76621  tcctggccac cagcagtcct gtgcactatg ctcttacctt tggtctcacc ccagcctgca
76681  atctcacact tggtccctgg aggcaccaca taccattcag gcggcaggca gatcagggcc
```

-continued

```
76741  acacgctggt tcagggtcac agatctttaa caagaatggg ggcactcagg gtctgaggcc
76801  acaaggctca gccccacctc acatcctccc aggttgtcca catacctctc cagcttgagc
76861  aggacaagct gggagcctga gggcccacac agcatcttgg ctactgggac ccgctgtagg
76921  cctggctctc catgttgtgg gttctggaac agggtgccca accatacctc atagcccgtg
76981  agaggcatat ggctgggaga gaagctctgc taggtcattt gtgactctca gtccgttgcc
77041  ccaaggctca cttgttagct tgcctgggga aaggggaaag tgggatgaga ctgggtcccc
77101  aaacacaagg gaggctcacc aggaggagaa gcactgccgg gcagtcagta tccactgctc
77161  ctttactaga gaccccgcgc agaaatgctg gccctgccta gaggagtggg gaattaggac
77221  agggaacaga ctcctgggac agatgctaga cctgccatct tctggctagg acctctgggg
77281  gcagggatag attcccagcc cccagtggca taaccacaga ggacacaacc tcagctcctc
77341  tctgtgggag acaggcagtt gtgcctcacc gattccgcaa gctgactgtc cagggtgagt
77401  tgcccggatg gccccagcc acgcgcagct tggaacgacg ctgatccagc cgatccaccc
77461  tcttgccaca cttctcaaac tgcacctggt ctgtaggatg gggtgggctg gatgaaaccc
77521  agactgtgtg gatgtcgtgg gctaaagggc ctgacccata actggcccaa ctcgtaacct
77581  gggggggtcc aggattgatg gcggctggtc atcagctgaa agacaaagtt cactggggtt
77641  aagggagcca gcctttggtg gtgagggctg aggtaaggtc atggggcaag cgtcactagt
77701  gctcaccgca gcgtcgcagg gcacagtagt cgaatggggt ccttgggtcc atcgtgtagc
77761  accagggccc atggctatcc ccatctgggt ctggcagaag ttctcctcca gttgtgcatg
77821  cggttcggag gtaaatgtga accgaggcgg gagcgggagc aaaatcgtgg cagggtagtc
77881  tcaaccattt ccaggctctg gtcccagaca tcaaagcatg ccgccccagg gttagggccc
77941  tggcggggcc gggagcacca gggactcact gcagcttgtg cggcgtctca gcgaccagc
78001  gctggcactg gacacccttg cgggtcttgc tgaccgtgcc gcggtactgc tcccccgcgc
78061  cgtggtagca gtctgcggcc ggtgcgggca gccatcaggc cgagacctcg ccccggccct
78121  ccggttccag gcttccagcc ccggctctgt agccccccaag cttgggcctc accctgggc
78181  cgcacgtcgt ctgtacaacg ccggatctgg tagcaaaagc ccacgcgcgt gccgggccgc
78241  agggtgaagc accaggcgc ctctgagccg tcgaggttcc agcagaagtt ctcccgaagg
78301  tctctaagca ggcgctccac tcagcctag cccgccagcc tccagcccta agcccgtgac
78361  taccctcctc ccgtctcacc cgcagcagca cgtcccaacg cccgccccc cgcccacctc
78421  acttgcacgc gtatttttct ggcgtaaatc ggtgctgatg tgggatttgc gcgtcccaac
78481  gctggcaagg tacgccgcgg tggtggtatt ggctgtgccc cggtagccct caccccttcc
78541  gcggaagcag ctgacacttg tggcctcttg gcggggctgt gcctcggacc cttagatgga
78601  ccgagatagg tcggcccccg agcgacagct gagatccctc tggggctggg accaaacccg
78661  cctttcccag gtgtacggta ctccacggga tatgctctca ggtcacgccc agcccctctg
78721  acctccccgg ccaagccacg cccctcccca aggttccag gtaccctccc aggcctggtc
78781  cccgccgcct accgcagcgg gggaggtcac agaactctcg ctcgatctgc ggatccgtag
78841  tgtagcacca tggccgctcg gagccgtcag gattccggca atagttgtcg tccagaccctt
78901  ggtcgaggaa cctgggggcg gtaatggggc gtgaagaaga ccctggtact ctggcttatc
78961  tggcccccgcc cagttgccct acacggagcc ctgccctgg agtcctggac cttccctagc
79021  ccggccccca gggcgccgat accgcctacg cgtacttgcc cggctcgaag gggtgctggt
79081  gcgggtgctg aagatcccag cgctggcact cgcgccctga ctcggtgcgg tctaccgcgc
79141  cgcggttattc ctcgccattg caccagacac acgcggctgg agacaaagag ccagtgggtt
79201  cgtggatggg cgtgggcttg cccctccact ctcccagctt gacccggcgc cgcttaccca
79261  cccggcagga tttgatgctg cagctctgga agcgcacggc agggtctgtt gtgtggcacc
79321  aaggacctcc ggggtcgcca tcagggttac ggcagaagtt ctcttccagg ccattccgga
79381  gctgtgggcat gtacctgagg gcccagagca tcactatagt gtgtgctggg ggaaggtccc
79441  aggccgggac ggagggaagg tgtttgtctc acttgtgatc gttcgggaac ttgtggctcc
79501  aagcctggca ggacaggcca cccacggtcg tggccatggt gccccggtac ccaaccccat
79561  tgttcatgat gcaggtccgt atgtagtctg ggagcaagag acagaagatc aacttgggct
79621  gaggtcccct gtctcccacc ctgccccctct ccaccccccac tcgccttttct cctggaagag
79681  gtcacagcgc ccagaatgcc acagccttga gtggggcgag tgttgagtcc atggcagcag
79741  ttggcaacca tggctgctca cattgtagtg gaacgccctg gagagaagaa ggcacagggt
79801  aacgccacgg cccaggctcc cctgcccca gtcttatcta ggcccagtgg ccactcacca
79861  gcagtccatt aagggcccac agcgaccagc acactcttca gcatctgcca catctcctg
79921  ccaaggcccg ggcaccaccg catgtagcag gtgctgtagc tctgtgcccc ggagccacctg
79981  gaagtcattc gatgcgagc gctgccctgc agagtgggca tgagtgggtg caggtcaggt
80041  gggcatacat gtcagtaatg tgtattggca tgtccacact ttgttcattc aggggatcaa
80101  agctacaagg cttctgggat ggaccctgta tgcactttca agggccagtc tagccccct
80161  gcacagatac ttgtcaaaaa aatttcccct gggaagcagg cccagacttg gtagttatca
80221  ccgtgcctc tgtgtagtgg cccaggcact gggctcagat ctaacacata cgctctgtga
80281  gagcagtggg tgatggagct tgccccatct catctctcaa atgagaatgc taaggctcag
80341  agccatcaca ttacccagcc aggggccctg gctaggcatt cagactccaa atctgggctc
80401  tcacctgcac aaaaggcatac gctaggttag aggggtagat caggctcagg aggggtcatt
80461  tcctgctgtg tgcgtgcatc tgtgtggtcc taacactgct tcagtgctag agcagacgtg
80521  ctaatagagg cctaagtggg ccgtgtctgt gtgttcctag ggcttcccag ctgtgctcaa
80581  gaggccaagg tcactgcccc atgcccactg agcctctggc tccccgactt ttttctcatc
80641  ccagaatagg agaataggggc caacccctc ctgaaggcag atggggatca gggttggggg
80701  cactcaccag ggacccctaa gtattgagtc agaagcagca ggagtgggag ccactcctcc
80761  aggatgactt catccttaact aattatatga ctatgttgac tgcaacatat gtatgaagtt
80821  tcatatactc aattccttta ctgcttcctt gagcctatga accccctcct gcatctccta
80881  gtcttcactg aacattatgt caattctcag cctcagctct aaatgctcat ggtttccaaa
80941  aacatattta caacccacca taggtcctga gcaccaaagc ctgatgtcca gttgcccagt
81001  ggacagacat ctccactggg acatctcata agcactaaaa atctcaatgt actgaaacct
81061  gaatttatat ttctctcccc aaatgtgctc catttccatc ttcccttttct caacatccat
81121  ccagtggaaa tgttgctcaa acccaagtcc agagccaccc ttggcacgct catcttcctg
81181  agcccccccac ttccatcggca cacccaggtg cttgtcagtt tgcccacttt ctcccctctcc
81241  acagcccttt tcctagttca gaccttctgt ctcccttgtt gggatcatgt caacctcttc
81301  ctcactcgcc tctggctctg ggcttgtgcc ttcaaccgac tcttcaaacc gtagcaagag
81361  ggatgcctcc aatcacagat cagatcccctc tctccttaaa gccctgcagc agcttcctgt
81421  ggctctcagg atagaattca aacacttcca ggatctgggc atcctctgcc cctccacagc
```

-continued

```
81481  cctgcctcgc cctgcattcc agccccacca aaccacagtc agtcccttcc atggttttgg
81541  atctcttgtc tgggaacttt gcacctgctg ttctctctgc ttaaactctc gctttcaccc
81601  atgcgacctg gttcactcct cattctcctg catgtctcag cttggaagtc acctcttcca
81661  gaaagccttc cctgaccctc aggtccaggt tagatcccc acctggattc ccacagcacc
81721  gtgttttcc cctaccacaa ccctagtcat gccctttagc gaacagccaa cagttactaa
81781  gcacctgctg tgttaggctg tttcttagga ctttataaga aagatcacat ttaatcctac
81841  gaagtaggta ctgctattat cctatttttt agatgaacaa actgaggcaa gagcagtcac
81901  acacacatag agtcagtaag tggtaaagtt gggatagaaa ccaagacaat ctgactcatg
81961  gatgttacac cgtgtgttag aactagcctt gaaaaaaaga cacaagcttg tgccctgtgc
82021  caagaaagtt tctgataatg gtggcggtgg tggtggtggt gggatttaat cagttggcag
82081  aagtctgtat ttctaacaat ctctgattca aatgggcagg acccatgtcc atttctcttt
82141  attgcaattg tactatgttt cttaccttca ctctgcaaca agcttggtga agacagagaa
82201  catgtatctg aggcccttca tctccctca gttcctagac cagcactagc ccatagtcaa
82261  ccctccatca aagtagaggg agaaagtaag tggcttttac cctgtgcttt ctgaactcct
82321  gggatgctag gaagagccag aaaaccttgt ccaccgaacc cacaaattca ctctcttcat
82381  cccttcctca ctccacttcc ttcccagtag ttgttggagt ttttgaattt tccctctgtg
82441  agcccttgcc ctcccctgcc atgttctcag caaaggccct ggcctccagg tccatgagaa
82501  caggattccc tgtagtaaga gctcttccct agcctcctcc acttccaaag gggctggaat
82561  cttcaccct tgatcccttc ccttttaga gcacagagga agcggagccc tcctcctgcc
82621  ctgggctccc atgccccaca tgttcctgga gagcaccctt gggccactgt tgtaactaca
82681  tggtgacttg cttgctctca tccttcatga ccccccctcc tcccatgccc cactttgtta
82741  atttcactct cctctcaaaa ctccccacag tgccagtgat ggggtataaa tgcagctggg
82801  caacgaggct cccacagaca gacccaaacc tatcttccaa gtgttaattt cttttctctc
82861  ctcttcttca aataggtctc ttccttacac atttctgcca ttccttttctc tctctgcctt
82921  gcctctccct tttctcccgg ccacagcctt atccaactc ccagcccagc ttggactcag
82981  cttcctagg aggctcccag acaatccagt gggctctcat ttttttgagt gtattcagca
83041  gttggctgat gctgcatctc cagcacttgc cctaggttgt tttatctccc taatgcctg
83101  taaacccctt gagggcagga tctgtgcctt gtactctaaa aaggtcttcc tactagagaa
83161  tgctccacac atgtgtgatg cttcggggag tcccaacctt catcagagat tcccactggt
83221  gccagctcat agctcatcat gacgtgtccc agatggtgac tgggagtagc ctatgccaag
83281  caggagtttt tccccgaagt cttcctgttt attgcaccgg gctggctgca agacattgag
83341  gatgctgccc caggggccag caggggtgact ggggcaggcg ccatgatggc tgtgcctggg
83401  tgctggccag tgtggccca agaaagaggcc gggagccaga gctgcatgcc ctctgtcagc
83461  accagcctcc taaaaacact ctcgactttc tccaagcatg gattgcctga gctcccctcc
83521  tgctccccaa agaggccggg gaacaagtca gacagggat aagtcagaca ggctcagctg
83581  tgggaggctg gaggaaaaag accaataaaa ctgactttat ttgtaatgtt cccatgtttg
83641  tgattttgtt atttctactc tgtttcctca gagcaatgaa acaaggaaac ggaacaaaaa
83701  ataacaaaac ccagctctaa gtatacgtga actgtaaggc ctcccctctgg cctcctctct
83761  tcctccttcc tcaccaggtt tgcctggctg acccttccag ccagtgaatt ccttttcccag
83821  gttgagtgtt ttccatttta attttgtgg catttccctg gattaatggt taacgcattc
83881  attttctccc ctccagcctc cattatcaaa gagtgctttg aataaccatt aactctctgg
83941  ttaagcgaaa gaaacacgtt aatcatctac aagtcctggg gcaggaaat tattcttggt
84001  aaccttctcc caatggcaag aaaaccactg tccctgagca gctcaacttc agccacacct
84061  gggtctacaa gcttgcaaaa cccctccggt aaccttgtta caaggacttg gtaaactgag
84121  gtcataaact gctgaatggc taagcgctgt gcttttcaac ccagccacca ccggttctct
84181  aggaccctat aaagagacaa ggctgggctg ctgcttctcc ctttactttt aaaaattgtt
84241  ttgccagtaa agtctcatct attgtacatt cctgttacg gggaaactca agtggctgta
84301  caggctgttc ttggagccac agttaaaagc gctttgactc aaacacacat gtgcgctcat
84361  cctgagcctcc gtttgcgtgg ggccggaaca ccggactagg aaacctctcc ctgcttagc
84421  aactgagtgt ggctagattg agggaccaca ggggggtggct ctggatgcag caatccaagt
84481  cccctttca gggagggtga cctcttccg aagttcagtg gatggcccc ttcagggtt
84541  agggagacag gaggaggagg aagaagaaaa ggaggaggaa agctctcaac agcccccac
84601  ccccaaccca tccaggagag aaggactgca gtccccgaga ccagctggag gagtggcgtg
84661  tgcatggtgt gccctcaggg tagagcgcgc catctggag agatgcctct ttcattcaca
84721  aagccggatct gttgcagagc ccagagcccc ggggagagca gggcgcgctc caagtgcttg
84781  ctgggttttgg cttgcactcc ctctcccctta aagaagacag aggcggaagg gagaggctgt
84841  tcttcggagg cgagcctcag gcactgctag acttagtagg aaagatattg ctggggtctt
84901  ggcaagccgt aggtgcagcg ctccccatcg tcattccggt gcggctggtt actgtcaccc
84961  tgcctcctcc ccgccggcct gagagcctct ctgttccaga tccaaacatt tccacattag
85021  gcagcctgca tgtgcatttc cctggcagtg gagggaaagg caccctgtg acctgggatg
85081  accgacgacg gggacttgcc ctcctccccc acaggtgcac ttgctctttt ctgggccagc
85141  cttgtgatct ggtgtccggg cacttggcag catttagcaa atgttcctca gtgctctgtt
85201  tggtagttaa tgctgttgac acggacacct ttgggagcac gtgggagaag ctgctgcctc
85261  cgtttccccc gggttacagc gcctggcgca gtctgttgtc ccctcagaag tggtgggcga
85321  cattatctcc tttttcatcc ctagccctct ccttgaagc tgtcctgatc tctcttttgg
85381  acccaggaac gtgagcagag gttactactc actatatata cacactgcat ctagactcat
85441  gcatgccttc ttggtgtcaa ggacacctca catttcaaag acttcatgaa aaagaacgtg
85501  aggtatctca cacggtgaca tgataaagct ttggacaacg tgggttaagc taaaaacagg
85561  tcattacaat taattgtatc tctgtctttt gacccttcag tggctcctga aatccatcac
85621  acatgtgggct tgcaagtatt ttggtcggac aacgctgccg tagattgtcc cactctgaaa
85681  tggttccctc tgggcttacg ggactgctat agaagggtcc taaggtcctg tgcctccctg
85741  cttttcaagt ggctgcaaac ttctgtgcct accgcttcct ccactggatg tttccttcct
85801  gccctcctcc ctgaggacct cctagtccct cttcaggatg cagagctgga gcctccactc
85861  caggaaagcc actcatgttg ttgccaacac aaccccctgc acacatgcag tattaggcat
85921  tggtctgcct ggctgtccct gggctgtgct gtccttgagg gcagttttttg tgtctaattc
85981  ccagagagtg caagaacaca agcatgctca tccagacgtt agtaagctgc cctaagggt
86041  ggagcagtca gattccggtt ttattttatt ttcccctgca aggagcaatc aattattaac
86101  cgaagtcacg atactttggt tgctgttatc agcacatgaa aatatcagtc aaggctgggt
86161  ttcagacccg cctggcacta ttcaaaggaa attttttagt aattcttatt ttattaagag
```

-continued

```
86221  cactagtata ttcagatcaa gtaaaacttc acatataaca ggttcactct tctatatgaa
86281  atgtttgtgg gaaatctatc atgcatcagg tgctctcaaa aggtggtgag gtgtaaatgt
86341  cagcctcaaa ggctgcagtg tccaacatgg cacacagctt gtgtggctct tagcacctga
86401  agcatgcctc gtccacagtg agatgtgccg aaaatgtaat atacatccag attttgaaga
86461  cttggtaaaa tatctcacca gcaattttt atattgatta catgaggaag tgataatgtt
86521  ttgggttggt taagttaaac gtattattaa aattcatctc acctgtttct tttaaaagt
86581  ggcttctaga gaattttaaa taacatgtag ttcacattat attctatga gacagtgctg
86641  ctctaaggcg attatgcttt gtttgttttg agacactcac aggtgtatgt gagcatttca
86701  accgggttta taacagctta ggaaactggg aactttgact tggaactttc ccgccaagtg
86761  acaaaacatc cgtccagtga tagaagtttt aattctactt cctccagcta gatcttgcct
86821  ggaggaccca cgttgactta ctctctccag aaacggcccc actggctctc tgggggaact
86881  cctgggttct gcagggactt gctaggtagt aattacaggt gtgtagagac cctcctgctt
86941  catacgctca gtcatcatta tttacttta ccaggcacca ggggcgtgat gagagcttag
87001  ctgaaaggag agaagactca gcaagcacat caccttgaag ctgacctgtc agccagattt
87061  cgcagcacct gcctgttcca gcctgagggg ctgcgattca ttccttggga aagagagctg
87121  caaattccct ctctaggcca cagtccaaat ccttgctctt ctctctcagg ttctggaaga
87181  cagaatggag gcatctacag agcaaggaca tgttttctac ctgaattagc ttttctgaca
87241  ccttgaaacc atctctaaga aattgatttt ttaacataca catatacagg taaacattta
87301  aatctgtgcc ataatgtatt tgcacttcga gtccccctga agtcctaagt cacatgcttc
87361  tcttcctagg ggttctgtct gaagcagaga ccctgatt ggagcagtgg gaagaatcct -
87421  gatgaatcag gtgttcctgc ctgtttacat taactgggca ccctgcctgc ccacccaca
87481  tgctgaatac tgctggggag aagagaagaa acatttatta aaggcaagga aaaattagag
87541  ccttttcatt gaggtcagaa gattttttgag gttggatcgg ctggccaggt gcatgaccaa
87601  ttttcttggc tccttagaag cagcaaagta tttgaaaaat aatggagccc ttcgtcctac
87661  aagtaaaagc ccatttatat tgggaatttt ttaaaaagtg ctggcgatgg aaaatttccg
87721  atgagatgca tttcttcctg cctgaatgtc ttgaatgcct gctcgatttg tctccctgct
87781  aagacactca cacttgcaaa tctgtgcttt tcaaggtggg gagatgaaaa taaaaagtct
87841  gtgacatgta tttctgggag gcctgaaaac aggaagcaaa ttggaaccac agcatgtggg
87901  gcacggatgc tggattctgg gggatatttg cttatttgga aaggctgcaa acattccatc
87961  ctacccactg ctaggagctc tgcactttgc taacgtccca tggaaaccaa ggttctctt
88021  aggactcgac aggactgggt tattttctc agcttaaatt gtttttatat ggttatcctc
88081  agtactcttt tctgttttgg gatattttca tacttttat ttttaaaaa ccccagaata
88141  tcttgattt gaaaaggtac attcacccaa ataaagtgcc cagcgcatag acaaggctgc
88201  ctcaatattt cacgtgtcaa cagccaatgc ccccggtacg tgcagaaaag cctgagaaca
88261  aggaaggaag aaaagggtct ggtccttgct gtgcgggtat ttaagcattt ctcagccccc
88321  tcctctgact tctcaactat gttcacctat atggcctcaa atggagagaa ctggggttat
88381  aaaagaggat attagctatg cctgctatag aatgaggaag gcatttcagg atgtgcttgg
88441  ggaggagatg gaatgaatgg caaaggggat gtttgtccgt gagggtggtc tgtgatctgt
88501  gggtggggga tgtctgtgca gctcccttca tggcctctca tggcccacac agtaggcagt -
88561  gtttgccaca cacagaccct ggacaaagtc acagagtggt gttggtacca tttcatagga
88621  ggggtcctag gggacattct aggaagttct tcatcagctt aggaaggtgc agcctctgca
88681  gtcattaaac acagtctacc agccagagaa gcccaaaagc tgctgctcct gctgttctgc
88741  gtggtgtggg aaactacggc attggcacaa ctttgggagc tctctttgat ctcttgtttg
88801  tctgcatttc ccatactctt ccagtcacca agtgtcatca ttcttcccca ggttgtctct
88861  gtctcccttc cttttctgtc cccatgactc ttacctgtat ccaaaactat ggcgtttaag
88921  gtgaaagagc cagtctgtag gagctgcttc gaggaaagtc ttgcaagact gccttcttga
88981  acttggtgct caaactcccc tctggcttca caacctgcat agttgcctgg gtcagaaaca
89041  ggttcctcag gcaacttggt gttgcattaa ccaagtgaca ctgattgtca cttggaagac
89101  actcagtgac tgactattag agatcatctg cctctcattt tggggatgtg aaggttgaga
89161  ctcagagagg tcaggcaaca tgtctgaggt cattgagcca actagcagca gccccagagt
89221  tgtcacccag atttccgac tccccattca ttccagaaaa cctaccccatg gggaatgttc
89281  tgccaggctg ttcacatca ccagtagaga gaagttgcct tgagtattcg gtttggtttt
89341  gaagttaacc tattcagaca cacttgagca tgcagtgagt cactgactgg attcattccc
89401  agacctatgg actcagcaca tcagctcacc aagcctcctg catactctgc ttctacgctg
89461  gacaactgtg cattttgaga agctggagga aattgtttgg catactgttc taggccagca
89521  gtcatgcgat actgagctag gcctggctcc tataggctgg tgaaagccaa gtgttaactg
89581  ttcaggattt ttttgagttg gttaactatt gatagcttca aagtcgccat ggcaggggta
89641  ttttataccat agaaattggt acatgttaca aattagggtt tcattttca ccatccagag
89701  atctgattta ctaactcact actgattctg aggtaggacc ccagcttagg aaggcactttt
89761  caggcaagac tgttctgcgg taattagaaa atggagagtg gccctgtcag atgcaaagga
89821  gaatatcaaa tttggaaaaa agtactgcct attgcacaag aggtaagagt cactgagaca
89881  tcttgcacca gacccaagtg agggatggaa ggggccctga tggtcatctt gggacagctt
89941  cttagggtca cccaggagcc caggagccag gtatgccact ccgtggtggg acagaaaccc
90001  ctgtaaagag caagcagaca ctcagtcacc caggaccctc cccaacactc ccattccctg
90061  caatctatca gcgcatccta tcaatcccgt ctggagtaga tatctgatca tgcctctct
90121  cccttgtgac tgccatcacc caagtccagg ttcctgctac atccttccta aaaggccttc
90181  ccctgcaagc ttgcctacct cacatcgact ttccccacat agctgcaaaa gtggacgtct
90241  gagaagaagg gggaggaaga ggagaagaag gaagaagatga agaaggcgaa gatgaagaaa
90301  aagaagaaga ggaggaagaa gaagaaggag gaagaggggg aaaagaggag gagatgatgt
90361  tatgtcatcc cttcacccctt cccctgcaca cacacacaca cacacacaca cacacacaca
90421  cacacagaca cacacacaca cacacacaca ccacgaaaac ccttcaagag cttcccattg
90481  tacttagaat aaaatccacg cttgagtaaa gctctgcatg atttggcccc tgcaaacctc
90541  tccagcctcc tcttgcttgg gagcctctgt gctcacaact ctcctgtcac cctggtcttc
90601  ttcaggtcc ttgaatgccg gctaagctct ttgctgcccc aggaccttcg cacctggtct
90661  tctactggca ggaatactgt ttcctgagtc ttccctgac tggctccttc atttccttta
90721  ggtctcagct tgagtgtaac ctcacagggc catttcctgc tcacctggtg aaaagtcagg
90781  cctcgtctgt tctctgtttt agctcctaag tttcttatg acaattattt cagcccacag
90841  ttcttttatt tactgtctg cttacatttt gttttaatct tttcttact tccccccact
90901  tcaacagatg ctccatggag aaatgggtta accactgcat tgccagagcc tggcatatag
```

-continued

```
90961  gggtgctcaa ataaagactt gatgagtggg ctgggtgtgg tggctcacac ctgtaatctc
91021  agcactttgg gaggcaaagg cgggcagatc acctgaggtc aggagttcga gaccagcctg
91081  gacaacatgg tgaaaccctg tctctactaa aaatacaaaa gttagctggg tgtggtggtg
91141  agtgcctgta atcccagcta ctctgggagg ctgaggcagg agaatcgctt gaacctggga
91201  gacagggatt gcagtgagct gagaccgcac cactgcactc cagcctggga gacagagcga
91261  gactccatct caaaaaaaaa aaagttgat gagtggttca ttctactgcc accacctatg
91321  ggaagacagg tcaggaatgt tgaaatgaaa gaagtgcttg gcttcctctg agccccagct
91381  ggacacaggc atctgtgatg catccagatt caggctgctc atggactctg aggactcaac
91441  gctcccggag ggctagcagg gagctttgca cacatacaac cagttctcac caagcaactg
91501  gggattaata gtgcaagggg ttaaatgggt tcaaactgtt cctcttaagc tccccaagat
91561  ggtgaaccgc acttcaaagc tgcttgaaaa ttcttacttg gtgagcatgc tgttctgtgt
91621  ccctttgggg cagaggattg ggaaggcagc caccaaggcc gcctgccgag tgaacagggg
91681  gagggggcac tccaggtgac gtgtgtgcag agacccgctc atgcctgacc cacagttagt
91741  gcacgctcac agtggttcca gtcttgtccc agcgacccga ctggcctgct ttgttattgg
91801  aactagagct gatgattcac tttaaataga tccttaacct cacaatttgt ttttcttgaa
91861  acggtcctga gaggtgcttt ccaagaaaca aggaaaaaac tgactgcaca gtggtgactt
91921  tgagtctgtc tgcagaaagc agtgtgagtg gatggttcat tcccatggca aagccttcc
91981  ctgtcacccg gtgtcaggga cagtgaaaaa aacgggccgt agcttgggaa acagggggtgc
92041  tctgcagttg ccgtagcagg tcttcaggga gagcttacgg gaacccacgg tgtaggggcg
92101  gggggagggg actgggtgtg ttcatttccc gggatgctg taacaaatta ccacaaactg
92161  ggggccttaa aacaacagaa atgtattgtc tcacatttct ggaggctgga agtctgaaat
92221  caatgtgtcg caggaccaca cttcttcctt gccgctttct ggcttctggc gcttgccagc
92281  agtccttggc agttctcggc cggcggttgc atctctccag tctctgcctt tgctgtcgtg
92341  tggccatctt ccctctgtct ctgtctctgt ctccgtattc aaatcttttt ctctttgtga
92401  gaacaccagt cattggattt agggctgcc ctaatccagt aggatcttat tttaacttga
92461  ttacatctgc aattatatcc tattttctaa taggtcata ttcacaggca tcagagttag
92521  gacatcagca tatcttttgg ggctggggac tcaattcaac ccaccacagg agaggtcccc
92581  ttgctactag gcgggtagtc atatcacacg cacatgtcgt aaacatgctg agcagacgag
92641  aacccaaaat ctctgatttg ggtaagatgt gattccaaaa tgtagagtgc agaatttact
92701  aaaacgtttt gaggcttaga gtaagagact gctgcagttt aggaagactt cctcattaaa
92761  agattccaaa agacatattc catgagtcac cagggtagac tgaataatga gcgctcaaag
92821  atgtccgtgc tgtaatcccg ggagcctgtc actatgttac cttgcatgac aaaagggact
92881  ttacagatgt gtttaaattc aggattttgag atgagatgat cctggattct ctgaatggat
92941  cttctaagaa tcacaagggt cttcacagga gggaggcagg aaggtcagag ttagagaagg
93001  agacgtgatg gctgaagcag agatcagagc gcgaggggtt ggaggatgga gggaggatct
93061  agaagaggaa agcaggcagc ttctagaaac tggaacaggc aaggaaatag attttcctt
93121  cagagcctct ggaaggagct gaccctgctg gacgcttcaa tcctagcccg gtgagactga
93181  tttttttctt catgacaagt cagttgatgt tgttttaagc tccctaaattt gataattggt
93241  tacagcagca ataggaagca ttgcagtcac atagcccagt ttggcatctt gtattatttt
93301  aacaaactct ccatcaatcc acctgtgtat catttagtc tgctaacacc aagaacaata
93361  tgttgcatgt ggaagacctt aataactact tgttggatgc ataactctgag agcttattat
93421  acactcggta gtatgctaaa ccctttggat acatccctgt cctcctatct atcagtgtgg
93481  aggagaattg gacattgaac aaataatttt acaaataaaa cagacattga tttatgtgac
93541  aagtgctgtc acagaaaaac cacagggaga catgacaggg tagagtcggg gaaacctaac
93601  ttcaacgtgg ggtcaggcag agccttccag gacactccca gctgaagcca ggactggtca
93661  taccctcgct tggttccagt tttaaagaca agacactttg cccaaggagg tgacccgagt
93721  tgagcactcg gagcgtccac catctttct gaatggtgcg aggttgtctg ttgttcatgg
93781  agctcgtgtg gggtaggcca atccctggtc tgaacttgag gcggtgacac attttcatct
93841  tggttctgcc gtaggtttag cgggtgacct ttgcatatc gtctgccctt cctgcatgtc
93901  gtttgtgctc tggctgacaa acaacgatct caccagccat cagcgctcca caggaatgaa
93961  aagagtgagt gacaggaca gggagggagg aaagaagaag ttgccttgtt gccacggcct
94021  tcctcagatg tgcctccgtg ccttgggtca ccctggggc tactggcacc ttctgagaca
94081  gagccgggc tgagggctag attgtcgttc actgggcacc tctgcaccgg ggaagggggac
94141  gggagctgag gaggggggcac tgagcaaggc agaatcctta tccccaagca gttgctgaca
94201  ggtggagaga caaatgcaaa cactcagaat gcaaacacac agtgtccaaa gcagaagcag
94261  caggagggggc gtgggctctg ccccaggaat tcaggtcac agaaggagct gggcctgcag
94321  ggatactttg gggtttggta aatgaaggcg gggtcgtgca ctctgcggtg gacaacaaga
94381  gagaagcctc cccacacatc aggttacac gtggcttggg gtatggcttg ccaccttctc
94441  ccgtttctcc ccacatgagc aaggcggtg tcattatct ctcaagcaat tcctacctcc
94501  ctggcactgg tagatgctgc acacatggta cctcctccag cctcacaaca acactgtcac
94561  atcgtcacct ccatttctca gatgaaactc aaagaggtga cacttgtcca gtgtcaggtg
94621  gctgtgaaga tcccagcaca gtctccttgc atccagaagcc ctagcctcta ccacattgtt
94681  gatcctgggt tgatggtgaa ggttaagct gggggttcctc cccagcccct acctgtcgtg
94741  tgcacacctg gccttctctg ggggtgcatt tcccagctga ggagactgtc tgcgtgtgtg
94801  gctccgaagg aagcctagct ggtgagttca gaacaggccc tgtgtgtgat gtggtgacct
94861  gaggtcatag gatacagact gcgtcccagg agcacctgcc attttaggg tggctcagga
94921  aagcctctga gctccctgga ggaagttgcc ccctctccac tgctgcaaag gagagttggt
94981  catgggggcca ggccagacact ctctggacat gctcgtggaa gagctctttg ggagaaaaga
95041  cactcgagca tgccaacaag gggacttagg ggccagaatg ttctgccact tgccactcgc
95101  caacctgaaa tctgcaccctc ctaatcacct cctctcagcc ctgcctcatc aagtggggtc
95161  ttgcaggaac tgctggcagc tcggccacca tcggggaaaa caccccagtc aaacacaggc
95221  tctcctgtgc cttggcatag agggaagagc cagcctgcc ccgcccctg cccactatgg
95281  tctcaggatt cactccttgc tgaagccttt acagggggagc caaatgccct ctcacccaag
95341  gccttccaa ggccctccca catcctttgg gtgaatctgt ttcaggagca cccattttgag
95401  ggaaaacttc gtccccagga gaaatggcaa cggagagggtg aaggggtgga ggtacgcttt
95461  ggagcagggc caaggcacat gggggtgggc tccagcctcg agcctgtcct tctccatgat
95521  cctgaacatg actcttctgg aacctggccg gaagttgccc ctcaggagac agcgggggaa
95581  ggaagttgtg gtccagaaac tccagaatgc aggggtgccct tcccattcaa tcacggaggc
95641  tggtccaggc caagagcatc ctcggccttt gtttaagctc ccgtgagttc ttggttgacc
```

-continued

```
95701   tggagaggct gagagaggcc cacaggacct ctttccttct gacccttcat tgcctttgga
95761   tccagctcac ctcagtgcaa gcctgtggcc tgcaggggag gccctgaggt agaggcactc
95821   agccctgata ccgtgaggga cccttgaaag tttgtgctct tgtttatggt ctcaaagaca
95881   agaggccaaa ttcctcagct gacatttttta ctgtcaggac gtgccaatgt tgttcacttt
95941   ttgttttgct ttgcttatga ttgtctggca ccttgagatg atgctgagta tgccaggcta
96001   taggatggag atgtgggtgg gagcaggcaa cagactggcc ctgatcttcc agagctgatc
96061   acattctctg acgtcagctc tctctgttca tgtccttga agggcaatgg actccgtgag
96121   gggagacccg aagtctgtga atgcccagct tctgagatac cgtcaatact gttgactgca
96181   tgaatggatg aattgcaagt gagttgttga acacagtggc aaggaggctc cttactagct
96241   tggaaccccc tcctccggca gggaaagtga ttaccaacct ggaggtcagc caggccaaga
96301   gggctttgag atctacaaca ccatctccat ctactgggtt tgggttacgt gttttaagtg
96361   gctcaacctt cctctgaaat catgcaata gcaatgaatg atgtcccatc aggcactgcc
96421   ctggtttttt tgcacacact atctttcatc cctataagga cgatgtggga tggccattgt
96481   catgttcctt tcacagaggt gaaaattaac actcagagag agtaggcatc ttgctcaagg
96541   ctagaatggg gtaaagccat tcatttaatt tatttattca acaaatattc attgccaacc
96601   tgctataggc caagcccctg gcactattcc aggtatcgga aaaatagcag tgagcaaaat
96661   ggacgagaat tcctgctctc cgggagcttc acttctaatg gggggaagcag agcaacacac
96721   aagataaaat acacacgcatg ccagaggttg ttaagtgcca aggaggaaaa gtggagaagg
96781   tggagggggaa gggaagggct ggtgggcaga gggatatgcc tactgctgag gaagctccca
96841   ccatgaaggt gacatttgca aacaaacctg aaggaggtgg aagactggcc aagcagagac
96901   ctccggaag aggggctagg cccagaccca agcatgaggg tggccagagt gttctgggaa
96961   cacgaagacc agcgctgctg caggtgggag gggatgtggg gaagataaga tgagacagag
97021   taagggtgtg ttgggggtg acagattatg gaggggccca gaggccatcc tgaggatacg
97081   ggagccattc tctgagcaga gaagtgacat aatccaattt cagtttctgc agggtccttc
97141   tgggctctag gctgagagtg gactgaggga tgaggggtgga gtcaggggca tggattagga
97201   ggctatggct agtccaggca aggggatgg cagtctaaat cagggcagca gcagagtcag
97261   gttttggaaa tgttttgaaa atagagccag taggatttgc caacattggc aaagattgga
97321   tgtgaggtgc cagaccaagt gttgtcctca gcaactggga aaaaagagtt aacgttctgc
97381   attaggctgt tccagcattg ccataagaa ataccagaga ctgggaagtc tataaagaac
97441   agaggttttaa ttggctcacg gttctgcagg ctgtacagga agcatggtgc tggcatctgc
97501   ttttccttctg gggaggcctc aggaagcttc caatcatggt ggaaggcaga gggagagtgg
97561   gcatgtcaca tggccagagc aggagcaaga cagcaagggg ggaggtgcca cacacttttta
97621   aacaaccaga tctcatgaga actctctctc tatctgcagg atggccaccaa gagagatggt
97681   gctaaaccat tcatgagaaa tctgcccccca tgatacaatc gcctcccacc aggccccacc
97741   tccaacattg gggattacag tgaacatgag gtctgagtgg ggacacagat acaaaccata
97801   tcatgttccc tgagatagga tggctggggg ttgggggtga acagtatttg ggagggaaaa
97861   tcagggactc tgttttggac acaatccatt ggagttgcag gtaacgttc cagtggagaa
97921   gacaagtggc tggctggctc tctgagcctg gagttgaggg ggtgatgtgg gctggagatt
97981   ggactttggc atcatcagtg ttggtgaggc agctacaatc atgactctgg atgagctcat
98041   tgatgggggc agcaagtgtg gacagagaag caggaggtct gaagactgag gtctgaggtg
98101   tttggggaga agaggaggaa cctgcaaagg agatagggag caagcaagga ggcaggagga
98161   gagccgggca ggtgggctgc agccaagcaa ggagaggggg aggaggaagg ggggaaggg
98221   aaaggcgggg agtgggaaga gggtaggagg gggaggagga gaggggggaag aggagagcag
98281   ggggagtagg ggtaggagga gaaggggagg aaggggagga ggaggggggg aaggggggtga
98341   gggagaggaa ggggaggaaa ggagggggtaa gggggggagga ggagagggga agaggggaga
98401   aggagtgaaa tatacctgtc gtgggatttg acctatatta gagaatcact gtgcagtgca
98461   ccaagtggca ctggagaagt catccccgaa ataattgga ttgtgtgaca agatgtgggt
98521   tcagcagatg caacacacag ggaggaggga aactggacca gccttggctg tggattggct
98581   gcgcgatctt ggacaaatca cccatcatgt tttccttccg tgttacgtgg aaatgtctct
98641   gatatctact gcccttacct cacagagtaa agacccaaag gagatgtcat gaaagcatttt
98701   tgaaatgctg ctgaacactc agcacagtgg ctgcacacga gtgggtagaa ctcaatggtt
98761   ggaaaatgta cttggctgtt attgtgcctt tttcatgaaa atatgaaaag ctaaataaac
98821   ctgaaacatg ttggggactg agtgaggga gatgagcacg ttctgagagt cctaggacca
98881   tgcactctca gagtgccttt gctattgttt cgcctcccgt cctacagagg aagggcttag
98941   gtttgctgtg aatttccccc ttgcctacca gcattgcgcc aattaaggtt tctacttcac
99001   cgcacgtttc agccaaggat gtcaagggaa tccactgctg ctccagtgag acaaataaca
99061   tatccagcat caacactgcc atcatcatta gcatcattgt ggccattagg atggttggca
99121   aggcaatagg ttggcactac tgatgggcag caccattagt cttcttagtg attttttcaaa
99181   atggacagtc tggagctaaa agcgtgagcc ctggaggagc tcatttcatc agacctgctg
99241   caggcaaaca ctcttctctt catacctttc ccgcctgtac gtgtgggggtg atgcctgtct
99301   tgggaggaaa tatagatgca gtgcctagat attccaaagc ccaggttcgg aatctgtgtt
99361   ccctttgttt tttgatattt ccctcctttt cctcctgccc tttagatctt gtgcatttgt
99421   gggttttttcc ctttctgctc agctctgatc acttatttgc tttttgttttt ggagagctgc
99481   gtcctctctt tactcaccca cctgcttcat tagagattgc tactcacctg cagtatccat
99541   gctcacccttc ttccacgata attgaaaagg tgtccggcac acggctgtct acttaaaaac
99601   tgctttctct agtatccctt gcagcctggt gtggtcatgg gactgatttc tgcaagaaga
99661   gtttgagctt cagtgtggtg tgacctctgg acctttgaaa agagggtttt attccttcca
99721   ttctcccacc tttctcttcc ttcctccttg ttggagtgtg gctatcatgg tgatggtgaa
99781   ccatccttgga ccacatggat gagggccaca cactccaggat gctggagcaa caaggtggaa
99841   ggtacctggg tctcgactgc ccacccttgt gaaaggtaaa tgcagttcca tcttatctga
99901   accctagtat tttgaggttc tgttagaatt gctgcacctg tattctaact aataccttct
99961   ttaggctctt tgacccactt gccagattgc aggtgcagg aagacagaac atggttttgc
100021  tcaccattag gtcatcaggg ctggcacaga ttgctcaaca cataataaat acttgttgga
100081  agtgttaatg agttatggtt ttactctggt atctggactt ctgctttcca aaggatgagt
100141  ggcccttgac gcattgttcc cttgggcaac tgcagcctct gtcatgggcc aagtatggaa
100201  tgtccctggg aaataaaatc tcagaggaag agactcctcg cccagccgaa attctccctg
100261  gaattgtgag cctccaatta ggctagaaga tacagtcttc ccatctgttg tagaaacaga
100321  aagttatttta gagtataaaa caatctcccg gcttcatgtg tgaagcctat ttgagagtca
100381  gaggggttcca gcagagggag gaggaacatc agctacacct ggagctctgg ggatgaaaga
```

-continued

```
100441  acccatgagg gcctcataga ttatagggct ctgactcctc cagggaaaga tgatccagtg
100501  ttctggccta tcttggcctg tggttctttg tgatccatgg agtgagagtg tccacaatcg
100561  cctgctgtgt ggtatttccc tgacttgagc ctttgctcat aaccagcata gcccacaaac
100621  accagccgta tccctcaatt cctgacttct gcttcctgt ctttacagaa gaaccccagc
100681  tgtgctaatg gtcctgtaac ctctcagctc agggccatga gaccttctct ctgcatgaat
100741  ctcgcctcct ctgcacccca cacttccaca ccacttcctc atataacgtg ttatctgact
100801  acacaaccct ggaaatgatg ttcctcctga tgtgttccca agcattcttg ctattctgct
100861  tcctctagaa gccagggaac tttagctgac caggtctgtg tcttgggcac ctgccttggt
100921  gagcgacctc tgagaatttc tcactaaaca tttgttgaat gaactaggag atatataagg
100981  gaatgcctct tctgcctacc atgagcatgg ccttaagtgt tatctttgtt gcttggccaa
101041  gtcatggcct tgagtcccaa gtgaggtgcc cagcccttat tcctgatcaa taaatacttt
101101  tagactcctg attattctct tgcttgcttg cttgcttgct aatctctaat agattagatc
101161  tattccctaa tctaattctc tgatcttcct cctgaaactt ggctccatat tgagttcctt
101221  gccctatatc cgtacttgca cggccgctat ttgccaccca gagtccctgt gctggcaaat
101281  tcaacacccg gagcattatc attttggtgc aattcctgag cacagcttgc tgactcttca
101341  gtacttattg tttctatctg gaatacaaga gggagtatat tatggaggatg atggtaaacc
101401  cagatcatgg tgctcagagc agatctgaaa ctctggcagc gtaacacctc tctccagcat
101461  ggacagataa gggtgattat tatttaattg gacttttcat tttgagagaa attgtaggtt
101521  cacatgcaaa tgtaagaaat gatgtggaga cctatgtacc ttttatacag tttctcccaa
101581  aggtaatacc ttcaaaacta ttgtatgatt tcacaaacag gacactgaca ttgatagagt
101641  ccagattcag aacatgtccg tcatccaccaa ggtccctcat gttgcccttt tgtggccgca
101701  cctgcgtcct cttactctcc ccatctctgc cccatcttta actcctgaca actactaaac
101761  tgttctttgt ataactacta aactgttctt tgtataacta ctaaactgtt ctttgtataa
101821  ctaaagtttat aattttgtca tgtcaagaat ttcatatgaa tggaattaca cagcatgcaa
101881  ccttgactttt tcttactcag cacaaccgtc tggaggttca cccaggttgt ggcatgtgtc
101941  aatagtttc tcttttgttg ctgagtagta ttccataata gagatgtact gcagtttgtt
102001  taaccactca ccttccacct gaagggcagc tggttttttc cactttgggg ggattacaaa
102061  caaagctgct gcagacattc acatgtgggt ttttgtggga acctaagttt tttgtgtttt
102121  tttttttttt tttcctggga tgaatgctca ggagtgcatg ccaggttgca cagaccttgc
102181  atgtttagtt ttataagaaa ctgtcagact gttttctaga gtgattgcac cattttacat
102241  tctcaccaac aatgtatgag ggatccagtt tctccacatc cttgccagca tttgtggttg
102301  tcactcttt agccattcaa tagtcatgta atgatatctc attgtggttg taatttgtat
102361  ttcctaatg gctaatgatt ttaaattacc tcttcatatg cttatttgcc acctgtatat
102421  tttcctcttc agttaaaatat ctcttcatgt cttttctcat ttcttcaaat ttaaaaattc
102481  ttatttattt atttttatt tttttactg tggagttttg agagttcttt ctatattcta
102541  catactagtc ctttgtcaga taggcagttt gcaagtattt tctcccagtc tgtagcttga
102601  cttttcatcc tcttaacagg gtcttcata gagcaaatgt ttaacttga tgaagtctaa
102661  tttaaccatt tttcctctta tggctcatgc ttttggcatc aagtctaaga attccttgcc
102721  tggccctagc tttcaaatat tttctctttt ttctctata agttttatcg ttttatgttt
102781  tacatgtaaa tccatgatca atttggagtt aatttctgca tgaagcgtga gactagattg
102841  aggttatttt atttatttttt tgcttatgaa tatcgattgc ttccatacca tttgttgaaa
102901  agggtatctt tcctccattg aattgcctt gtaccccttat ctaaagtcag ttggaaattt
102961  tgcgtgggcc tatttctatt aacttccact ggtctgtgta tctatcccctt cactaatagc
103021  atgtagcctt gatcactgta gctatacagt aaatcttgac attaggtaga ctaatctatc
103081  ccatttcatt tttcttttc aaaattgttt tagctattct agtttctctg ccattttata
103141  tacatttagg ataatcttgt ctagatctat gcaataatat tgctgggatt ttgtttgcag
103201  ttatattgac ccatatatca agatgggag aattgacatc tttactgttg agtcttctga
103261  ttcatgaatt tgtaatgctt cttccatgtat tttagctctt attttggttct tttttgtagga
103321  attttaagca cacaagtact gcacatattt tgttagattt acacctacgt attttcattc
103381  tcttgagtga ctgcaaatgg cattgcattt gtaattttgg tgtccacttg ttcattgcag
103441  tatacagaaa tagaattgag ttcatgtgtt tatctcttat tctgtaacat tgctgaactc
103501  attagttcta gggtttttt tttggtttgt tttatagatt ctttgggatt gtctatgttc
103561  acaatcatag ggatggtttt atttcttcct ttccaaacta tctgctttta ttttatttttc
103621  ttattttatt gcactggcag aacttccagt aggaagttga ataggagtgg tagagtggtc
103681  attcttgcct ctccttgatc ttatgtggaa agcattcagc ctttcatcat caagtatatt
103741  gttagctata gggttttata gatgctttt agtaagttga ggaagtcccc ctctattcct
103801  atttttctga gaggttttct aatgaatggg tgttgaattt tgtcaaatgg ggcaagaggg
103861  tggtaattct tcattattcc ttactgtaat tagtctgtca atgttaatga gcatgctatt
103921  attaagcacc tattggatgt tcagtgttgt gctaggccct gtgagacata taggaaccta
103981  aaaatttgag ccttgccctc aagcactaag gaaacacact ttctaaacca caatttagca
104041  tataccataa gtgctgcaga aggccccagg cagcggaggc cagtgttgcc ctggcctagaa
104101  ggtgtcactt aggttggcct ttgggctgga gtagaaccta gatacacaag agaggggagt
104161  gaattagaga aaattcaacg gcctaaaatt ctattttcta acaaggacaa tggtaagttg
104221  ataattagta ggatagagat agcttttgat taatgaagtt ggattatctc tattctgtgg
104281  attatccctg acaaatgctt aatcctgaac ttcctcccctt tttgagcatt tgggctctct
104341  tttctgccat ccgtcaacat gttcagggga atgcaaaacta atattactat tagctaaaga
104401  aaaacataat taaggaggc aatctgctgt ccctaaattg tatcatcttt tccaaactaa
104461  atatgagtga tattggtact atcttttgtt tggagagatc cacaccactt ctctccctct
104521  taaggctcaa gaagaattga ctgtgaccat gatatacaca atacattttat taagctgtct
104581  ctctaacaag gtagctaaac acttgggaag taagagtaat gccttagaga atttggaacc
104641  catgacatct gattcattgg tattgtccat atttgtacat gtttactcta atataaagta
104701  ataatataat agtgctgtca tttgcaaaat taaaaatcct ggcacattac tcatgggtca
104761  tgctttgggt tgtcattcta acggggtttgg tggatttgta tagatctggt cctctatctc
104821  actttgtcct gctggtgacc agtggctcct cttggaggca gacggccagg gttaagggtg
104881  gaatctgagg ccgtgaggga gagtgaaatt aactgctccc ttcacaaggg aattgaaccc
104941  ctgaccttca cctcattagc acagcactcc aatgcagcaa ttcctaacct caatttttata
105001  tcaccccagg gtgtctccac ttatctcaag cgggagctgc agaattcctc caacaaaatt
105061  aatttttaatt caccttaatt taaacattaa atacgggacta tgaggcagca acttgcagga
105121  gtggggaaga atggctgttg ttaataaatc ccaccaccac aatgcactgt tatccaaaca
```

-continued

```
100581  ccccaaaaca ccctctcgaa cccactgagc caaacagtgt ggggaggaag aagtctataa
105241  gtaagcagca ggcatggaag gcttttaaat tgcggggaa gcaacaccca accctaccaa
105301  acatctgcat ttcatagaga ctgtttcatg tggtcagctg gggtgcactc tgacattcac
105361  tgggccagat ggacatattt cagctcccgt ccagccagcc catcccttt tcctcctagg
105421  gactgtgatg ctttgcatag tcccaggagt ttgctgcagg aacattttgt gatttactaa
105481  gaaaataaat tggtctttgt tgctgggggct ttctcctggg tcaatacaaa agatttatca
105541  cctccatgcc ggcccacgga gaggttggct caaaggattc tctggccact ggcttattct
105601  ggagacaagc agagtcccag cagaaccttt gcagggcagg ccagcagcct gagtgtaagg
105661  caggggaagt aaccgtagga atcagttatt gatgaacatc cttaaaactc tgtttgtttg
105721  tttgtttgtt tgttttgaga tggagtctca ctctgtcgcc caggctggag tgcagtgacg
105781  cgatctcggc tcactgcaag ctcctccttc caggttcaca ccattctgcc acctcagcct
105841  cccgagtagc tgggactaca ggcgcccgcc accatggcca gctaattctt ttttgtgttt
105901  ttagtagaga ctgggtttca ccgtgttagc caggatggtc ttgatctcct gacctcatga
105961  tccaccggcc ttggcctccc aaagtgctgg gattacaggc gtgggccacc gcgcccggcc
106021  gaacatcctt aaaactcttc atggtctttt actgataaca acatccacat gcattttta
106081  aaggagaata agcatagttc cttaccctga cagtgcactt tatataattt gtcaaagagt
106141  ttcacatgca ttgtatctca attgttttct acctacccag aattaccaac ttcattttat
106201  tgaagagcaa atagacttgg aaaagttaaa tgccttgccc aaggtcgcat agctagtaaa
106261  tcatggttgt agcaccagat cccatgtctt ctcatatact gcactctttt ctctatacta
106321  atcttatctt ggttttattat caacatccat ttgctttttgg caggggaaggg tccagaatct
106381  tcattttaca gaacaacgaa ttgaggtaag taagcgtttt gggtcctgcc tcttttctg
106441  ctggcaccat gtgccttct tgctgaaggg caaggagttc ttttgcaggc acactcattt
106501  ctgctctcag aggccaggct ctcaaccatc atcatcagtg ccatcctgct cattgggccc
106561  cacctgccc tctgtgtcca gtgggggct acatctgtga ttctgggca gtgagggggt
106621  catacgtgaa cagttccttc gcatcctctt aaaattgctc tttcagctcc ataagtttca
106681  actagtcaaa acactctcct tcacacttct tcaaagatga gcatttgttc tacatatttt
106741  tttgtagtca tattctgcga gtgcacactt tccctcttgg gtccttagac acaccctttt
106801  ccaggcatga ttcacttcct caagctccgt tctggacaca tacatctggt gccacctgga
106861  agagggctta tcaggtcctc ccacctggaa tacagcttaa ccagagttga tttctaaggc
106921  atgcaaccaa gaaaccagac tgatataaat gggatattat tgattttatc tgcctaaccg
106981  agtctataaa tttctgaaag ccatggaaggg aactctattt tgttgcattc ctcataacat
107041  ctagaacggt gcttgtgcata tactgagtgc tcaaggcata tttgcagatg gtgacgagga
107101  tgatttgatg tcgttttaaa ggccggacat ccaagaggag gtctgttctc tacatgtgca
107161  tgcacgtaca cttacacaca ctctctgact tgtaagatgc cctttgcaag agtccatttg
107221  ggaaatgcag tgggcccact ggaagaaatt caaggccatg ggccagctac accacgggaag
107281  ccctacaccc agccaaacgt gctcactggc aagtcaaacc caaaaactgt catcaaattc
107341  tgcttcctgg cagcccggat ccaacaatac tctgaaagac aaaagaagca gaaactcaag
107401  tgaagatcac caacgtgtct ttttgggcaa ctagcagatt gagcagaggg tcagcacaga
107461  caccagcaga gaagaacatt ctcctggcag gactctgcct ccaaattcgg caccacttca
107521  caggatctca gcctcacacc ttatgggatt tattttttta aaaaagatcc aacatttgtt
107581  cctaattatt cttagtaaaa ctgcctttct tgatgtggca cccattacct cattcattca
107641  gtcactcatt cattcattca atgaaacccc tgtcatccac gctctgggct cttctacag
107701  ccccacgaga tgatcaagaa ctctggaaaa caggtaagcc attatcatca gtgtatatga
107761  aattatcatc agtgtatacg aaatatgaag aaacccaatt agatggagat atctcctaca
107821  acacattgaa atcagaactc agacaagact cagatgttct aactccaaat tctgagcagt
107881  ggcccctgga taaaggatta tggagaaata ctgaccagaa aaaatactct taatggcat
107941  attgtggtgt tttaaggcaa ggttattggt agtgcttgta actctcaaaa tactgttttg
108001  gaagtttgta gtgattttgc agaacggctt tgagttacct ctgggtgtta tcaatcattg
108061  gatagttttc agaagaaatc caccttaatt tgagttaaat aatatgtcat ttagccagat
108121  ttcctcctgc ccccaatccc cataggagtg agaagccatg gcttggggca tatctcagc
108181  atcatgggaa ttgcagagag ggtaccacag ctttagagtt tgaggtgttg agcctgaaca
108241  aaaggaaagg gtaagaaact tggggtggat gaaacgtgga actactatga agagcttatt
108301  gcatagaaaa agagaaattt gagtttaaaa aaaaaatgga agaaagtaaa gggagcccaa
108361  atgggaacag ttaccagagg agattccctg gaatttgaag gaaccaggtt gaaggatggt
108421  ttcccaattt gaataattat aagaatcacc tggtactctt tttaaaacta taagttccta
108481  gagccccagt cttagacatt gcatttagtg tgtctgggtt gaggcccaga aatctgtatt
108541  tttaacagaa acccaggtga tttttataat caggaaaagat ttgggcaatg tctgcatttg
108601  aagatgctgt ctctcaaaat gaagaaatac ctggacaaag ccaagtccaa gacaggggct
108661  ctaagtcaaa aaggcaagag caaaacaac atgagccttt acaaaatgtg aattggcaaa
108721  aaagcagctg tagctcatat ttaataacct cccatggctt ccaaagaagc agctgggtct
108781  gcagagtcct gtttgtgcac aggatgaatg gagtctgtgt gccactcggg atgccccac
108841  aataccccaca ttatcactga ggtgctccag cgaggcattc attatgcact ccctgccac
108901  ccaaagcctc aggtcaggtt tgccttggac actctccctt tcccttctc tgaggctgag
108961  gggctgcagg ggcgggtgcc tgaactccct ccctctctca gggatgcctc agctctatgg
109021  gacttcctct ggttcacatg attgcatttt cctgccttgg ggcaccctaa aggcctgcct
109081  ctgggaagca gggtctagag gcatgagctt gtctggacaa cagaagctca atctcagcat
109141  cctaaaggcc tacctctggg aagggggggg tcacagaggc atgaactgt ctggacaaca
109201  gaagctcaat ctccatctcc aagcagttcg atcccccaac actcttggta ttaggagggg
109261  agcctctgca agtgtgagga ccggggggcct ctaaacaggg tttttttctt tttctttttt
109321  tcttgagatg gagtcttgct ctgttgtcca agctggagtg cagtggtacc atctccactc
109381  actgcaacct ctgcctcctg ggttcaagag atttctggct aattttttgta ttttagtag
109441  agacggggtt tcaccatgtt ggccaggctg gtctcaaact cctgacctca agtgatctgc
109501  ccacctcggt ctcccaaagt gctagtatta aaggcgtgag ccaccacacc aagccctaaa
109561  cacagcctga ggctggtatc ccaggaggcc ttgaaaaatc tcaggtttgc tgctgacagg
109621  tgtgccagga agagacctgg ctgctgtctg caagtgggcca aaccctgata atcccggaaa
109681  taaacaataa aataaactcc tcaatggtga ttataaagta ctattgttta tcagccagga
109741  cctgtgctaa gcttttcacc tacattattt catttatatt tcagagcagt cctttgaagc
109801  agtcatgttt atatcagttt tatggatgag gtcagagact tctgctggtt aagtaccttg
109861  ccactatcac acagctagct agtaaataaa cttttaaaaaa ttgaagtatt atgtacataa
```

```
109921  agacaggcat agtgtacaac taagtgggtt atcataaaag tgaacatacc tgtgtaacca
109981  tccacccaaa tcaagagcta gactattacc agcctcagaa aaatcccaga ccctctccaa
110041  taacctcctc ttccccaatg gtgaccattt ttgtcaccga gtattagatg gctagtttgt
110101  gaattttata aaaacagaat tctacattat atgttctttt tgtctgactt ttttctccac
110161  tcagtatgac atctgtaatg ctgatctaat gtcattcatg tacaagtagt ttggtcattt
110221  ttaatgctat aaagatgttc atagtatgaa tgtatcacaa tttatttata cattttcat
110281  tttgctggtt atttgagtag attttaattt tgccccatga caaataatgc tacttggaat
110341  gttcttggat agttgaccct tgaacaatga gggtcggagc agtaaaaaat tcatgtataa
110401  cttttggctc tcccaaactt aactagtaat agcttactat tgaccagaac ccttactgat
110461  gacataaata attgattaac acatattttg aatgtatata ctgtattctt acagtaaagt
110521  gagctagaaa atagaaaata cttttaagaa aattataaga atgagaaaat atatttacta
110581  ttcattaagt aaaagtgaat catcataaag gtcttcatcc tcaccgtctt cacattgagt
110641  aggctgacga ggaggaggaa gaggagggggt tggtcttgtc tcagggatgg cagaggtgga
110701  ggaaaatctg tgtataagtg gacccacgca gttcaaaccc atgttgctca agggtcacct
110761  gtacatgtgt cttggtgtac atatttcggc ataggatata ccaagaaatg taattgatgg
110821  gtcataaggt gtgtggattt tcagcttag tagatactgt ttacatagtt ttgcaaagtg
110881  gctgtaccag ttcactttca gctatgagag tcctggggga tccacatcct caccaacact
110941  tgatactgtt ggtctctttt tactttgcc atcctgatga atgtgtttca gtttgcattt
111001  ccctgatgac taatgaaatt gagcagcttt tcaaatgcta ttggccattt ggatatctac
111061  tggcttattc aggtctcttg cctgttttc tactgggttt tctgtctttc caggtgattt
111121  gtaggagttc tttatatttt ccggttatga atcattgtc atttatatgg attgtaaacg
111181  tcttctctat ggcttttctt ttcattctta atagtatctt ttggtgaaaa gaagactcaa
111241  attttaatgt agtccaattt ttcaatgttt tcttttttga ttctgttttt gtttctgtta
111301  tatataagta caactgactt tgtatattga tatttcaatc caagaaccttt gctgaattta
111361  cttattaatt ctgttagttt ttctataaat tatttttgtat tttctgcata tgcagtgata
111421  tagtctgtca ataatggcag tttttttct ttctatttct taaaattta tttgtttct
111481  tgctttactg caaaggctag gacctccaaa acaataatga ataagaagtgg tgatagatag
111541  gaagcatctt tcttttattc tcagtattag gggaaaagta tcaatatttg aacatttata
111601  tgatatttgc tggagggttt ttttgtagat actctatcat gttaaggcat ttcccttta
111661  gtcgtacttt cctaaatact tcttttttcc ttttactatc gccaggggtt gaattttatc
111721  aaatgccttt tctgaatcta ttgagctgat caacgatttt cttctttatt ctgtactgt
111781  ggtaaattac atagactgat ttccgaacac tgaaataatc ttgcatttct ggaaaaaaat
111841  atcatcttgt ttgtgatgta ttgtcctgt tatatattgc tgaattcagt ttgataacat
111901  tttgtttagg attagcatcc atgttcagga gaaagaaatc accattttct ttccttgtca
111961  ggtattaagg ttataaagct ctcaaaaatg agtcaagaag tcattttat tttctagaag
112021  agcttttgta aagactgatg ttatttcatc tttaaaggtt ttgaagaatt cactgatgaa
112081  gccatctggg cctggaggtt tgtttttgtt tttgttttgg tggaaaggtt tttcattatg
112141  gatttatttt ctttaatagg tacaaggcta ttatatcaga tattctttt ttatttgggt
112201  cagtttaat aagttgtgtt ttccaaagaa tttgtctatt tcacctagat ttaaacattt
112261  atcatcataa attggttctg aacagctttt tgtcttattt aggagccaca gattctattg
112321  ttagggcttc ctttccattc ctgataatat ttgggactct tctttaaaaa aattaatctt
112381  atgggcttat cggttgtatt aatctctttt gttgtttgtt tgtttgtttg agatggagtt
112441  tcgctcttgt tgcccaggct ggagtgcaat ggcgtgatct tggtcactg caacctcagc
112501  ctcccaggtt caagcgattc tcctgcctca gcctcccagg tagctgggat tacaggcgcc
112561  tgccaccatg cctggctact tttttgtttt tttagcagat ttctccatgt cggtcaggct
112621  ggtctcaaac tcctgacctc aggtgatccg ccccaccttg gcctcccaaa gtgctgggat
112681  tacaggcatg agccacagca cctgtccctg tatttgtctt ttttaaagac ttgtttttat
112741  tttatttt tcactttgtt ggttttcttt gttgtattat tgttttctac tttattaatt
112801  cctgctattt attatttcca ttcttatgct atcttaggat ttaatatgct gttttttat
112861  taaaatcttg agatggaaac ttagttcatt gtttcttcat cttttcttct tttcttgtaa
112921  agcattcaag gttttaaatt tctcttaagc attctttggc tgcatccctt acattttgat
112981  atgttttagt tttattacct ttttattgaa atatttccta atttccacgg taattcttat
113041  tttgactcat gggttgttta gatatgtatt agttcatttt acatcaccttt aatccgacca
113101  agaactgagc tctttaaaga tggttcaggc tttctgcagg ctgagttctt cctggatcac
113161  cccttgtgg ggagtctcaa cagaagacca gtggtatta acccagctct tcctccttgc
113221  tgggctctga attccttct gtgcctcagc cccatgagag tcctggcaac tctgctcaac
113281  ttctcagttt ccgagccact gctggggaat ccatgcacgc caaggagaaa agtggctggc
113341  acctctccgc tcacgccttg tttctgggat cttagtgcct tagttctctca ttgcgttagt
113401  agttttttt ttttaaatt cttattcatt tatttaggag acagaggtct tgcatgtgttg
113461  ctcaggctgg cctcaaactc ctgggctcaa gtgacccctcc cacctcagcc tcctgagtag
113521  cagggactac aggctactat tagctggtgg tttttgatgc cttcaaatag atttgaaaaa
113581  gatgttttgt ccacattatc cagtgttctt ggcacgaagg gcgtctgata agccaatcta
113641  tccttaccac caggggacat cccctggaac caggatttag gcacaggtct gtgcacaccc
113701  agactccaga gcccacaccg ctgcgtggca gggggagttg ccatgttgga gtacaggccg
113761  ccaaatgcgg agtagaaaag gaatgtgaag ccctcttgct ctccagctct cttcttcatc
113821  atcttcatta ttctggatct agtcaagcat tgccatttat ctaatctcag ttctaaaatg
113881  tgttgaacac aaattttcta gtttcttagt aaaattaatc ttttaaatca cttactttct
113941  aacggttgtt cacagggcat ctgggacctc ttttttcaagt tcaccttctc ctggtctgaa
114001  accaaaatga aaacaaatag aatccaagtg tgctgtagct cctgacatcc ctccgtgggc
114061  tccgccagcc cctgcatgga agcctccaca tgggttcacc aggctgttct tcgggctctc
114121  ccaaagtggc tgcttttccg tcaatatgaa tggcatgact ggccacatct ccctttttc
114181  ttcgggtgcc aggaagcctg tgctgttgag ctaactttac ggtccaacca tagcaactat
114241  gtcagtgtgc agataactga aggtgccttt ccctccctgg cttggcttct ccctcttact
114301  tctcttccca agctctcaat ttgctttatt ttgtatatt ttaccacgat attgtctctc
114361  tgtgtgtctt tatataaaac ttgagttatt ccagttctgc caatctgtgt aatcacttgg
114421  cattttatt tgtgttcata attttcagcc atggagacat ttgaaagaca acaaaatcga
114481  tcctggagaa acagagatgt gggcactatt gcaatttata gaattttattg taaaattgga
114541  ctttgatgaa tctttgccat acatattctg ttgcttaaga ttttttgtaa caatttatgt
114601  gtctattgct ttatgtgaaa gacgcttttc aaaattaaaa tcagtaaaca gtgttctgtg
```

-continued

```
114661  attaaccagg aacaaaagta gatggacaac tgctcaatga acatgaaacg atgaagatca
114721  attttcttc taggtcatgg acaaattaaa gtagttaagt gttaaaaaca gagaccatga
114781  tgtcattcct catgactaca atagaccaat atttaactct aagcgtattt ccttaaaaa
114841  aaaaaaagt taactacaaa aatgtagtta aaggtgctaa tctactactt ttttggtact
114901  gtaatattta ctgtattatt tattttcta ttttatgggc ataaccatcc acagaagggt
114961  cagtaagaga gaaatatcac tgctttcctc ttctatccat tattttgtt gtttcgtttc
115021  atggctacta ctaaaaataa tgttgtcaca gagaagcaag gtgataaaag gattctctct
115081  gggggtcaat ccatgaagaa agctggagaa atatctgctg aacagagttc atggcttcat
115141  gttctatctg agcaagtctc atcctgcagt cagctctctt gaggctgagc caggtctttg
115201  cacaccttc tctggctga tgctttaaa ttccctctgt cttcgtctct gctattgagt
115261  tcggtctcct ccgtgagtcc cccacggggc ctggtgagga caggctctgt gggagcagct
115321  ttctgttttg agcctgtgat gtctggccaa ggagcgcctg tcagctgctt gggctccatc
115381  tcagcccaga gacgtcgtgc tgtgtggtct taaagcaggt cacttcacct ctcggtatct
115441  ctctctgtaa aacccagata ataatacttc ccaaataaag aaagggtttt cttttaagccc
115501  tttgagctcc tcagatggag cgcaccacag aaatgccaaa tgcggcattg tgatccgcgc
115561  tgcctccatg tgattaggta atgtgagatt gtggttcatt atgctttgtc tggaatgaat
115621  gcgagcccgc ccacaaagca ctgggaactc tcagttacac agaaaccca tggtaagctt
115681  ggattggctt acacttaaat aaagcacacc agaaaagagc agtagttttg acgaacccag
115741  ctctgaatta acactcattt gatttcttct gctgagtgcg ggcgataagt aagagatgac
115801  ccagttacag gtgcggggg cacaaccaac actgaggtga ctgagtcggg ggaagggcag
115861  cccctctgca aaatgcttca ggctcccaag gaggcaggcc cagagtgggc aggtctggac
115921  ttactgctgt acagacaagg gggaaattca atagctacca tttattgagt ttctgctagg
115981  tgccaggaac tctgcaatgt atgccattct tctaaaccct ccagacaacg gtattaaacc
116041  atattaatat tctgaaaacc aaaacaaaca cccactacac ttgacacatt ttttttgta
116101  ccataatgaa agcctatgtg tttgggccca cagtttcagc caggattttg acctggggcc
116161  tcctcactga tcctgaggct ttaagaccac acagcatggg tctgcgaatt gcaaatggga
116221  ggcttacttt tcccattctt atccaagcct ccagaagtgg ctctggagct ggatccagcc
116281  tcctttctta cgaagccttg gatacatccc acttagcttg acaaactttt accggaattc
116341  tctgatccca tttcacagct gttgcaaagg taggggtcttg gttgtgtctt ccttcaagct
116401  gcttatgaac caggggtgga gactaggaag taaggaaccc tggaatcaga gaagtcagga
116461  gcaagcatct tgttggcttg aggttctcca ggcaccataa accaagtagt gcgcatacta
116521  agaaacaag ctggacaaca agaggagagc aggagggtcc ttaggattgg ctgcttgtac
116581  catggcccc agtggctcag tagagacaag gggaatccca ggtaagtaga ctccttcgct
116641  ccccagagag gaatctattg tgtcaattgc tgggaaacac gctcagttga actgaccctc
116701  tatagccgta tgtgcatgtg gaatccattg ttagggaaac catggtgaga agggaagtga
116761  gatgctctgg atgggtgctg agctgagtgc tgatggaaca gaccttccag aaaaggttgc
116821  atattatcca aggaaatatc attgcctgga gagtcctagg ctgacttgct ctcttgggag
116881  ctgatgttta gggaatggga gaagcagctg gtttaaagca tcaaacaatg aaatgaactt
116941  cagaatctgc caaatcctaa acatttcttg ctaagcacca ttttttctgt attgtgaacc
117001  catctgtgct tcaaaagcaa ttttgtttaa atggcttctt ccccttactc ctaatccttg
117061  ggaagctgta atacacaggt ggtaaagggg actccccaag agatgctcac taggactgct
117121  gtgagccaga tactgggcta acactgcata gcaccgaggg tgtgggagat cagaagtcag
117181  gagcctgcat tctcagggga gggactggat ccctgcaagg aaacaaagtg tggtgtgtgt
117241  ggcttcatga tccactggcc taggtctaat agcggatctt tttgcaaatt tatttatttt
117301  tcttttcttt tctttcttt tcttttct ttctttct ttctttct ttctttct
117361  tttctttct tttctttctt cctccttcc ttctttctt ccttcccttc tttttctt
117421  ctttctttcc ttgctttttt ttttttga tggagtttg gtcttgtcac ccaggctgga
117481  gtgcagtggt gtgatcttgg ctcactgcaa cctctgcctc ccaggttcaa gcgattctcc
117541  tgtctcagtc tcctgagtag tggggactaa aggcaggcaa caccaagcct ggctaatttt
117601  gtatatttgg tagagacagg gtttcaccat gttggccagg ctagtctcaa actcctgact
117661  tcaggtgatc ctgacctgg cttcccaaag tgctaggatt ccaggcgtga gccaccgcac
117721  ctggcttgca aatttctatt tctaattgag ccagtatttc ttcccaaagg ttcactggaa
117781  aatcactgac atgaagaaga ttgattaata ggaaaaaagg catacacatt tatttaacgt
117841  gtatacacag gagccttcag aatgaagacc caaagataga ggggaaattg tccacttta
117901  cacttaggtt caagacagta tggatagtca catagaaata tgactggaca aaaagggtct
117961  gatggaatgc tagactagac tgagtggaaa gcgcagcaag gcctgtctgc ctagattctt
118021  ccaggcatcc atgcagcatt ccttccttct gggtatggga caggatc
 2341  tctttatcct ttcttctgtc ctgtgctagg cataaagata cagaacttga attttgttgc
 2401  attgaagtta gagagtagga agggaatttt gtcacaaata aacccaagaa caacatagag
 2461  tgaatttggg agaaactttg ggggaaatta taaattgacg ctaagaaaga aaagcagaat
 2521  aacacagtaa ttaaaagcat aggctgtgca attgactact tagagtcaaa tcccagctct
 2581  attttacttg ccagtaaatt agattctgag cctcagtgtc ctctgtaaaa taatggtaag
 2641  agtacttatc ttagagactt gttttaagga ttaaataagt aaatacttaa agctctgaga
 2701  acgctgccca acatacagta aacattatat aaatgtcagg taaataaagt gagcaaaatc
 2761  tggactaggc actctactat tctgggattt gttgaactaa gtgagaagga tgaataattg
 2821  ttggaatgga gctgctagtt ttgtgtttat ctgaagtcat ctactcctac tcacaaatgc
 2881  aggttgaggg attttagtca tctctaactt taataacatt cattcacaga aatatttatt
 2941  gggcacagaa ctggtagctg catcatcact gggaatagca ttcatatgtt tttattagta
 3001  gtctactaaa atgtaatgat tttgaatgtc atttaactca tatttgatta agaatcatgt
 3061  aataaacaaa agtaattggc gaaacacaca ccccaatttg tttcaaatcc caatttgttt
 3121  caaagctgac aattgaaggc atattgtagt gtggtagag gaaatagtag gcatttgatt
 3181  ctatgatcct taaaagagtt tttttttt ttttgtttgt ttgtttta aggagtctca
 3241  ctctgtcaac caggctggag tgcagtggcg cgatctcggc tcactgcaac ctccgcctcc
 3301  cgggttcaag cgattattct gcctcagcct cctaagtagc tgggaccaca ggcgtgtgcc
 3361  accacggctg gctaattttt tgtattttta gtagagacag ggtttcactg tgttagccgg
 3421  gatgatctcg atctcctgac cttatgatcc acctgccttg gcctcctaaa gtgctggtat
 3481  tacaggtgtg ggccaccgtg cctggccaaa gtgctcttg tataagct actatcattc
 3541  ctgtataagc aatgctacaa gcattaataa agtgatgggc atgtgagttt ccactgagtt
 3601  ttctgactta cagcaagatt gactcttcct tccattagca gaactgagtt gtagaaataa
```

-continued

```
3661   aaggtacaca cacatacgtt aagataatag ttttttcat ataacaagta ataatcatca
3721   tatatattca tgattaactc accaggagtc agtgggattt cttcacctat tatataaaag
3781   acaaaatcgt ttggaagtga attttcccga cttgtatgtt accaccaagt ttcaattcc
3841   agctctacta cttaccagct gtgtgaactt gagaacttcc tttgtccttt ctgtgctcaa
3901   gtttcgtcat ctatcaaatg ggtctagcgg ctgttaacta cctcagaagg cttttgtgag
3961   gagtcatata agtgaagcat ttggaacagc gcctggcaca ttctcacttc ctgatatatg
4021   ttacaatgac tacttcttcc actcttatta atactgctaa gctactatta ataaagttcc
4081   ttttggctgga tgctggaagg agaacatggg tcaaggttct gatgaactaa cttcctga
4141   cagcccctc ccctcccctt ctgcctgcct cccaggcaga agcagtggat attcaggtag
4201   gagtggagga gcagggaaat ggcaactctt tcctctctgt tcaccatgat taataacatg
4261   gttcatactc ccttataata tatttttgt taaaaaaggg aatggagaaa tgagaaacaa
4321   atggcagtgg gagtgtagcc aagtggagaa actcagggcc ggacagacct ggcaccagca
4381   ctaagtagct gtgtgctgtt ggtgtgtttt tgacctggcc aaccctcagc ttcttcatct
4441   gtgaaaagga gctaagcaca gcccttactc aggggggttca ccaagagtac atgaaataat
4501   gcctgtaatg catttgttgt actgacaaat aatgagtttg aatgagctat tgtttaaaat
4561   gattcaaaaa tgacacttca aagtaaagca tgagttttct cccttatcta ctcccaaggg
4621   cctcctgtcc tgtttttgtt ttgttttttg tttttgaga tgtctgttgc acaggctgga
4681   gtgcagtggt gtgatcttgg gtcattgcaa cctccacctc ctgggttcaa gtggattctc
4741   ctgcctcagc ctgccgagta gatgggatta caggcgcctg acatcacgcc cagctaattt
4801   ttgtactttt agtagagatg ggatttcctc atgtcgggca agtcctgacc tcaagtgatc
4861   cacccacttt ggccttccaa agtgctggga ttataggtgt gagccactgc tcccagccct
4921   ggttttctta atggccattt ttgtatttcc tcttataagc atggtcttct actgagagaa
4981   tcaatattca gaggattcat taatagctgt tcaacataat tttagcatcc ttcacgaatg
5041   ttaatccatt taggaagagg atataagtaa tcactaattt ggaatctaaa ctgtatgtct
5101   taaacgtata tactttaaaa tatttctgta acatatgtgt agctaatgaa gaatatatct
5161   aaaacattgt tattttataa atttgtaagc aacttttaaaa aaaattccaa atacaaagga
5221   ctatgcagtt tcttaatata agtatctgac ttctttattt agtgttttca ttttctattt
5281   aattgatatt taggagaaat taaaagatca gataagtgag gcagggaggg cattttattt
5341   tattttattt tattattttt tattttttat ttttttttga gacagtctca ctcagtcacc
5401   caggctggag tgcagtggcg caatctcggc tcattgcaag ctctgcctcc cgggttcact
5521   gctaattttt tgtatttta gtagagacga ggtttcacca tgttagccag gatggtctcg
5581   atctcctgac cttgtgatcc tcccgtctcg gcctcccaaa gtactgggat tacaggtgtg -
5641   agccaccgca caggcagggc attttagtat tggtctctta taattggcta taaaacaatg
5701   tctttactac tgtgtattat aaatatagtc ttagtacaaa aaacaaagat tgttatgaaa -
5761   cattatccag cattctactt ttccttccac acctatgtca tttttcatgtg ctaaggttac
5821   atttatagat tcctacctga cacctccact ggcaacttct tttaactgct gttggatata
5881   cagaaatcag agagattgtc tgcagaatga ctctactgag ccccagaaaa aacaaacgct
5941   aaacaaaaaa tggagcccat ttagtctgag caactaggca atataggagt gttggtggag
6001   aattaagaaa gcggatggaa atcctatgac tctactgatg atgctccaaa catttctggc
6061   ttcttagcca gtcccaacac caccctcct tcttttgatt ccagcatgtg cgaggatgca
6121   ggactcaact actatgcatt caggctatgt tctgcgactg cacggtgcac tgcttttgta
6181   atgcaaatag gaggcacaaa gtgtctcttt gataatgtgc agtcagaaga caaaaaagca
6241   ttcactgaaa cagtaaaact aattcataaa gctgaaagac aatagggaag cattatggat
6301   ttttttaaag gaaaaaagta tcctagatca atgtaattgt cacagtgtaa gctattcaca
6361   gtcaatgcag gaggggaaaa tggctgcaag tttatttaaa ggtgggagaag ttttataggc
6421   aaaaaaccat tatgttaaac aaatataaat atatttggtt aacaagttc tgcttagtct
6481   cttagaggtc aaatatatag ctggttattt tcatttagat ccacagtatt cccttagtga
6541   caaaaactca gtagaagttt taaaagagca cagagatca atagttaaaa accatatggt
6601   agattttttt ttttctttta aagggagtat ctcccccatca cataccagag tttagctcaa
6661   ggtcaactta tattaatgca ttaaacttag ctgtggagga ggcaaagggc tggaggaaaa
6721   aggataaaag aagttctgaa attgttcttc caacatattc agccaagcaa cagaacattg
6781   cctggataag gctatatattg gacagttgcc ataattcctc ctgttagatc agctcctctg
6841   gtaccttattc ccatacctt taaagtatag catgtaacat tttgcttgaa aattgcttct
6901   acctctattg ctttgttata gccgttttgc agtttcggta tagaggcagt tctgtgtcac
6961   aagaaattac taatctgagg cttgagaagg ggcagtgtag ccttccatta tctcaccagc
7021   aagctctgta caggattatt ttcaaatttt ctgctgccat tacaatgtgc tattagagtg
7081   gccaaggtgg tgagggaggg gatgttattg aaacttggtt accagggtag ataagataaa
7141   cttcatcact ttcttggcat ccacatttgt agccaagggt ggaaattttg atgaaagaag
7201   tacatttggt caaagatatt aaggtgtaaa gctggatatt ttctaactgc attctacaga
7261   gtctgtctct tccccattga tgctcatctg aaatagtctg cttgattgtt tcaataaaca
7321   cactttcttt caatgtattg taaacttgta aataccagat aaccaactta aaatccccct
7381   cccatcccag tctcaagaaa taacactggt tatgtgcaga cataacttc ttgagtaagt
7441   caccattttc tgtcactttc tatttgcggc tggtaaaatg acagctcagg cttaactttt
7501   acataagcta tttttagatt tttctcagac atcctttaac tatttctttt atacaggatc
7561   ctaccctaag gatcattta ttcttttgacg gggtcattaa gcaatcactc tatactggtt
7621   cattattgga agtcactgca atatccagaa atacatgaag agtggcaagt ggtttatatt
7681   tcagcaagag atttatgcta gaaaggagaa gtcaaggtgt tgacgattga aataaggatg
7741   atcatttcat gagttattcc ctttcgctgg ggttccactg cccacaagcc acttagtttc
7801   cctttgaggc cagcatctct tctctctgca gccaaaccag cctaatacac atgtgcaggt
7861   ttaatgctgg aagggagggg ccagctttac ccatacataa tcactgtttt atggcttca
7921   ctcattcctg aggtgttaat gcagatcaaa tgggaaacac tcgagaaaga acccttgcag
7981   ctactgcatt gcctggctct ccctctcaa tcgttaattc ttattgtaag atctaaaggt
8041   aattttgttt gctctcttaa tgtgttgcag ttctcccagt ggcccttgca tatcctttct
8101   caaattccca tcttgatcaa ttgtttgcaa ataattaagc ttttaaaaga taatagcatg
8161   aggctaatgt acacaacaaa ggcgaggtct ccctcactgt ctatgggact gtggtcaaat
8221   ttgctttgat atcccgaagt gattaggttg attggtatat ctgggaagtg ccatccatct
8281   tgccttcaca agagccactc gatcttcct aaactgtgtc cttgagatgc aataacagca
8341   aaggtgtttg gaggatggc aaggagtgac ataggccttt agttgcaaag gtttggaatg
8401   aatttcccat tttctcccta aaaacagcac ttctcggaga ttactcttta tctcttttgc
```

-continued

```
 8461   aaagtgacgt ctgcctttgc ccattgcatg gcctcactag acctgtgggc agaaggcaac
 8521   agggctttca atgttttttt ttcagcagcc atgcctgtgg catgctgggt ttttgtcaag
 8581   tcattttttt ttaagtctat aaaagaataa ctcatactgt ccacaaaaag cttatttag
 8641   taaagatgca taggatttaa gatattgaaa catattaggt ttcagtttaa aagcctactt
 8701   ctttgtgaat ttttggctgg ttaaggatta actacatgaa gtcacggctt tcatgtgatt
 8761   ctagcaatta cagacttttt tcagggaatt gaaagtttgt gggacactaa ggccaagaac
 8821   tatgagaaaa agaaatacat tcagttgacc taccatagac aagggtttag gaatgttgtt
 8881   gataccttt tctcctctta acaatggcca gattattgtg acattaatt tgtccaggct
 8941   cattcatttg tattaaaaaa atatatatat atcccgaaca actgaaaatt tcttaatgga
 9001   gacagagtgc tgagcctcca tagcttgagg ctgccctagca attatgctgc atgaaattag
 9061   atacagtttg ttccaattac ttaaaatcag atcacatgaa aagtgacaga ggaaaaaaag
 9121   ggtagaactt tctaattttg tgatatttaa attatgaaat cagaaactat atgatgtgaa
 9181   gaaacaactg aaatttgcac tgaaattttg agagccatat tactaccctt tgaagctcca
 9241   ggtagtggta atgattcaaa gagaattttt gtgacaccac ttgcataaat aaaatgtgaa
 9301   ttccattttgc tttgtaagaa tgtttgtaaa acttgctcat aaacaggcat gcaaaagtac
 9361   tcttgaaaat acaggaaaat aaattactgt gacaattttc agttttcaaa gtaactaaag
 9421   ataaatggta taaataataa tttttatcca gttctggtca taatattaag acataactaa
 9481   taagacaggg caaaaggttt tgccatctga ctatactaaa gaaggactgt tgacatattt
 9541   attaattcta ttaaaaatca ctgcaagtga tttctgtaag acctggacaa ctgtcagcaa
 9601   ataattttac aggaaatgtt atagattgga agttgcttgt gtacttcagt gtacaacttt
 9661   atatgacaca tagtgccagt ggtgggatgc taatattgc atatttcaaa attgagcttg
 9721   tcttctggca ctgcaatatt gtaagaactg ctagcctggg taatcttta cctcaatgga
 9781   tcttagaact ctggatgaca aaattgagga taagaaaagt tgtctgttgt tcaagtccc
 9841   atagttaatg agtggcagca tcatttatac aatctaatag agtcacctat attaggtaca
 9901   attcttcaac tagtagagac atagacctac tgtatatcaa gctgtaattc agcattctat
 9961   ccatgggata agaaattcat ttggtttgta ttgtgtgcca aatctttata cagtgggagt
10021   tatgttttaa accttagggt aatggattcc tttgagctca gtagccagtc atgagacttt
10081   ggctgcaatg gctggcattc tgttgagtag tcacttatga tcttagccta ttaggaggtt
10141   tatataccct cattgaaga aagtgggtca acatcactt tgtgaatgaa gcaagaaag
10201   tagtgtcatg gatcttaaat tggattgtt ctgctttgtt atacaatttg atgttgcatc
10261   tgagtggaga gtgtctgtca tggcatggta cagccattcc tttgttccac aaatatttag
10321   tgattttctg ttatgtccca gtctgggctt tgaggataaa cagaaagcaa ggcaaggggt
10381   ttattagcat tggtagatga gtgagaaaag acacaccaac aaggaaataa acaattaaag
10441   caggtgcttc agagagtgat gcttgctatt agggaaataa gaaaaagatg aatgtgagcg
10501   tgataaggcg gggtgctggg aggtggggag ggtaaagctg aacatttgag ctgagagcta
10561   aaagtgacat tggggtaaga atctgagtga cgggaaaagc tggtggtgtt aggaaaacag
10621   aaagaaggat ggtgtggctt ggtataggg taggaagcgg gtgagaagaa ggtatcaaaa
10681   tctgagaagt gggcaaggct ggatggtgac aggccttgca ggccatggta accagtctga
10741   aggttattc acaggggaca tgaatgggga ttatgaaagg cgtctgctac atcctttggt
10801   catggtgagg cttaggcact gaaagggaag caggaaatat cactgactta tgtctgcctc
10861   tgtccatctc ttcccctggc cagtttcctc acctgtaaaa cagaagggat gatgattcc
10921   atttatgtca ctcaaaggga tataatgggg attaattacc atcctgtctg taatatactt
10981   ggagctcttt agaaaaggc actatattcc atgaaagcaa agccttattc taattgtgta
11041   tttattgatt aagtgacaat catagacaat gcttatggga aaaattgtga tctctctgct
11101   gttcacaaac aaatcccctg tgtatagata tagagcatat ttaaacttac atataagagt
11161   actgaagtgg tcattaacaa gccttttag catctaatca gacattatta attaaattaa
11221   aagctatgtc aattagcatt caatagacga caatttagtt tccatggcac agatagttaa
11281   attaagggtt ggggggtgcac ttttccattc ataatagaat agagggttga ctctcagaag
11341   aattttatct tgggataatt tattgagatg tggtgtttca agcaagctaa tgtctctata
11401   gatggaaacc atatcctcag ctcctccccct aagcttaga aatatgtatt tcaaattaga
11461   tatatttgat cagtgaacag aaagcatttg tgccaaaact aatttcagta gaattccaaa
11521   cgttcttaca ggaaggtatg aatttcactt tattatctaa tcctgtaata cttttatcta
11581   ctatgactct tgaggaacat agctgggctt gttcttagca tgcaaaatat gctggtcttt
11641   gaccttatat tggcctgtgt tcagaatctc agcatgtgtt gacattcaga tttggaaacc
11701   aacattggtg aattttgttt ttttgctga ggactgaaaa tgaatagtgt atgtgtgtgt
11761   gtgtgtgttt aatagcaccc actttagatt tgatatttgc atctggcaat atggtgtttt
11821   agagggagaa cgtcactatg tggacctcag ctgagattgt tggtccaaat gggtcagctt
11881   tagaaattta tggttcaatg aatatattaa gttagggcag tatacttta ggtggtaaca
11941   aatggcttgt ccttatttta atcctataaa atacagtgaa gatcatacta aactttctgt
12001   gtttgcaaca aataaagctg ttaaaggata aactcagtgt caaggttctg caagtatcct
12061   aagtagctat ttatacactt cattaatctt tgtaattggc ttgtcttta ctgccattaa
12121   ttagatgatg tagtattcca ttaataagag tgacacacct cagcattttt acctttaatt
12181   atagacttca tgagacactt aggctattga caaaatggct aaatattgcc tgatgcacac
12241   gtatctttt tattctcttt cagcacccct accctctga agaacagaaa aagcagttgg
12301   cacaagacac gggactcacc atcctcaag tgaacaattg gtaagtaatt tggctttgtg
12361   tttacacaca atctgttcc ccctctggca acctgcagct catgttttgc attaagaaga
12421   cacacccagt tgccactgct ttccctggtg gcttgttgat tcaaaagtga aaacaaactg
12481   ttgactgata tgtgagaaca tttgctagta tgggaaataa aacattgtat tgtcttctac
12541   ctccttata agttgacaat tttatgcata gtataagtat gtgtgtaatt cacattcact
12601   atggctctgt caatgtatct ctctctatgg cttttttttt ccccccttcag ggtaatcgat
12661   agagtagtat catcctattt tctacaaaac aagaaaatcc accatcacat atcagtcagg
12721   tttaaattca ttgaataact aaattcagtt agattttgtt agggctatgc attcaaggat
12781   agcctctcct ttgctcttat ctcctgaata ctgaaaggaa gaaattattt gtttctcttt
12841   gaggctattc caaacctgag gcatctcgtg gctgtgcaat actgtttcta aataaagtgt
12901   aaattcctga tttggggcga agctgagatt atgtaccaag taccagccaa caatattctg
12961   actcaatgta cagcagtgtg gcaatgaggc tttgagaaag tatgatttat taccctttgt
13021   gaatgtgctg aaagccaggt ttcatataat cacccaggac tagtgtcata tttgaagggt
13081   atcgaaatcc aatatcctct aaagtaagt gtatctaatt aattgtccta atattttag
13141   attagtgttt atgatgggga aaccttatcc tctttgaagt aaaatccaga aaaggcccaa
```

-continued

```
13201  agcctgggct ggggaagggg agaactagga atgccagttt gcagacagaa gtatttcttt
13261  ctgttcaata agtgtcaaag attaatatta cagaatctct gattacatgg cctaatccat
13321  tttggtgaat aaatttgttc ttgatgtcta ttgcacctac attaacagac ccttctctgt
13381  tagagagcct gggagccttt gggagagatt tcagatatat taaaccccat tacagaaaat
13441  gtaatttctg tcaatataat cccatgtatt cttcaattta gtattttaga gataacaagc
13501  tacttacaat atatttgcct ttggaggatt aatttacaaa gtgcactatc tgcaagacac
13561  agacagactc acataagaat tgcttgtaag ggttatcaat ttctatgacc ttactgctgc
13621  cttgagagat caattttttgc agccctttttc atcagtggat ggtaaaccaa gcaaaggcat
13681  actacatcta aatgtgttac tacgagttgt gtggctgctg aggtttttttg tttgcctatt
13741  tctacctgct actgtgtctt aattttcaag gctgttaata ctacatattg gaaatttcaa
13801  atatgtaata atttcatatt tgaaatatga aatttcaaat atgtaatatt tgaaatataa
13861  tatcctggat gatatattag gggagaccat caatttttgcg tgcacatcta gattcatata
13921  tctgtatttt aaaacttaaa gctgatgttg agacagtttt aatacaatgg aggctgcaca
13981  aatgtccgca tttccctggg aagtgttcct gtttgcgggc aaaggagtgg caggacaagc
14041  tctctagtta agaaacgaaa agcgctgtca ttcaggggat ctatcctgtg agccatctct
14101  cttcctctgc agggttgcta gcaaactcca ctcataaaca cagttaccag agaacaaatc
14161  ccaatacaag ttgcttacta tgggtggacg gccttattat gggatatttc ctgtgaatgc
14221  aggaagagga aggcattctt gtgacttcaa gcaatatata tatcacaca gttttctaaa
14281  ttctatgcac agtctctgcc ggagagcaat cttcctaatc agtccatgat cacaattcga
14341  ctttctcagt tttgtaacca gaagggagag aaaggatgtt taaaaagttt taattcacac
14401  tctaaaataa ttttaaagta tatgcagact ttaccctaaa cttcacactg ctattcaatt
14461  ctgcacgggt aaataactta aaaatagctt ttaattagtt atttgggaca gaaacacaat
14521  tctgtgctta actgccactt tgtgcagtgt gtggtttctc tctacttgta tatatatgga
14581  gttagaagtg gcttttgctt gcaccacagt gctttgcatt tggcaattgt ttcaacattt
14641  aacatgttg tttgctgtag aaaatgtccc tcaagtaact aaaagttgta agagagattg
14701  tttttctttta gtttgacaaa taatgacaat accatgtttg atttgaattt ttaatggttt
14761  attaattttt atagaaacct cttcctgttt tgttttgttt tgttttgttt tgttttgttt
14821  tgttttgttt tgttttgata ccgagtcctg ctctgttgtc cgggctggag tgcagtggtg
14881  tgaacatggc tcactgcaac ctccaactcc tagctcaagt aatcctcctg actcagcctc
14941  cccagtagtt gggaatacag gcatatgcca ccatgcccag ttaatttttt tttcttttgt
15001  tgaggcaggg gttttgctat gttgcccagg ctggtctcta actccagggc tcaagagatc
15061  cacccacttc agcctcccaa agtgctggga ttacaggcgt gagctactgc acccacttat
15121  aaacatttt tataaaaaat gtttttcatc ttagctatac tgagcatcgg tacaagttat
15181  tttctactaa aaataataat tttgaaaatg tcatcattag tatttctgtg tttcccttc
15241  attttattat ccacaacttt taaacatctg tgtcttcctt cttggatttc ttaaaacttg
15301  ttaatacaca tgtacatttt tgtatgaact atgagtcact gttgaaatgc aattcaataa
15361  aatgctgaag gacaggttga gtgtgatca gtcataatta ttagcagtaa cataatgtat
15421  caaatatat aatatgtaag tgaaaaatat aaactcatgt ctagttgtta gagtgtcata
15481  gaaatcctgg ctgatgcagt tttaagttag gctttgactg aaaaatagac aagaagtttg
15541  ctacatttta atggttcttt cacttcatca ctgaactaat tttacattc tcgaattgac
15601  agtgatatat actacctgcc tcaggtggct aaggctaaag tacatgggat ttgaggggag
15661  aaaggcaaaa gaggagagaa cttaaaagta aaacaataag actgatttga ttaattaaga
15721  gaaaatctgg aaaaaagaaa atctcgttat aactctctatt ttggtccaat tgtcagaata
15781  aaaatggaga gaaagaatct taaaatggtt ggcatcagta cttacagcat gtgggcccta
15841  ggatggaatg tgaaatttat tagatgtgac attgtggaaa aagtctatgc caataaattt
15901  tttgagaatt gaggcaatta tgtaaataat ttgagtaaaa tatttttaaa taaattatct
15961  aagtatttga tgtgactgca tattttttaaa aaatcaacct ccataactag ttgtctaaat
16021  atttcaatct agtatgttgt ggttgactta gatttaaaag tgtaatcatt ttcgaaacat
16081  aatatgcacc agagatttat gtattcttcc ttctttggtc ccttgctccc aattataatt
16141  ttatccaaaa atgataaata atagcatcag gggctttttgt ctctttgctt tttttactgtt
16201  gttgtggttt taacaaatac ttatgttata tcagcagtgc aaacattacc aatatgcaaa
16261  tgttttagta atttaagtag aaacatctta aattttgaga ttagatggtt gtttagacct
16321  ttaagtattt aagtagaact ttatggaaga cacacacaca cacacacaca cacacacaat
16381  caatacttgg ttgtttttttc tcctgaataag accaacttta tttttttata ttgaaaatgt
16441  gagtgtagaa tggtcagata aaaatttccct tatacatgat cacaccagtg ttgcggacct
16501  gggaattccc tgtgatgaaa acttatctct tgtacttgtg tcgtacttac tggatgcctc
16561  agttgcctcc tgcctcagca gagtttttggc ctagggtgta ctgaatacat tttacagttt
16621  ctttgtttac tactcctcat ccaaacactt tcctattaag ttctgatatt aaatgattat
16681  cccttatgc tctgagaagg caatatgggt tttaggtgca aaatatatag tgtatgtgaa
16741  atacagtatt tatatataga gaaaaattat tctccatcaa gagagcatat aaaattccag
16801  gttccatcct agcagccaag atgacactgt tcagaactat ggtactctac atttcttaga
16861  tttagtgctc ataccagatt ttcctagtta tttcattttat tgctttcaaa gctgcaaagc
16921  attcaggcat cacttcccat ttattatgag tgggaaaaaaa gtatgttatc cttggagatt
16981  tatgccactg gcaagtaaaa atgtaaactt atttttttaaa aataagatct cctttattat
17041  aataaacaga ttcagctgtt aaaggtcaag tttcctttctg agttatggta ataatatagc
17101  aaatacttt acaaatatc aaagattcta taaatatagg tacctgttta gatgtaaatg
17161  ttaaaacatt cacaaattat ccttttcaact tctgtgatct aaaaatcaat aggggtcata
17221  gggtttcata gaattgttct gcttttttctt ccaacataat ttaataatac attttacaga
17281  tgttgtttga atattagaca cagattgttt tgtcaataaa gttaaacaga ggtatgacac
17341  aaaagcaagg aaaacagatg taaaaaaaag aaaaaaacag tacacgatgc aagaagctct
17401  gggtcacttg tttgctattc aactacaaaa ttaaagtgtg ggctgtatgg tgattttcct
17461  tgcctaggaa tcacctaggg atggaacagc ttcacacata gaaagtaatt gtattaagca
17521  ggtggtttaa cttttttccct tgagaattga agtgtaacct acatttaaag tagacttcct
17581  aattgatcaa tggagtaaca ggtgcggtat attaaaaaga aaaaggagaa atataaatgg
17641  aagaactccc cagaatattt cagaatgggt tgttgttctt caagcctcgg ttaattgcta
17701  tgcttttcac cttgagtgtc aattctaata atattaccttt tacagacgct tactctgggc
17761  ttagattata gcaatcagta atactcacta gataaaatac tgtctagttg ctcataagaa
17821  aatattgaaa tcagtcaaaa aatgtttagc ttgcatattg cctgagacag agctggcggg
17881  gcgccagaca ggcagggtat tataggaaaa gctgagcaaa tagctcgcag ggaaaagagc
```

-continued

```
17941  tgtgaattta gaaaccttca ggtattgtca tgtcagagag tcttaagagt tcaacagaga
18001  cactgctttt tttttccttc agatttaaaa aatttccaac aaacaatctt ctttgaaaat
18061  gactctgcag tctgttaaat atactttgtt gtaagtttta caccataagt ttactcagag
18121  cttttcccca ctgcataaaa tcacatcgtt aatactgtta aagacgaaag ctccttatga
18181  aagagtacac tttgaaacac tgtgctggct ggaaaaaccc tgcccttcc accatgggc
18241  cctaagtcta ggtgagaaaa gaaatgaagg tctaggatgt aggaagggtg gatttgaaag
18301  tccaaatatg gttttgtgta accactgttt ctcctccagc cagcattcaa aggcagttgc
18361  tgagcttctc aggaggacaa gacactagct ggaagctgca atccagctgg tacaacctga
18421  ggaattatgt cgggaccctg tagggttggg gttcaagtga ggctcagagt tgagtgagtt
18481  gggagactga tttaccagc agggacccaa tgtttctgaa tatccatgat tcatttcaag
18541  gcaatgaaac cagtgacaac ggaggttgac tttgaacatg gtatgcaggt cagcacaact
18601  tgttgcaaat cctaattaag ccagtcttct tgttttcagt gtgtctgtaa gtatctggtc
18661  agagaaatgc aaacaacagg ctgtgggtca tgcaacccga tggggcagga ccttgactcc
18721  atttccctgg agagggcata gggatgaggg gctgagaggt gtcacggtca aggggggaaga
18781  gcttggctac gcctcatcca taggtggcta aggtgtaagc ctcatgacaa tttaaaattt
18841  acacagggca agtatgggaa ggggaaatgc agggacaggt cgctgcaatc aaaacatttc
18901  atccctcatc cctactcctt ggatttgggc gacagtgtcc tctggtttaa aatggacaag
18961  taggacgaat tagtcaggac tcaaaggact cttttagctg taatattcta gactgtgtaa
19021  taatgtgaat caaagagaag taaagtgtgc gctctgaaac tctcattcca gctttatcct
19081  aggagtgggg aaggaaaaaa aatactttga taaggagaca aacagagaaa ttaattaaaa
19141  agttgtagtt gtaactttcc tcatcttaca taagcaaatc aaacactgta aaataaaaac
19201  tagatgaaat taaacattat cacaagacat gaaaaagatg tgtgctgtca ttaggatt
19261  cataataaag ataaatcagt tgtttttagc agtgtgctat gagtctatga agggcatgac
19321  agataatagg ctcgaaattt ctgaagttat tgtacagcaa aatttgtttt ttcctcaggc
19381  attcaatctt tttctccagt aattttgaac atgacaaact ttttagtgga tgcattaata
19441  atctataagt aatgggttgt caggtgtcag ttagataaga ttaaaagact gtttaagcat
19501  tatccatttg cttctttgca tgagtttttat aggtcagcag aaataacttt ttgaattgtg
19561  gttgtgtgta cgtgttctct ctctctctct ctctctctct cgtctctctc caccccccaa
19621  accccctcc ctctttcatt tggctccact ccaagcatac gtggaagaac cgtattacat
19681  tccataaatc ctgtatgtaa gagcagattt gaaactcact atgtgaatca aggggacaaa
19741  tgtctcagct gtcttctgta aatgtatttt agttttttaaa atgttactct tcatcttctc
19801  aaaggaagct ctgtaagggg aaacaaactc ggctaagagg ggcattgaag ctttagacat
19861  tagtagtttc ctagcaagtc aggtttaggt ctattcttgt caaatatgtc ttaagtgtgt
19921  ttacatatag tttgccttc tggtattttc tgcttgcaca gacctgatct ccacctattt
19981  tgtgtcaaca gttgctgagg ctggtgttgg gtgattaacc gttaagcacg gaagcgcagt
20041  acccagagag accctctctc tcctctcact tacatcatca tctggcttca ggctgtgcct
20101  acagaaaaca aacagcattt ttgagtggtt aaaaagtcag cctgaaatat taaaaaatgg
20161  ggcaaatgtt gcctcctggt tgaatagaac agttttcttg aaaaatggag tggagccagg
20221  ggctcggggg aaggaagtgt ttccgagggc aaacgttggt cttagatccg gtctgcattg
20281  ctccagtgtg tgcacgccga ggagctttct gtagacgctg agggttatgt tctgcttcgt
20341  ttttgatttt caaggggaaa gaggacatac aaaacaaaaa caaaaaaaaa cctacaacaa
20401  catggatgcc tgtaactttg gcaaatataa ggctgtcctg ttcaatgccc tcataaatca
20461  ttaatatttt cctgtctatt ttattttcat tcttacaacg ctcttagcct gaccccttaa
20521  tatggaaaat aattaactct ttcatgctcc tgatgcctga acaataacaa ataaacaaaa
20581  gaatattaat ctgttccgac atatttgaga ggttttcttt cctttttacc ctcttaacta
20641  accagtgcct cacaagatta gatccctatg ttgaagaagg ggaaaagtat ttcctttttc
20701  aaacacatta actcctccag gtctggggga gatgattgga gctacatgta acttagctca
20761  aaaataaatg tcctgccttt ggtgagatct ggcttaatat tgataaagtc acttttttt
20821  ttttttcaaa aacaatatgt tgcctacgga tggaagttaa tgcaccatat aattatacac
20881  acatacacac gtgcatgtaa gttttcagta tttttactct aggatgctaa ctaaatcaaa
20941  tgcaaaccag tagtcttgag gtttgttgtc tggttgaagg gttttgttgg cctatatcac
21001  taggacatct gcagtggttg acttgtttg tttgctagtt tgggtcatag ttcagatgta
21061  cttggaaagg gccggggagt gggtaggggg atgttttaaa agcttatgga aagaattgaa
21121  catgtacaaa aagatatagg atctcagccc cctggctggt tacctgacaa tactgtttac
21181  agaaaggaaa gtatagtagg ttatggcaga gattccatc ctcaggactt ggggcggggt
21241  gggagggggc gcagagaggg ggtagcgggg cacataagaa gcatgtcaca atcattttga
21301  gtgaatatga tatttaaaaa gcatatcgag aattaaattt tgtttttagt catgctattt
21361  cttttgaaat tgcaaataac aaaggaatat aagattttg atgtgtcaaa agggagcatg
21421  gattaaaatt ttagaaaccc tatgctacag aaccataaag taaaaatcct ggggaggagg
21481  gaatttatgc atcatacgac agatgaggct cagggctaat tagaggcagg gctaggactg
21541  gttcctagtc cagtgcttct tccagtccac tagaatgtac ttatttttaa cagcttttatt
21601  gagatataat tcataaacca tcatttcacc catttaattc aatggttttt agtgtgttca
21661  cagagttgtg taaccatccc catagtcaat taaaagacat tttcaccacc ttaaaagaa
21721  gccttgtacc ctttagctat tgcccctctt tatacttccg tctctctctc caacagctcc
21781  tggcaaccac taatctactt tctgtctcta tatttgccta ttctagacat ttcaccaatg
21841  tgatcatgga atacgtggta tttgagact ggcttttttc actaagcata atgttttgcaa
21901  ggttcatcca tgtcatagca tgtattatca gcacttcatt cccttttcaag gctgagcaat
21961  gttccattgt atggatataa ggtatctttt tttacctat ttatcagtgg atgggcattt
22021  gatattcatc tcttaccatt ataagcgttc atatacaagt tttggtacca ttaagtattt
22081  ttgggaatga cagtatagca acaaagacct tcttaggtt tgtataattt ggaaagcact
22141  tttcattcga tcatcccaat ttcagcacct aaacactgct agaaaacttg ccggtgagtg
22201  gcagttttcc cactcagttc tcatattctt ctcactacac actgctctca ctttccccgc
22261  cactgggtag tgttttgact gtgataatta cgagtgatgt tcaaagaaaa ggaaagttgg
22321  ctgggcacag tggctcacgc ctgtaatccc agcatttgg gaggccgagg gaggcggatc
22381  acctgaggtt gggagttcaa gaccagcctg atgaacatag aaaaaccccg tctctactaa
22441  aaatataaaa ttagctggga gtggggggtgc atgcctgtaa tcccagctac ttgggagact
22501  gaggcaggag aatcgcttga acgcataagg cagaggttgc tgtgagccga gattgcgcca
22561  ctgcactcca gcatgggcaa caagagtgaa actccatctc aaaaaaaaaa aaaaaaaaa
22621  aaaagaaaa aagaaaaga aaagaaaaa ggatagtcac actgaaatcc agcaactcag
```

-continued

```
22681  cagtaaaatg cacaaagttc cctcgaaatg acttagatga ccataagcat tttcaaagat
22741  ttgacagatt ccaagatgtc attttgctaa tgttattgtc tttattcgag agattgtttt
22801  cctttaagtg tgtttccatt tgtattttaa aggtctacag gttacatatt gacatatatt
22861  attacataga gcttaggttt caagcttttac tcattaaaac agaggtcaca gtgaacattc
22921  caaggatgca tgcaagcctc cattcaagtc aaatcatctt cattgtgcca ttctatagcc
22981  taatttcata accagacgga actagaaatc aagctaaatt ttgagatatc ctctcttgac
23041  atgagcagag actccaggtc tagaggttta tggttgctga agacttggag aactgaggca
23101  actacaggca agatcctaga gaaaggaagg agctcaaagg tactccaata tggagctaag
23161  attctttaat acctgattag ggccaggcac agtggcttat gcctgtaatc tcagcacttt
23221  gggaggctga ggagggcaga tcacctgagg tcaggagttt gagaccagcc tggacaacat
23281  ggcgaaaccc tgtctctact aaaaatataa aaattagctg ggcatgttgg tgggtgccta
23341  taatctcagc tactagggag gctaaggcag gagaatcact tgaacccagg aggcagaaat
23401  tgcagtgagc tgagatcgaa ccactgcact ccagcctggg tgacagagag agagagagag
23461  agagagagag agactctgtc tcaaagacaa acaaacaagt aaacaaaaaa acctgatgta
23521  tatgggggct ggttgccatt ctaacacaac ggggttttaa attatttggg ggaaactttc
23581  tttggaaaat aaaacatatt tgatcattaa ggtgaccatg catcccactt tcctgggagg
23641  ctcatggttt atgcctgttg cccagtgtaa ttgttaacag tgcctcttca ctctcaaacg
23701  tgtcccagtt tagatgacaa attatctgct catcatattt ataatagaga ttggcagaaa
23761  actagaattt gctttaaata gatacattta ttcagtaatg tgtaagggat gttttgttag
23821  attcaattt attgacttct tgtgaatatg gaaaaattgg aatttaaatg aaaaatggtt
23881  catctattaa actaaagaga gacacttctg ttctttgaag acattattat acctattta
23941  gcttttttcat tagtagagga agtttttgcta tattatccta gatcatgcta ttgcttctac
24001  attgtgctaa taatcatttt aaatctatat tctaaaccac tattttttt agctccataa
24061  ggttatacaa actcaaattt ggcaaattgt ctgttacatg taagtaaata tttatgttt
24121  acttaaatat aaatataaac cctgtctcat tctgttgcct aggccggaat gccatggtgt
24181  gatcatgatt cactgcagcc tccacctcct ggatttaagc aatcctccca cttcagcttc
24241  cctagtagct gggactacag gtgtgcacaa ccagacccag caatttttta ccatttttgt
24301  agagacaggg tttttaccatg ttgcccatgg tgatcttata ctccaggctc aaatgatcct
24361  cctgccttgg cctccaaaag tgctggtatt ataggcataa gccacaactc cctgccatca
24421  ctttttttt tttttttt tttaggatg aagtcatttc aaaatttgct ttcaaggaaa
24481  atttctgta atatatacca agtgatgaat tatttgaaat ttatttttaat gcctaaggcc
24541  aaaataatac atgagttttg atattacttt gcatcatcat tgtcaactag tgattggttc
24601  atttcacaag ctgctttaaa gagaattta gtggctgggt gcagtgtctc cacccagca
24661  ctttgggagg ccgaggaggt tggatggctt gagctcagga gtttgagatc agcctgggca
24721  acatagtgaa accttgtctc tacaaaaaaa acaaaacgac aaaaactagc taggcatggt
24781  gatgcataac tgtagtcctc ggaggctgaa gtgggaggat cactcgagcc agggaggtgg
24841  aggttgctaa gctgtgatag tgccactaca ctccagcctg ggcaacagag tgagactctg
24901  tctcaaaaaa aaaaaaaga aagaaaagaa aagaaaattg tatatgtaat taccttcctc
24961  aactgtggta gacaattttca gttcttttca aagtaaatttg gcaaatacccc ccaacactgt
25021  tagagaagga aaactttca tgtggctgat tgatggactt cttatgattt gaccaaattt
25081  caatatattg tttatcaagt gggtagagaa gagaggtgct ccctttcccc ctcctgtcta
25141  ttctcctcct gccgctgttc tctacctccc ctacccgcag acacactgat gatgtattgc
25201  aatcttggaa ctgttggatc ctgaggagg ttaagaaact agaaaaaggt gccaaaaaca
25261  tgatttcata aggtttgact tgagaatgaa tcaactttct tgaatatctt aaaatcatgt
25321  ttcatgaaat tttattttcac aaagaaaggg agtgtagaag acttgaactc tgaagaccaa
25381  cagttatgga tcattaaatc caatatgtaa atgtaaatct aaaataaaga gttccaacag
25441  aaaaatttca gagtgatttt tttattgttg tttaaaagaa cagagagtta catgggagat
25501  aactagacct ctttccctga gggtttgttt ataaaacatg ccttaaaagt tattaaggga
25561  tgctgacttt aaaaaaaagt agtagatatg attttattta aatgactatg atatagatga
25621  aggaaatgct atggtgagga aattcctgga ataaaaaaat aacaaaatgt tgggatttga
25681  caactacctt ccaatgataa attttatatt tgaagattt tcatgaggtt taaattctaa
25741  aatttgaaaa tatttataga aatcacaaaa atgaattata tcaattat catctgtgca
25801  tgttttttt ctattgaata aagaatagta tatgcagaaa tcttatattt aagaatgcac
25861  agtgttaatt tttattacta agtttttata gagatattcc taacgctagc taaatattaa
25921  taaaagatta ttataatcag cacttccctt aagggatagt gtaggtatag aaggcattgc
25981  cactaatcaa tctaactaat taacaaaatc ttttcttaat agttgattag cttcttaggt
26041  acttgcagat gttgtaaaat gatatttctc tgtctagtta ggaaccttct gaagtaattc
26101  tatgtccacc actatcctgc tgacagttca cttacgccta gttggcaaga aacacgacgg
26161  ggggtgaagc agagccatgt cattgtttgg aggcaacacc attgtgattt tctgtggttt
26221  accaagttgg ctgtggcatg ctaacataac caaatgtggg cttcctttaa ttatcaggga
26281  gtaagtagag tggtaaacac tgaggaataag aactaattga gtaaaggtga aaatgctatt
26341  tctgaaagtg agcaagtaat tttttttt tttttttt tttttttt tactttttatc
26401  agtattacag agagccatac aagggaggaa aagggcaaag gtatgtggaa aatgttgcct
26461  gtgaaactgg gaaactacct tgtgttttgg ctcctaacag atgcccactg tgatctcctc
26521  acctctcctg gttctcacag agggaaacta aacttagcaa ttcagttttg ggggaagaga
26581  ccagggaaag gagtggagga taaactaaag gacaaaggtc agtttcaaaa agctgttctg
26641  ccagatcttg ctcagaaaac tattcaggta tccaaagact gagaataaaa ggagatagat
26701  gaaattagtc cagtggaaaa aaaaaaagcc taatgataaa taaacatctg gggacaaaaa
26761  agaaagaaca aagcaaaact tcctgtattt cttttttaaa catgagtcac agtcacttcc
26821  cattctcctt gtcagattcc tataaaaaat tcaaaataaa attcaattt tagatgatcc
26881  aggtctcaga tttttggaga tttttgctccc ctgccaactt tcctctttcg cttttaggga
26941  cttgagtctt aaacaaacaa ctaagtaaaa aagaaatata tttctatttg gacatgaaaa
27001  aaagctatag agcaaaccca ttatcttcct ttcctttgta aagcttttg ttttgagact
27061  ggagatagtt tggtcagaag aagaaattct aactcatgat tctatgaaaa aaaggaaata
27121  taaagattct tctcctaatt cagtcttcca ccacctgcag ggagtccaat tcttaaaaag
27181  tcattcacaa aagaagactg tgtttcaaa gcaaactaga ttttaagaaa ccctatgttc
27241  gaatgtaaat gaaaaagcaa acgagacatt ttctaacctt aaagcatact aaaagattta
27301  ctttttcaag aatcccaatg tatggcaaat ttgaattata tttcattaaa ccaaggtgtg
27361  taactatcta tttaatgag tgagcaaaac tgtcatgtgg ctgtgtactc ctgacattcc
```

| | |
|---|---|
| 27421 | atatctgagt tttaagggct atgtaatatt aggaccttaa ttgtaaaagt acaaaagttt |
| 27481 | cctcttacat cttaaacta acatactttg taaaagagac cttatcagta tggaaaattc |
| 27541 | taagattgtg tgtatttcat agatatgtat ttgtatttta tctcaaacca ttttgtggct |
| 27601 | gttggagaat gtattttta tagtatattc aaattggaat tttgtcattc tttttatat |
| 27661 | ttctcttcca aaacactatt tcttctatgt tgaatctcta atatatattt gtgttcatac |
| 27721 | ataaatgtag atatatattt gaacacacag acacacacac atacatatag gattaagata |
| 27781 | actattttac ttatgcctct taaaatgaca ggattttaaa gtgacaatat gttcatttaa |
| 27841 | gttcacatca tatgtacagt tcttttttg gttcggtgtt tagagaattc ttgataattt |
| 27901 | agactcttcc acaatgaaaa gtaaagcatt ctgtcacaaa agcagggagg atgagacaca |
| 27961 | aggtcaaagg gcatttaga aacaaacagc tggaccaatt tatttaaaca gatagaggga |
| 28021 | tggggaactg acctcagttt gacttatagt gggaggagca agaatgtcat tttattactt |
| 28081 | tgcccagaag gaaaatgttt ttgtatctga attcaccctg aagccatcta aacatggctc |
| 28141 | tgctgtgtgt agcataattc caaagagaga ggatgtataa aatgtctgg gataatgata |
| 28201 | aaatacacta aagagaatca aatgtggaga ttgtttaagg tcgaaaaggt gatgttgttt |
| 28261 | taaaaataaa atattttgct atttactttg ttgttttcac atagatgtcc atcatgaccc |
| 28321 | caaataatta gttgttcata taagtgtagt aattgtaatt cagtaacgtt ctgagagatt |
| 28381 | actacatcct atatgtacta atgatatttc attatattga atttttaaa ttaaatgttt |
| 28441 | cacaagtaag aagttgcagg tagacctact aatgtggtca aacagctcag aaaaggtgat |
| 28501 | tagtttttct caggttttca gtgtttttgt ttatgtttta ttttttaatt aaaggttttcc |
| 28561 | cccttttgata tctacacatt ctaggggtag ctgacatctg tgttcttaat aacaacaaac |
| 28621 | agttcttgcc accaaaaaga agcaaataac atctagtacc tgtgggcagt tggctaagag |
| 28681 | gctgtggtat ttttgtgtg tatttgcttt ctacctgggg atcagagcag gcctggaata |
| 28741 | aatgtcgttg gtgttgtcca ctgcaaggct tcaggaggac atagacaaag atcagcctac |
| 28801 | tgagcagaga gtggtccagg tattgaatgg actcaatatc ctagaaggac tcacattcta |
| 28861 | gcaggcactt tttaagaatc actaatgttt aacctaagga ttagaggga gaaggctata |
| 28921 | aagcataatg gctatgttta actatttgaa gggctatcct gtggaagtaa aattagaatt |
| 28981 | gcttacagta ccccaaggag ttgtgctgat aaaactatta ggttgggtgc aaaagtaatt |
| 29041 | gttttttttt tttttaatta tactttaagt tctagggtac atgtgcacaa cgtgcaggtt |
| 29101 | tgttacatat gtatacatgt gccatgttgg tgtgctgccc ccattaactc gtcatttaca |
| 29161 | ttaggtatat ctcctaatgc tatccctccc ccctcccct gtaattgttg ttttgccac |
| 29221 | tgaaagtaat ggcaagaccg caattacttt tgcaccaaca taaatatttt tgatctagta |
| 29281 | aggcagaacc ttctaacagc cttgtttata gatggggtgg cctcttaagt aaggtggtga |
| 29341 | gtgctgtatt agttcagcag aggttaccta tgtactttg ggggacagat atcatatagg |
| 29401 | ggattcatgt cagtgaccaa acgaagtgac cattacagcc cttttgaaac ctgaggtgta |
| 29461 | atttttaaaa atgaactcac gactttaata gtcatagact caaacctgag ttgattatta |
| 29521 | tgaattagtt tatgggagtc tcaatatgtg aaatatgatgg agacaagttt tggaatacag |
| 29581 | ataaatcaag tcactgtatt cactctctct ctctctctt gaatagctt atctttgcct |
| 29641 | atacacacaa acagtgcagc catcaaaatt ttcaatttac aaaatgttca cagtcatgct |
| 29701 | tcttccttga ctaaacactg gggttgctgc cagtggtaat tggcttgaaa ccagctaatt |
| 29761 | tttatatatc tatttagtct ggatattcta gatgagtggc actatagttg cggtgctcta |
| 29821 | gtcactgtgc cagagcacca gggaggaggg tgcttgctac cactgacagc tgtgtgtcat |
| 29881 | ttagcaaatt attaacatct cttttggtaac atgtgacctc aaagaagtca cctaatttct |
| 29941 | ctgagcccag gcttctcatc tgttaaaaat gtctcttcct atttttaggt aagtagtata |
| 30001 | agtcacatcc ataaaagatt atgtttttaa aaagtctgga aaaagaaagt taatagacag |
| 30061 | aattccttcc ctctaagagt ctgcagataa tgaacagtac catagataaa gagatgtttt |
| 30121 | tgctctctta cctacattag ttactatgaa aattactttt ggtatatgca gaatattaat |
| 30181 | attaaataat tttctaattg gtcatgcagt gaaggcagct aatgaaaaaa cagattttt |
| 30241 | ttcattttaa ttggttattt cacatggtgt ttgtgctaca cctgtgctta taatgagaat |
| 30301 | ggagaattaa tctaaccttc tgctcacatg attccagttt tcatggttta tacaagataa |
| 30361 | tgataaccctg atttgcaaca caatttgttg tagacctgtg tttaaatat ttttattagc |
| 30421 | agttcaggga cttcatatac aagaactgat ataatatgta ttgccaacaa gaattagcac |
| 30481 | aaacagtata ccttttagtt agattctagt ttcattattt gtttcaatta cttctcagat |
| 30541 | aatgaaagaa cacaaggata caggatattg agaatcttaa aatgttatga agtatgcatt |
| 30601 | tttgttttga aaacctgtcc ctgtctgttt aatggtttgg ttttaggaa ctattttcct |
| 30661 | tcctgaagtg ggcagattta caaactagaa ttcactactgg actatgatc ctttaatcat |
| 30721 | taatagagcc ttattaaact tttcattgta tttttatgt cctgctcaga tttgatctga |
| 30781 | gttgggaact aaaaggaatt tactatttca gaatctaata tgtcctcttc attttctgga |
| 30841 | tttgatacgt aatttttaat attatgcaga acaaacgtat cttaagagaa tctcatgcgt |
| 30901 | atgactctgg agagcgtata ttaaatacttt tttacatgtc agtgacttgt cacttttgga |
| 30961 | gaggctacaa aaataattgt acaaaactat cttattaagg cacttaaagt aacttaagtg |
| 31021 | ccttaataag atgttataa atttcagta ctagctggag aaagcaaaac tataagttca |
| 31081 | attactgtat atctgtgacc ttgccttgac ctcacagctt acataaagag caaaaaaaaa |
| 31141 | aaaaacaaca acaacaaaaa aagccacccc aagaaatctc tacaaggaat gcatttctct |
| 31201 | gaagtcctaa gcagtgtgag ttagtggtga taaactccag acattctctc atttgatggt |
| 31261 | gtgctgccat cccagttcat tatcttaata gtgggcatta aaatagaatt aggtttgcaa |
| 31321 | gaggtagggg tggttttgat aaaaattgta caaaagaagt cagagaacat aagattgaaa |
| 31381 | tgtcactaat taggagaggt aacagatgcc cttatgagca tctaactctt tacaccaatt |
| 31441 | ttctctcttt gcaaatgaaa ggagtggtgg ctagtattgt ttcctgaaaa ctctgctaat |
| 31591 | tcccccatga aaagatgaaa tggaagtgtc caactgtggt aaaacaggca aacataaatc |
| 31561 | aactcagaaa ccccaagcct gtgtactcaa aggtcactgg gggttacagg ttttccagca |
| 31621 | cgtgaggctg cacatagagc aatggagaga actgaaggag tcccatttg ccaagatcta |
| 31681 | gttttactcc aactgcgatt catctttcc tcttcctcaa ccccccttt tatttttaag |
| 31741 | gaataacgat ttgtttcact ttcttggtta caggtttatt aatgcccgga gaagaatagt |
| 31801 | gcagcccatg atagaccagt ccaaccgagc aggcaagtcc cccatagtga ctgtattcaa |
| 31861 | gtcacgcaag cgaaaaccat cctcaagcca ttcccggga ggtccgctac ctggtaaata |
| 31921 | aactgggagt gagtatagga acgcctggca attaaaatta aaccagtttc gtttcataac |
| 31981 | aacactaatc aatttaacat cattataaaa cgtttggaga aggtggaaaa aaaaagccaa |
| 32041 | cagagaaaag taactcttaa ataatatgct cagttacaat attcttttgta cacattcaat |
| 32101 | atattaatgt tatttttttt ctgagtttgc cttcccagct ctttctgcta ctatgaccac |

-continued

```
32161   tccctggtgc atggcttggt gtggaattgc tgtaaacttt attacctgtc aaaagggcaa
32221   aggggtcagg attgcttgtg ggactcagta aagttcaaag acattcaatg aggtagagct
32281   tttgtgtgct ttaataaccc aaggcagctt acttctgaag cagcttttca tgtacagtta
32341   aaacacggga ttcaggtagt ggtataaata catggttctt atttctcaga cttctcttg
32401   ttaatatcca tcttctggtg ttcgactttt tttttttta ataacagtct ttttgtttg
32461   tttttaaatt atgagcttaa aatggcgata cttctatggg atcctggctt gtggatctaa
32521   aaatccaaga aacatctctc taggatttgt tttgcatta taatatgcca gtaagataac
32581   aagagtattt gctaggggtg atgtgagtct ttactttctt tatgaaatac tctctcatct
32641   cttagggagc actatggaaa actatgttag catcgcattg aggcaacaca catttactcc
32701   tgtaacttt ttcttccaa cacccatatt gtggtcacca gacaaaaccc aagcagaaag
32761   tttccacacc ttaactgttc cctctttgag ctagatgttt taaaaactca gtcacagagg
32821   tgtgtagatc tagtctgaga gaaatttcac tttgaatgtt taaaaatta tactagcctg
32881   ctatgttctg tctctttctc tggtatgttc tcctcttagt ctctcttggg ctatttcttt
32941   tgctctcaga gactgttatt aaaaaaccac attctgtact tttgtagtaa gtcaaggaac
33001   accttataat cctgatggac agcccatggg aggtttcgta atggacggtc agcaacatat
33061   gggaattaga gcaccaggta agactttgtt tttgtggtag ttcctcattt ttgactccaa
33121   gagtgtcatc ccctcatcaa cacaggtaaa tccgcctcat ccttttctgt tatctcaagc
33181   tggctgcctt gccttgtctg ctatctgtgc atctaagata ttgcagaggg gaagccagga
33241   tctttatgca ctgaagatct cactatttct caaccctcta gatcctgttt tttttttaag
33301   ggtctttgg cactatctgt tgactttgct catttctgg cctcttcttg gattttatc
33361   tcctctag gacctatgag tggaatgggc atgaatatgc gcatggaggg gcagtggcac
33421   tacatgtaac cttcatctag ttaaccaatc gcaaagcaag ggggaagtaa gtacaaatgg
33481   ggtctttgtt ttcactttgt cctaggaata tttttcctct tgcatttct tatgttctcc
33541   ttgcccatag cttcatgctt gttcattcct ttccattaaa ctcctggttt cttgcttcca
33601   tcatttctt tttggttgtg atcaagcttt taagcttata aatactgtgt atgatgtaca
33661   tttatcctgt gtgttgctat tgtacagtac tgaccacatg acaaaacaag aagcagtcag
33721   gaggtggggg agtgggttgt catagcaaca gactgatttg caaatgtaa gcagtctgca
33781   gcagtgcaag gagagggaag agcatgtccc caaagtgtca taaatctgtc taaccgcagt
33841   tgatgcatga gttacatttc tacactaacc tgcaagacac cgaaaagcta aacagagact
33901   tcttttaggt aaaataaaca caagctttac ttagggtaag taaaggcata ttttgagctc
33961   cagtcaacta aactttgatt ttttttctta gtttattcct ttgtctgtcc atcataatgg
34021   gattacgtgt ggcaatggga aaaggggagaa tacaaaatag aggtgtgcac agcagggctgc
34081   ggggcttagc ccaggctaat tgactatatc caaattaagt atgccatcac ttgcagtgtg
34141   acaaatggat ttgacttatt cagtatacaa aaatagagat cattaatgca atcatcagtg
34201   gcaggcctag tgaagtgggc ctaggaaaac tgtcccagat tctcactctt gcattttctc
34261   tcctataaag acactccagc aattcgagtt caaacaagta aaactgtttt gaacaccaag
34321   gctcttgttc acttcctaaa ttaccctaa tagcactgtt cttgctttgt ttttgaaatt
34381   aaaagcagtt atttcagagt cttgcttgtg tctctgatta tatttatgca ctatttaaaa
34441   tcactgctga ggccagggg aattcgtact ggtcatcttc tctgggtgtg agtcaaatat
34501   aagtttaaca attagctctg aaaacattcc attgagctgg ggaatgcaac agtcttatta
34561   cctcatcatg gaattctcta gcttagttaa tttaaatatt gtttcttagt ttctgggtca
34621   attaaattta aatgatgtat tttatgcttc gtgaccaatt aaattactag gttattacaa
34681   aaaaaattat catctttttt gattaaagag ctgtgggtac agtatattt ataagcaatt
34741   ttcattagtt caaaaatgtt cctttaggct agattaagca gccattcatt gttagagcct
34801   ggagaccta ttcgaaggtg ttcatcgtat tcacagtgca ctattactta gaactaaagc
34861   caattgaacc tacttagcaa tagcgttatg cctttcaccc ttgatgatta tggagtttat
34921   agctctcaga aacaatacac ctgtcagttt ccatcaacta tagcaatcca tgcagaagac
34981   aagaggcccc ctcaaagcag gaggggtatt gttttaggtc caatttttct tattgttctc
35041   aaaatcatta taaggtggac agtgttttgt gaagattttc tttcccag ctctaagaaa
35101   ccatgtggaa agaattcatt gataactgtt ttgattttt tcttttttta agtacaggtt
35161   ttgctaagta atcaccctta gtgagcctgt gtagttcagc tgcctgtgag atgttggtg
35221   accagctcag tgtattcttg tattcttgat agagaatatt tcaggagaca aaagtgcttc
35281   ttcagaccag acctcaaata acaattttat tcttttaat aaataagacc tcagtaggcg
35341   gacctgataa cagtgacaat gaaaggaaaa tagtggcaaa atgtgagttt ccagcatgat
35401   gtttctcatt ttattttctt ctgtatgaat caaagaatg cttacaaaa ccatgttccc
35461   ttaatcacag ggttctctgg cttttatagg attgtcatag ccaggaccac actattgctt
35523   tttcataaca tttctttt gtttcttct tttgaatttc ttacaggcgt gcaaagtatg
35581   ccaggggagt atgtagcccg gggtggtcca atgggtgtga gtatgggaca gccaagttat
35641   acccaacccc agatgccccc ccatcctgct cagctgcgtc atgggcccc catgcatacg
35701   tacattcctg gacaccctca ccacccaaca gtgatgatgc atggaggacc gccccaccct
35761   ggaatgccaa tgtcagcatc aagccccaca gttcttaata caggagaccc aacaatgagt
35821   ggacaagtca tggacattca tgctcagtag cttaagggaa tatgcattgt ctgcaatggt
35881   gactgatttc aaatcatgtt ttttctgcaa tgactgtgga gttccattct tggcatctac
35941   tctggaccaa ggagcatccc taattcttca tagggacctt taaaaagcag gaaataccaa
36001   ctgaagtcaa tttgggggac atgctaaata actatataag acattaagag aacaaagagt
36061   gaaatattgt aaatgctatt atactgttat ccatattacg ttgtttctta tagatttttt
36121   aaaaaaatg tgaatttttt ccacactatg tgtgttgttt ccatagctct tcacttcctc
36181   cagaagcctc cttacattaa aaagccttac agttatcctg caagggacag gaaggtctga
36241   tttgcaggat ttttagagca ttaaaataac tatcaggcag aagaatcttt cttctcgcct
36301   aggatttcag ccatgcgcgc gctctctctc ttctctctc ttttcctctc tctccctctt
36361   tctagcctgg ggcttgaatt tgcatgtcta attcatttac tcaccatatt tgaattggcc
36421   tgaacagatg taaatcggga aggatgggaa aaactgcagt catcaacaat gattaatcag
36481   ctgttgcagg cagtgtctta aggagactgg taggaggagg catggaaacc aaaaggccgt
36541   gtgtttagaa gcctaattgt cacatcaagc atcattgtcc ccatgcaaca accaccacct
36601   tatacatcac ttcctgtttt aagcagctct aaaacataga ctgaagattt attttttaata
36661   tgttgactt atttctgagc aaagcatcgg tcatgtgtgt attttttcat agtcccacct
36721   tggagcattt atgtagacat tgtaaataaa ttttgtgcaa aaaggactgg aaaaatgaac
36781   tgtattattg caattttttt ttgtaaaagt agcagtttgg tatgagttgg catgcataca
36841   agatttacta agtgggataa gctaattata cttttgttg tggataaaca aatgcttgtt
```

-continued

```
36901  gatagccttt ttctatcaag aaaccaagga gctaattatt aataacaatc attgcacact
36961  gagtcttagc gtttctgatg gaaacagttt ggattgtata ataacgccaa gcccagttgt
37021  agtcgtttga gtgcagtaat gaaatctgaa tctaaaataa aaacaagatt attttgtca
37081  tgctgactcc actgcttgaa aaatttgttt actgcccccc agattttaa agattaatac
37141  agtaaatata aaaattaatt ttggctccct aagccatata tgtatttgac aattttaacc
37201  gcaaagtaag ttgtttaata ataaccactg atttcttaa gctgacttaa tgaactccta
37261  atatcagcaa atttgaggcc taaaggcact aaactaactc tagactcaga attacatcca
37321  acagaattac tcatctaata tcagtgaaat tattcttgca cataaaggca aacctaagta
37381  caaagttaag tcttttacta aaggatgtta cctaggatga gcagtatatg tttattagga
37441  aattaactac atgaattgaa gagaccagac ttcaaaatct aatttttata aatatgctct
37501  atgttctcat tggataaaac tggttattaa ccaattttcc agaacagctg tacaagattt
37561  ctgcatggca gccggctaaa tggtagaaaa taatatgttt aagctggaat agcttataat
37621  tttatttaaa taaaattgct gctataaaaa gtgcttccca aagctaagga aaatatacaa
37681  atattttaat taaggcaaat tcgttttaaa aaataagcct ttcagtagtg attgctttgt
37741  aaacaaagga tgggtcggag gagagagagc cttaaactca agtctgacat tcaggcccaa
37801  gtcaccctat aaaccggccc ttagcaattc tattttctat tcgaaaagag aaaccagctg
37861  tgggttggct ttactaggtg atgtgtgatt gactgactca cctgctggag tagcaatgca
37921  ttctcaccctt ttgctgatgg ggccttgttt ctaaacacgt ggatgcgcag agagcaaggc
37981  tcagcctact gcagccatct ctggcagcgc ttctacccct ccccagccca tagatgggat
38041  tgtttaaatc tcccttgttg acctagtggc aattcttcct ctacctaaat agtcgatgtg
38101  agtgaaatca ttctctttg ataggtggtt gctagcagtt aacaaccatt tatttacttt
38161  aacaattaat aataaacttt ataaactgtc tatttgctcc tcctctccag tacatgcccg
38221  ggtgagttgg ttattttcag cctttattcc tgaggaggct caggatgggt gggggaggga
38281  aagaaggggg aggaggtgtg gtggggagag ggagagaggc gagagggaga gacagagaga
38341  aagagagagg cgctagggga gggaggttta caagtgaaga gtagttaggg aaatatggtga
38401  ctctgaagaa tcgagatcag cagtgtccag gaattagaaa aaataaactg ctatttccgt
38461  gagttccccc tctgtgagcc atttaggtga gagcctcgct cttcgcagtt cctttcttcc
38521  cctgcctcga tgccctcccc tcttaatgct attttagctt ttcctcttgt aaatttcaga
38581  gccagctcga aggttattga ggacacttat ccgaaagagg caaataatag aggtgctgag
38641  agtgttttg atgtttccta aaaggcaaaa acaaaacgcc ctcctctaaa caagggcaca
38701  aaattgtacc tggtttttat ttttatttgg tggtgggggg gtgggggggt ggggggggggg
38761  tggaaagggg gctggctctg gctgaatgag actactttt aatatgattt aaattttttt
38821  ttcaaaaaat taaaaatatt ttaccctatc atatttaatc agctgtaatt ataacacatt
38881  caaaatgaat aatatgcctt gacagtattt ttattgttat tgttcattgc atgatgttcg
38941  actgctttag aagcacagga aagagaagta aacgcgctac aaatggggaa ttaccctcgt
39001  ttagcattaa aattcattta gataaaattg ccacaaacat ttaaatggga agattagttc
39061  cccctcacgc cttattgcac tcgctcaatg gttccgttaa gaacatttta cacgttggaa
39121  attccgtctt ctcagacggc ttgctgtttc ctagttaccc acattcaaag caaaggcagc
39181  agcaaaggca gccgcagcag cagcagcagg gaaaaaaaaa aagtttggc aactggtctg
39241  caattcatcc gctgctcgcc ccagtctccc ctccgcccgc tgcagtctgc ccccacccct
39301  tccccttccc caccccctacc tctttccccct cattatgtaa ttcgcagagt ccagtcctcg
39361  aggaaacacg ttgccctagtt gtgtagtatt tatatacaat gttaaaatac aaagaaagac
39421  cctaaagtca gtcgagtcgg ttcctctctg ggtctccctc tccctctcct gttctaaaat
39481  gaagatttag cttgaatgtg ctgagtttct cacatcccgt acctgaggc cacaaggcac
39541  gttttttggc tttcatttct gccaggactt ttccaggaaa ttcaccactg cttttcgctt
39601  gtattagaaa cgtgtgaaag aattcgtctg aaaagtccat gcaccgtcta gctttctct
39661  cccccctttt ttcttctcc ttctcctcct cctcctctc tctctctgtc tctctctctc
39721  tctccgcccc ccactctcgc actcccccat cctcctctct cccctccct tcgcagagcc
39781  acaggaaaag aggaaagtcg gcttcgactg ccatcttttg gggatttcga aaaacgactc
39841  ggtaggaaac ggagggaggc ggaggcgcgg gagtggggga aaccccctta ttatccagtg
39901  tcggaactgg ctccccttaat ctgatgctta aatatttgat gtggaaaaat tacccataaa
39961  attagttact aacaatttca aattgaaatc acttatcgaa ttataaacgc attaaagctg
40021  tatggatggt attaggagtt cctcgggagg cagcgggtgt ctccttgaag tgagccaggc
40081  gggcgagttt cgcccccgggg aaaagagccc ccagccgagc ccgggggcaa ggccgggagg
40141  gcggcgctgc aacctgggcg cagggtccgg gtcaggggga tcgagcgggc ggccgggtcc
40201  tggtggaggc tgcggctgct tcggctcgcg ggggcgggga gaaggggagg ggaaggagcc
40261  ttggtgggag gctccgaccc cggagcagag gcgcctacca gcaaacttcg tagtgaagtc
40321  gaaggattct gaaaaggaaa aacgcaagcc ctgccctccc cctccctctc gcgtctccca
40381  cgccggcgtgc agacttcgcg ctcgactttg cgatcggggt tagttgctgt gtgcagtgtc
40441  ccccaagtct gcgggaggag cggaagggta taggctccag tcctggggtt gggcccggct
40501  ccgtgccccg agaggaaatc cagcgggcaa ctgcgcagag ctccagccag gacgtgctac
40561  ccctgagtcc ctcgatgcgc tgggtcccgg cctagccccc agtgcgtggg cgggcaggtc
40621  tttgcccaga gaccacagct ctggtcgcgg gggtggcgg gggtgggggg gctgcacggg
40681  cgcctgcctt accctcctgc cctcacccccc atctgagtct agtctaaggg actgttgact
40741  ttgtctctgg agatggggcg accagggggtc tgcgaaggag gttgtggaga ggcacctcct
40801  gggtgcaggt ccgggcgctc tttcctgcgga acctcacgga gtgctttgta gtagcctgaa
40861  gacttcctaa tagactttgc cacatcgggg gccccagact ccagagtccc atagtgggcc
40921  tgggagcgcg acccagagag cctgggggct ggagggcaca tggaacgcgt gcacggccca
40981  ctaggagggc gttgggagga gagtgcccga gtctggagcc gcagccggga agccgtagac
41041  agcaccccga cgccttaggc agaagctcct caggatcact ttaaaagctc tgcaaacttt
41101  ccccagcctt tcggataccc tcaggcccctt ggcccaccgg aaggcagtaa aaacgtaact
41161  tcatgctgca aagctcccgg gtaggcgctt ggacgccgat ggagagaggc gtgaactggg
41221  gtagtggggc gccctgcctg gctgggcact tttccttgtc tcattctcgt ctcccatgcc
41281  atgccttacc cactggctgc tagcggcgcg tttcacttaa ggtggccacg gtgcggagac
41341  tacaggagcc tgggaatccc agggtttggg gaaaaagtag tgagcgagaa aggtgggtc
41401  ggggacctga ggaagacagc tgatggctgg gagagggagg gctcccttt cggcccgctc
41461  tacccgccaa gggagtctgaa acattctctc cctaggcgga gctgaaagga aaacaaaca
41521  acgtattgag caatcagttc gccaacattt gagctttaaa gcgcctttgc tctgaaaata
41581  gtaccctggg ggtctcagtg gggagatggg ggaagcattt ttagggcctt gattctggct
```

-continued

```
41641  tgccgcgccc cacgggtcac ccctccgcgc gctgcctcct gacatcccgg cgctctcagc
41701  ccactgaggg gaaacccggg cggtgcagcc ctggagaaaa gggatttagt tttaagccag
41761  tctcccatcg atcgggtcgg taatttctac ccctgcccac tcgcagacac actcacctct
41821  accctaaagc attaaggtca ttacgcgagc aatgtcatta atttccaggc ggaaaacgag
41881  tcccgggacc tcgccgattg gggaagcagt gaataaagtc acctgcttca ggcacccgct
41941  tggcccgctc ctcccggtgg gggccgtgtg tggcagggag cgccgagcgg gggtccctag
42001  ctccacgccg aggcggaccg ggcaggggtc agaaaccctg tgtctgtttt ctgcggggtg
42061  acgacctcct gtaagggtgg gattgctttt gcttgctttc cttctcccct ccctctgcct
42121  ttcttcctag gcctccctca catctcagta ctctttcttc ctcctcccct cccccaaagt
42181  ggcaagttcc ccttctccac ctagtgtcca gaggttctgc ccctctccta gtccccgct
42241  gcctcagggc cgtcgcagaa gtctggtagc ccgacgcctt tttgcgccca tctacctcgc
42301  ccacctttct gggcatgggt ggggtggggga atgttcagtg aggccctttt gaagccgctt
42361  gctgagggca ccctgaggct ttaaagaacc agatttctcg atttagggac gatctctgcg
42421  cccattgata actccatccc aaagaaaccc agcacagcag caaacacccc cagcagtcgc
42481  ctgctcctca gcccccgcct tggcacagag cagcgtctgg cactgcgggg agatggaggc
42541  gagccacgcg cacccgttcc cttactggcc gacccgcgag gcgccagctt gttctggaga
42601  ctcagtttcc actggacaaa agcaggggaa acacaacgca agggctgtgc aaatccacgt
42661  tcccgacgcc cctccacccc atcccaatct gattttgag acgtgcattt tcaggtagtc
42721  ctaaactgtg aacagcgagc tttgtgtgtt atctagtggg ggtggggatg aaagggggagg
42781  agactcccac tgcccgttcc agtctttaat gtttgaaata acgaaatgcc ttgtgtagca
42841  gctgctgctt gagccaaaac taactctttg gaagacggaa aagagtgaaa ggcaaagaaa
42901  gactgttcat ttttttttctt ttggtgccgt ttgggatgtc atctgtttcc ttggcgactg
42961  tgttcagccc ccggagcccc tgggctcctg gattgttagg ggggaaaagc atgctatttc
43021  tgcaccgtca tttatcactg tcaccgcata atgattcccc ttgcagcccc ttattgatgt
43081  ttgtaattgc attatctcat aaaggaggat gatcaatgaa actgagccgt gcattctggg
43141  gtcagaggaa gccaaagtac tgtttgtccc ctttaataca acaagtactc attatctta
43201  ggtctgcatt caaaaaatga tctgatctag ggctgaccct gtcggacatc ccaacactt
43261  ctaaaacgcg gtttgtgtaa ccttttgctt aaatgctaaa tcaagtacct gtcttgcatt
43321  tcaacgaaac aagatgctaa aactgaatga aaaaaaagca tttctttttt tttttcccc
43381  ctgggaggggg tgcgatcgtc tgaaggtgca tgagatttta cactgtaact gcttggtaat
43441  ataatacaga aaaggcaatc ccaatccaca tgagtcctaa taaatagaaa aaaaattggg
43501  gatgagggga aaaaggcagg tagctgggag cttttaacaa ggtcggtact aaaagatcag
43561  aataaaacca catccagttt aattaataat agctataaac tgaaataatt ccccatgatt
43621  ctgcccttgc ttctcctttt tacagagtca tatctcttca gtttagagaa atgacttttg
43681  tggctgttcg attctcacaa caacaataac taaatcagtt gcacactgtt atctaaaacc
43741  atctacaaac tccagcaaat aaaaagaagt tcatttgtct attaaggcaa gcatttagtt
43801  gagcagaaat atcccagtaa cactgaatag agttcgtgta atcctatgga aatcaagtca
43861  tcttgttgca ctgaagtaaa tgaaaaaata caaaggagaa aaggtccaag tgtaattgta
43921  attttaaact aaatgcatta ttggactgtc acagtgaaaa cgtgattgtt cggctgcggg
43981  gggggggggcg ggggcggcg agtggacata aacttagctc acatttaact taaaggtttc
44041  agaaaggaaa tatgtattcc atatttggtg atcatttgtg gaaagaggag aaattgaaac
44101  aattctaacc catcattta gtatactagg gggaatcatt ccttcaaaag cagaattaag
44161  caaaaagctt attttaaaca ttgcaagtct gtattagcag aaaaaaaaag tttcaaattt
44221  tctgaaaatg tatgtcctct ctatgttaat aagatgttga cagagagaaa gagagagaga
44281  gagagaaact aagttcaggt gttttattt ttaagttcta gatacttcta aattaacgat
44341  ataaattaat gtttacata aaaagatcta aatgaaaagt tttcattata gttgagaaaa
44401  tgagtactta gagtgtgctc tgataattg acacattgac ataaaaccttt aaattgaata
44461  ataaaacaaa cggctaaaat attcccccctt ggaaaaataa ctttaataat aaagctagaa
44521  aagtttaac tgtgttgaac catcacttt ttctctggaa ggcagattat cctaaagagt
44581  attattttcc agaaattctg tcaaggcact ttgaaatat atatgtttgt attattttaat
44641  attctgacac ttccgttctt tgaaaatgct cagactggaa tggatacgta gccatgcata
44701  tatttaatat aaatggtatc ttgtcgttaa cataaaatat taaagagaaa ataaaactt
44761  gggctttgtc agttaagata gaattttta gcataatact ctgattttca aaacataaaa
44821  ttgaaacccc ttgattttaa ccaatcaaca caagtctttc tcttatttgg ttggggatct
44881  gcatcatata ctctttctat ttttaatatt tagtgttgta gcccactgtt aaaataatga
44941  aaaattagtc tcgtttcaaa attatttatt tatggaacga acatgattaa aacataaaca
45001  cacaaactgc agctgcaaca gaaaaaaaac ttgatttatg gttattaaat cttttgatcgc
45061  catgttaatg tttctttttc taccttcat ttgcatttta atctatcgaa tctttacagt
45121  tttgctgcct cctatttcaa tgattgatta cagatctgaa ataagaaaaa ccaagcctag
45181  cttttctttt ccttcttcg ctttcttttt tctctttttc tttccccccc ctcccttttcc
45241  cccgggtag atttctgaaa cttctctca atgctaatgt agacaggaca aattaattct
45301  gctcttttaa atgtcaaaga tataaataaa aaatgttttc tgtcccaaac gtgaatattt
45361  tcccagctgc ttgtttcga gtcgtaaaag atcatcccag caaaatgcaa ttaacagcga
45421  aacacacaca catacactca cacactcggc ggtgcggaat ttttttaaag gacgtgttgt
45481  tctgagttga agaaaggtga gaagttcacc gtccctccac catcagtagc ctcgctgcgg
45541  ctctcctctc tctctctctc tctctctctc tcacacacac acacacacac acacactggg
45601  aggtttggtc cctagttcta tctgtgatct aagtcacaca aacaaaaaca agcttggtgg
45661  cagcttgttg ttgttgagtg ttgttgagtt gatttcttga gataagcagt gtaaagacaa
45721  aagggggagc gatgcaggtc tgtttgtttt ctttccccgc cgccccactg tcccttttct
45781  cgtctccccg cgcacctccc cagacgcccct gccggggtgg ctccgcggat gaggcggtca
45841  tttgctgtcc gcttttgcggg gacgggtcac ttttccgcgct ggcgtgaaag caatgtggga
45901  gctgctttttg gaaggcgccg gccggacgtc ggctaggcctc cttctccccg cgggctgggg
45961  gccctggggc tctgcaaggc tctggctccg aacagattgc gcctccccgcc tggctgccag
46021  taggaactgg ggtggggagcc gcgtaactaa cagttgcgcg caggaggcga gccccaggtg
46081  tgagcgcaga ggctctctcc ccagcccgcg ggtctgggaa cctttcagga cgcctccctc
46141  cccaactcct acccatgcgt ctgctcccta ggccgagccc ccctcgtgag gtttttaatga
46201  ccgcggacgc aggggagccc gcacttgagc gaggaccgac ttctctggcg ggtccacgct
46261  gctcgcgctt gcgtccgcgg gtagcgcgct gtgcccgggt caggggggcga gctgcgagaa
46321  gtaggagggg tcaagacccc cagaaatccc tccatgggca cacacacaat caagaatagg
```

-continued

```
46381  gttgagggtc ttgagaggta gaactaccct aggcagggct tctccaactc ggcctttgga
46441  ccccgcgcgc gcccaagggc gtgcccaccg cggaagcaca gatcatcttc ccgggactgg
46501  gtctcctgga ccctgcgttg ctcccttttt cctagcggcc ccgtagctgg ctgccgcatg
46561  tagggcgatc ttcattaact tggacgccca acgtgattga aatagagagg aggaaaaaac
46621  acatttgatc tgggccgacc ctttgtcttg aagcagatta ggcagcctag aaataggagg
46681  aaaaacagaa agtctaggca ggaaaactta ttgtgttcac aacatataaa aatgatccga
46741  gcggtctggt acctcaaggg gtgaagatag atcctgtag acgagtgtga agacatgact
46801  gggaagattt aaagtgaaag aaacggcaga ttattaagaa agtaatagta aggtgtccca
46861  tacactacag ttttattgtt gggtagtaac tacccgattt atttattgcc ggggctatat
46921  aatagagata atgaccacaa actcaagata aattcttatg cgcccagccg gtcaattctt
46981  ttttatttaa gagagtgagc ctgaagggtg agcctcatcc cctcccctcc tcgaagatcc
47041  gtcttgcttt ctaccatatt ataagcatga catgcaaata aataagtgct gctgggtctg
47101  tgtgggtagg ccggcaggat ttatttcagg tgacggagga acatacacgg aatatgaatt
47161  tccgcaggag tggcgccgtg attccttccc tctccctctc ggccgccctc tcctcagggt
47221  ctccctcctt ttctgtggga gcagagagca tcccctgtta aaaacattaa cgtgtcatgt
47281  ctcagctccc tattccttga catataggtc tggggaggga tgggggcact gcaaaatgca
47341  aaacgcatgc ccaaagtagg ttgacttgct gggactgctc aaagcgattc tggtggacaa
47401  agagaagggt gagttgtaat tatgacttcc agtaggggag cagtatagga agtatgttaa
47461  tatcattttg aaatatgcac aatggtccaa aagtttactg tcccggatct ggcatgggtc
47521  ctccccagcc ggatggaccc caagggggagc cctcctggca ccttgggaca tgcccgcctc
47581  tcttggccct cggtttctct ctctgggagc caggtaaaca ccccccctggc caggtgatgg
47641  agttaaagat gaccttgctc gttgaccgcc aaggtcggaa gagagctggc ggcctcaggt
47701  gtaggttcca cctgacgccc tggctgcaat catagtcacc ggctggcctt taagggggcg
47761  gcctcccaga actgctctcc ccacctgcac tctgcgacca ctcaggcaga tccggaacct
47821  gccaagacga agtcagtcag catcctcttc cgatcttctt attttcttcc tcatttttg
47881  gataatattc agacatacag tgtttcagtc tcacaataac cacttacatg cagaacttcc
47941  tttgatctgt ttggccagag tcggggggaa acacctgaca gtgaagaact gcgatgaaaa
48001  agaggggttc aggggagatg ggagagccag acgcgtgggg cgagggagaa ggaggtgcgt
48061  gtggggagat ggagacctag agacagcaag aagtagcaga tgggggagga aggtaaggcg
48121  agaaagtgaa gagcagctgc gagcgggaag agaaggggct gctcctgtaa tttggtggtt
48181  tgtgtgaagg atggtattat gaggctgaaa gagaggacaa tcctcgtcaa tcttttacaa
48241  tattggtgtc attcaagcac aactttatct ttgaaccaga ttatctgttc caatgatttc
48301  cataagaaca taaattataa ccttcagagc cttcaatatt tcttcggta ctttattaag
48361  tgttgttgca gaggctattt atgaagtgag tgattcaact tttaatcttt tgaacattaa
48421  agtgtattcc tccgagtttc cttttcaaaa taatctaaaa taacaaaaag aaactaagct
48481  cattacatga aaaagtgaca agcgttttg ctcgcagcct ggcaagttgc cttattcact
48541  tcaaaggatg atgaactaat tgtttccaga gtttataagt aattaagcta ttatttgggg
48601  aatttatgta acagttttat tcacattaga acttctatt taaaatagcc tgagacaaat
48721  actatttta ttttaaaaag cactggaaaa tgtaaacaaa tatagtttc tccagagtat
48781  atgataagtg gagatcatta tggataatta acgctgaaag gaaaatgaac atgtaatggc
48841  ttccaaaaat taaaacattt gtaactatca agttaagttc taaaaagtta attttaaat
48901  cagctggatt tatctaaata tgcctggcaa ggaaaaagat atatatatat atatatatat
48961  atatatatat atatatatat atatatatat ctatttactg tccttttaga actctataaa
49021  gaaagtttaa aaccttaaat aattttagca tttttaaacc aacttttggt gcctaggcaa
49081  taagattaa tgcccagaaa tgctaagtgc tgtagtttct ccaattttgc aacaaagaaa
49141  tatatttatt caccccctaga ttaaataaa gaaatattc taaaaatctt ttgaaatata
49201  taattcaaac accacttcca taatatttca atgcatgttt gttagtttta aataattagg
49261  tttgccataa atgaaacaaa attcattaaa ggaaaaagta ggactttaaa aggagtgatg
49321  aattattttg taaaattcag caaaatatac aacacttag tttaataggc atttgtatac
49381  ataacaatat accatttta tataattttc ccatccaaggt ggtattagct ctgtgtgtta
49441  gaaaatgcct gtttcattgt cacatgaaga atttcaaaaa taataaaatt ttcatattag
49501  gaggaaatat ctttgaagaa taacaaacac aaatgtgaaa atccaagtaa atgcctataa
49561  aatcttatat gaggtaaaat atattttctg gaagttatct ggaaaaaatt aaagcatgtg
49621  gtagttcaat attaattccc ctcaccacaa aaaattggg agttgtctgt agcaattatt
49681  acaagaggta gaatatatgt attaaataga aaaaaaatt taggacatat ccacttgttt
49741  caagtaaaat tcctctaaaa caaagtctg gaatttgatg gaaattgtat ataaaatgct
49801  ttgtataatt catggtcagt gttgttttgt ggactctgta taaactgtgg caatttagat
49861  ctgtcatggt atcacaatgt ctgattcaat atttgctgta atatgttctc tttattagta
49921  cagactagca ttgcattatt aaaaacaaaa actaaagcac cctggttagt agtaatgcaa
49981  tcccaatggt ctaaccccct gcgataattg accttctgga caccagacac tgggattcac
50041  tttcagacac ttagctgttt aaactgactt cattacagga ggacaatggt gactctgttg
50101  caactgacac ctgcactatt tcacacaacg catgggccat accttgccaa gtcagccacc
50161  accatgattc gcaccagagc aggaagtcag ctcgagacaa attttataat atgaatatac
50221  tgttacgatt aaggagaaat gaattcgttt tgcatagccc tctacaatct taaggagaca
50281  attagaagcc tgttttctgg tttccttgtg ttacaatatt gccatatgca aagatgtttc
50341  cattacttta cgctgaagtt taaaagttaa ggattttatg gtacacagca ttcaaggtgt
50401  ccatagtaat acagcatata gatagaaaa tactgttgtg ggaggctgag gcaggagaat
50461  ggcatgaacc cgggagacgg agcttgcagt gagccgagat ggcgccactg cactccagcc
50521  tgggcgacag agcaagactc cgtctcaaaa aagaaaaag aaaaatacag ttgtatcaca
50581  cctatgtcct agttgaaaag agtccattag tggaaaggtt tggggggcgg aggtggttag
50641  ctcactgacc agacttgcag gcactctgat tagttatcct aaatgaattg ctagaacata
50701  tgcaattcat tctccatgga tctttctcct aatctctaaa taataataat atatttcttt
50761  ttataaatc attttgtgtt gcagaatatg gtaaagcatt gttttaaatt atattgacta
50821  aaataaaatc tcagagggtt ctagatttt tctgaactca tagagagttc tagatgtgag
50881  ttctagattt ttttctgact cataagggaa tattactctg tcctcaaagt tctaagcatc
50941  tcagaattct gagatacttt ccttttgctct tctctggcca ccagaaggaa agtgacagtg
51001  cctattgtt ccaaagtatt tgctgaaggt aattaatacc tttattgatt aagttgcttc
51061  actgaaataa aaggtgactt ttcaccaat gactagattg tgatctaaca gactgaaaaa
51121  taacatgcca tattccaaag agagaagccc agcttctaag gcagaactcc atccctcccc
```

-continued

```
51181  agcttgtaaa aatccacaga tttactagtt tttatttaaa ttttgtgtta tgctaggctg
51241  gatcttgtct taaatccttg aacatttcta gcatattcca tcaaatgctt tgtaagactg
51301  aaaaaattct ctgtatgtgg gcttagaat cttaagcagt cagcaggaca ctgtagatac
51421  caccccacaa tccaaatcca tagcagtata cacaggtgct gtgcaatcac aaaagttaaa
51481  ccagaaaat ggaagaaggg agcccccaaa agtctttgtc gtgggctaag gtgagggga
51541  gtagagatca gggtatgttt ttaaatcaga gtttaaacaa gtaaacagaa accactctga
51601  gtgtatacaa gggaaggaat cgaatgcagg aaattggtta cacagggtat aggagaggct
51661  gcaaagccca ccagctggca gcaaggcaac cttgaggcag gaaatagcag gaaactctaa
51721  ccactcctag actggaggga cagagggcgc aggtgagtca ccagactcca ggggttggga
51781  ctacttggta gaagatgtaa ccggggaagg catgtccagt gggagctgga gctatggaag
51841  gaataaggga gggatacata ttctggagtc ctgcaatcta gagcagagca aggaagggcg
51901  aagaatagct ttgaaaggag acagttccag gagtggcatt tcttattata ttttttcaaa
51961  tgaaaatctt tcatattcat ttctgaagat actcatttga gaatgctgga gaaggaagag
52021  aagaatgttc caggcaaggg tactgaattg gaaaagaaag tgacttattt agaaagtcac
52081  aagtttgcca gtgcagcccg agtaaagagg aagatgtggg acattgtagg acatgagttg
52141  aagattctaa cagccaaaga catgaaatga ccagtggctt ctgtaacagc tttacttgct
52201  ctcaatcatt aagccccaga ggcccggata atagagacta caggggttaa cattgcaaaa
52261  cgctgcaaaa atagagacat gggtctccat acaggtgcaa tgctgcccac caacaaatgg
52321  catttctatg aagaaataca gtcatcatcc tgggctgcct tcagttaact tacattgtta
52381  tctgattcag ccacaaagcc agtgggacat cgattctgtc atttaatga acaaattaga
52441  tattgctcac taacccaaag gaaccatcct tgtggccagt ttggtgttca gagggctaga
52501  taaaaggttt tgtctactcc caggtaatag gaatagctca gtccatgacc tcacaggtgt
52561  cagtctcatg aataatagtt tgaagtagag ccagggagct aagaaaccag tgaaaacact
52621  attgtgatga tggtggggat gggaggtaag cgtgatgatt accagaagat attaggtgat
52681  agaagcacag aggagggga tgagatattg agaaccatgg catggtttct ggtttggaaa
52741  attctgcaga ttgtggttcc atttgctgga aagataacct tagaagaagg aacatattag
52801  aaaggaggat gttaaacttg ttttaggtat tttgagatta agatacttt gatttatcaa
52861  gatagagatg ctcattagga caatgaaaat atgggtctgc gttttagtgg agggagtctg
52921  ggctggagat aaaaatttgg gaggagtcat tggagtagat gagatcattc acaatctctt
52981  tcaagtggtt tatggtgaaa gaaaagaaag gaacaggccg tcagtaataa agggaacaa
53041  ggatatataa ttttgaagat gggaaagact tgaacatatt tgtataatga agggaaggaa
53101  gaggatatgc tgatattaca agaaagagtg ttaaataatg gagaaatcca tcatccaggt
53161  ggggaatgga ggaacggagc tattcctcag caggggaaga gcctggcctt caaggtcgaa
53221  ggcaggtaat gggtagagtt gtatgtccag gtcagggta gtggaggaag aatttggtag
53281  cagttcatac ttaaaaactt acgccttttt tttttttga gatatgggta gagatgtcat
53341  ttgatgagtg aggaagtagg aggggtgacca ggttgtagca cttaaaggcc tgtcccccag
53401  gaaccccttc agtcctggac aagctgagaa atttggtcac cccaaagagt aaaggaaagg
53461  gaaaggcttg agataaatgt gaaacattaa cagtcatcac aggaagtggg agagggagct
53521  gaccagaaat gcgaagctta ctggctggta tcgagaactt acatggaatt ggagattaag
53581  gggcaaggtt ttgtgcacgg ctgtggggtt ttcttcagca acacctaagc atactgagtt
53641  atcattccag gagagagtgt gttcatgcat ccaggtgtgt gtttgaagta ctttttagaa
53701  cccaaaagta tgtagtatca gagttccgt tctgggaaca ggaaaacaga gtgaaattag
53761  cagcaaggtt gccagaaccc tgttaggtag aagatcattc tgtcaacgat gtacatcact
53821  cttgcttcat gttttgcagtc gacaaatggc agttttcaca atccacaata tcttgaggta
53881  cccctgccat gcgggcatgt attcataata cctcttctct ctggaagggt aatttagaca
53941  ctgcagtcat taagcagtgt cttgaggtaa aaagcaccca catgcctgtg ggtgaacatt
54011  atctgttacc ccagctcatc cacaaggcgt gtcatgagaa tatttttgcct gtgtcattga
54061  ctaagttatg tacctttata ctggtaggaa tttcacctgt tgttggttat atgaacaaag
54121  aaaaatgtaa atatgtgatt gtctggctgg tcatagggca aatggggcaa tgagctccca
54181  taagtagatt caagtaaata tctggagttt tgactttct ttttgcagca catgcagttg
54241  gatagctccc aaatagatga agggttgttt tctctggtt gtgccctata tctaggacaa
54301  accagtacct ctaagtttcc aatacaggac agacaataag ccacaaaggg gaccaaacta
54361  catgatgaaa atctgaaact aagcttgggt tgaggaaggt actcaaatct tgtctgaaat
54421  ttgatgcagc ttggctcaaa actttccagg aattggctga ggctttagac aatagactga
54481  atggtgttcc tcaaaattca tgtgttgaag tcctatccca gtacctcaga atatgactgt
54541  gtttggagac agggtcttta aagaagtaac tgaggttaaa tgaggtaata cgtgtgggcc
54601  ctaacccaat ctaaccggtg tcttataggg agaggaagtt tagacataaa aagaggcact
54661  agggatgctg gagcacagag gaagcaccct gtaaggacac agtgagaaaa cagccaactg
54721  caagccagga agcaaggccc cagaagaaag ctacccacc catacccttgc atattagtcc
54781  attttcacgc tgctgataaa gacatacca agactgggta atttataaag aaaatgaggt
54841  ttaatggact cagagttcca cgtggctggg gaggccttac aatcatggct gaaggtgaaa
54901  ggcacatctt gcatggtgga agacaagaga taaatgagag ccaaacaaaa ggggaaaccc
54961  cttataaaat catcagatct catgagactt attcactacc acgaggacag tatggggaa
55021  accgtcccca tgattcaatt atctcccacc aggtcccttc tacaacacat gggaattatg
55081  ggacctacga ttcaagatga gatttgggtg gggacacagc aaaaccatat caccttgatt
55141  tcagacttca agcctccaga atgcaagaac ataaattttt gttaagtcac caggtctgtg
55201  gtatttgct atggcaaccc tcgtgaagca atacaggag gtttagagtt tgaattctca
55261  acaacttcag aaattgtgga tgcatcaatt atttttaac gtgaaatga atctaggaga
55321  tatctactga gaaactctgt ttttacctca acttatta tcaaatattt accaaacatt
55381  tttgtagcac ttagcaggag aggtgccttc attattcttt tcagctctta aacctttctt
55441  actctccttc acctcgtcct gcatgtctat aagcgcgaac tctattgaag tcattttaaa
55501  aatacactat ttttcaaatg acaatactgc atttttttc ttttctttc tttcttttct
55561  tttttttt tgagacggaa tcttgctctg ttgccaggct ggagtacagt ggcgccatct
55621  cggctcactg caagctccgc ttcccaggtt caagtgattc tcctgcctca gcctctcgag
55681  caactgggac tacaggcgca caacaccaca ccaagctaat ttttgtattt ttagtagata
55741  cggggtttca ctatgttggc caggatggtc tcaatctctt gacctcgtga tccacctgcc
55801  ttggcctccc aaagtgctag gattacaggt atgagccact acacccagcc gacaatactc
55861  catttttaac gaagtttagt tatgagtct gtaggcaggg ttttcattat gtttagtagg
55921  aattaagcct gtatgtgagc ataaagctat agtcaataat tttaccccct ttatgactgt
```

```
55981  aaaatttggg ccagtcaccc tacctggtta attctctgca gtatttaagg tatctatctc
56041  aagttgattc taaggttagg cacttttaat taaaaatgca tttctaaaat actttagaac
56101  atttagaaat gtcagcatga cgatgttgac aggggaatct ccatggcatt aagttgtgtg
56161  ttctgtgtt gagagcagat gctactaaaa gtatcgcaga agcgcaaaaa catctgacat
56221  tgcccggtga gcctatttgt agctgttggc ttagaataat ctatactgac ctgtaaggtc
56281  cgctttagta acaataacag gtaatgtact gaacctgcta taagcaaaag gatgttcatt
56341  aaatgtttgc ctttggtgaa ttttcctggt cattgttctt ggaaataata cggaggactg
56401  gaaattggga aattttataa actaatccta gtgttcccag gctgggcgca gcagctcaag
56461  cctgtaaacc cagcactttg ggaggccgag gcaggcggat cacgaggtca ggagatcgag
56521  accatcctgg ctaacacggc gaaacccccgt ctctactaaa aatacaaaaa aattagccag
56581  gcgtggtggt gggcacctgt agtcccagct gctggggagg ctgaggcagg agaatggtgt
56641  gaacctggga ggcggagctt gcagtgagcc gagatcgtgc cactgcactc cagcctgggt
56701  gacagagcaa gactccgtct cgaaaaaaaa ataaaaaaat aaaaaaataa atccagtgt
56761  tcctatttac ttattgtgtg gttttggtaa agtcaatcat agtgaacatc agtttgttca
56821  cctgtaaaat ggggaagatt ctatctttga atgctactt aaaggtgtta tgagaagaat
56881  attaaaagac caacgtgtat gtggtgcttt taaaacatgc tatccaaatt taaatattat
56941  attgttattg taattgccat taaatggttt aatttagcaa cacttttgaaa tggctttctc
57001  caattctaat tgaagtagca acttgggatc ccttcagtga tgaaaatcat agcaaacaca
57061  atctctatt gatcaggttt cccagaaaga cccctggttc caccatattt cagggagtat
57121  ctactggagc ttggtcaaca tcaacttttg ttttagtct tacattagac aatgctgttt
57181  ttctacaaat gtccccaata ttaccttttt aaaactcagt tgaagatgta aatgttatct
57241  cagatgaaaa actttcagaa cctaatgtca agttgcatgc gggaatgtgt catctcaaag
57301  tgttgtgaga aaggctcttt ccctagggt ctctgattct atccatgctg tacaacacca
57361  gtctccaacc cctgggccac ggaccctac ttgtctgtgg ctgttaggaa ccagggcacc
57421  cagcaggagg tgagccacgg gcaagtgagt gaaccagtaa atcttcatct gtatttacag
57481  tccctcccca tcacttgcat tactgcctaa gctctgcctc ctgtcagatc aactgtggca
57541  ttagattctc acagaagcat gaacctatt gtgaactgtg catgtgaggg atctaggctg
57601  tgcactcctt atgagaatct aatgcctggt gatctgttac tgtctcccat catccccaga
57661  taggaccatc tagttgcagg aaaacaagcg caggggctccc actaattcta cattatggta
57721  ggttgtataa ttatttcatt atatattaca atgtaataat actaatagaa atgaagtgca
57781  caataaatgt aatgcacttg aattatccga aaattatccc tccacatcat gcgagtccat
57841  gggaaaattg tcttatatga aactggttcc tggtgccaaa aaggttggag actgctgccg
57901  tactacattt atttgaatag attaatgaat ataagcctta tcactatgtt ttgttttttt
57961  ttttttttgag acagagtctc ttgcccatgt cacccaggct ggagtgcaat agcacaatta
58021  cgactcactg caacctctga ctcctgggtt caagcaattc tcctgtctca gcttcccaag
58081  tagctgggat tataggagcg agccaccaca ccagctaatt ttttttttggt atttttagta
58141  gagatggggt tttaccatgt tggccaggct ggtcttgaac tcctgacctc aggcgatctg
58201  cccacctcgg cctcccaaag tgctgggatt acaggcatga gccaccacgt ccaggctatg
58261  tattaacaaa gtgcattaag catgttgctg tcacttcctg tgttgagaca taggtaaatg
58321  ttcattaaat atgaaataat tcccataaaa tgctgctttt gaacccaaat tataatttgg
58381  gcaatgatcc aaaccatctg gagtctttgt catggatctc aggagtgtgg gcaaactaga
58441  gtacatgtgt atgtgtgtgg aagtgtgggt taggggagt tgtcattgct gggattggag
58501  gcttggcata gatttagagg agtttaacat ttgaaaaccc ctctattatg gaaagttttc
58561  aaatgtacac aaaagtcaag agactggtat aacagacttc catgtattca tcactctact
58621  tcaagaatta caatgatcaa cattttgcat cattttg gtccttttt tttttattt
58681  ttgagatgga gtctcactct gtcactcagg ctggaggggca gtggcgcgat cctggctcac
58741  tgaaaactct gcctcccagg atcaagcaat tctcctcctg cctcagtctc ttgagttgct
58801  gggatcacag gtgcgcacca ccaccctggg ctaagtttttg tgttttagtt agagatggga
58861  tttcaccatg ttggccaggc tggtcttgaa ctcctgacct caagtgatcc acctgcctcg
58921  ggctcccaaa gtgctaggat tgcaggtgtg agccactgtg ccaggcctga catttggta
58981  cttttgttc atgtattccc tccctcctc aagtctgtca cacacactct ctctctcgct
59041  cgctctctct cttcctccac ttgctctaat attttaaatc aatcaaacac tagatatcag
59101  tttatctcac ttttaaatat ttcagaatgc atatttaact agtagtgatt ttgttttgtt
59161  ttaatttaaa aaataaacttt ttcatttttga tgtaatttta aacttataga gaaattgcaa
59281  acatcttaat tttcctttat cactctgttt ttcatataat tgatatactt tgttttctga
59341  atcatttgaa gttaagttgg tgacaatata tatatcttt ttttttttt tttttgaga
59401  tggagtctca ctctatcacc cgagctggag tgctgtggtg tgatcttggc tcgctgcaac
59461  ctctgcctcc caggttcaag cgattctcct gcctcagcct cctaagtagc tgggattaca
59521  gctgtgtacc aacacgccca gctattattt tatttttattt tttttatt tatttattt
59641  cctgacctcg tgatctgccc accttggcct cccaaagtgt tgggattaca ggcttgagcc
59701  accgcaccta gcctaacatt atactctttt actattaaat cagtatgtat gttctatgaa
59761  caaagaaatg ttgttatata accacaggat aactatgaaa atcaggaaac ttaatatcaa
59821  tacaatacta ttatctcaatc cccagcccat atttaaatgt tatcaattgc cacaataata
59881  tcctttatat cattttacc cctaatccag agtctactcc aggattgtac attacttctt
59941  gtcacgtctc tttagtttcc tttaatctgg aacaagctgt tcctcagcct tttttggttt
60001  ttgttgacct tgacatttt gaagagtaca gaccagttgt tctgtggaat gtcccttagt
60061  tgggtttgt ttgatatttc cttttgattg gatttaggtt atgctttgtt ggcaggagca
60121  ctgcagaagg gatgttgtgc cttcagtaca cagtatcagc tggcacataa tgtccgtttg
60181  tctcagcaat ggtgacattt acttttaatta tttttgatcac aagttactgt ctgccaaata
60241  agagttattt tgagattatt atagaaatat tctgttctgc atcaaacgtt ggtccattag
60301  tgttaacacc cattgatgat tctctaactc cattattta atatattat cagttggcat
60361  tctattgtaa ggaagcattt tgccttttc caactttatt tattcatgca ctttttttct
60421  attaaaatgg gctaatggat tctttattt aatgggttat gatttattac tatattatt
60481  attttttgat gcttttttt tcttttaga tttggtcaat ggaaaccact ccaagttacc
60541  tcctgtgtct ttcgatgtc ctaaagagg cttaacttg taccttccat gttgaaatgg
60601  agactgagct cagctctcct attcacatgc taagttccaa gttacaatag actttctatc
60661  caaatccttc cttttttttt tttttttaa aagtacatcc ttggagtgag tcagtgtggt
60721  tagttgagta gcaggaaaag atttaactgt tctcatgtag gggaaagccc agttgatagt
60781  ctcttttggc ccctcatggc cgctatcacg agaaacattc cccactaaaa agtcaagcaa
```

-continued

```
60841   caggcttcct aatttctggc ttctgtctga aacaggcttt ttgagccagt taattgaaca
60901   taaattacaa ctgaccttgg agggattaac ttgcattttg gggtcatctc agctgcatag
60961   ctatttgggt gctttctgac tgcttgtgct tttatatact tttcagctaa gttagagatg
61021   aaaatgtacc actcagtgac attacaggaa ttgttgacct tctctggtca gtttgaggtc
61081   aaggaattaa tgcagagaat taccagaaga tctataaata cacgtttctt acatgagagg
61141   tatcattaaa aaatgatgtt cattttactt aactgtttca gatccatgtg tagtatgtga
61201   atagcagtca tataaaggga actctagttt tggggaacaa taaaataaga tttaaattaa
61261   acgtttaaaa aactacacta gcagtaggtt tcctaaaatt ccccttgtgac tgagccattt
61321   taatgttaaa aataggatga taaacccata ttcaaaagaa gaattattgt tcatgtcaaa
61381   ggctaaaaac attctttga ggtcaagtca gtcctgaaag taatcagtgt ggcccatgtc
61441   ttatgttttg ctctgcctct ttggtatatc aagaggttga attagaaatt ggtatgccag
61501   cttctccttg atgaatgagt gggaagagca tgacccttcag aaacacagac ctgggaccaa
61561   ataacactac tgacattgat tagttctcca tctttggcaa gttcttttat cattctaagt
61621   gtctgttttc tatctatgaa gaaaatgtct cagtctgtgc cactataaca aaaatacccca
61681   agactaggca attaataaga ataggaattt attccatacc attctggagg ctgggaagtc
61741   caagatcaag gcaccagtag agtctgtgtt tgtgacaact gctgtctgct tccaagacgg
61801   taccttgttg ctgcatcctc atatggcaga agaggcagtc tgtgtgtcct cacatggcag
61861   aaaagcagaa ggacaaaaaa gggcctacct agttccccca gtccttctaa aaggtcatta
61921   atttcattca taagggctct cttctcatga cttaatcact tccaacacct cacatttaa
61981   tgctgttgct ttgggggatt aaatttttaag atgaggctgg gcgcggtggc tcatgcctgc
62041   ctgtaatccc agcactttgg gaggccaagg cgggtggatc gcctgaggtc aggagtttga
62101   gaccagcctg gccaacatgg tgaaaccctg tctctattaa aaacacaaaa attagccaga
62161   tgtgctggca ggtgcctgta atcccagcta ctcgggaggc tgaggtagga gaattgcttg
62221   attcgggagg cagaggttgc agtgagccga gaatgtgcca ttgcactcca gcctgcgtga
62281   caagagtgag acttcatctc aaaaaacccc agaaaaacaa aaaaacaaaa tttaagatgg
62341   attttagagg agacacaat gccaagccat cagcaaatca acaatgtgca gggtagtgc
62401   aaggaatgaa agctatataa aactttata ccaagtataa tgccaacaca gaggcataga
62461   ggaggctctc catgattgtg atttctcttt ttttcccacc ctttcttcta atagcataac
62521   aatcaccacc atttattaat tgcttaaaac atgccagaat ctgatttgag tgctttacat
62581   gcatgatttg tgagagagga actattatct tcaatttgca gatgagaaaa ccaagattta
62641   gacatgttaa ggaccccttga ccaaatgttg gtgctggggt tttacatttg atgccagagt
62701   ccaagccctt aatcatcatg ctctcctgcc tctcataact atgtctcttt taaaccatac
62761   acttctctcta aatttgaagt agtaactcac gggtttacac aatactattg agtgggtgca
62821   gttgagagtc ctaaggtgtg gcaagggaga cttaaaaacc tgaactagaa gcagaaataa
62881   ttaagagtgc aggagaaaag acagggaaag gtcagagata aacttatcag gtaacaggg
62941   gctgaatacc actctctgtg tctctggagc ctttgattgc ttacttgaag ttagagatta
63001   aaaatataca tgattatcct acatgtttat ctatgtaaca aacatgcaca tcctgcatat
63061   gtatcccaga actaaaaata aaaattaaaa gaaagaaaat gataaaaata cacatgatta
63121   gtcctaatat taggtaggtg caaagtaat tgtggttttt gccattaaaa gtaatgctac
63181   tatttagcta ctgtttcttg aacatgtata catcaggcat tatgtgcttt atgggattgt
63241   cactttaaag ttacaggagc cctatgaggc atatttcccc cttgttctta gagtacgcct
63301   tgaaaaatat ttcacacccc agtcatttaa gcattctgt agcagaggct gcttgttgtc
63361   taccccaaca ttgactttcc cttccttctt aagaagggaa cctgagtttt agtcaggccc
63421   cttgccaggc agaattcgag ataattccca gcctctcctg cagctaagtg tggacatgtc
63481   tgaactctgg ccaagcagat agaaacagaa gtgctctgtg gggttctggg aaagctgttt
63541   aaaaggagtg gactctgctt gggggaaacc cctttgtctc tctttttttg aactttatt
63601   ttaggtttgg ggatacatgt gaaggtttat tatgcagtta aactcatgtc agggggggt
63661   tgctgtacag attatttctt cacttgggta ttaagcccag tacccaatag ttatatttctc
63721   tcctcctctc cctcctccca aactccattc tcaagtagac cccagtgtct gttgtttctc
63781   ttgcccttct ttttatttct acttgttagg tagcaattgg aatgttacag ctaagtttta
63841   gcaactatcc taaccatcg agtggcattg acgatagaaa ccacctggta agatggcaga
63901   gcagaaagag agaagactag gttactgatg acatcttaaa gttgctttac cagtcctggg
63961   ctgcctccct ctagttttac acaagaagga aacttaattt cttcttctct tcttctac
64021   ctcccttcgt tcctctctcc tctcccttcc ttccctccat tccttccttc cttcctctct
64081   tcttccttcc cttccacct ctccttgctc ttttccttcc tctctcccct tccttcctcc
64141   ctctctcttt atttctgttt gccactgtta gcttgcttt ttctcttata tataaccaag
64201   taattctaat tacagcttcc aaatatatgc ctagcttcct gtgggcatat cttgatatat
64261   tgggaaagcc tgtaaagctc tgaggttact ggttcaacct ttagttgaat acacttaact
64321   tacaaaatat taagctcatca tggaaataca cacagttgaa tattttgggc ctttatgtcc
64381   tttaacatct ttttgggcta cagcactttt agcagttaga atatattgac agcaaactca
64441   cagtgttttcc tccattttaat tcaaagaaag atgcattttgg aagaaaatta aagtcttgct
64501   gctctaaact attcctataa agtccatcag agactgcaca tcgttcaagg tcatgctgca
64561   aacagattcg gaatgggcaa gatgcttttg tgatgaaagt tattgcatca aacaaaactc
64621   aaaatttatt ccaggtggga tccaccaccc ctccccatgc tatcttaaca tcaaacacaa
64681   aactgacaca aaacaattct gtcctcctga tatactgaac tttgggcaca agtagagggt
64741   gcattacaaa gacatggttt catacttgag tacatgtgtt gggaaaaag ttttccactt
64801   aaatgtgatc catttaagga tagctaaata tatgctctcc tgctctattat atttacaatc
64861   atttttatct cagcaaaaga tgctgttatg gtgaaaatat attacacatg tcctttgctg
64921   actgagagag ttaaatgaa tagaacaata aagaaaaaaa gaagaagaaa aaaggaagaa
64981   atcctaaact ttattgccaa agccttacaa agacaaatat gggcagaaca tatatttaga
65041   gaccttggca aaagaaaatg gaaatatgag caattagctg aatatatttta gccaaaaatg
65101   gttgagaata tttattctct tttaaaatct taattgtcca tccccgtcgta ggctagattg
65161   actgaatttt ctgacacaaag tcataaagtt tccttaactt tgtgggaaca tgggttgtaa
65221   ctactcagta accactacca gtgactattt gttaaaaata caccatttgc aagcactga
65281   attagctttg tggtcataaa tgtattgtcc tatgagttaa atgaagattg ttaatggact
65341   cataggatca tacaatctca gtattttcag gaaatttaga tatatctatt tcaatccttt
65401   aaatccctcc cccagcacca ttttaaagat gaggaaactg aggccctaga gacttttcaa
65461   aatctcacaa cttgtacata aactccactt gtaaaataat ggtgttttgt acttttact
65521   agttttctaa agtggcccag tggagaaaag gaagcttttg ttcattactt tgaatttgtt
```

-continued

| | |
|---|---|
| 65581 | tctagttatg tttggtatca tgcttttctt ctggaaagat ttatcaataa gaagattata |
| 65641 | agatcaaaac cttccaaggg tgagttacct taaccttgtt gaaaattatt gatattagat |
| 65701 | attattacct ataagagaca tggactatga gaaaagactt cttttatttt cagtgatagt |
| 65761 | acactaagcc ttgtagcaaa acagaaatag taaactgcat attgattcca aagcaaatca |
| 65821 | agttaagtat cttctatgga catatagtca gataataaaa ctcaagaaaa taatgtatgt |
| 65881 | tcttctctgt tttccactaa actagggaat ctcctttaaa ctttgtatgc agtatggaaa |
| 65941 | taaggtttct gaagtaacca ttacaacatg tttcatgag tgtttattaa gaagccccaa |
| 66001 | acattttca gtaataaatc ggctgacata tccatagatt taaatctttt attggttact |
| 66061 | gattaacata actgctctgc ctgacaaatc tttataataa ataagccaac cagtgagcat |
| 66121 | ttcacaatga aaccaacttt gtttaaagga ctatcactaa aacaggattt atgcgctaat |
| 66181 | gaattttgca atcagcatgt ggtggtgtac aagtttcaac atgaatctaa aatgcagaaa |
| 66241 | tctgaagaca ctgaagttat taaaaatcac accacaacac aactacttt aattaaaaag |
| 66301 | aaatatatta cattcgtatt tagcagcagc attatagcgt atgaaaagga gaactcaggg |
| 66361 | ttactctttg aacatattct aacaaaatac agctgttgct gctatacagg ttaatgattc |
| 66421 | cttctcaaaa taaaattcct tgctatagtg attctgattt ttaaaaaaat caaaataagg |
| 66481 | aacaatgttt tttgtataca cataagccaa gtaaatagac aagatgatcc atgatggtga |
| 66541 | ttcagtaaaa taaaagttgc tgatggatat atatatatat atacatatat atatatatat |
| 66601 | actttcagtt tgattgaatt cttcttggaa agcctataga agtcactgga cttcttgtct |
| 66661 | ctgtttgaat taattaaatt gttgacagtg aaattgtcaa aagtagcttt ggtataaaaa |
| 66721 | atgattccca gatcttttc tctaaaactt aaaaaaaaat cctgacaaac ttgaaaagt |
| 66781 | tttaaacatc tgtctggaca gatgtcaaaa tgctgagtgt tataccatta tactgtgtca |
| 66841 | gtatctgaca ctatgttatt actcttcagt taaatattca cagtgagatt ttatgatctt |
| 66901 | ttttaaaagaa aacttgcatg agagagtaac tttatctgc acaacacata agcactttaa |
| 66961 | acaaatgaat ttcagagtaa acaatgaaaa ataacttttt gtgctagttt ttataccata |
| 67021 | ttttaatcac ttgggatttt cacatcagga ttttacaaat cattcaacag tatgtaatgg |
| 67081 | ataatgaacc atgttattaa ttttgaatat ttccctggaa agagaactt agtgagaatc |
| 67141 | atacataaat agcatagaga attacatatg gggaaaagat ggcattgcta aatcctaatt |
| 67201 | gttgtggagt atatattata gtaaaataaa caatgtttt caagaaatga gagatgaaaa |
| 67261 | ctgtcacgat attataaaat gcaacagtaa tttagcaagg aagacttcac tgaaagcaat |
| 67321 | atttagatcc agacactggg ttgctgagat gttatttcat tctgtgttca tctctacccc |
| 67381 | aaatcttcta gattagatat attatagtta gtttatttga tgaacatttt catattggga |
| 67441 | ttataagtgc ctgaaaatag aatttttaat gctttttaatg tgattaagga agcaaaacct |
| 67501 | ctcttttctc cctagaaatt actagccct tttgcactaa atacctacat cagacaaacc |
| 67561 | gccacaattt ccttgtattg ccagagagaa ttcttcaata aaacactgca attctctgtc |
| 67621 | aaagagacta acaatagcaa gagcatctca ctatttttct aatgagatgt gaatggaagt |
| 67681 | gtgaaggtga aaagacagat tctaggttgg cagattctag gttgactggc aaggtgagac |
| 67741 | cacttcttta gcaaaaggaa cccccctcct tgaaatgtca tgtttgatat aaacagaatc |
| 67801 | ttccctccct tcctgccttc cttcttctct tccttttcat cctttacttg gggagtcctc |
| 67861 | ctcatttgtc ttaaaaattc tgagatgaat tcatttgccc tcgaagccat cagatttgat |
| 67921 | gttgataaat ttaagtggtt taactttgga aaacatcaac ttatgtgtta atttccttcg |
| 67981 | tagcgatagc ctggcctcca ggtcacactg cgtagcctac ctgctatcaa tatcatcatt |
| 68041 | attgttttaa tcgttaaatt aaactgaatg aagttggtga tgagctgtca agaagtctca |
| 68101 | gagacaaggg caggccagtg ccccatttct tcttctaaac actttgtacc tattcataaa |
| 68161 | aattgaatga gattgtgtct gggaaactat tgtacactgc aaagcacaaa cataagggca |
| 68221 | gatgatgcca gtggtgatta tgatgatgcc cagcaatgtt gttcatttt aggctagaga |
| 68281 | tctggtagca gccttatgtt ttctgcttag gatacagtct tgaatagcat aatttgtact |
| 68341 | gatataaact agatttagcc attccctggg attctaaact attctcttat gatgcctctt |
| 68401 | ccactattgt acagaactat ttagctagga caagaaaaat tgattatttt tcccttctta |
| 68461 | gttttctaaa tgacattgcc cagattaatt agaaaattgc ccaaatctct cttttctcta |
| 68521 | ctctgctatg tagcacttgc aagaaaaaaa aaaagccaat ttcatgcaga agttgcttaa |
| 68581 | aattagtcaa aagcaaccc tgttctagtc ctgtacacat taagtaattc tcattgatca |
| 68641 | aaataggaag tgagcctgag aacaagggag aagagaggaa gtttgcagat ggacttctc |
| 68701 | ccccagtgtc attttcaacc aggtaaaatg gagttcgaaa ggcccaaatt ctcagcagat |
| 68761 | ttgcacagca cagtaatagc ctttatgctt ggaaatttat gggccatgga cagtttataa |
| 68821 | gaaacgatgt agttcatcag agagctagac tgatggggca tatgggagca ttctgcacag |
| 68881 | gaagttgggt tttggaataa tacttacttt gatagagttg ttttgttagc taagtaaaac |
| 68941 | agtagggaag ccaatggcca cttaggcttc agacataaat atatatttat aagtcaccca |
| 69001 | gctgcctaat tgagagccat agtgttttca ctgagtatat cttcaccaga aagcagtaga |
| 69061 | aacaacaata tcaccaagaa aaccccagtc ttggcataga tttattttaat cagtctttga |
| 69121 | tactttttgag ataattgaat tgctctctaaa tgtcgctctt ttaaagccag agggtgaggg |
| 69181 | gatggttaaa aagaagtttt ttgtttttt gtttttttaa gttggggttc ttttgtattt |
| 69241 | aaggtgcaaa gatacgaagt taaggtttat gttacacttg gggtagcaga gggctattac |
| 69301 | cagagatttg aaattgtggt tctatggact cctgatggga agagtgggga agctcagagg |
| 69361 | agcaagggtt gggcgtacaa ttgtctggtg ctttcaggtt tcacagaaga aggttaagca |
| 69421 | ggaggtggcc tgttaaattt gagcagagaa ctggaaaata agatttcaca ctcctgagac |
| 69481 | gccggaaggct ggtgagtttg gagtttgtct gggagatttg aaaaaggtcg agtgtgctat |
| 69541 | aaagtttctg aaattctatt ttagtgctta cgaacacgaa aaaagtaggt gttatgaaaa |
| 69601 | aaagcaaagg gcattttaaa actcaaataa gtatttggca tgtcgaaata aaatacacat |
| 69661 | ccacttctgc ttggctggac ctcctagaat tcaggcctta ctaacgatgt cttgttactg |
| 69721 | tgtcctccat tcaagcccct tcttcttt cttaagcttt tttttttt ttcctcttta |
| 69781 | tggccactgc tttaattatt tctctctttg cgttaagacc ctgagctgaa cttgtgttgc |
| 69841 | aagtggcagc atgggagtca gagatttggg ttctagtctg aggtctgttt cttgtgtga |
| 69901 | tcttaaggca ggacaccaac tctcatttgg cccttgcctt ccaacttgga ggaactgggg |
| 69961 | gtcaggtccc tgaggtcttt cttagtctg acattatttt atcttagagt cagttttgtt |
| 70021 | acttcaattc ttcctcctc ttctgggaca agcgtgaccc ttttattcaa ttgcttgctt |
| 70081 | tcttctttttc ttttcttttc cttttttta attaaaaaaa gatggatctc actatgttgc |
| 70141 | tcaggctggt ctcgaacccc caggctcaag agatcctccc acttcagctt cccaaattgt |
| 70201 | taggattaca ggtgcgagcc accatgccca gccaatcaat tgcttttttt tttttttt |
| 70321 | ggcgcaatct cggctcactg caagctccgc ttcccggggtt cacgccattc tcctgcctca |

-continued

```
70381  gcctcccgag tagctgggac tacaggcgcc cgccaccgcg cccggctaat tttttgtatt
70441  tttagtagag acggggtttc accttgttag ccaggatggt ctcgatctcc tgacctcatg
70501  atccaaccgc ctcggcctcc caaagtgctg ggattacagg cgtggccac cgcgcccggc
70561  cctcaattgc tttttataaa agtattcatt aatgctattt gatctctgtt tacatttaat
70621  tctctttgtc aattgtttt ctatttttt gcttctgatt ttacttgtat tctctttgct
70681  ccttggttcc ctctttgag gctgatttta tctttaaatt gttatctaat gtagaatata
70741  atattccgtc tcttcaagca tttatttttt ccttgtcttc aatgtttgat ctttaagagc
70801  taaagtacaa ctaaacacat tttaggcatt ttataaatat ttcttgattg attgattggt
70861  ttaataagat tccccaggtt tcagaccgcc catcttttca atttggcttt ggactcaggg
70921  ctatctcctg tgttttgga attagagtta aagccatccc tcacctagta taatatgatc
70981  actgggtcag gcaactcaca cctgtgcaat ctctagtctt aaatcctcta ttcttaaggg
71041  gctgacttaa aagatgactc agtctcattt cttttgctcc catccaaaat gaacaggaaa
71101  cataaaaggc attaagtaca ttggatagca gtcaaatttc taatagttca gttgtgctag
71161  gaaaattaaa cctatagtg tcagaaactc ccaaatgctt ttttttttt tttcaacttg
71221  caggactata aaataagagg tgtctctact aagagttaca aaatgttctg aaataacaac
71281  tcactggaga aatacagata agagtcctta aaagtataac ctcgaattag atccacattt
71341  ccctgtacta tggaacatta aaataattta atagcttgaa ggaaatgtta ctcgttgccc
71401  attatcttgc tactaatcta cgtatttcta tgaaaatgtc atacattttg tgctatatta
71461  agcacatttt agcatacact taaatagata ttatttattt tttaaatcct gaatggccaa
71521  tgattggtct ttgttaatta acattttatt aaatggaact catgatagag taaaatagaa
71581  aaaaacctgt ttctccatac tgctacagta ggtagctagt caggcatgag cagggcagga
71641  gagggctccc caacaccaca tcaggaatgc caggtgacca tcaggtgatg gtcacgtggt
71701  tgttaactct cgctgtaaaa taataattgg tcacagctgg caccagggaa cggccatctt
71761  ccaataggta gaaacacctg aaactggtga tcagcagctt cccagtaaaa tctcaggagt
71821  tgggagagtg gactcaagca tgccgcattaa gaggcaaaat ggtggagttt aactggtata
71881  tgaccttcct ctaggaatgt taggctggta agggaaaaac gtctcaagtg agcatgtgta
71941  caactccagt aaacacactg catgtgctcc cctcccaagg gctagcaggc cactgtgcat
72001  gtggacagcc caccccaagg gaagaataag gagagaagta acacaagacc tcagaagtat
72061  gccaacgtat aaaactccaa gtcaaaatgt caaaccacgc acttgactct ctcaagtcgc
72121  ctgcttggcc cgcttccaag tgtatgttac ttcttcgtat tcctgattca aaactttta
72181  gtaaaggttc actcctgctc taaaacttac ctcagtctct ccctctgcct tatgcacctc
72241  actctaattc tttcttctga ggaggcaaga attgagattg ctgcagaccc ttatggatat
72301  ggatttgctg ccggcaacta gtattattta actcattttg ctaagatttt ccaagaggtt
72361  tcatgttttt cgcagtccga ctataatctg gttctcagtc ttgccatttc aaatttcctt
72421  taaggaggca ttgggtttg ctttgaaagg cctacaagtt ggttgtcact agaggctagg
72481  gccaagctct tgcattaaga gacatactaa agagcaatca gaactttttg ataaaatagg
72541  ggtttgtaaa ttaatttact aacggttcat tatggtattc ccgtaatata ttttcctata
72601  actttaccga taattttttt tggcttgcat aacatttag aaatacttacg cttgttggaa
72661  atgccatgat tatattaaaa aattttttgtt gttatctatc caatactcat gatgctaggc
72721  taaattctgc tgaaaagaaa tacaaacata ttgcaaaaag ttacagacat agtaaaacct
72781  tggaagacag ggactggtta atgaaattac tgaaaaaccc aactatatag tattactctt
72841  ttacatatat aaaattaaat aaaaagaatt gatcagaatc ttcttaatta aagtttgctg
72901  gtatatgtca gtagatgtca atattataaa gtgcaaaata agattttccc atcgattcag
72961  tgaattgttg tctaattata tttatttat ttatttttga gatggagttt tgctctgttg
73021  cccaggctgg agtgcagtgg cacaatctca atcttgggc actgcaacct ttgcctccca
73081  agttcaagaa attctcctgc cttagcctcc tgagtagctg ggattacagg tgcacagcac
73201  ggtctcaaac tcctgacctc aagtgatctg cccaccttgg cctcccaaga tgctgggatt
73261  acagatgtga gccaccacgc ccagcctgtt gtctaattct aaacagtttg atgcctatga
73321  tgtatacatt tgttcatcaa aacaaattta gaacagtgaa cctcaaggga tgtgaaatta
73381  tttttttaaag acgagacaga atgatggta tttttgctct aagaaaaagg agattagatt
73441  gttctgcaac ccatttttg ggaaggtctg tgtcctggct cttttccttc taattatgtt
73501  gggaagtgca atgacatgat aaggttttt aaatatatat aaatgaaagt attgtcttaa
73561  tgtagtagtg cattcagcct tgatgtctac aaaccttcag tatgttgcag tgatttaaaa
73621  gtatccttac aattcatatg taaggatgtt atatgtattc caaaagaaaa tgtattaatg
73681  ctaatcctga gtaaagctgt gagtcttaaa ggatgccttg tccaccaaaa agggattaga
73741  ataggcccat tggttcaggg atgtgggaag gatcttggca tacacttggg tttcaggtga
73801  aaaaatatga gagtaaccctg atggaaatgg aaacaccacg accaggaaag ggatctgaaa
73861  gtttcctgct gtcatgatgt ggataattca aatcaacaaa ttatcctaaa agaagtcaca
73921  aaataggtga aacatttagg attctagcag gagtcaatga aaactgttt ttttaaaat
73981  tatactttaa gttctagggt acctgtgcac aatatggagg tttgttacat atgtaaacat
74041  gtgccatgtt ggtatgctgc acccatcaac ttatcattta cattaggtat ttctcctaat
74101  tcctatccctc ccctgcccc ccaccccagg acaggcccca gggtgtaata ttccccgccc
74161  tgtgtccatg agttctcatt gttcaattcc tacctatgag tgagaacatg cggtgtttgg
74221  ttttctctcc ttgtgatact ttgctcagaa tgatgatttc cagctgcatc catgtccegg
74281  caaaggacat gaactcatca ttttttatgg ctgcatagta ttccgtggtg tatatgtgcc
74341  acattttctt aatccagtct atcattgatg gacatttggg ttggttccaa gtctttgcta
74401  ttgtgaatag tgccacaata aacatacctg tgcatgtgtc tttatagcag catgatttat
74461  aatcctttgg gtatataccc agtaatggga tggctgggtc aaatggtatt tctagttctg
74521  gatcctgag gaatcaccac actgtcttcc accatggttg aactagtta tactcccacc
74581  aacagtgtaa aagcattcca atttctccac atcctctcca gcatctgttg ttcctgact
74641  ttttaatgat tggcattcta actggtgtga gatggtatct cattgtggtt ttgatttgca
74701  tttctccgat gaccagtgat gatgagcatt tttcatgtc tgttggctgc ataatgtct
74761  tcctttgaga agtctctgtt tatatccttc acccacttt tgatgggctt gtttgtttt
74821  tcacgtaaat tgtttaagt tctttgtaga ttctggatat tagcccttg tcagacaggt
74881  agattgcaaa aatttttcttc cattctgtag gttgcctgtt cactctgatg atagttcctt
74941  ttgctgtgca gaagctcttt agtttagtta gatcccattt gtctattttg gcttttgtgg
75001  ccattgcttt tggtgtttta gtctttgccc atgcctatgt cttgaatggt attgcctagg
75061  ttttcttcta gggtttctat ggtttaggtc taacatttaa gtctttaatc catcctgaat
75121  taattttga ataaggtcta aggaagggat ccagtttcag ctttctacat atggttagcc
```

```
75181   agttttccca gcaccattta ttaaataggg aatccttcc ccatttcttg ttttttgtcag
75241   gtttgtcaaa gatcagatgg ttgtagatgt gtggtgttat ttctgaggcc tctgttttgt
75301   tccattgctc tacatgtctg ttttggtacc agtgccatgc tattttggtt actgtagcct
75361   tgtagtgtag tttgaagtca ggtagtgtga tgcctccagc tttattcttt ttgcttagga
75421   ttgtcttggt aatgtgggct ctttttttggt tccatatgaa ctttaaagca gttttttcca
75481   actctgtgaa gaaagtaatt ggtagcttga tgggggatggc actgaatcta caaaatacct
75541   tgggcagaat ggccattttc attatattga ctcttcctat ccatgagcat ggaatgttct
75601   tccatttgtt tgtgtcctct tttatttttgt tgggcagtgg tttgtgggtt tccttgaaga
75661   ggtccttcac atcccttata aattagattc ctaggtattt tattctttt gtagcaatta
75721   tgaatgggag ttcactcatg atttggctct gtttgtctgt tgctggtgta taggaatgct
75781   ggtgattttt gcacattgat tttgtatcct gagactttgc tgaagttgct tatcagctta
75841   aggagacttg gggctgaggc gatggtgttt tctaaaatata caatcattta ttctgcaaag
75901   agggacaatt tgacttcctc ttttcctaat tgaataccct ttatttcttt ctcttgcctg
75961   attgccctgg ccagaacttc caacgctatg ttgaatagga gtggtgaaag agggcatccc
76021   tgtcttgcca gttttcaaag ggaatgcttc cagttcttgc ccattcggtg tgatattggc
76081   tgtgggtttg tcataaatag ctcttattat tttgagatat gttccatcaa taccttgttt
76141   gttgagagtt tttagcatga agcactgttg attttttttc aaaggcctt tctgcatcta
76201   ttgagataat catgtggttt ttgtcattgg ttctgtttat gtgatggatt atgattattg
76261   atttgcgtat gttgaaccag ccttgcatcc catggatgaa gttgacttga tcatggtgaa
76321   taagcttttt gatgtactgc tggattcagt ttgccagtat tttattgagg attttttgcat
76381   cgatgttcct cagggatgtt ggtctaaaat tctctttttt tgttgtgtct ctgccaggct
76441   ttggtatcag gatgatgctg gcctcataaa atgagttagg gaggattccc tcttttttcta
76501   ttgattggaa tagtttcaga aggaatggta ccaactcctc tttgtacttc tggtagaatt
76561   cggctgtgaa tccgtttggt tctggactt ttatggttgg taggctatta attattgcct
76621   taatttcaga gcctgttatt gatctattca gagattcaac ttcttcctgg tttagtcttg
76681   ggaggctgta tgcatccagg aatttatcca tttcctctag attttctagt ttatttgcgt
76741   agaggtgttt atagtattct ctgatggtag tttgtatttc tgtgggattg gtgatgatat
76801   ccctttatc acatttatt gcgtctattt ggctcttctc tcttttcttc tttattagtc
76861   tcattagctg tctatcagtt ttgttgagct tttcaaaaaa ccagctctg gattgattga
76921   ttttttgaag agttttttgt atctctatgt ccttcagttc tgctctgatc ttagttattt
76981   cttaccttct gctagctttt aaatttgttt gctcttgctt ctgtagttct tttaattgtg
77041   atgttagggt gttgatttta gatctctcct gctttctctt gtgggcattt agtgctataa
77101   attcccctct acacactact tcaaatgtac gttgtatctt tgttctcatt agtttcaaag
77161   aacatcttta tttctgcctt cacttcatta tttacccagt agtcattcag gagcaggttg
77221   ttcagttccc atgtagttgt gcggttttga atgagtttct taatcctggg ttctaatttg
77281   attgcactgt tgtctgagag acagtttgtt gtgatttctg ttcttttaca tttgctgagg
77341   agtgccttac ttccaactat gtggtcaatt ttggaataag tatgatgtgg tgctgagaag
77401   aatgtatatt ctgttgattt gggatggaga gttctgtaga tgtctattag gtctgcttgg
77461   tgcagagctg agttcaagtc ctggatatcc ttgttaacca tctgtctcgt tgatctgtct
77521   aatattgaca gtggggttgtt aaaatctcca attattattg tgttggagtc taagtctctt
77581   tgtaggtctc taaggacttg ctttatgaat ctgggtgctc ctgtattggg tgcatatata
77641   tttaggatag ttagcacttc ttgttgaatt gatcccttta ctattatgta atggccttct
77701   ttgtctcttg atctttgttg gtttaaagtc tgttttatca gagactagga ttgcaacccc
77761   tgctttttt tttgcttttcc gtgtgcttgg tagatcttcc tccattttt attttgagcc
77821   tatgtgtgtc tctgcacgtg agatgggtct ccttataga gcacactgat gggtcttgac
77881   tctttatcca atttgccagt ctgtgtcttt taattggggc agttagccca tttacattta
77941   aggttgatat tgttatgtgt gaattttgttc ttgtcattat gatgttatct ggttattttg
78001   cccattattt gatgcagttt cttcctagca tcgatggtct ttataatttg gcatgttttt
78061   acagtggctg gtattggttg ttccttttcca tgtttagtgc ttccttcaga agctctttta
78121   gggcaggcct ggtggtgaca aaatctctca gcattttgctt gtctgtaaag gatttttattt
78181   ctcttcactt atgaagctta gtttggctgg atatgaaatt ctgggttgaa aattcttttc
78241   tttaagaatg ttgaatattg gccctcactc tcttctgggt tgtagagttt ctgctgagag
78301   atcagctgtt agtctgatgg gcttccctt gagggtaacc caaccttct ctctggcctgc
78361   ccttaacatt tttccttcat ttcaacctttg gtgaacctga caattatgtg tcttggaatt
78421   gctcttcttg aggagtatct ttgtgctgct ctctgtattt cctgaatttg aatgttggcc
78481   tgccttgcta ggttgggaaa gttctcctaa cagtgtttc caacttggtt ccattctccc
78541   catcacttttc aggtacaccg atcaaaggta gattttggcct tttcacatgg tcccatattt
78601   cttggaggct ttgttcgttt cttttttactc ttttttctct aaacttatct tctcacttta
78661   tttcattaat ttgatcttca atcactgata cccttttcttc cacttgattg aattggctat
78721   tgaagctgtg catgtgtcgt gtagttctca tgccatggtt ttcaactcca tcaggtcatt
78781   taaagtcttc tctacactgt ttattctagt tagccattca tataatcttt tgtcaaggtt
78841   ttttccttcc ttgcaatgag ttcaaacatc ctccttttagc tcggagaagt ttattattac
78901   cgaccttctg aagcctactt ctgtcagctc gtcaaagtca ttctcagtcc agctttgttc
78961   tgttgctggc gaggggctgc aatccttttgg aagagaagag gtgctctggt ttttagaatt
79021   ttcagctttt ctgtctctggt ttctccccat ctttgtggtt ttatctacct ttggtctttg
79081   atgttggtga cctacagctg gggtttttggt gtggatgtcc tttttgttca tgttgatgct
79141   attccttttct gcttgttaagt tttccttcta acagtcaggc ccctccacctg cagatctgtt
79201   ggagtctgct agaggtccac cccgaccct gtttgctggg gtatcactag cagaggctgc
79261   agaacagcaa atattgcaga acagcaaata ttgctgccta atccttcctc tggaagcttc
79321   atcccagagg agcaccgcct gtatgatttg tcagtcagcc cctactggga ggtgtctccc
79381   agttaggtta cacgggggtc agggacacac ttgaggaggc agtctgtttg ttctccgagc
79441   tcaaacacca tgctggggga accactgctc tcttcagagc tgtcagacag ccatgtttaa
79501   gtctgcagag gtttctgctg ccttttgttc agctatgccc tgcccccaga gatggagtct
79561   actgaggcag gaggccttgc tgagctgaga tgggctccgc ccagtttgag ctttcctggc
79621   tgctttgttt acctactcaa gcctcagcaa tggtggatgc ccctcccct gccaggctgc
79681   tgcctcgcag gttgatctca gactgctgtg ctagcagtga gccaggctct gttggtgtgg
79741   gacccgccaa tccaggcatg ggatataatc tccggtgtg ctgtttgctg agaccattga
79801   aaaagtgtaa tatttgggca ggagtgtccc attttttccag gtactgtctg tcatggcttc
79861   ccttggctag gaaagggaaa ttccccgacc ccttgtgctt cctgggtgag gcaatgccct
```

-continued

| | |
|---|---|
| 79921 | gccctgcttc ggctagccct ccatgggctg cacccactgt ccaaccagtc ccagtgagat |
| 79981 | gaaccaggta cctcagttgg aaattcagaa atcacccgtc ttctgcatca atcacactgg |
| 80041 | gacctgcaga ccagagctgt tcctattcag ccatcttgga acagaacgtg aaaactgctt |
| 80101 | tgttaatatg ctttctttac ctccagattt ctcccaaatg aactcccata gacctcataa |
| 80161 | tgtgaagata caaacctcta tgaggaaaaa tcagcagaca caacaaacag gagatttttt |
| 80221 | atgtaatgta atggcccca aactggatat tatagaataa tgtaaatgag attatgtatt |
| 80281 | caatatgtta attaattaag gaaaacagaa ggaacagaaa tcacaaagaa acattagaaa |
| 80341 | gtcatggaaa aagtagggcc ctatttataa aatagcaaaa tagaagatat agaaataaaa |
| 80401 | aaatcattga aattaaaaaa tgtaaataca ttattaattt atgctaattt aaatgttaga |
| 80461 | caaatagaat aataagacag aaatgtatcc aagcatgtat aaagatttat tgtttaacag |
| 80521 | gtcaatgaag aaaatgattg aatatttagc aattaccact gtgtcaaatg atagtcatct |
| 80581 | ggaaagaaga aaactggatt tctgctttat agcaaataaa aaaatcaaag ttgagataga |
| 80641 | ttaaagatct aaaaaacacc catatttca acaccttgg gaaaattata ggaaaatatt |
| 80701 | atgtcagggt gtacaagaac tttataagta gtcgcaaata aaatagtatc ctgcaaaaga |
| 80761 | aagaatttag accctacct cacatcatat atgaaattaa ctaaaaaatg gatcaaagac |
| 80821 | ctaaatataa gaacctcaaa ctataaaatc cttagaagaa aaaaagtgta gatctttatc |
| 80881 | agcttggatt aggcaatggt ttcttagcta tgacagaaaa aggataaaca acaaaataaa |
| 80941 | tggataaatt gtactttatc aaacttaaaa acgtttatgt ttcaaaggat accatcaaga |
| 81001 | aggtgaaaag aaaacctaca aaatgtgaaa aatatttgca aacatatatc taacaaagta |
| 81061 | cctgtatcca gaatatataa tgaacactta gcaataacaa ataaaaagac aaataaccca |
| 81121 | attaaaaatg ggcaaaagat ttcactagac atttatccaa agaagattta taagtgacca |
| 81181 | ataagctcat gaaaggatgt tcagcattga tagagaaacg caaatcaaag tcacaataag |
| 81241 | atgccataaa attttacact cactaggatg gctataataa aaaagatggg ctgttggagt |
| 81301 | tttgaagagt atgtgaaaaa ttttgaacac tcatcatga atggtggaaa tgtaaaatgc |
| 81361 | tccagctgct ttggaaaaca gtctggtact tcctgaaaat tttaaataca gagtttttctt |
| 81421 | ttatatacat atatatattt atttaagttg tagggtacat gtgcaaaatg tgtaggttta |
| 81481 | ttacatatgt atacatgtgc catgttggtg tgctgcaccc attaactcat catttacatt |
| 81541 | aggtatatct cctaatgcta tccctccccc tgcccccac cccacgacag gccccagtgt |
| 81601 | gtgatattcc ccttcctgtg tccatgtgtt ctcatgttcc aattcccacc tatgagtgag |
| 81661 | aacatgtggt gtttggtttt ttgtccttgt gatagtttgc tgagaatgat ggtttccatc |
| 81721 | ttcatccatg tccctacaaa ggacatgaac tcatcatttt ttatggctgc gtaatattcc |
| 81781 | atggtgtata tgtgccacat tttcttaatc cagtctatca ttgttggaca tttgggttgg |
| 81841 | ttccaagtgt ttgctattgt gaatagtgcc acaataaaca tatgtgtgca tgtgtctta |
| 81901 | tagcagcatg acttataatc ctttgggtat atacccagaa atgggatggc tgggtcaaat |
| 81961 | ggtatttcta gttctagatc cctgaggaac caccacactg tcttccacaa ggggttgaact |
| 82021 | agtttacagt cccaccaaca gtgtaaaagt gttcctattt ctccacatcc tctccagcac |
| 82081 | cttttgtttc ctgactttt aatgattgcc attctaactg gtgtgagatg atatctcatt |
| 82141 | gtggttttga tttgcatttc tctgatggcc agtgatgatg agcatttttt catgtgtctg |
| 82201 | ttggctgcat aaatgtcttc ttttgagaag tgtctgttca tatccttcac ccacttgttg |
| 82261 | atggggttgt ttgttttttt cttgtaaatt tgtttgagtt cttcgtagat tctggatatt |
| 82321 | agcccttttgt cagatgagta gattgcaaaa attttctccc attttgtagg ttgcctgttc |
| 82381 | actctgatgg tagtttcttt tgctgtgcag aagctcttta gtttaattag atgccatttg |
| 82441 | tcaattttgg ctttgttgc cattggtttt ggtgttttag acatgaagtc cttgcccatg |
| 82501 | cctatgtcct gaatggtatt gcctaggttt tcttctaggg tttttatggt tttaggtcta |
| 82561 | acattaaagt cgtttatcca gcttgaatta attttgaat aaggtgtaag gaagggatcc |
| 82621 | agtttcagct ttctacatat ggctagccag ttttcccagc accatttgtt aaatagggaa |
| 82681 | tcctttcccc atttcttgtt tttgtcaggt ttgtcaaaga tcagatagtt gtacatgtgt |
| 82741 | ggtatttaaa tacagagttt tcatatgacc cagaaattct actcctaggc agagtctcaa |
| 82801 | ggtaattgaa aatgtatgtc caccaaaaac ttgtagtgaa tgttcctact ggtgttaatt |
| 82861 | atcatagccc tgaagtggaa acaacccaaa tttccatcag ttgatgagtg gataaacaaa |
| 82921 | atgtggtaaa tccttgcaat ggaatattat ttggccataa aatggaagta cagctacatg |
| 82981 | ttacagcatg catgaatgtt aaagccatta tacttagtga aggaagccat cacaaagagt |
| 83041 | cacatattgt cagatttcct gtatatacat catccaaaat gggtaaatcc atagagacag |
| 83101 | taggagattc atgggttgcca agggctgggg gtgggcaaaa tgggaagtga ttgctaatgg |
| 83161 | gtatgagatt tttttgggg aggggtgata aaaatgttct gaaattaaat aatggtgata |
| 83221 | attgcacaac tttaaatata ctaaaaaacg tggaattgca tactttgaaa ggataagttt |
| 83281 | tttgttatgt gaattccatc tgaatttaa aagaagaga aaaactaaaa aagattgatt |
| 83341 | aacttgatgt tgaatttta acagcttat gaaagagcat atataacaag ctgtgtatca |
| 83401 | ttatccagga tatataaatg actcctacaa ataatgaaa taaaggcaaa atttccacca |
| 83461 | aataatatgc aaacatttgc atatgcaaat aataagcaaa cgtggctagc cagttttccc |
| 83521 | agcaccattt attaaatagg gaatcctttc cccattgctt gtttttgtca gatttgtcaa |
| 83581 | agatcagata gttgtagata tgtggcatta tttctgaggg ctctgttctg ttccattggt |
| 83641 | ctatatctct gttttggtac cagtaccatg ctgttttggt tactgcagcc ttgtagtata |
| 83701 | gtttgaagtc aggtaacatg atgcctctag ctttgttctt ttggtttagg attgacttgg |
| 83761 | caatgcgggc tctttttgg ttccatatga aatttaaagt agtttttccc aattctgtga |
| 83821 | agaaagtcat tggtagcttg atgggggatgg cattgaatct ataatgacc ttgggcagta |
| 83881 | tggccatttt cacgatattg attcttccta cccatgagca tggaatgttc ttccatttgt |
| 83941 | ttgtatcctc ttttatttcc ttgagaagtg gtttgtagtt ctccttgaag aggtccttca |
| 84001 | catcccttgt aagctggatt cctaggtatt ttattctctt tgaagcaatt gtgaatggga |
| 84061 | gttcactcat gatttggctc tctgtttgtc tgttattggt gtataagaat gcttgtgatt |
| 84121 | tttgcacatt gattttgtat cctgagactt tgctgaagtt gcttatcagc ttacatagat |
| 84181 | tttgggctga gacgatgggg ttttctagat atacaatcat gtcatctgca aacagggaaa |
| 84241 | tttgacttcc tcttttccta attgaatgcc ctttatttcc ttctcctgcc taattgccct |
| 84301 | ggccagaact tccaacacta tgttgaatag gagtggtgag agagggcatc cctgtcttgt |
| 84361 | gccagttttc aaagggaatg cttccagttg ttgtccattc agtatgatat tggctgtggg |
| 84421 | tttgtcatag atagctctta ttattttgag atacgtccca tcaatacctaa atttactgag |
| 84481 | agttttagc aggaagactt gttgaatttt gtcaaaggcc ttttctgcat ctattgagat |
| 84541 | aatcatgtgg tttttgtctt tgattctgtt tatatgctgg attacgttta ttgatttgca |
| 84601 | tgtattgaac gagccttgca tcccagggat gaagtccact tgatcatggt cgataagctt |

-continued

```
84661  tttgatgtgt tgctggattt gttttgccag tattttattg aggattttg catcaatgtt
84721  catcaaggat gttggtctaa agttctcttt ttttgttgtg tctctgccag gcttggtat
84781  taggatgatg ctggcctcat aaaatgagtt agggaggatt ccctcttttt ctattgattg
84841  gaatagtttc agaaggaaca gtaccagctc ctccttgcac ctctggtaga attcggctgt
84901  gaatccatct ggtcctggac tttttttggt tggtaagcta ttaattattg cctcaatttc
84961  agggcctgtt attggtctat gcagagattc aacttcttcc tggtttagtc ttgggagagt
85021  gtatgtgtct cggaatttat ccatttcttc tagattttct agtttatttg cataaaggtg
85081  tttatagtat tctctgatgg tagtttgtat ttctgtggga tcagccggtga tatcctcttt
85141  gtcattttt attgtgtcta tttgattctt ctctctttc ttctttatta gtcttgctag
85201  cggtctatca attctgttga tcttttcaaa aaaccagctc ctggattcat tgattttttg
85261  aaggggttttt gtgtctctat ttccttcagt tctgctctga tcttagttat ttcttgcctt
85321  ctgctagctt ttgaatgtgt ttgctcttgc ttctctagtt cttttaattg tgatgttagg
85381  gtgtcagttt tagatctttc ctgctttctc ttgtgggcat ttagtgctat aaatttcgct
85441  ctacacactg ctttgaatgc gtcccagaga ttctgatgtg ttgtgtcttt gttctcattg
85501  gtttcaaaga acatctttat ttctgccttc atttctttat gtacccagta gtcattcagg
85561  agcaggttgt tcagtttcca tgt gttgag tggttttgag tgagtttctt aacctgagtt
85621  ctagtttgat tgcactgtgg tctgagagac agtttgttat aatttctggt ctttcacatt
85681  tgctgaggag tgctttattt acaactatgt ggccaatttt ggtccatata tctaccagta
85741  cattgctgtt ttggttactg taggcttgca gtatagtttg aataaggtag catgatgcct
85801  ccagctttgt tctctttgct taggattgtc ttggctatat ggggtctttt ttggttccat
85861  atgaaattaa agtattttt ctaattctgt gaagaaagtc agccggtagct tgatgggaat
85921  ggtatcgaat ctataaatta ctttgggcag tatggccatt ttcatgatat tgattcttct
85981  tatccatgag catggaatgt tcttccattt gtttgtgttc tttcttattt ccttgagtag
86041  tggtttgtag ttctccttga agtcctccac atcccttaa gttgtattcc taggtatttt
86101  attatttttg tagcaattgt gaatcagagt tcattcatga tttggctctg tttgtctatt
86161  attgatgtat aggaatgctt gtgattttg cacattgatt ttgtatcctg agactttgct
86221  gaagtttaag gagtttttgg gctgagacaa tgggttttc taaatataca ataatgtcat
86281  ctgcaaacag agataatttg acttatcttc ctgtttgaac acccttatt tcttctctt
86341  gcctgattgc cctggccaga acttccaata ctatgttgaa taggagtggt gagagagacc
86401  atcttttctt gtgcaggttt tcaaagggaa tgttttcagc ttttgcccat tcagtatgat
86461  attgactgtg ggtttatcat aaatagctct tattattttg agatacattc catcaatacc
86521  aagtttattg agtgtttgga acatgaaggg gtgttgaatt tttatgaaag gactttctg
86581  catctattga gataatcatg tggtttgtgt cactggttct gtttatgtga tggattacat
86641  ttattgattt gcatatgttg aaacagcttt gcatcccatg gatgatgcca acttgatcat
86701  agtggataag cttttaatg tgccactgga tttggtttgc cagtatttta ttgaggattt
86761  tcacatcaat attcatcagg gatattcgcc tgaaattttc ttttttgt gtgtctgc
86821  taggttttgg tatcaggatg atgttggtct cctaaaatga gttaggggagg agccctctct
86881  ttctattgtt tggaatagtt ttagaaggaa ttgtaccagc tccttttat acctatggta
86941  gaatttggct gtgaatccat ctggtcctgg gctttttg gttggttggt attaattact
87001  gcctcaattt ccgaacttgt tattggtcaa ttcagggatt caccttcttt cttgtttagt
87061  cttgggaggg tgtatgtgtc caggaattta tccattctt ccagagtttc tagtttattt
87121  gtgtagagct gtttatagta ttcctctgatg gtagtttgaa tttctgtggg atcagtggtg
87181  atatccccctt tatcattttt tattgtgtca atttaattct tctttcttt cttcttatt
87241  agtctggcta gcagtctatc tattttgtta atcttttcaa aaaatcagct cctgaattca
87301  ttggtttttt ttgaaggggtt tttttttgt gtctatctcc ttcagttctg ctctgatgtt
87361  agttatttct tgtcttctgc tagcttttgg gtttgtttgc tcttgcttct ctagttcttt
87421  taattgtgat gttagggtgc tgatttagaa tcttttctgc ttctccttgt gggcatttag
87481  tgctataaat ttcctgctac acactgctgt agctgtgtcc cagagattct tgtatattgc
87541  atctttgttc tcattggttt caaagaatgt attatttct gccttgcagg ttgttgagtt
87601  tgcatgtagg tgtgtggttt tgagtgagtt tctgaatcct gagttctaat ttgattgcac
87661  tgtggtctga gagactgttt gttatgattt ctgttctttt gcatttgcag aggaatgttt
87721  tacttccaat catgtggtca atttagaat aagtgctatg tggtgctgag aagaatgtat
87781  attctgttcc cttgtggtgg agagttctgt agatgtctat taggtctgca ttgtgggagag
87841  ctgagttcaa gtcctgaata tccttgttaa ttttctgtct cattgatctg tctaatactg
87901  acagtggggt gttaaattt cccactatta ttgtgtgggg gtctaagtct ctttgtaggt
87961  ctctaggaac ttgctttatg aatctgggtg ctcttgtatt gggtgcacat gtatttagga
88021  tagttagctc ttcttgttgc actgatcctt taccattatg taatgctctt cctgtcttt
88081  ttaaaccttt tttggttga agtcgttttt agcagagact aggattgcaa cccctgcttt
88141  tttttttgc tttccgtttg cttggtaaac ttcctccatc cctttgtttt gagcctatat
88201  gcatcttgc atgtaagatg ggtctcctga atacagcaca ccaatgggtc ttgactcttt
88261  atcaaattcg ccagtctgtg tctttaatt ggagcattta gcctgttac gtttaagatt
88321  aatattgtta tgtgtgaatt tgatcttgtc attatgatgc tagctggtta ttttgcccat
88381  tagtagatgc aggttcttca cagtgtcaat ggtcttttaca attggtatg tttttgcagt
88441  ggctggtacc ggtgttttcct ttccatattt aatgcttcct tcaggaactc ttgtaagtca
88501  ggcctggtgg tgacaaaatc accagcattt gcttgtctgt aaaggattt attcttctt
88561  cacttttgaa gcttagtttg gctggattttg aaattctggg ttgaaaattc tttcctttaa
88621  gaatgttgaa tattggcccc cactctcttc tggcttgtaa ggtttctgca tagagatctg
88681  ctgttagtct gaatggcttc ccttttgtggg taacccgacc tttctctctg gctgccctta
88741  acatttttcc tccattcaa ccttggtgaa tctgacaatt atgtgtcttg gggttgctct
88801  tcttgaggag tatcttttgtg gtgttctctg tatttcctga atttgaattg ttggcctgtc
88861  ttgctaggtt ggggaagttc ttctggataa tacctgaagt gtgtccaac ttggttccat
88921  tctcctcgtc actttcaagt acaccaataa aatgtaggtt tggtctcttc acagtcccta
88981  tatttcttgg aggctttgtt tgttcctttt cattcttttt tctctagtct tgtcttcttt
89041  gtttatttca ttaagttggt cttcaatctc tgaaatcctt tttttcactt gatcaatttg
89101  gctattgata cttgtgtatg cttcacgaag ttctcgtgct gtgttttca gctccatcag
89161  gtcattttatg ttcttctcta aactggttat tctagtcact agttcctgta acctttttatc
89221  acagttcttta gcttccttgc actggggttag aacatgctcc tttacctctg aggagtttat
89281  tattacccac cttctgaagc ctacttcttc aattcgtcaa actcattctt catcctgctt
89341  tgttcccttg ctggtgagaa gttgtgattt ttggaggag aaggggtact ctggttttg
```

-continued

```
89401    gaattttcag cctttcgag ctggttttc ctcattttcg tggatttatc tccctttcat
89461    ctttgatgtt ggtgaccttc agatggggtt tttgagtgag ggttcttttt gttgatattg
89521    atgctattgc tttctgtttg ttagttttcc ttctaacagt gaggcccctc ttctgcaggt
89581    ctgctggagg tccactccag accctgtttg tgtgggtatc accagtggag gctgcagaac
89641    agcaaagatt gctgcctgct ccttctctg gaaggtttct tgcagagagg cacctgccag
89701    atgccagcca gagctctcct gtatgaggtg tctgttgact tttgctgaga gttgtctctc
89761    tgtcagaagg catgggggcc agggatccac tcgaggaggc agtctgtccc ttagcagagc
89821    tcaagtgctg tgctgggaga tcttctgttc tcttagagc cagcaggcaa gtacatttaa
89881    gtctgctgat gctgcattca cagccacccc ttcccccagg tgctctgtcc cagggaggtg
89941    ggagttttat ctataagccc ctgactgggg ctgctgcctt tctttcagag attccctgcc
90001    caaagaggag gcatctagag aggcagtctg gctacagcgg ctttgcggag ctgcagtgtg
90061    cttcacccag ttctaacttc ccagtggctt tgtttacact gtgaggggaa aaacacctac
90121    tgaagcctga gtaatggcac atgcccctct ccccaccaag ctcgagcagg tcaacttcag
90181    actgctgtgc tggcagcgag aatttcaagc cagtggatct tagcttgttg ggcaccatgg
90241    gggtggaatc tgctgggcaa gaccactcag ctccctggct tcagcccccgt ttccaggga
90301    gtgaatggtt ctgtctcact ggtgcttcag gcaccaatgg ggtatgaaaa aaaactcctg
90361    cagctagctt ggtgtcttcc caaacggctg gtgagtttta tgcttgaaac ccaaggccct
90421    ggtggcatag gcacctgagg aaatctcctg gtatgagggt tgcaaagact gtgggaaaaa
90481    cgtagtatct tggcctgaat gcactgttcc tcatggcaca gtctctcaag gcttcccttg
90541    gcaaggggag ggagttcccc aaccccttgt gcttctgagg tgaggcaatg cccaccctg
90601    ctttggcgtg ccctctgtgg cctgcaccca ctgtgaaacc agtcccaatg agatgaactg
90661    ggtaccttag ttggaaatgt agaaatcacc tgccttctgt gttggtgttg ctgggaactg
90721    cagaccagag ctgttcctat tcggccatct tgcctggaag ccaactcttc tttttttaat
90781    ttaacttatt ttaagttcag gggtacatac gcaggtttgt tatagaggtg aacttgtgtc
90841    ataattattt cattactcag gtagtaagct tagtacctat tagttatttt ccctgatcct
90901    ctccctcctc ctaaccctcc accctccaac aggcccccagt gtgtgttgtt cccctctatg
90961    tgaataaaag gacacttcta ttgcatttta tttcttttga aaggtcaaaa gaggacgggc
91021    actgtggcac acacctgtaa ttccagccct ttgggaggct gaggtgggca gatctcttga
91081    tcccagaagt tcaagaccag cctaggcaac atggtgaaac cctttctgta caaaaaata
91141    ccaaaactag ctgtgcgtga tggtgcatgc ctgtagtcca agctactgg gaggccgagg
91201    tgggagaatc acctgagcct gggtaggttg aggctatagt gagccatgat tgtaccattg
91261    cattccagcc tgggtgacag agtgagaccc tcttaacag caatacccaa tttcaaaaaa
91321    agtaaagaaa aaaaaacatc cagaagaagg tatagcataa taaaaataat tgttacattt
91381    ggtaattatc aaatatggtg tttattttat tttattatta ttatacttta agttttaggg
91441    tacatgtgca caatgtgcag gttagttaca tatgtataca tgtgccatgc tggtgcgctg
91501    cacccactaa ctcgtcatct agcattaggt atatctccca atgctatccc tcccccctcc
91561    tcccatccca caacagtccc cagagtgtga tgttccctttt cctgtgtcca tgtgttctca
91621    ttgttcaatt cccacctatg agtgagaata tgcggtgttt ggcttttgt tcttgcgata
91681    gtttactgag aatgatgatt tccaatttca tccatgtccc tacaaaggac atgaactcat
91741    cattttttat ggctgcatag tattccatgg tgtatatgtg ccacatttc ttaatccagt
91801    ctatcattgt tggacatttg ggttggttcc aattctttgc tattgtgaat agtgccacaa
91861    taaacatacg tttgcatctg tcttatagc agcatgattt atagtccttt gggtatatac
91921    ccagtaatgg gatggctggg tcaaatggta tttctagttc tagatccctg aggaatggcc
91981    acactgactt ccacaagggt tgaactagtt tacagtccca ccaacagtgt aaaagtgttc
92041    ctatttctcc acatcctctc cagcaccgt tgtttcctga cttttaatg attgccattc
92101    taactggtgt gagatgggtat ctcattgtgg ttttgatttg catttctctg atggccagtg
92161    atggtgagca tttttcatg tgttttttgg ctgcataaat gtcttctttt gagaagtgtc
92221    tgttcatgtc ctttgcccac tttttgatgg ggttgtttgt tttttcttg taaatttgtt
92281    ggagttcatt gtagattctg gatctcagcc ctttgtcaga tgagtaggtt gcgaaaattt
92341    tctcccattt tgtaggttgc ctgttcactc tgatggtagt ttcttttgct gtgcagaagc
92401    tctttagttt aattagatgc gatttgtcaa ttttggcttt tgttgccatt gcttttggtg
92461    ttttagacat gaagtccttg cctatgccta tgtcctgaat ggtaatgcct aggttttcat
92521    ctaggggttt tatggttta ggtctaacat ttaagtcttt aatccatctt gaattaattt
92581    ttgtataagg tgtaaggaag ggatccagtt tcagcctttct acatatggct agccagtttt
92641    cccagcacca tttattaaat agggaatcct ttccccatttg cttgtttttc tcaggtttgt
92701    caaagatcag atagttgtag atacgcagca ttatttctga gggctctgtt ctgttccatt
92761    gatctatatc tctgttttgg taccagtacc atgctgtttt ggttactgta gccttgtagt
92821    atagtttgaa gtcaggtagc gtgatgcctc cagctttgtt cttatggcctt aggattgact
92881    tggtgatgca ggctctttt tggttccata tgaactttaa agtagttttt tccaattctg
92941    tgaagaaagt cattggtagc ttgatgggga tggcactgaa tctataaatt accttgggca
93001    gtatggccat tttcacgata ttgattcttc ctacccatga gcatgggata gtcttccatt
93061    tctttgtatc ctcttttatt tccttgagca gtggtttgta gttctccttg aagaggccct
93121    tcatgtccct tgtaagttgg attcctaggt atttattct ctttgaagca attgtgaatg
93181    ggagttcatt catgatttgg ctctctgttt gttattggtg tatatgaatg cttgtgattt
93241    ttgtacatgg attttatatc ctgagacttt gctgaagttg cttatcagct taagtagatt
93301    ttgggctgag acgatggtgt tttctaggta tacaatcatg tcatctgcaa acagggacaa
93361    tttgacttcc tcttttccta attgaatacc ctttatttcc ttctcctgcc taattgccct
93421    ggccagaact tccaacacta tgttgaatag gagtggtgag agagggcatc cctgtcttgt
93481    gccagttttc aagggaatg cttccagttt ttgcccattc agtatgatat tggctgtggg
93541    tttgtcatag atagctctta ttattttgag atacgtccca tcaatacctac atttattgag
93601    aggttgtagc ttgaagggtt gttgaatttt gtgaaaagac ttttctgcat ctattgagat
93661    aatcatgtgg ttttcgtctt tggttctgtt tatatgctgg attacattta ttgatttgcg
93721    tatattgaaa cagccttgca tcccacggat gaagcccact tgatcatggt gaataagctt
93781    tttgatgtgc tgctggattt ggtttgccag tatttattg aggatttttg catcaatgtt
93841    catcaaggat attggtccaa aattctcttt tttggttgtg tctctgccag gctttggtat
93901    taggatgatg ctggcctcat aaaatgagtt agggaggatt ccctctttt ctattgattg
93961    gaatagtttc agaaggaatg gtaccagttc ctctttgtac ctctggataga atttggctgt
94021    gaatctgtct ggtcctggac tcttttttggt tggtaagcta ttgattattg ccacaatttc
94081    atagcctgtt cttggtctat gcagagattc aactttccc tggttagtc ttgggagtgt
```

```
94141  gtatgtgtcg aggaatttat ccatttcttc tagattttcc agtttatttg catagaggtg
94201  tttgtagtat tctctgatag tagtttgtat ttctgtggga ttggtggtga tatcccctt
94261  atcatttttt atggcgtcta tttgattctt ctctcttttc ttctttatta atcttgctag
94321  tggtcatca atttttgttga tcttttcaaa aaccagctc ctggattcat taattttct
94381  aaggttttt tgtgtctgta tttctttcgc ttctgctatg atgttagtta tttcttgcct
94441  tccgctagct tttgaatatg tttgctcttg cttttctagt tcttttaatt gtggtgttag
94501  ggtgtcaatt ttggatcttt cctgctttct cttgtgggca tttagtgcta taaatttccc
94561  tctacacact gcttttaatg tgccccagag attctggtat gttgtgtctt tgttcttgtt
94621  ggtttcaaag aacatctta tttctgcctt catttcgtta tgttcccagt agtcattgag
94681  gagcaggttg ttaagtttcc atgtagttga gcggtttgca tgagtttctt aatcctgagt
94741  tctagtttga ttgcactgtg gtctgagaga cagtttgtca taatttctgg tctttcacat
94801  ttgctgagga gagctttatt tccaactatg tggtcaattt tggaataagt gtgatgtggt
94861  gctgaaaaaa atgtatattc tgttgatttg gggtggagag ttctgtagat gtctattagg
94921  tctgcttggt gcagagctga gttcaattcc tgggtatcct tgttaacttt ctgtctcatt
94981  gatctgtcta atgttgacag tggggtgtta aagtctccca ttttattgt gtgggagtct
95041  aagtctcttt atagatcact caggacttgc tttatgaatc tgggtgctcc tgtattgggt
95101  gcatatatat ttaggatagt tagctctctt tgttgaattg atccctttac cattatgtaa
95161  tggcctttt tgtctctttt gatctttgtt tgtttaaagt ctgttttatc agagactagg
95221  attgcaaccc ctgccttttt ttgtttttcca tttgcttggt agatcttcct ccatcctttt
95281  attttgagcc tatgtgtgtc tctgcatgtg agatgggttt cctgaataca gcacactgat
95341  gggtcttgac tctttatcca atttgccagt ctgtgtcttt taattggagc atttagtcca
95401  tttacattta aagttaatat tgttatgtgt gaatttgatc ctgtcattat gatgttagct
95461  ggtgattttg cttgttagtt tatgcagttt cttcctagcc tcgatggttt ttacaatttg
95521  gcgtgatttt gcagtggctg gtaccggttg ttcctttcca tgtttagtgc ttccttcagg
95581  agctcttta gggcaggcct ggtggtgaca aaatctctca gcatttgctt gtccgtaaag
95641  tattttattt ctccttcact tatgaagctt agtttggctg gatatgaaat tctgggtcga
95701  aaattcttt ctttaagaat gttgaatatt ggcccccact ctcttctggc ttatagagtt
95761  tctgccaaga gatgagctgt tagtctgatg ggcttccctt tgtgggtaat ccgaccttc
95821  tgtctggctg cccttaacat tttttccttc atttcaactt tggtgaatct gacaattatg
95881  tgtcttggag ttgctccttct caaggagtgt cttttgtggtg ttctctgtat ttcctgtatc
95941  tgaatgttgg cctgccttgg tagattgggg aaattctcct ggataaatatc ctgcagagtg
96001  ttttccaact tggttccatt caccccgtca ctttcaggta caccaatcag acgtaaattt
96061  ggtcttttcc catagtcccg tatttcttgg aggcttttgt cattctttt tattcttttt
96121  tccctaaact tctcttctcg cttcatttca ttcatttcat cttccatcac tgatacccctt
96181  tcttcagttg atcgcttcgg ctcctgaggc ttctgcattc ttcacgtggt tctcgagcct
96241  tggcttcag cccatcagc tcctttaagc acttctctgt attggttact ctagttatac
96301  attcgtctaa atttttttca acgttttta cttcttttgcc tttgtttga atttcctcct
96361  gtagctcgga gtagtttgat cgtctgaagc cttccttgtct gaactcgtca aagtcatact
96421  ccgtccagct ttgttctgtt gctggtgagg aagtgtgttc ctttggagga gaggcactgc
96481  gcttttaga gtttccagtt tttctgctct gtttttttccc catctttgtg gttttatcta
96541  cttttggtct ttgatgatgg tgatgtacag atggggtttt ggtgtggatg tcctttctgt
96601  ttgttagttt tccttctaac agacaggatc ttcagctgca agtctgttgg aatttgctag
96661  aggtccactc cagactctgt tttcctgggt aacagcagca gtggctgaag aagagtggat
96721  ttttgtgaac tgcgaatgct gctgtctgat cgttcctctg gaagttttgt ctcagaggag
96781  taccggccg tgtgaggtgt cagtctgccc ctactagggg gtgcctccca gttaggctgc
96841  tcggggtca ggggtcaggg acccacttga ggaggcagtc tgcccgttct cagatctcca
96901  gctgcatgct gggagaacca ctgctctctt caaagctgtc agacagggcc atttaagtct
96961  gcagaggtta ctgctgtctt tttgtttgtc tgtgccctgc ccccagaggt ggagcctata
97021  gaggcaggca ggcctccttg agctgtggtg ggctccatcc agtttgagct tccagctgc
97081  tttgttacc taagcaggcc tgggcaatgg caggtgcccc tccccagcc tcgctgccac
97141  cttgcagttt gatctcagac tgctgtgcta gcaatcagcg agactctgtg agcgtaggac
97261  agtgcagcat taggatggga gtgacccgat tttccaggtg ccccatctgt caccccttc
97321  tttgactagg aaagggaact ccctgacccc ttgcacttcc cgagtgaggc aatgcctcgc
97381  cctgcttcgg ctcgcgcacc atgcgctgca cccactgtcc tgcgcccact gtctggcact
97441  cactagtgag acgaaccccgg tacctcagat ggaaatgcag aaatcacccg tcttctgcat
97501  cggtcacgct gggagctgta gaccggagcc attcctgttc agccattttg gctgctactg
97561  cctcaaatat ggtgttttaa atattattct ctattgtcaa catgacagct aaacatggtg
97621  tcatgtttat atttatgtaa taataataat gtaataactt ttttcataga tgcaccccaat
97681  gtttgccttt tttttgttatt gttaaattgc ctgtttgaat cctttgccta catttctatt
97741  agtatgactg atgtatcact tgggaattgt gtttggctgt gaataacaca aacctggaaa
97801  cagtggatta aataaagact tttatttttt tctctcagaa tgaaaagtcc aaaagtcaaa
97861  aacctaggac gggtacagtg tctccatgat gccagtaggg aaatggactt gtatctttcc
97921  actaagccac ccctggcata tgcttttcac ccttgggatt atgagatggc tgctttgttt
97981  ccagaatcaa gtccatgttt caggcaggaa gaaatgaaag agccaaggac gaaatgtcca
98041  ttccagcgaa gtctgccctc tccctccctt cccatacatc cacatattt aaagagcctt
98101  cctggaagtc ccatcaaaaa ctccctgctc ccttttttt cagttgccag aactaggtca
98161  gatgatgact tgtatccagg aattcagcag tgtttgattta atcttttccc caaactggag
98221  ttaagtggac aggaataaga atggatactg ggaagagacc actaggcttt cgtagctgcc
98281  aaacaatgat gataacaata gtgatgatga tcataataaa aatcatcata gttaccattt
98341  attatgtgct gtgtgccagg tgtgtaagct ttgtacattt ttcttgttta gtccccccaa
98401  tccttaaagt acttgtgttg gcacccattt agaactgagg ctattgagac tcattaatgt
98461  gtagtaacat gttgaaagtc atgcgagggg caatacaaac ttgaatccag tcctatttga
98521  ctatgaagat cgtctgggac tgtactggct ttagcagtga aagtctcaca ttctaggaca
98581  cctgtcagtc atggaacagt gtggcagggg tcacccactg aagctcaaac agtattaggg
98641  tatgagttca attaaggttt tttgaatggt taatttaata agtattattt atcatttctc
98701  ataagttat agacttgcaa tacattaaga atacaacctt tggccgggcg cggtggctca
98761  cgcctgtaat cccagcactt tgggaggccg aggcgggcgg atcacaaggt caggagatcg
98821  agaccatccc ggctaaaacg gtgaaaccc gtctctacta aaatacaaa aaattagccg
98881  ggcgtagtgg cgggcgcctg tagtcccagc tactgggag gctgaggcag gagaatggca
```

-continued

```
 98941  tgaacccggg aggcggagct tgcagtgagc cgagatccca ccactgcact ccagcctggg
 99001  cgacagagcg agactccatc tcaaaaaaaa aaaaaaaaaa aaaaaaaaaa aaaaaaaaaa
 99061  aaaaaaaaaa gaatacaacc tttaagttgt atgtattttc ttttgctttg tagcttttat
 99121  gactcttctt gatatacaga tatttaaaaa ttttatgtat caaatatgtt ttcctttata
 99181  attttttcct tttcttttat gtttagatat tcttccccat gctattgacc aaaagttatc
 99241  tgcattttct tctggtcctt ttataatcta ctttgcaatt cacagtgtaa aatggggata
 99301  tgcaggaatg ggcaagactt tcatgcacat gttccatctc ccaggtttgg gtgagtgttt
 99361  caaaactgta tgcttgtatg tttgaaatgt tcatctcagg aactgattta aaatccataa
 99421  cttaaaggga tgaaaactct ttccaatgca tttccaatgt gcagtgcaca tgtatctgat
 99481  ctgcaattgg aaaatgtcaa aatgtgtcag ctcatttcat actcttttaa gctatccttt
 99541  gattaaggga gtgctgtatc aacttatgtg agcctgcagt caaatctacc ttcaaattat
 99601  tagcacctgg tgagaaatgt ccttcccatt ctaaacacta gttcatcatg tcttatttgt
 99661  aattcatttg atgattttga tataacatta taaatattat acgtgactaa gcctttacac
 99721  tgaagctttg ttcttgtaaa aatggcagaa actgtgaatt gcatactctg tctctgatac
 99781  agatgtgtgg atctagacta agcaggtgtg gtgctaggct gagtaaatca ccagtccaa
 99841  atgtctttat gttgggaaac atgatgtcat taatgtttat cttgtactac tgagtctaac
 99901  ttagtttttct agcctatgga gtgggaaaat ctttgtgaat tcactgttat tgacaaataa
 99961  ttattagaaa ataaaattaa tactctagtc caagtgttgg caaacttttt gtaaagggcc
100021  agatgatagc tattttaggt tttgctggcc ataagatttc gattgcaacc actcaagtct
100081  tccttttgtag cagcagtaga caatacataa acaaatgggc ttggctgtgc tccagtaaaa
100141  cttatttac aaaaacaggt ggtctacacg gttcggtctg cagactgtat tttgccaact
100201  actgtgtagt caaataattg cttctttcag agttctttct ttttttcag aattctttga
100261  aaactatgta ttagattcct cattgttata taaaaactgt ttattatttc aaaagtggga
100321  atttgttgct atcctggaaa atattaaaca agttctccta taattgatac tttaagactt
100381  tgacttgaat gtcttaaagt taaattggaa agtccttga aaatttatttg aagggaagta
100441  tcatggtgta aacatttcag aattgtttgt taggaatagg ttgtgccaat tgcaaatgaa
100501  aagttagttt ctcaaatctt ctttcatatt agtggcccat agctttcttc ctaaacaaat
100561  ctttctatct tcttccaaaa agctggatat agctcttagt ttcagtgggg tccacgctta
100621  aagacaggaa agcatatggg tgccatacat ttgttagtat ttgtctctac aaaatcacaa
100681  aaattgaaca ctccagagct ctaaattaca aatttggatg gtgtgcctta ttgcagatca
100741  taaaggccac gtgtgcaaga ttcatcgtca atagcattgc ttcatgtttt agtaaatcag
100801  aatgactgac tggaactttt acatctttt ttgatggatt ctctcatggt atagactgta
100861  acctgtgtgt caatctctaa ctggatatca ttaatcacat ttcaaagcta aatacaattg
100921  ggggatgtaa gttttatatt tatacatcaa aatatgtaca tttttaggg taggcaatat
100981  acaaacatat atatatatgt atatgaacaa acaatattta tatatataat gtttaataat
101041  cagcctccca tgggccctga atatccatga atttttattt atgcaaaatt tcaatgctat
101101  tagtgctgaa aagaggttgg aattcatgct ttgaaagact ttacagtcta tgataaggct
101161  tttgttgttg ttcttgtatt ttttgtttgt ttttatagtc ttggcagaca cttgtttagt
101221  gtttggtggt tggcttattt ttggaagcac cctcaaaaca attggagata atatattaca
101281  aataaagtgg atgttcaagc tggggatttt tatctttgtt caaaaataaa gtgtaatgtt
101341  atagtaatag gacttttcc tgttttataa tgtaacttaa aaaatttata gcaataaatg
101401  cccacaggag aaagcaggaa agatctaaaa tcaacaccct aacatcacaa ttaaaagaac
101461  tagagaagca agagcaaaca aacccaagag ttagcagaag gcaagaaata actaaggtca
101521  gagcagaact gaaggagata gacacaaaaa aacccttcaa aaaatcaatg aattcaggag
101581  ctggtttttt gaaaagatta acaaaatagg tagaccgcta gccagactaa taaagaagaa
101641  aagagagaag aatcaaatag acacaataaa aaatgataaa ggggatatca ccactgatcc
101701  cacagaaata cgaactacca tcaggtgtgt atatactata cacacctcta tgcaaataaa
101761  ctagaaaacc tagaagaaat ggatacattc tggacacact cacccctccc aggactaaac
101821  cagaaagaag gcaaatccct gaatagacca ataacaagtt ctgaaattga ggcagtaatt
101881  aatacctacc aaccaaaaaa agcccaggac cagtaggatt cacagccaaa gtctaccaca
101941  ggtataaaga ggagctggta ccattccttc tgaaactatt ccaaataata gaaaaagagg
102001  gctcctccct aactcatttt aggaggccag catcatcctg ataccaaaac ctagcagaga
102061  caagaaaaaa aaaacaacaa aatttcaggg ccgatatcct tgatgaacat cagtgagaaa
102121  atcctcaata aagtactggc caactgaatc cagcagcaca tcaaaaagct tatccaccag
102181  gactttcaa gtgctttaag cagtggaagg gtcactgaaa tatgtattgc ctcctaacat
102241  taattttga agaacaactt tcatttgagc atggaagcta aggtctgttt tgaaagtctc
102301  attactctat attcatatct tgtaaaaata cacttataca cttccttaga aatgtaattt
102361  ggacaaaaat tacatttcca aaaagaatat tttcaaataa tcaagcttat ttttagtaat
102421  aaactaagtt tatcagtaaa actaaggggc tgaaattttg ccaaacgtaa caagtgaat
102481  atatgaaaac aacaaagtag acaatattat caacaggatt tataattttt gttttcaag
102541  atatccatgg atgctttgct gctaatttct cagaccagtg caacactatg tgatttgata
102601  atgggagttt ccctcccaag tacctgtaac ttctacagta ttatctttgt gggtggtatg
102661  ctgggatatt ctgaaaagtc gtcctttatt cctcacataa tggaaccaag agctggaaga
102721  gagcaagaag agcatagtca ggaaagagag aagaaacatt cagagaaaca cctcatgggg
102781  tttaaaaatt ttataataga tttaacctga ggaagataaa gtcttgtatt aacaaataaa
102841  tagaagcaac tgcaaatatg tttgaatgga gactatgggg catatttttc tttgctccat
102901  ttctttttct ctcttaaaat acatgtgtgc tccttcatac aaaaatttat tgttaatttt
102961  ccaattgcaa aagtacttaa taaagagcac tttgaaaaca aagtaaaaca gtaagaatta
103021  cctatcattg atgacctaga gatataaatg gtaaaacttg aattcatgcc ttctttttc
103081  cttaacttat atatttttg ttttacaaa aagaggatcc atcacatcac atgtgtttca
103141  taagttgccc ttttgtatag caatgtactt aaatatctct gactacatct tgtcaatgtg
103201  ctttttttctc aaaataattt taaaaatagt tttatctagc tcatttttta aatcttaaaa
103261  gcaatgcata tttactgcaa aataattcag aaaacataca ttaaaagat atcgtctttc
103321  gtactactgc caaaagttgc tgaagctgtt tttacagggc acttgaaaga aggtatttat
103381  aagccaggcg cggtggtgcg tgcctgtaat ctgagcattt tggaaagcag aggtgggcag
103441  atcacctaag gtcaggagtt caagaccagc ctggccaaca tggtgaaacc ctgtctctac
103501  taaaaataaa aaaattagct gtgtgtggtg gcgggagcct gtaatcccag caacttggga
103561  ggctggggca ggagaatcac ttgtcccggg gaggtggagg ttgcagtgag aagagatcga
103621  gccactgcac tccagcctag gtgacagagc gaggctccat ctgaaaaaaa aaaaaaaaaa
```

-continued

```
103681  aaaaaaaaaa aaaagaaggt atttatgcta aaataggttt aggaaattgg gggttaaatg
103741  cacataaaca ggttttcttt tattacagga cttctcagag cctttaatat gctgatgtgt
103801  actatgatat tcacagaagg gaggtaaaat gtagagtttc ccaaacttat ttgatgagag
103861  aagctttatt tcaatagatt agttttcctt agaaccacact ttggtataca gtgttcttta
103921  tacacacaca cacacacaca cacacacaca cagaggcata ctcaaacaat cttttatttac
103981  ttattactag gtgattaata attggataat gagtttaata tatcatggtc atctattcac
104041  attaataaat gatccacata atcattttaa tgactgccaa gtataccact gtttttcatgc
104101  atcctaattt ttcaaaacaa ctccttcctg atgtacattt aagctgtttc catctttttt
104161  gcatttgcaa atcatgctga atcaatacct ttgtacattt ctgtatattt gttcaataat
104221  ttctttagga tatatgccta acaaagagac agtatgggcc ttttcatctt atctgtattc
104281  ccagattcgt ttctttgcct aggaatgaca gttttaata caattaggat agttttttcct
104341  aattaggata aggaattgtc cactcatgaa gtatgaatag gatcagagta agctatcaga
104401  aatatagttt cttaaatact tgcaattatt cacaagaatg atatgtattt atgaaggagt
104461  aattattaac attgtttagg agggaagctt aatacaaatt atgtaaaaaa ttagaaacca
104521  aattccaaaa atattattcg cccccttcct tctagagaat aaaataggtt aaaaggaaca
104581  ataccttctg aattttaagt gaaaaagaaa cacattttaa gtccaagtta agatgtagaa
104641  atataccct attgattgt ctctctcat taattaaaac ctgaaatacc ctatccagtg
104701  ttttattatg actacattct atcaaaaatc ccataagtta ttccattgga gtttacatag
104761  gctgatatct catcctgctt tcaataaaaa gtcagaaagc aaatctgttt gatcagattt
104821  gctctgagta ttggagtcta cacttaagct tttgaacaat tatatacagg actgagcaaa
104881  ggctattgtt tgcttatgtg gtagattgga atcgcgaatg ttaatctcat ccccaagaac
104941  actttttaat ttatatcaaa attgtataaa cagggtcacc agtgctaaat gggatgtcaa
105001  tgacctatga agatcagaaa gtaaacaaag atcttaaaat aagcatgtaa cctgaacacc
105061  tcaagaattg ttgtatattg aaaggcattt gtttacataa agaaagggaa aattacttag
105121  tgctaattca gtttgtggca ggttccttct ttctcaatcc atcagcaaaa tggtgatgga
105181  caaaagtttc accctgtcta ttttaaaggg ccgtggagaa aaccaacatg aaccaatggt
105241  tcattcacgt cctttgaaat cgcgggcatt cagaagccta cctacttcct ttatgggcta
105301  tttaacttca ggccaatttc tttttcagg atgagcatcg aggaaagagg atagccagga
105361  aacttgatta agattaaagg agtaagatac agccggcagg aagaggtagg tagattcact
105421  gaggacatgt tcagggattt ctttgaagcc caaactccca actgtaaaag gaattccagc
105481  cagatggaga acaaatggga acatgttttg gggtgagtga gccacatgtt ttggtttcag
105541  gggtgaagga ttgatgagtc caaaaaacgt ttgtgtaaaa agaggagaat gaattaagaa
105601  aaagaaacgc tattttttat tatgactat tagatacata taattatgga tctgaaactg
105661  aggcaaatta aaaattcacc aacatattga catcctccct tatccgtggg gataaattcc
105721  aagaacctca gtggatttct gaaaccgcag gtggtgccaa acctggttgc tgctaatgga
105781  aacacgtttc tgttcatttc ttccacaaag ttaatgcctt ttctatctta tttatcactc
105841  actgtagcct taacatttgt agctaaggtg taacagcaaa actggcacaa atttgttttt
105901  ccttcttcac aatttaatgg atagaagact tattcttact gtagatctta gcatcctcag
105961  cataggattt tttttcttc tttcttaagt ccagaactt catcttttca cctaaaggaa
106021  gtagtttata ccttcttttt ggtgtattcg aatggctagc atcgttactc ttgccatttg
106081  gagccattat taagtaaaag aagggttact tgaacacagc actggggttgc tgcaagagtc
106141  catttgataa ccgcgccagt tactattaat aagtgactga ctgaggggta gtgtacacag
106201  ctttccaagt caccaaggac atgattccag aggcagtgta gcctagcgac tatggctctg
106261  tggtcctact gcctagattt ggatccaggc tcttcgagtt acactgagtg actctcagga
106321  ggtaatttga cctctctttg cctgactttc ctatcacta aaatgaaaat aatagtttcc
106381  acctgctagg ttagttgtgg agagtaaatg agctattaga tgcaatgagc ttagaacagt
106441  gcttgacaca tgtggtaagt aagtcctcag tgaatgttag tcattggttt gaacatttaa
106501  agacccacta agctggatac acttctctctt gttctccctc gctccctccc ttctttcctt
106561  cctgcctgcc tgccttcttt ccttccttcc ttccttcctt ccttcctttcc ttccttcctt
106621  ccttccttcc ttccttcctt ccacttctt tctttctgtc tttcgacagg gccttgctta
106681  attgcctagg ctgagtgca gtggctccat ttcggctcac tgaggcctca tactccttgg
106741  tttaagcaat cctccccct cagcctctca agtagctggg atcacagtca tgtgccacca
106801  tgcctggcta atttttgat tttttttt ttggtagaga tggagtctca ctatgttgct
106861  cctgggctcg agcgatcctc cggcctcagc ctccaaaat gctgggatta caggtgtgag
106921  ccacagggcc tagccacctt tccttttgat atcttaattt atttggttct ttttttcttta
106981  attatacttt aagttttagg gtacatgtgt acaacatgca ggttagttac atatgtatac
107041  atgtgccatg ttggtacgct gcaaccatta actcgtcatt tagcattagg tatatctcct
107101  aatgctatcc ctcccccatc accgccccc ccacaacagt ccccggtgtg tgatgttcac
107161  cctcctgtat ccacgtgttc tcattgttca attcccacct atgagtgaga acatgtggtg
107221  tttggtttt tgtccttgcg atagtttgct gagaatgatg gtttccagct tcatccatgt
107281  ccctacaaag gacatgaact catcattttt tatggctgca tagtattcca tggtgtataa
107341  gtgccacatt ttcttaatcc agtctatcat tgttggacat ttgggttggt tccaagtctt
107401  tgctattgtg aatagtgcca caataaacat acatgtgcat gtgtctttat agcagcatga
107461  tttataatcc tttgggtata tacccagaaa tgggatggct gggtcaaatg gtatttctag
107521  ttctagatcc ttgaggaatc gccacactga cttccacaag ggttgaacta gtttacattc
107581  ccaccaacag tgtaaaagtg ttcctatttc tccacatcct ctccagcacc tgttgtttcc
107641  tgactttta atgatcacca ttctaactgg tgtgagatgg tatctcattg tggttttgat
107701  ttgcatttct ctgatggcca gtgatgatga gcattttc atgtatcttt tggctgcata
107761  aatatcttct tttgagaagt gcctgttcat atcctttgcc cactttttga tgggggttgtt
107821  ttttcttgt aaatttgtt gagttagccc tttgtcagat gagtagattg caaaaattt
107881  ctccccattt gtaggttgcc tgttcactct gatggtagtt tcttttgctg tgcagaagct
107941  ctttagttta attagatccc aattgtcaat tttggcttt gttgccattg cttttggtgt
108001  tttagacatg aagtccttgc ccatgcctat gtcctgaatg gtattgcctg ggttttcttc
108061  tagggtttt atggttttag gtctaacatt taagtcttta atccatctta attaattttt
108121  gtataaggtg taaggaaggg atccagtttc agctttctac atatggctag ccagtttcc
108181  cagcaccatt tattaaatag ggaatccttt cccccattgct tgttttgtc acatttgaca
108241  aagatcggat agttgtagat atgtggcatt atttctgagg gctctgttcc attggtctat
108301  atctctgttt tggtaccagt accatgctgt tttggttact gtagccttgt agtatagttt
108361  gaagtcaggt agcgtgatgc ctccagcttt gttctttcgg cttaggattg acttggcaat
```

-continued

```
108421  acgggctctt ttttggttcc atatgaactt tgaagtagtt ttttccaatt ctgtgaagaa
108481  agtcattggt aacttgatgg ggatggtgaa tctataaatt accttgggca gtatggccat
108541  tttcatgata ttgattcttc ctacccatga gcatgaaatg ttcttccatt tgtttgtatc
108601  ctcttttatt tccttgagaa gtggtttgta gttctccttg aagaggtcct tcatgttcct
108661  tgtaagttgg attcctaggt attttattct ctttgaagca attgtgaatg ggagttcact
108721  catgtttggc tctctgtttg tctgttattg gtgtataaga atgcttgtga tttttgcacg
108781  ttgatttttgt atcctgagac tttgctgaag ttgcttatca gcttaaggag attttgggct
108841  gagatgatgg ggttttctag atatataatc atgtcatctg caaacaggga caatttgact
108901  tcctcttttc ctaattgaat gcccttttatt tccttctcct gcctgattgt cctggtaaga
108961  acttccaaca ctatgtggaa taggagtggt gagagagggc atccctgtct tgtgccagtt
109021  ttcacaggga aagcttccag tttttgccca ttcagtatga tattggctgt gggtttgtca
109081  tagattgctc ttattatttt gagatatgtc ccatcaactac ctaatttatt gggagtttt
109141  agcatgaagg ttgttgaatt ttgtcaaagg ccttttctgc atctattgaa ataatcatgt
109201  ggttttttgtc cttggttctg tttatatgtt ggattacgtt tattgatttg cgtatgttga
109261  gccagccttg catccaaggg atgaagccca cttgaccatg gtgaaaaagg tttttgatgt
109321  gctgctggat ttggtttgcc agtatttat tgaggatttt tgtattgatg ttcatcaagg
109381  atattggtct aaaattctct tttttgttgt gtctctgcca ggcttttgta tcaggatgat
109441  gctggcctca taaaatgagt tagggaggat tccctctttt tctattgatt ggaatagttt
109501  cagaaggaat ggtaccagct cctccttgta cctctggtag aattcggctg tgaatccatc
109561  tggtcctgga cttttttttgg ttggtaagct attaattatt gcctcaattt cagagcctgt
109621  tattggtcta tgcagagatt caacttcttc ctggtttagt cttgggaggg tgtatgtgtc
109681  aaggaattta tccattctt ctagattttc cagtttattt gcatagaggt gcttgtagta
109741  ttctctgatg gtagttcgta tttctgtggg atcagtggtg atatcctctt tatcatttt
109801  tattgcgtct atttgattct tctctctttc cttattagtc ttcctagtgg cctatcaatt
109861  ttgttgatct tttcaaaaaa gcagctcctg gattcactga tttttttgaag ggttttttcgt
109921  gtctctatat ccttcacttc tgctctgatc ttagttattt cttgccttct gctagctttt
109981  gaatgtgttt gctcttgctt ctccagttct tttaattgtg atgttagggt gtcaattta
110041  gatctttcct gctttctctt gtggacattt agtgctataa atttccctct acacactgct
110101  ttgaatgtgt cccagagatt ctggtatgtt gtgtcttttgt tctcattggt ttcaaagaac
110161  atctttattt ctgccttcat ttcattatgt acccagtagt cattgaggag caggttgttc
110221  agtttccatg tagttgagtg gtttgtgtga gttcttaat cctgagttct agtttgattg
110281  cactgtggtc tgagagacag tttgttataa tttctggtct ttcacatttg ctgaggagtg
110341  ctttacttcc aactatgtgg tcaattttgg aataggtgtg gtgtggtgct gaaaagaatg
110401  tatattctgt tgatttgggg tggagagttc tgtagatgtc tattaggtct gcttggtgca
110461  gagctgagtt caattcctgg gtgtcctgt tagctttctg tcttgttgat ctgtctaatg
110521  ttgacagtgg ggtgttaaag tctcccattt ttattgtgtg ggagtctaag tctctttgta
110581  ggtcactcag gacttgcttt atgaatctgg gtgctcctgt attgagtgca tatatattta
110641  ggatagttag ctctccttgt tgaattgatc ccttaccatt atgtaatggc cttttttgtc
110701  tcttttgatc tttgttggtt taaagtctgt tttatcagag actaggattg caaccttgc
110761  cttttttttgt tttccattttt cttggtagat cttcctccat cccttttattt tgagcctatg
110821  tgtgtctctg caggtgggat gggtttcctg aatacagcac actgatgggt cttgactctt
110881  tatccaattt gccagtctgt gtcttttaat tggagcattt agcccattta catttaaggt
110941  tgatattgtt atgtgtgaat ttgatcctgt cgttatgatg ttagctggtc attttgcttg
111001  ttagttgatg cagtgtcttc ctagcctcga tggtctttac aatttggcat gtttttacag
111061  tggctggtat tggttgttcc tttccatgtt tagtgcttcc ttcagaagct ctttttagggc
111121  aggtctggtg gtgacaaat ctctcagcat ttgcttgtct gtaaagtatt ttatttctcc
111181  ttcacttatg aagcttagtt tggctggata tgaaattctg ggttgaaaat tcttttcttt
111241  aagaatgttg aatattggcc ctcactctct tctgacttgt agagtttctg ctgcgaaatc
111301  cgctgttagt ctgatgggct tccctttgtg ggtaaccccga ccttctctc tggctgcccct
111361  taacattttt tccttcattt caagacaatt atgtgtcttg gagttgctct tctcgaggag
111421  tatctttgtg gcgttctctg tatttcctga atctgaatgt tggcgtgcct tgctagattg
111481  gggaatttct cctggataat atcctgcaga gtgttttcca acttggttcc attctccctg
111541  tcacttttcag gtacaccaat cagacgtaga tttggtcttt tcacatagtc ccatatttct
111601  tggaggcttt gttcattct ttttattctt ttttctctaa acttctctt tcacttcatt
111661  tcattcattt gatcttccat cactgatact ctttcttcca gttgatcgat tcggctactg
111721  aggcttgtgc attagtcacg tagttctcgt gccttggttt tcagctccat caggtcctt
111781  aaggaattct ctgcattggt tattctagtt agccattcat ctaattttt ttcaaggttt
111841  ttaacttctt tgccatgggt taggacttcc tccttttagct cggagtagtt cgattgtctg
111901  aagccttctc tcaactcgtc atagtcattc tctgtctagc tttgttccgt tgctggtgag
111961  gagctgtgtt cctttggagg aggagaggtg ctctgatttt tagagtttcc agtttttctg
112021  ctcttttttt tccccatctt tgtggttttta tctaccttttg gtcttttgatg atggtgacgt
112081  acagatgggg tttttggtgtg gatgtccttt ctgtttgtta gttttccttc caacagtcag
112141  gagcctcagc tgcaggtctg ttggagtttg ctggaggtcc actcctgacc ctgttttgcct
112201  gggtatcagc agcggaggct gcagaacaga ggattttggt gaacagcaaa tgttgctgcc
112261  tgattgttcc tctggaagtt ttgtctcaga ggagtaccca gccgtgtgag gtgtcagtct
112321  gccccctactg ggggggtgcct ccgagttagg ctactcggag gccagggacc cacttgagga
112381  ggcagtctgt cccttctcag atctccagct gcgtgctgaa agaaccactg ctctcctcaa
112441  agctgtcaga cggggacatt taagtctgca gaggattctg ctgcctttg tttggctgtg
112501  ccctgcccc agaagtggag tctacagagg caggcaggcc tccttgagct gcggtgggct
112561  ccacccagtt tcagcttccc agcagctctg tttacctact caagcctcgg caatggcggg
112621  cacccctccc ccagccttgc tgccgccttg cagtttgatc tcagactgct gtgctagcaa
112681  tgagcgatgc tccatgggca taggacccctc tgagccaggc acggttgtaa tcgcctggtg
112741  tgccgtttgc taagagcatt ggaaaagcgc agtattaggg tgggagtgac cggattttcc
112801  aggtgccatc tgtcacccct ttctttgact aggaaaggga attccctgac cccttgcact
112861  tcccaggggga ggtgatgcst cgccctgccc tagctcacgc tgggtgcgct gcacccactg
112921  tcctgcaccc acttccgac actcccccagt gagatgaacc tggtacctca gttggaaatg
112981  cagaaatcac ccatcttctg tgtcgctcat gctgggagct gtagactgga gctgttccta
113041  ttaggccatc ttggctccac cccccaattt atttggttct taatgaccct ttttttttttt
113101  taagagtcac ttctcaaaat atgaatagtc tgttaattat ttatatttca gtggacccac
```

-continued

```
113161    cgcaaagctg ctatcaatta ataatacta cagcaggatt taatttgttc tcatacttac
113221    tcaatgggat accactttgg gggaagagca agaagtgatg agccagtggg aagcatccta
113281    ggacaaacct aacccacct tttctacttt atactaaaca gtccaccaat tatagtttg
113341    ctaattgcaa ggaaaatgtt aagcctataa tgtgtcaatg caaagcacta aagaaagtac
113401    gtgctaatac aattctgtga gataaagtag aaggctgtga tacattttct ggctccttgc
113461    cttaaccatg ggaagaaaaa agtgtcttat ttgaaggcag tcatgaaagg ggaggaactc
113521    atgaaagagt ctcgtaggtt gattgtgaaa aagacgatgt agaggaattc cagagtctct
113581    gttttagttg catgctgtgg aaagccaagt tagcgtagag ctgaggatga agcccaaaca
113641    accacatgct tgaggcatca aaggacagaa acaggaaagg aaggacaggc agacacacac
113701    acacagagac acagacacac acacacagac acacacacac acactcaaag gaattatttt
113761    aaagcagtaa acatatcttt tactgaaata ccaaatttca ttttatgggc attttttgtt
113821    tttgagttac atatgtcaga gaagggtact ctcatcctct caatgtttga gtttgtttct
113881    gtgttgatcc aatcctaact gcaggatttg ttcagtgaac caagacatgt atctttaaag
113941    ccaaaggtgg tttcactaaa acagtgattc tcaaactttt tgatctcata tccttataca
114001    actttttaa attattgaga attttcattt tgttattata cccattgata tttaccatat
114061    tagaaactgg aactgagaaa aaactactta ttcacttatc taaatcccat tttacattt
114121    gataatttt tttgtgaaaa cattttcaa aacaaaaaa taatgagaac agtggcaaaa
114181    tgttcagctg aatagatgac agattctcat atctgttct ggatttgtt tttgtatca
114241    tgtagtctct ggaaaactct tatgtactat aatgagagaa cagaaacgaa aatggaaaga
114301    acactttagt atttgggga aaatagtttt gaattcatag acttcctgag aatgtctcag
114361    gaatacccca ggaatctcca taccacactt ggagaactac tatcccaaga caaagtcgta
114421    tgcttggtcg agactgagtg gcctgattta attgttgctg ttgttattgc atcactatag
114481    gttattggtt ttaaaaagcc catctcttca cactctgaat ttggaatatg tcttatattg
114541    atagtgactt acaacagctg ttggcccccgt ggcagttgtg atgtagttat tacctgcaca
114601    agcatgaatt tggtcatagc tattcacggc atcagtattt ttattgaatt atttgcattg
114661    ttgttatgtg ttgagagttt agttgtcatt taagtctct ttctttcaga atttatagta
114721    taacatagtt ctgagatgag aagttactgt agatgcagaa aggcaagcag agagcagtgg
114781    ggcatatatc tgacattagg aaagcgattt tgggagaagg aataggattc tatatttct
114841    tgcataagaa caacaacgta cttcatggta tcaaaaaagg tactaaatcc acacgcatct
114901    atggctgaat tgtgtgttgt tagtgagaaa tgtgcaaaat gattgccttt catgtgccaa
114961    accacacacc tgaagacaca aaaacttgcc aaatctcttg gtatcgagga aagatgctgc
115021    acagcaatga gaggatgatg tgaccaattt acgtgtcatg caggattatc attaaggtag
115081    ggtgtcatta cttaattggc agccttttc ctttcttaga ggtccattaa ataattcatg
115141    tcttcccatt gatgacatct tagattgagt acaatagtca taacaatatt tttgactggt
115201    gtacttgttt cctagacttg tgatcacagg ttaccacaaa ccaggtggct taacacaaca
115261    gaaatttatt ctctcacagt tttggggact agaagcctga actcaaggtg tcagcagagt
115321    catgcaccct ctaagactgg tggaatccct ccttcctcc ttctagtttc tgatggtggc
115381    gtaattcctt ggtgtttct ggcatgcagg tgtatcatcc cagtctttgc ttctgtcatc
115441    acaggatggt ctccttgtgt acctctgtct tcacatggtg tttttccctt tttgtaggga
115501    caccagtgat attggattaa ggactcaccc aactccaata tgacctcatc ttaactaatt
115561    acaactataa aaactctatt tccaaaaacg tcacattctg gggtactggg ggttaggact
115621    tcaacatgtc ttttggggag ctataattca acccataaca acagataagg aacataatat
115681    ttctatgtct gtggcagaga aaattctatg ggtttccaaa ttctgttttg tattcctccc
115741    tcctgggcac aataaaaatt ttattttcca gttcccttgc agtaaagcaa gagtgtgtga
115801    ttaattatgg gcaatgaaat ttgagaataa gtggcatgtg tcactctgg gctgaggcag
115861    taaaaagctg ctgtgtgact tttcagtttc ttgattttcc tcaggtagtg agtgtaagag
115921    caatgtgttg agatagcaaa cccacaagat cacagcagcc tggatctctg agttactata
115981    tggatgatga agcactacac tgttgagtct gacctaaagc aatctttata ttgtgagaaa
116041    tttgtgtgtg ttaaaccact gagattttgg agtcatatgt cacagaagca taatctagtc
116101    tatcctgatt aacacatgaa gatgcaccaa gaggtagagg atggcatgaa gtgatgaatt
116161    tccaattaac tttctgtagc catatctatg aattctttct aagggtgaaa tacttctttt
116221    aacattcaaa aatcaatcaa tgttacacac cacatcaata gaataaagga caaaaaccac
116281    atgattatct caatagatgc agaaaaaaaa attgacaaca tccaacactt tattatgatg
116341    aaaacactga acaaacgaag gcaagtcaac ttcctcaacc taataaaggg catctacaaa
116401    aaaatccatc actatgatca tatataatgg tgatttcctc ctaagattaa gaacaatatg
116461    agaatgtcca ctctctcatc agtttcgttc aacatttgta ctggaggttc gctagccaga
116521    gcaattaagc aagaaaacaa gataaaggca tccagacagg aagggaaaaa gtaaaattat
116581    ttttattcac atatgatatg gtcttatgta taaaaaaatt ttaaggaact cacacaaaat
116641    gattaaatct aatataaatg aattcagcaa agttgcaagg tacaagctca atatatgaaa
116701    tcaattttat ttatatgtac tagcaatgaa caagcccaag tgaagttaag aaaacaattc
116761    aatttataat agaattaaaa gaataaaatg cttgggaata catttaaaaa gtataagatg
116821    tatacactga aaacaataaa acattattga aagtattaaa agaagatcta aataaatgga
116881    aagatattcc atgttcatag attgaagtc ggtattgggt tttttgttt gtttgtttgt
116941    tttttgcttt cttaacttgt attttaggtt caggggtaca tgtgaaagtt tgttacatag
117001    gtaaattcat gtcacggggt ttgttataca gattatttca ttacccatga attacgccca
117061    gtgcccaata gttatctttt ctgctcctga taatattgct gaggtgataa tactctccca
117121    aattgatcta cagattcaca caattcctat taaattccaa ctaccttttt ttttggtaa
117181    aagttgataa ctcatgttaa aatacctatg gaaattcaag gaacccagaa cacctagaac
117241    aaccctgaaa aacagcaaag ttggagggct cactcatcag aataaaatta acaggctcac
117301    acatactgtt ttttagaaaa gcaacatctt tattttaaac ataaaattaa tatattctta
117361    cttgtactag taaggatagg caaggtcatt ttcatgaac aaactctcca aatctctaaaa
117421    gtttagaata ataagagtta attttttgct ctaattaagt gtccactggg gattggctga
117481    gagctccgat ccacatctca tttccgaatc taggctgatg gagcagccgc tatctcaaac
117541    ttgagccacc atctcaaggg tttgtgtcaa aagaaaagag ctcaggagga tcctgcacca
117601    gcaattaaac attccagcct ggaagtgaca catgccattt ttgctcataa ctctttagac
117661    agaaccaatc acatggtgcc acccaaccac aaggggtcct ggtataattc tttcatgggc
117721    tcacataaca agtaaatgca actctgtagt aaagagatag attatctgtt gtaagaaaat
117781    caaatgatac aaaaccattt cactcagtaa tacccccagag atgatcaccg ttaacaaggt
117841    agcatatatt ttctagactc ttataggaat atacatatcc acacatacac aatttaattt
```

-continued

```
117901  aaaaatcaca ctagaaatgt cattctaaaa tctgttcctt cctgggcccc cagtcatata
117961  acaatcacat ttctccatga aaagacatat aattttacct catatctttt agctgctaca
118021  ggctaggatg gactgtgatt tacttcattc actctgtata gagtaatatt tagtttcttt
118081  ctagattttg atattattaa acactttga atcaatactt ttgcacctgt atcttagcta
118141  acagtaaatg tttatgactg actgaataaa gatgtcaaca aatgaatgaa tgaaaaccaa
118201  tcaccagtga tttaagactc caaacacatg gcgagagaag taaaaaatgc attattccaa
118261  ccttctcat gttgtttagc atgcttcaga atggcaataa aggcagagga attcttacct
118321  acgttaatgt agcaggtcat tcacattagc atttctagag tttgttaaac ccctggattc
118381  ctgttcaagt aaaacatttg ttttgattat aaaacttaat atccactctg agagcctgtg
118441  gaaatagaag gtagatggca atgttactgc cgtaagtctg aagctcctga gacatgaaca
118501  agatggtaat gtgactcctc atttatttt tatcttcagt ttcaatttt ttaatcatca
118561  tgtatctaga atgactagtg attttaaatg agaaattgga atctaaagat aatcagagtt
118621  ttagcagttt aaaccaatca ccagtgcacc agcttgaaaa gctttgtgac tttgactgtg
118681  aaggcattta cagtcccagg aggaaagtgg ctttggcagc tctcagtttt gatgggttaa
118741  gtagtttgta gttggttttg gaggggtgt tactgtggaa gataaatgaa ttcctcagtt
118801  tatgaactta ctccccaggc tgctcaactc agctaagctc tcatggcaac tgctcgatgg
118861  ggttctcact gtgagacagt cagccaccacg cttgaagccc tgcaggaaaa acaaacccca
118921  ctgaatcaac caaaatattg gagagaactt cagtagtttc agtaaatcct aaatcagaga
118981  agaagatggt gtgtgtgtgt atgtgcttat cgtacatcct tattcacatg agcttttataa
119041  ggactcatca taaaagatga ctgaaagcaa ccagaaaaac attcttctta ggctgatcta
119101  tttcatttc aattcaagct gtatatagta tgcaaagcat attttaaaga tatgtttaat
119161  tttgccaatt gtatttgagt agttattttc ttagtctgtg tgtgtgtgtg tgtgtatgtg
119221  tgatgagaga gagagagaga tttggccaag gagataataa gggagaaggt aaataatatg
119281  aggaattata gcaaattatt acgtctgatt tgggaataa gaacaggaat gtatcaatta
119341  actacaatg cactacaaaa tgccatagac tgggcttatt tcttacagtc ctagagatag
119401  agaattttaa gatcaaggtt ccagcaaagt gggcttcatt ctgaggcttc ttctcgtggc
119461  ttgtaggcag ccaccaactg aatgtgtgct cacatgactt ctttgtatga gcacacggag
119521  agaaaggtgg agagaggcgt gggagggagc aggcagcaca ttagctctcc agtgtcctttt
119581  cttataaggg cactaatccc atcatgagtg ctcctctcat tatttcatct aatcccaatg
119641  atctccccaa atcccatctt caaacactgt cacactgggg tttaggggttt caaccaatga
119701  atttagggat gcacaaacat tcattccata ataagaggtg ttaaattctt tgctcactaa
119761  tcagtcccca aaaagttcct aggaaattga agtttaaaac atttctattt tggataatct
119821  ccaggtttaa aaatctccac tctgaaaatg atgtctacac aaacattcat tgttgcccct
119881  ccatcttaca caggggttgaa cgtcttcacc ttcattccca ccctcatctc ttacatcaaa
119941  tccttgtgaa tttttaaaa tggtagagtc agataaagat taaagacaga aacagggtaa
120001  agcaaatttg agaaactgtt tccaggagcc aacccctgga tattcccctg tttgccaatt
120061  tcctactgct actacccaaa cctttaattt gacttcactt tcttatctga aatttgacaa
120121  ttaaagatgc atttaagcta acaagcatta acatttaaaa aatgcaaatg tgtatgtgtg
120181  tgtttgtgtg tgttttgagg agaatgccat gttaatagac tattaatttt tttgacaata
120241  gtgggatatt ggtgaatcca agtccttttc tttctagcgg atggttgaag ctaactgcac
120301  tgagatcaca gaagttgtat gaaggggaag agacggagta tggagaagtg gatgtgggga
120361  gaggtcagaa tggtgcacca atgcattcac cccagtacat acagcaactc aaaaggctca
120421  tgtcccatat aatggacact gtataaatat ttgttggatg agtaaaatga agaaagacta
120481  ttgaagtgtc tgcggaaaat actaaaattt gggtgttggg tcttataaaa ggatgctgac
120541  atggtataac aacttctttt caccttgcc aagatttcct gagtgtaact ccttgtttat
120601  cttctttg attttgtatc agtacatcct gagcttgatc ttgggggtta tccaacatgt
120661  tattattact tagataaact gttcactctc tgtaacttgc acctgaaaat gaacaaggcc
120721  attgagaaaa cccaatgctg aaaagctcct taagctgata aacaacttca gcaatctcag
120781  gatacaaaag caatgtataa aatccattac attcctatac accgacaaca accaagctgc
120841  aagccaaatc aggaatgcaa tcccattcac aattgccaca aaaagaataa aatacctagg
120901  aatacagcta accaggaaag tgaaagatct ctacagggag aattaaaaaa cactgttcaa
120961  agaagtcaga gatgacacaa acaaatggaa aaacttaaca tgctcatgga ttagcctctt
121021  gcagaaaagg gaagaccttt gtcatatgca ttatttgcaa atgttttccc tattctgtag
121081  gttgtttatt tattctgttg atggtttctt tcatgtgta tgcagaagct ctgttgttta
121141  gctagatccc attcgtcagt ttttgcttgc aattgttttt ggcatcttca tcatgaaatc
121201  tttgcttgtt cctgtgtcca gtatgttatt gcctaggttg tcttccagga tttttatagt
121261  tttgggtttt acatttaatt ctttaatcca tattgagttt attttttgtat gtggtataag
121321  gaaggggtcc agttttggta ttctgcatgt ggctagccag ttatcccaga accatttatt
121381  gaataggaa tccttcccc attgcttgtt tttgtcagct ttgttgaaga tcatataatt
121441  gtaggtgtgt ggcctttctc ataagcgctc tctattctgt tccgttggtc taggtgtcgg
121501  ttcttgtacc agtaccatgc tgtttgggtt actgtagccc tatagtagag tttgaagtca
121561  ggtaacgtga tgcctccagg ttttttttt tttttttgc ttaggataac gttagctatt
121621  caggctcttt tttggttcca tattaatttt aaagtagttt ttttctagtt ctgtgaagaa
121681  tgtcattggt agtttaatag gaatagcatt gaatctataa attgctctgg gcagtatggt
121741  ctttttatta atatagattc ttcctatcca tgagcatggt atgtttttcc atttgtttgt
121801  gtcatctctg atttctttga acagtgtttt ttaattctct ctgtagagat ctttcactttt
121861  cctggttaac tgtattccta ggtatttta tcttttttgtg gcaattgtga atgggattgc
121921  attcctgatt tggcttgcag cttggttgtt gttggtgtat aggaatacta gtgattttac
121981  acattgcttt tgtatcctga gattgctgaa gttgttttat agcttaagga gcttttggtc
122041  agagactatg gggttttctc aaatatagaat catgtcatct gcaaagagtg acttcctctt
122101  ttcctatttg gataccttta ttcttttctg ttgcctgatt gcccctgcca ggacttcaa
122161  tacaaatgtt gaatagcagt ggtgagagag agcatccttg tcttgtgcca gttttcaagg
122221  ggaatgtttc cagcttttgc ctgtaaagta tgatgctgac tgtgggttg tcatagattg
122281  ctcttattac tttgaggtat gttccttcaa cacctagttt gttgataatt tttaatgaaa
122341  gcggtgttga atttatccg aagacttttc tgcatttgtg gttttgtctt tagttctatt
122401  tatgtgataa agcatatata ttgatttgcg tatgttgaac caacttgca ttctctcaag
122461  tagggataag gccaacttga ttgtagtgga taaacttttt gatgtgctgc tggattcaat
122521  ctgtcagtat gttgttgagg gattttttgca ttgatgttca tcaaggatat tggcttgatg
122581  ttttcttttt ctgttgtgtc ttccaggttt cagcatcagg atgatgctgg cctcatataa
```

-continued

```
122641   tgagttaggg aggagtccct ccttctcaaa ttttggaata gtttcagtag gaaaggtacc
122701   agctcttctt tgtacatctg atagtattca gctgtaaatc catctggtcc tgggcttttt
122761   tagttggtag gctatttatt actgattcca tttcagagct tgttattggt ctgttaatgg
122821   attcactttt tcctggctca gtcttgggag ggtgtatgtg ctcaggaatt tgtcaatttc
122881   ttctagattt tctagtttgt gtgcatagtg gtgttcataa tattctctga tggttatttg
122941   tatttctgtg gggtcagtgg tattatctcc tttgtcattt ctaactgtgt ttattttgat
123001   cttctctctt ttctccttg ttgtcagct agtggtttat catttatttt cattttttca
123061   aaaagccaac ttctggattc actgatattt ttaatgtttc ttcctgtctc aacctctttc
123121   agttcagctc tgattttggt tatttcttgt cttctgctag ctttgggggtt ggttttctct
123181   tggttctcta gttctttag ttgtgatgtt atgttgttaa attgagatct ttctaactct
123241   ttgatgtagg catttggtgc tataagtttt cctcttaaca ctgccttagc tgtgtcccag
123301   agattctagt atgctgtatc tttgttctta ctactttcaa aataacttct tgatttctgc
123361   cttaatttca ttatgtatcc aaaagttatt caggagcagg atactcaatt ttcatatagt
123421   tgtatgattt tgagcaaatt tcttagtctt gatttctaat ttgattgtgc tgtggtctga
123481   gagagtgctt gttatgattt cagttctttt gcatttgctg agcagtgttt tgtgtttatg
123541   tgattgattt tacagtatgt gccatgtggc aatgggaaga atgtatcttc tgttgttttt
123601   aggtggagag ttctatagat gtctagcagg tccatttgat ccagtgctga gttcaggtcc
123661   tgaatatctt tgttaatttt ttatcttgat gatttatcta gtactgtcag tggagtgttg
123721   aagtatccca ctattattgt gtgggactct aagtctttt gaaggtctca aaaaacttgc
123781   tttatgaatc tgggtgctcc tgtgttggtt gtatacatac ttaggatagt taggtcttct
123841   tgtacaatct gacccttac cattatgtaa tgcccttct tgtcttttt gatatttgtt
123901   tgtttaaagt ctgttttgtg tgaagttatg attgcaacac ttgcttttt tctgttttct
123961   atttgcttag attttcttc tttccttaat tttgaactta tatgtgtcat tgcacgtgag
124021   gtgtgtctct taaagacagc ataccaatgg gtcttagttc tttatctacc ttgccatttt
124081   gcactttta attaaggcat ttagcccact tatattcaag gtgagtattg atatgtgtag
124141   attttggtcct ggcatcatgt tagctggtta ttttgcagac ttatttatgt gtttgcttta
124201   cagtgtcatt ggtctgtgta cttaagtgtg ttttgtagt aactggtaat gaccttcct
124261   ttcacattt agtgcttctt tcaggagacc ttgtaaggca ggtctaatgg taatgaattc
124321   tctcagcatt tgcttgtctg aaaaggatct tatttctcct ttgaatataa agcttagttt
124381   ggctagatat gaaattctgt gttggaattt gttttcttta agaatgttga ctataggctc
124441   ccaatttctt ctggcttata aggtttcagc tgggaggtct gctgttggtc tgatgattcc
124501   ctttgtaggt gaccttacct ttctctctag ctgcctttaa catttttct tgcatttga
124561   cctcgaagaa tctgatgata atgtgtcttg aggatgatct tgtgaagtat cttacatggg
124621   ttctctgcat ttcctgaatt tgaatattga cctctctagc taggctgggg aagtgctcat
124681   ggatgatatc ctgaaatatg tttccaagt tgcttatact ctccccattt ctttcaggga
124741   taccaatgag tcatagattt ggtctcttta cataatccca tatttctcag agatttgtt
124801   cattcctttg tattctcttt tctctattct tgtctgactg ctcatttcag aaagccagtc
124861   ttcaagctct gagactttt cttccactta gtctattctg ctattaatac ttgtgactcc
124921   attatgaaat cacttagtgt gttttcagc tctgtcaggt tggttatgtt cttttctata
124981   ctggctattt tgtctgtcag ctcctgcatt agtttattgt gatccttagc ttccttggat
125041   tgggtttcaa tgtactcctg catctcaatg atctttgttc ctattcatat tctgaatcat
125101   atttctgtca tttcacccat cttagcctgg ttcagaaccc ttgctggtga tgtggtgtgg
125161   tcatttggag gaaaggaggc actctggatt tttgagttgt cagggttttt gcattgcatt
125221   ggttccctct catctttgtg ggctgacatt ccctcagttt ttgaagttgc tgaccttga
125281   atggggtttt ttcttctttt atcttatttg atgaccttgt gagtttgatt atggtgtaag
125341   gtaaatttcag ctgactggct taatttctgg aagatttag ggggccagtg ctcagctccc
125401   aacctctaaa ctgtgtgctc taaatctggg ggacttgtat caggctcctg agtgttctta
125461   ctgaaacac tcaggctcca ggctcctgag tgttcttact ggaaacactc aggctccaac
125521   tttgttcttt ggctccctcga ggttaggaat ccactgtggt ggggtgctg aggtggtccc
125581   agaccactgg tcattacact ctaataagta gtgtcatcca gagtttcata gtgtggtgac
125641   agtgggatct gtcctaggtc acatatgcca gcagcagctg cagtggcagt gaggtggggt
125701   gcaccctcct cagctgcagc agggtgctag tgggtgccag ggtgcctgcc tctgtgcggg
125761   tgttcaccac agtagtggag gcaacataac tcaaggggac caggggctcc tgctggccac
125821   tgtgtacaca gttgtctga tggtggtgtt ggcacggggt ggagcactgg caggcatagg
125881   tctgtgtgtg ttctctgcac cacaggcagg ggtggtcgct cagggcaggg aagggtttgc
125941   tgttttctgt acctagtttc actctcgcag cagtgttggt gcaagagcag ggcactggtg
126001   gggttggggc ttgctggctc tgtgcctgtc agggctctaa ctgcaacggc agtcagtgtg
126061   gggaagtggg atgggctgca ctctcactgt agcaggggca gggcagggca gggtgtatgc
126121   acacgcggca ctggtggggt aaggaagaca cacgtgcct gtgcagacac gtcagcaaa
126181   ataatgtggg tggttgctgt gggcacaggg gaagctgctg tgtggggagt ggttgagctg
126241   atgcatggcc atgggggcca ccctgctgga gcactccact ggtcaggcat ggttgccagt
126301   acaggagcta tgatgtgggt tctcagggca cctgaggctg ccttgcaagc aggctgggca
126361   aggctggggc ttcaggagag gccaggagaa caaggagtgc ccaaatcaga ccaggctggt
126421   ctgatgggta agaccaatct gcaaagttca ggtccgacag ttctcctagg gctaaagtct
126481   cctatgggag ctacttgaac ctaggggat ggccgtctct ggctgtgctt tgctacagat
126541   gcactgccac caaaccatct gagttccacc tcattgctgc ccctaccact tctgtaagca
126601   gctctccctg ccaactcagg tggcggtcga ggggtctcct cctgcagtga ttccagagcc
126661   ctgtggtgag agccatttgc tccttgccag gagttattgg gagccacgaa taagtcctgg
126721   tgtgcagtag ccctgtgcag ggttcccagc ttcctctccc ttcagcccag cttctgtgtc
126781   ttccctctgt ccatcctcag ggccttccct ctgaagatct gttaggagtt gtcttggtcc
126841   ctctgtggca gctgttccag ttggctgcat ctagtcagcc aacttgcgct ctctctgaat
126901   ccatgctttc tatggaaaga ttttcctagc caaacccatc tttggcgtaa tttcactttat
126961   atatttattt ttatgtaacc tttaaaaaaa gtgcattaga agttatctat aaatcaccta
127021   taataaaatg cacagatctt aaaggtccat ttgatgaata ttgacagtca cagtttcacg
127081   tgtaaccacc acacaaaaca atataacaaga catttctatc attcagaaac ttccatcctt
127141   ccactttcct gtcaactgcc acccccact cacatataac tgcttctaa caactataac
127201   taaagattag tagtgcctgt tctcagactt catgtaaatg gaaacataga gtgtatatat
127261   atatatatat atatatatat atatatatat atatatat atatgtgtgt gtgtgtgt
127321   gtgtgtgtgt gtgtgtgt gtgtttctct cttctttgta tcagtatgat aattttgagg
```

-continued

```
127381  ttcattcatg atgttttgtg taacagtata ttgtgccttt ttattgttgt gtagtattcc
127441  attgcacaga tttgcttgca ttttaaaggg gctttgcagg aagaagagcc ttttctcaaa
127501  atatgaatta gaatataatg actgaaagag aagtgtagaa ctaaagggca taatgatctg
127561  tgttgagtac tcactgtgga tttcctgtca tatctctctc cttatttagg gactcatcat
127621  taatagtgtc agtggatttc ttctttcttc tgtgtgtcaa cagcagacct acacttgata
127681  gcattttggc cactaaccct gcttgaccct gcactaaccc tcttgctatc aatttcagac
127741  tcccacatct ggggccagac ccacacaact gttcctatca ctgctactcc agctcctcag
127801  acattccatc agccaaggag ctccttgccc caattccctc taagaactgc aagatgcagc
127861  agcagtccca catcctcggc tgcatgtatc tggcatgcag gtgttagttt ttatagtgca
127921  ccaggtagga gagatgccac tggagtaggc gaggttccca ggccccttt tttggggatt
127981  gttcttttcg tgtcctcaca catactgatt tgaatgtcaa gacagacaga gctgggtagc
128041  tgaggacaga ggggaaggaa aactgctcat cttggggctt gtctttgaga ggcaactgaa
128101  caattttga tcaattactg aatagcacaa gcctggattc tccagagagg tgattatgac
128161  atgaaataag cacactctac aggtgtttct gggatgcata actccaaata tacagtttta
128221  aagaaatgat aaaataaatg attttcccag agaaactgaa attgcattct gaagggtgac
128281  ttggcatgat gttcagttag ctgatatatg gcctcttgca ggtattcctt tgcatcccta
128341  gtgcagtgaa gaaagccatt actaccaggg agaagcatgg gagtagtcag tggcacatgg
128401  ctgtcaccac ttgtcttaca ctgttgttaa tttgtttaac aattctgctt agccacttat
128461  tcacacagta ttctttagca gcaaggagaa aagtatcagg gcaaccaagc catggcttgg
128521  agccgtgacg tgtgtaaatg gaagggttag ttttatctga ctgttctttt cttccctgtc
128581  attctttctc ctctcttgaa actcaggctc tcaatgggtg aatatcatat ggcatattta
128641  cataatggaa taatatgtga tggtgaaaaa tgtgtaaact agagtaacat gtatcaaaat
128701  ggatatatct ttaaaagtac agagtaaaac aaaaactaaa ttacatatgt atgatatgat
128761  gccattcatg caaaatttta aaatatgcaa aatgattctg tacattgtct agggatagtt
128821  acatatatgt aaagctataa aaatatgctt cagattaata tcctccaaat tcagaatcag
128881  ggtttccttt ggttggcggg ttggagagag atgcacttgg aaggagtaca caactatgct
128941  tgtaatgttt aattttctac actaggccat gacccaaatg tatttggtat attgttattc
129001  agatattttt atatattcaa aaatatttta caatacatga ataaaaatta ataaaataag
129061  atcattgttg gtttatattg tctaaatcat taaacttcca aaggtttaat attcattcat
129121  tttcaccagc tgccaaactc aagattttgg caaaaaatga gattggtgtg gaagtgggtg
129181  ttctccgtgt tctctgattt tacaacttt aaatgtcaat gaattgttat tagaaggtag
129241  tttgacactc tgagacagat acatggtatt atgtccactt aattaatgat ataggacaca
129301  ggattttaga taaatgctgg tgtaaccccc tttctcatag aatttctgtaa ttcctgtatt
129361  catttatgaa atatttattg aggctgctat gtctattgct gtggagtagg tatcaggaca
129421  ggtgcaggta gaaaaaatgt cactttacaa aatgtagaat acaaatgag aagtagagaa
129481  aaaaccatga tgaattctag ccagcttgca aaaaggaaat gcagcaaagt acaatggaca
129541  taaatccgtt aggagcatct gtaccagatt ggataaatgg ggtttgctga gtcatttcac
129601  tttgtctgag tctggtatgg gatgctgcaa gctggacatg ggtcagggcc ttctggagct
129661  gagatcaaac ctctcagacc tcagtccagg gcttgcattc ctttctggat tctcaagatc
129721  ctgtagctca gatcctgtga gaagagccct tgtctaatga aacctatgaa atccattctg
129781  gggaccatgc tggcctggtc tagagatgtg ggcaatgctg acatccagca cgcttgagga
129841  tgcaaggagc accctacgag aatagagatg caaaggcaga ggaagagaaa tgatgcaatt
129901  tcctttttcag ctagggagaa ggatagcaga aatgaacaag atctgtgagg aaatttatat
129961  taggggataa acaaatgagt tctgtgcctg cctcttttaag tctcttcaat gccatgttca
130021  tttctctttt ttgattacca ggtagtgctg tcctcagtct cttggggcat acttctttcc
130081  cgatctggca caaatgaccc ctcagggctt aaagacttga gaatgacaga tgatcaaggt
130141  atgcatctct taatcaagct gctgtatttg cccatataaa gaactgttta agaaacacat
130201  ctagcagatc tctgcctcca atgctcacat attatttaac tccaacttt acttttgaaa
130261  aatctaaaga aaatcttatt caggctgcga ccaaaggaga gggaaagcta aaatgtcct
130321  atgcagggga aggactttt tttttaatt ttaaattcag ttggtgattt tattagctgc
130381  tggtctgacc ttccagctaa cttcaggatt gtttaggtta agattgaaaa tgtaaatttg
130441  catggcaaga gtgcttttcc aaaggatgct gtttagatag ctcttcaaat tgttggatga
130501  taatgactat tgtcccttac ctttcaaagc tgaaggaagg tctgcagcct gtttacctgc
130561  ccagcttatc tagtgagaac ctaccatgtg tccagccatg ggctaggtcc tttccatcca
130621  attaaacccc tttgccagaa tagcaaagat cacatttcaa aaatatatt ctcacgtatt
130681  tacagatatt agggaacaat ccaacaaaaa acaaaaccat attggtaatg ctattctaga
130741  aaattcaact tgttttactc ttcctggcat tttccttcag gaaaagtagt ttgatagtga
130801  agatagtgag atgatgggac tttacaagga gattaggtcc acagatttaa aaaaaaaagg
130861  gccagatgtg caggtccatg tctgtagtcc cagctactca ggaaatcact tcctgatagt
130921  gggaggattg cttgagccca ggagttata tcagcctggg caatgtaaaa agccttacct
130981  agtaaatctc caagcaagtg cctctagaag tattctgggt gcaacagttg ccctctatgg
131041  gacttctgtc ttaggcatta cactgtcaga ttgatcccca tctctgaaag ccactgttgg
131101  gtccctgctg cagtctgaac tcctgggaaa tgtagcatag ctattcctct tcaaccaaag
131161  attgggagca ctcacttaaa ggtaggttta tggaatgaga ggaagtaggt atttgaccat
131221  tacttgccat tcttcccgct tggaacattt gggccttcct tgagctgttc gaagtgatga
131281  gatgacataa taagccagat ttctaccta ctgtgtgttg tgcataatat gcttttactgc
131341  gtacttcaaa ttcactaata tatgcactga actagtcatc caatgtacat taattatcta
131401  ctgagaccaa gaccagagtg atctgctcaa tcaaaaacca ttcatatttt tgaaaaataa
131461  aatttactgc ttttatacaa tttataattg ttctcctttt tttgggcact tggtatgtgt
131521  caagccctga catggtgttt ttttcatacg ttactgttaa ccatggcaac aatacagaga
131581  ggttggtatt agcataccta tttcatagat gaagaaactg gggctgagaa atattacgcg
131641  acttgctcag acttgtatag acagccagtg gcagcattag ggtaaaaacc catttcttat
131701  catatcttgg agtctgttct ctttccattg aaccaaactt ccttcctgtt caaaccatca
131761  acgtggtcag tccagacctg gttagatccc tgcagctgct gaatccacat gcctcgttta
131821  gagcaaccag aacagagatg tgtttcattg gcttgagtga ggaaaaatgc attacaatag
131881  atgtgcttta tgtaaagtgg cctccttttaa aagggatttg cctttctcat acagtgtaag
131941  acattagaag ggtttttgcca aagtaatatg ctttccagta tgaatccttt tcagggaact
132001  tttggttgtt tctctcatca ttacacgggg tatcaagctg aaagctttgc tatcctggct
132061  actgaatcct cagtcacagt aaagttttaa ttttagattt tactagcatt gaaaatgtgg
```

-continued

```
132121  caataagaca cataaacagg acatctaatc catgaagtct tttcaggggc aggaaaattg
132181  cttctctgtg gtacaaggga gattttctat ctgccacttg gaaaacttgt atgaaataaa
132241  ccccaatttg ggatgttttt ggagggcaaa gggtgatgtc ccctatctga ttggacttag
132301  tggtacattt taacctgtga tttatgcaac ttgacattga ggttcattta gctcaaatta
132361  caagtaaagt aattcaatcc ctaatgaagt gtaccctgca tgacatattg accatgggag
132421  ctgacaatca ttgcttaaaa acagacatag gttccatttt cttttgtcat tcaaagtagg
132481  ttatcagtta ataaacttaa aacagggcct gctgacctgc cattcttcca gaagtatttt
132541  attagagcat cagaaaagca cataccaaaa tttacattgt aatggaaaaa agagtaaaaa
132601  actgcatgaa ctcactgttg ttcagaggaa tagctttcc atgcatttat acaagttcct
132661  tccaactttt tattttggaa atcttcaaac ctatagaaaa gcagaaaaca tagtaacatg
132721  aacagctgtg tactcttcgc ttgattaat cagttgttaa tattttgtca catgtgtgta
132781  ctctctcttt cacgtgtaca cacacacaga cacacaattt taaagtaaat tacagacatc
132841  atgacacttc actcctaaat actttagcat gaatcatcta agaatcagga cattcttcta
132901  tattaccaaa atatcattat catacaccta agaaaattaa caattcaaca acataatcta
132961  atataaagtc tgtattccag tgtcctcaat agtctccaaa atgtatttta aacttatctt
133021  ttaaaaatga gaatgcaata aaaaatttca ccttgcattt ggttgttatg catttataca
133081  taattttgtg gggaataaaa atgaaaacaa aggagctttg agccacagtg attgaaagca
133141  cagtgataca gtgttggtta tgtcttatgc caaagtattc ttcaaggatc tctcttataa
133201  agtatgtaac ccatgatagt ggtcattttt ttttccaaaa tgtttcaatc agtaccccat
133261  tttactgtat ttaaattggt aggcacatgg aatatgctat tacctattca tatttttaga
133321  aacctcagtc tcattgaaga gttgagtgtt ttattctgtt tccatataaa ctgtaggatt
133381  agagttccaa atctagagga tttgttccaa ctccactcaa aaagaaaaaa aaacatgatc
133441  tttcctgcat aaaatgtttt tcagcattat gtttagaatg aattatgttt caaataattg
133501  aattttcttc taatttagac ttttccttat tctcctgaaa gcaaaatgtg ttgtaattaa
133561  aaatggaaag aaaaatgaat attcactagg gaaaatgtaa ttgttttatt actgccatgg
133621  acatttggag atcaagttta agaaaatgtg gttgaattca gtgttgcaag tgcacttctc
133681  atctataatt acacatgtct aaggtctgt aaagtgacta taattgcttt agagttgaat
133741  ttaaggaaa tattgagaaa ctgcatttca tgaattacag tttgcatgga tcttatgtac
133801  tttattttat gtctttgtac tttcattagc agtgcaaaag ctattgcaga aaatagaaga
133861  ggggaactat gaccttttat gttcactttg cagaagatag taacttggtt tttaaagaag
133921  caaaacaata ttatcctctt ccataataaa tcataaaaag gcttatgaac aatgcaatat
133981  attttgaaac aaaaacaaaa atatctgtc cattggtgat tgctattgaa ttttaaaatt
134041  agctagaagt ttttcctcc agctatatat atatataatt actatttctt ttttgagat
134101  agaatctcgc tctgtcaccc aggctggagt gcagtggtac gacctcggct cactgcaagc
134161  tccgcctccc gggttcacgc cattcctctg cctcagcctc ccgagtagct gggactacag
134221  gtgcccacca ccacgctggc taatttcttt ttgtattttt agtagagatg gggtttcacc
134281  gtgttagcca ggatgatctc ggtctcctgt tctcgtgatc tgcctgcctc ggcctcctta
134341  tatttatagt ttttagagac tgcctcactc tgtcaaccag tctggagtga catgataata
134401  gttcactgca gccttgatct cttgggctta agcaatcctc ctacctcagc ttctagagta
134461  gctgggacta caggtgtacc acactgcact ggccaggatc acttcttatt atagaaagta
134521  gaatgtagac tggtggtgtt gtaaggactg cttacctgtt ccggtccaca gggccttcca
134581  catacacaca catgtcctgt tagctacaca tactttctat aaagtttagg gttattctag
134641  cctctcataa gaaaattctg ggcttaaaac atagcttcaa agtgctgcac tgctcccatc
134701  actaacagat ggtcaaacta aatacatgtc catgtcagcc tggctaaatt gggttgcaac
134761  tccaactcta gagtatcaat ttagcatgtg cagagatctt taattgtttc acaaaaaaca
134821  aaaacaaaaa ccctagagct gtctacacaa ttgtctgtaa taaatccaag gtcttcttgg
134881  agaaacattt tgcctcatac tcccagacgg tgcttcactt ggtgggagaa ttaggacctt
134941  cctttattat ttttagtttt gagtaccttc ttggaggcaa gctatagaaa gaaaagtgca
135001  caaatgataa gcttagtgag ttttcaccaa ttgaatgtcc ctgcataacc agcctccaga
135061  ttaaaaaaag aaaaaaaaaa tctgaaccatt tccagcacct aggtgacctc cctcatgtcc
135121  cttcaattcg ggaaccccaa caggaacttt agtaccttac tgattgtaat ctcagcaaat
135181  gagcttgctc tacttttgc ccagtcccat taattaactc ttcttcattt ttagtaacaa
135241  cagaaatgca gatgacacga cttcttcatt tctcgaagct atcttcaagg ggttggtaga
135301  catgatggga aaactcttga gtgatgcaaa tgtggctttt caccttcatg cttgcggagt
135361  gactgctact tcatactccg gaggcagtgc ccaaaaggat tataataggg gcagaaggga
135421  ttgtcctggg gcaagtatac agttgtattg atataggtac cttagttaca gcagataaaa
135481  aactaaaatt ttcttagtca aataagcaga gtatttaaat gcattaaatg ctggggaaat
135541  ctatagctag gaggaaatcc tgggtaatta actctttaaa tgtcaaaagg taatgcggac
135601  ttctttctgt atctacgagt cttactctcc acatcgagtg ttacttctcc aaccagaaga
135661  atcgctttgt gaaataattt gggctctctt tcttgctatt aatgggacaa caaggaatgg
135721  gatgggggag gcagagggga aggggcggtc agttaggccc agcccttcat gctgatgggt
135781  gggcataaaa ggaaatggac tggaaccatc catacctttt caaggagttg tcaactcaaa
135841  cttaagaaaa taattctagg gatgttaata ttttacccta agccttttga ttgtgcatga
135901  aatggaagtg ggtgaggttt agcatgtcac tgaaatttcc cgttgatgca tatctaccat
135961  tctgagaact gtatcctgcc tctttgattt agtgtgacaa ctggatttta tttatacaat
136021  taattaatgt ttgcttgacc acttttttcc aatttctttc cgtatgcacat aaaagagaac
136081  ctgatataaa tttctcttc aaaacaattg acttagcaac tgctgaccttt ctgttctgtc
136141  attctaagga ttgattggat attgttgaat tgtttcattc tacagtaatt aaacataaaa
136201  ttaattatgc tagtaaccca ttattttttct gaaccaagga ctaagtcatt tgttttcact
136261  tggttactca gagaatctgc cattagttga acagggaaaa ggaaattgta ctgttgcaaa
136321  cagaaactaa atattttaag gcatatttta atggctaaaa tataatctga aagcttctca
136381  tttccatatg cacagcatat tgaatttgtt taatgtaatt taggccataa atctttacc
136441  ttatgatatg gtcatttaaa tattttctca ggtggctaat catttagaaa acatgtcgaa
136501  gaagaatata tgttaagaaa gagggggcagg tgaataaaac tggaagcatc cataaagcca
136561  tcatgaatct ctaattcttg atttggtttg ctgctcacct gaaatgaaat ttacttcaca
136621  agtcatttct ttgttagttt tttatagaaa atgcttaaaa ttaccctgat atatgagga
136681  ttgaatttgg tattgacagg caaacaagta tggcaggact aaattatcaa aatgtatgtg
136741  ctgatagaga ccaaaatagg tttttacagt tttcattagt gcaggccata ttaatttaat
136801  taacttgatt gaagacagta tcactagatg aggcagcaga tacctagcct tggcctatta
```

-continued

```
136861  ctcacccata ggctataaaa tgatgcacct gacacatggg tatgcaatct cacatatttc
136921  acatttggac tctgccttt actgcaaggt tcctatggct ttggaatatg tggtgaactt
136981  catcagatga aattcctgat gcttttaca attcaagatc ccaatcagta ttttaaacat
137041  tgagcaaatc cttggcttat acttttactt tatgcaattt ggactgtcat atttattatc
137101  tagcctgctg agcaccctgt ttctttatct gactattgtc cttcctcctt agtttagacc
137161  cctctcctcc taacctgctt gtgggtctgg ttgggtctgt gaatcataat agcccactgt
137221  cctggccaca agagtgtgtg cggggactaa gagagccaat taatggctct tttcaggatt
137281  tgtctggttg gaaataatag agaagaccag ttacctaccc aacatccatt ctttccttt
137341  cccctgtgaa gaaaatccca ttaaaaaaat tgtggcagtg tttccatttg aaaatattca
137401  tctcctcaca ttctactgga gccaaatgta ttcacgttcc catttctggc caatgtgatt
137461  caaatggaag tctgcagtgt agggcttctg gaatgatatt ggtgtcctga caaaagactc
137521  agctgacaag tgactttgc acttaatctt cttccatttt ctgcctgaaa cttgcacacc
137581  atggactagg cttaagcctg ctaagaacaa tggagtagga atcgacagga ccctggataa
137641  ttgataactg gctcaagtag ctgtaccagc cttggtctac tctgtttcag aattcttgtt
137701  atgagaaaaa taaaacttct gtttagttat gctcatgtga gtgggtcgct gtcatgctca
137761  gtaggacatt gccctaattg ttgtaattct tttcctatac taaggtggct ttgtagagga
137821  ggccagcctg agaaaatgag tcaacctaca aagagccaag agaccaatag caagacctgg
137881  tcttgtgccc tgaattttta cacagcctgg ggtatatta tgtgagcctg tgcagccctg
137941  ctctgctgaa ctttgctaaa gttggtttct gtcacaaata caagaattct tggaaatatg
138001  agaataaaaa cacactctac gcaacagata ttcaaaacct tgaattagtt tttcttagca
138061  ctaattccct attttctggg atgggaagga ggaggcctga gttcttaagc tgacagtata
138121  ggtttagggg ctttggaaca tcacccagca ttttgaacc tcagtcttct catctgcgaa
138181  acaatgtgaa cagattagaa gttctctagg gtagcttcag ttctaaatga ctatgactcc
138241  atgcacattt tccacaaata tgggctgaaa gggagggatg taaaatacag aattcaatta
138301  tgaaagaaat gtactcagag atttaccata aacacctact cctacagagt aataaaaaaa
138361  agaaagttac agcacaagta gagattttct gtggatgagg ttgcacaggc tctggttatc
138421  agtctataaa ggtagtgtgc acagagttag ggaaagaaac agacttttcc tcaggattaa
138481  attacttcta agcattgatt tttagatctg aagaagactt tcatcctcaa atatgaaaac
138541  tatcatacta ataacaataa ttacagataa ctacatacta tcaactctgc tattttgcat
138601  gcatcatcac atttcatcct cagtgatgct ttgagataga gaatcatatt attccattt
138661  tataactatt cgcttttttt agttacaatc agaataattc caaatttgta aatagttaag
138721  gcttattatt tgctgttttc aacaaagcag agaaatctga atatcagtgt tgattccaaa
138781  gatatttctc cattttctca ctacatatat taaaggaaat aatgggctcc aaaggaaatg
138841  ttgattggga attaattgtg taactgcctg caaaacaatt ttgcctatta ataccagt
138901  gcaagagagg attttcctat tgtatagatc agtggaaatc cagaggcact cagtgatgca
138961  aagttgcatt gaccttggag aagatctgag atagacaaaa tctacatatt taaatacaaa
139021  attgtctttg taacaaatgt tgattagact taagaggctt cagggactgg gttttaagaa
139081  gagtaaaaat cctaacattt gttgagcccc ttctgtggag caggcattgg gctacatcct
139141  cttcacactg catctcattt agtcaccaag gaagcccagc gtagtagata taattgatcc
139201  attttacaga ggaagaacag agggactaac ttgctgaagg tacacaggtg ggaaacagtg
139261  aaaggggctg tgagctcagc tcttcagct gccagagtct gagctcttgc agcagatggg
139321  agtgtgagtg tcagtttc aaattccatg atgggaaccc tggaaaaatt cagatgtcta
139381  gtgaatgaag gggaagaatg agttgtagat tgtgactggt cttgtattct gagcaggcaa
139441  agagctgaga ttaaagagtt taacctgcgg aaaatttgtt gtgttggcta ctaaccaaat
139501  ctgttttcat tctcctggaa gctctggacc catgttgaaa gcagacttct ggtaagtttt
139561  cctgagttga tgtctgggct ttttcctcaa aggagataga tgtgaagctc ttaatctggt
139621  tccttctagc atggggagca gaaagtcaga agccaagatg ccctggctga tctgtttcttc
139681  tgtcttgagg aa gagtata cgttaaacta tttccatctg atgtaaatct gaaacactct
139741  ctgcggtaag ggaagacagg ggaaaaattt cttatcactc caaatgagga acaaaagaag
139801  gtaaaataat taccctcagtc caccaaaagg tagagaaatg ggtctgggcc cacctgaaag
139861  tacggtgtgc cttgtgttct ctctctcttt ccctctatt caagtaagac ctggaaactc
139921  ttaaaaacct ccggggaggt aggtaacaaa cactttctct tagtaactct ctaaggccat
139981  catagttctt aataacccctt atgtaaggat gtttcccctc tagagcaaac ataaatcatt
140041  tggctgcagg ttaattctat tttctctctt ctctctagtg aggagaaaga acagctgttt
140101  accatcttcc cagagtcaaa ttgaacacac tggaacagag aggtatcaaa tcacccccag
140161  actttcatca ttcaggcaaa atggcattga catgtcagta gttctcaaag tggttctctg
140221  aacagcagga acagtatccc ctgggaactt gttagacatg caaattctca ggccccacac
140281  caggcctgct gaatcagaaa ttcaggaggt ggccccagaa gttggtgttt taacaagcct
140341  tccaggtaat tttcatgcta tctgaagttt gggaactcaa tagttatgaa tgatatcata
140401  tgtagatatt ttgatcagat atgggtgact attactaata atcatttgaa taattcgtaa
140461  tgttttttct acatttgtgt gtatgtctgt atataagaat gtatataatt atgtattgat
140521  ttaagtgaga tttctagttt ggaatcagtt attcttgtaa gatacggtga aaccagtgag
140581  catgagaatt gaacctttgg ctctggcctc atgagtatac gactagagaa agtctaagaa
140641  tttcagttgt gttatgactt gtgttaaaga gttatggtct gcagaaagtt ttgagtttct
140701  tccaaacatt ttaaatactg ttgctgtgca atggtagtcc ttgcacagtt cgtaacatcc
140761  ccgtttcaaa tcttactctt tacagaaact ctcatgatac catgaccaac gagatgctaa
140821  gctgacatga cccatgggcc cgctatagct ttctttctaa ctcttgataa agttgaccta
140881  tattaaagga ccttctcctt gttttcact caagcttagc tttgggaatc ttgcctatac
140941  taaagtgaga ttatgtttt gaaacattac ccagaccct taatttgtct tgattattct
141001  cagattgtgt tgcacagtca atataactcc tgtcttccc ccacaagctt taatgaggta
141061  taattgacca ataaaattgt ataaatttaa gatcttccat gtgatgatt gatatactta
141121  tatatcccta tttttgaag aagctgagaa aacacatcca ggctgcaaga ctaggacaaa
141181  agatttcca ccattttat atgggtgtac ataagccagc aggaaatctt tgtcaaccat
141241  accctttag gcatagatca tgtctgtttc gttcactgca gcataactgt aactaacctt
141301  gggcttagca caggtatgtt gtcaatgaaa acttgctgaa agaatgaatg aaggaaaaca
141361  tttttatgac tatttcaatg gggcaactag gaattctgct ttaatgaca cctggaagga
141421  tatatgagaa atcttgtaaa aaactttata gaaccttta gaacacattc acccagaagc
141481  cgatatttt aatctttaaa atgagcatgt tcattagtta taaaaaatat gtatatatat
141541  gtgctgctaa aatatttgtt ttgggatctc aactcaggtc attaagatgt tccaaaaaat
```

-continued

```
141601   ggtatttatc tgttcaaatc caactttag taataaatat ttgccaaggt agatgtaccc
141661   taaatatcca acagtttatt tagcaaaata acttgtctag aataatcaag agttctcaaa
141721   gaattactgg ttatgactaa gattggctat taagacatga aacacatcat attcttttcc
141781   aaatgttttg aaccttaat gatatacttt tcatgttttt cacttacttg caatttttt
141841   gtcatgcata ttcttcaaac aaaatcttct cttatcatgt tacatgttat ctctttttctt
141901   cccctgctgt cagcttaaga tataaagtac tttttcttc aacaaagttg gggggaaag
141961   atcttatttt taaactaact tggaatggtg taaatttttt taaaaatcaa acattggtat
142021   attgatagca tgtactcaac atcagacagt attgtatttc acaaatatta actcatttat
142081   ttttcacaag aattaggtac aaacactatc ctcatttttgc aggaaaattt aggcacagaa
142141   aggttaggtg attttcccaa ggtcacacag tcaggaaaaa gaagaactgg gactcaaaca
142201   tagatagttt ggctatagtc catgtacttc ctattgaacc atgaagcctt tctgggatta
142261   tggctctatt taggtcatcc tagggtattg ccttcaatcg tgggtttggg gtggagaggt
142321   tcatgttgag gatttatgga ttaggagctg tagcagctgc ccagattttc aattttctg
142381   atattaaagt ggtgagttta aaaagctgac atttgtaaaa gataatcatt tctgaattgg
142441   gagggggat ttttccacta tttaaatggg attttacaa gcataaataa atctactgag
142501   aaaaatgtga tgttttacct gaattgcaat tactttattt ttaaaataga agttaaaagt
142561   ctcagagaga gttgtcaata agggcttcgg ctggaactag tatgttttgca cacacctccc
142621   tctccttcgg ctctttttcct tcacccaacc ctgtggaaag taaaaatgcc aagaagaaaa
142681   atggggaaag tgatgctatt aaatatagca caggtgctgt tttcataggt ggtgggaagt
142741   tttagcttt ctatctttta cattctctgt ggagctttat taccatttct cagagataca
142801   catactgaaa gagagtccag gattactggg gaattgggtt ttattcactt cacttgtttc
142861   aggtagggg ggaattgtg aaagagtgag aaaacagcaa gagcctacta gatcagtatc
142921   tgttttaaa gtggcattca attgaataaa attttagag tgcaggagta gagttttctg
142981   attttactta tttattatgg caaatcttat tcaactttgt tatagaaaaa tcgaaaaag
143041   ataactgtca tgagtttcag ctttcttaaa tcagaactta atttgggaac tgccccaaa
143101   aaatcccctc aagaaaaatc taccaatacg attttcaact aaaattggta aggaaagata
143161   ttataaagta ttaaaatcat aaggaatgcc ttttatttt gagagaaagt aaggttttat
143221   ataattcacc ttgcagagtt caacattttg caaattaagg cagcaacatg ttggagcctt
143281   tccactcaag tcaatggata aagtcttgac ccttaatatg taatgaacat atgcaaataa
143341   tggaaaatat tttccaacca ctgattcctt tgctgatgtt accaaaggtc atttcatagt
143401   ttcaatcatt aaagttagtt ttgcttcctt ctcttacctt agtaaaaata ttctaaattt
143461   gtattcaaaa tctccatatc ctcttggctt ccaaccgaga gctgacgaat attacaaga
143521   agcagttaaa acctgtccat taaaactat gacacttaga ctatttgtat acacatgacc
143581   ttcaaggtta tatgaaggta gtccattaat ccctctgtct ggtctttatg ttttcccttt
143641   actcttaaaa tgaatgaagt tgataaggaa taaatatcac tagaaccatc atgatttttgg
143701   accaagttac ctgaatttcc tgtttgataa tattctgttg aagaaccatt tactggagga
143761   gccaaatgca catgttcatg gtggtggtga ggaggaggtg gtcagggatg gggaaggaag
143821   gtgggggtgg gtggggtgga gagcagtaca aaaagagacc acagtgttct accccgcgct
143881   gctggtgttt tcagattaag atggggggatt aaggaatttt actcagcaat ttgagatgct
143941   ttgttaggga ctgaggagat ttgagctgct ttgttctcaa accacatgtt agtgaaaag
144001   caaacaggca cttaatcctg acagacaaaa gaacttgaca tcaatttgcc ccttgggagg
144061   tgaccaggag ttctctatga agggctaaaa tggccagccc ttgttttcct ggagcctaat
144121   gccaacattc catcctaaac tgtattcctc agcagtgggg ctataactta tttggtttga
144181   ctaaccaaga gtttctagag actatggact tttacattat ttttaaaaac aaaacaaag
144241   accttttaaa ggcaaataac ctacaaggtg ccaaatattc aaagagtttt caaacatgtc
144301   taatatttg gtcactcagt cttgaagtga aatatagaaa ggctgagatt cttttttttt
144361   ccttttgaaa ataatggttt cctctaacaa taaaatcaca gggcaacata tcaatttgg
144421   agcccatggt tatgaaataa acatcaattc ttatgtagat gtttgaagga gattctactg
144481   aataaccagt tatattctaa ggtcatgtcc ttccaagtca ctgaagtagg acaaaagcaa
144541   acaaaatgaa taggaaagaa attaatggct tcttcaattg aattttatac attataaaac
144601   ttaagtatac atagttagat agtctggcac acaatctgaa attgtgggat aaaggctcac
144661   ttttccatct tgagtttgtg ccaccctaat ccgttgacca aaagtgaact tttagtggcc
144721   tattgattta ctaaacgttg gcatgcatag ggaagccatt tttaaaaatc agaattgaag
144781   cagcaaattt ataaaacaca tttcagagca aatccttaca ttctaaagag tttctagttg
144841   aatattcagc ttgaatcaat agttactgta ctctggtagg atgtaaaaat ctgctatatc
144901   ttaataatta aaaagcaagt ttgtcacaa ttgcaaaatt gctacatatt gcactatta
144961   aacacagaac tttgagtcaa gtcaagcctc tgctcctgct caccctatc tctccctgt
145021   aaactcaaag gaaaacttat ctctttatat cgactctata ggtgattttc tccattctgc
145081   tataaactca acattttatt cttaaataac catagagttg ttcaaataat cttttcttc
145141   aggattggtg cagccctctt tatgtttaca tggcactaaa ctaattttta aatgaccatg
145201   aacacatgat gatagaatat cttataaga aagttaatgt cagctgagcc tggcagctca
145261   cagctatat cccagcagtt gggaggatga ggaaggaaaa tcacttgagc ccaggagttt
145321   gagaccagcc tagacaacat ggcaaaacct catctgtaca aagaatacaa aaattagctg
145381   ggtgtggtgg catgcaactg tagtcccagc tactcaggag gctgagttag gaggatcacc
145441   tgagcccggg aggttgaggg tgcagtgagg tgacagaga tgacccaact gcatcccagc
145501   atgagcaaca aagtgagaaa ttgtcttaaa aaaattttatg tcactttata tttccaaaga
145621   aatggaatga gcataaaaaa gtgtttgtat tattagttgc caatttggga gatgagacaa
145681   tttccaatat tttgtatatc cttaattatt tattataaaa accagtggga cagaaatctg
145741   aaattaaaa tattataaag agatactttc attatttta tttaaaacat tatatgcttg
145801   gctttagatg acttctgagt tgtgttgttt ctctctcctt tatgaaggtt taccaggcat
145861   attaaaagga tcaaatacaa ggtgaagtaa aagcagaaac acaatattca tttatttaac
145921   tctggtacag tagagcaaat tcagggtgac tcaagggaca cagtgtcttg taaacatat
145981   gtacttaata taagggtcat aaaacttatt aaattaaaag ctaggttaaa aataggaaga
146041   aaatttatgc tgctgtctaa aatgcaata atttccctt ggccttttccc tttccaagta
146101   atatggggttc tggtcaggag gaaaaaaaaa aggcaactta taaatctcc atttggagg
146161   accaaatgca aatctttgtt aactacacca tgcattttaa caggcaagtg atacggctga
146221   aaatagagta gtaagaagat aaaatgttta gccttaaaaa gtgtacttgt gatgaggatt
146281   caaggatata ggtggcatta ttcctgagtg caaacaataa actccattct tgttagctgg
146341   tatccaggaa gaatagcttt agggtatggg gacagtagaa aaaatattaa aaaatagttg
```

-continued

```
146401    atttggcttt gtggcagcag gacagtgagt agggagcaca aagtgtgcat tgctgttcag
146461    tcagggcaca gcagtgcttc cctggacaaa accttccacc cttgtcccag caaaatttgg
146521    gctgtaacaa aatctatgta agccagaaaa tttgaagtga agattgacct cctatttgtg
146581    tctcactctg ctgcctgtgg gccactggtg taggaaagga cacattaccc ttataaacaa
146641    cttcagggtt tgagagtaag tgtggcctca actttgtaag cacttgtatt tttttttaat
146701    ccatgcagct aaaatatatt gggcttgctt aaatgtttat tctcaacatg atagccattt
146761    tcctacctgg ggttcctagg tataacacct tagtaatttg aaaccaaaat aaatatcaat
146821    ttccttctac tgtagtcaca tggggggttg tttggaattt tatcttcaca cgaaagtctt
146881    acggctgttg agaagggctg tgccggtcat ttatctgttt actctcagac tcactctcat
146941    cctttccttg ctcttttgtc ttccaggcgg cttaaccctg caaagtacat taccatctgg
147001    cttccacaaa ggctctgcaa agggagatgc tttttaggg agtaggagag aggctaggat
147061    agccattctc ccactctccc acctgcattg aaagtgcttc tgcaatgcct acctctcccc
147121    tgaggtctca gacctgcctt cttctctttg tccttctagt caaggggtgg cagtggcttt
147181    acgtctttgc caaactcttg ttgatctcat catccccatt tggactttca gttcttccaa
147241    cactttgta actacctccc tagattaaat ctctaggttg aactacttgg tagtgattct
147301    gtttttcctg actaatgcca ggaccaactg ctttaaaaaa attatttcta ggttattagt
147361    ttgaaagata agagattctg cttgacgtct tgaggggtct ttgcctgttg gccagtgggt
147421    aggctgttga gtcataatag tcacttttggc aaggttctct ttttggttga agtgaagcaa
147481    acctgtttga aggtgaaatg agaaagtaag aactagtcaa ggtctttaca gggtggacat
147541    tttaggaata caagagaagt tgaactgaaa gggccgtgtg gatatgttgt tgatcttggc
147601    gaactctcct gagctgtata gcactgacaa tggagtgcta ttatagccct tggaaaaact
147661    cagctaaaac ctcataatcc attttctttt catccttgca atctctttt ttttaattc
147721    tgtaatgaac tagcctgata gtgtaaatag cctcatttga gctaagatgg gcaatataaa
147781    cacacacact cagagatcag tagaggaact ctgaaaatca tacaccagtt tctctttctt
147841    tctcttttc ctctttctct tctcactcac aattgctaac aaagttaaaa gttggttctc
147901    atgatgaaac ttcataggct gctgtctgga atgaattttc ctgaaagagc tctaactgct
147961    gggggaggga gggaatgtag ggtggggtgg gggagaatcc agacctcaaa cccaatagcc
148021    ttgccattca aaataccagc ttgaaggttg acatttgcag ggaccttggg agtatagcac
148081    gtggggactt ttatcctgct acttcagtga cagctgggcc tggtccaaac aacactgcca
148141    gtaacattgt catcgagtag gttaagcgga gctggagggg aacttccttt tagctttaga
148201    ctttagacta caaagtctca gagcctttgg gtattcattc accattcagt gaacttagac
148261    tggcctgaag tttatttca tcaggatgtt agtagggctt gggaaacctt gaaaatggaa
148321    tgctcagttt ttgtgaagac tttcttttaa acctacagat ttaatgaagt ttaaacacat
148381    tgttcattgt gtaattatag atgaaatatt agagaagtgg actaattata caatgcac
148441    tcaaacccaa ttaaattaac atctgtggtg aatgtaagga tattctcttt tactaataag
148501    aaatatttc taaacaacag agaataaaat cattaaattg gatatgctgt agagattata
148561    aatatcctat tagcatataa aatgaggatt aaccttattt aatcactgca tgtcagatca
148621    tcaaaagtca tgttgcaccc ccataatgtt gctgtattaa ttctacagaa ataacaataa
148681    aaaaccctac tattaatcaa catagctctc aatgaatgct gttcttgtct actaaattaa
148741    actgttggag aaattcaagt attcccataa ttgcttaaca aaatagcaaa aatactttta
148801    cctattcatt gtggtattat ggctgattca gatttacgtc atctactggc tgaagaggtg
148861    tgtcttcctg gctaggcaaa ttagcctacc tcaaaataaa taaatatac tatccattcc
148921    agctagcacc acaagtgacc ttttgaaaat gtaaattaag tgattgcaaa taccaagagt
148981    gtattcaaaa tgaaaacgta tggacttgag acatagtgcc accattgctc cagggattaa
149041    ttggcagact atgaatccag ggatttctac ctttcaatct ggggcattca atattccatt
149101    ggaagatact catgaccatt gttactgtga ttaaataatc aaatctgggt ggagcgacaa
149161    caaagtggac ttggggttat ccagattcat gttatagctt attatgaata ttgattggat
149221    gcagtaacaa aaaacaaatg acagcaaagt tgaaggtagc catttcatat atcatgttca
149281    tagattgccg ttttcacag ctgagggaca gaaatcagtc aacagggatg gttgattcga
149341    gggagtcttt gtcagaagag agtgaaagag ctaaaatcaa tctttcttgc ttttctttc
149401    ttccctgttt ctctttcatc tctccttccc tccctccctt cctttgtttt ttccttcctt
149461    ccaaagagtt cttctttata tttcttccaa aatttgaagg gcgtttttt ctttcattct
149521    tgtgaaaacc ataattacag ggcctggaat ataaatgtac ttataaatat tgagaataat
149581    tatggctatt acaactttgt atttctaatt tggtgaatta aaaaaaaatc aacacataca
149641    attcttttc agttgaaccc ttccacttag ttttgcctact catccttatc tgaggaagta
149701    agttcagttt aaaatgtaaa aattcagatg taattggaaa gaaatttaga ataaactgga
149761    ggtaacctgt ctgcgggggc atggtagggc acactgtgat gggcccacgg gcagggactg
149821    aatccaggaa tacatgtgga gggcagaaaa gtctacctgg gaaactgaaa tttaataaac
149881    acatcaaaca catgaaagaa aatgtgattt tatcacacta gaagtatatc tctcagaaag
149941    ccacttcaaa gaaagcaagc agaatgcatg cgcaagtcaa agtccttttt cgtcctcagg
150001    accaaagctg cttagccaag aagttttct ttctgtccag gtgccataca ccatttaagt
150061    ttttttccag tttccttaag attttaaagc cacttgcact acatatatgt agtgcaaaaa
150121    gaatatatat atatatattt tttttttt tttttttttg agatggagtc tcgctctgtt
150181    gccctggctg gagtgcagtg gcacgatctc agctcactgc aacttttgca tcccgtgttc
150241    aagtgattct cctgcctcag cctcctgagt agctgggatt acagacgtgt ggcaccatgc
150301    ccggataatt tttgtatttt tagtagagac ggggcttcac catgttggcc agcctagtct
150361    cgaactactg acctcaagtg atccaccctc ctcggcctcc caaagtgtta ggattacagg
150421    agtgagccca gtgggcccgg tcaatatatg tatatttaga aaatcttctg tggcttcttt
150481    attctataga gagagcaata tgttgtgaat acagtgttaa taataactac tattttgcc
150541    cttttgaac aaaccaacaa ttgtgagttt tagctttat ttttgttctc tttaagctca
150601    attaaaaagt acttttgcct tccaggagcc attttacaa ttattgaa gtgctgggtg
150661    aattaaagaa aatcctatgc cttcaaattt tagttgaact tatagatttt ccataacaat
150721    attactttaa aagactcttt ttcttccccc ttcttccagg tctcactggc ccagcaattt
150781    agccttgcct cagaattgtt acattacggt caaatggttt ggttgtgaca caggatggtt
150841    ttcagaaaag cagcagacag tgtctagaag tgggaaaaaa ggtctttatt gagaaggtca
150901    aagggacat aaaggcaaaa actgactttc accgaaacag aactggagac caggcctcca
150961    gtgtcctttt tgtaattcat tgcttgtttt caggtcccgt gatagaattc ttccataaca
151021    gaagaggact ttgttaaatt gtaaatgagt attacttcaa gcactctgtg gaaatatatt
151081    ctccccctat agcccataca ttatttctgc ttagttatag tggctcacct ttcctgtaac
```

-continued

```
151141    tatcaaagag aacttaattc aactcacacc acatcacttt acaattgtgc agctctctta
151201    atcaacctt gtgtcagcca cgaatgtgca gtatgaccta atttgaaaat gtctcaaagt
151261    gctgactcaa actgttagtg aataaaggct ggtcattacc attatgcac taatgtgatg
151321    caaaataaaa ttgagttgca tcagctgaac attagttggc aaaaatatca gtgattgaat
151381    ccattttctg ttcatatttt atttatactt agatatgtat acatatatat ataggcacat
151441    attttttgtt tgtttgaaac aggcttgcgg caaaattttt gagggtagag gaaggaagcc
151501    acattttaac actggaaaaa gacacagggt taaaggctga tcatatgtgt atcatgatct
151561    cctctctata acatgaagac atgttgttga aatcttatta ggatatttat atgcacataa
151621    gcataacat atgaaaatta tcatctgtc gtgtactttg gtgctagatt ccaaggtttc
151681    taacagccct ggcacttctt actacttcgt attactccaa aattctgact ttgtattcgc
151741    aagtaacaaa aatttgagat tttttttcttt catgggactt ctttccttct tctttacttg
151801    acaaaagtt actttgagat ggaaatacct ttaatacaca ctgtcgttaa ttacttgtga
151861    acaaaagaaa gtgagatata aaactagaca ttatttagcc tcatccctac tgataatact
151921    ttgtggaaag caacatcaat gatcttttt ttacacaatt cagatggttt tgaggaaaaa
151981    ctcatgggct taattaatac ctgtgcatcc taaaactagc attggttca aattctaagc
152041    tgataagtag tcattgaaaa taaatcagca ggaaactttc ttaatttaga gaaattttcc
152101    taatggtaaa tgagaaactc caccctgtat ctcattttgg gtctccagaa ttctgaaaat
152161    cctgaacata aaagtgaggt attagtgata aaatactcts gatttttatt ctttaatggt
152221    tctaacaaac ctagcacaca aatgcaaagg agatatgttg tcctttaaaa tggtcaagga
152281    caagaagttt tggctatcag gaaattattt aacctgcttc caattgagag agtatatgtc
152341    ttcataatat atcaccataa gcgatcagta gagaatacag ctaaattaaa atgctggcaa
152401    gctcagttca ttcactttt agaaaagcaa gtaaaacctt ccagcaagat gtgtagaaat
152461    tttctattac gtgatgactt tcatatttga atccattta cattgtgtaa tatgtgactt
152521    gggctgtttt tatgacctgt gcttattac cacattaaga caatcgacat ttcaaaaaag
152581    aaaaagtttg aataatttca aagtgaactt gccaaaatca gcattcagaa gcatgggtgc
152641    tcgcgcgctc aaacacaggc acactttcaa tttacctaaa aacggggatc acctttgta
152701    gctaaaatgc aatctttctt atttttaggt taccctgaga aaaggtatgt gggtgtgatt
152761    cctgcaaatg gattgccagt ttcttaacag ttcatcattc ttaaatgata gaagtatagc
152821    agcacccttc tgagaaacat cttttctgta gattttactt tgtccatgcc aggacaaatt
152881    gcgtgctaag ttgaataatt ctgagatgtg agacacctcc ataactgtcc ttggactacc
152941    aaggagctgg catttctctt tggaagatga ggggagaatg ctccctgctc tcttaattga
153001    tgatttactg tgcttttccct tgggaccaca accgatgatc tgtaagcttg ttgaattttg
153061    aggtagatac taaatataat caatatataa aaatatttaa aaaaggagag aaaaaatgca
153121    atgaaaattt atgaccttaa cattccttca gggtcaagca atttatcaaa ttctctcact
153181    ttctggtttc aattacacag ccattgtgga aggaacttat tttagcaggt tcatttgcct
153241    cagtggggaa tacaggactt tggcctaatg cttcaccttt agtgcaggcc attttgagcct
153301    tagaacaaat accaatcatc actctttggg aaaaaagaat ctgcatcggc gtggcctatt
153361    ggaatggggt ttctgtcaag gtaaacggtt gtcggcaatg actgtggtag agtggcgata
153421    aatcccattt tattgctgaa aaattccagc ttctctccat gcctgacagc tccccacatt
153481    ctcatacca tttgggcaat ttctgcacta tgtccatctg gttctcatta cctctcaacc
153541    tccctgcgtc tgatccagaa aaagagcagg tcagaaatgg ggctgggggt gacgaaacca
153601    aggtgatgaa caaaacagaa agcagggga tggcccatgg ggttcgggga agagttgagg
153661    ttgggtggag tagggattcc agctaagaat ctgagtggtt ttgagaaggg gccatgtcaa
153721    ttattaaaaa tgatcatgac agagctggag ccagaagcca gagaaacctg tatctttaga
153781    ctcaggcatt aaaaagacac ctgttttaag gtgaaagaga gagtagagag agagaatgtg
153841    gtaggtagag gagggtggga aggcatctct attaagggca ctgccagctg gattatcaga
153901    gtagcggacc tgttctagaa aagcacggag ccctgtgtac acagttggca ggcttctaaa
153961    tatgctgatc aaactctgct ggagattaga ttttggttca aaaacatatg ttttgagga
154021    caaagaaaac ttttggcct ccaaccttat tgtctccatc tttcgaagaa gaataatatt
154081    taaaaactaa cttgtcttaa ttagggcatt tagaatgaca ggactagcac tgactcactt
154141    gggaattcat aaccctacat ataatcactt ttggaatgga gtgcatttat gccttcaaaa
154201    agttggcctc attttctgaa gctgaaatcc ttttgatcat aattacttct gacctaaaat
154261    tacccacagt caccatacaa tgccacgctg ggacaaaaaa gaaatacata ttgtaagtat
154321    ctgataacag atataaacta tcgccaaact taaatagtaa cattaattag actaggatga
154381    aactataca ctatatattt ctgaatataa cattaatca ttattattat tcttttggtg
154441    cagtggttgg ggccgttgtc ataatgcta aataagagt tgttaaagta tattgaagta
154501    taaatgataa agacctgaga actttgcata aaaatgagaa tcagatgaat gactgccattg
154561    atgtagttat ttcaccacct gttttgaagt caatttttat atgcaaatgt cttaaaacca
154621    gatatgattg tgtattctta aatacgttgg agagctgtgg cattattatg atttgtagac
154681    agaatctctc atgttagata tgtttggatg gacatatga atggtctctt agtgccttct
154741    ggatcccagg gatccagagt gtatttcagg tcctaaaaat ggacattttt gacagtcaga
154801    accccagta ctgcactgaa tatctgttt tttatgggtt gaattcccaa tatcgaaatt
154861    acgttaaatt ttagttgctg agccagatcc tttagacaag aaatactggc ttccagtaat
154921    caggattta tttctaaatt ttcaagtcat gaatgctcaa aggaggtttt atgaaatgta
154981    cctgaaattg taaatgaatc ccacgtagac acttaaattg agaaattgtt gctaaaaatt
155041    ttaaattaaa acgacaagat aatttggact gacgtacatt agaaatcata aaaatggaag
155101    tttgttaact ttaaaatgaa tattttagtc aacaaataaa atttcaaaac agacgtttc
155161    acatgcacat attaaaaggc ataaacctt agctagggtc acgtatctat taaacggtc
155221    ttgattttaa tggtgtctct aatttggaaa gtaatttcag attcttagcc aagaagaatc
155281    ttgcttgaac tttacttttc taggctgtac atataccaga gaaacatgat catttaaatt
155341    ctaaaggatg tttgtttctt ttaatagcat agcagagaat taatgcatg gggagggg
155401    acgtgacaac ttaacctgat gtttgatagc tgtttactta tgaatgtgtg ccacagattt
155461    cagtgtctgt aaaagaaggg gaaataaaca aaccgatggc ttttagggaa cttaagacac
155521    atggaagaaa gtgcttagaa ggctattgaa atatttacaa aacaaatcat ttacattaac
155581    tttcttatgt gtagaaactg gagtgcccat gaaaagacag agcccaatttt ggctatgaga
155641    agtatttcag catcaaaatg gttaacagta ttatagcttc aaaagagcct attggctcac
155701    cctcaaggat gccctgcagt tgttgttaaa gtcatcagat gaagctagcc ttctcagcta
155761    gccttcagat ttgtctgcta acagtaaaaa tactataata aatcggtaac atatgttgcc
155821    aggcaaggaa aagtgatata aataaagaga ctgggagacc caaaccaagt acaatgtgaa
```

-continued

```
155881  aagaatttaa atttcaatct atttgctggc taattaccat ttgaaaagta atttgaaagt
155941  tttactgtta tttgctgata ttcttcctca tttttctttt tttcctcttc agattgcatt
156001  cttacccaaa tactcttcgt gattgcctgc tttgcggctt tggggtaagt cccagttttc
156061  cacaacctta agaaaaaaat gcataacata aaagatgcca gaaagactta tgtgtcctga
156121  tagtcggggt ctgtgaaata tacatgggtt tgttacgggg gtgggaggca taatgaaata
156181  aagaaaagcg atttgtttct gcaaggatca aaagtgtgcg aaagtgtgca tatgcaaacg
156241  aggctcccat caggaaagcc acctctggaa tgtaaatgac aaagcttgga acacacacaa
156301  tcaattattt tcaccagcat ttaaaatata gaaaacaaaa tctgctttgg gaattgactg
156361  aatatttat ttagctttt ttattgagac atccttttgaa aaatggcata atataaatag
156421  ttttacaaag caacaatata atcaatctct aaactagaat ataaatcaag gatttcatta
156481  actgctggta gccagtttaa attgtagtct tgtccataat gtctatctat ctatgtatgt
156541  ccaagttata ttaaaaacct ttaaatggct ttgtaatatc agctacatct agctattata
156601  ataattaatg gtactgtttt ataaatcaat acatgtattc ttgataaatt catatccagt
156661  taatggtgta atttaaataa aaaattaatg taataaagga catacagaag cgggcaggaa
156721  atctttaaag gttaagagcc aaatttgtct aaattcattt ttaacctgtt ttggaaaagt
156781  ttatatttaa aatcagctga gacttacctt gtttcgtgaa aactaactctt gccatttctg
156841  gtggtatcta gtattaaatt tgtaaggtgt tttctgacgt tgttttaatt acgtagttac
156901  aatactgtgg aatatttac tgtcgttgca ctattttgtg actattgcat attctttagt
156961  aaaatagaac aaaacaaact aaaaacatca caccagcaat ttatttttaa tacacaaatg
157021  catgtaaatg atttatttt tgaaaatctc caaaactata cacacatttt atttaagggg
157081  aaaaatgact gactagttca ataatttgc atgtggaaga gccgagcatt ttcactgctt
157141  ccgctgagtg aacattccaa gaattttaga aagaaaagaa aaatgcatga aagagtctga
157201  aatgtatttt aacgctgcac ccgggtacag gaacattcta ccaaaagatg agtgtattac
157261  agttctaatg taaagaatac ataccaaaga catatttaaa aaataacaag attttagaaaa
157321  acaactgaag gttgtatgtt atcaaataca atatcaaatc tttccaaata aaatttcatt
157381  tggttcataa gagtacgcgt tttacaaaaa atatctttca aaattatgca gaccagtctg
157441  ccctgccatc ctccttgaca tgatgcagaa atgttccttt aatccactga gctttttctg
157501  acatttttct taacattgct gagccttatt tagagcacca aaggaggcgt gtgcagtttt
157561  ctttgacact gatgggtatt tcaaaatgtt acagagagag ggggaaaaa aaagaaagaa
157621  aagatttgct gccagtcact tcatcaatag agctacagaa gcaattacta tttgttaaaa
157681  gtttacattt caaatgaagc taaatttaa agaagtctca tccttttaga aggactggtg
157741  cttggaagag agaggaagag aatgcacatt agtgattaca tgttaaagtg cactcaagta
157801  ctggaaccat ttaaaatgta ttgtgttttt agttgaaacc tgcagcaaaa ccactcctaa
157861  gaggcttaat ttaggtttta taggaggaac ataaaaaaga ccaggttaca gcaacatgct
157921  gaaatatggg gtacatttta aatatcttca tttaaaaacg tatgtttatt tcccctcctg
157981  ggatcactaa cgtgtgtctc cacagagaaa gcaaggacat gcattcttaa aaattatctg
158041  ttaaagggat cacattccaa gacaggttg agcattttta ttactacaga taacctctta
158101  attgtgtcac tgccttccac ttgttaatca gggacattca acatagttaa ccatgcagtg
158161  gttgtcttta gaagaataca ttatcattaa ggattagaaa cacattttat tcctataatc
158221  atattgcatg tatggttta gcactgctaa aacccttatt acctgcttta aatacataac
158281  acctaagaaa ggattgagat gcctataaca atgttgttca ctactctcaaa ctatgcagtc
158341  catgaaaagc tttaagagac agataatttt actttttcttg tccccctcct ccacctcccc
158401  catgtcccac gcaattccta tttgaattga ttttaggttt cttgtgtagc caccagcatc
158461  tgagatactc aggtactctt tcagagacca aggtgtaagt gtgaagtaaa taaaatcatg
158521  tttcactgtt gctttatcaa ccctcctagg tagttttct gccagccaac ctgcgctgtt
158581  aagacccata aaattatgca atagtgactt ctttggaggt tctctaatca gataatggct
158641  ggtgttggga ggcaagggcc caaggcaatg ttgctggtac ttaacactgt ggttggtcat
158701  tacttgtcta gtagagacca ataaacagct gattactgtc ctatatggag ccaatatttt
158761  acatttatcc tagttatttt ttccttttct ttttaagttc ttataacagg aagtatttgt
158821  caagaagata tatgagtaat agcctcccag gcacccttaaa aataagaatt ttcctaccat
158881  gaaatgatgc cttttgtgga aaggtgggaa tgattctggt ttttacaaga gcaaaggttt
158941  gattcgtttc aagcccactt ctttcagaca gggacactcc acgacaccat ccctgctgct
159001  ccttgtccct ttcccccctct atgacaggtt cacaggctgc aaccaaggga ttttaaaatg
159061  caaaggttta cattcatatt tgcactctgg caataacagg cccattttgc ttcctctgta
159121  agcctgtgat aattgatgct tcatacctgg aactatgttt catttatctc tttactcatg
159181  aagatagtat ataaataaa ggtaatgtat ggaaaggaac caaccatctg aaatataagt
159241  cctaaatcca actagataat cttttaaagc tgtaagagtc agagatggag atttctaaac
159301  tttcaaagaa aacttgattg caaatgagaa acctgtgcat ttttgaatgc ttattgaatt
159361  tgaatgtctg tgtgggccaa aaagaatcag agggacaaat ggaaggcagg aaagaaaagg
159421  tgtaaatttt agatgtgttt taaattaatg tatttaatga catattagac tcattacaat
159481  tttattgact ttcccttttac atttgaatgt aattttttac tagccgatgc aagctgcaaa
159541  atggcgagtc ttctaaggtg cctttccttc cctgggatcc tcatcttaga atgagcagag
159601  gcacatcgat aagaactgga ccttgatttc acaacctcat acaaagccag gcaattcttg
159661  agccaaacaa aggggtgta agctatttca tttatttga taatcctcct cttgcacggg
159721  agcatttgc tgtctttgtc aaagtgaatg acaacaattt ggccaactct ctctgagctg
159781  cactcaacag tgacaggcaa attatcagag gccctgcct tcttattatc agaggaagag
159841  ccatcagggg gacgcatgga ggatacctct ccctgtcac tatttgtcag tgggacaagg
159901  gccactgcta tgggtagctg acaggtaatt tcaacaataa caattactcc tattactggt
159961  gtcataaaca attcgcccaa ggcatgacaa tagcaaagct ttataattca atgccatata
160021  aataaatgcc agcaggtaac aagtaattta gctccaatca agctttcacc ccggcattaa
160081  tattgttatt gcaagaaaat ggaaaattga aaaaattcaa tatgttaatg aattaagaga
160141  ggttcaaggg ctagacaaga cgagttggaa aaaggaaaca aaaattattg tggtatcata
160201  ttttggtgcca tcctggaggc caaacatcag tataattact ttaagacaag aaggggaact
160261  ggagtgcctt agatctcaga gcagggaaaa atgtgacatg agctttcaaa aaatccacct
160321  aactccaatt tctgaagaat ataaggagaa atatgagagt gtatatatat aatgtagcat
160381  ttcactggct ttctttttct acctgaaata tttcatatga agcagaagca tgagtatcaa
160441  agaaacgttt ccatctgttt aagaaaattg tatcagcacc tgcttccttt acattaagtc
160501  tcataatgaa actattttaa taatccttt tttttaatc tggggtgaag gtaaagctga
160561  aagtcatctt tgctctccag ctgtccacct tttggaagtg gactagagga tacagtgtta
```

-continued

```
160621  tcttcatacg taaaacttcc tgatcaagcc aatttgcaat tttagtattt gtccagcaag
160681  acaatgtgcc atcatggtga cagcagtaaa agaatttgaa aatctctaat taggagagct
160741  gcacaccaat taacgcatgt caaatttcac ttcatcaagt gccactctaa ttttccctct
160801  aaaaattaat ggattttttt tcttttggta tgtgtgtgtg tccccttaag gcaatgttga
160861  ttcaaatctg ctcgagatgc agtgttgcac agctaagcat cttcttgatt acaatccgcc
160921  acacttctaa ctgcgctcat tcgcactgcc acggatactt tgtcaacagt caaattacac
160981  cacgctgata acaatgcata atggtgttcc tcctccagtc ccctgtcagg agaggggctt
161041  cataaaaatg tgatgttttc ttctcaactg tatctaaagg aagtttgtat gaccaggtcc
161101  ccagtcaggt gttgattttt aaaattagtt tgttaatttc aaaaaaaaaa aaaaaaagaa
161161  gaagaagaag aagaagcaaa ctgatggcat ataaaaagtc ctcattgaaa aaaaaatcag
161221  caaagaatga ggaatggaga atatctatgg ccaaagtttt gcttaaacac tttgttctga
161281  gacattttca agagcactat tcttggttaa ataccagatt tttttttct ttacttatgg
161341  tctataaaca ttggaagcct ctcttgaaca gactgtattt agattgtgct agaagtttgt
161401  ttaactgcca tatttgccag aatcctcaaa acatcacagg acatagaaga caaatgactt
161461  tgtgtgttgc ggggaggggg gtgggggga gtgcgtaagg gggtcaggac tgtatattcc
161521  agataaatgt tgattcactt ttaactattt tttatcctag ttgcttgttg cagattggtg
161581  tgtctgaggc atcagcacgc gtggtaatat ttctcactga aaaatgaaag aaagaaatgt
161641  agtgattaga agatgatttt acatttagtc ttttagaga ttatttagat ttcttatttt
161701  tcaaaaacaa tcagaaccag aacaaaaaca aggaaattaa acaaaatttt aaatatattc
161761  tctcatagat tcttcaggga gtagagaaca ttcacacggg ttgacatccc agttttctca
161821  gcatgtaagc atattgtaat cctatttatt cactaaaaat ttaaattcat gagatctaca
161881  ctttatttc tttaatctgc aggccgaata cagcttctta ttcactgatg actaactcaa
161941  aatttaaaa cgatatttt aggtttgtat ttccgaatat taaaagtgtc ttccttatct
162001  tatggcccca ccccagcatg ttcttaagtg gtctatttca aacaaaagaa aatgacatcc
162061  ccctttcaac tagccaaaca ttagattctc tcagaactga ttggggggttc actagaagtt
162121  ttgcaattag attcatacaa attgaattat tttctttttt tccaaacatc gttcttagaa
162181  cttataaat atagcaatac tggcttcaca gtttcatgtg gctcgtttac aaataaaggt
162241  attttaataa aaccaagttc tgtgtacctt tgaaaaacaa aaagctggaa caatctcaca
162301  ttaaaacatt acaaaaggat tgtaaaggga aatttaaagg gagaaaactt gatcatataa
162361  tgcaatccag cagtaatcaa ttttaccttc aatatcttgc tttgtttttc aaaatgctaa
162421  ataacaata cataatgcat ccctcatcag ccaaaccatg gaggctctgt gctcaaataa
162481  caggaaacat attcaattt cctaacagaa gacagttcat taagctgtgc cacatcaaat
162541  aaaactttaa tttctccagc atcagagtcg caatgaaagc aattgaagaa gatgagccat
162601  atggtacttc tatcagcaaa cacatattgc tcattccccc aaagttttct aattctgctc
162661  cccagacctg tgtaatatag ataatgtgct ccgagagcag caaccatgag ctatctagtg
162721  tacacttcca atactgtatt taatgggaaa taatgaatca taaaagccta gagaagacgg
162781  cttttgctaa cctaaatctc agctgtaatt tcattgttct gtgcctaaga tgctgtttgc
162841  cctttccaaa caacagcagt tgaacataat tatgctgctt cgaagctggg tttgaaaaag
162901  catccctaat ataaccaact ttctattaac tcctgaaatt tgaatttaa tgatgcactg
162961  atacaggcat tgagataacc aagcatgtgt catttaaaaa tccaaacagc attttctcc
163021  ttcttctctt tggtcagact gctcaatgct tttacgcttc ctcctccgcc ccctgcttgc
163081  gtccatcccc caccccacac cccacccat gcaacaggag tggcatgatt aaaaatgatg
163141  agatttcttt gttattagca aatttgacat ttgcctgatg aaatgcacat aaaatgtgaa
163201  agctacacag tactcagaag aatgtctcca ctccaatcct agctaccaag atgaaataat
163261  ttaggtaaag gaaatgtaaa ggtccttgta catctcttgc tgcagaatgc taggggttgcg
163321  ttataaatga aagaaccaaa tattgctgag cttttagagt gatagtatt tgacacatgt
163381  gaagcacata gtgtttcttc tctcaccttg gctgctttga caatttactt aaacataata
163441  cacatgctca aaagcagcaa tttacatgtc gtgagcccag cctttctctg gtttgagatc
163501  ttggggctgg ggctttgttc atttttagga aaaaatgttg cttttcctc taactaggtc
163561  aataattcca gcttttccat ttttaaagct tatcaaatca ttatttttacc aacatgatgc
163621  taatttagaa catcatcaga taacaccgtg gatacatatt gaaaacatat tttaatggtt
163681  ttgtttgttt tggcatcata tgaaccaaga acaattaaat taaaagaga cttttaaaag
163741  ttagagattg ccttttaaa gcttattaaa atcagcatgt taacatgcct gtctctgaat
163801  tagctctcac acttgattgc catcattaaa acgagttgtt cgggtgctgc tcaaagccga
163861  ttcttactag ttattaactt gaaatctctt tccattgaaa tgtaaaaaaa aaaaaaaaaa
163921  tcattctcac tagtggaaga aacagtcacc aaaacatgaa ctagcacagc aagccagcaa
163981  cattaaacca cgaaaagacc aacaggtaaa ataactacag taacatctaa aacacactca
164041  gggaaaaaaa aaaatcacaa caacaacaaa gaagcagttc attgattata tttcatgaat
164101  gccttaaaac aaatgtttaa acagttttct gaaacagtgc agaaaacctc tgcatgctcc
164161  actgggttgc aatgacaatg gtctattgca atgtaaaaca cgctggagga taaaaggtg
164221  ctttttgtta ccatttatc aaagctgttc atcttcgagc tgcaggcagc attttgctgg
164281  aattgcagat atttctctgt ccaggcttct ttgtttgtgc atctcatttg catatattta
164341  tctccagctg agggtgcgtt ctgctcatta aggcctcct tcacattatt tcataagcca
164401  gctgctgaga gggatttcac ctgtggtgac tgagaaaaga ggggtgaaaa actaaattct
164461  tcataaaaag gaaatcttca gagtctcttc ccctataaat gggcaccatt tgtgttaaac
164521  agcctcttgt catgatagat gcctccagag gtcagggggt aagttgatt tgaaggtcag
164581  cagtaaaaca acagacaaac cagacgccaa actggttcct tagctgtcgg tgggagctgt
164641  ggtacaacca ggtcttgaac cttttcaac ctctaataaa acaggggatg aatctgaagt
164701  ggatcaacca ggcccctgag gaagcagcac agaaaaacac aaataatatc aatatcaggc
164761  agcccacaggg aaacaatggg gcatttctcc gtgctacatg catgctgcta ttgtttcaag
164821  ggctggggaa ttaattccac ttatttattt aaggcgtgtc aactcactgc ctaaacctgt
164881  ttcagtgtca agatggataa aactttatg gctcataaaa tagagccatt catctcaatg
164941  ttctttgtgg tgggtttct tttctttct tttctttct tttctttt tttttttct
165001  ggcatactga gctagaacctc tgctctgaaa cggttacatc tgaacccatt gctgctatga
165061  tccacaccat ttaaaaaaaa aaaattatt tcactggcaa atggatctca acagaaatga
165121  cacagggagg catttttagct acgatgtaat agctccaaaa attctctaa acagtctgca
165181  tgcagttgca tctgttttga gcatgcatta tttacaaagc agaagtttta ctatttttaga
165241  ggaaaagttc aaaagagata gcagtaaaga tattagtttt ctagaatact atgtcacata
165301  tttcatttta cttagaaaat gcaaccttgt taggatagct ctttcccatt catcatttt
```

-continued

```
165361  tgcccaagtt tccactgttc cgtagtcagc ttatactgat gtaataatca aatgccttct
165421  ttaacttgac tgctcagaat tttatgttta attttctgca taaatagca cacataaatg
165481  gaaaagaaaa tgcatttata tgcttttgt attatacatt ttttaaaagt tcagttatag
165541  aattaatttt acttttgatt ttctgacaaa tgactttaat aataatataa ataaacaggt
165601  taacatttct aaagtgccac acacaatgtg aagcacatgt attttctcat gcaattatta
165661  attcaatcta agtcacacag gtccacttag aatggactgt aataacactc tttattatcc
165721  acaacatatt ttagttgaaa caaaatgttc cagtcacaca atatcatcac cgtagtagat
165781  cattatagct ttaacagatg acatcatggg aacacagttg ctttatattg aaatgagtaa
165841  aaagaagcaa tttgatgata tttcacaaat tttctaatca cagcctcagc catgtatatt
165901  acacgttttt gctccattgt aatgtaaatt gatttgtgga ggattcactt actgtcttat
165961  cctagttgct ttgtttttga gttctctatt gaatattgta gactttacat atgatgctag
166021  attattctg atgtagtcag ttggtaggta aggtgtttcc cacatgaact caagttttc
166081  cagtaagtag atcatttgag aatggctcca aataaaagtg gtgctttcac attttgctgg
166141  tacacaaaca tatggccctg aggaagacgg attcattttg gggtgctaag cactgctcaa
166201  gatgtaagtg ctttttattt cccatttgaa ctggtgcatg caccttacag atggaccagt
166261  tgcttacat actggtggcc catttacaaa gcagccctgt ttgaaaacag atgctttcaa
166321  gtgggtcacc aggctctaag aaaaatattt aaaccctttaa ttattggctt ttggtcgtct
166381  atggcaatgt gttctcattt aaacatagag caggggattt ttcttctata accaattaca
166441  gtttaaaaaa tgcaacgaat cttgcttcac acaaggagct taacttgtgg ttggagaaat
166501  tttccaactt attaaatgtt gtttatatcc tcattttgt cttcccaaag cattttataa
166561  ctccctctgt aactgactta tcaattttct ttctgacctt tcatattaaa tttaaccaca
166621  cccccacccc caaacccaga gcctccaagc aactagccta gagcaaaat atacaattta
166681  ctctctccat atctccaccg acgtctttcg tttttcttgt actctaatct aatcggtaat
166741  tcgtaagctt tggccaaata gttaaaaatg ttaagtgcta gcaaagcctt ttacctcccc
166801  ctcagatctg tctctgttta tggaatgggt cccagtttcc tcctcttctc cttcagcctg
166861  gggtcttcag gtcagaacac agtaaataca cacagccctt gctggaccca taatctgag
166921  caaagggcag gcctatatat tcagataagc aggggcagag atagggggctt gaaaggaggg
166981  agaactagcg gagtctgagg ctctgcagcc ctgttcagag aactgaactc aaaagaccaa
167041  gaatccttag tgcagaagga ggaattttgc cttgaaacat ctccccctat ttctaatgga
167101  tgagattggc actgcttcct cttcgtttat ttattttttt ccacgttgct tatattcaca
167161  tccttaccaa atgtattatc ttaaaggcaa tcaagttaaa caataaattt aatttatttc
167221  caatgtcttt ttttcttaag tgtgtttgtg ttttgacctg tgtgtgtgtg tgtatatcag
167281  tgatatgaac tgaagtcatt ttactagaaa gtctctcta ctgtaattt tcagtcccaa
167341  agtttttgac tgtataactg tattcttact gaccacattg aatccccaag aaaaataccat
167401  ctaaaggagg aatgacaaag tgacaaataa atgcttacat atccttcagt cttccaggct
167461  tctattttat tcctgggttc aaatattttc tgttggattt tcacttcttg aaattttcag
167521  tgactcctgg aagaccaccc ttcttgggg atgtaccat tgtgaccaca gataatgtca
167581  ccatgaaaa tcctgggcaa gatgaccatg gctgagaagg tcctttctat cacacttgac
167641  agaatcactg cctgattctt ctttagatgc aatgagtcac accacagatt cgtctgggtc
167701  atttcagact ccaggaaaat gtgtcactcg atttgtttcc gagcaatgtt ttgtatttta
167761  ttgtatacat gtatatctaa ttgtaatctg atttctctag gttattcttt ttggctaata
167821  gagaatagat ttttaaaaaa tgctaattca tgttcctcaa aaggggcttc tttttttctt
167881  ttcctcggtt gaaaagttag tgataattcc aggtaattaa gaacatttta tggaaaaaaa
167941  ttgccaagaa agtaattggg ctgggagccc agtgtgttac acctacacta gagcctcatt
168001  tttgacaaat ctctgaaatg ataacaataa tgataataat cattatgtat cgtttatcaa
168061  gcacttactt ttggtaagca atgtactagg aacttaagat atatattaat ttttgtcttt
168121  acaagtggta agtgatgtac tactctatag tctcaatctt ataaatgaaa aaaaccctcc
168181  gatttgaaaa gtaagaaac ttaatccaga acacacatgg aagcccagaa tttgaaagtg
168241  gttttggctg cagagggctg tcttctgagc tgcctctcca tagcctcagg ttctgcatct
168301  tcaggatgag tgtcttgggt gggagggtgt ctatgtagtg gtgatcttcc atggccagtt
168361  gattttctcc cgcccctact ctcctgagcc tagccttggc attttcaata gctctctggc
168421  atctgggcct gtctctcaaa gaccttctgg accacatgtc tgaaacggaa ctcactgatt
168481  ctctagctgc catgtctcta ctctgtgatc catgtgatgt ttaatgggag ggagtaccct
168541  cgattctgta gtccgaactt aaggctctct aactaccac cttttttcac ctgtcatgat
168601  tattatccaa cctggcagag aagtgacctg tgcaggaggc attacagtct gaccacctgg
168661  gtttgaaccc tgacttccct gtttaccagc tgtgcagtgc tggacaagtt acttactcc
168721  tctgcgcctt gatttttttt catctgtaaa atggagtcta aaatattatt tatttataa
168781  ggttgtctag ttcagattgt tggtaatgtt tgacagaact attaaaatag ccttcaggct
168841  gctgtttctg cagtgaggct cctccttcca taatccagcc cctctggatt acagaataaa
168901  ataaataata aacatgataa tttcctgctt aaaaatcttt aagactccct attgccctca
168961  ggtcgaacta ttgaatcagg aaaaggccttt cattattttc ctccaactgc ccttttccaga
169021  gtcattttcc accatgaccc tctaagcaat ttccactcta gcagcaaaaa attatacata
169081  tgatgttctt ttatttctcc agactttttga ctgtgctgtg ctctctctat caggaatgcc
169141  cttccttttca atttccatgt agcaaaagta catttatctt gcatggctca gttcaaaaga
169201  cacttttttt ttaaaggcag cataaattga gacagtcact tctagaatgc attcctctgt
169261  tttagaacct agtatgttga taacaatcat atgcatggta attatttgtc taccactagg
169321  ctgtggactg ctgtggggag ggactatgtt ttttttaaact taatatcttt tgttctaggg
169381  cctcacatgt agtgggagcc tcccaaattt agattaatat ataaaatatc tttcctcact
169441  cctaaaaatg acttagagca aatgtgaatc aaatgactgt aatgttgtta actagttgaa
169501  ttaactcctg ttagcttaag ataataaagg cagtgaactt gtaacaaaat taaattaaaa
169561  actgaagtgc aattatagtg ttcttactgt ctcccaagata aaaccatgat acattttttt
169621  cctagcacac gttacattttt ttctgacatc ataagaaaat ctgagaacag aaatccttc
169681  aagcatttcg tttgatagag aacatctata ttccatacag cattccatta ggaaaggagc
169741  ctgcttttct cttatctgtc cttactctaa acgtaatatc ttatgggaga cagtatatta
169801  gcggttaaga tcataagctc tggatctgga atgtctgggt ttaaatgctg gtgctgccat
169861  ttataagatg tgtaatggct ggaaacagtt ttcttgggac ctgctatctc atctgtaaaa
169921  tgggtaccat agtaacattc agtgtagtga gtggttatga ggatcaaatg agttaatgca
169981  tctagcactt agatgagagt tcatgtatct tgcacttaga tgagagcctg gctatacta
170041  ggtgctctaa aaatgtgtct tcttatttgg ttggtgttta taagagaggc acctgaaatc
```

-continued

```
170101   ctgatagaaa ggtgaggagg atttcatcat cagggaacag tggaaagaga tggagaagtc
170161   ttgagagctt gtgagaatgt ccattcacct gtgcaaggac cagtttatct atttcagata
170221   taattccaac acttccatga ttcagtgctt catttcatca ttttacacat ggaattacgt
170281   gtaggaacga acccaagtgt aaacttagcc atcaggaaag ttagctccag aactatcttg
170341   cctgagtttg aatcccagct ccatgacatg ctggctgtct caccctgggc aagtgttttc
170401   atttattaaa gattaaattt tttcatctgg caaatgagga aaaaagagt aattttttgcc
170461   ttttacctgt ggtgagaatt aaatgaaaaa ccatcactca acatgcttat cacagtgcct
170521   gtcgtatagt aagtgcttaa tgtgttgact actattttca tgttgcaaat attattgaat
170581   attttttacca catggtgtgg ttttttcaag tagttattga agagagtaaa aacatttatt
170641   tatgtagact taaaaatgta aggtgagcac ctctatactc accatcccag gttataaaat
170701   gaaaggttgc cactttctta gaagtctctg caggcctttc tgggcacatt cccatctctc
170761   tctccagcgc gttactgttc tcctggcctt tgaatcatcg tatacttgct ttactttata
170821   atttttagttc ttataaatgt accactaaac agtatgttat ttggttttgt cttttatgaa
170881   tattatagta atgtaattga tatatatttt atattctgtg ttttgcactc agcagatgca
170941   gctggattga tgcatgcact gtagttcatt cagtgtcatg ctgaatagta ttttatgata
171001   tcaacatcct acaatttact ttgctattat tttttctatt gatggacatc tggactgtta
171061   tttatttatt gctatcacaa agcctgctat atagaacatt cttgtacatg tgcccctata
171121   ggagactttc tatatataca ccccggtgtc tatataaaga ctttctttag gaagttagac
171181   ctaggagtgg agttactcac ttgtaagatg tgggaatatt caaatttact tggtaatggt
171241   aaactctttt ctaagtggca gcacatgaag gagtttttcag cagaagatta ttaggtacat
171301   atttcagatc ctcataaaaa ttatatatgt ggtagttagt ctccaagatt ccacagtttc
171361   aacataaaat ccaaatcatc cacttctctt ggtgttcata ccctttgtgtg gtccctccc
171421   acattatgcc aaggctggtc tgtgtgacca gtataattca ggaagagtga tggtattgtt
171481   gcttctgttt tggacatctt tcttcttgtc tcttttttgcat ctctcactct ggggggacaca
171541   gcttccctgt tggaagcaat tctatggaga ggcccatgag gtgaggagca gaggcctcca
171601   gcaaacagcc agtgaggagc tgtggcatgc caccagccat gtgactgagc ataggagcca
171661   atttctagct ccttggatct tgagatgact gcaatttgag agcttgacta taatctcatg
171721   aaagatcctg aaccagaatt gccctgctaa gctgcacctg gtcatgagtc ccccccgccc
171781   cccccccca cacacaaatg tgagattaa agtattttgtt gtcttgagct aagcctttgag
171841   gtaattttttt atgcagcaaa gataactaat acatattcta ttaaaaaggt gaaaaattcc
171901   aagttccctt aaggaatatg tgaataaag caggatatta aaacaaatag atttgaaaat
171961   ggataacatt aaaagttgat gcacctgtaa ttctaggtgc tattaagtta gttagccatg
172021   taaaaaaaaa cccatagaaa tgggagacca aggtaaattt gtgattcata acctgtaaca
172081   acgcatgtca agcgtgttca cgtttttttta gttgatcttg atttatcatt attagagtcc
172141   tttagatgtc tttataagtt attcttgatg caaaaacatt cattataaca taatagcaaa
172201   aaagaagcca tttagttata cagaaataag agaaaagtta aatatgtcat atatctacta
172261   aagagaatat tataaagtca tgacaaatat atacatattt tttaagtgac atattccaag
172321   cataatgtta agtgacaaca gcgggatatg ctatacaaac agtataaaac caactattca
172381   gtgacttaag ggtgaaaatg gcatctcctta gttgtgagat tatgtgggaa tttgtttttct
172441   tcattaaact tctggactt caaagtctaa taaacatacg ttaagactac tattgttaga
172501   aaaaagtgta tttagcattg aagaaattac ttttaattca tttttagtaa tacaaagaaa
172561   tgcggacagc aaactttgcc ttcagattgg gcagaaaatc cctatcaaat atatatcaac
172621   aatgagcatc tggaaaggtt ccggttgcta tttcgagttg gcttcctttc aaattatctt
172681   gatctttgga tctaatcata gtcctctatc ttgttataat tgctggtcct tttgatttct
172741   cttacagaag tgaagatata ttctaagaag tgtatcctta gatgatttcg tggttgtgta
172801   aacattatag catgtatttta caccaaccta aatattatag tatagcctac tacacaccta
172861   ggctgtggtg gtctagcctt ttgcttctag gctacaaacc catacagtat gttactattc
172921   tgaatactgt aggcaattgg aacacaatgg taagaatttg tatatttaaa cataaatgta
172981   taagaattgg tacatccaaa catgcaaaag gaaatatttt atgataaat cttattatgg
173041   cttcaatgtc actaggccat agagaggaat ttttcagctc tattatactc ttatgggacc
173101   accatcatat acgtaatcca ctgttggtgg aaatgtcatt ggaaggcatg actttttttat
173161   tcatcgtttt gtggacttca gagctattgg agaatcagag ggtaaattca cagaatactc
173221   taaatttaaa tgtgactaaa gtttatattc ttcagttttct gctcatgaag ttgagaagaa
173281   taagataaat gcgatttcac ggaggcattg tggaggcaag ggttgcctaa tacctttta
173341   tatcagaaag gattttttatc taaggcagcc aatgctggca taattgaaga aggaatttaa
173401   gttgaatagg agctggagtc attgcctgca cagtgacact tcatggcata ataagtatag
173461   aaattttttga tattagttta aaaagaaaaa ttctcaaaac ttagtgtttg aatagactga
173521   aagtgttctt tttttgtttt aaaaatgctc tttataacca tattttttgcc cattaaatta
173581   agcttggaaa agaccttaaa atagagtatt taatttggaa gaattaagca aagttccatc
173641   acgcaggaac tgcttcaaca tgttggtgta tttcttctga tatttatatt tcctttctgc
173701   atttccatta caccctgtac ttttagcttg catgctttgt tattactgaa tatttcctcc
173761   tagactgtca gttccctgag gacagaggct atgcctttct ggcttatcat cttttcctca
173821   ccttagagtt tagtaggtgc ttaataaaaa catgttgaat gagtaacttg gttggacaat
173881   tacacggaaa agaggaaatc catgagtaga aaataagtg aagtaaagc tctatgccag
173941   ttgagactat tggcaatttg aagtgtcagt gtccttctgt tcttggtccc aggtgccatc
174001   aaaggtaggt ggaaccaagg ccaggtacca ggtgccacct gagtgctcca gggccagtgc
174061   caagtggaag ttctgggaag gtttctgtga gggtgctcag tcagtgccaa ggaaagagat
174121   cacacctggg tttctgaact ccaaaagggc aaagcagaag aaggagcttt gggtttagca
174181   ggaaaatatc atggcttttg gctttatttg aaacctcgaa cactgaatca tatttgcttc
174241   tcaaagcagt gagctatttt gttttatcat gtacaaaata ctgatctcag gtatttcaag
174301   caatagaaa acattaccag ttatggcaag cactgaattt tataatttgg tgactctgca
174361   aagatctaat cattccaaca tcattattcc aagcgttatt tgattaatca ttgcatttat
174421   agagaatctc ttaccagtat ttattgttta gatttttcca atgccctcat cactgaggtc
174481   tctggttgca tgtgtagaag attaagagat acaataagct aggaagaata gatcaagcaa
174541   cacacactag acctaggcca aactaaataa atatgtctat ttctaaggcc tggaattcag
174601   caagaacaga cacaaattct tgcatatata aaaaagtaaa attttttacaa gaaagagatt
174661   tcagccttaa tttgatctga ttttgcttaa gttaagcagt ttttatcta taagccagtg
174721   ttcataatta tttttttcgta ttattttttcc aatcatggtt tgaagataat aggagccatg
174781   aggaagcaga accaagaaat taaaaataaa attctccaag ttgtgaattg aggacaaagc
```

-continued

```
174841    atgtgtttcc aactcaaaac aaatagttta aaatcctttt tgaatctggt gttaataaaa
174901    tcaaccagaa caaattacag ctaaacgcag ttcttcctag tgtcagttac aagccaaatc
174961    ccctagttta gattctgaat tttaatttct gatcatgggt gaattactca cctccttgtg
175021    cctcggtttc ctctcctata aactagggac aataacagta tccatctcat aggattgctg
175081    tgaggatccc acaaggtaat atgtgttaag ttctgagaat aatgatgac aataataag
175141    tgctatataa atagctataa ttacgattaa acaatgaagc aaaacacttg cctatcgttc
175201    tagatcattt catctttttt tcttacaag agaatgcatt tgttactctt tatagcttta
175261    tagttcattt tatactcatt cttatccttc tatacaagac tgcttctctt gttcttctgt
175321    tggtaagtct gatttctttt aactagcctc ttataaggta gaatgctaca atatgctggg
175381    gccagaaagg tgtctttgtg ttttttgaca ttctagaatc agccacagca tgtgatccac
175441    attagaaatc tgtaggaaaa taagagcaat ttcttaaaat cctttgtgt tcttatttt
175501    atttttaag acaggttctc actctgtcac tcaagttgga gtgcagtggc aaaatcacac
175561    ctcactgtag cagttatcaa cctcgctggc tcaagcaatc ctctcatgtc agcctcccaa
175621    gtagctgaga ccacaggtcc catcatgcct ggctaattt ttaaatttt cttagagatg
175681    ggtgtctcct tatgttgccc tggctaaact cctaggctca agcaatcctc ccacctcagc
175741    cttccaaagt gctaagatta caggcctgag ccactgtgac cagcctttct ctgctcctaa
175801    aatacattc tttatatatt tgtgtcctgg aatgcaggtg attgaatacc tcatttgct
175861    actatttaaa aatggagaat aagagagaaa tttttttatg tgagtatcat tattgacatg
175921    actgtgcata agaaagctgt atatactggt tctttcctgg gagatccgaa gtgagaaacc
175981    agttgtccat ttcactggct cttcacttgg ccatctcctc catggtgaag ctgtgcagtg
176041    gacagaggtc tctgacagc agaagctgca ccctgatgct ctacctatta ttgcaggctc
176101    tattacatgg atggttattt cagttcccaa gcctcagtta ccctggctat cctatgtgag
176161    ctgtacatcc ctgcctacat caaagcaaga acttggccca ggaggcagtg gaccaagtgg
176221    tccaggaccc aactcttagg tctatgactc agtttactgg aaaagccttg taattcttcc
176281    tacctataga aacatcttta aaatccagca gtcaagcaag gatatctctt gccacggact
176341    ttttctaaat ctatttgcct tcagctatgg aactgggaag gctctttcaa agggacattt
176401    ttctcctccc acccaaggtg atggtaacat tgctaaatgc catttggatc atgtcgcttc
176461    ccctcgagaa atcctccagt tgctttcct tgagtatggg gtaacatatc agtatctaca
176521    tgtcattcac agcccctttgt actgacctc tggggtctac tttcccacaa gtatcttggc
176581    tttgaccccta ataagtgtga cactttcctt catttgctgt cttttctctt cctcatgcct
176641    tgcctttggc tggattattt tttctgttgt tgagatattt cttgatttt ttgctaggct
176701    aaatcctccc cttcctatac attaaactca ggtgtcttgt cctctgagaa gtctgtcctg
176761    aactctaggc tgagctggat gacgccctct gtacccatcc agtgctcaca gcattagcta
176821    cactgtgttg tacctgcctt ttggtgttca tgttgttcat tggtctggaa gcttctgagg
176881    acagggactg aaactttgt tttggcaact cttgcatgca gcccagagcc tggcagatgg
176941    taagaaggtc aataaatgtt tattgaataa ataaaagaat gaagcctaaa ttgataagt
177001    tctcccatat gataattaga gacaccataa acctagagga cattatgatt ttaggcagat
177061    ttatagctag aggaaaactg ttcccaaaga atttagagaa gggagaacta gatcagacga
177121    taaatgcatg atggtttata agaattagaa agaatataag gtaagatgta ggggctcctg
177181    aacctgggga ggagttttca gtaggtaaca tattcaaatg agttagcttt gaaacagatg
177241    aagtgaacag ttctgatttt agggattaaa aagttcatta aattaataca aattgttgga
177301    gaagaacttg tttgaaagtg ctcaaaatga gctaagagtg taatagaagc tctctaaact
177361    tttattatta ttaacggcat attgagcacc cagtacctac tgagcatttt caataagtgc
177421    tttaaaggca taaactcata ggatttagcc ctcatcacat ctctatgaag taggtcattg
177481    gtaatattag ccctgttttgt ggatgaggag gctgaggcctg aagtattgta acccacatgc
177541    cgaagcttac agggttggaa aatgtgggtc tgactgagtg agtccaaaag ccatggattg
177601    caggagggac ggtctcactt cattctgcat tgtcagatca tggggaaaga ttggttctat
177661    tttgagtgcc cattttaaga tggttacaga caaactagag tgcattctgt aggggaagc
177721    tgttgtgaat ttaggaatga ccattaatca catcttgttc ttttactcag attctgaac
177781    caacttacgg atacatgaag aagtcagaca aggccgggtg cggtggctca cgcctgtaat
177841    tccagcactt tgggaggccg aggtgggcag atcaggaggt caggagattg agaccatcct
177901    ggctaacacg gtgaaacccc gtctctacta aaaatacaaa aaaattagcc aggtgtggtg
177961    gtggatgcct gtagtcccag ctactcagga ggctgaggca ggagaatggc atgaacctgg
178021    gaggccgagc ttgcagtgag ccaagatcac gccactgcac tccagcccgg gctacagagc
178081    aagactccat ctcaaaaaaa aaaaaaaaaa aagtcagaca aatagaaatc tagaaatcca
178141    aatgtcagct ttttcagagg aaacttgtgt tatggttaaa tagatgggct actcctgtac
178201    ccctagcccc acattaagtg tagccatcag aagtgcagat tcaccctgta agggcctaag
178261    cctgcctgct aaactcacca caggcaggga gaaaattgaa ctctgcaggc aggtccaaag
178321    cagcaggcgc cgtagaccta taaggactta gccagccatg cccagggatg tccctcagat
178381    tcaacaatca ggcaagctat tcctttctt atgggcagga aggaatcaga gagaggtcaa
178441    aagtgtgact ctaaatcttc gtagagacac ataaatccca ggaataaagt cctcatcctt
178501    agccatggcc aggatgctaa tgtcacatc agtgggacca aggggtggaa agactgttgt
178561    aagggttaaa tttatgtgtc caattgactg ggctgtggta cccagatttg gggtaaaaca
178621    tcaattgaat tgctgtgaag gtgttttgta gatgtgttta acactcgaat tagtagactt
178681    tgagtaaagt agatgaactt ccatgatatg tgtgggccat atccaatcag ttgaaggtct
178741    caggggctag gagaaatact cctcaagact acaatatcaa ctctttcttg aatttccagc
178801    ctgcctgcct gccctacaga tttcagagct gccagtcccc aaaattctgt gagccattct
178861    ttaaagccag tctctctctc tctcactctc tgtctctctc tagacatagg tatacatata
178921    tatatatata tggatggatg gatatataca catatacaca catatatata tggatggatg
178981    tatacacata catatatatg agtatctcct attggttctg tttctctgaa gagttctgat
179041    taatacaatg tggaatgtgg gaatgtggaa tctgtagctg aggagtcaag atggtgatca
179101    tggaagctgt tttcacattt ctgagggggtt cccacaggac aagctatgta gcatctgaga
179161    tggttaaat ggagtgtgat aactttgttg gtcgtactat agaagaagtg ctcatgttat
179221    gagaaggctg actcatggct ggctgttagg gtcactttga actcttttaa gagtagtgaa
179281    gctattttat gcttctgtta aataatctaa tgccacaggt ttttttttc acatttcatt
179341    gtttgtgaat ttcttcaca tctcttagtt tattggtttt cccgtagtgc atagcacaca
179401    agtaggcaat tatggaattg aattaagagt ttaataatgg ctcattagga accaaatttc
179461    aactttaaat gagcacatat ttctctattt tttgtgttgc tttgttccta tatgtatttc
179521    ttttaaagta ttcatttgta aaaataaacc agcatattgg taatgtccag tattacttgg
```

-continued

```
179581  ttatttaatt ataaattaaa ctacatagct cacaggattt ttgaccagaa caaagcaaga
179641  aattaaaata ctaacaagaa aataacctaa tttgtaaaat aacgttctct gaaatcaatt
179701  atcttatttt cacaggaaat aaaattagga gaaatctgct aaattcatcc aaaataatac
179761  aagagtttgg gaatataaaa aaagtactac ttctttaaat gctaatgaac accagcttta
179821  tcatttctaa agaagaggat tttggtgtta tttttcttct cccagtgaaa aatttactgc
179881  tcctacctgg caaagggaca tgggcttgag cctgatattt gagactgtat aaatagctga
179941  tctggaaatt tcaagccaat tttatcctct ttccttcaac tgcagtttca tgctctcccc
180001  tctactcctt gaattatccc atcaacattc ttggtcattc agggttgatg aagccatcat
180061  gccatgatca gctgcttaac ttggcactct gtgagggagg ggggatcttt ttgaagccct
180121  gacaccattc ccctgtccag ctcgtcttgc agggcagtga acaagaggct gagcagaagg
180181  tatcagaatc tttggaaatg ggacccatca gatgtttcac aagtcaaagt attctgatgc
180241  atactcaagt ttgagagcta ctggtttata gcagttcagc tcctcacaaa cacaaatata
180301  tgcacatttg tggtattcct tcagtgaaga tggctctggt cacattgaaa cagtgaatat
180361  gtgcctttgt gtgtgtgtgc gtgtgtgtgt gtgtgtgtgt ctgtgtgtgt gtctggtgtt
180421  tgggggtaga agtgataacc aggaaatgtc ccatgaaatg tctcatgaag caaaggcagg
180481  ggtattttct atgaactatc tccattaatc tgtgggcctg cattcctgga aaatcttcac
180541  tcaggatccc taaggcttcc tagagcaaag gtggcccagc ctgggtcttg gcatagtatg
180601  acctcagggt gtccaggctg aggacaaggt gaatgtcctg cctctgctgc gctgggtctg
180661  ggtgccctgg tgtgctcctg ccctctcctt gtcagggaac cttggactgg gtctggggcc
180721  tgagctcaat tcccagaccc acctctattg agctatgtga ccttgggtcc tatgctccct
180781  gggccatctg tggtgagtgg gccatatgac aggccatctc agggaggtgg gcagggatgg
180841  tgctcaccat acaggcctcc ctcacttctc ttcacctcca attgtatgca gaagacttca
180901  gtattacaca tccttccatg aaggacctct cctaccagaa aaaaaaaaa ataaaagcaa
180961  aaggaaatga tttctcgttc actttcagct cggaaactcg acaggcaggc cttggcttgg
181021  tgtcttaact cggcagccct gtggtgctga gtttataca ttatttcaaa gggctagagt
181081  tccctctga agatttgttt tctggtggtg ggcttagcaa ctctattttt ttctccttaa
181141  tctattttct tacacaaaga acaaatgcct ccaagtacaa ttgcacccag attactagac
181201  tctccttaaa cattaccaaa agctataatt ttgaaattct tttatctatc ccaagctaat
181261  agcagttttg catgtcttta tattgttttc atctgtttct tagctgcccc ctcctcttgg
181321  gttattgtct ctggaatatg tgcgggcttg ttttaatttta gtgctgaatt tgggatatgg
181381  aaaagattat tcctaattat attacttatt tgttgaaaca taatatattt atatggacct
181441  tctgtgctcc agaagcagtg tgttcttttg tgaagacatt gctggagttg ccaaggcggg
181501  gatctgaatt gaacaggatc tgaatctaaa gcaatctagg agtagatcta tccttcagca
181561  tcttcaaacc aacttatcaa atatttcttt caacatgaaa cattcacccc agccctgtag
181621  ccaactagtt cagtgctatt ttttctacaa ttcaatgaac ccgtgaggcc ccatctaaaa
181681  caatcaccac agcagaacct tggggtctaa caaagatttc cctcccaggg agaataaggc
181741  atgttgaatt ggtttgaatc aatgggggcat tttttctctt gttggcctgg tgattacaac
181801  cctgtctctt aaactgcact caactcaaat gactttttt aaatgatata atgctactaa
181861  agaatagaaa atacattctt ggtcaagcta ttaccaagca gaaaagaaaa aaaactccat
181921  cactttgaat ttctcactt gtcaataaaa ttatcaacct cgacttcctt tatgtttctt
181981  ggtgcctgct gttaagccat gagtcagaaa ccccccagctt tggatgttgt catagagccc
182041  agacaccata tgctcctctg tcatgagagc aggaccagct atatgatttg tgggggagcc
182101  caatgcaaaa tgaaagtgtg aggcccccctg ctcaaaaatt atgtaggatt tcaagacggc
182161  gacagcagag cattaaagga agtgctgggc ccttcggaac cacacaggac acatgtgcat
182221  gaagctagcc cttgttcaaa gacagaccta gttgaggagg aggaagagtc catttccttc
182281  tctcctgctt gtcagcccaa gttatttagg tttatctcag aggtctgcat tcaattctcc
182341  caactcaatg aactgcctct ctccttccca aatttgctct gcatttgggga ctctctctaa
182401  acaaggtgtg cagcttcgtg caagttaag tcacactgcc aagtcctcta aggcctgatg
182461  aaagccttgg ggcaccagga ggggcagaga ggcagccctc gtgcctcacc acgctgctct
182521  gctctgccag aggtaatcgc tttgcagatt ctcaactaca tctccaactg tggtgttttc
182581  tctcctttgt ccttctgaca aagactttta taattctctt taaatgttcc agggattttt
182641  ttgctctttc aaataattgt tatcaatccc taccaaatgc cttagatctt ctcctcctcc
182701  ttgtctttac tgtaaatatt ttccctctc ttcagcagca acgttatgcc tatacatgt
182761  aacaaaatct ctacagctat cttagtttct ttattcttgt gtcttcaaag actcccaaat
182821  cttgctctgt tggtgtttgt tgaactttc taataagatg acttttaaaa gaaagctaaa
182881  tacatatatt ttttttatga tactttaagt tttaggggtac atgtgcacat tgtgcaggtt
182941  agttacatat gtatacatgt gccatgctgg tgcgctgcac ccactaactc atcatctagc
183001  attaggtata tctcccaatg ctatccctcc ccctcccccc caccccacca cagtccccag
183061  agtgtgatat tccccttcct gtgtccatgt gatctcattg ttcaattccc acctatgagt
183121  gagaatatgc ggtgtttggt tttttgttct tgcgatagtt tactgagaat gatgatttcc
183181  aatttcatcc atgtccctac aaaggacatg aactcatcat ttttatggc tgcatagtat
183241  tccatggtgt atatgtgcca cattctta atccagtcta tcattgttgg acatttgggt
183301  tggttccaag tctttgctat tgtgaataat gccacaataa acatacgtgt gcatctgtct
183361  ttatagcagc atgatttata gtcatttggg tatatacca gtaatgggt ggctgggtca
183421  aatggtattt ctagttctag atccctgagg aatggccaca ctgacttcca caatggttga
183481  actagtttac aatcccacca acagtgtaaa agtgttccta tttctccaca tcctctccag
183541  cacctgttgt ttcctgactt tttaatgatt gccattctaa ctggtgtgag atggtatctc
183601  attgtggttt tgatttgcat ttctctgatg gccagtgatg gtgagcattt tttcatgtgt
183661  ttttgtctg cataaatgtc ttcttttgag aagtgtctgt tcatgtcctt cgcccacttt
183721  ttgatgggggt tgtttgtttt ttcttgtaa atttgtttga gttctttgta gattctggat
183781  attagcccct tgtcagatga gtaggttgca aaaattttct cccatttttgt aggttgcctg
183841  ttcactctga tggtagtttc ttttgctatg cagaagctct ttagttttaat tagatgccat
183901  ttgtcaattt tggctttttgt tgccattgct tttggtgttt tggacatgaa gtccttgccc
183961  atgcctatgt cctgaatggt aatgcctagg tttttctcta gggtttttat ggttttaggt
184021  ctaacattta aatctttaat ccatcttgaa ttgattttttg tataagggggt tgcaatccta
184081  gtctctgata aaacagactt taaccaaca aagatcaaaa gagacaaaga aggccattac
184141  ataatggtaa agggatcaat tcaacaagaa gagctaacta tcctaaatat atatgcaccc
184201  aatacaggag cacccagatt cataaagcaa gtcctgaatg acctacaaag agacttagac
184261  tcccacacat taataatggg agactttaac accccactgt caacattaga cagatcaatg
```

-continued

```
184321  agacagaaag tcaacaagga tacccaggaa ttgaactcag ctctgcacca agtggaccta
184381  atagacatct acagaaagct aaatatgtat ttataactct tccatgaaag tctgcctgct
184441  ctccccactc ctaaatatat tagtgatttc tgagcataaa aaatagattg attttgtgac
184501  attatgaact ggtagtcata gtttgcctac tgataacttt gccaaacaca ggagcatgtg
184561  gacattgttg cctctaaacc cagctgcatt ccctgcaaac tggatgccct cagaggagaa
184621  gggtgagagg gtcctttata gaatatttt gctgatagtg gttgccacta ggcaatgaca
184681  ttcacagatg ttcgcaaatg ggtagttcaa ttaaaagttt tcataaatca agttcaggac
184741  ctctgaatca ccctaccaca gaaaattgac agatgcattg aaaatgaaaa ttaaatgcca
184801  gggctgcatg aaccatttct tcctgttctg ttcaatgtta ctacttgttt gcggagggga
184861  acacttggaa tttccacttc tgcaagtggg acccatttct ctctgggcct taattcctcc
184921  tgatgacagg ctgaatatgg tagtgactat agtctcagga agatacatca gaagccatgc
184981  agtcagcttc tccaatactt tctttgccta ttaatttcta catgactttg gtcagatcac
185041  cagatgcctt gatttccaca ttttaaaaat gataattgta cctgtgatca tggataattt
185101  ttttctttgc agggaggtga gtaatgtgga taaaagaaat acctgtgaga gaatttagaa
185161  atatttgaaa ggaagaactc ttccttcaaa tgtgttttgt tttagagat ggggtcttgc
185221  tatgttgtct aggcaggact tgaactcctg ggcttggacc atcctatcac ctgagcttcc
185281  agagtaactg agactacagg tgcatgccac catgcccaac tcacatgtga cttttttttt
185341  ctctctagat cttattatgg gatttcccac tcatttctta gttattttga aagacaagac
185401  agtgaggttc acacctctga atgttttctc attatgtaag caaatttgga cttagctttt
185461  gcatccatgg cttcttgaaa agaaagtctc cttgagcctc tgaggctgaa ttcttagtac
185521  attaacctc ctcttctgtg ttgcaactgt gatataggaa agtctagtta gcatcctgat
185581  ttatttggtt ttgttgagtg tgtgtgtctc tgtgtttgtg tgtgtgtgtt ttccttgaag
185641  tattcttggc gtgggcatgt gtgtctaatt aaaaaagtaa attgacagag ttgaggccac
185701  tgggctctta catagattgt tttcccattc ccagtccagg catacctcat tttatcgtgc
185761  tttgctttat tgtacttcac agatattgag cttttgaaga attgtatatt tgtgtaaccc
185821  tgctttgaac aagtctatca gtaccatttt ttcaacaaca tgtgctcact tcatgtcact
185881  acgtcacatt ttggtaattc tcacagtatt tccaactttt tcattacaat tatatctgtt
185941  atggttgtct gtcatcagca atttttaatg ttactgttat acttgtttta ggacatcaca
186001  aactgtaccc atataagatg acagactta ctgataaatg ctgcttttgt tctgactgct
186061  ccactgacta gcaagtccct catctctctt cttctccttg ggcctcccta ttccctgaga
186121  cacaacaata ctgaatttag gccaattaat aaccctctcaa tgatctctaa gtgttcaagt
186181  gaaagagtca catgtctctc actttaaatc aaaagctaca aatgattaag tgaggaggga
186241  agttgaaagt caagataggc tgaaggctag gcctcttgtg ccaaatagtc aagttgtgaa
186301  tgtaaaggaa atgttcttgc aggaaattaa aagttctact ccaatgaaca catgaatcat
186361  aagaaagcaa aacagcctta ttgttgatat ggagaaagtt tgaatgattt ggatagaaga
186421  tcaaccaac cacgacactc ccttaagcca aagcctattc cagagcaagg ctctaactct
186481  cttcaattct gtgaaggctg agagaggtga ggacactgcg gaagaaaatt tcaaagctgg
186541  cagaggttgg ttgatgaggc ttaaggaaag acaccatctt cataacataa aagtgcaagg
186601  tgaagcagca agtgctgata tagaagtggc aacaggttat ccaggagatc tagctaagat
186661  cattgatgac ggtggttaca ctaaacaaca gcttttcaat gtagacagaa gagccttcta
186721  ttggaagatg ccatctagga ctttcttagc tagagagaag ccaatgccta gcttcaaagg
186781  acaggctgac tctctgttta ggggataatg cagatggaga ctttcagttg aagccaattc
186841  tcattacca ttttgaaaat cctatcgccc ttcagaatta tgctaaatct actctgcctg
186901  ttctctataa atggaaccac aaagtctata ttacagcaca tctgctggtc atccaagagc
186961  tctgatgggg atgtacaagg agattaatgt tgttttcatg cctgttacca caacatctat
187021  tctgtagccc atggatcaag gagtatttt aactttcaag tctttttatt taagaaatac
187081  atttcataaa gctatcgctg ccttagatag tgattcctct gatggatctg ggcaaagtaa
187141  actaaaaatc tactggaaat gacttaccat tctaaatgcc gtaaagaaca tttgtgattc
187201  ataggtagag gtcaaaatat caattaac aggaatttgg aagaagttga tttcaagctt
187261  catgaatgac tttgaggaat tcaagacttc agtggaggaa gtaactgcag atgtggtgga
187321  aatagcaagt gtgctagaat tagaattgga gcctgaagat gtgattgaat tcctgcaatc
187381  tcctgatgaa acttgagtgg atgagaaatt gcttccttga gatagaatct attcctggtg
187441  aaaattctgc gaatattgtt gaaatggtaa caaaggattt acaatatcac ataaacttag
187501  ttgataaagc agttgcaggg tttcaaagga ttgactccaa ttttgaaaga agttctgctg
187561  tgggtaaaat gctactaaac agctttgcat gctagagaca tctttcctga aaggaagaat
187621  cattcaatgt ggcaaacttc cttattgtc atatttgctt tattgcagtg gtctggaact
187681  caacctaaaa tatctcagag gtatgcctat acatcagctc cttgaagagt gacactttat
187741  taaatgtcct tttgttataa cgttgatgaa aaaaacactt cctggctgga gccacagttc
187801  ttgtcaagtt tgcatgtttt ctctatgtct acatgggttt tctctgggtg tactcagctt
187861  cctcccacat ctcagagatg tgcatgtcag gtgaatgggc gtgtctacat ggtcccagtg
187921  taagggagtg tggagatgtg tgtgtgtgtg agtgcactt gagatgggat ggcggctttt
187981  ccaggaccga tttctgccct gcctcctgag ctgctgggat aggctccagc cactggcgat
188041  gctgaactga aatgagaggg ttggaaaata agtgaatgaa gaatgattga atgaatacac
188101  attattgtaa aataacagtt caaaacttct acaacaataa tgcaaatgca ccacagtaaa
188161  caatgcattc tgaacgcgct cagtaagcct gccagatttg ttcttgtttg tttgtaaact
188221  gcatggtggt ggtaggtact ccttacaatt tttccttttgc aaacatttac tgcttggttc
188281  aatccaccat cactaggact gctgtcactc actgattcac caaaaaaatt gggtaattat
188341  cttgtttcta ttaatctttt ttaagtatct atatctcacg tgtatttcac tgtttaacat
188401  tagaagtgtt ttggtttgga cttttttaga agtttggtga tattttgggg accagacata
188461  ggccgtagga acttaattct tgtttatatc aattagctca tagtaaaatt ggttttgctt
188521  aatgtggcag tttccaaaaa catatgaata ttgttaagtg aggacttact gtaattgtta
188581  tgcaacttct gttctgataa caacccagtt gttgttcttt ttaatgaaat gatactggaa
188641  ggaaatagca cttttgcattg ctgtaaacta acaaggcgtc ctcctatccg tggcttactt
188701  atgattcctc agcactttgc tgctcttcgg cactgtgggc agcagatctc attctgctgg
188761  tgttttttcct tcactttgtc atgccgtcaa gtacttcttg ctaatatggc tcagtttcag
188821  tttgtttcac cagaaaataa atttttattc acagcttcac agcttttcat ccttcccatg
188881  ttactccaaa cacatgctca ctgggtttcc ataactcatc gagtaatctc ttacagactc
188941  tttctacgtt ataagaacat tccctgtttg ccttccttga catctctttc ttaaactctt
189001  ttccaacatc aaaatcctca cttcctggga gaaaagagtt gtgttgtgaa aagagcatac
```

-continued

```
189061   atgggattca gagttttcag attccagtat tacctccttc tgcaactccc tagctgtgaa
189121   aatttaagcg attgctcggt ctcagtttcc ttagttgcaa atgggaatga caaacaggac
189181   tttccccaca gaggcactgt gaggattact tgagatagta catgtcaaaa gctgttccta
189241   gagatttcaa aatgtgttca ttgttatttc agcaggtcga ttttcttcta atttttactt
189301   tgatagactc tcaattcatg caaataatac atggcctatt tgcagtttaa atttaattac
189361   tgattcacaa aatatgtatt tactttctcc taacattaat cattggtacc aagccaggtt
189421   ttgacctttt ttacctgagg aatttagagt tggaaataaa aggcaaaatt ataaggagga
189481   gaacgaagta tagttcaagt cctaaagtat gctgattaac acatttgttt gcctttggaa
189541   catctgggaa agcaactata tactaattct cttaaaaatg atttatttaa acatttgtgg
189601   aagattcagg tgtgtgattt taattgcaca attaattaat tattggtgag gtccttttat
189661   ttcttcctag taatcaacat aataaaacgc tgtagtataa attatggcag aaaagaaaat
189721   taataaatgt agttgcagct tttaatttt attctgaaag tatgtttaaa caattgatta
189781   ttaatttta gctagatttt tcttcttcct tgctcttttcc tttccccctt ctccctcttt
189841   ttgctgatta attcattcct ttcttcttc cttcagttta cacaaacaaa acacaataat
189901   gagaacaatg ctatatgaaa ggccttccct aaaaatattt aagctgtgaa aaaatgaaaa
189961   caaaggaatg gacagcaata gctaatctga tatttgtcta tgaattaaca ggtaagaagg
190021   aaaaaaggtt gctgagtgtg tgtatgtgtg tgtgtgtgtg tgtgtgtgtg tgtgtattta
190081   tgtttgtttg ttttataaaca atccggcgca ttcatgccca gtgaagggtt aattactttt
190141   gacgttttgt taatggcaat gtcgttctct tacttattat tgcttatctt tttagatcag
190201   ctatttttaa acttctatca gactttgaat gaacttatca attttcagtt aataaaacgt
190261   tgaatttgat atccttacaa acttaccagt ggtaaatatt atctcctaag tagtactgtt
190321   tgaaaatcac atctactcgt cttccagtgt atctggtacc tggactatct aactggtacc
190381   tggaccgttc tccacttatg tttcctttgg gtgaagattt caaagatttc tggtaaaacc
190441   aaatgtgctc ttggggaaag tatatcatga aaacgtattt accagtcagt actgaaggat
190501   gtagatggtt ttaagcaagt tttttggaac catgcaattc tacctcccct gctgattagc
190561   tgcacagcct gaatagttgc taaaatttct gaagctgttt tctcatctgc cagatgtgta
190621   tggtggtatc ttttttctg ggttatgata atgattaaaa gtagtcatgt ttataaagta
190681   catagcacag tacccagcct gtactcaata aacatcaata aactgtatat tcacataaat
190741   actatatcga tagctaattc tgtgcctctt aatatgtctt gaattgcctg taacaggaaa
190801   atctgattca aactttacta taaaggctga aaccatacag agactcattg gctcacataa
190861   gtggtaagca gagttagtca ggcctccagg ttggtttgct tcagtggtgt ggtaaggtaa
190921   tatcatcaag gcccactcac catctttctc tccccacttt acttctgctg ttagctttat
190981   cctaaggctg gcttctcttt gcggttggga ggtggccgtg aacacttcct gggtctacat
191041   gtttccccct ccaggagcct ctcgaaaacg ttaagaactc tcctttccta gaagctcccct
191101   gtgtctcttt gatccaactt ggcctatata tttagcctat atattcatcc caggccccaa
191161   agctataact agaagtagga ataaaattga taagtttaag cttagtcac cagctctaac
191221   ttgatgtcag cttctctcaa aacacagggg ttacaaagga gaatgtggat atcctgggaa
191281   gcagggcatg aataatgagg aggagaccac agcatcaatt acagtgttaa ttacacctaa
191341   agcaccacca gcaaatctgt gtatctctat gggacgtgag ttctgacaag gcagggcact
191401   agagcaaac gttacccttc ccagtgtagc ttaggacttg tgatttcccc tgtagaatgt
191461   ttggaagag gtaggggtct tagaggtcac ctagacttta agaggctgtc ttaaatctgg
191521   tatcacagag cttgttattg gtacacttag gagcagaaca tagttgtcct gatggtatat
191581   tggatctctt ttccccattc agcgcagctc tgcctcttaa gctcttcctc tattttctga
191641   tattacatct ggaaaagtca cacagctagt gtgtggcagt cttggaactg gacctgccac
191701   ttcagcccca tgcttcattt aaggcaccag tggaacatgg cgtattttgg aaaatatgtc
191761   cagaatgtgt atatactaac ctgggcaggc aagaacttg ttcttatatt acaatggaga
191821   ccgggaatgg tgctcacac ctgtaatccc agcactttg gaggctgagg cagaagaatc
191881   atctgagatc aggagttgga gactagcctg gctacatggt gaaaacctgt ctctaccaaa
191941   aaatacaaaa attagctagg catggtggta gcacctgtag tcccagctac tggggaggct
192001   gagctgggag aatcgcttga gcccaggagg tggaggttgc agtgagcaga gatcacatga
192061   ctgtactcca gcctgggcaa cagactgaga ccctgtctca acaaaacaa aacaaaacaa
192121   aacaaaacaa aacaaaacaa aacaaaacac accaatggag aactagaagc tggcattcac
192181   agggtattct tgtgactgta gccattggat ttagtggctc ttacaagagc cctaatcagt
192241   tattaggact cttgtaagaa aatagtgtca tgtacatgga tattcatttc agcattcttt
192301   ataatgacag atccctagaa acaacttaaa cacctaccaa tgaggaaatg gtaaaatcca
192361   ttatattgca acattaggac aatggcatag ctccatttgc gatggaaatg tttacataaa
192421   tgttcatcaa gctacaggtt atgtgaagaa agctttgctt agaagaacat ggtattatgc
192481   ccctaatcat tgtgtgtgtg tgtgtgtgtg tgtgtgtgtg tgtgtgtgtg tatgtatgtt
192541   tatatgtagc taagcttata tttcttaag agtattagag aatctgtaga cagtaattac
192601   ctggggaagg aaattagagg tctgattgag acaaagacat tttcactaat tgattttaa
192661   aaaaacaagc atatatacta cattttcact taaaatacta cttataaaag aacttattct
192721   tggtttcaga acttgagtat caatctaggg tctatcattt cttggcatca tgatcttaag
192781   caagacattt tatttctcag tttctcacc tgtaaaatga agacgatgat gtttgtcaca
192841   cgagtgttat gcaaattaac tctctgtgaa agtgctttct aagctctcaa gggggtgatc
192901   ctatgggga cttttcttga taatcacctt cttcctccta ttccacacag ttcccccaca
192961   gcccactgcc tcagggaaga tgtctgtcat taaagggcaa ataatctcat tggaatttct
193021   ggttggccgg gagcactgac tgagaaggaa ggctgaggaa ttcagggaag gtttaagttg
193081   gattccacca acctttccc acaatttgat gagcatttta atctgtgca actggactca
193141   gtgttcccag gtcctaactc aactctgaaa tgggattcag aaatcctcac tgcattctca
193201   cctgtccaga caagatggaa aagtctaatt ccatttcaat tcattatttg ttcaaccagt
193261   agttattgaa caccaactgt atgctaggtg ctcaggggaa ttc
  2341   tctttatcct ttcttctgtc ctgtgctagg cataaagata cagaacttga attttgttgc
  2401   attgaagtta gagagtagga agggaatttt gtcacaaata aacccaagaa caacatagag
  2461   tgaatttggg agaaactttg ggggaaatta taaattgacg ctaagaaaga aagcagaat
  2521   aacacagtaa ttaaaagcat aggctgtgca attgactact tagagtcaaa tcccagctct
  2581   attttacttg ccagtaaaatt agattctgag cctcagtgtc ctctgtaaaa taatggtaag
  2641   agtacttatc ttagagactt gttttaagga ttaaataagt aaatacttaa agctctgaga
  2701   acgctgccca acatacagta aacattatat aaatgtcagg taaataaagt gagcaaaatc
  2761   tggactaggc actctactat tctgggattt gttgaactaa gtgagaagga tgaataattg
```

-continued

```
2821  ttggaatgga gctgctagtt ttgtgtttat ctgaagtcat ctactcctac tcacaaatgc
2881  aggttgaggg attttagtca tctctaactt taataacatt cattcacaga aatatttatt
2941  gggcacagaa ctggtagctg catcatcact gggaatagca ttcatatgtt tttattagta
3001  gtctactaaa atgtaatgat tttgaatgtc atttaactca tatttgatta agaatcatgt
3061  aataaacaaa agtaattggc gaaacacaca ccccaatttg tttcaaatcc caatttgttt
3121  caaagctgac aattgaaggc atattgtagt gtggttagag gaaatagtag gcatttgatt
3181  ctatgatcct taaaagagtt tttttttttt ttttgtttgt ttgttttta aggagtctca
3241  ctctgtcaac caggctggag tgcagtggcg cgatctcggc tcactgcaac ctccgcctcc
3301  cgggttcaag cgattattct gcctcagcct cctaagtagc tgggaccaca ggcgtgtgcc
3361  accacggctg gctaattttt tgtatttta gtagagacag ggtttcactg tgttagccgg
3421  gatgatctcg atctcctgac cttatgatcc acctgccttg gcctcctaaa gtgctggtat
3481  tacaggtgtg ggccaccgtg cctggccaaa agtgctcttg tatataagct actatcattc
3541  ctgtataagc aatgctacaa gcattaataa agtgatgggc atgtgagttt ccactgagtt
3601  ttctgactta cagcaagatt gactcttcct tccattagca gaactgagtt gtagaaataa
3661  aaggtacaca cacatacgtt aagataatag tttttttcat ataacaagta ataatcatca
3721  tatatattca tgattaactc accaggagtc agtgggattt cttcacctat tatataaaag
3781  acaaaatcgt ttggaagtga attttcccga cttgtatgtt accaccaagt ttcaaattcc
3841  agctctacta cttaccagct gtgtgaactt gagaacttcc tttgtccttt ctgtgctcaa
3901  gtttcgtcat ctatcaaatg ggtctagcgg ctgttaacta cctcagaagg cttttgtgag
3961  gagtcatata agtgaagcat ttggaacagc gcctggcaca ttctcacttc ctgatatatg
4021  ttacaatgac tacttcttcc actcttatta atactgctaa gctactatta ataaagttcc
4081  tttggctgga tgctggaagg agaacatggg tcaaggttct gatgaactaa ctttccctga
4141  cagccccctc ccctcccctt ctgcctgcct cccaggcaga agcagtggga attcaggtag
4201  gagtggagga gcagggaaat ggcaactctt tcctctctgt tcaccatgat taataacatg
4261  gttcatactc ccttataata tattttttgt taaaaaaggg aatggagaaa tgagaaacaa
4321  atggcagtgg gagtgtagcc aagtggagaa actcagggcc ggacagacct ggcaccagca
4381  ctaagtagct gtgtgctgtt ggtgtgtttt tgacctggcc aaccctcagc ttcttcatct
4441  gtgaaaagga gctaagcaca gcccttactc aggggttca ccaagagtac atgaaataat
4501  gcctgtaatg catttgttgt actgacaaat aatgagtttg aatgagctat tgtttaaaat
4561  gattcaaaaa tgacacttca aagtaaagca tgagttttct cccttatcta ctcccaaggg
4621  cctcctgtcc tgtttttgtt ttgttttttg tttttttgaga tgtctgttgc acaggctgga
4681  gtgcagtggt gtgatcttgg gtcattgcaa cctccacctc ctgggttcaa gtgattctc
4741  ctgcctcagc ctgccgagta gatgggatta caggcgcctg acatcacgcc cagctaattt
4801  ttgtactttt agtagagatg ggatttcctc atgtcgggca agtcctgacc tcaagtgatc
4861  cacccacttt ggccttccaa agtgctggga ttataggtgt gagccactgc tcccagccct
4921  ggttttctta atggccattt ttgtatttcc tcttataagc atggtcttct actgagagaa
4981  tcaatattca gaggattcat taatagctgt tcaacataat tttagcatcc ttcacgaatg
5041  ttaatccatt taggaagagg atataagtaa tcactaattt ggaatctaaa ctgtatgtct
5101  taaacgtata tactttaaaa tatttctgta acatatgtgt agctaatgaa gaatatatct
5161  aaaacattgt tattttataa atttgtaagc aactttaaaa aaaattccaa atacaaagga
5221  ctatgcagtt tcttaatata agtatctgac ttcttttattt agtgttttca tttctattt
5281  aattgatatt taggagaaat taaaagatca gataagtgag gcagggaggg cattttattt
5341  tattttattt tattttttt tattttttat ttttttttga gacagtctca ctcagtcacc
5401  caggctggag tgcagtggcg caatctcggc tcattgcaag ctctgcctcc cgggttcact
5461  ccattcttct gcctcagcca cccgagtagc tgggactaca ggtgcccacc accatgccca
5521  gctaattttt tgtattttta gtagagacga ggtttcacca tgttagccag gatggtctcg
5581  atctcctgac cttgtgatcc tcccgtctcg gcctcccaaa gtactgggat tacaggtgtg
5641  agccaccgca caggcagggc attttagtat tggtctctta taattggcta taaaacaatg
5701  tctttactac tgtgtattat aaatatagtc ttagtacaaa aaacaaagat tgttatgaaa
5761  cattatccag cattctactt ttccttccac acctatgtca ttttcatgtg ctaaggttac
5821  atttatagat tcctacctga cacctccact ggcaacttct tttaactgct gttggatata
5881  cagaaatcag agagattgtc tgcagaatga ctctactggg ccccagaaaa acaaacgct
5941  aaacaaaaaa tggagcccat ttagtctgag caactaggca atataggagt gttggtggag
6001  aattaagaaa gcggatggaa atcctatgac tctactgatg atgctccaaa catttctggc
6061  ttcttagcca gtcccaacac caccctcct tcttttgatt ccagcatgtg cgaggatgca
6121  ggactcaact actatgcatt caggctatgt tctgcgactg cacggtgcac tgcttttgta
6181  atgcaaatag gaggcacaaa gtgtctcttt gataatgtgc agtcagaaga caaaaaagca
6241  ttcactgaaa cagtaaaact aattcataaa gctgaaagac aatagggaag cattatggat
6301  tttttaaag gaaaaaagta tcctagatca atgtaattgt cacagtgtaa gctattcaca
6361  gtcaatgcag gaggggaaaa tggctgcaag ttatttaaa gtgggagaag tttataggc
6421  aaaaaaccat tatgttaaac aaatataaat atatttggtt aacaagtttc tgcttagtct
6481  cttagaggtc aaatatatag ctggttattt tcatttagat ccacagtatt cccttagtga
6541  caaaaactca gtagaagttt taaaagagca cagagatcta atagttaaaa accatatggt
6601  agattttttt tttttcttta aagggagtat ctccccatca cataccagag tttagctcaa
6661  ggtcaactta tattaatgca ttaaacttag ctgtggagga ggcaaagggc tggaggaaaa
6721  aggataaaag aagttctgaa attgttcttc caacatattc agccaagcaa cagaacattg
6781  cctggataag gctatattg gacagttgcc ataattcctc ctgttagatc agctcctctg
6841  gtacctattc ccataccttt taagtatatg catgtaacat tttgcttgaa aattgcttct
6901  acctctattg ctttgttata gccgttttgc agtttcggta tagaggcagt tctgtgtcac
6961  aagaaattac taatctgagg cttgagaagg ggcagtgtag ccttccatta tctcaccagc
7021  aagctctgta caggatatt tcaaatttt ctgctgccat tacaatgtgc tattagagtg
7081  gccaaggtgg tgagggaggg gatgttattg aaacttggtt accagggtag ataagataaa
7141  cttcatcact ttcttggcat ccacatttgt agccaagggt ggaaattttg atgaaagaag
7201  tacatttggt caaagatatt aaggtgtaaa gctggatatt ttctaactgc attctacaga
7261  gtctgtctct tccccattga tgctcatctg aaatagtctg cttgattgtt tcaataaaca
7321  cacttctttt caatgtattg taaacttgta aataccagat aaccaactta aaatcccct
7381  cccatcccag tctcaagaaa taacactggt tatgtgcaga cataactttc ttgagtaagt
7441  caccattttc tgtcactttc tatttgcggc tggtaaaatg acagctcagg cttaacttt
7501  acataagcta ttttagatt ttctcagac atcctttaac tatttctttt atacaggatc
```

-continued

```
7561   ctaccctaag gatcatttta ttctttgacg gggtcattaa gcaatcactc tatactggtt
7621   cattattgga agtcactgca atatccagaa atacatgaag agtggcaagt ggtttatatt
7681   tcagcaagag atttatgcta gaaaggagaa gtcaaggtgt tgacgattga aataaggatg
7741   atcatttcat gagttattcc ctttcgctgg ggttccactg cccacaagcc acttagtttc
7801   cctttgaggc cagcatctct tctctctgca gccaaaccag cctaatacac atgtgcaggt
7861   ttaatgctgg aagggagggg ccagctttac ccatacataa tcactgtttt atggctttca
7921   ctcattcctg aggtgttaat gcagatcaaa tgggaaacac tcgagaaaga acccttgcag
7981   ctactgcatt gcctggctct cccctctcaa tcgttaattc ttattgtaag atctaaaggt
8041   aattttgttt gctctcttaa tgtgttgcag ttctcccagt ggcccttgca tatccttct
8101   caaattccca tcttgatcaa ttgtttgcaa ataattaagc ttttaaaaga taatagcatg
8161   aggctaatgt acacaacaaa ggcgaggtct ccctcactgt ctatgggact gtggtcaaat
8221   ttgctttgat atcccgaagt gattaggttg attggtatat ctgggaagtg ccatccatct
8281   tgccttcaca agagcctact gatcttcttt aaactgtgtc cttgagatgc aataacagca
8341   aaggtgtttg ggaggatggc aaggagtgac ataggccttt agttgcaaag gtttggaatg
8401   aattttcccat tttctcccta aaaacagcac ttctcggaga ttactcttta tctctttgc
8461   aaagtgacgt ctgcctttgc ccattgcatg gcctcactag acctgtgggc agaaggcaac
8521   agggctttca atgttttttt ttcagcagcc atgcctgtgg catgctgggt ttttgtcaag
8581   tcattttttt ttaagtctat aaaagaataa ctcatactgt ccacaaaaag ctttatttag
8641   taaagatgca taggatttaa gatattgaaa catattaggt ttcagtttaa aagcctactt
8701   ctttgtgaat ttttggctgg ttaaggatta actacatgaa gtcacggctt tcatgtgatt
8761   ctagcaatta cagactttt tcagggaatt gaaagtttgt gggacactaa ggccaagaac
8821   tatgagaaaa agaaatacat tcagttgacc taccatagac aagggtttag gaatgttgtt
8881   gataccttt tctcctctta acaatggcca gattattgtg acatttaatt tgtccaggct
8941   cattcatttg tattaaaaaa atatatatat atcccgaaca actgaaaatt tcttaatgga
9001   gacagagtgc tgagcctcca tagctgagg ctgccctagca attatgctgc atgaaattag
9061   atacagtttg ttccaattac ttaaaatcag atccatgaaa aagtgacaga ggaaaaaaag
9121   ggtagaactt tctaattttg tgatatttaa attatgaaat cagaaactat atgatgtgaa
9181   gaaacaactg aaatttgcac tgaattttttg agagccatat tactaccctt tgaagctcca
9241   ggtagtggta atgattcaaa gagaattttt gtgacaccac ttgcataaat aaaatgtgaa
9301   ttccatttgc tttgtaagaa tgtttgtaaa acttgctcat aaacaggcat gcaaaagtac
9361   tcttgaaaat acaggaaaat aaattactgt gacaattttc agttttcaaa gtaactaaag
9421   ataaatggta taaataataa tttttatcca gttcctggtca taatattaag acataactaa
9481   taagcagggg caaaaggttt tgccatctga ctatactaaa gaaggactgt tgcatatatt
9541   attaattcta ttaaaaatca ctgcaagtga tttctgtaag acctggacaa ctgtcagcaa
9601   ataattttac aggaaatgtt atagattgga agttgcttgt gtacttcagt gtacaacttt
9661   atatgacaca tagtgccagt ggtgggatgc taatatttgc atatttcaaa attgagcttg
9721   tcttctggca ctgcaatatt gtaagaactg ctagcctggg taatctttaa cctcaatgga
9781   tcttagaact ctgatgacaa aaattgagga taagaaaagt tgtctgttgt tcaaagtccc
9841   atagttaatg agtggcagca tcatttatac aatctaatag agtcacctat attaggtaca
9901   attcttcaac tagtagagac atagacctac tgtatatcaa gctgtaattc agcattctat
9961   ccatgggata agaaattcat ttggtttgta ttgtgtgcca aatcttata cagtgggagt
10021  tatgtttttaa accttagggt aatggattcc tttgagctca gtagccagtc atgagacttt
10081  ggctgcaatg gctggccattc tgttgagtag tcacttatga tcttagccta ttaggaggtt
10141  tatataccctt catttgaaga aagtgggtca acatcacttt tgtgaatgaa gcaaagaaag
10201  tagtgtcatg gatcttaaat tggattgttt ctgctttgtt atacaatttg atgttgcatc
10261  tgagtggaga gtgtctgtca tggcatggta cagccattcc tttgttccac aaatatttag
10321  tgattttctg ttatgtccca gtctgggctt tgaggataaa cagaaagcaa ggcaaggggt
10381  ttattagcat tggtagatga gtgagaaag acacaccaac aaggaaataa acaattaaag
10441  caggtgcttc agagagtgat gcttgctatt agggaaataa gaaaaagatg aatgtgagcg
10501  tgataaggcg gggtgctggg aggtggggag ggtaaagctg aacatttgag ctgagagcta
10561  aaagtgacat tggggtaaga atctgagtga cgggaaaagc tggtggtgtt aggaaaacag
10621  aaagaaggat ggtgtggctt ggtataggg taggaagcgg gtgagaagaa ggtatcaaaa
10681  tctgagaagt gggcaaggct ggatggtgac aggccttgca ggccatggta accagtctga
10741  aggttatttc acaggggaca tgaatgggga ttatgaaagg cgtctgctac atcctttggt
10801  catggtgagg cttaggcact gaaagggaag caggaaatat cactgactta tgtctgcctc
10861  tgtccatctc ttccctggc cagtttcctc acctgtaaaa cagaagggat gatagattcc
10921  atttatgtca ctcaaaggga tataatgggg attaattacc atcctgtctg taatatactt
10981  ggagctcttt agagaaaggc actatattcc atgaaagcaa agccttattc taattgtgta
11041  tttattgatt aagtgacaat catagacaat gcttatggga aaaattgtga tctctctgct
11101  gttcacaaac aaatcccctg tgtatagata tagagcatat ttaaacttac atataagagt
11161  actgaagtgg tcattaacaa gccttttttag catctaatca gacattatta attaaattaa
11221  aagctatgtc aattagcatt caatagacga caatttagtt tccatggcac agatagttaa
11281  attaagggtt gggggtgcac ttttccattc ataatagaat agagggttga ctctcagaag
11341  aattttatct tgggataatt tattgagatg tggtgtttca agcaagctaa tgtctctata
11401  gatggaaacc atatcctcag ctcctcccct aagctttaga aatatgtatt tcaaattaga
11461  tatatttgat cagtgaacag aaagcatttg tgccaaaact aatttcagta gaattccaaa
11521  cgttcttaca ggaaggtatg aatttcactt tattatctaa tcctgtaata cttttatcta
11581  ctatgactct tgaggaacat agctgggctt gttcttagca tgcaaaatat gctggtcttt
11641  gacctatat tggcctgtgt tcagaatctc agcatgtgtt gacattcaga tttggaaacc
11701  aacattggtg aattttgttt ttttgctga ggactgaaaa tgaatagtgt atgtgtgtgt
11761  gtgtgtgttt aatagcaccc actttagatt tgatatttgc atctgtgccaat atggtgttt
11821  agagggagaa cgtcactatg tggacctcga ctgagattgt tggtccaaat gggtcagctt
11881  tagaaattta tggttcaatg aatatattaa gttagggcag tatacttta ggtggtaaca
11941  aatggcttgt ccttatttta atcctataaa atacagtgaa gatcatacta aactttctgt
12001  gtttgcaaca aataaagctg ttaaaggata aactcagtgt caaggttctg caagtatcct
12061  aagtagctat ttatacactt cattaatcct tgtaattggc ttgtcttttca ctgccattaa
12121  ttagatgatg tagtattcca ttaataagag tgacacacct cagcattttt acctttaatt
12181  atagacttca tgagacactt aggctattga caaaatggct aaatattgcc tgatgcacac
12241  gtatctttt tattctcttt cagcacccct acccttctga agaacagaaa aagcagttgg
```

```
12301  cacaagacac gggactcacc atccttcaag tgaacaattg gtaagtaatt tggctttgtg
12361  tttacacaca atctgtttcc ccctctggca acctgcagct catgttttgc attaagaaga
12421  cacacccagt tgccactgct ttccctggtg gcttgttgat tcaaaagtga aaacaaactg
12481  ttgactgata tgtgagaaca tttgctagta tgggaaataa aacattgtat tgtcttctac
12541  ctccttata agttgacaat tttatgcata gtataagtat gtgtgtaatt cacattcact
12601  atggctctgt caatgtatct ctctctatgg cttttttttt cccccttcag ggtaatcgat
12661  agagtagtat catcctattt tctacaaaac aagaaaatcc accatcacat atcagtcagg
12721  tttaaattca ttgaataact aaattcagtt agatttttgtt agggctatgc attcaaggat
12781  agcctctcct ttgctcttat ctcctgaata ctgaaaggaa gaaattattt gtttctcttt
12841  gaggctattc caaacctgag gcatctcgtg gctgtgcaat actgtttcta aataaagtgt
12901  aaattcctga ttttggggcga agctgagatt atgtaccaag taccagccaa caatattctg
12961  actcaatgta cagcagtgtg gcaatgaggc tttgagaaag tatgatttat taccctttgt
13021  gaatgtgctg aaagccaggt ttcatataat caccccaggac tagtgtcata tttgaagggt
13081  atcgaaatcc aatatcctct aaaagtaagt gtatctaatt aattgtccta atattttag
13141  attagtgttt atgatgggga aaccttatcc tctttgaagt aaaatccaga aaaggcccaa
13201  agcctgggct ggggaagggg agaactagga atgccagttt gcagacagaa gtatttcttt
13261  ctgttcaata agtgtcaaag attaatatta cagaatctct gattacatgg cctaatccat
13321  tttggtgaat aaatttgttc ttgatgtcta ttgcacctac attaacagac ccttctctgt
13381  tagagagcct gggagccttt gggagagatt tcagatatat taaacccccat tacagaaaat
13441  gtaatttctg tcaatataat cccatgtatt cttcaattta gtattttaga gataacaagc
13501  tacttacaat atatttgcct ttggaggatt aatttacaaa gtgcactact tgcaagacac
13561  agacagactc acataagaat tgcttgtaag ggtatcaat ttctatgacc ttactgctgc
13621  cttgagagat caattttttgc agcccttttc atcagtggat ggtaaaccaa gcaaaggcat
13681  actacatcta aatgtgttac tacgagttgt gtggctgctg aggtttttttg tttgcctatt
13741  tctacctgct actgtgtctt aatttttcaag gctgttaata ctacatatg gaaatttcaa
13801  atatgtaata atttcatatt tgaaatatga aatttcaaat atgtaatatt tgaaatataa
13861  tatcctggat gatattatag gggagaccat caattttgcg tgcacatcta gattcatata
13921  tctgtattt aaaacttaaa gctgatgttg agacagtttt aatacaatgg aggctgcaca
13981  aatgtccgca tttccctggg aagtgttcct gtttgcgggc aaaggagtgg caggacaagc
14041  tctctagtta agaaacgaaa agcgctgtca ttcagggat ctatcctgtg agccatctct
14101  cttcctctgc agggttgcta gcaaactcca ctcataaaca cagttaccag agaacaaatc
14161  ccaatacaag ttgcttacta tgggtggacg gccttattat gggatatttc ctgtgaatgc
14221  aggaagagga aggcattctt gtgacttcaa gcaatatata tatacacaca gtttctaaa
14281  ttctatgcac agtctctgcc ggagagcaat cttcctaatc agtccatgat cacaattcga
14341  cttctcagt tttgtaacca gaagggagag aaaggatgtt taaaaagttt taattcacac
14401  tctaaaataa ttttaaagta tatgcagact ttaccctaaa cttcacactg ctattcaatt
14461  ctgcacgggt aaataactta aaaatagctt ttaattagtt atttgggaca gaaacacaat
14521  tctgtgctta actgccactt tgtgcagtgt gtggtttctc tctacttgta tatatatgga
14581  gttagaagtg gcttttgctt gcaccacagt gctttgcatt tggcaattgt ttcaacattt
14641  aacaatgttg tttgctgtag aaaatgtccc tcaagtaact aaaagttgta agagagattg
14701  ttttctta gtttgacaaa taatgacaat accatgtttg atttgaattt ttaatggttt
14761  attaatttt atagaaacct cttcctgttt tgttttgttt tgttttgttt tgttttgttt
14821  tgttttgttt tgttttgata ccgagtcctg ctctgttgtc cgggctggag tgcagtggtg
14881  tgaacatggc tcactgcaac ctccaactcc tagctcaagt aatcctcctg actcagcctc
14941  cccagtagtt gggaatacag gcatatgcca ccatgcccag ttaattttt ttctttttgt
15001  tgaggcaggg gttttgctat gttgcccagg ctggtctcta actccagggc tcaagagatc
15061  cacccacttc agcctcccaa agtgctggga ttacaggcgt gagctactgc acccactat
15121  aaacatttt tataaaaaat gttttttcatc ttagctatac tgagcatcgg tacaagttat
15181  tttctactaa aataataat tttgaaaatg tcatcattag tatttctgtg tttcccttc
15241  atttatttat ccacaacttt taaacatctg tgtcttcctt cttggatttc ttaaaacttg
15301  ttaatacaca tgtacattt tgtatgaact atgagtcact gttgaaatgc aattcaataa
15361  aatgctgaag gacaggttga gtgtagatca gtcataatta ttagcagtaa cataatgtat
15421  caaatatat aatatgtaag tgaaaaatat aaactcatgt ctagttgtta gagtgtcata
15481  gaaatcctgg ctgatgcagt tttaagttag gctttgactg aaaaatagac aagaagtttg
15541  ctacatttta atggttcttt cacttcatca ctgaactaat tttacatttc tcgaattgac
15601  agtgatatat actacctgcc tcaggtggct aaggctaaag tacatgggat ttgaggggag
15661  aaaggcaaaa gaggagagaa cttaaaagta aaacaataag actgatttga ttaattaaga
15721  gaaaatctgg aaaaaagaaa atctcgttat aactctttatt ttggtccaat tgtcagaata
15781  aaaatggaga gaaagaatct taaaatggtt ggcatcagta cttacagcat gtgggcccta
15841  ggatggaatg tgaaatttat tagatgtgac attgtgggcc aagtctatgc caataaattt
15901  tttgagaatt gaggcaatta tgtaaataat ttgagtaaaa tattttaaa taaattatct
15961  aagtatttga tgtgactgca tattttaaa aaatcaacct ccataactag ttgtctaaat
16021  atttcaatct agtatgttgt ggttgactta gatttaaaag tgtaatcatt ttcgaaacat
16081  aaatatgcacc agagatttat gtattcttcc ttctttggtc ccttgctccc aattataatt
16141  ttatccaaaa atgataata atagcatcag gggctttttgt ctctttgctt tttactgtt
16201  gttgtggttt taacaaatac ttatgttata tcagcagtgc aaacattacc aatatgcaaa
16261  tgttttagta atttaagtag aaacatctta aatttggagc ttagatggtt gtttagacct
16321  ttaagtattt aagtagaact ttatggaaga cacacacaca cacacacaca cacacacaat
16381  caatacttgg ttgttttttc tcctgaatag accaacttaa ttttttata ttgaaaatgt
16441  gagtgtagaa tggtcagata aaattccct tatacatgat cacaccagtg ttgcggacct
16501  gggaattccc tgtgatgaaa acttatctct tgtacttgtg tcgtacttac tggatgcctc
16561  agttgcctcc tgcctcagca gagttttggc ctagggtgta ctgaatacat tttacagttt
16621  ctttgtttac tactcctcc ccaaacactt tcctattaag ttctgatatt aaatgattat
16681  cccttatgc tctgagaagg caatatgggt tttaggtgca aaatatatag tgtatgtgaa
16741  atacagtatt tatatataga gaaaaattat tctccatcaa gagagcatat aaaattccag
16801  gttccatcct agcagccaag atgacactgt tcagaactat ggtactctac atttcttaga
16861  tttagtgctc ataccagatt ttcctagtta tttcatttat tgctttcaaa gctgcaaagc
16921  attcaggcat cacttcccat ttattatgag tgggaaaaaa gtatgttatc cttggagatt
16981  tatgccactg gcaagtaaaa atgtaaaactt atttttaaa aataagatct cctttattat
```

-continued

```
17041   aataaacaga ttcagctgtt aaaggtcaag tttctttctg agttatggta ataatatagc
17101   aaatactttt acaaataatc aaagattcta taaatatagg tacctgttta gatgtaaatg
17161   ttaaaacatt cacaaattat cctttcaact tctgtgatct aaaaatcaat aggggtcata
17221   gggtttcata gaattgttct gcttttttctt ccaacataat ttaataatac attttacaga
17281   tgttgtttga atattagaca cagattgttt tgtcaataaa gttaaacaga ggtatgacac
17341   aaaagcaagg aaaacagatg taaaaaaaag aaaaaaacag tacacgatgc aagaagctct
17401   gggtcacttg tttgctattc aactacaaaa ttaaagtgtg ggctgtatgg tgattttcct
17461   tgcctaggaa tcacctaggg atggaacagc ttcacacata gaaagtaatt gtattaagca
17521   ggtggtttaa cttttttccct tgagaattga agtgtaacct acatttaaag tagacttcct
17581   aattgatcaa tggagtaaca ggtgcggtat attaaaaaga aaaaggagaa atataaatgg
17641   aagaactccc cagaatattt cagaatgggt tgttgttctt caagcctcgg ttaattgcta
17701   tgcttttcac cttgagtgtc aattctaata atattacctt tacagacgct tactctgggc
17761   ttagattata gcaatcagta atactcacta gataaaatac tgtctagttg ctcataagaa
17821   aatattgaaa tcagtcaaaa aatgtttagc ttgcatattg cctgagacag agctggcggg
17881   gcgccagaca ggcagggtat tattaggaaa gctgagcaaa tagctcgcag ggaaaagagc
17941   tgtgaattta gaaaccttca ggtattgtca tgtcagagag tcttaagagt tcaacagaga
18001   cactgcttt ttttccttc agatttaaaa aatttccaac aaacaatctt ctttgaaaat
18061   gactctgcag tctgttaaat atactttgtt gtaagttta caccataagt ttactcagag
18121   cttttcccca ctgcataaaa tcacatcgtt aatactgtta aagacgaaag ctccttatga
18181   aagagtacac tttgaaacac tgtgctggct ggaaaaaccc tgcccttcc accatggggc
18241   cctaagtcta ggtgagaaaa gaaatgaagg tctaggatgt aggaagggtg gatttgaaag
18301   tccaaatatg gttttgtgta accactgttt ctcctccagc cagcattcaa aggcagttgc
18361   tgagcttctc aggaggacaa gacactagct ggaagctgca atccagctgg tacaacctga
18421   ggaattatgt cgggaccctg tagggttggg gttcaagtga ggctcagagt tgagtgagtt
18481   gggagactga tttacccagc agggaccccaa tgtttctgaa tatccatgat tcatttcaag
18541   gcaatgaaac cagtgacaac ggaggttgac tttgaacatg gtatgcaggt cagcacaact
18601   tgttgcaaat cctaattaag ccagtcttct tgttttcagt gtgtctgtaa gtatctggtc
18661   agagaaatgc aaacaacagg ctgtgggtca tgcaacccga tggggcagga cttgactccc
18721   atttccctgg agagggcata gggatgaggg gctgagaggt gtcacggtca aggggggaaga
18781   gcttggctac gcctcatcca taggtggcta aggtgtaagc ctcatgacaa tttaaaattt
18841   acacagggca agtatgggaa ggggaaatgc agggacaggt cgctgcaatc aaaacatttc
18901   atccctcatc cctactcctt ggatttgggc gacagtgtcc tctggtttaa aatggacaag
18961   taggacgaat tagtcaggac tcaaaggact cttttagctg taatattcta gactgtgtaa
19021   taatgtgaat caaagagaag taaagtgtgc gctctgaaac tctcattcca gctttatcct
19081   aggagtgggg aaggaaaaaa aatactttga taaggagaca aacagagaaa ttaattaaaa
19141   agttgtagtt gtaactttcc tcatcttaca taagcaaatc aaacactgta aaataaaaac
19201   tagatgaaat taaacattat cacaagacat gaaaaagatg tgtgctgtca ttttaggatt
19261   cataataaag ataaatcagt tgttttagc agtgtgctat gagtctatga agggcatgac
19321   agataatagg ctcgaaattt ctgaagttat tgtacagcaa aatttgtttt ttcctcaggc
19381   attcaatctt tttctccagt aattttgaac atgacaaact tttagtgga tgcattaata
19441   atctataagt aatgggttgt caggtgtcag ttagataaga ttaaaagact gtttaagcat
19501   tatccatttg cttcttttgca tgagttttat aggtcagcag aaataactttt ttgaattgtg
19561   gttgtgtgta cgtgttctct ctctctctct ctctctctct cgtctctctc caccccccaa
19621   acccccctcc ctctttcatt tggctccact ccaagcatac gtggaagaac cgtattacat
19681   tccataaatc ctgtatgtaa gagcagattt gaaactcact atgtgaatca aggggacaaa
19741   tgtctcagct gtcttctgta aatgtatttt agttttttaaa atgttactct tcatcttctc
19801   aaaggaagct ctgtaagggg aaacaaactc ggctaagagg ggcattgaag ctttagacat
19861   tagtagtttc ctagcaagtc aggtttaggt ctattcttgt caaatatgtc ttaagtgtgt
19921   ttacatatag tttgcctttc tggtattttc tgcttgcaca gacctgatct ccacctattt
19981   tgtgtcaaca gttgctgagg ctggtgttgg gtgattaacc gttaagcacg gaagcgcagt
20041   acccagagag accctctctc tcctctcact tacatcatca tctggcttca ggctgtgcct
20101   acagaaaaca aacagcattt ttgagtggtt aaaaagtcag cctgaaatat taaaaaatgg
20161   ggcaaatgtt gcctcctggt tgaatagaac agttttcttg aaaaatggag tggagccagg
20221   ggctcggggg aaggaagtgt ttccgagggc aaacgttggg cttagatccg gtctgcattg
20281   ctccagtgtg tgcacgccga ggagctttct gtagacgctg agggttatgt tctgcttcgt
20341   ttttgatttt caaggggaaa gaggacatac aaaacaaaaa caaaaaaaaa cctacaacaa
20401   catggatgcc tgtaactttg gcaaatataa ggctgtcctg ttcaatgccc tcataaatca
20461   ttaatatttt cctgtctatt ttattttcat tcttcacaacg ctctagcct gaccccttaa
20521   tatggaaaat aattaactct ttcatgctcc tgatgcctga acaataacaa ataaacaaaa
20581   gaatattaat ctgttccgac atatttgaga ggttctttt ccttttttacc ctcttaacta
20641   accagtgcct cacaagatta gatcctatgg ttgaagaagg ggaaaagtat ttccttttc
20701   aaacacatta actcctccag gtctggggga gatgattgga gctacatgta acttagctca
20761   aaaataaatg tcctgcctt ggtgagatct ggctaatat tgataaagtc acttttttt
20821   tttttttcaaa aacaatatgt tgcctacgga tggaagttaa tgcaccatat aattatacac
20881   acatacacac gtgcatgtaa gttttcagta tttttactct aggatgctaa ctaaatcaaa
20941   tgcaaaccag tagtcttgag gtttgttgtc tggttgaagg gttttgttgg cctatatcac
21001   taggacatct gcagtggttg acttgttttg tttgctagtt tgggtcatag ttcagatgta
21061   cttggaaagg gccgggggagt gggtaggggg atgtttaaa agcttatgga aagaattgaa
21121   catgtacaaa aagatatagg atctcagccc cctggctggt tacctgacaa tactgtttac
21181   agaaaggaaa gtatagtagg ttatggcaga gattcctatc ctcaggactt ggggcggggt
21241   gggagggggc gcagagaggg ggtagcgggg cacataagaa gcatgtcaca atcattttga
21301   gtgaatatag tattttaaaaa gcatatcgag aattaaattt tgttttagt catgctatt
21361   cttttgaaat tgcaaataac aaaggaatat aagattttg atgtgtcaaa agggagcatg
21421   gattaaaatt ttagaaaccc tatgctacag aaccataaag taaaaatcct gggagggagg
21481   gaatttatgc atcatacgac agatgaggct cagggctaat tagaggcagg gctaggactg
21541   gttcctagtc cagtgctct tccagtccac tagaatgtac ttattttaa cagctttatt
21601   gagatataat tcataaacca tcatttcacc catttaattc aatggttttt agtgtgttca
21661   cagagttgtg taaccatccc catagtcaat taaaagacat tttcaccacc ttaaaagaa
21721   gccttgtacc ctttagctat tgcccctctt tatacttccg tctctctctc caacagctcc
```

-continued

```
21781  tggcaaccac taatctactt tctgtctcta tatttgccta ttctagacat ttcaccaatg
21841  tgatcatgga atacgtggta ttttgagact ggctttttc actaagcata atgtttgcaa
21901  ggttcatcca tgtcatagca tgtattatca gcacttcatt ccctttcaag gctgagcaat
21961  gttccattgt atggatataa ggtatctttt ttttacctat ttatcagtgg atgggcattt
22021  gatattcatc tcttaccatt ataagcgttc atatacaagt tttggtacca ttaagtattt
22081  ttgggaatga cagtatagca acaaagacct gtcttaggtt tgtataattt ggaaagcact
22141  tttcattcga tcatcccaat ttcagcacct aaacactgct agaaaactg ccggtgagtg
22201  gcagttttcc cactcagttc tcatattctt ctcactacac actgctctca ctttcccgc
22261  cactgggtag tgttttgact gtgataatta cgagtgatgt tcaagaaaa ggaaagttgg
22321  ctgggcacag tggctcacgc ctgtaatccc agcattttgg gaggccgagg gaggcggatc
22381  acctgaggtt gggagttcaa gaccagcctg atgaacatag aaaaaccccg tctctactaa
22441  aaatataaaa ttagctggga gtgggggtgc atgcctgtaa tcccagctac ttgggagact
22501  gaggcaggag aatcgcttga acgcataagg cagaggttgc tgtgagccga gattgcgcca
22561  ctgcactcca gcatgggcaa caagagtgaa actccatctc aaaaaaaaa aaaaaaaaa
22621  aaaaagaaaa aaagaaaaga aaaagaaaaa ggatagtcac actgaaatcc agcaactcag
22681  cagtaaaatg cacaaagttc cctcgaaatg acttagatga ccataagcat tttcaaagat
22741  ttgacagatt ccaagatgtc attttgctaa tgttattgtc tttattcgag agattgtttt
22801  cctttaagtg tgtttccatt tgtatttaa aggtctacag gttacatatt gacatatatt
22861  attacataga gcttaggttt caagctttac tcattaaaac agaggtcaca gtgaacattc
22921  caaggatgca tgcaagcctc cattcaagtc aaatcatctt cattgtgcca ttctatagcc
22981  taatttcata accagacgga actagaaatc aagctaaatt ttgagatatc ctctcttgac
23041  atgagcagag actccaggtc tagaggttta tggttgctga agacttggag aactgaggca
23101  actacaggca agatcctaga gaaaggaagg agctcaaagg tactccaata tggagctaag
23161  attctttaat acctgattag ggccaggcac agtggcttat gcctgtaatc tcagcacttt
23221  gggaggctga ggagggcaga tcacctgagg tcaggagttt gagaccagcc tggacaacat
23281  ggcgaaaccc tgtctctact aaaaatataa aaattagctg ggcatgttgg tgggtgccta
23341  taatctcagc tactagggag gctaaggcag gagaatcact tgaacccagg aggcagaaat
23401  tgcagtgagc tgagatcgaa ccactgcact ccagcctggg tgacagagag agagagagag
23461  agagagagag agactctgtc tcaaagacaa acaaacaagt aaacaaaaaa acctgatgta
23521  tatgggggct ggttgccatt ctaacacaac ggggtttaa atttatttggg ggaaactttc
23581  ttttggaaaat aaaacatatt tgatcattaa ggtgaccatg catcccactt tcctgggagg
23641  ctcatggttt atgcctgttg cccagtgtaa ttgttaacag tgcctcttca ctctcaaacg
23701  tgtcccagtt tagatgacaa attatctgct catcatattt ataatagaga ttggcagaaa
23761  actagaattt gctttaaata gatacattta ttcagtaatg tgtaagggat gttttgttag
23821  attcaatttt attgacttct tgtgaatatg gaaaaattgg aatttaaatg aaaaatggtt
23881  catctattaa actaaagaga gacacttctg ttctttgaag acattattat acctatttta
23941  gcttttcat tagtagagga agttttgcta tattatctta gatcatgcta ttgcttctac
24001  attgtgctaa taatcatttt aaatctatat tctaaaccac tattttttt agctccataa
24061  ggtatacaa actcaaattt ggcaaattgt ctgttacatg taagtaaata tttatgttt
24121  acttaaatat aaatataaac cctgtctcat tctgttgcct aggccggaat gccatggtgt
24181  gatcatgatt cactgcagcc tccacctcct ggatttaagc aatcctccca cttcagcttc
24241  cctagtagct gggactacag gtgtgcacaa ccagacccgc ctaatttta cattttttgt
24301  agagacaggg ttttaccatg ttgcccatgg tgatcttata ctccaggctc aaatgatcct
24361  cctgccttgg cctccaaaag tgctggtatt ataggcataa gccacaactc cctgccatca
24421  ctttttttt ttttttttt tttaggatg aagtcatttc aaatttgct ttcaaggaaa
24481  attttctgta atatatacca agtgatgaat tatttgaaat ttatttaat gcctaaggcc
24541  aaaataatac atgagtttg atattactt gcatcatcat tgtcaactag tgattggttc
24601  atttcacaag ctgctttaaa gagaattta gtggctgggt gcagtgtctc acacccagca
24661  ctttgggagg ccgaggaggt tggatggctt gagctcagga gtttgagatc agcctgggca
24721  acatagtgaa acctgtctc tacaaaaaaa acaaaacgac aaaaactagc taggcatggt
24781  gatgcataac tgtagtcctc ggaggctgaa gtgggaggat cactcgagcc agggaggtgg
24841  aggttgctaa gctgtgatag tgccactaca ctccagcctg ggcaacagag tgagactctg
24901  tctcaaaaaa aaaaaaaaga aagaaaagaa aagaaaattg tatatgtaat taccttcctc
24961  aactgtggta gacaatttca gttctttcta agtaattttg gcaaatacc ccaacactgt
25021  tagagaagga aaactttca tgtggctgat tgatggactt cttatgattt gaccaaattt
25081  caatatatg tttatcaagt gggtagagaa gagaggtgct cccttttccc ctcctgtcta
25141  ttctcctcct gccgctgttc tctacctccc ctacccgcag acacactgat gatgtattgc
25201  aatcttggaa ctgttggatc ctggaggagg ttaagaaact agaaaaaggt gccaaaaaca
25261  tgatttcata aggttgact tgagaatgaa tcaacttct tgaatatctt aaaatcatgt
25321  ttcatgaaat tttatttcac aaagaaaggg agtgtagaag acttgaactc tgaagaccaa
25381  cagttatgga tcattaaatc caatatgtaa atgtaaatct aaaataaaga gttccaacag
25441  aaaaatttca gagtgatttt ttattgttg tttaaaagaa cagagagtta catgggagat
25501  aactagacct ctttccctga gggttgttt ataaaacatg cctttaaaagt tattaaggga
25561  tgctgactt aaaaaaaagt agtagatatg attttattta aatgactatg atatagatga
25621  aggaaatgct atggtgagga aattcctgga ataaaaaaat aacaaaatgt tgggatttga
25681  caactacctt ccaatgataa attttatatt tgaagatttt tcatgaggtt taaattctaa
25741  aatttgaaaa tatttataga aatcacaaaa atgaattata tatcaattat catctgtgca
25801  tgtttatttt ctattgaata aagaatagta tatgcagaaa tcttatattt aagaatgcac
25861  agtgttaatt tttattacta agttttttata gagatattcc taacgctagc taaatattaa
25921  taaaagatta ttataatcag cacttccctt aagggatagt gtaggtatag aaggcattgc
25981  cactaatcaa tctaactaat taacaaaatc ttttcttaat agttgattag cttcttaggt
26041  acttgcagat gttgtaaat gatatttctc tgtctagtta ggaaccttct gaagtaattc
26101  tatgtccacc actatcctgc tgacagttca cttacgccta gttggcaaga aacacgacgg
26161  ggggtgaagc agagccatgt cattgtttgg aggcaacacc attgtgattt tctgtggttt
26221  accaagttgg ctgtggcatg ctaactaaac caaatgtggg cttcctttaa ttatcaggga
26281  gtaagtagag tggtaacac tgaggaatag aactaattga gtaaagttga aaatgctatt
26341  tctgaaagtg agcaagtaat tttttttt tttttttt tttttttt tactttatc
26401  agtattacag agagccatac aagggaggaa aagggcaaag gtatgtggaa aatgttgcct
26461  gtgaaactgg gaaactacct tgtgttttgg ctcctaacag atgcccactg tgatctcctc
```

-continued

```
26521   acctctcctg gttctcacag agggaaacta aacttagcaa ttcagttttg ggggaagaga
26581   ccagggaaag gagtggagga taaactaaag gacaaaggtc agtttcaaaa agctgttctg
26641   ccagatctg ctcagaaaac tattcaggta tccaaagact gagaataaaa ggagatagat
26701   gaattagtc cagtggaaaa aaaaaaagcc taatgataaa taaacatctg gggacaaaaa
26761   agaaagaaca aagcaaaact tcctgtattt cttttttaaa catgagtcac agtcacttcc
26821   cattctcctt gtcagattcc tataaaaaat tcaaaataaa attcaatttt tagatgatcc
26881   aggtctcaga tttttggaga ttttgctccc ctgccaactt tcctctttcg cttttttagga
26941   cttgagtctt aaacaaacaa ctaagtaaaa aagaaatata tttctatttg gacatgaaaa
27001   aaagctatag agcaaaccca ttatcttcct ttcctttgta aagctttttg ttttgagact
27061   gggagatagtt tggtcagaag aagaaattct aactctgat tctatgaaaa aaaggaaata
27121   taaagattct tctcctaatt cagtcttcca ccacctgcag ggagtccaat tcttaaaaag
27181   tacttcacaa aagaagactg tgttttcaaa gcaaactaga ttttaagaaa ccctatgttc
27241   gaatgtaaat gaaaaagcaa acgagacatt ttctaacctt aaagcatact aaaagattta
27301   cttttttcaag aatcccaatg tatggcaaat ttgaattata tttcattaaa ccaaggtgtg
27361   taactatcta ttttaatgag tgagcaaaac tgtcatgtgg ctgtgtactc ctgacattcc
27421   atatctgagt tttaagggct atgtaatatt aggaccttaa ttgtaaaagt acaaaagttt
27481   cctcttacat ctttaaacta acatactttg taaaagagac cttactcagta tggaaaattc
27541   taagattgtg tgtatttcat agatatgtat ttgtatttta tctcaaacca ttttgtggct
27601   gttggagaat gtattttta tagtatattc aaattggaat tttgtcattc ttttttatat
27661   ttctcttcca aaacactatt tcttctatgt tgaatctcta atatatattt gtgttcatac
27721   ataaatgtag atatatattt gaacacacag acacacacac atacatatag gattaagata
27781   actatttttac ttatgcctct taaaatgaca ggatttttaaa gtgacaatat gttcatttaa
27841   gttcacatca tatgtacagt tcttttttg gttcggtgtt tagagaattc ttgataattt
27901   agactcttcc acaatgaaaa gtaaagcatt ctgtcacaaa agcagggagg atgagacaca
27961   aggtcaaagg gcattttaga aacaaacagc tggaccaatt tatttaaaca gatagaggga
28021   tggggaactg acctcagttt gacttatagt gggaggagca agaatgtcat tttattactt
28081   tgcccagaag gaaaatgttt ttgtatctga attcaccctg aagccatcta aacatggctc
28141   tgctgtgtgt agcataattc caaagagaga ggatgtataa aatagtcgg gataatgata
28201   aaatacacta aagagaatca aatgtggaga ttgttaagg tcgaaaaggt gatgttgttt
28261   taaaaataaa atattttgct atttacttttg ttgtttttcac atagatgtcc atcatgaccc
28321   caaataatta gttgttcata taagtgtagt aattgtaatt cagtaacgtt ctgagagatt
28381   actacatcct atatgtacta atgatattc attatattga atttttttaaa ttaaatgttt
28441   cacaagtaag aagttgcagg tagacctact aatgtggtca aacagctcag aaaaggtgat
28501   tagttttct caggtttttca gtgtttttgt ttatgttttta ttttttaatt aaaggtttcc
28561   cccttttgata tctacacatt ctaggggtag ctgacatctg tgttcttaat aacaacaaac
28621   agttcttgcc accaaaaaga agcaaataac atctagtacc tgtgggcagt tggctaagag
28681   gctgtggtat ttttttgtgtg tatttgcttt ctacctgggg atcagagcag gcctggaata
28741   aatgtcgttg gtgttgtcca ctgcaaggct tcaggaggac atagacaaag atcagcctac
28801   tgagcagaga gtggtccagg tattgaatgg actcaatatc ctagaaggac tcacattcta
28861   gcaggcactt tttaagaatc actaatgttt aacctaagga ttagaggga gaaggctata
28921   aagcataatg gctatgttta actatttgaa gggctatcct gtggaagtaa aattagaatt
28981   gctactagta ccccaaggag ttgtgtcgat aaaactatta ggttgggtgc aaaagtaatt
29041   gtttttttt tttttaatta tactttaagt tctagggtac atgtgcacaa cgtgcaggtt
29101   tgttacatat gtatacatgt gccatgttgg tgtgctgccc ccattaactc gtcatttaca
29161   ttaggtatat ctcctaatgc tatcccttcc ccctcccct gtaattgttg ttttgccac
29221   tgaaagtaat ggcaagaccg caattacttt tgcaccaaca taaatatttt tgatctagta
29281   aggcagaacc ttctaacagc cttgtttata gatgggggtg cctcttaagt aaggtggtga
29341   gtgctgtatt agttcagcag aggttaccta tgtactttttg ggggacagat atcatatagg
29401   ggattcatgt cagtgaccaa acgaagtgac cattacagcc cttttgaaac ctgaggtgta
29461   atttttaaaa atgaactcac gactttaata gtcatagact caaacctgag ttgattatta
29521   tgaattagtt tatgggagtc tcaatatgtg aatatgatgg agacaagttt tggaatacag
29581   ataaatcaag tcactgtatt cactctctct ctctctcttt gaatagcctt atctttgcct
29641   atacacacaa acagtgcagc catcaaaatt ttcaatttac aaaatgttca cagtcatgct
29701   tcttccttga ctaaacactg gggttgctgc cagtcggtaat tggcttgaaa ccagctaatt
29761   tttatatatc tatttagtct ggatattcta gatgagtggc actatagttg cggtgctcta
29821   gtcactgtgc cagagcacca gggaggaggg tgcttgctac cactgacagc tgtgtgtcat
29881   ttagcaaatt attaacatct ctttggtaac atgtgacctc aaagaagtca cctaattct
29941   ctgagcccag gcttctcatc tgttaaaaat gtctcttcct attttttaggt aagtagtata
30001   agtcacatcc ataaaagatt atgtttttaa aaagtctgga aaaagaaagt taatagacag
30061   aattccttcc ctctaagagt ctgcagataa tgaacagtac catagataaa gagatgtttt
30121   tgctctctta cctacattag ttactatgaa aattactttt ggtatatgca gaatattaat
30181   attaaataat tttctaattg gtcatgcagt gaaggcagct aatgaaaaaa cagattttt
30241   ttcattttaa ttggttattt cacatggtgt ttgtgctaca cctgtgctta taatgagaat
30301   ggagaattaa tctaaccttc tgctcacatg attccagttt tcatggttta tacaagataa
30361   tgataacctg atttgcaaca caatttgttg tagacctgtg ttttaaatat ttttattagc
30421   agttcaggga cttcatatac aagaactgat ataatatgta ttgccaacaa gaattagcac
30481   aaacagtata cctttttagtt agattctagt ttcattattt gtttcaatta cttctcagat
30541   aatgaaagaa cacaaggata caggatattg agaatcttaa aatgttatga agtatgcatt
30601   tttgttttga aaacctgtcc ctgtctgttt aatggtttgg tttttaggaa ctattttcct
30661   tcctgaagtg ggcagattta caaactagaa ttcatactgg actatggatc ctttaatcat
30721   taatagagcc ttattaaact tttcattgta ttttttatgt cctgctcaga tttgatctga
30781   gttgggaact aaaaggaatt tactatttca gaatctaata tgtcctcttc attttctgga
30841   tttgatacgt aattttttaat attatgcaga acaaacggat cttaagagaa tctcatgcgt
30901   atgactctgg agagcgtata ttaatactt tttacatgtc agtgacttgt cactttttgga
30961   gaggctacaa aaataattgt acaaaactat cttattaagg cacttaaagt aacttaagtg
31021   cctaataag atgtttataa attttcagta ctagctggag aaagcaaaac tataagttca
31081   attactgtat atctgtgacc ttgccttgac ctcagacttt acataaagag caaaaaaaaa
31141   aaaaacaaca acaacaaaaa aagccacccc aagaaatctc tacaggaat gcatttctct
31201   gaagtcctaa gcagtgtgag ttagtggtga taaactccag acattctctc atttgatggt
```

-continued

```
31261  gtgctgccat cccagttcat tatcttaata gtgggcatta aaatagaatt aggtttgcaa
31321  gaggtagggg tggttttgat aaaaattgta caaagaagt cagagaacat aagattgaaa
31381  tgtcactaat taggagaggt aacagatgcc cttatgagca tctaactctt tacaccaatt
31441  ttctctcttt gcaaatgaaa ggagtggtgg ctagtattgt ttcctgaaaa ctctgctaat
31501  tcccccatga aaagatgaaa tggaagtgtc caactgtggt aaaacaggca aacataaatc
31561  aactcagaaa ccccaagcct gtgtactcaa aggtcactgg gggttacagg ttttccagca
31621  cgtgaggctg cacatagagc aatggagaga actgaaggag tcccattttg ccaagatcta
31681  gttttactcc aactgcgatt catcttttcc tcttcctcaa ccccccttt tattttaag
31741  gaataacgat ttgtttcact ttcttggtta caggtttatt aatgcccgga gaagaatagt
31801  gcagcccatg atagaccagt ccaaccgagc aggcaagtcc cccatagtga ctgtattcaa
31861  gtcacgcaag cgaaaaccat cctcaagcca ttcaccggga ggtccgctac ctggtaaata
31921  aactgggagt gagtatagga acgcctggca attaaaatta aaccagtttc gtttcataac
31981  aacactaatc aatttaacat cattataaaa cgtttggaga aggtggaaaa aaaaagccaa
32041  cagagaaaag taactcttaa ataatatgct cagttacaat attctttgta cacattcaat
32101  atattaatgt tatttttttt ctgagtttgc cttcccagct ctttctgcta ctatgaccac
32161  tccctggtgc atggcttggt gtggaattgc tgtaaacttt attacctgtc aaaagggcaa
32221  aggggtcagg attgcttgtg ggactcagta aagttcaaag acattcaatg aggtagagct
32281  tttgtgtgct ttaataaccc aaggcagctt acttctgaag cagcttttca tgtacagtta
32341  aaacacggga ttcaggtagt ggtataaata catggttctt atttctcaga ccttctcttg
32401  ttaatatcca tcttctggtg ttcgactttt ttttttta ataacagtct ttttgttttg
32461  ttttaaatt atgagcttaa aatggcgata cttctatggg atcctggctt gtggatctaa
32521  aaatccaaga aacatctctc taggatttgt ttttgcatta taatatgcca gtaagataac
32581  aagagtattt gctagggtg atgtgagtct ttactttctt tatgaaatac tctctcatct
32641  cttagggagc actatggaaa actatgttag catcgcattg aggcaacaca catttactcc
32701  tgtaactttt tttcttccaa cacccattat gtggtcacca gacaaaaccc aagcagaaag
32761  ttttccacacc ttaactgttc cctctttgag ctagatgttt taaaaactca gtcacagagg
32821  tgtgtagatc tagtctgaga gaaatttcac tttgaatgtt taaaaaatta tactagcctg
32881  ctatgttctg tctctttctc tggtatgttc tcctcttagt ctctcttggg ctattctt
32941  tgctctcaga gactgttatt aaaaaaaccac attctgtact tttgtagtaa gtcaaggaac
33001  accttataat cctgatggac agcccatggg aggtttcgta atggacggtc agcaacatat
33061  gggaattaga gcaccaggta agactttgtt tttgtggtag ttcctcattt ttgactccaa
33121  gagtgtcatc ccctcatcaa cacaggtaaa tccgcctcat cctttctgt tatctcaagc
33181  tggctgcctt gccttgtctg ctatctgtgc atctaagata ttgcagaggg gaagccagga
33241  tctttatgca ctgaagatct cactatttct caaccctcta gatcctgtt tttttttaag
33301  ggtctttgg cactatctgt tgactttgct catttttctgg cctcttcttg gattttatc
33361  tcccttctag gacctatgag tggaatgggc atgaatatgg gcatggaggg gcagtggcac
33421  tacatgtaac cttcatctag ttaaccaatc gcaaagcaag ggggaagtaa gtacaaatgg
33481  ggtctttgtt ttcacttttgt cctaggaata ttttttcctct tgcattttct tatgttctcc
33541  ttgcccatag cttcatgctt gttcattcct ttccattaaa ctcctggttt cttgcttcca
33601  tcattttctt tttggttgtg atcaagcttt taagcttata aatactgtgt atgatgtaca
33661  tttatcctgt gtgttgctat tgtacagtac tgaccacatg acaaaacaag aagcagtcag
33721  gaggtgggg agtggttgt catagcaaca gactgatttg caaaatgtaa gcagtctgca
33781  gcagtgcaag gagagggaag agcatgtccc caaagtgtca taaatctgtc taaccgcagt
33841  tgatgcatga gttacatttc tacactaacc tgcaagacac cgaaaagcta aacagagact
33901  tcttttaggt aaaataaaca caagctttac ttagggtaag taaaggcata tttgagctc
33961  cagtcaacta aactttgatt tttttctta gtttattcct ttgtctgtcc atcataatgg
34021  gattacgtgt ggcaatggga aaagggagaa tacaaaatag aggtgtgcac agcaggctgc
34081  ggggcttagc ccaggctaat tgactatatc caaattaagt atgccatcac ttgcagtgtg
34141  acaaatggat ttgacttatt cagtatacaa aaatagagat cattaatgca atcatcagtg
34201  gcaggcctag tgaagtgggc ctaggaaaac tgtcccagat tctcactctt gcattttctc
34261  tcctataaag acactccagc aattcgagtt caaacaagta aaactgtttt gaacaccaag
34321  gctcttgttc acttcctaaa ttaccctaa tagcactgtt cttgctttgt ttttgaaatt
34381  aaaagcagtt atttcagagt cttgcttgtg tctctgatta tatttatgca ctatttaaaa
34441  tcactgctga ggccaggggt aattcgtact ggtcatcttc tctgggtgtg agtcaaatat
34501  aagtttaaca attagctctg aaaacattcc attgagctgg ggaatgcaac agtcttatta
34561  cctcatcatg gaattcctcta gcttagttaa tttaaatatt gtttcttagt ttctgggtca
34621  attaaattta aatgatgtat tttatgcttc gtgaccaatt aaattactag gttattacaa
34681  aaaaaattat catcttttt gattaaagag ctgtgggtac agtatatttt ataagcaatt
34741  ttcattagtt caaaaatgtt ccttaggct agattaagca gccattcatt gttagagcct
34801  ggagacctta ttcgaaggtg ttcatcgtat tcacagtgca ctattactta gaactaaagc
34861  caattgaacc tacttagcaa tagcgttatg cctttcaccc ttgatgatta tggagcttat
34921  agctctcaga aacaatacac ctgtcagttt ccatcaacta tagcaatcca tgcagaagac
34981  aagaggcccc ctcaaagcag gaggggtatt gttttaggtc caattttct tattgttctc
35041  aaaatcatta taaggtggac agtgttttgt gaagattttc ttttccccag ctctaagaaa
35101  ccatgtggaa agaattcatt gataactgtt ttgattttt tcttttttta agtacaggtt
35161  ttgctaagta atcaccctta gtgagcctgt gtagttcagc tgcctgtgag atgtttggtg
35221  accagctcag tgtattcttg tattcttgat agagaatatt tcaggagaca aaagtgcttc
35281  ttcagaccag acctcaaata acaattttat tcttttttaat aaataagacc tcagtaggcg
35341  gacctgataa cagtgacaat gaaaggaaaa tagtggcaaa atgtgagttt ccagcatgat
35401  gtttctcatt ttatttttctt ctgtatgaat caaaagaatg ctttacaaaa ccatgttccc
35461  ttaatcacag ggttctctgg cttttatagg attgtcatag ccaggaccac actattgctt
35521  tttcataaca ttttctttt gtttcttttct tttgaatttc ttacagggct gcaaagtatg
35581  ccagggggagt atgtagcccg gggtggtcca atgggtgtga gtatgggaca gccaagttat
35641  acccaacccc agatgccccc ccatcctgct cagctgcgtc atggggcccc catgcatacg
35701  tacattcctg gacaccctca ccacccaaca gtgatgatgc atggaggacc gccccaccct
35761  ggaatgccaa tgtcagcatc aagccccaca gttccttaata caggagaccc aacaatgagt
35821  ggacaagtca tggacattca tgctcagtag cttaagggaa tatgcattgt ctgcaatggt
35881  gactgatttc aaatcatgtt ttttctgcaa tgactgtgga gttccattct tggcatctac
35941  tctggaccaa ggagcatccc taattcttca tagggacctt taaaaagcag gaaataccaa
```

-continued

```
36001  ctgaagtcaa tttgggggac atgctaaata actatataag acattaagag aacaaagagt
36061  gaaatattgt aaatgctatt atactgttat ccatattacg ttgtttctta tagattttt
36121  aaaaaaaatg tgaatttttt ccacactatg tgtgttgttt ccatagctct tcacttcctc
36181  cagaagcctc cttacattaa aaagccttac agttatcctg caagggacag gaaggtctga
36241  tttgcaggat ttttagagca ttaaaataac tatcaggcag aagaatcttt cttctcgcct
36301  aggatttcag ccatgcgcgc gctctctctc tttctctctc ttttcctctc tctccctctt
36361  tctagcctgg ggcttgaatt tgcatgtcta attcatttac tcaccatatt tgaattggcc
36421  tgaacagatg taaatcggga aggatgggaa aaactgcagt catcaacaat gattaatcag
36481  ctgttgcagg cagtgtctta aggagactgg taggaggagg catggaaacc aaaaggccgt
36541  gtgtttagaa gcctaattgt cacatcaagc atcattgtcc ccatgcaaca accaccacct
36601  tatacatcac ttcctgtttt aagcagctct aaaacataga ctgaagattt atttttaata
36661  tgttgacttt atttctgagc aaagcatcgg tcatgtgtgt attttttcat agtcccacct
36721  tggagcattt atgtagacat tgtaaataaa ttttgtgcaa aaaggactgg aaaaatgaac
36781  tgtattattg caattttttt ttgtaaaagt agcagtttgg tatgagttgg catgcataca
36841  agatttacta agtgggataa gctaattata ctttttgttg tggataaaca aatgcttgtt
36901  gatagccttt ttctatcaag aaaccaagga gctaattatt aataacaatc attgcacact
36961  gagtcttagc gttctgatg gaaacagttt ggattgtata ataacgccaa gcccagttgt
37021  agtcgtttga gtgcagtaat gaaatctgaa tctaaaataa aaacaagatt attttgtca
37081  tgctgactcc actgcttgaa aaatttgttt actgccccccc agattttaa agattaatac
37141  agtaaatata aaaattaatt ttggctccct aagccatata tgtatttgac aattttaacc
37201  gcaaagtaag ttgtttaata ataaccactg atttcttaa gctgacttaa tgaactccta
37261  atatcagcaa tttgaggcc taaaggcact aaactaactc tagactcaga attcatccca
37321  acagaattac tcatctaata tcagtgaaat tattcttgca cataaaggca aacctaagta
37381  caaagttaag tcttttacta aaggatgtta cctaggatga gcagtatatg tttattagga
37441  aattaactac atgaattgaa gagaccagac ttcaaaatct aattttata aatatgctct
37501  atgttctcat tggataaaac tggttattaa ccaattttcc agaacagctg tacaagattt
37561  ctgcatggca gccggctaaa tggtagaaaa taatatgttt aagctgaat agcttataat
37621  ttatttaaa taaaattgct gctataaaaa gtgcttccca aagctaagga aaatatacaa
37681  atattttaat taaggcaaat tcgtttaaa aaataagcct ttcagtagtg attgctttgt
37741  aaacaaagga tgggtcggag gagagagagc cttaaactca agtctgacat tcaggcccaa
37801  gtcaccctat aaaccggccc ttagcaattc tattttctat tcgaaaagag aaaccagctg
37861  tgggttggct ttactaggtg atgtgtgatt gactgactca cctgctggag tagcaatgca
37921  ttctcaccttt ttgctgatgg ggccttgttt ctaaacacgt ggatgcgcag agagcaaggc
37981  tcagcctact gcagccatct ctggcagcgc ttctaccccct cccagccca tagatgggat
38041  tgtttaaatc tcccttgttg acctagtggc aattcttcct ctacctaaat agtcgatgtg
38101  agtgaaatca ttctcttttg ataggtggtt gctagcagtt aacaaccatt tatttacttt
38161  aacaattaat aataaaactt ataaactgtc tatttgctcc tcctctccag tacatgcccg
38221  ggtgagttgg ttattttcag cctttattcc tgaggaggct caggatgggt gggggaggga
38281  aagaaagggg aggaggtgtg gtgggagag ggagagaggc gagagggaga gacagagaga
38341  aagagagagg cgctagggga gggaggttta caagtgaaga gtagttaggg aaatatggta
38401  ctctgaagaa tcgagatcag cagtgtccag gaattagaaa aaataaactg ctatttccgt
38461  gagttccccc tctgtgagcc atttaggtga gagcctcgct cttcgcagtt cctttcttcc
38521  cctgcctcga tgccctcccc tcttaatgct attttagctt ttcctcttgt aaatttcaga
38581  gccagctcga aggttattga ggacacttat ccgaaagagg caaataatag aggtgctgag
38641  agtgttttg atgtttccta aaaggcaaaa acaaaacgcc ctctctcaaa caagggcaca
38701  aaattgtacc tggtttttat ttttattttgg tggtggggg gtggggggt gggggggggg
38761  tggaaagggg gctggctctg gctgaatgag actacttttt aaatatgattt aaattttttt
38821  ttcaaaaaat taaaaatatt ttaccctatc atattttaatc agctgtaatt ataacacatt
38881  caaaatgaat aatatgcctt gacagtattt ttattgttat tgttcattgc atgatgttcg
38941  actgctttag aagcacagga aagagaagta aacgcgctac aaatggggaa ttaccctcgt
39001  ttagcattaa aattcattta gataaaattg ccacaaacat ttaaatggga agattagttc
39061  cccctcacgc cttattgcac tcgctcaatg gttccgttaa gaacatttta cacgttggaa
39121  attccgtctt ctcagacggc ttgctgtttc ctagttaccc acattcaaag caaaggcagc
39181  agcaaaggca gccgcagcag cagcagcagg gaaaaaaaaa aagttttggc aactggtctg
39241  caattcatcc gctgctcgcc ccagtctccc ctccgcccgc tgcagtctgc ccccacccct
39301  tcccctttccc caccccctacc tctttcccct cattatgtaa ttcgcagagt ccagtcctcg
39361  aggaaacacg ttgcctagtt gtgtagtatt tatatacaat gttaaaatac aaagaaagac
39421  cctaaagtca gtcgagtcgg ttcctctctg ggtctccctc tccctctcct gttctaaaat
39481  gaagatttag cttgaatgtg ctgagttttct cacatcccgt accctgaggc cacaaggcac
39541  gttttttggc tttcatttct gccaggactt ttccaggaaa ttcaccactg cttttcgctt
39601  gtattagaaa cgtgtgaaag aattcgtctg aaaagtccat gcaccgtcta gcttttctct
39661  ccccccttttt tttcttctcc ttctcctcct cctcctcctc tctctctgtc tctctctctc
39721  tctccgcccc ccactctcgc actcccccat cctcctctct cccctccct tcgcagagcc
39781  acaggaaaag aggaaagtcg gcttcgactg ccatcttttg gggattttcga aaaacgactc
39841  ggtaggaaac ggagggaggc ggaggcgcgg gagtgggga aacccccta ttatccagtg
39901  tcggaactgg ctcccttaat ctgatgctta aatattttgat aataaacgc attaaagctg
39961  attagttact aacaatttca aattgaaatc acttactcga ttataaacgc attaaagctg
40021  tatggatggt attaggagtt cctcgggagg cagcgggtgt ctccttgaag tgagccaggc
40081  gggcgagttt cgccccgggg aaaagagccc ccagccgagc ccggggggcaa ggccgggagg
40141  gcggcgctgc aacctgggcg caggggtccgg gtcaggggga tcgagcgggc ggccgggtcc
40201  tggtggaggc tgcggctgct tcggctcgcg ggggcgggga gaaggggagg ggaaggagcc
40261  ttggtgggag gctccgaccc cggagcagag gcgcctacca gcaaacttcg tagtgaagtc
40321  gaaggattct gaaaaggaaa aacgcaagcc ctgccctccc cctccctctc gcgtctccca
40381  cgcggcgtgc agacttcgcg ctcgacttg cgatcggggt tagttgctgt gtgcagtgtc
40441  ccccaagtct gcgggaggag cggaagggta taggctccag tcctgggggt gggcccggct
40501  ccgtgccccg agaggaaatc cagcgggcaa ctgcgcagag ctccagccag gacgtgctac
40561  ccctgagtcc ctcgatgcgc tgggtcccgg cctaggcccc agtgcgtggg cgggcaggtc
40621  tttcccagaa gaccacagct ctggtgcgg ggggtgcgg gggtggggg gctgcacggg
40681  cgcctgcctt accctcctgc cctcacccccc atctgagtct agtctaaggg actgttgact
```

-continued

```
40741   ttgtctctgg agatggggcg accaggggtc tgcgaaggag gttgtggaga ggcacctcct
40801   gggtgcaggt ccgggcgctc tttcctcgga acctcacgga gtgctttgta gtagcctgga
40861   gacttcctaa tagactttgc cacatcgggg gccccagact ccagagtccc atagtggccc
40921   tgggagcgcg acccagagag cctgggggct ggagggcaca tggaacgcgt gcacggccca
40981   ctaggagggc gttgggagga gagtgcccga gtctggagcc gcagccggga agccgtagac
41041   agcaccccga cgccttaggc agaagctcct caggatcact ttaaaagctc tgcaaacttt
41101   ccccagcctt tcggataccc tcaggcccct ggcccaccgg aaggcagtaa aaacgtaact
41161   tcatgctgca aagctcccgg gtaggcgctt ggacgccgat ggagagaggc gtggaactgg
41221   gtagtggggc gccctgcctg gctgggcact tttccttgtc tcattctcgt ctcccatgcc
41281   atgccttacc cactggctgc tagcggcgcg tttcacttaa ggtggccacg gtgcggagac
41341   tacaggagcc tgggaatccc aggggtttggg gaaaaagtag tgagcgagaa aggtggggtc
41401   ggggacctga ggaagacagc tgatggctgg gagagggagg gctcccttt cggcccgctc
41461   tacccgccaa ggagtctgaa acattctctc cctaggcgga gctgaaagga aaaacaaaca
41521   acgtattgag caatcagttc gccaacattt gagctttaaa gcgcctttgc tctgaaaata
41581   gtaccctggg ggtctcagtg gggagatggg ggaagcattt ttagggcctt gattctggct
41641   tgccgcgccc cacgggtcac ccctccgcgc gctgcctcct gacatcccgg cgctctcagc
41701   ccactgaggg gaaacccggg cggtgcagcc ctgagaaaaa gggattagt tttaagccag
41761   tctcccatcg atcgggtcgg taatttctac ccctgcccac tcgcagacac actcacctct
41821   accctaaagc attaaggtca ttacgcgagc aatgatctta atttccaggc ggaaaacgag
41881   tcccgggacc tcgccgattg gggaagcagt gaataaagtc acctgcttca ggcacccgct
41941   tggcccgctc ctcccggtgg gggccgtgtg tggcagggag cgccgagcgg gggtcctag
42001   ctccacgccg aggcggaccg ggcaggggtc agaaaccctg tgtctgtttt ctgcggggtg
42061   acgacctcct gtaagggtgg gattgctttt gcttgctttc cttctcccct ccctctgcct
42121   ttcttcctag gcctccctca catctgtcta ctctttcttc ctcctccct cccccaaagt
42181   ggcaagttcc ccttctccac ctagtgtcca gaggttctgc ccctctccta gtcccccgct
42241   gcctcagggc cgtcgcagaa gtctggtagc ccgacgcctt tttgcgccca tctacctcgc
42301   ccacctttct gggcatgggt ggggtgggga atgttcagtg aggcccttt gaagccgctt
42361   gctgagggca ccctgaggct ttaagaacc agattctcg atttagggac gatctctgcg
42421   cccattgata actccatccc aaagaaaccc agcacagcag caaacacccc cagcagtcgc
42481   ctgctcctca gccccccgcct tggcacagag cagcgtctgg cactgcgggg agatggaggc
42541   gagccacgcg cacccgttcc cttactggcc gacccgcgag gcgccagctt gttctggaga
42601   ctcagtttcc actggacaaa agcaggggaa acacaacgca agggctgtgc aaatccacgt
42661   tcccgacgcc cctccacccc atcccaatct gattttgag acgtgcattt tcaggtagtc
42721   ctaaactgtg aacagcgagc tttgtgtgtt atcgtagtggg ggtggggatg aaaggggagg
42781   agactcccac tgcccgttcc agtctttaat gtttgaaata acgaaatgcc ttgtgtagca
42841   gctgctgctt gagccaaaac taactctttg gaagacggaa aagagtgaaa ggcaaagaaa
42901   gactgttcat ttttttttctt ttggtgccgt ttgggatgtc atctgttttcc ttggcgactg
42961   tgttcagccc ccggagcccc tgggctcctg gattgttagg ggggaaaagc atgctatttc
43021   tgcaccgtca tttatcactg tcaccgcata atgattcccc ttgcagcccc ttattgatgt
43081   ttgtaattgc attatctcat aaaggaggat gatcaatgaa accgagccgt gcattctggg
43141   gtcagaggaa gccaaagtac tgtttgtccc cttaataca acaagtactc attatctta
43201   ggtctgcatt caaaaaatga tctgatctag ggctgaccct gtcggacatc ccaacactttt
43261   ctaaaacgcg gtttgtgtaa ccttttgctt aaatgctaaa tcaagtaccct gtcttgcatt
43321   tcaacgaaac aagatgctaa aactgaatga aaaaaaagca ttctttttt tttttcccc
43381   ctgggaggg tgcgatcgtc tgaaggtgca tgagatttta cactgtaact gcttggtaat
43441   ataatacaga aaaggcaatc ccaatccaca tgagtcctaa taaatagaaa aaaaattggg
43501   gatgagggga aaaaggcagg tagctgggag cttttaacaa ggtcggtact aaaagatcag
43561   aataaaacca catccagttt aattaataat agctataaac tgaaataatt ccccatgatt
43621   ctgcccttgc ttctcctttt tacagagtca tatctcttca gtttagagaa atgacttttg
43681   tggctgttcg attctcacaa caacaataac taaatcagtt gcacactgtt atctaaaacc
43741   atctacaaac tccagcaaat aaaaagaagt tcatttgtct attaaggcaa gcatttagtt
43801   gagcagaaat atcccagtaa cactgaatag agttcgtgta atcctatgga aatcaagtca
43861   tcttgttgca ctgaagtaaa tgaaaaaata caaaggagaa aaggtccaag tgtaattgta
43921   attttaaact aaatgcatta ttggactgtc acagtgaaaa cgtgattgtt cggctgcggg
43981   gggggggcg ggggcggcg agtggacata aacttagctc acatttaact taaaggtttc
44041   agaaaggaaa tatgtattcc atatttggtg atcatttgtg gaaagaggag aaattgaaac
44101   aattctaacc catcattta gtatactagg gggaatcatt cctttcaaaag cagaattaag
44161   caaaaagctt attttaaaca ttgcaagtct gtattagcag aaaaaaaaag tttcaaattt
44221   tctgaaaatg tatgtcctct ctatgttaat aagatgttga cagagagaaa gagagagaga
44281   gagagaaact aagttcaggt gttttatttt ttaagttcta gatacttcta aattaacgat
44341   ataaattaat gttttacata aaaagatcta aatgaaaagt tttcattata gttgagaaaa
44401   tgagtactta gagtgtgctc tgataatttg acacattgac ataaaacctt aaattgaata
44461   ataaaacaaa cggctaaaat attcccccctt ggaaaaataa ctttaataat aaagctagaa
44521   aagttttaac tgtgttgaac catcactttt ttctctggaa ggcagattat cctaaagagt
44581   attattttcc agaaattctg tcaaggcact ttgaaataat atatgtttgt attatttaat
44641   attctgacac ttccgttctt tgaaaatgct cagactggaa tggatacgta gccatgcata
44701   tatttaatat aaatggtatc ttgtcgttaa cataaaatat taaagagaaa ataaaacttt
44761   gggctttgtc agttaagata gaatttttta gcataactact ctgattttca aaacataaaa
44821   ttgaaacccc ttgattttaa ccaatcaaca caagtctttc tcttatttgg ttggggatct
44881   gcatcatata ctcttttctat ttttaatatt tagtgttgta gcccactgtt aaaataatga
44941   aaaattagtc tcgtttcaaa attatttatt tatggaacga acatgattaa aacataaaca
45001   cacaaactgc agctgcaaca gaaaaaaaac ttgatttatg gttattaaat ctttgatcgc
45061   catgttaatg tttctttttc tacctttcat ttgcatttta atctatcgaa tctttacagt
45121   tttgctgcct cctatttcaa tgattgatta cagatctgaa ataagaaaaa ccaagcctag
45181   cttttctttt cctttcttcg ctttctttt tctctttttc ttttccccccc ctccctttcc
45241   ccccgggtag atttctgaaa ctttctctca atgctaatgt agacaggaca aattaattct
45301   gctctttaa atgtcaaaga tataaataaa aaatgtttc tgtcccaaac gtgaatattt
45361   tcccagctgc ttgttttcga gtcgtaaaag atcatcccag caaaatgcaa ttaacagcga
45421   aacacacaca catacactca cacactcggc ggtgcggaat tttttaaag gacgtgttgt
```

-continued

```
45481  tctgagttga agaaaggtga gaagttcacc gtcccttcac catcagtagc ctcgctgcgg
45541  ctctcctctc tctctctctc tctctctctc tcacacacac acacacacac acacacttgg
45601  aggtttggtc cctagttcta tctgtgatct aagtcacaca aacaaaaaca agcttggtgg
45661  cagcttgttg ttgttgagtg ttgttgagtt gatttcttga gataagcagt gtaaagacaa
45721  aaggggggagc gatgcaggtc tgtttgtttt ctttccccgc cgccccactg tcccttttct
45781  cgtctccccg cgcacctccc cagacgccct gccggggtgg ctccgcggat gaggcggtca
45841  tttgctgtcc gctttgcggg gacgggtcac tttccgcgct ggcgtgaaag caaatgtgga
45901  gctgcttttg gaaggcgccg gccggacgtc ggctaggctc cttctccccg cgggctgggg
45961  gccctggggc tctgcaaggc tctggctccg aacagattgc gcctcccgcc tggctgccag
46021  taggaactgg ggtgggagcc gcgtaactaa cagttgcgcg caggaggcga gccccaggtg
46081  tgagcgcaga ggctctctcc ccagcccgcg ggtctgggaa cctttcagga cgcctccctc
46141  cccaactcct acccatgcgt ctgctcccta ggccgagccc ccctcgtgag gttttaatga
46201  ccgcgacgc aggggagccc gcacttgagc gaggaccgac ttctctggcg ggtccacgct
46261  gctcgcgctt gcgtccgcgg gtagcgcgct gtgcccgggt caggggggcga gctgcgagaa
46321  gtaggagggg tcaagacccc cagaaatccc tccatgggca cacacacaat caagaatagg
46381  gttgagggtc ttgagaggta gaactacccc aggcagggct tctccaactc ggccttgga
46441  ccccgcgcgc gcccaagggc gtgcccaccg cggaagcaca gatcatcttc ccgggactgg
46501  gtctcctgga ccctgcgttg ctccctttt cctagcgcc ccgtagctgg ctgccgcatg
46561  tagggcgatc ttcattaact tggacgccca acgtgattga aatagagagg aggaaaaaac
46621  acatttgatc tgggccgacc ctttgtcttg aagcagatta ggcagcctag aaataggagg
46681  aaaaacagaa agtctaggca ggaaaactta ttgtgttcac aacatataaa aatgatccga
46741  gcggtctggt acctcaaggg gtgaagatag atccttgtag acgagtgtga agacatgact
46801  gggaagattt aaagtgaaag aaacggcaga ttattaagaa agtaatagta aggtgtccca
46861  tacactacag ttttattgtt gggtagtaac tacccgattt atttattgcc ggggctatat
46921  aatagagata atgaccacaa actcaagata aattcctatg cgcccagccg gtcaattctt
46981  ttttatttaa gagagtgagc ctgaagggtg agcctcatcc cctcccctcc tcgaagatcc
47041  gtcttgcttt ctaccatatt ataagcatga catgcaaata aataagtgct gctgggtctg
47101  tgtgggtagg ccggcaggat ttatttcagg tgacggagga acatacacgg aatatgaatt
47161  tccgcaggag tggcgccgtg attccttccc tctcccctctc ggccgccctc tcctcagggt
47221  ctccctcctt ttctgtggga gcagagagca tccctgtta aaaacattaa cgtgtcatgt
47281  ctcagctccc tattccttga catataggtc tggggaggga tgggggcact gcaaaatgca
47341  aaacgcatgc ccaaagtagg ttgacttgct gggactgctc aaagcgattc tggtggacaa
47401  agagaagggt gagttgtaat tatgacttcc agtaggggag cagtatagga agtatgttaa
47461  tatcattttg aaatatgcac aatggtccaa aagtttactg tcccggatct ggcatgggtc
47521  ctccccagcc ggatggaccc caaggggagc cctcctggca ccttgggaca tgcccgcctc
47581  tcttggccct cggtttctct ctctgggagc caggtaaaca ccccccctggc caggtgatgg
47641  agttaaagat gaccttgctc gttgaccgcc aaggtcggaa gagagctggc ggcctcaggt
47701  gtaggttcca cctgacgccc tggctgcaat catagtcacc ggctggcctt taaggggggcg
47761  gcctcccaga actgctctcc ccacctgcac tctgcgacca ctcaggcaga tccggaacct
47821  gccaagacga agtcagtcag catcctcttc cgatctctctt attttcttcc tcattttttg
47881  gataatattc agacatacag tgtttcagtc tcacaataac cacttacatg cagaacttcc
47941  tttgatctgt ttggccagag tcgggggggaa acacctgaca gtgaagaact gcgatgaaaa
48001  agaggggttc aggggagatg ggagagccag acgcgtgggg cgagggagaa ggaggtgcgt
48061  gtgggagat ggagacctag agacagcaag aagtagcaga tgggggagga aggtaaggcg
48121  agaaagtgaa gagcagctgc gagcgggaag agaaggggct gctcctgtaa tttggtggtt
48181  tgtgtgaagg atggtattat gaggctgaaa gagaggacaa tcctcgtcaa tcttttacaa
48241  tattggtgtc attcaagcac aactttatct ttgaaccaga ttatctgttc caatgatttc
48301  cataagaaca taaattataa ccttcagagc cttcaatatt tctttcggta ctttattaag
48361  tgttgttgca gaggctattt atgaagtgag tgattcaact tttaatcttt tgaacattaa
48421  agtgtattcc tccgagtttc cttttcaaaa taatctaaaa taacaaaaag aaactaagct
48481  cattacatga aaaagtgaca agcgttttg ctcgcagcct ggcaagttgc cttattcact
48541  tcaaaggatg atgaactaat tgtttccaga gtttataagt aattaagcta ttatttgggg
48601  aatttatgta acagttttat tcacattaga actttctatt taaaatagcc tgagacaaat
48661  cttcaaaaat gccaagattt taataattga aaagccttct cattattgtt aatagtgaaa
48721  actatttta ttttaaaaag cactggaaaa tgtaaacaaa tatagttttc tccagagtat
48781  atgataagtg gagatcatta tggataatta acgctgaaag gaaaatgaac atgtaatggc
48841  ttccaaaaat taaaacattt gtaactatca agttaagttc taaaaagtta atttttaaat
48901  cagctggatt tatctaaata tgcctgcaa ggaaaaagat atatatatat atatatatat
48961  atatatatat atatatatat atatatatat ctatttactg tccttttaga actctataaa
49021  gaaagtttaa aaccttaaat aattttagca tttttaaacc aactttggt gcctaggcaa
49081  taagagttaa tgcccagaaa tgctaagtgc tgtagtttct ccaattttgc aacaaagaaa
49141  tatatttatt caccctaga ttaaataaa gaaaatattc taaaatctt ttgaatata
49201  taattcaaac accacttcca taatattca atgcatgttt gttagtttta aataattagg
49261  tttgccataa atgaaacaaa attcattaaa ggaaaaagta ggacttaaa aggagtgatg
49321  aattattttg taaaattcag caaaatatac aacacttag tttaataggc atttgtatac
49381  ataacaatat accattttaa tataattttc ccatcaaggt ggtattagct ctgtgtgtta
49441  gaaaatgcct gtttcattgt cacatgaaga attttcaaaaa taataaaatt ttcatattag
49501  gaggaaatat ctttgaagaa taacaaacac aaatgtgaaa atccaagtaa atgcctataa
49561  aatcttatat gaggtaaaat atattttctg gaagttatct ggaaaaaatt aaagcatgtg
49621  gtagttcaat attaattccc ctcaccacaa aaaaattggg agttgtctgt agcaattatt
49681  acagaggta gaatatatgt attaataga aaaaaaaatt taggacatat ccacttgttt
49741  caagtaaaat tcctctaaaa caaagtctg gaatttgatg gaaattgtat ataaaatgct
49801  ttgtataatt catggtcagt gttgttttgt ggactctgta taaactgtgg caatttagat
49861  ctgtcatggt atcacaatgt ctgattcaat atttgctgta atatgttctc tttattagta
49921  cagactagca ttgcattatt aaaaacaaaa actaaagcac cctggttagt agtaatgcaa
49981  tcccaatggt ctaacacccct gcgataattg accttctgga caccagacac tgggattcac
50041  tttcagacac ttagctgttt aaactgactt cattacagga ggacaatggt gactctgttg
50101  caactgacac ctgcactatt tcacacaacg catgggccat accttgccaa gtcagccacc
50161  accatgattc gcaccagagc aggaagtcag ctcgagacaa attttataat atgaatatac
```

-continued

```
50221  tgttacgatt aaggagaaat gaattcgttt tgcatagccc tctacaatct taaggagaca
50281  attagaagcc tgttttctgg tttccttgtg ttacaatatt gccatatgca aagatgtttc
50341  cattacttta cgctgaagtt taaaagttaa ggattttatg gtacacagca ttcaaggtgt
50401  ccatagtaat acagcatata gatagaaaaa tactgttgtg ggaggctgag gcaggagaat
50461  ggcatgaacc cgggagacgg agcttgcagt gagccgagat ggcgccactg cactccagcc
50521  tgggcgacag agcaagactc cgtctcaaaa aagaaaaag aaaaatacag ttgtatcaca
50581  cctatgtcct agttgaaaag agtccattag tggaaaggtt tgggggggcgg aggtggttag
50641  ctcactgacc agacttgcag gcactctgat tagttatcct aaatgaattg ctagaacata
50701  tgcaattcat tctccatgga tctttctcct aatctctaaa taataataat atatttcttt
50761  tttataaatc attttgtgtt gcagaatatg gtaaagcatt gttttaaatt atattgacta
50821  aaataaaatc tcagagggtt ctagatttt tctgaactca tagagagttc tagatgtgag
50881  ttctagattt ttttctgact cataagggaa tattactctg tcctcaaagt tctaagcatc
50941  tcagaattct gagatacttt ccttgctct tctctggcca ccagaaggaa agtgacagtg
51001  ccttattgtt ccaagtatt tgctgaaggt aattaatacc tttattgatt aagttgcttc
51061  actgaaataa aaggtgactt ttccaccaat gactagattg tgatctaaca gactgaaaaa
51121  taacatgcca tattccaaag agagaagccc agcttctaag gcagaactcc atccctcccc
51181  agcttgtaaa aatccacaga tttactagtt tttatttaaa ttttgtgtta tgctaggctg
51241  gatcttgtct taaatccttg aacatttcta gcatattcca tcaaatgctt tgtaagactg
51301  aaaaaattct ctgtatgtgg gctttagaat cttaagcagt cagcaggaca ctgtagatac
51361  tgaaattaac aggacgttgt ctgtgtcctc aagagctcat cttagggtag agctgataaa
51421  caccccacaa tccaaatcca tagcagtata cacaggtgct gtgcgaatac aaaagttaaa
51481  ccaagaaaat ggaagaaggg agccccccaaa agtctttgtc gtgggctaag gtgagggga
51541  gtagagatca gggtatgttt ttaaatcaga gtttaaacaa gtaaacagaa accactctga
51601  gtgtatacaa gggaaggaat cgaatgcagg aaattggtta cacagggtat aggagaggct
51661  gcaaagccca ccagctggca gcaaggcaac cttgaggcag gaaatagcag gaaactctaa
51721  ccactcctag actggaggga cagagggcgc aggtgagtca ccagactcca ggggttggga
51781  ctacttggta gaagatgtaa ccggggaagg catgtccagt gggagctgga gctatggaag
51841  gaataaggga gggatacata ttctgagtc ctgcaatcta gagcagagca aggaagggcg
51901  aagaatagct ttgaaaggag acagttccag gagtggccatt tcttattata ttttttcaaa
51961  tgaaaatctt tcatattcat ttctgaagat actcatttga gaatgctgga gaaggaagag
52021  aagaatgttc caggcaaggg tactgaattg gaaaagaaag tgacttattt agaaagtcac
52081  aagtttgcca gtgcagcccg agtaaagagg aagatgtggg acattgtagg acatgagttg
52141  aagattctaa cagccaaaga catgaaatga ccagtggctt ctgtaacagc tttacttgct
52201  ctcaatcatt aagcccccaga ggcccggata atagagacta caggggttaa cattgcaaaa
52261  cgctgcaaaa atagagacat gggtctccat acaggtgcaa tgctgcccac caacaaatgg
52321  catttctatg aagaaataca gtcatcatcc tgggctgcct tcagttaact tacattgtta
52381  tctgattcag ccacaaagcc agtgggacat cgattcgtc attttaatga acaaattaga
52441  tattgctcac taacccaaag gaaccatcct tgtggccagt ttggtgttca gagggctaga
52501  taaaaggttt tgtctactcc caggtaatag gaatagctca gtccatgacc tcacaggtgt
52561  cagtctcatg aataatagtt tgaagtagag ccagggagct aagaaaccag tgaaaacact
52621  attgtgatga tggtggggat gggaggtaag cgtgatgatt accagaagat attaggtgat
52681  agaagcacag aggagggga tgagatattg agaaccatgg catgttttct ggtttggaaa
52741  attctgcaga ttgtggttcc atttgctgga aagataacct tagaagaagg aacatattag
52801  aaaggaggat gttaaacttg ttttaggtat tttgagatta agatactttt gatttatcaa
52861  gatagagatg ctcattagga caatgaaaat atgggtctgc gttttagtgg agggagtctg
52921  ggctggagat aaaaatttgg gaggagtcat tggagtagat gagatcattc acaatctctt
52981  tcaagtggtt tatggtgaaa gaaaagaaag gaacaggccg tcagtaataa aggggaacaa
53041  ggatatata ttttgaagat gggaaagact tgaacatatt tgtataatga agggaaggaa
53101  gaggatatgc tgatattaca agaaagagtg ttaaataatg gagaaatcca tcatccagtt
53161  ggggaatgga ggaacggagc tattcctcag caggggaaga gcctggcctt caaggtcgaa
53221  ggcaggtaat gggtagagtt gtatgtccag gtcaggggta gtggaggaag aatttggtag
53281  cagttcatac ttaaaaactt acgccttttt ttttttttga gatatgggta gagatgtcat
53341  ttgatgagtg aggaagtagg aggtgacca ggttgtagca cttaaaggcc ttcccccag
53401  gaacccttc agtcctggac aagctgagaa atttggtcac cccaaagagt aaggaaagg
53461  gaaaggcttg agataaatgt gaaacattaa cagtcatcac aggaagtggg agagggagct
53521  gaccagaaat gcgaagctta ctggctggta tcgagaactt acatggaatt ggagattaag
53581  gggcaaggtt ttgtgcacgg ctgtggggtt ttcttcagca acacctaagc atactgagtt
53641  atcattccag gagagagtgt gttcatgcat ccaggtgtgt gtttgaagta ctttttagaa
53701  cccaaagta tgtagtatca gagttctcgt tctgggaaca ggaaaacaga gtgaaattag
53761  cagcaaggtt gccagaaccc tgttaggtag aagatcattc tgtcaacgat gtacatcact
53821  cttgcttcat gtttgcagtc gacaaatggc agttttcaca atccacaata tcttgaggta
53881  ccctgccat gcgggcatgt attcataata cctcttctct ctggaagggt aatttagaca
53941  ctgcagtcat taagcagtgt cttgaggtaa aaagcacccca catgcctgtg ggtgaacatt
54001  atctgttacc ccagctcatc cacaaggcgt gtcatgaaa tatttgcct gtgtcattga
54061  ctaagttatg taccttata ctggtaggaa tttcacctgt tgttggttat atgaacaaag
54121  aaaaatgtaa atatgtgatt gtctggctgg tcatagggca aatggggcaa tgagctccca
54181  taagtagatt caagtaaata tctggagttt tgactttct ttttgcagca catgcagttg
54241  gatagctccc aaatagatga agggttgttt tctctggttt gtgccctata tctaggacaa
54301  accagtacct ctaagtttcc aatacaggac agacaataag ccacaaaggg gaccaaacta
54361  catgatgaaa atctgaaact aagcttgggt tgaggaaggt actcaaatct tgtctgaaat
54421  ttgatgcagc ttggctcaaa acttccagg aattggctga ggctttagac aatagactga
54481  atggtgttcc tcaaaattca tgtgttgaag tcctatccca gtacctcaga atatgactgt
54541  gtttggagac agggtcttta aagaagtaac tgaggttaaa tgaggtaata cgtgtgggcc
54601  ctaacccaat ctaaccggtg tctttatagg agaggaagtt tagacataaa aagaggcact
54661  agggatgctg gagcacagag gaagcaccct gtaaggacac agtgagaaaa cagccaactg
54721  caagccagga agcaaggccc cagaagaaag ctaaccccacc catacctgc atattagtcc
54781  attttcacgc tgctgataaa gacatacccca agctgggta atttataaag aaaatgaggt
54841  ttaatggact cagagttcca cgtggctggg gaggccttac aatcatggct gaaggtgaaa
54901  ggcacatctt gcatggtgga agacaagaga taaatgagag ccaaacaaaa gggggaaaccc
```

-continued

```
54961   cttataaaat catcagatct catgagactt attcactacc acgaggacag tatgggggaa
55021   accgtcccca tgattcaatt atctcccacc aggtcccttc tacaacacat gggaattatg
55081   ggacctacga ttcaagatga gatttgggtg gggacacagc aaaaccatat caccttgatt
55141   tcagacttca agcctccaga atgcaagaac ataaatttt gttaagtcac caggtctgtg
55201   gtatttttgct atggcaaccc tcgtgaagca atacagggag gtttagagtt tgaattctca
55261   acaacttcag aaattgtgga tgcatcaatt attttttaac gtgaaaatga atctaggaga
55321   tatctactga gaaactctgt ttttacctca actttatta tcaaatattt accaaacatt
55381   tttgtagcac ttagcaggag aggtgccttc attattcttt tcagctctta aacctttctt
55441   actctccttc acctcgtcct gcatgtctat aagcgcgaac tctattgaag tcattttaaa
55501   aatacactat ttttcaaatg acaatactgc atttttttc ttttttcttt ttcttttctt
55561   ttttttttt tgagacggaa tcttgctctg ttgccaggct ggagtacagt ggcgccatct
55621   cggctcactg caagctccgc ttcccaggtt caagtgattc tcctgcctca gcctctcgag
55681   caactgggac tacaggcgca caacaccaca ccaagctaat ttttgtattt ttagtagata
55741   cggggtttca ctatgttggc caggatggtc tcaatctctt gacctcgtga tccacctgcc
55801   ttgcctccc aaagtgctag gattacaggt atgagccact acacccagcc gacaatactc
55861   catttttaac gaagtttagt tatggagtct gtaggcaggg ttttcattat gtttagtagg
55921   aattaagcct gtatgtgagc ataagctat agtcaataat tttacccct ttatgactgt
55981   aaaatttggg ccagtcaccc tacctggtta attctctgca gtatttaagg tatctatctc
56041   aagttgattc taaggttagg cacttttaat taaaaatgca tttctaaaat actttagaac
56101   atttagaaat gtcagcatga cgatgttgac aggggaatct ccatggcatt aagttgtgtg
56161   tttctgtgtt gagagcagat gctactaaaa gtatcgcaga agcgcaaaaa catctgacat
56221   tgcccggtga gcctatttgt agctgttggc ttagaataat ctatactgac ctgtaaggtc
56281   cgcttagta acaataacag gtaatgtact gaacctgcta taagcaaaag gatgttcatt
56341   aaatgtttgc ctttggtgaa ttttcctggt cattgttctt ggaaataata cggaggactg
56401   gaaattggga aattttataa actaatccta gtgttcccag gctgggcgca gcagctcaag
56461   cctgtaaacc cagcactttg ggaggccgag gcaggcggat cacgaggtca ggagatcgag
56521   accatcctgg ctaacacggc gaaacccgcgt ctctactaaa aatacaaaaa aattagccag
56581   gcgtggtggt gggcacctgt agtcccagct gctggggagg ctgaggcagg agaatggtgt
56641   gaacctggga ggcggagctt gcagtgagcc gagatcgtgc cactgcactc cagcctgggt
56701   gacagagcaa gactccgtct cgaaaaaaaa ataaaaaat aaaaaataa atccagtgt
56761   tcctatttac ttattgtgtg gttttggtaa agtcaatcat agtgaacatc agtttgttca
56821   cctgtaaaat gggggaagatt ctatctttga atgctacttt aaaggtgtta tgagaagaat
56881   attaaaagac caacgtgtat gtggtgcttt taaaacatgc tatccaaatt taaatattat
56941   attgttattg taattgccat taaatggttt aatttagcaa cactttgaaa tggctttctc
57001   caattctaat tgaagtagca acttgggatc ccttcagtga tgaaaatcat agcaaacaca
57061   atctcttatt gatcaggttt cccagaaaga ccctccggttc caccatattt cagggagtat
57121   ctactggagc ttggtcaaca tcaactttg ttttagtct tacattagac aatgctgttt
57181   ttctacaaat gtccccaata ttactttttt aaaactcagt tgaagatgta aatgttatct
57241   cagatgaaaa actttcagaa cctaatgtca agttgcatgc gggaatgtgt catctcaaag
57301   tgttgtgaga aaggctcttt cccctagggt ctctgattct atccatgctg tacaacacca
57361   gtctccaacc cctgggccac ggaccttac ttgtctgtgg ctgttaggaa ccagggcacc
57421   cagcaggagg tgagccacgg gcaagtgagt gaaccagtaa atcttcatct gtatttacag
57481   tccctcccca tcacttgcat tactgcctaa gctctgcctc ctgtcagatc aactgtggca
57541   ttagattctc acagaagcat gaacccatt gtgaactgtg catgtgaggg atctaggctg
57601   tgcactcctt atgagaatct aatgcctggt gatctgttac tgtctcccat catcccaga
57661   taggaccatc tagttgcagg aaaacaagcg cagggctccc actaattcta cattatggta
57721   ggttgtataa ttatttcatt atatattaca atgtaataat actaatagaa atgaagtgca
57781   caataaatgt aatgcacttg aattatccga aaattatccc tccacatcat gcgagtccat
57841   gggaaaattg tcttatatga aactggttcc tggtgccaaa aaggttggag actgctgccg
57901   tactacattt attttgaatag attaatgaat ataagcctta tcactatgtt ttgttttttt
57961   ttttttgag acagagtctc ttgcccatgt cacccaggct ggagtgcaat agcacaatta
58021   cgactcactg caacctctga ctcctgggtt caagcaattc tcctgtctca gcttcccaag
58081   tagctgggat tataggagcg agccaccaca ccagctaatt tttttttggt attttagta
58141   gagatggggt tttaccatgt tggccaggct ggtcttgaac tcctgacctc aggcgatctg
58201   cccacctcgg cctcccaaag tgctgggatt acaggcatga gccaccacgt ccaggctatg
58261   tattaacaaa gtgcattaag catgttgctg tcacttcctg tgttgagaca taggtaaatg
58321   ttcattaaat atgaaataat tcccataaaa tgctgctttt gaaacccaaat tataatttgg
58381   gcaatgatcc aaaccatctg gagtctttgt catggatctc aggagtgtgg gcaaactaga
58441   gtacatgtgt atgtgtgtgg aagtgtgggt taggggggagt tgtcattgct gggattggag
58501   gcttggcata gatttagagg agtttaacat ttgaaaaccc ctctattatg gaaagttttc
58561   aaatgtacac aaaagtcaag agactggtat aacagacttc catgtattca tcactctact
58621   tcaagaatta caatgatcaa cattttgcat ttgcattttg gtccttttt tttttattt
58681   ttgagatgga gtctcactct gtcactcagg ctgagggca gtggcgcgat cctggctcac
58741   tgaaaactct gcctcccagg atcaagcaat tctcctcctg cctcagtctc ttgagttgct
58801   gggatcacag gtgcgcacca ccacccctggg ctaagttttg tgttttagt agagatggga
58861   tttcaccatg ttggccaggc tggtcttgaa ctcctgacct caagtgatcc acctgcctcg
58921   ggctcccaaa gtgctaggat tgcaggtgtg agccactgtg ccaggcctga cattttggta
58981   cttttgtttc atgtattccc tccctccct aagtctgtca cacacactct ctctctcgct
59041   cgctctctct cttcctccac ttgctctaat attttaaatc aatcaaacac tagatatcag
59101   tttatctcac ttttaaatat ttcagaatgc atatttacat agtagtgatt ttgttttgtt
59161   ttaatttaaa aaataacttt ttcattttga tgtaattta aacttataga gaaattgcaa
59221   gaatagtaca agaaactcct gtaatccttt aattcttac tcagatatca ctaattgtat
59281   acatcttaat tttccttat cactctgttt ttcatataat tgatatactt tgtttctga
59341   atcatttgaa ggtaagttgg tgacaatata tatattcttt ttttttttt ttttttgaga
59401   tggagtctca ctctatcacc cgagctggag tgctgtggtg tgatcttggc tcgctgcaac
59461   ctctgcctcc caggttcaag cgattctcct gcctcagcct cctaagtagc tgggattaca
59521   gctgtgtacc aacacgccca gctattattt tattttatt tattttatttt tattttattt
59581   tattttgta ttttagtag agatggggtt tcaccgtgtt ggcggggctg atctcgaact
59641   cctgaccctg tgatctgccc acctggcct cccaaagtgt tgggattaca ggcttgagcc
```

```
59701  accgcaccta gcctaacatt atactctttt actattaaat cagtatgtat gttctatgaa
59761  caaagaaatg ttgttatata accacaggat aactatgaaa atcaggaaac ttaatatcaa
59821  tacaatacta ttatctaatc cccagcccat atttaaatgt tatcaattgc cacaataata
59881  tccttatat cattttacc cctaatccaa agtctactcc aggattgtac attacttctt
59941  gtcacgtctc tttagtttcc tttaatctgg aacaagctgt tcctcagcct ttttggttt
60001  ttgttgacct tgacatttt gaagagtaca gaccagttgt tctgtggaat gtcccttagt
60061  tgggggtttgt ttgatattc cttttgattg gatttaggtt atgctttgtt ggcaggagca
60121  ctgcagaagg gatgttgtgc cttcagtaca cagtatcagc tggcacataa tgtccgtttg
60181  tctcagcaat ggtgacattt actttaatta ttttgatcac aagttactgt ctgccaaata
60241  agagttattt tgagattatt atagaaatat tctgttctgc atcaaacgtt ggtccattag
60301  tgttaacacc cattgatgat tctctaactc cattatttta atatatttat cagttggcat
60361  tctattgtaa ggaagcattt tgcctttc caactttatt tattcatgca cttttttct
60421  attaaaatgg gctaatggat tctttattt aatgggttat gatttattac tatattattt
60481  atttttgat gctttttt tcttttaga tttggtcaat ggaaaccact ccaagttacc
60541  tcctgtgtct tttcgatgtc ctaaaagagg cttaactttg taccttccat gttgaaatgg
60601  agactgagct cagctctcct attcactgc taagtttcca gttacaatag actttctatc
60661  caaatccttc cttttttt ttttttta aagtacatcc ttggagtgag tcagtgtggt
60721  tagttgagta gcaggaaaag atttaactgt tctcatgtag gggaaagccc agttgatagt
60781  ctcttttggc ccctcatggc cgctatcacg agaaacattc cccactaaaa agtcaagcaa
60841  caggcttcct aatttctggc ttctgtctga aacaggcttt ttgagccagt taattgaaca
60901  taaattacaa ctgacctgg agggattaac ttgcatttg gggtcatctc agctgcatag
60961  ctatttgggt gctttctgac tgctgtgct tttatatact tttcagctaa gttagagatg
61021  aaaatgtacc actcagtgac attacaggaa ttgttgacct tctctggtca gtttgaggtc
61081  aaggaattaa tgcagagaat taccagaaga tctataaata cacgttctt acatgagagg
61141  tatcattaaa aaatgatgtt cattttactt aactgtttca gatccatgtg tagtatgtga
61201  atagcagtca tataaaggga actctagttt tggggaacaa taaaataaga tttaaattaa
61261  acgtttaaaa aactacacta gcagtaggtt tcctaaaatt cccttgtgac tgagccattt
61321  taatgttaaa aataggatga taaaccccata ttcaaaagaa gaattattgt tcatgtcaaa
61381  ggctaaaaac attcttttga ggtcaagtca gtcctgaaag taatcagtgt ggcccatgtc
61441  ttatgttttg ctctgcctct ttggtatatc aagaggttga attagaaatt ggtatgccag
61501  cttctccttg atgaatgagt gggaagagca tgaccttcag aaacacagac ctgggaccaa
61561  ataacactac tgacattgat tagttctcca tcttttggcaa gttctttat cattctaagt
61621  gtctgttttc tatctatgaa gaaaatgtct cagtctgtgc cactataaca aaaataccca
61681  agactaggca attaataaga ataggaattt attccatacc attctggagg ctgggaagtc
61741  caagatcaag gcaccagtag agtctgtgtt tgtgacaact gctgtctgct tccaagacgg
61801  taccttgttg ctgcatcctc atatggcaga agaggcagtc tgtgtgtcct cacatggcag
61861  aaaagcagaa ggacaaaaaa gggcctacct agttccccca gtccttctaa aaggtcatta
61921  atttcattca taagggctct cttctcatga cttaatcact tccaacacct cacatttaa
61981  tgctgttgct ttggggggatt aaattttaag atgaggctgg gcgcggtggc tcatgcctgc
62041  ctgtaatccc agcactttgg gaggccaagg cgggtggatc gcctgaggtc aggagtttga
62101  gaccagcctg gccaacatgg tgaaaccctg tctctattaa aaacacaaaa attagccaga
62161  tgtgctggca ggtgcctgta atcccagcta ctcgggaggc tgaggtagga gaattgcttg
62221  attcgggagg cagaggttgc agtgagccga gaatgtgcca ttgcactcca gcctgcgtga
62281  caagagtgag acttcatctc aaaaaacccc agaaaaacaa aaaaacaaaa tttaagatgg
62341  attttagagg agacacaaat gccaagccat agcaaactca acatgtgca gggttagtgc
62401  aaggaatgaa agctatataa aacttttata ccaagtataa tgccaacaca gaggcataga
62461  ggaggctctc catgattgtg atttctcttt tttccacc ctttcttcta atagcataac
62521  aatcaccacc atttattaat tgcttaaaac atgccagaat ctgatttgag tgctttacat
62581  gcatgatttg tgagagagga actattatct tcaatttgca gatgagaaaa ccaagattta
62641  gacatgttaa ggaccccttga ccaaatgttg gtgctgggt tttacattg atgccagagt
62701  ccagcccctt aatcatcatg ctctcctgcc tctcataact atgctctttt taaaccatac
62761  actttctcta aatttgaagt agtaactcac gggtttacaa atactattg agtggggtgca
62821  gttgagagtc ctaaggtgtg gcaagggaga cttaaaaacc tgaactagaa gcagaaataa
62881  ttaagagtgc aggagaaaag acaggggaaag gtcagagata aacttatcag gtaaacaggg
62941  gctgaatacc actctctgtg tctctggagc ctttgattgc ttacttgaag ttagagatta
63001  aaaatataca tgattatcct acatgtttat ctatgtaaca aacatgcaca tcctgcatat
63061  gtatcccaga actaaaaata aaaattaaaa gaaagaaaat gataaaaata cacatgatta
63121  gtcctaatat taggtaggtg caaaagtaat tgtggtttt gccattaaaa gtaatgctac
63181  tatttagcta ctgttcttg aacatgtata catccggcat tatgtgcttt atgggattgt
63241  cactttaaag ttacaggagc cctatgaggc atatttcccc cttgttctta gagtacgcct
63301  tgaaaaatat ttcacacccc agtcatttaa gcatttctgt agcagaggct gcttgttgtc
63361  taccccaaca ttgactttcc cttccttctt aagaagggaa cctgagtttt agtcaggccc
63421  cttgccaggc agaattcgag ataattccca gcctctcctg cagctaagtg tggacatgtc
63481  tgaactctgg ccaagcagat agaaacagaa gtgctctgtg gggtctgggg aaagctgttt
63541  aaaaggagtg gactctgctt gggggaaacc cctttgctct tcttttttg aactttatt
63601  ttaggttgg ggatacatgt gaaggttat tatgcagtta aactcatgtc aggggggtt
63661  tgctgtacag attatttctt cacttgggta ttaagcccag tacccaatag ttatattttc
63721  tcctcctctc cctcctccca aactccattc tcaagtagac cccagtgtct gttgtttctc
63781  ttgcccttct ttttatttct acttgttagg tagcaattgg aatgttacag ctaagttta
63841  gcaactatcc taaaccatcg agtggcattg acgatagaaa ccacctggta agatggcaga
63901  gcagaaagag agaagactag gttactgatg acatcttaaa gttgcttttac cagtcctggg
63961  ctgcctccct ctagttttac acagaaggga aacttaattt cttctttcct tcttctac
64021  ctcccttcgt tcctctctcc tctcccttcc ttcctccat tccttccttc cttcctctct
64081  tcttccttcc cttccaccct ctccttgctc ttttccttcc tctctcccct tccttcctcc
64141  ctctctcttt atttctgttt gccactgtta gcttgctttt ttctcttata tataaccaag
64201  taattctaat tacagcttcc aaatatatgc ctagctcctt gtgggcatat cttgatatat
64261  tgggaaagcc tgtaaagctc tgaggttact ggttcaacct ttagttgaat acacttaact
64321  tacaaaatat taagctatca tggaaatacc cacagttgaa tattttgggc ctttatgtcc
64381  tttaacatct ttttgggcta cagcactttt agcagttaga atatattgac agcaaactca
```

-continued

```
64441   cagtgtttcc tccatttaat tcaaagaaag atgcatttgg aagaaaatta aagtcttgct
64501   gctctaaact attcctataa agtccatcag agactgcaca tcgttcaagg tcatgctgca
64561   aacagattcg gaatgggcaa gatgcttttg tgatgaaagt tattgcatca aacaaaactc
64621   aaaatttatt ccaggtggga tccaccaccc ctcccatgc tatcttaaca tcaaacacaa
64681   aactgacaca aaacaattct gtcctcctga tatactgaac tttgggcaca agtagagggt
64741   gcattacaaa gacatggttt catacttgag tacatgtgtt ggggaaaaag ttttccactt
64801   aaatgtgatc catttaagga tagctaaata tatgctctcc tgcttattat atttacaatc
64861   atttttatct cagcaaaaga tgctgttatg gtgaaaatat attacacatg tcctttgctg
64921   actgagagag ttaaaatgaa tagaacaata aagaaaaaaa gaagaagaaa aaaggaagaa
64981   atcctaaact ttattgccaa agccttacaa agacaaatat gggcagaaca tatatttaga
65041   gaccttggca aaagaaaatg gaaatatgag caattagctg aatatattta gccaaaaatg
65101   gttgagaata tttattctct tttaaaatct taattgtcca tcccgtcgta ggctagattg
65161   actgaatttt ctggacaaag tcataaagtt tccttaactt tgtgggaaca tgggttgtaa
65221   ctactcagta accactacca gtgactattt gttaaaaata caccatttgc aagacattgc
65281   attagctttg tggtcataaa tgtattgtcc tatgagttaa atgaagattg ttaatggact
65341   cataggatca tacaatctca gtatttttcag gaaatttaga tatatctatt tcaatcctt
65401   aaatccctcc cccagcacca ttttaaagat gaggaaactg aggccctaga gacttttcaa
65461   aatctcacaa cttgtacata aactccactt gtaaaataat ggtgttttgt acttttact
65521   agtttttctaa agtggcccag tggagaaaag gaagcttttg ttcattactt tgaatttgtt
65581   tctagttatg tttggtatca tgcttttctt ctggaaagat ttatcaataa gaagattata
65641   agatcaaaac cttccaaggg tgagttacct taaccttgtt gaaaattatt gatattagat
65701   attattacct ataagagaca tggactatga gaaaagactt cttttatttt cagtgatagt
65761   acactaagcc ttgtagcaaa acagaaatag taaactgcat attgattcca aagcaaatca
65821   agttaagtat cttctatgga catatagtca gataataaaa ctcaagaaaa taatgtatgt
65881   tcttctctgt tttccactaa actagggaat ctccttaaa ctttgtatgc agtatggaaa
65941   taaggtttct gaagtaacca ttacaacatg tttcatgag tgtttattaa gaagcccaa
66001   acattttca gtaataaatc ggctgacata tccatagatt taaatctttt attggttact
66061   gattaacata actgctctgc ctgacaaatc tttataataa ataagccaac cagtgagcat
66121   ttcacaatga aaccaacttt gtttaaagga ctatcactaa aacaggattt atgcgctaat
66181   gaatttttgca atcagcatgt ggtggtgtac aagtttcaac atgaatctaa aatgcagaaa
66241   tctgaagaca ctgaagttat taaaaatcac accacaacac aactacttt aattaaaaag
66301   aaatatatata cattcgtatt tagcagcagc attatagcgt atgaaaagga gaactcaggg
66361   ttactctttg aacatattct aacaaaatac agctgttgct gctatacagg ttaatgattc
66421   cttctcaaaa taaaattcct tgctatagtg attctgattt ttaaaaaaat caaataagg
66481   aacaatgttt tttgtataca cataagccaa gtaaatagac aagtgatcc atgatggtga
66541   ttcagtaaaa taaaagttgc tgatggatat atatatatat atacatatat atatatatat
66601   actttcagtt tgattgaatt cttcttggaa agccactaga agtcactgga cttcttgtct
66661   ctgtttgaat taattaaatt gttgacagtg aaattgtcaa aagtagcttt ggtataaaaa
66721   atgattccca gatctttttc tctaaaactt aaaaaaaaat cctgacaaac ttgaaaaagt
66781   ttaaacatc tgtctggaca gatgtcaaaa tgctgagtgt tataccatta tactgtgtca
66841   gtatctgaca ctatgttatt actcttcagt taaatattca cagtgagatt ttatgatctt
66901   tttaaaagaa aactgcatg agagagtaac tttatcttgc acaacacata agcactttaa
66961   acaaatgaat ttcagagtaa acaatgaaaa ataactttt gtgctagttt ttataccata
67021   ttttaatcac ttgggatttt cacatcagga ttttacaaat cattcaacag tatgtaatgg
67081   ataatgaacc atgttattaa tttttgaaatat ttccctggaa agagaacttt agtgagaatc
67141   atacataaat agcatagaga attacatatg gggaaaaagat ggcattgcta aatcctaatt
67201   gttgtggagt atatattata gtaaaataaa caatgttttt caagaaatga gagatgaaaa
67261   ctgtcacgat attataaaat gcaacagtaa tttagcaagg aagacttcac tgaaagcaat
67321   atttagatcc agacactggg ttgctgagat gttatttcat tctgtgttca tctctaccc
67381   aaatcttcta gattagatat attatagtta gtttatttga tgaacatttt catattggga
67441   ttataagtgc ctgaaaaatag aatttttaat gcttttaatg tgattaagga agcaaaacct
67501   ctcttttctc cctagaaatt actagcccct tttgcactaa ataactatct cagacaaacc
67561   gccacaattt ccttgtattg ccagagagaa ttcttcaata aaacactgca attctctgtc
67621   aaagagacta acaatagcaa gagcatctca ctatttttct aatgagatgt gaatggaagt
67681   gtgaaggtga aaagacagat tctaggttgg cagattctag gttgactggc aaggtgagac
67741   cacttcttta gcaaaaggaa cccccctcct tgaaatgtca tgtttgatat aaacagaatc
67801   ttccctcccct tcctgccttc cttcttctct tccttttcat cctttacttg gggagtcctc
67861   ctcatttgtc ttaaaaattc tgagatgaat tcatttgccc tcgaagccat cagatttgat
67921   gttgataaat ttaagtggtt taactttgga aaacatcaac ttatgtgtta atttccttcg
67981   tagcgatagc ctggcctcca ggtcacactg cgtagcctac ctgctatcaa tatcatcatt
68041   attgttttaa tcgttaaatt aaactgaatg aagttggtga tgagctgtca agaagtctca
68101   gagacaaggg caggccagtg ccccatttct tcttctaaac actttgtacc tattcataaa
68161   aattgaatga gattgtgtct gggaaactat tgtacactgc aaagcacaaa cataagggca
68221   gatgatgcca gtggtgatta tgatgatgcc cagcaatgtt gttcatttt aggctagaga
68281   tctggtagca gccttatgtt ttctgcttag gatacagtct tgaatagcat aatttgtact
68341   gatataaact agatttagcc attccctggg attctaaact attctcttat gatgcctctt
68401   ccactattgt acagaactat ttagctagga caagaaaaat tgattatttt tcccttctta
68461   gttttctaaa tgacattgcc cagattaatt agaaaattgc ccaaatctct cttttctcta
68521   ctctgctatg tagcacttgc aagaaaaaaa aaaagccaat ttcatgcaga agttgcttaa
68581   aattagtcaa aagcaacccc tgttctagtc ctgtacacat taagtaattc tcattgatca
68641   aaatggaag tgagcctgag aacaaggggag aagagaggaa gtttgcagat ggactttctc
68701   ccccagtgtc attttcaacc aggtaaaatg gagttcgaaa ggcccaaatt ctcagcagat
68761   ttgcacagca cagtaatagc ctttatgctt ggaaatttat gggccatgga cagtttataa
68821   gaaacgatgt agttcatcag agagctagac tgatgggggca tatgggagca ttctgcacag
68881   gaagttgggt tttggaataa tacttacttt gatagagttg tttgttagc taagtaaaac
68941   agtagggaag ccaatggcca cttaggcttc agacataaat atatatttat aagtcaccca
69001   gctgcctaat tgagagccat agtgttttca ctgagtatat cttcaccaga aagcagtaga
69061   aacaacaata tcaccaagaa aaccccagtc ttggcataga tttatttaat cagtctttga
69121   tactttttgag ataattgaat gctctctaaa tgtcgctctt ttaaagccag agggtgaggg
```

-continued

```
69181  gatggttaaa aagaagtttt tttgtttttt gttttttaaa gttggggttc ttttgtattt
69241  aaggtgcaaa gatacgaagt taaggtttat gttacacttg gggtagcaga gggctattac
69301  cagagatttg aaattgtggt tctatggact cctgatggga agagtgggga agctcagagg
69361  agcaagggtt gggcgtacaa ttgtctggtg ctttcaggtt tcagagaaga aggttaagca
69421  ggaggtggct tgttaaattt gagcagagaa ctggaaaata agatttcaca ctcctgagac
69481  gcggaaggct ggtgagtttg gagtttgtct gggagatttg aaaaaggtcg agtgtgctat
69541  aaagttctg aaattctatt ttagtgctta cgaacacgaa aaaagtaggt gttatgaaaa
69601  aaagcaaagg gcattttaaa actcaaataa gtatttggca tgtcgaaata aaatacacat
69661  ccacttctgc ttggctggac ctcctagaat tcaggcctta ctaacgatgt cttgttactg
69721  tgtcctccat tcaagcccct tctttctttt cttaagcttt ttttttttt ttcctcttta
69781  tggccactgc tttaattatt tctctcttg cgttaagacc ctgagctgaa cttgtgttgc
69841  aagtggcagc atgggagtca gagatttggg ttctagtctg aggtctgttt ctttgtgtga
69901  tcttaaggca ggacaccaac tctcatttgg cccttgcctt ccaacttgga ggaactgggg
69961  gtcaggtccc tgaggtcttt cttagttctg acattatttt atcttagagt cagttttgtt
70021  acttcaattc tttcctcctc ttctgggaca agcgtgaccc ttttattcaa ttgcttgctt
70081  tcttcttttc ttttctttc ctttttttta attaaaaaaa gatggatctc actatgttgc
70141  tcaggctggt ctcgaacccc caggctcaag agatcctccc acttcagctt cccaaattgt
70201  taggattaca ggtgcgagcc accatgccca gccaatcaat tgcttttttt tttttttt
70261  tttttttt tttgagacgg agtctcgatc tgtcgcccag gccggactgc ggactgcagt
70321  ggcgcaatct cggctcactg caagctccgc ttcccgggtt cacgccattc tcctgcctca
70381  gcctcccgag tagctgggac tacaggcgcc cgccaccgcg cccggctaat tttttgtatt
70441  tttagtagag acggggtttc accttgttag ccaggatggt ctcgatctcc tgacctcatg
70501  atccaaccgc ctcggcctcc caaagtgctg ggattacagg cgtgagccac cgcgcccggc
70561  cctcaattgc tttttataaa agtattcatt aatgctattt gatctctgtt tacatttaat
70621  tctctttgtc aattgttttt ctattttttt gcttctgatt ttacttgtat tctctttgct
70681  ccttggttcc ctctttttgag gctgatttta tctttaaatt gttatctaat gtagaatata
70741  atattccgtc tcttcaagca tttatttttt ccttgtcttc aatgtttgat ctttaagagc
70801  taaagtacaa ctaaacacat tttaggcatt ttataaatat ttcttgattg attgattggt
70861  ttaataagat tccccaggtt tcagaccgcc catctttca atttggcttt ggactcaggg
70921  ctatctcctg tgtttttgga attagagtta aagccatccc tcacctagta taatatgatc
70981  actgggtcag gcaactcaca cctgtgcaat ctctagtctt aaatcctcta ttcttaaggg
71041  gctgacttaa aagatgactc agtctcattt cttttgctcc catccaaaat gaacaggaaa
71101  cataaaaggc attaagtaca ttggatagca gtcaaatttc taatagttca gttgtgctag
71161  gaaaattaaa ccttatagtg tcagaaactc ccaaatgctt tttttttt tttcaacttg
71221  caggactata aaataagagg tgtctctact aagagttaca aaatgttctg aaataacaac
71281  tcactggaga aatacagata agagtcctta aaagtataac ctcgaattag atccacattt
71341  ccctgtacta tggaacatta aaataattta atagcttgaa ggaaatgtta ctcgttgccc
71401  attatcttgc tactaatcta cgtatttcta tgaaaatgtc atacattttg tgctatatta
71461  agcacatttt agcatacact taaatagata ttatttattt tttaaatcct gaatggccaa
71521  tgattggtct ttgttaatta acatttatt aaatggaact catgatagag taaaatagaa
71581  aaaaacctgt ttctccatac tgctacagta ggtagctagt caggcatgag cagggcagga
71641  gagggctccc caacaccaca tcaggaatgc caggtgacca tcaggtgatg gtcacgtggt
71701  tgttaactct cgctgtaaaa taataattgg tcacagctgg caccagggaa cggccatctt
71761  ccaataggta gaaacacctg aaactggtga tcagcagctt cccagtaaaa tctcaggagt
71821  tgggagagtg gactcaagca tgcgcattaa gaggcaaaat ggtggagttt aactggtata
71881  tgaccttcct ctaggaatgt taggctggta agggaaaaac gtctcaagtg agcatgtgta
71941  caactccagt aaacacactg catgtgctcc cctcccaagg gctagcaggc cactgtgcat
72001  gtggacagcc caccccaagg gaagaataag gagagaagta acacaagacc tcagaagtat
72061  gccaacgtat aaaactccaa gtcaaaatgt caaaccacgc acttgactct ctcaagtcgc
72121  ctgcttggcc cgcttccaag tgtatgttac ttctcgtat tcctgattca aaacttttta
72181  gtaaaggttc actcctgctc taaaacttac ctcagtctct ccctctgcct tatgcacctc
72241  actctaattc tttcttctga ggaggcaaga attgagattg ctgcagaccc ttatggatat
72301  ggatttgctg ccggcaacta gtattattta actcattttg ctaagatttt ccaagaggtt
72361  tcatgttttt cgcagtccga ctataatctg gttctcagtc ttgccatttc aaatttcctt
72421  taaggaggca ttgggttttg ctttgaaagg cctacaagtt ggttgtcact agaggctagg
72481  gccaagctct tgcattaaga gacatactaa agagcaatca gaactttttg ataaaatagg
72541  ggtttgtaaa ttaatttact aacggttcat tatggtattc ccgtaatata tttttcctata
72601  actttaccga taatttttt tggcttgcat aacatttag aatacttacg cttgttggaa
72661  atgccatgat tatattaaaa aattttttgtt gttatctatc caatactcat gatgctaggc
72721  taaattctgc tgaaaagaaa tacaaacata ttgcaaaaag ttacagacat agtaaaacct
72781  tggaagacag ggactggtta atgaaattac tgaaaaaccc aactatatag tattactctt
72841  ttacatatat aaaattaaat aaaaagaatt gatcagaatc ttcttaatta aagtttgctg
72901  gtatatgtca gtagatgtca atattataaa gtgcaaaata agatttccc atcgattcag
72961  tgaattgttg tctaattata ttttattat ttatttttga gatggagttt tgctctgttg
73021  cccaggctgg agtgcagtgg cacaatctca atcttgggc actgcaacct ttgcctccca
73081  agttcaagaa attctcctgc cttagcctcc tgagtagctg ggattacagg tgcacagcac
73141  cacacccagg taattttttgt gtttttagta gagacagggt ttcaccattt tcaccaagct
73201  ggtctcaaac tcctgacctc aagtgatctg cccaccttgg cctcccaaga tgctgggatt
73261  acagatgtga gccaccacgc ccagcctgtt gtctaattct aaacagtttg atgcctatga
73321  tgtatacatt tgttcatcaa aacaaattta gaacagtgaa cctcaaggga tgtgaaatta
73381  ttttttaaag acgagacaga atgatggtta tttttgctct aagaaaaagg agattagatt
73441  gttctgcaac ccattttttg ggaagtgctg tgtcctggct cttttccttc taattatgtt
73501  gggaagtgca atgacatgat aaggtttttt aaatatatat aaatgaaagt attgtcttaa
73561  tgtagtagtg cattcagcct tgatgtctac aaaccttcag tatgttgcag tgatttaaaa
73621  gtatccttac aattcatatg taaggatgtt atatgtattc caaaagaaaa tgtattaatg
73681  ctaatcctga gtaaagctgt gagtcttaaa ggatgccttg tccaccaaaa aggattagaa
73741  ataggcccat tggttcaggg atgtgggaag gatcttggca tacacttggg tttcaggtga
73801  aaaaatatga gagtaacctg atggaaatgg aaacaccacg accaggaaag ggatctgaaa
73861  gtttcctgct gtcatgatgt ggataattca aatcaacaaa ttatcctaaa agaagtcaca
```

-continued

```
73921   aaataggtga aacatttagg attctagcag gagtcaatga aaactgtttt tttttaaaat
73981   tatactttaa gttctagggt acctgtgcac aatatggagg tttgttacat atgtaaacat
74041   gtgccatgtt ggtatgctgc acccatcaac ttatcattta cattaggtat ttctcctaat
74101   gctatccctc cccctgcccc ccaccccagg acaggcccca gggtgtaata ttccccgccc
74161   tgtgtccatg agttctcatt gttcaattcc tacctatgag tgagaacatg cggtgtttgg
74221   ttttctctcc ttgtgatact ttgctcagaa tgatgatttc cagctgcatc catgtcccgg
74281   caaaggacat gaactcatca tttttatgg ctgcatagta ttccgtggtg tatatgtgcc
74341   acattttctt aatccagtct atcattgatg gacatttgag ttggttccaa gtctttgcta
74401   ttgtgaatag tgccacaata aacatacctg tgcatgtgtc tttatagcag catgatttat
74461   aatcctttgg gtatataccc agtaatgggga tggctgggtc aaatggtatt tctagttctg
74521   gatcctgag gaatcaccac actgtcttcc accatggttg aactagttta tactcccacc
74581   aacagtgtaa aagcattcca atttctccac atcctctcca gcatctgttg tttcctgact
74641   ttttaatgat tggcattcta actggtgtga gatggtatct cattgtggtt ttgatttgca
74701   tttctccgat gaccagtgat gatgagcatt ttttcatgtc tgttggctgc ataaatgtct
74761   tcctttgaga agtctctgtt tatatccttc acccactttt tgatgggctt gtttgttttt
74821   tcacgtaaat ttgtttaagt tctttgtaga ttctggatat tagcccttg tcagacaggt
74881   agattgcaaa aattttcttc cattctgtag gttgcctgtt cactctgatg atagtttctt
74941   ttgctgtgca gaagctctt agtttagtta gatcccattt gtctattttg gcttttgtgg
75001   ccattgcttt tggtgtttta gtctttgccc atgcctatgt cttgaatggt attgcctagg
75061   ttttcttcta gggtttctat ggtttaggtc taacatttaa gtcttttaatc catcttgaat
75121   taattttga ataaggtcta aggaagggat ccagttcag ctttctacat atggttagcc
75181   agttttccca gcaccatta ttaaatagg aatcctttcc ccatttcttg tttttgtcag
75241   gtttgtcaaa gatcagatgg ttgtagatgt gtggtgttat ttctgaggcc tctgttttgt
75301   tccattgctc tacatgtctg ttttggtacc agtgccatgc tattttggtt actgtagcct
75361   tgtagtgtag tttgaagtca ggtagtgtga tgcctccagc tttattctt ttgcttagga
75421   ttgtcttggt aatgtgggct ctttttggt tccatatgaa cttttaagca gttttttcca
75481   actctgtgaa gaaagtaatt ggtagcttga tggggatggc actgaatcta caaatacct
75541   tgggcagaat ggccatttc attatattga ctcttcctat ccatgagcat ggaatgttct
75601   tccatttgtt tgtgtcctct tttatttgt tgggcagtgg tttgtgggttc tccttgaaga
75661   ggtccttcac atccctata aattagattc ctaggtattt tattcttttt gtagcaatta
75721   tgaatgggag ttcactcatg atttggctct gtttgtctgt tgctggtgta taggaatgct
75781   ggtgattttt gcacattgat tttgtatcct gagactttgc tgaagttgct tatcagctta
75841   aggagacttg gggctgaggc gatggtgttt tctaaatata caatcattta ttctgcaaag
75901   agggacaatt tgacttcctc ttttcctaat tgaataccct ttatttcttt ctcttgcctg
75961   attgccctgg ccagaacttc caacgctatg ttgaatagga gtggtgaaag agggcatccc
76021   tgtcttgcca gttttcaaag ggaatgcttc cagttcttgc ccattcggtg tgatattggc
76081   tgtgggtttg tcataaatag ctcttattat tttgagatat gttccatcaa taccttgttt
76141   gttgagagtt tttagcatga agcactgttg attttttc aaaggcctt tctgcatcta
76201   ttgagataat catgtggttt ttgtcattgg ttctgtttat gtgatggatt atgattattg
76261   atttgcgtat gttgaaccag ccttgcatcc catggatgaa gttgacttga tcatggtgaa
76321   taagctttt gatgtactgc tggattcagt ttgccagtat tttattgagg attttttgcat
76381   cgatgttcct cagggatgtt ggtctaaaat tctctttttt tgttgtgtct ctgccaggct
76441   ttggtatcag gatgatgctg gcctcataaa atgagttagg gaggattccc tctttttcta
76501   ttgattggaa tagtttcaga aggaatggta ccaactcctc tttgtacttc tggtagaatt
76561   cggctgtgaa tccgtttggt tctggactt ttatggttgg taggctatta attattgcct
76621   taatttcaga gcctgttatt gatctattca gagattcaac ttcttcctgg tttagtcttg
76681   ggaggctgta tgcatccagg aatttatcca ttcctctag atttctagt ttatttgcgt
76741   agaggtgttt atagtattct ctgatggtag tttgtatttc tgtgggattg gtgatgatat
76801   ccctttatc acatttatt gcgtctattt ggctctctc tctttcttc tttattagtc
76861   tcattagctg tctatcagtt ttgttgagct tttcaaaaa ccagtctctg gattgattga
76921   tttttgaag agtttttgt atctctatgt ccttcagttc tgctctgatc ttagttattt
76981   cttaccttct gctagctttt aaatttgtt gctcttgctt ctgtagttct tttaattgtg
77041   atgttagggt gttgatttta gatctctcct gcttttctct gtgggcattt agtgctataa
77101   attcccctct acacactact tcaaatgtac gttgtatctt tgttctcatt agtttcaaag
77161   aacatcttta tttctgcctt cacttcatta tttacccagt agtcattcag gagcagagttg
77221   ttcagttccc atgtagttgt gcggttttga atgagtttct taatcctggg ttctaatttg
77281   attgcactgt tgtctgagag acagtttgtt gtgatttctg ttcttttaca tttgctgagg
77341   agtgccttac ttccaactat gtggtcaatt ttggaataag tatgatgtgg tgctgagaag
77401   aatgtatatt ctgttgattt gggatggaga gttctgtaga tgtctattag gtctgcttgg
77461   tgcagagctg agttcaagtc ctggatatcc ttgttaacca tctgtctcgt tgatctgtct
77521   aatattgaca gtggggttgtt aaaatctcca attattattg tgttggagtc taagtctctt
77581   tgtaggtctc taaggacttg ctttatgaat ctgggtgctc ctgtattggg tgcatatata
77641   tttaggatag ttagcacttc ttgttgaatt gatccctta ctattatgta atggccttct
77701   ttgtctcttg atctttgttg gtttaaagtc tgttttatca gagactagga ttgcaaccc
77761   tgctttttt tttgcttcc gtgtgcttgg tagatcttcc tccattttt attttgagcc
77821   tatgtgtgtc tctgcacgtg agatgggtct ccttatagaa gcacactgat gggtcttgac
77881   tcttatcca atttgccagt ctgtgtcttt taattggggc agttagccca tttacattta
77941   aggttgatat tgttatgtgt gaatttgttc ttgtcattat gatgttatct ggttattttg
78001   cccattattt gatgcagttt cttcctagca tcgatggtct ttataatttg gcatgttttt
78061   acagtggctg gtattggttg ttcctttcca tgtttagtgc ttccttcaga agctcttta
78121   gggcaggcct ggtggtgaca aaatctctca gcattgctt gtctgtaaag gattttattt
78181   ctcttcactt atgaagctta gtttggctgg atatgaaatt ctgggttgaa aattctttc
78241   tttaagaatg ttgaatattg gccctcactc tcttctgggt tgtagagttt ctgctgagag
78301   atcagctgtt agtctgatgg gcttccctt gagggtaacc caacctttct ctctggcctg
78361   ccttaacatt tttccttcat ttcaaccttg gtgaacctga caattatgtg tcttggaatt
78421   gctcttcttg aggagtatct ttgtgctgtt ctctgtattt cctgaatttg aatgttggcc
78481   tgccttgcta ggttggggaa gttctcctaa cagtgttttc caacttggtt ccattctccc
78541   catcactttc aggtacaccg atcaaaggta gatttggcct tttcacatgg tcccatattt
78601   cttggaggct ttgttcgttt cttttttactc ttttttctct aaacttatct tctcacttta
```

-continued

```
78661  tttcattaat ttgatcttca atcactgata ccctttcttc cacttgattg aattggctat
78721  tgaagctgtg catgtgtcgt gtagttctca tgccatggtt ttcaactcca tcaggtcatt
78781  taaagtcttc tctacactgt ttattctagt tagccattca tataatcttt tgtcaaggtt
78841  ttttccttcc ttgcaatgag ttcaaacatc ctcctttagc tcggagaagt ttattattac
78901  cgaccttctg aagcctactt ctgtcagctc gtcaaagtca ttctcagtcc agctttgttc
78961  tgttgctggc gaggggctgc aatcctttgg aagagaagag gtgctctggt ttttagaatt
79021  ttcagctttt ctgctctggt ttctccccat ctttgtggtt ttatctacct ttggtctttg
79081  atgttggtga cctacagctg gggttttggt gtggatgtcc ttttttgttca tgttgatgct
79141  attcctttct gcttgttagt tttccttcta acagtcaggc ccctcacctg cagatctgtt
79201  ggagtctgct agaggtccac cccggaccct gtttgctggg gtatcactag cagaggctgc
79261  agaacagcaa atattgcaga acagcaaata ttgctgccta atccttcctc tggaagcttc
79321  atcccagagg agcaccgcct gtatgatttg tcagtcagcc cctactggga ggtgtctccc
79381  agttaggtta cacggggggtc agggacacac ttgaggaggc agtctgtttg ttctccgagc
79441  tcaaacacca tgctggggga accactgctc tcttcagagc tgtcagacag ccatgtttaa
79501  gtctgcagag gtttctgctg ccttttgttc agctatgccc tgccccagaa gatggagtct
79561  actgaggcag gaggccttgc tgagctgaga tgggctccgc ccagtttgag ctttcctggc
79621  tgctttgttt acctactcaa gcctcagcaa tggtggatgc ccctcccct gccaggctgc
79681  tgcctcgcag gttgatctca gactgctgtg ctagcagtga gccaggctct gttggtgtgg
79741  gacccgccaa tccaggcatg ggatataatc tcctggtgtg ctgtttgctg agaccattga
79801  aaaagtgtaa tatttgggca ggagtgtccc atttttccag gtactgtctg tcatggcttc
79861  ccttggctag gaaagggaaa ttccccgacc ccttgtgctt cctgggtgag gcaatgccct
79921  gccctgcttc ggctagccct ccatgggctg cacccactgt ccaaccagtc ccagtgagat
79981  gaaccaggta cctcagttgg aaattcagaa atcacccgtc ttctgcatca atcacactgg
80041  gacctgcaga ccagagctgt tcctattcag ccatcttgga acagaacgtg aaaactgctt
80101  tgttaatatg ctttctttac ctccagattt ctcccaaatg aactccccata gacctcataa
80161  tgtgaagata caaacctcta tgaggaaaaa tcagcagaca caacaaacag gagattttt
80221  atgtaatgta atggcccccca aactggatat tatagaataa tgtaaatgag attatgtatt
80281  caatatgtta attaattaag gaaaacagaa ggaacagaaa tcacaaagaa acattagaaa
80341  gtcatggaaa aagtagggcc ctatttataa aatagcaaaa tagaagatat agaaataaaa
80401  aaatcattga aattaaaaaa tgtaaataca ttattaattt atgctaattt aaatgttaga
80461  caaatagaat aataagacag aaatgtatcc aagcatgtat aaagatttat tgtttaacag
80521  gtcaatgaag aaaatgattg aatatttagc aattaccact gtgtcaaatg atagtcatct
80581  ggaaagaaga aaactggatt tctgctttat agcaaataaa aaaatcaaag ttgagataga
80641  ttaaagatct aaaaaacacc catatttca acaccttggg gaaaattata ggaaaatatt
80701  atgtcagggt gtacaagaac tttataagta gtcgcaaata aaatagtatc ctgcaaaaga
80761  aagaatttag acccctacct cacatcatat atgaaattaa ctaaaaaatg gatcaaagac
80821  ctaaatataa gaacctcaaa ctataaaatc cttagaagaa aaaaagtgta gatctttatc
80881  agcttggatt aggcaatggt ttcttagcta tgacagaaaa aggataaaca acaaaataaa
80941  tggataaatt gtactttatc aaacttaaaa acgtttatgt ttcaaaggat accatcaaga
81001  aggtgaaaag aaaacctaca aaatgtgaaa aatatttgca aatatatatc taacaaagta
81061  cctgtatcca gaatatataa tgaacactta gcaataaaca ataaaaagac aaataaccca
81121  attaaaaatg ggcaaaagat ttcactagac atttatccaa agaagattta taagtgacca
81181  ataagctcat gaaaggatgt tcagcattga tagagaaacg caaatcaaag tcacaataag
81241  atgccataaa attttacact cactaggatg gctataataa aaaagatggg ctgttggagt
81301  tttgaagagt atgtgaaaaa ttttgaacac tcatacatga atggtggaaa tgtaaaatgc
81361  tccagctgct ttggaaaaca gtctggtact tcctgaaaat tttaaataca gagtttttctt
81421  ttatatacat atatatattt atttaagttg tagggtacat gtgcaaaatg tgtaggttta
81481  ttacatatgt atacatgtgc catgttggtg tgctgcaccc attaactcat catttacatt
81541  aggtatatct cctaatgcta tccctccccc tgccccccac cccacgacag gccccagtgt
81601  gtgatattcc ccttcctgtg tccatgtgtt ctcattgttc aattccccacc tatgagtgag
81661  aacatgtggt gtttggtttt ttgtccttgt gatagtttgc tgagaatgat ggtttccatc
81721  ttcatccatg tccctacaaa ggacatgaac tcatcatttt ttatggctgc gtaatattcc
81781  atggtgtata tgtgccacat tttcttaatc cagtctatca ttgttggaca tttgggttgg
81841  ttcaagtgt ttgctattgt gaatagtgcc acaataaaca tatgtgtgca tgtgtcttta
81901  tagcagcatg acttataatc ctttgggtat atacccagaa atgggatggc tgggtcaaat
81961  ggtatttcta gttctagatc cctgaggaac caccacactg tcttccacaa gggttgaact
82021  agtttacagt cccaccaaca gtgtaaaagt gttcctattt ctccacatcc tctccagcac
82081  cttttgtttc ctgactttt aatgattgcc attctaactg gtgtgagatg atatctcatt
82141  gtggttttga tttgcatttc tctgatggcc agtgatgatg agcatttttt catgtgtctg
82201  ttggctgcat aaatgtcttc ttttgagaag tgtctgttca tatccttcac ccacttgttg
82261  atggggttgt ttgttttttt cttgtaaatt tgtttgagtt cttcgtagat tctggatatt
82321  agcccttttgt cagatgagta gattgcaaaa attttctccc atttttgtagg ttgcctgttc
82381  actctgatgg tagttctttt tgctgtgcag aagctctta gtttaattag atgccatttg
82441  tcaattttgg cttttgttgc cattggtttt ggtgttttag acatgaagtc cttgccccatg
82501  cctatgtcct gaatggtatt gcctaggttt tcttctaggg tttttatggt tttaggtcta
82561  acattaaagt cgtttatcca gcttgaatta attttttgaat aaggtgtaag gaagggatcc
82621  agtttcagct ttctacatat ggctagccag ttttcccagc accattttgtt aaatagggaa
82681  tcctttcccc atttcttgtt tttgtcaggt ttgtcaaaga tcagatagtt gtacatgtgt
82741  ggtatttaaa tacagagttt tcatatgacc cagaaattct actcctaggc agagtctcaa
82801  ggtaattgaa aatgtatgtc caccaaaaac ttgtagtgaa tgttcctact ggtgttaatt
82861  atcatagccc tgaagtggaa acaaccccaaa ttttccatcag ttgatgagtg gataaacaaa
82921  atgtggtaaa tccttgcaat ggaatattat ttggccataa aatggaagta cagctacatg
82981  ttacagcatg catgaatgtt aaagccatta tacttagtga aggaagccat cacaaagagt
83041  cacatattgt cagatttcct gtatatacat catccaaaat gggtaaatcc atagagacag
83101  taggagattc atggttgcca agggctgggg gtgggcaaaa tgggaagtga ttgctaatgg
83161  gtatgagatt tttttgggg aggggtgata aaaatgttct gaatttaaat aatggtgata
83221  attgcacaac tttaaatata ctaaaaaacg tggaattgca tactttgaaa ggataagttt
83281  tttgttatgt gaattccatc tgaattttaa aaagaagaga aaaactaaaa aagattgatt
83341  aacttgatgt tgaattttaa acagctttat gaaagagcat atataacaag ctgtgtatca
```

-continued

```
83401  ttatccagga tatataaatg actcctacaa ataaatgaaa taaaggcaaa atttccacca
83461  aataatatgc aaacatttgc atatgcaaat aataagcaaa cgtggctagc cagttttccc
83521  agcaccattt attaaatagg gaatcctttc cccattgctt gtttttgtca gatttgtcaa
83581  agatcagata gttgtagata tgtggcatta tttctgaggg ctctgttctg ttccattggt
83641  ctatatctct gttttggtac cagtaccatg ctgttttggt tactgcagcc ttgtagtata
83701  gtttgaagtc aggtaacatg atgcctctag ctttgttctt ttggtttagg attgacttgg
83761  caatgcgggc tctttttgg ttccatatga aatttaaagt agtttttccc aattctgtga
83821  agaaagtcat tggtagcttg atggggatgg cattgaatct ataaatgacc ttgggcagta
83881  tggccatttt cacgatattg attcttccta cccatgagca tggaatgttc ttccatttgt
83941  ttgtatcctc ttttatttcc ttgagaagtg gtttgtagtt ctccttgaag aggtccttca
84001  catcccttgt aagctggatt cctaggtatt ttattctctt tgaagcaatt gtgaatggga
84061  gttcactcat gatttggctc tctgtttgtc tgttatttggt gtataagaat gcttgtgatt
84121  tttgcacatt gatttttgtat cctgagactt tgctgaagtt gcttatcagc ttacatagat
84181  tttgggctga gacgatgggg ttttctagat atacaatcat gtcatctgca aacagggaaa
84241  tttgacttcc tcttttccta attgaatgcc ctttatttcc ttctcctgcc taattgccct
84301  ggccagaact tccaacacta tgttgaatag gagtggtgag agagggcatc cctgtcttgt
84361  gccagttttc aaagggaatg cttccagttt ttgtccattc agtatgatat tggctgtggg
84421  tttgtcatag atagctctta ttattttgag atacgtccca tcaataccta atttactgag
84481  agtttttagc aggaagactt gttgaatttt gtcaaaggcc ttttctgcat ctattgagat
84541  aatcatgtgg ttttttgtctt tgattctgtt tatatgctgg attacgttta ttgatttgca
84601  tgtattgaac gagccttgca tcccagggat gaagtccact tgatcatggt cgataagctt
84661  tttgatgtgt tgctggattt gttttgccag tatttttattg aggattttg catcaatgtt
84721  catcaaggat gttggtctaa agttctcttt ttttgttgtg tctctgccag gctttggtat
84781  taggatgatg ctggcctcat aaaatgagtt agggaggatt ccctctttt ctattgattg
84841  gaatagtttc agaaggaaca gtaccagctc ctccttgcac ctctggtaga attcggctgt
84901  gaatccatct ggtcctggac ttttttttggt tggtaagcta ttaattattg cctcaatttc
84961  agggcctgtt attggtctat gcagagattc aacttcttcc tggtttagtc ttgggagagt
85021  gtatgtgtct cggaatttat ccattcttc tagattttct agtttatttg cataaaggtg
85081  tttatagtat tctctgatgg tagtttgtat ttctgtggga tcagcggtga tatcctcttt
85141  gtcattttt attgtgtcta tttgattctt ctctcttttc ttctttatta gtcttgctag
85201  cggtctatca attctgttga tcttttcaaa aaaccagctc ctggattcat tgatttttg
85261  aagggttttt gtgtctctat ttccttcagt tctgctctga tcttagttat ttcttgcctt
85321  ctgctagctt ttgaatgtgt ttgctcttgc ttctctagtt cttttaattg tgatgttagg
85381  gtgtcagttt tagatctttc ctgctttctc ttgtgggcat ttagtgctat aaatttcgct
85441  ctacacactg ctttgaatgc gtcccagaga ttctgatgtg ttgtgtcttt gttctcattg
85501  gtttcaaaga acatctttat ttctgccttc atttctttat gtacccagta gtcattcagg
85561  agcaggttgt tcagtttcca tgtagttgag tggtttttgag tgagtttctt aacctgagtt
85621  ctagtttgat tgcactgtgg tctgagagac agtttgttat aatttctggt ctttcacatt
85681  tgctgaggag tgctttattt acaactatgt ggccaatttt ggtccatata tctaccagta
85741  cattgctgtt ttggttactg taggcttgca gtatagtttg aataaggtag catgatgcct
85801  ccagctttgt tctctttgct taggattgtc ttggctatat ggggtctttt ttggttccat
85861  atgaaattaa agtatttttt ctaattctgt gaagaaagtc agcgggtagct tgatgggaat
85921  ggtatcgaat ctataaatta ctttgggcag tatggccatt ttcatgatat tgattcttct
85981  tatccatgag catggaatgt tcttccattt gtttgtgttc tttcttattt ccttgagtag
86041  tggtttgtag ttctccttga agtcctccac atcccttaa gttgtattcc taggtatttt
86101  attattttg tagcaattgt gaatcagagt tcattcatga tttggctctg tttgtctatt
86161  attgatgtat aggaatgctt gtgatttttg cacattgatt ttgtatcctg agactttgct
86221  gaagttaag gagttttgg gctgagacaa tgggggttttc taaatataca ataatgtcat
86281  ctgcaaacag agataatttg acttatcttc ctgtttgaac accctttatt tctttctctt
86341  gcctgattgc cctggccaga acttccaata ctatgttgaa taggagtggt gagagagacc
86401  atctttttctt gtgcaggttt tcaaagggaa tgtttttcagc ttttgcccat tcagtatgat
86461  attgactgtg ggtttatcat aaatagctct tattattttg agatacattc catcaatacc
86521  aagtttattg agtgtttgga acatgaaggg gtgttgaatt tttatgaaag gacttttctg
86581  catctattga gataatcatg tggtttgtgt cactggttct gtttatgtga tggattacat
86641  ttattgattt gcatatgttg aaacagcttt gcatcccatg gatgatgcca acttgatcat
86701  agtggataag cttttttaatg tgccactgga tttggtttgc cagtatttta ttgaggattt
86761  tcacatcaat attcatcagg gatattcgcc tgaaattttc tttttttgtt gtgtctctgc
86821  taggttttgg tatcaggatg atgttggtct cctaaaatga gttagggagg agccctctct
86881  ttctattgtt tggaatagtt ttagaaggaa ttgtaccagc tccttttat acctatggta
86941  gaatttggct gtgaatccat ctggtcctgg gcttttttg gttggttggt attaattact
87001  gcctcaattt ccgaacttgt tattggtcaa ttcagggatt caccttcttt cttgtttagt
87061  cttgggaggg tgtatgtgtc caggaatta tccatttctt ccagagtttc tagtttattt
87121  gtgtagagct gtttatagta ttctctgatg gtagtttgca tttctgtggg atcagtggtg
87181  atatccccctt tatcattttt tattgtgtca atttaattct tctttctttt cttctttatt
87241  agtctggcta gcagtctatc tattttgtta atcttttcaa aaaatcagct cctgaattca
87301  ttggttttttt ttgaagggtt ttttttttgt gtctatctcc ttcagttctg ctctgatgtt
87361  agttatttct tgtcttctgc tagcttttgg gtttgtttgc tcttgcttct ctagttcttt
87421  taattgtgat gttagggtgc tgattttaga tcttttctgc tttctcttgt gggcatttag
87481  tgctataaat ttcctgctac acactgctgt agctgtgtcc cagagattct tgtatattgc
87541  atctttgttc tcattggttt caaagaatgt atttatttct gccttgcagg ttgttgagtt
87601  tgcatgtagg tgtgtggttt tgagtgagtt tctgaatcct gagttctaat ttgattgcac
87661  tgtggtctga gagactgttt gttatgattt ctgttctttt gcatttgcag aggaatgttt
87721  tacttccaat catgtggtca attttagaat aagtgctatg tggtgctgag aagaatgtat
87781  attctgttcc cttgtggtgg agagttctgt agatgtctat taggtctgca ttgtgggagag
87841  ctgagttcaa gtcctgaata tccttgttaa tttttctgtct cattgatctg tctaatactg
87901  acagtggggt gttaaatttt cccactatta tgtgtggggg gtctaagtct ctttgtaggt
87961  ctctaggaac ttgctttatg aatctgggtg ctctgtatt gggtgcacat gtatttagga
88021  tagttagctc ttccttgttgc actgatcctt taccattatg taatgctctt cctgtctttt
88081  ttaaacctttt tttggtttga agtctgttttt agcagagact aggattgcaa ccccctgcttt
```

-continued

```
88141    tttttttgc tttccgtttg cttggtaaac ttcctccatc cctttgtttt gagcctatat
88201    gcatctttgc atgtaagatg ggtctcctga atacagcaca ccaatgggtc ttgactcttt
88261    atcaaattcg ccagtctgtg tcttttaatt ggagcattta gcctgtttac gtttaagatt
88321    aatattgtta tgtgtgaatt tgatcttgtc attatgatgc tagctggtta ttttgcccat
88381    tagtagatgc aggttcttca cagtgtcaat ggtcttttaca atttggtatg ttttgcagt
88441    ggctggtacc ggtgtttcct ttccatattt aatgcttcct tcaggaactc ttgtaagtca
88501    ggcctggtgg tgacaaaatc accagcattt gcttgtctgt aaaggatttt atttcttctt
88561    cacttttgaa gcttagtttg gctggatttg aaattctggg ttgaaaattc tttcctttaa
88621    gaatgttgaa tattggcccc cactctcttc tggcttgtaa ggtttctgca tagagatctg
88681    ctgttagtct gaatggcttc cctttgtggg taacccgacc tttctctctg gctgcccta
88741    acattttcc tccatttcaa ccttggtgaa tctgacaatt atgtgtcttg gggttgctct
88801    tcttgaggag tatctttgtg gtgttctctg tatttcctga atttgaattg ttggcctgtc
88861    ttgctaggtt ggggaagttc ttctggataa tacctgaagt gtgtccaac ttggttccat
88921    tctcctcgtc actttcaagt acaccaataa aatgtaggtt tggtctcttc acaagtccta
88981    tatttcttgg aggctttgtt tgttcctttt cattctttt tctctagtct tgtcttcttt
89041    gtttatttca ttaagttggt cttcaatctc tgaaatcctt ttttcactt gatcaatttg
89101    gctattgata cttgtgtatg cttcacgaag ttctcgtgct gtgttttca gctccatcag
89161    gtcatttatg ttcttctcta aactggttat tctagtcact agttcctgta accttttatc
89221    acagttctta gcttccttgc actgggttag aacatgctcc tttacctctg aggagtttat
89281    tattacccac cttctgaagc ctacttcttc aattcgtcaa actcattctt catcctgctt
89341    tgttcccttg ctggtgagaa gttgtgattt tttggaggag aaggggtact ctggttttg
89401    gaattttcag cctttcgag ctggtttttc ctcattttcg tggatttatc tcccttcat
89461    ctttgatgtt ggtgaccttc agatgggggtt tttgagtgag ggttcttttt gttgatattg
89521    atgctattgc tttctgtttg ttagttttcc ttctaacagt gaggcccctc ttctgcaggt
89581    ctgctggagg tccactccag accctgtttg tgtgggtatc accagtggag gctgcagaac
89641    agcaaagatt gctgcctgct ccttctctg gaaggtttct tgcagagagg cacctgccag
89701    atgccagcca gagctctcct gtatgaggtg tctgttgact tttgctgaga gttgtctctc
89761    tgtcagaagg catgggggcc agggatccac tcgaggaggc agtctgtccc ttagcagagc
89821    tcaagtgctg tgctgggaga tcttctgttc tcttagagc cagcaggcaa gtacatttaa
89881    gtctgctgat gctgcattca cagccacccc ttcccccagg tgctctgtcc cagggaggtg
89941    ggagttttat ctataagccc ctgactgggg ctgctgccctt tctttcagag attccctgcc
90001    caaagaggag gcatctagag aggcagtctg gctacagcgg cttgcggag ctgcagtgtg
90061    cttcacccag ttctaacttc ccagtggctt tgtttacact gtgaggggaa aaacacctac
90121    tgaagcctga gtaatggcag atgcccctct ccccaccaag ctcgagcagg tcaacttcag
90181    actgctgtgc tggcagcgag aatttcaagc cagtggatct tagcttgttg ggcaccatgg
90241    gggtggaatc tgctgggcaa gaccactcag ctccctggct tcagccccgt ttccagggga
90301    gtgaatggtt ctgtctcact ggtgcttcag gcaccaatgg ggtatgaaaa aaaactcctg
90361    cagctagctt ggtgtcttcc caaacggctg gtgagttta tgcttgaaac ccaaggccct
90421    ggtggcatag gcacctgagg aaatctcctg gtatgagggt tgcaaagact gtgggaaaaa
90481    cgtagtatct tggcctgaat gcactgttcc tcatggcaca gtctctcaag gcttccctg
90541    gcaagggggag ggagttcccc aaccccttgt gcttctgagg tgaggcaatg ccccaccctg
90601    ctttggcgtg ccctctgtgg cctgcaccca ctgtgaaacc agtcccaatg agatgaactg
90661    ggtaccttag ttggaaatgt agaaatcacc tgccttctgt gttggtgttg ctgggaactg
90721    cagaccagag ctgttcctat tcggccatct tgcctggaag ccaactcttc tttttttaat
90781    ttaacttatt ttaagttcag gggtacatac gcagtttgt tatagaggtg aacttgtgtc
90841    ataattattt cattactcag gtagtaagct tagtacctat tagttattt ccctgatcct
90901    ctccctcctc ctaaccctcc accctccaac aggcccccagt gtgtgttgtt cccctctatg
90961    tgaataaaag gacacttcta ttgcatttta tttctttga aaggtcaaaa gaggacgggc
91021    actgtggcac acacctgtaa ttccagccct ttgggaggct gaggtgggca gatctcttga
91081    tcccagaagt tcaagaccag cctaggcaac atggtgaaac cctttctgta caaaaaaata
91141    ccaaaactag ctgtgcgtga tggtgcatgc ctgtagtcca agctacttgg gaggccgagg
91201    tgggagaatc acctgagcct gggtaggttg aggctatagt gagccatgat tgtaccattg
91261    cattccagcc tgggtgacag agtgagaccc tctttaacag caatacccaa tttcaaaaaa
91321    agtaaagaaa aaaaaacatc cagaagaagg tatagcataa taaaaataat tgttacattt
91381    ggtaattatc aaatatggtg tttattttat ttattatta ttatacttta agttttaggg
91441    tacatgtgca caatgtgcag gttagttaca tatgtataca tgtgccatgc tggtgcgctg
91501    cacccactaa ctcgtcatct agcattaggt atatctccca atgctatccc tcccccctcc
91561    tcccatccca caacagtccc cagagtgtga tgttcccttt cctgtgtcca tgtgttctca
91621    ttgttcaatt cccacctatg agtgagaata tgcggtgttt ggcttttgt tcttgcgata
91681    gtttactgag aatgatgatt tccaatttca tccatgtccc tacaaaggac atgaactcat
91741    catttttat ggctgcatag tattccatgg tgtatatgtg ccacattttc ttaatccagt
91801    ctatcattgt tggacatttg ggttggttcc aattctttgc tattgtgaat agtgccacaa
91861    taaacatacg tttgcatctg tcttatagc agcatgattt atagtccttt gggtatatac
91921    ccagtaatgg gatggctggg tcaaatggta tttctagttc tagatccctg aggaatggcc
91981    acactgactt ccacaagggt tgaactagtt tacagtccca ccaacagtgt aaaagtgttc
92041    ctattctcc acatcctctc cagcacctgt tgttcctga ctttttaatg attgccattc
92101    taactggtgt gagatggtat ctcattgtgg ttttgatttg catttctctg atggccagtg
92161    atggtgagca tttttcatg tgttttttgg ctgcataaat gtcttctttt gagaagtgtc
92221    tgttcatgtc ctttgcccac ttttgatgg ggttgtttgt tttttcttg taaatttgtt
92281    ggagttcatt gtagattctg gatatcagcc ctttgtcaga tgagtaggtt gcgaaaattt
92341    tctcccattt tgtaggttgc ctgttcactc tgatgtgtagt ttcttttgct gtgcagaagc
92401    tctttagttt aattagatgc gatttgtcaa ttttggcttt tgttgccatt gcttttggtg
92461    ttttagacat gaagtccttg cctatgccta tgtcctgaat ggtaatgcct aggttttcat
92521    ctagggtttt tatggttta ggtctaacat ttaagtcttt aatccatctt gaattaattt
92581    ttgtataagg tgtaaggaag ggatccagtt tcagctttct acatatggct agccagtttt
92641    cccagcacca tttattaaat agggaatcct ttccccattg cttgttttc tcaggtttgt
92701    caaagatcag atagttgtag atacgcagca ttatttctga gggctctgtt ctgttccatt
92761    gatctatatc tctgtttgg taccagtacc atgctgtttt ggtactgta gccttgtagt
92821    atagttgaa gtcaggtagc gtgatgcctc cagctttgtt cttatggctt aggattgact
```

-continued

```
92881  tggtgatgca ggctctttt tggttccata tgaacttta agtagttttt tccaattctg
92941  tgaagaaagt cattggtagc ttgatgggga tggcactgaa tctataaatt accttgggca
93001  gtatggccat tttcacgata ttgattcttc ctacccatga gcatgggata gtcttccatt
93061  tctttgtatc ctcttttatt tccttgagca gtgggttgta gttctccttg aagaggccct
93121  tcatgtccct tgtaagttgg attcctaggt attttattct ctttgaagca attgtgaatg
93181  ggagttcatt catgatttgg ctctctgtt gttattggtg tatatgaatg cttgtgattt
93241  ttgtacatgg atttatatc ctgagacttt gctgaagttg cttatcagct taagtagatt
93301  ttgggctgag acgatggtgt tttctaggta tacaatcatg tcatctgcaa acagggacaa
93361  tttgacttcc tcttttccta attgaatacc ctttatttcc ttctcctgcc taattgccct
93421  ggccagaact tccaacacta tgttgaatag gagtggtgag agagggcatc cctgtcttgt
93481  gccagttttc aaagggaatg cttccagttt ttgcccattc agtatgatat tggctgtggg
93541  tttgtcatag atagctctta ttatttgag atacgtccca tcaataccta atttattgag
93601  aggttgtagc ttgaagggtt gttgaatttt gtgaaaagac ttttctgcat ctattgagat
93661  aatcatgtgg ttttcgtctt tggttctgtt tatatgctgg attacattta ttgatttgcg
93721  tatattgaaa cagccttgca tcccacggat gaagcccact tgatcatggt gaataagctt
93781  tttgatgtgc tgctggattt ggtttgccag tattttattg aggattttg catcaatgtt
93841  catcaaggat attggtccaa aattctcttt tttggttgtg tctctgccag gctttggtat
93901  taggatgatg ctggcctcat aaaatgagtt agggaggatt ccctctttt ctattgattg
93961  gaatagtttc agaaggaatg gtaccagttc ctctttgtac ctctggtaga atttggctgt
94021  gaatctgtct ggtcctggac tcttttggt tggtaagcta ttgattattg ccacaattc
94081  atagcctgtt cttggtctat gcagagattc aactttccc tggtttagtc ttgggagtgt
94141  gtatgtgtcg aggaatttat ccatttcttc tagattttcc agtttattg catgagaggtg
94201  tttgtagtat tctctgatag tagtttgtat ttctgtggga ttggtggtga tatcccctt
94261  atcatttttt atggcgtcta tttgattctt ctctcttttc ttcttatta atcttgctag
94321  tggtctatca attttgttga tctttcaaa aaaccagctc ctggattcat taattttct
94381  aaggtttttt tgtgtctgta tttctttcgc ttctgctatg atgttagtta tttcttgcct
94441  tccgctagct tttgaatatg tttgctcttg cttttctagt tctttaatt gtggtgttag
94501  ggtgtcaatt ttggatcttt cctgctttct cttgtgggca tttagtgcta taaatttccc
94561  tctacacact gcttttaatg tgccccagag attctggtat gttgtgtctt tgttcttgtt
94621  ggtttcaaag aacatctttta tttctgcctt catttcgtta tgttcccagt agtcattgag
94681  gagcaggttg ttaagttcc atgtagttga gcggtttgca tgagtttctt aatcctgagt
94741  tctagtttga ttgcactgtg gtctgagaga cagtttgtca taatttctgg tctttcacat
94801  ttgctgagga gagcttatt tccaactatg tggtcaattt tggaataagt gtgatgtggt
94861  gctgaaaaaa atgtatattc tgttgatttg gggtggagag ttctgtagat gtctattagg
94921  tctgcttggt gcagagctga gttcaattcc tgggtatcct tgttaactt ctgtctcatt
94981  gatctgtcta atgttgacag tgggggtgtta aagtctccca tttttattgt gtgggagtct
95041  aagtctctt atagatcact caggacttgc tttatgaatc tgggtgctcc tgtattgggt
95101  gcatatatat ttaggatagt tagctctct tgttgaattg atccctttac cattatgtaa
95161  tggccttttt tgtctctttt gatcttgtt tgtttaaagt ctgttttatc agagactagg
95221  attgcaaccc ctgccttttt ttgtttttcca tttgcttggt agatcttcct ccatccttt
95281  attttgagcc tatgtgtgtc tctgcatgtg agatgggttt cctgaataca gcacactgat
95341  gggtcttgac tcttatcca atttgccagt ctgtgtcttt taattggagc atttagtcca
95401  tttacattta aagttaatat tgttatgtgt gaatttgatc ctgtcattat gatgttagct
95461  ggtgattttg cttgttagtt tatgcagttt cttcctagcc tcgatggtt ttacaatttg
95521  gcgtgatttt gcagtggctg gtaccggttg ttccttcca tgtttagtgc ttccttcagg
95581  agctcttta gggcaggcct ggtggtgaca aaatctctca gcatttgctt gtccgtaaag
95641  tatttatt ctccttcact tatgaagctt agtttggctg gatatgaaat tctgggtcga
95701  aaattctttt ctttaagaat gttgaatatt ggcccccact ctcttctggc ttatagagtt
95761  tctgccaaga gatgagctgt tagtctgatg ggcttccctt tgtgggtaat ccgacctttc
95821  tgtctggctg cccttaacat ttttccttc atttcaactt tggtgaatct gacaattatg
95881  tgtcttggag ttgctcttct caaggagtgt ctttgtggtg ttctctgtat ttcctgtatc
95941  tgaatgttgg cctgccttgg tagattgggg aaattctcct ggataatatc ctgcagagtg
96001  ttttccaact tggttccatt caccccgtca ctttcaggta caccaatcag acgtaaattt
96061  ggtcttttcc catagtcccg tatttcttgg aggcttttgtt catttctttt tattctttt
96121  tccctaaact tctcttctcg cttcatttca ttcatttcat cttccatcac tgatacccctt
96181  tcttcagttg atcgcttcgg ctcctgaggc ttctgcattc ttcacgtggt tctcgagcct
96241  tggctttcag ccccatcagc tcctttaagc acttctctgt attggttact ctagttatac
96301  attcgtctaa attttttca acgttttaa cttcttttgcc tttgttttga atttcctcct
96361  gtagctcgga gtagttgat cgtctgaagc cttccttgtct gaactcgtca aagtcatact
96421  ccgtccagct ttgttctgtt gctggtgagg aagtgtgttc ctttggagga gaggcactgc
96481  gcttttttaga gtttccagtt tttctgctct gtttttttccc catcttttgtg gttttatcta
96541  cttttggtct ttgatgatgg tgatgtacag atgggttttt ggtgtggatg tcctttctgt
96601  ttgttagttt tccttctaac agacaggatc ttcagctgca agtctgttgg aatttgctag
96661  aggtccactc cagactctgt tttcctgggt aacagcagca gtgctgaag aagagtggat
96721  ttttgtgaac tgcgaatgct gctgtctgat cgttcctctg gaagttttgt ctcagaggag
96781  tacccggccg tgtgaggtgt cagtctgccc ctactagggg gtgcctccca gttaggctgc
96841  tcgggggtca ggggtcaggg acccacttga ggaggcagtc tgcccgttct cagatctcca
96901  gctgcatgct gggagaacca ctgctctctt caaagctgtc agacagggcc atttaagtct
96961  gcagaggtta ctgctgtctt tttgttgtc tgtgccctgc cccagaggt ggagcctata
97021  gaggcaggca ggcctccttg agctgtggtg ggctccatcc agtttgagct tcccagctgc
97081  tttgttacc taagcaggcc tgggcaatgg caggtgcccc tccccagcc tcgctgccac
97141  cttgcagttt gatctcagac tgctgtgcta gcaatcagcg agactctgtg agcgtaggac
97201  cctccgagcc aggtgcggta tataatctcc tggtgcgccg ttttttaagc ccgttggaaa
97261  agtgcagcat taggatggga gtgacccgat tttccaggtg ccccatctgt caccccttc
97321  tttgactagg aaagggaact ccctgacccc ttgcacttcc cgagtgaggc aatgcctcgc
97381  cctgcttcgg ctcgcgcacc atgcgctgca cccactgtcc tgcgcccact gtctggcact
97441  cactagtgag acgaacccgg tacctcagat ggaaatgcag aaatcacccg tcttctgcat
97501  cggtcacgct gggagctgta gaccggagcc attcctgttc agccattttg gctgctactg
97561  cctcaaatat ggtgttttaa atattattct ctattgtcaa catgacagct aaacatggtg
```

-continued

```
 97621   tcatgtttat atttatgtaa taataataat gtaataacct ttttcataga tgcacccaat
 97681   gtttgccttt ttttgttatt gttaaattgc ctgtttgaat cctttgccta catttctatt
 97741   agtatgactg atgtatcact tgggaattgt gtttggctgt gaataacaca aacctggaaa
 97801   cagtggatta aataaagact tttattttt tctctcagaa tgaaaagtcc aaaagtcaaa
 97861   aacctaggac gggtacagtg tctccatgat gccagtaggg aaatggactt gtatctttcc
 97921   actaagccac ccctggcata tgcttttcac ccttgggatt atgagatggc tgctttgttt
 97981   ccagaatcaa gtccatgttt caggcaggaa gaaatgaaag agccaaggac gaaatgtcca
 98041   ttccagcgaa gtctgccctc tccctccctt cccatacatc cacatatttt aaagagcctt
 98101   cctggaagtc ccatcaaaaa ctccctgctc ccttttttt cagttgccag aactaggtca
 98161   gatgatgact tgtatccagg aattcagcag tgtttgttta atcttttccc caaactggag
 98221   ttaagtggac aggaataaga atggatactg ggaagagacc actaggcttt cgtagctgcc
 98281   aaacaatgat gataacaata gtgatgatga tcataataaa aatcatcata gttaccattt
 98341   attatgtgct gtgtgccagg tgtgtaagct ttgtacattt ttcttgttta gtcccccaaa
 98401   tccttaaagt acttgtgttg gcacccattt agaactgagg ctattgagac tcattaatgt
 98461   gtagtaacat gttgaaagtc atgcgagggg caatacaaac ttgaatccag tcctatttga
 98521   ctatgaagat cgtctgggac tgtactggct ttagcagtga aagtctcaca ttctaggaca
 98581   cctgtcagtc atggaacagt gtggcagggg tcacccactg aagctcaaac agtattaggg
 98641   tatgagttca attaaggttt tttgaatggt taatttaata agtattattt atcatttctc
 98701   ataagtttat agacttgcaa tacattaaga atacaacctt tggccgggcg cggtggctca
 98761   cgcctgtaat cccagcactt tgggaggccg aggcgggcgg atcacaaggt caggagatcg
 98821   agaccatccc ggctaaaacg gtgaaacccc gtctctacta aaaatacaaa aaattagccg
 98881   ggcgtagtgg cgggcgcctg tagtcccagc tactgggag gctgaggcag gagaatggca
 98941   tgaacccggg aggcggagct tgcagtgagc cgagatccca ccactgcact ccagcctggg
 99001   cgacagagcg agactccatc tcaaaaaaaa aaaaaaaaaa aaaaaaaaa aaaaaaaaaa
 99061   aaaaaaaaa gaatacaacc tttaagttgt atgtattttc ttttgctttg tagcttttat
 99121   gactctctt gatatacaga tatttaaaaa tttatgtat caaatatgtt ttcctttata
 99181   attttttcct tttctttat gtttagatat tctttcccat gctattgacc aaaagttatc
 99241   tgcattttct tctggtcctt ttaataatcta ctttgcaatt cacagtgtaa aatggggata
 99301   tgcaggaatg ggcaagactt tcatgcacat gttccatctc ccaggttttgg gtgagtgttt
 99361   caaaactgta tgcttgtatg tttgaaatgt tcatctcagg aactgattta aaatccataa
 99421   cttaagggga tgaaaactct ttccaatgca tttccaatgt gcagtgcaca tgtatctgat
 99481   ctgcaattgg aaaatgtcaa aatgtgtcag ctcatttcat actcttttaa gctatccttt
 99541   gattaaggga gtgctgtatc aacttatgtg agcctgcagt caaatctacc ttcaaattat
 99601   tagcacctgg tgagaaatgt ccttcccatt ctaaacacta gttcatcatg tcttattttgt
 99661   aattcatttg atgattttga tataacatta taaatattat acgtgactaa gcctttacac
 99721   tgaagctttg ttccttgtaaa aatggcagaa aatggcagaa gcatactctg tctctgatac
 99781   agatgtgtgg atctagacta agcaggtgtg gtgctaggct gagtaaatca ccagttccaa
 99841   atgtctttat gttgggaaac atgatgtcat taatgtttat cttgtactac tgagtctaac
 99901   ttagtttct agcctatgga gtgggaaat cttttgtgaat tcactgttat tgacaaataa
 99961   ttattagaaa ataaaattaa tactctagtc caagtgttgg caaactttt gtaaagggcc
100021   agatgatagc tattttaggt tttgctggcc ataagattc gattgcaacc actcaagtct
100081   tccttttgtag cagcagtaga caatacataa acaaatgggc ttggctgtgc tccagtaaaa
100141   ctttatttac aaaaacaggt ggtctacacg gttcggtctg cagactgtat tttgccaact
100201   actgtgtagt caaataattg cttcttttcag agttctttct tttttttcag aattctttga
100261   aaactatgta ttagattcct cattgttata taaaaactgt ttattatttc aaaagtgggga
100321   atttgttgct atcctggaaa atatttaaaca agttctccta taattgatac tttaagactt
100381   tgacttgaat gtcttaaagt taaattggaa agtcctttga aaattatttg aagggaagta
100441   tcatggtgta aacatttcag aattgtttgt taggaatagg ttgtgccaat tgcaaatgaa
100501   aagttagttt ctcaaatctt ctttcatatt agtggcccat agcttttcttc ctaaacaaat
100561   ctttctatct tcttccaaaa agctggatat agctcttagt ttcagtggggg tccacgctta
100621   aagacaggaa agcatatggg tgccatacat ttgttagtat ttgtctctac aaaatcacaa
100681   aaattgaaca ctccagagct ctaaattaca aatttggatg gtgtgccta ttgcagatca
100741   taaaggccac gtgtgcaaga ttcatcgtca atagcattgc ttcatgtttt agtaaatcag
100801   aatgactgac tggaactttt acatctttt ttgatggatt ctctcatggt atagactgta
100861   acctgtgtgt caatctctaa ctgatatca ttaatcacat ttcaaagcta aatacaattg
100921   ggggatgtaa gttttatatt tatacatcaa aatatgtaca ttttaggggg taggcaatat
100981   acaaacatat atatatatgt atatgaacaa acaatattta tatatataat gtttaataat
101041   cagcctccca tgggccctga atatccatga atttttattt atgcaaaatt tcaatgctat
101101   tagtgctgaa aagaggttgg aattcatgct ttgaaagact ttacagtcta tgataaggct
101161   tttgttgttg ttcttgtatt ttttgtttgt ttttatagtc ttggcagaca cttgtttagt
101221   gtttggtggt tggcttatt ttggaagcac cctcaaaaca attggagata atatattaca
101281   aataaagtgg atgttcaagc tggggatttt tatctttgtt caaaaataaa gtgtaatgtt
101341   atagtaatag gactttttcc tgtttataa tgtaacttaa aaaatttata gcaataaatg
101401   cccacaggag aaagcaggaa agatctaaaa tcaacaccct aacatcacaa ttaaagaac
101461   tagaaagca agagcaaaca aacccaagag ttagcagaag gcaagaaata actaaggtca
101521   gagcagaact gaaggagata gacacaaaaa aaccccttcaa aaaatcaatg aattcaggag
101581   ctggtttttt gaaaagatta acaaaatagg tagaccgcta gccagactaa taaagaagaa
101641   aagagagaag aatcaaatag acacaaataa aaatgataaa ggggatatca ccactgatcc
101701   cacagaaata cgaactacca tcaggtgtgt atatactata cacacctcta tgcaaataaa
101761   ctagaaaacc tagaagaaat ggatacattc ctggacacat acaccctccc aggactaaac
101821   cagaaagaag gcaaatccct gaatagacca ataacaagtt ctgaaattga ggcagtaatt
101881   aatacctacc aaccaaaaaa agcccaggac catgtggatt cacagccaaa gtctaccaca
101941   ggtataaaga ggagctggta ccattccttc tgaaactatt ccaaataata gaaaagagg
102001   gctcctccct aactcatttt aggaggccag catcatcctg ataccaaaac ctagcagaga
102061   caagaaaaaa aaaacaacaa aattcaggg ccgatatcct tgatgaacat cagtgagaaa
102121   atcctcaata aagtactggc caactgaatc cagcagcaca tcaaaaagct tatccaccag
102181   gactttttcaa gtgcttttaag cagtggaagg gtcactgaaa tatgtattgc ctcctaacat
102241   taattttga agaacaactt tcatttgagc atggaagcta aggtctgttt tgaaagtctc
102301   attactctat attcatatct tgtaaaaata cacttataca cttccttaga aatgtaattt
```

-continued

```
102361  ggacaaaaat tacatttcca aaaagaatat tttcaaataa tcaagcttat ttttagtaat
102421  aaactaagtt tatcagtaaa actaaggggc tgaaattttg ccaaacgtaa caaagtgaat
102481  atatgaaaac aacaaagtag acaatattat caacaggatt tataattttt gtttttcaag
102541  atatccatgg atgctttgct gctaatttct cagaccagtg caacactatg tgatttgata
102601  atgggagttt ccctcccaag tacctgtaac ttctacagta ttatctttgt gggtggtatg
102661  ctgggatatt ctgaaaagtc gtcctttatt cctcacataa tggaaccaag agctggaaga
102721  gagcaagaag agcatagtca ggaaagagag aagaaacatt cagagaaaca cctcatgggg
102781  tttaaaaatt ttataataga tttaacctga ggaagataaa gtcttgtatt aacaaataaa
102841  tagaagcaac tgcaaatatg tttgaatgga gactatgggg catattttc tttgctccat
102901  ttcttttct ctcttaaaat acatgtgtgc tccttcatac aaaaatttat tgttaatttt
102961  ccaattgcaa aagtacttaa taaagagcac tttgaaaaca aagtaaaaca gtaagaatta
103021  cctatcattg atgacctaga gatataaatg gtaaaacttg aattcatgcc ttcttttc
103081  cttaacttat atattttttg tttttacaaa aagaggatcc atcacatcac atgtgtttca
103141  taagttgccc ttttgtatag caatgtactt aaatatctct gactacatct tgtcaatgtg
103201  ctttttctc aaaataattt taaaaatagt tttatctagc tcattttta aatcttaaaa
103261  gcaatgcata tttactgcaa aataattcag aaaacataca ttaaaaagat atcgtcttc
103321  gtactactgc caaaagttgc tgaagcttgt tttacagggc acttgaaaga aggtatttat
103381  aagccaggcg cggtggtgcg tgcctgtaat ctgagcattt tggaaagcag aggtgggcag
103441  atcacctaag gtcaggagtt caagaccagc ctggccaaca tggtgaaacc ctgtctctac
103501  taaaaataaa aaaattagct gtgtgtggtg gcgggagcct gtaatcccag caacttggga
103561  ggctggggca ggagaatcac ttgtgcccgg gaggtggagg ttgcagtgag aagagatcga
103621  gccactgcac tccagcctag gtgacagagc gaggctccat ctgaaaaaaa aaaaaaaaaa
103681  aaaaaaaaaa aaaagaaggt atttatgcta aaataggttt aggaaattgg gggttaaatg
103741  cacataaaca ggtttcttt tattacagga cttctcagag cctttaatat gctgatgtgt
103801  actatgatat tcacagaagg gaggtaaaat gtagagtttc ccaaacttat ttgatgagag
103861  aagctttatt tcaatagatt agttttcctt agaacacact ttggtataca gtgttcttta
103921  tacacacaca cacacacaca cacacacaca cagaggcata ctcaaacaat ctttatttac
103981  ttattactag gtgattaata attggataat gagtttaata tatcatggtc atctattcac
104041  attaataaat gatccacata atcattttaa tgactgccaa gtataccact gttttcatgc
104101  atcctaattt ttcaaaacaa ctccttcttg atgtacattt aagctgtttc catctttttt
104161  gcatttgcaa atcatgctga atcaatacct ttgtacattt ctgtatattt gttcaataat
104221  ttcttagga tatatgccta acaaagagac agtatgggcc ttttcatctt atctgtattc
104281  ccagattcgt ttctttgcct aggaatgaca gtttttaata caattaggat agtttttcct
104341  aattaggata aggaattgtc cactcatgaa gtatgaatag gatcagagta agctatcaga
104401  aatatagttt cttaaatact tgcaattatt cacaagaatg atatgtattt atgaaggagt
104461  aattattaac attgttagg agggaagctt aatacaaatt atgtaaaaaa ttagaaacca
104521  aattccaaaa atattattcg ccccccttcct tctagagaat aaaataggtt aaaaggaaca
104581  ataccttctg aattttaagt gaaaaagaaa cacatttaa gtccaagtta agatgtagaa
104641  atatacccct attgatttgt ctcttctcat taattaaaac ctgaaatacc ctatccagtg
104701  ttttattatg actacattct atcaaaaatc ccataagtta ttccattgga gtttacatag
104761  gctgatatct catcctgctt tcaataaaaa gtcagaaagc aaatctgttt gatcagattt
104821  gctctgagta ttggagtcta cacttaagct tttgaacaat tatatacagg actgagcaaa
104881  ggctattgtt tgcttatgtg gtagattgga atcgcgaatg ttaatctcat cccaagaac
104941  actttttaat ttatatcaaa attgtataaa cagggtcacc agtgctaaat gggatgtcaa
105001  tgacctatga agatcagaaa gtaaacaaag atcttaaaat aagcatgtaa cctgaacacc
105061  tcaagaattg ttgtatattg aaaggcattt gtttacataa agaaagggaa aattacttag
105121  tgctaattca gtttgtggca ggttccttct ttctcaatcc atcagcaaaa tggtgatgga
105181  caaaagtttc accctgtcta ttttaaaggg ccgtggagaa aaccaacatg aaccaatggt
105241  tcattcacgt cctttgaaat cgccgggcatt cagaagccta cctacttcct ttatgggcta
105301  tttaacttca ggccaatttc ttttttcagg atgagcatcg aggaaagagg atagccagga
105361  aacttgatta agattaaagg agtaagatac agccggcagg aagaggtagg tagattcact
105421  gaggacatgt tcagggattt ctttgaagcc caaactccca actgtaaaag gaattccagc
105481  cagatggaga acaaatggga acatgttttg gggtgagtga gccacatgtt ttggtttcag
105541  gggtgaagga ttgatgagtc caaaaaacgt ttgtgtaaaa agaggagaat gaattaagaa
105601  aaagaaacgc tatttttat tatgacttat tagatacata taattatgga tctgaaactg
105661  aggcaaatta aaaattcacc aacatattga catcctcct tatccgtggg gataaattcc
105721  aagaacctca gtggatttct gaaaccgcag gtggtgccaa acctggttgc tgctaatgga
105781  aacacgtttc tgttcatttc ttccacaaag ttaatgcctt ttctatctta tttatcactc
105841  actgtagcct taacattgt agctaaggtg taacagcaaa actggcacaa atttgttttt
105901  ccttcttcac aatttaatgg atagaagact tattcttact gtagatctta gcatcctcag
105961  cataggattt tttttctttc ttcttaagt ccagaacttt catcttttca cctaaaggaa
106021  gtagtttata ccttcttttt ggtgtattcg aatggctagc atcgttactc ttgccatttg
106081  gagccattat taagtaaaag aagggttact tgaacacagc actgggttgc tgcaagagtc
106141  catttgataa ccgcgccagt tactattaat aagtgactga ctgagggta gtgtacacag
106201  ctttccaagt caccaaggac atgattccag aggcagtgta gcctagcgca tatggctctg
106261  tggtcctact gcctagatt ggatccaggc tcttcgagtt acactgagtg actctcagga
106321  ggtaatttga cctctcttg cctgactttc ctatcacta aaatgaaaat aatagttcc
106381  acctgctagg ttagttgtgg agagtaaatg agctattaga tgcaatgagc ttagaacagt
106441  gcttgacaca tgtggtaagt aagtcctcag tgaatgttag tcattggttt gaacatttaa
106501  agacccacta agctggatac acttcttctt gttctccctc gctccctccc ttcttcctt
106561  cctgcctgcc tgccttcttt ccttccttcc ttccttcctt ccttccttcc ttccttcctt
106621  ccttccttcc ttccttcctt ccactttctt tctttctgtc tttcgacagg gccttgctta
106681  attgcctagg ctggagtgca gtggctccat ttcggctcac tgaggcctca tactccttgg
106741  tttaagcaat cctccccct cagcctctca agtagctggg atcacagtca tgtgccacca
106801  tgcctggcta atttttgat ttttttttt ttggtagaga tggagtctca ctatgttgct
106861  cctgggctcg agcgatcctc cggcctcagc ctcccaaaat gctgggatta caggtgtgag
106921  ccacagggcc tagccacctt tcctttgat atcttaattt attggttct ttttcttta
106981  attatacttt aagtttagg gtacatgtgt acaacatgca ggttagttac atatgtatac
107041  atgtgccatg ttggtacgct gcaaccatta actcgtcatt tagcattagg tatatctcct
```

-continued

```
107101    aatgctatcc ctcccccatc accgcccccc ccacaacagt ccccggtgtg tgatgttcac
107161    cctcctgtat ccacgtgttc tcattgttca attcccacct atgagtgaga acatgtggtg
107221    tttggttttt tgtccttgcg atagtttgct gagaatgatg gtttccagct tcatccatgt
107281    ccctacaaag gacatgaact catccatttt tatggctgca tagtattcca tggtgtatat
107341    gtgccacatt ttcttaatcc agtctatcat tgttggacat ttgggttggt tccaagtctt
107401    tgctattgtg aatagtgcca caataaacat acatgtgcat gtgtcttat agcagcatga
107461    tttataatcc tttgggtata tacccagaaa tgggatggct gggtcaaatg gtatttctga
107521    ttctagatcc ttgaggaatc gccacactga cttccacaag ggttgaacta gtttacattc
107581    ccaccaacag tgtaaaagtg ttcctatttc tccacatcct ctccagcacc tgttgtttcc
107641    tgactttta atgatcacca ttctaactgg tgtgagatgg tatctcattg tggttttgat
107701    ttgcatttct ctgatggcca gtgatgatga gcatttttc atgtatctt tggctgcata
107761    aatatcttct tttgagaagt gcctgttcat atcctttgcc cacttttga tggggttgtt
107821    tttttcttgt aaatttgttt gagttagccc tttgtcagat gagtagattg caaaaatttt
107881    ctcccatttt gtaggttgcc tgttcactct gatggtagtt tcttttgctg tgcagaagct
107941    ctttagttta attagatccc aattgtcaat tttggctttt gttgccattg ctttggtgt
108001    tttagacatg aagtccttgc ccatgcctat gtcctgaatg gtattgcctg ggttttcttc
108061    tagggtttt atggttttag gtctaacatt taagtcttta atccatctta attaatttt
108121    gtataaggtg taaggaaggg atccagttc agcttctac atatggctag ccagttttcc
108181    cagcaccatt tattaaatag ggaatccttt ccccattgct tgtttttgtc acatttgaca
108241    aagatcggat agttgtagat atgtggcatt atttctgagg gctctgttcc attggtctat
108301    atctctgttt tggtaccagt accatgctgt tttggttact gtagccttgt agtatagttt
108361    gaagtcaggt agcgtgatgc ctccagcttt gttcttttcgg cttaggattg acttggcaat
108421    acgggctctt ttttggttcc atatgaactt tgaagtagtt ttttccaatt ctgtgaagaa
108481    agtcattggt aacttgatgg ggatggtgaa tctataaatt accttgggca gtatggccat
108541    tttcatgata ttgattcttc ctacccatga gcatgaatg ttcttccatt tgtttgtatc
108601    ctcttttatt tccttgagaa gtggtttgta gttctccttg aagaggtcct tcatgttcct
108661    tgtaagttgg attcctaggt attttattct ctttgaagca attgtgaatg ggagttcact
108721    catgtttggc tctctgtttg tctgttattg gtgtataaga atgcttgtga ttttgcacg
108781    ttgattttgt atcctgagac tttgctgaag ttgctatca gcttaaggag attttgggct
108841    gagatgatgg ggtttctag atatataatc atgtcatctg caaacaggga caatttgact
108901    tcctctttc ctaattgaat gcccttattt ccttctcct gcctgattgt cctggtaaga
108961    acttccaaca ctatgtggaa taggagtggt gagagagggc atccctgtct tgtgccagtt
109021    ttcacaggga aagcttccag tttttgccca ttcagtatga tattggctgt gggtttgtca
109081    tagattgctc ttattatttt gagatatgtc ccatcaatac ctaatttatt gggagtttt
109141    agcatgaagg ttgttgaatt ttgtcaaagg ccttttctgc atctattgaa ataatcatgt
109201    ggttttttgtc cttggttctg tttatatgtt ggattacgtt tattgatttg cgtatgttga
109261    gccagccttg catccaaggg atgaagccca cttgaccatg gtgaaaaagg tttttgatgt
109321    gctgctggat ttggtttgcc agtattttat tgaggatttt tgtattgatg ttcatcaagg
109381    atattggtct aaaattctct ttttgtgt gtctctgcca ggcttttgta tcaggatgat
109441    gctggcctca taaaatgagt tagggaggat tccctctttt tctattgatt ggaatagttt
109501    cagaaggaat ggtaccagct cctccttgta cctctggtag aatcggctg tgaatccatc
109561    tggtcctgga ctttttttgg ttggtaagct attaattatt gcctcaattt cagagcctgt
109621    tattggtcta tgcagagatt caacttcttc ctggtttagt cttgggaggg tgtatgtgtc
109681    aaggaattta tccattcatt ctagatttc cagtttattt gcatagaggt gcttgtagta
109741    ttctctgatg gtagttcgta ttctgtggg atcagtggtg atatcctctt tatcatttt
109801    tattgcgtct atttgattct tctctctttc cttattagtc ttcctagtgg cctatcaatt
109861    ttgttgatct tttcaaaaaa gcagctcctg gattcactga ttttttgaag ggttttttcgt
109921    gtctctatat cctttcacttc tgctctgatc ttagttattt cttgccttct gctagctttt
109981    gaatgtgttt gctcttgctt ctccagttct tttaattgtg atgttagggt gtcaattta
110041    gatctttcct gctttctctt gtggacattt agtgctataa atttccctct acacactgct
110101    ttgaatgtgt cccagagatt ctggtatgtt gtgctttgt tctcattggt ttcaaagaac
110161    atctttattt ctgccttcat ttcattatgt acccagtagt cattgaggag caggttgttc
110221    agtttccatg tagttgagtg gtttgtgtga gttcttaat cctgagttct agtttgattg
110281    cactgtggtc tgagagacag tttgttataa tttctggtct ttcacatttg ctgaggagtg
110341    cttcactcc aactatgtgg tcaattttgg aataggtgtg gtgtggtgct gaaaagaatg
110401    tatattctgt tgatttgggg tggagagttc tgtagatgtc tattaggtct gcttggtgca
110461    gagctgagtt caattcctgg gtgtccttgt tagctttctg tcttgttgat ctgtctaatg
110521    ttgacagtgg ggtgttaaag tctcccattt ttattgtgtg ggagtctaag tctctttgta
110581    ggtcactcag gacttgcttt atgaatctgg gtgctcctgt attgagtgca tatatattta
110641    ggatagttag ctcttcttgt tgaattgatc ccttaccatt atgtaatggc cttttttgtc
110701    tcttttgatc tttgttggtt taaagtctgt tttatcagag actaggattg caaccccttgc
110761    cttttttgt tttccatttt cttggtagat cttcctccat cccttttatt tgagcctatg
110821    tgtgtctctg caggtgggat gggtttcctg aatacagcac actgatgggt cttgactctt
110881    tatccaattt gccagtctgt gtctttaat tggagcattt agcccatta catttaaggt
110941    tgatattgtt atgtgtgaat ttgatcctgt cgttatgatg ttagctggtc attttgcttg
111001    ttagttgatg cagtgtcttc ctagcctcga tggtctttac aattggcat gttttacag
111061    tggctggtat tggttgttcc tttccatgtt tagtgcttcc ttcagaagct ctttagggc
111121    aggtctggtg gtgacaaaat ctctcagcat ttgcttgtct gtaaagtatt ttatttctcc
111181    ttcacttatg aagcttagtt tggctggata tgaaattctg ggttgaaaat tctttctttt
111241    aagaatgttg aatattggcc ctcactctct tctgacttgt agagtttctg ctgcgaaatc
111301    cgctgttagt ctgatgggct tccctttgtg ggtaacccga ccttctctc tggctgccct
111361    taacattttt tccttcattt caagacaatt atgtgtcttg gagttgctct tctcgaggag
111421    tatctttgtg gcgttctctg tatttcctga atctgaatgt tggcgtgcct tgctagattg
111481    gggaatttct cctggataat atcctgcaga gtgttttcca acttggttcc attctccctg
111541    tcactttcag gtcaaccaat cagacgtaga tttggtcttt tcacatagtc ccatatttct
111601    tggaggcttt gttcatttct ttttattctt tttctctaa acttctctt tcacttcatt
111661    tcattcattt gatcttccat cactgatact ctttcttcca gttgatcgat tcggctactg
111721    aggcttgtgc attagtcacg tagttctcgt gccttggttt tcagctccat caggtccttt
111781    aaggaattct ctgcattggt tattctagtt agccattcat ctaattttt ttcaaggttt
```

-continued

```
111841  ttaacttctt tgccatgggt taggacttcc tcctttagct cggagtagtt cgattgtctg
111901  aagccttctc tcaactcgtc atagtcattc tctgtctagc tttgttccgt tgctggtgag
111961  gagctgtgtt cctttggagg aggagaggtg ctctgattt tagagttcc agtttttctg
112021  ctctttttt tccccatctt tgtggttta tctaccttg gtctttgatg atggtgacgt
112081  acagatgggg ttttggtgtg gatgtccttt ctgtttgtta gtttccttc caacagtcag
112141  gagcctcagc tgcaggtctg ttggagtttg ctggaggtcc actcctgacc ctgtttgcct
112201  gggtatcagc agcggaggct gcagaacaga ggattttggt gaacagcaaa tgttgctgcc
112261  tgattgttcc tctggaagtt ttgtctcaga ggagtaccca gccgtgtgag gtgtcagtct
112321  gccctactg gggggtgcct ccgagttagg ctactcggag gccagggacc cacttgagga
112381  ggcagtctgt cccttctcag atctccagct gcgtgctgaa agaaccactg ctctcctcaa
112441  agctgtcaga cgggacatt taagtctgca gaggattctg ctgccttttg tttggctgtg
112501  ccctgccccc agaagtggag tctacagagg caggcaggcc tccttgagct gcggtgggct
112561  ccacccagtt tcagcttccc agcagctctg tttacctact caagcctcgg caatgcgggg
112621  caccctccc ccagccttgc tgccgccttg cagtttgatc tcagactgct gtgctagcaa
112681  tgagcgatgc tccatgggca taggaccctc tgagccaggc acggttgtaa tcgcctggtg
112741  tgccgtttgc taagagcatt ggaaaagcgc agtattaggg tgggagtgac cggatttttc
112801  aggtgccatc tgtcacccct ttctttgact aggaaaggga attccctgac cccttgcact
112861  tcccagggga ggtgatgcct cgccctgccc tagctcacgc tgggtgcgct gcacccactg
112921  tcctgcaccc actttccgac actccccagt gagatgaacc tggtacctca gttggaaatg
112981  cagaaatcac ccatcttctg tgtcgctcat gctggggagct gtagactgga gctgttccta
113041  ttaggccatc ttggctccaa cccccaattt atttggttct taatgaccttt tttttttt
113101  taagagtcac ttctcaaaat atgaatagtc tgttaattat ttatatttca gtggacccac
113161  cgcaaagctg ctatcaatta ataatacta cagcaggatt taatttgttc tcatacttac
113221  tcaatgggat accacttggg gggaagagca agaagtgatg agccagtggg aagcatccta
113281  ggacaaacct aacccaccct tttctacttt atactaaaca gtccaccaat tatagttttg
113341  ctaattgcaa ggaaaatgtt aagcctataa tgtgtcaatg caaagcacta aagaaagtac
113401  gtgctaatac aattctgtga gataaagtag aaggctgtga tacatttttct ggctccttgc
113461  cttaaccatg ggaagaaaaa agtgtcttat ttgaaggcag tcatgaaagg ggaggaactc
113521  atgaaagagt ctcgtaggtt gattgtgaaa aagacgatgt agaggaattc cagagtctct
113581  gttttagttg catgctgtgg aaagccaagt tagcgtagag ctgaggatga agcccaaaca
113641  accacatgct tgaggcatca aaggacagaa acaggaaagg aaggacaggc agacacacac
113701  acacagagac acagacacac acacacagac acacacacac acactcaaag gaattatttt
113761  aaagcagtaa acatatcttt tactgaaata ccaaatttca ttttatgggc attttttgtt
113821  tttgagttac atatgtcaga gaagggtact ctcatcctct caatgtttga gtttgtttct
113881  gtgttgatcc aatcctaact gcaggatttg ttcagtgaac caagacatgt atcttttaaag
113941  ccaaaggtgg tttcactaaa acagtgattc tcaaactttt tgatctcata tccttataca
114001  actttttaa attattgaga attttcattt tgttattata cccattgata tttaccatat
114061  tagaaactgg aactgagaaa aaactactta ttcacttatc taaatcccat tttacatttt
114121  gataattttt tttgtgaaaa catttttcaa aacaaaaaaa taatgagaac agtggcaaaa
114181  tgttcagctg aatagatgac agattctcat atctgtttct ggatttgtt ttttgtatca
114241  tgtagtctct ggaaaactct tatgtactat aatgagagaa cagaaacgaa aatggaaaga
114301  acactttagt attttggggga aaatagtttt gaattcatag acttcctgag aatgtctcag
114361  gaatacccca ggaatctcca taccacactt ggagaactac tatcccaaga caaagtcgta
114421  tgcttggtcg agactgagtg gcctgattta attgttgctg ttgttattgc atcactatag
114481  gttattggtt ttaaaaagcc catctcttca cactctgaat ttggaatatg tcttatattg
114541  atagtgactt acaacagctg ttggccccgt ggcagttgtg atgtagttat tacctgcaca
114601  agcatgaatt tggtcatagc tattcacggc atcagtattt ttattgaatt atttgcattg
114661  ttgttatgtg ttgagagttt agttgtcatt taaagtctct ttctttcaga atttatagta
114721  taacatagtt ctgagatgag aagttactgt agatgcagaa aggcaagcag agagcagtgg
114781  ggcatatatc tgacattagg aaagcgattt tgggagaagg aataggattc tatattttct
114841  tgcataagaa caacaacgta cttcatggta tcaaaaaagg tactaaatcc acacgcatct
114901  atggctgaat tgtgtgttgt tagtgagaaa tgtgcaaaat gattgccttt catgtgccaa
114961  accacacacc tgaagacaca aaaacttgcc aaatctcttg gtatcgagga aagatgctgc
115021  acagcaatga gaggatgatg tgaccaattt acgtgtcatg caggattatc attaaggtag
115081  ggtgtcatta cttaattggc agccttttc ctttcttaga ggtccattaa ataattcatg
115141  tctttccatt gatgacatct tagattgagt acaatagtca taacaatatt tttgactggt
115201  gtacttgttt cctagacttg tgatcacagg ttaccacaaa ccaggtggct taacacaaca
115261  gaaatttatt ctctcacagt tttggggact agaagcctga actcaaggtg tcagcagagt
115321  catgcacctt ctaagactgg tggaatccct cctttcctcc ttctagtttc tgatggtggc
115381  gtaattcctt ggtgtttctt ggcatgcagg tgtatcatcc cagtctttgc ttctgtcatc
115441  acaggatggt ctccttgtgt acctctgtct tcacatggtg tttttcccttt tttgtaggga
115501  caccagtgat attggattaa ggactcaccc aactccaata tgacctcatc ttaactaatt
115561  acaactataa aaactctatt tccaaaacg tcacattctg gggtactggg ggttaggact
115621  tcaacatgtc ttttgggagg ctataattca acccataaca acagataagg aacataatat
115681  ttctatgtct gtggcagaga aaattctatg ggtttccaaa ttctgttttg tattcctccc
115741  tcctgggcac aataaaaatt ttattttcca gttcccttgc agtaaagcaa gagtgtgtga
115801  ttaattatgg gcaatgaaat ttgagaataa gtggcatgtg tcactctgg gctgaggcag
115861  taaaaagctg ctgtgtgact tttcagtttc ttgattttcc tcaggtagtg agtgtaagag
115921  caatgtgttg agatagcaaa cccacaagat cacagcagcc tggatctctg agttactata
115981  tggatgatga agcactacac tgttgagtct gacctaaagc aatctttata ttgtgagaaa
116041  tttgtgtgtg ttaaaccact gagattttgg agtcatatgt cacagaagca taatctagtc
116101  tatcctgatt aacacatgaa gatgcaccaa gaggtagagg atggcatgaa gtgatgaatt
116161  tccaattaac tttctgtagc catatctatg aattctttct aagggtgaaa tacttctttt
116221  aacattcaaa aatcaatcaa tgttacacac cacatcaata gaataaagga caaaaaccac
116281  atgattatct caatagatgc agaaaaaaaa attgacaaca tccaacactt tattatgatg
116341  aaaacactga acaaacgaag gcaagtcaac ttcctcaacc taataaaggg catctacaaa
116401  aaaatccatc actatgatca tatataatgg tgatttcctc ctaagattaa gaacaatatg
116461  agaatgtcca ctctctcatc agtttcgttc aacatttgta ctggaggttc gctagccaga
116521  gcaattaagc aagaaaacaa gataaaggca tccagacagg aagggaaaaa gtaaaattat
```

-continued

```
116581  ttttattcac atatgatatg gtcttatgta taaaaaaatt ttaaggaact cacacaaaat
116641  gattaaatct aatataaatg aattcagcaa agttgcaagg tacaagctca atatatgaaa
116701  tcaattttat ttatatgtac tagcaatgaa caagcccaag tgaagttaag aaaacaattc
116761  aatttataat agaattaaaa gaataaaatg cttgggaata catttaaaaa gtataagatg
116821  tatacactga aaacaataaa acattattga aagatattaa agaagatcta aataaatgga
116881  aagatattcc atgttcatag attggaagtc ggtattgggt tttttgttt gtttgtttgt
116941  tttttgcttt cttaacttgt attttaggtt caggggtaca tgtgaaagtt tgttacatag
117001  gtaaattcat gtcacgggg ttgttataca gattatttca ttacccatga attacgccca
117061  gtgcccaata gttatctttt ctgctcctga taatattgct gaggtgataa tactctccca
117121  aattgatcta cagattcaca caattcctat taaattccag ctacctttt tttttggtaa
117181  aagttgataa ctcatgttaa aataccctatg gaaattcaag gaacccagaa cacctagaac
117241  aaccctgaaa aacagcaaag ttggagggct cactcatcag aataaaatta acaggctcac
117301  acatactgtt ttttagaaaa gcaacatctt tattttaaac ataaaattaa tatattctta
117361  cttgtactag taaggatagg caaggtcatt cttcatgaac aaactctcca aatcttaaaa
117421  gtttagaata ataagagtta atttttgct ctaattaagt gtccactggg gattggctga
117481  gagctccgat ccacatctca tttccgaatc taggctgatg gagcagccgc tatctcaaac
117541  ttgagccacc atctcaaggg tttgtgtcaa aagaaaagag ctcaggagga tcctgcacca
117601  gcaattaaac attccagcct ggaagtgaca catgccattt ttgctcataa ctctttagac
117661  agaaccaatc acatggtgcc acccaaccac aagggtcct ggtataattc tttcatgggc
117721  tcacataaca agtaaatgca actctgtagt aaagagatag attatctgtt gtaagaaaat
117781  caaatgatac aaaaccattt cactcagtaa taccccagag atgatcaccg ttaacaaggt
117841  agcatatatt ttcctagactc ttataggaat atacatatcc acacatacac aatttaattt
117901  aaaaatcaca ctagaaatgt cattccaaaa tctgttcctt cctgggcccc cagtcatata
117961  acaatcacat ttctccatga aaagacatat aattttacct catatctttt agctgctaca
118021  ggctaggatg gactgtgatt tacttcattc actctgtata gagtaatatt tagtttcttt
118081  ctagattttg atattattaa acactttgta atcaatactt ttgcacctgt atcttagcta
118141  acagtaaatg tttatgactg actgaataaa gatgtcaaca aatgaatgaa tgaaaaccaa
118201  tcaccagtga tttaagactc caaacacatg gcgagagaag taaaaaatgc attattccaa
118261  ccttcttcat gttgtttagc atgcttcaga atggcaataa aggcagagga attcttacct
118321  acgttaatgt agcaggtcat tcacattagc atttctagag tttgttaaac ccctggattc
118381  ctgttcaagt aaaacatttg ttttgattat aaaacttaat atccactctg agagcctgtg
118441  gaaatagaag gtagatggca atgttactgc cgtaagtctg aagctcctga gacatgaaca
118501  agatggtaat gtgactcctc atttatttt tatcttcagt ttcaattttt ttaatcatca
118561  tgtatctaga atgactagtg attttaaatg agaaattgga atctaaagat aatcagagtt
118621  ttagcagttt aaaccaatca ccagtgcacc agcttgaaaa gctttgtgac tttgactgtg
118681  aaggcattta cagtcccagg aggaaagtgg ctttggcagc tctcagttt gatgggttaa
118741  gtagtttgta gttggttttg gagggggtgt tactgtggaa gataaatgaa ttcctcagtt
118801  tatgaactta ctccccaggc tgctcaactc agctaagctc tcatggcaac tgctcgatgg
118861  ggttctcact gtgagacagt cagcaccacg cttgaagccc tgcaggaaaa acaaaccca
118921  ctgaatcaac caaaatattg gagagaactt cagtagtttc agtaaatcct aaatcagaga
118981  agaagatggt gtgtgtgtgt atgtgcttat cgtacatcct tattcacatg agctttataa
119041  ggactcatca taaaagatga ctgaaagcaa ccagaaaaac attcttcta ggctgatcta
119101  tttcattttc aattcaagct gtatatagta tgcaaagcat attttaaaga tatgtttaat
119161  tttgccaatt gtatttgagt agttattttc ttagtctgtg tgtgtgtgtg tgtgtatgtg
119221  tgatgagaga gagagagaga tttggccaag gagataataa gggagaaggt aaataaatg
119281  aggaattata gcaaattatt acgtctgatt tgggaatata gaacaggaat gtatcaatta
119341  actagcaatg cactcacaaa tgccatagac tgggcttatt tcttacagtc ctagagatag
119401  agaatttaa gatcaaggtt ccagcaaagt gggcttcatt ctgaggcttc ttctcgtggc
119461  ttgtaggcag ccaccaactg aatgtgtgct cacatgactt cttttgtatga gcacacggag
119521  agaaaggtgg agagaggcgt ggggaggagc aggcagcaca ttagctctcc agtgtccttt
119581  cttataaggg cactaatccc atcatgagtg ctcctctcat tatttcatct aatcccaatg
119641  atctcccaa atcccatctt caaacactgt cacactgggg tttagggttt caaccaatga
119701  atttagggat gcacaaacat tcattccata ataagaggtg ttaaattctt tgctcactaa
119761  tcagtcccca aaaagttcct aggaaattga agtttaaaac atttctattt tggataatct
119821  ccaggtttaa aaatctccac tctgaaaatg atgtctacac aaacattcat tgttgccct
119881  ccatcttaca cagggttgaa cgtcttcacc ttcattccca ccctcatctc ttacatcaaa
119941  tccttgtgaa ttttttaaaa tggtagagtc agataaagat taaagacaga aacagggtaa
120001  agcaaatttg agaaactgtt tccaggagcc aacccctgga tattccctg tttgccaatt
120061  tcctactgct actacccaaa cctttaattt gacttcactt tcttatctga aatttgacaa
120121  ttaaagatgc atttaagcta acaagcatta acatttaaaa aatgcaaatg tgtatgtgtg
120181  tgtttgtgtg tgttttgagg agaatgccat gttaatagac tattaattt tttgacaata
120241  gtgggatatt ggtgaatcca agtcctttc tttctagcgg atggttgaag ctaactgcac
120301  tgagatcaca gaagttgtat gaaggggaag agacggagta tggagaagtg gatgtgggga
120361  gaggtcagaa tggtgcacca atgcattcac cccagtacat acagcaactc aaaaggctca
120421  tgtcccatat aatggacact gtataaatat ttgttggatg agtaaaatga agaaagacta
120481  ttgaagtgtc tgcggaaaat actaaaattt gggtgttggg tcttataaaa ggatgctgac
120541  atggtataac aacttctttt caccttgcc aagatttcct gagtgtaact ccttgtttat
120601  ctttctttg attttgtatc agtacatcct gagcttgatc ttgggggtta tccaacatgt
120661  tattattact tagataaact gttcactctc tgtaacttgc acctgaaaat gaacaaggcc
120721  attgagaaaa cccaatgctg aaaagctcct taagctgata aacaacttca gcaatctcag
120781  gatacaaaag caatgtataa aatcactagt attcctatac accgacaaca accaagctgc
120841  aagccaaatc aggaatgcaa tcccattcac aattgccaca aaaagaataa aatacctagg
120901  aatacagcta accaggaaag tgaaagatct ctacagggag aattaaaaaa cactgttcaa
120961  agaagtcaga gatgacacaa acaaatggaa aaacttaaca tgctcatgga ttagcctctt
121021  gcagaaaagg gaagaccttt gtcatatgca ttattttgcaa atgttttccc tattctgtag
121081  gttgttatt tattctgttg atggttttctt tcattgtgta tgcagaagct ctgttgttta
121141  gctagatccc attcgtcagt ttttgcttgc aattgttttt ggcatcttca tcatgaaatc
121201  tttgcttgtt cctgtgtcca gtatgttatt gccctaggttg tcttccagga tttttatagt
121261  tttgggtttt acatttaatt ctttaatcca tattgagttt atttttgtat gtggtataag
```

-continued

| | |
|---|---|
| 121321 | gaaggggtcc agttttggta ttctgcatgt ggctagccag ttatcccaga accatttatt |
| 121381 | gaatagggaa tcctttcccc attgcttgtt tttgtcagct ttgttgaaga tcatataatt |
| 121441 | gtaggtgtgt ggcctttctc ataagcgctc tctattctgt tccgttggtc taggtgtcgg |
| 121501 | ttcttgtacc agtaccatgc tgtttgggtt actgctagcc tatagtagag tttgaagtca |
| 121561 | ggtaacgtga tgcctccagg tttttttttt tttttttgc ttaggataac gttagctatt |
| 121621 | caggctcttt tttggttcca tattaatttt aaagtagttt ttttctagtt ctgtgaagaa |
| 121681 | tgtcattggt agtttaatag gaatagcatt gaatctataa attgctctgg gcagtatggt |
| 121741 | cttttttatta atatagattc ttcctatcca tgagcatggt atgttttttcc atttgtttgt |
| 121801 | gtcatctctg atttctttga acagtgtttt ttaattctct ctgtagagat ctttcacttt |
| 121861 | cctggttaac tgtattccta ggtattttat tcttttttgtg gcaattgtga atgggattgc |
| 121921 | attcctgatt tggcttgcag cttgcttgtt gttggtgtat aggaatacta gtgattttac |
| 121981 | acattgcttt tgtatcctga gattgctgaa gttgtttatc agcttaagga gcttttggtc |
| 122041 | agagactatg gggttttctc aatatagaat catgtcatct gcaaagagtg acttcctctt |
| 122101 | ttcctatttg gatacctttta ttttctttctg ttgcctgatt gccccctgcca ggactttcaa |
| 122161 | tacaaatgtt gaatagcagt ggtgagagag agcatccttg tcttgtgcca gttttcaagg |
| 122221 | ggaatgtttc cagcttttgc ctgtaaagta tgatgctgac tgtgggtttg tcatagattg |
| 122281 | ctcttattac tttgaggtat gttccttcaa cacctagttt gttgataatt tttaatgaaa |
| 122341 | gcggtgttga attttatccg aagacttttc tgcatttgtg gttttgtctt tagttctatt |
| 122401 | tatgtgataa agcatatata ttgatttgcg tatgttgaac caaccttgca ttctctcaag |
| 122461 | tagggataag gccaacttga ttgtagtgga taaactttt gatgtgctgc tggattcaat |
| 122521 | ctgtcagtat gttgttgagg gatttttgca ttgatgttca tcaaggatat tggcttgatg |
| 122581 | ttttctttt ctgttgtgtc ttccaggttt cagcatcagg atgatgctgg cctcatataa |
| 122641 | tgagttaggg aggagtccct cctctcaaa ttttggaata gtttcagtag gaaaggtacc |
| 122701 | agctcttctt tgtacatctg atagtattca gctgtaaatc catctggtcc tgggctttt |
| 122761 | tagttggtag gctattttatt actgattcca tttcagagct tgttattggt ctgttaatgg |
| 122821 | attcactttt tcctggctca gtcttgggag ggtgtatgtg ctcaggaatt tgtcaatttc |
| 122881 | ttctagattt tctagttttgt gtgcatagtg gtgttcataa tattctctga tggttatttg |
| 122941 | tatttctgtg gggtcagtgg tattatctcc tttgtcattt ctaactgtgt ttattttgat |
| 123001 | cttctctctt ttctccttg ttgtcagct agtggtttat catttttatt catttttttca |
| 123061 | aaaagccaac ttctggattc actgatattt ttaatgtttc ttcctgtctc aacctctttc |
| 123121 | agttcagctc tgattttggt tatttcttgt cttctgctag ctttggggtt ggttttctct |
| 123181 | tggttctcta gttcttttag ttgtgatgtt atgttgttaa attgagatct ttctaactct |
| 123241 | ttgatgtagg catttggtgc tataagttt cctcttaaca ctgccttagc tgtgtcccag |
| 123301 | agattctagt atgctgtatc tttgttctta ctactttcaa aataacttct tgatttctgc |
| 123361 | cttaatttca ttatgtatcc aaaagttatt caggagcagg atactcaatt ttcatatagt |
| 123421 | tgtatgattt tgagcaaatt tcttagtcti gatttctaat ttgattgtgc tgtggtctga |
| 123481 | gagagtgctt gttatgattt cagttctttt gcatttgctg agcagtgttt tgtgtttatg |
| 123541 | tgattgattt tacagtatgt gccatgtggc aatgggaaga atgtatcttc tgttgttttt |
| 123601 | aggtgggagag ttcatagat gtctagcagg tccatttgat ccagtgctga gttcaggtcc |
| 123661 | tgaatatctt tgttaatttt ttatcttgat gatttatcta gtactgtcag tggagtgttg |
| 123721 | aagtatccca ctattattgt gtgggactct aagtctttt gaaggtctca aaaaacttgc |
| 123781 | tttatgaatc tgggtgctcc tgtgttggtt gtatacatac ttaggatagt taggtcttct |
| 123841 | tgtacaatctc gacccttttac cattatgtaa tgcccttctt tgtcttttt gatatttgtt |
| 123901 | tgtttaaagt ctgtttttgtg tgaagttatg attgcaacac ttgctttttt tctgtttttct |
| 123961 | atttgcttag attttttcttc tttccttaat tttgaactta tatgtgtcat tgcacgtgag |
| 124021 | gtgtgtctct taaagacagc ataccaatgg gtcttagttc tttatctacc ttgccattt |
| 124081 | gcactttta attaaggcat ttagcccact tatattcaag gtgagtattg atatgtgtag |
| 124141 | atttggtcct ggcatcatgt tagctggtta uttgcagac ttatttatgt gtttgctta |
| 124201 | cagtgtcatt ggtctgtgta cttaagtgtg tttttgtagt aactggtaat gaccttcct |
| 124261 | ttccacattt agtgcttctt tcaggagacc ttgtaaggca ggtctaatgg taatgaattc |
| 124321 | tctcagcatt tgcttgtctg aaaaggatct tatttctcct ttgaatataa agcttagttt |
| 124381 | ggctagatat gaaattctgt gttggaattt gttttctta agaatgttga ctataggctc |
| 124441 | ccaatttctt ctggcttata aggtttcagc tgggaggtct gctgttggtc tgatgattcc |
| 124501 | ctttgtaggt gaccttacct ttctctctag ctgcctttaa catttttct tgcattttga |
| 124561 | cctcgaagaa tctgatgata atgtgtcttg aggatgatct tgtgaagtat cttacatggg |
| 124621 | ttctctgcat ttcctgaatt tgaatattga cctctctagc taggctgggg aagtgctcat |
| 124681 | ggatgatatc ctgaaatatg ttttccaagt tgcttatact ctcccattt ctttcaggga |
| 124741 | taccaatgag tcatagattt ggtctcttta cataatccca tatttctcag agattttgtt |
| 124801 | cattcctttg tattctcttt tctctattct tgtctgactg ctcatttcag aaagccagtc |
| 124861 | ttcaagctct gagactttt cttccactta gtctattctg ctattaatac ttgtgactcc |
| 124921 | attatgaaat cacttagtgt gttttttcagc tctgtcaggt tggttatgtt cttttctata |
| 124981 | ctggctattt tgtctgtcag ctcctgcatt agttttattgt gatccttagc ttccttggat |
| 125041 | tgggtttcaa tgtactcctg catctcaatg atctttgttc ctattcatat tctgaatcat |
| 125101 | atttctgtca tttcacccat cttagcctgg ttcagaaccc ttgctggtga tgtggtgtgg |
| 125161 | tcatttggag gaaaggaggc actctggatt tttgagttgt caggggtttt gcattgcatt |
| 125221 | ggttccctct catctttgtg ggctgacatt ccctcagttt ttgaagttgc tgacctttga |
| 125281 | atgggggttt ttcttcttt atcttatttg atgacctttgt gagttttgatt atggtgtaag |
| 125341 | gtaaattcag ctgactggct taatttctgg aagattttag ggggccagtg ctcagctccc |
| 125401 | aacctctaaa ctgtgtgctc taaatctggg ggacttgtat caggctcctg agtgttctta |
| 125461 | ctggaaacac tcaggctcca ggctcctgag tgttcttact ggaaacactc aggctccaac |
| 125521 | tttgttcttt ggctcctcga ggttaggaat ccactgtggt gggggtgctg aggtggtccc |
| 125581 | agaccactgg tcattacact ctaataagta gtgtcatcca gagtttcata tgtggtgac |
| 125641 | agtggggatct gtcctaggtc acatatgcca gcagcagctg cagtggcagt gaggtggggt |
| 125701 | gcaccctcct cagctgcagc agggtgctag tgggtgccag ggtgcctgcc tctgtgcggg |
| 125761 | tgttccaccac agtagtggag gcaacataac tcaagggggac caggggctcc tgctggcaac |
| 125821 | tgtgtacaca gttgtgctga tggtggtgtt ggcacggggt ggagcactgg caggcatagg |
| 125881 | tctgtgtgtg ttctctgcac cacaggcagg ggtggtcgct cagggcaggg aagggtttgc |
| 125941 | tgttttctgt acctagtttc actctcgcag cagtgttggt gcaagagcag ggcactggtg |
| 126001 | ggggttgggggc ttgctggctc tgtgcctgtc agggctctaa ctgcaacggc agtcagtgtg |

```
126061  gggaagtggg atgggctgca ctctcactgt agcaggggca gggcagggca gggtgtatgc
126121  acacgcggca ctggtgggt aaggaagaca acacgtgcct gtgcagacac gtccagcaaa
126181  ataatgtggg tggttgctgt gggcacaggg gaagctgctg tgtggggagt ggttgagctg
126241  atgcatggcc atgggggcca ccctgctgga gcactccact ggtcaggcat ggttgccagt
126301  acaggagcta tgatgtgggt tctcagggca cctgaggctg ccttgcaagc aggctgggcc
126361  aggctggggc ctcaggagag gccaggagaa caaggagtgc ccaaatcaga ccaggctggt
126421  ctgatgggta agaccaatct gcaaagttca ggtccgacag ttctcctagg gctaaagtct
126481  cctatgggag ctacttgaac ctagggggat ggccgtctct ggctgtgctt tgctacagat
126541  gcactggcac caaaccatct gagttccacc tcattgctgc ccctaccact tctgtaagca
126601  gctctccctg ccaactcagg tggcggtcga ggggtctcct cctgcagtga ttccagagcc
126661  ctgtggtgag agccatttgc tccttgccag gagttattgg gagccacgaa taagtcctgg
126721  tgtgcagtag ccctgtgcag ggttccagc ttcctctccc ttcagcccag cttctgtgtc
126781  ttccctctgt ccatcctcag ggccttccct ctgaagatct gttaggagtt gtcttggtcc
126841  ctctgtggca gctgttccag ttggctgcat ctagtcagcc aacttgcgct ctctctgaat
126901  ccatgctttc tatggaaaga ttttcctagc caaacccatc tttggcgtaa tttcacttat
126961  atatttattt ttatgtaacc tttaaaaaaa gtgcattaga agttatctat aaatcaccta
127021  taataaaatg cacagatctt aaaggtccat ttgatgaata ttgacagtca cagtttcacg
127081  tgtaaccacc acacaaaaca atatacaaga catttctatc attcagaaac ttccatcctt
127141  ccactttcct gtcaactgcc accccccact cacatataac tgctttctaa caactataac
127201  taaagattag tagtgcctgt tctcagactt catgtaaatg gaaacataga gtgtatatat
127261  atatatatat atatatatat atatatatat atatatatat atatgtgtgt gtgtgtgtgt
127321  gtgtgtgtgt gtgtgtgtgt gtgtttctct cttctttgta tcagtatgat aattttgagg
127381  ttcattcatg atgttttgtg taacagtata ttgtgccttt ttattgttgt gtagtattcc
127441  attgcacaga tttgcttgca ttttaaaggg gctttgcagg aagaagagcc ttttctcaaa
127501  atatgaatta gaatataatg actgaaagag aagtgtagaa ctaaagggca taatgatctg
127561  tgttgagtac tcactgtgga tttcctgtca tatctctctc cttatttagg gactcatcat
127621  taatagtgtc agtggatttc ttctttcttc tgtgtgtcaa cagcagacct acacttgata
127681  gcattttggc cactaacctt gcttgaccct gcactaaccc tcttgctatc aatttcagac
127741  tcccacatct ggggccagac ccacacaact gttccatca ctgctactcc agctcctcag
127801  acattccatc agccaaggag ctcctttgcc caattccctc taagaactgc aagatgcagc
127861  agcagtccca catcctcggc tgcatgtatc tggcatgcag gtgttagttt ttatagtgca
127921  ccaggtagga gagatgccac tggagtaggc gaggttccca ggcccctttt ttggggatt
127981  gttcttttcg tgtcctcaca catactgatt tgaatgtcaa gacagacaga gctgggtagc
128041  tgaggacaga ggggaaggaa aactgctcat cttggggctt gtctttgaga ggcaactgaa
128101  caattttttga tcaattactg aatagcacaa gcctggattc tccagagagg tgattatgac
128161  atgaaataag cacactctac aggtgtttct gggatgcata actccaaata tacagttta
128221  aagaaatgat aaaataaatg atttccag agaaactgaa attgcattct gaagggtgac
128281  ttggcatgat gttcagttag ctgatatatg gcctcttgca ggtattcctt tgcatcccta
128341  gtgcagtgaa gaaagccatt actaccaggg agaagcatgg gagtagtcag tggcacatgg
128401  ctgtcaccac ttgtcttaca ctgttgttaa tttgtttaac aattctgctt agccacttat
128461  tcacacagta ttctttagca gcaaggagaa aagtatcagg gcaaccaagc catggcttgg
128521  agccgtgacg tgtgtaaatg gaagggttag ttttatctga ctgttctttt cttccctgtc
128581  attctttctc ctctcttgaa actcaggctc tcaatggtg aatatcatat ggcatattta
128641  cataatggaa taatatgtga tggtgaaaaa tgtgtaaact agagtaacat gtatcaaaat
128701  ggatatatct ttaaaagtac agagtaaaac aaaaactaaa ttacatatgt atgatatgat
128761  gccattcatg caaaatttta aaatatgcaa aatgattctg tacattgtct agggatagtt
128821  acatatatgt aaagctataa aaatatgctt cagattaata tcctccaaat tcagaatcag
128881  ggtttccttt ggttggcggg ttggagagag atgcacttgg aaggagtaca caactatgct
128941  tgtaatgttt aattttctac actaggccat gacccaaatg tattggtat attgttattc
129001  agatattttt atatattcaa aaatattta caatacatga ataaaaatta ataaaataag
129061  atcattgttg gtttatattg tctaaatcat taaacttcca aaggtttaat attcattcat
129121  tttcaccagc tgccaaactc aagatttttgg caaaaaatga gattggtgtg gaagtgggtg
129181  ttctccgtgt tctctgattt tacaactttt aaatgtcaat gaattgttat tagaaggtag
129241  tttgacactc tgagacagat acatggtatt atgtccactt aattaatgat ataggacaca
129301  ggattttaga taaatgctgg tgtaacccct tttctcatag aattctgtaa ttcctgtatt
129361  catttatgaa atatttattg aggctgctat gtctattgct gtggagtagg tatcaggaca
129421  ggtgcaggta gaaaaaatgt cacttttacaa aatgtagaat acaaaatgag aagtagagaa
129481  aaaaccatga tgaattctag ccagctgca aaaaggaaat gcagcaaagt acaatggaca
129541  taaatccgtt aggagcatct gtaccagatt ggataaatgg ggtttgctga gtcatttcac
129601  tttgtctgag tctggtatgg gatgctgcaa gctggacatg ggtcagggcc ttctggagct
129661  gagatcaaac ctctcagacc tcagtccagg gcttgcattc cttctggat tctcaagatc
129721  ctgtagctca gatcctgtga gaagagccct tgtctaatga aacctatgaa atccattctg
129781  gggaccatgc tggcctggtc tagagatgtg ggcaatgctg acatccagca cgcttgagga
129841  tgcaaggagc accctacgag aatagagatg caaaggcaga ggaagagaaa tgatgcaatt
129901  tcctttcag ctagggagaa ggatagcaga aatgaacaag atctgtgagg aaatttatat
129961  tagggataa acaaatgagt tctgtgcctg cctctttaag tctcttcaat gccatgttca
130021  ttctcttt ttgattacca ggtagtgctg tcctcagtct cttgggggcat acttctttcc
130081  cgatctggca caaatgaccc ctcagggctt aaagacttga gaatgacaga tgatcaaggt
130141  atgcatctct taatcaagct gctgtatttg cccatataaa gaactgttta agaaacacat
130201  ctagcagatc tctgcctcca atgctcacat attatttaac tccaactttt acttttgaaa
130261  aatctaaaga aaatcttatt caggctgcga ccaaaggaga gggaaagcta aaaatgtcct
130321  atgcagggga aggactttt ttttttaatt ttaaattcag ttggtgattt tattagctgc
130381  tggtctgacc ttccagctaa cttcaggatt gtttaggtta agattgaaaa tgtaaatttg
130441  catggcaaga gtgcttttcc aaaggatgct gtttagatag ctcttcaaat tgttggatga
130501  taatgactat tgtcccttac ctttcaaagc tgaaggaagg tctgcagcct gtttacctgc
130561  ccagcttatc tagtgagaac ctaccatgtg tccagccatg ggctaggtcc tttccatcca
130621  attaaacccc tttgccagaa tagcaaagat cacatttcaa aaatattatt ctcacgtatt
130681  tacagatatt agggaacaat ccaacaaaaa acaaaaccat attggtaatg ctattctaga
130741  aaattcaact tgttttactc ttcctggcat tttccttcag gaaaagtagt ttgatagtga
```

-continued

```
130801  agatagtgag atgatgggac tttacaagga gattaggtcc acagatttaa aaaaaaaagg
130861  gccagatgtg caggtccatg tctgtagtcc cagctactca ggaaatcact tcctgatagt
130921  gggaggattg cttgagccca ggagtttata tcagcctggg caatgtaaaa agccttacct
130981  agtaaatctc caagcaagtg cctctagaag tattctgggt gcaacagttg ccctctatgg
131041  gacttctgtc ttaggcatta cactgtcaga ttgatcccca tctctgaaag ccactgttgg
131101  gtccctgctg cagtctgaac tcctgggaaa tgtagcatag ctattcctct tcaaccaaag
131161  attgggagca ctcacttaaa ggtaggttta tggaatgaga ggaagtaggt atttgaccat
131221  tacttgccat tcttcccgct tggaacattt gggccttct tgagctgttc gaagtgatga
131281  gatgacataa taagccagat ttctaccta ctgtgtgttg tgcataatat gctttactgc
131341  gtacttcaaa ttcactaata tatgcactga actagtcatc caatgtacat taattatcta
131401  ctgagaccaa gaccagagtg atctgctcaa tcaaaaacca ttcatatttt tgaaaaataa
131461  aatttactgc ttttatacaa tttataattg ttctccttt tttgggcact tggtatgtgt
131521  caagccctga catgtgttt ttttcatacg ttactgttaa ccatggcaac aatcagaga
131581  ggttggtatt agcataccta tttcatagat gaagaaactg gggctgagaa atattacgcg
131641  acttgctcag acttgtatag acagccagtg gcagcattag ggtaaaaacc catttcttat
131701  catatcttgg agtctgttct ctttccattg aaccaaactt cctcctgtt caaaccatca
131761  acgtggtcag tccagacctg gttagatccc tgcagctgct gaatccacat gcctcgttta
131821  gagcaaccag aacagagatg tgtttcattg gcttgagtga ggaaaaatgc attacaatag
131881  atgtgcttta tgtaaagtgg cctccttaaa aagggatttg ccttttctat acagtgtaag
131941  acattagaag ggttttgcca aagtaatatg ctttccagta tgaatccttt tcagggaact
132001  ttggttgtt tctctcatca ttacacgggg tatcaagctg aaagctttgc tatcctggct
132061  actgaatcct cagtcacagt aaagttttaa ttttagattt tactagcatt gaaaatgtgg
132121  caataagaca cataaacagg acatctaatc catgaagtct tttcaggggc aggaaaattg
132181  cttctctgtg gtacaaggga gattttctat ctgccacttg gaaaacttgt atgaaataaa
132241  ccccaatttg ggatgttttt ggagggcaaa gggtgatgtc ccctatctga ttggacttag
132301  tggtacattt taacctgtga tttatgcaac ttgacattga ggttcattta gctcaaatta
132361  caagtaaagt aattcaatcc ctaatgaagt gtaccctgca tgacatattg accatgggag
132421  ctgacaatca ttgctttaaa acagacatag gttccatttt cttttgtcat tcaaagtagg
132481  ttatcagtta ataaacttaa aacagggcct gctgacctgc cattcttcca gaagtatttt
132541  attagagcat cagaaaagca cataccaaaa tttacattgt aatggaaaaa agagtaaaaa
132601  actgcatgaa ctcactgttg ttcagaggaa tagcttttcc atgcatttat acaagttcct
132661  tccaactttt tattttggaa atcttcaaac ctatagaaaa gcagaaaaca tagtaacatg
132721  aacagctgtg tactcttcgc ttggattaat cagttgttaa tattttgtca catgtgtgta
132781  ctctctcttt cacgtgtaca cacacacaga cacacaattt taaagtaaat tacagacatc
132841  atgacacttc actcctaaat actttagcat gaatcatcta agaatcagga cattcttcta
132901  tattaccaaa atatcattat catacaccta agaaaattaa caattcaaca acataatcta
132961  atataaagtc tgtattccag tgtcctcaat agtctccaaa atgtatttta aacttatctt
133021  ttaaaaatga gaatgcaata aaaaatttca cctttgcattt ggttgttatg catttataca
133081  taattttgtg gggaataaaa atgaaaacaa aggagcttg agccacagtg attgaaagca
133141  cagtgataca gtgttggtta tgtcttatgc caaagtattc ttcaaggatc tctcttataa
133201  agtatgtaac ccatgatagt ggtcattttt ttttccaaaa tgtttcaatc agtaccccat
133261  tttactgtat ttaaattggt aggcacatgg aaatatgctat tacctattca tattttttaga
133321  aacctcagtc tcattgaaga gttgagtgtt ttattctgtt tccatataaa ctgtaggatt
133381  agagttccaa atctagagga tttgttccaa ctccactcaa aaagaaaaaa aaacatgatc
133441  tttcctgcat aaaatgtttt tcagcattat gtttagaatg aattatgttt caaataattg
133501  aattttcttc taatttagac tttccttat tctcctgaaa gcaaaatgtg ttgtaattaa
133561  aaatggaaag aaaaatgaat attcactagg gaaaatgtaa ttgttttatt actgccatgg
133621  acatttggag atcaagttta agaaaatgtg gttgaattca gtgttgcaag tgcacttctc
133681  atctataatt acacatgtct aaggtctgt aaagtgacta taattgcttt agagttgaat
133741  ttaaaggaaa tattgaaaa ctgcatttca tgaattacag tttgcatgga tcttatgtac
133801  tttattttat gtcttttgtac tttcattagc agtgcaaaag ctattgcaga aaatagaaga
133861  ggggaactat gacctttat gttcactttg cagaagatag taacttggtt tttaaagaag
133921  caaaacaata ttatcctctt ccataataaa tcataaaaag gcttatgaac aatgcaatat
133981  attttgaaac aaaaacaaaa atatcttgtc cattggtgat tgctattgaa ttttaaaatt
134041  agctagaagt ttttcctcc agctatatat atatataatt actatttctt ttttgagat
134101  agaatctcgc tctgtcaccc aggctggagt gcagtggtac gacctcggct cactgcaagc
134161  tccgcctccc gggttcacgc cattctcctg cctcagccct ccgagtagct gggactacag
134221  gtgcccacca ccacgctggc taatttcttt ttgtattttt agtagagatg gggtttcacc
134281  gtgttagcca ggatgatctc ggtctcctgt tctcgtgatc tgcctgcctc ggcctcctta
134341  tatttatagt ttttagagac tgcctcactc tgtcaaccag tctggagtga catgataata
134401  gttcactgca gccttgatct cttgggctta agcaatcctc ctacctcagc ttctagagta
134461  gctgggacta caggtgtacc acactgcact ggccaggatc acttcttatt atagaaagta
134521  gaatgtagac tggtggtgtt gtaaggactg cttacctgtt ccggtccaca gggccttcca
134581  catacacaca catgtcctgg tagctacaca tactttctat aaagtttagg gttattctag
134641  cctctcataa gaaaattctg ggcttaaaac atagcttcaa agtgctgcac tgctcccatc
134701  actaacagat ggtcaaacta aatacatgtc catgtcagcc tggctaaatt gggttgcaac
134761  tccaactcta gagtatcaat ttagcatgtg cagagatctt taattgtttc acaaaaaaca
134821  aaaacaaaaa ccctagagct gtctacacaa ttgtctgtaa taaatccaag gtcttcttgg
134881  agaaacattt tgcctcatac tcccagacgg tgcttcactt ggtgggagaa ttaggaccttt
134941  cctttattat ttttagtttt gagtaccttc ttggaggcaa gctatagaaa gaaaagtgca
135001  caaatgataa gcttagtgag ttttcaccaa ttgaatgtcc ctgcataacc agcctccaga
135061  ttaaaaaaag aaaaaaaaaa tctgaacatt tccagcacct aggtgacctc cctcatgtcc
135121  cttcaattcg ggaacccaa caggaacttt agtaccttac tgattgtaat ctcagcaaat
135181  gagcttgctc tactttttgc ccagtcccat taattaactc ttcttcattt ttagtaacaa
135241  cagaaatgca gatgacacga cttcttcatt tctcgaagct atcttcaagg ggttggtaga
135301  catgatggga aaactcttga gtgatgcaaa tgtggctttt caccttcatg cttgcggagt
135361  gactgctact tcatactccg gaggcatgtc ccaaaaggat tataataggg gcagaaggga
135421  ttgtcctggg gcaagtatac agttgtattg atataggtac cttagttaca gcagataaaa
135481  aactaaaatt ttcttagtca ataagcaga gtatttaaat gcattaaatg ctggggaaat
```

-continued

```
135541    ctatagctag gaggaaatcc tgggtaatta actctttaaa tgtcaaaagg taatgcggac
135601    ttctttctgt atctacgagt cttactctcc acatcgagtg ttacttctcc aaccagaaga
135661    atcgctttgt gaaataattt gggctctctt tcttgctatt aatgggacaa caaggaatgg
135721    gatgggggag gcagagggga aggggcggtc agttaggccc agccttcat gctgatgggt
135781    gggcataaaa ggaaatggac tggaaccatc catacctttt caaggagttg tcaactcaaa
135841    cttaagaaaa taattctagg gatgttaata ttttacccta agcctttga ttgtgcatga
135901    aatggaagtg ggtgaggttt agcatgtcac tgaaatttcc cgttgatgca tatctaccat
135961    tctgagaact gtatcctgcc tctttgattt agtgtgacaa ctggattta tttatacaat
136021    taattaatgt ttgcttgacc acttttttcc aatttcttc cgtagcacat aaaagagaac
136081    ctgatataaa tttctctttc aaaacaattg acttagcaac tgctgaccct ctgttctgtc
136141    attctaagga ttgattggat attgttgaat tgtttcattc tacagtaatt aaacataaaa
136201    ttaattatgc tagtaaccca ttattttct gaaccaagga ctaagtcatt tgtttcact
136261    tggttactca gagaatctgc cattagttga acagggaaaa ggaaattgta ctgttgcaaa
136321    cagaaactaa atattttaag gcatatttta atggctaaaa tataatctga aagcttctca
136381    tttccatatg cacagcatat tgaatttgtt taatgtaatt taggccataa atcttttacc
136441    ttatgatatg gtcatttaaa tattttctca ggtggctaat catttagaaa acatgtcgaa
136501    gaagaatata tgttaagaaa gaggggcagg tgaataaaac tggaagcatc cataaagcca
136561    tcatgaatct ctaattcttg atttggttg ctgctcacct gaaatgaaat ttacttcaca
136621    agtcatttct ttgttagttt tttatagaaa atgcttaaaa ttaccctgat attatgagga
136681    ttgaatttgg tattgacagg caaacaagta tggcaggact aaattatcaa aatgtatgtg
136741    ctgatagaga ccaaaatagg tttttacagt tttcattagt gcaggccata ttaatttaat
136801    taacttgatt gaagacagta tcactagatg aggcagcaga tacctagcct tggcctatta
136861    ctcacccata ggctataaaa tgatgcacct gacacatggg tatgcaatct cacatatttc
136921    acatttggac tctgcctttt actgcaaggt tcctatggct ttggaatatg tggtgaactt
136981    catcagatga aattcctgat gctttttaca attcaagatc ccaatcagta ttttaaacat
137041    tgagcaaatc cttggcttat acttttactt tatgcaattt ggactgtcat atttattatc
137101    tagcctgctg agcaccctgt ttctttatct gactattgtc cttcctcctt agtttagacc
137161    cctctcctcc taacctgctt gtgggtctgg ttgggtctgt gaatcataat agcccactgt
137221    cctggccaca agagtgtgtg cggggactaa gagagccaat taatggctct tttcaggatt
137281    tgtctggttg gaaataatag agaagaccag ttacctaccc aacatccatt ctttcctttt
137341    cccctgtgaa gaaaatccca ttaaaaaaat tgtggcagtg tttccatttg aaaatattca
137401    tctcctcaca ttctactgga gccaaatgta ttcacgttcc catttctggc caatgtgatt
137461    caaatggaag tctgcagtgt agggcttctg gaatgatatt ggtgtcctga caaaagactc
137521    agctgacaag tgactttgc acttaatctt cttccatttt ctgcctgaaa cttgcacacc
137581    atggactagg cttaagcctg ctaagaacaa tggagtagga atcgacagga ccctggataa
137641    ttgataactg gctcaagtag ctgtaccagc cttggtctac tctgttcag aattcttgtt
137701    atgagaaaaa taaaacttct gtttagttat gctcatgtga gtgggtcgct gtcatgctca
137761    gtaggacatt gccctaattg ttgtaattct ttcctatac taaggtggct ttgtagagga
137821    ggccagcctg agaaaatgag tcaacctaca aagagccaag agaccaatag caagacctgg
137881    tcttgtgccc tgaattttta cacagcctgg ggtatatta tgtgagcctg tgcagccctg
137941    ctctgctgaa ctttgctaaa gttggtttct gtcacaaata caagaattct tggaaatatg
138001    agaataaaaa cacactctac gcaacagata ttcaaaaacct tgaattagtt tttcttagca
138061    ctaattccct attttctggg atgggaagga ggaggcctga gttcttaagc tgacagtata
138121    ggtttagggg cttttggaaca tcacccagca tttttgaacc tcagtcttct catctgcgaa
138181    acaatgtgaa cagattagaa gttctctagg gtagcttcag ttctaaatga ctatgactcc
138241    atgcacatt tccacaaata tgggctggaa ggggaggatg taaaatacag aattcaatta
138301    tgaaagaaat gtactcagag atttaccata aacacctact cctacagagt aataaaaaaa
138361    agaaagttac agcacaagta gagattttct gtggatgagg ttgcacaggc tctggttatc
138421    agtctataaa ggtagtgtgc acagagttag ggaaagaaac agactttcc tcaggattaa
138481    attacttcta agcattgatt tttagatctg aagaaggact tcatcctcaa atatgaaaac
138541    tatcatacta ataacaataa ttacagataa ctacacacta tcaactctgc tattttgcat
138601    gcatcatcac atttcatcct cagtgatgct ttgagataga gaatcatatt atttccattt
138661    tataactatt cgcttttttt agttacaatc agaataattc caaatttgta aatagttaag
138721    gctattatt tgctgttttc aacaaagcag agaaatctga atatcagtgt tgattccaaa
138781    gatatttctc catttctca ctacatatat taaggaaat aatgggctcc aaaggaaatg
138841    ttgattggga attaattgtg taactgcctg caaaacaatt ttgcctatta ataccagt
138901    gcaagagagg attttccctat tgtatagatc agtggaaatc cagaggcact cagtgatgca
138961    aagttgcatt gaccttggag aagatctgag atagacaaaa tctacatatt taaatacaaa
139021    attgtctttg taacaaatgt tgattagact taagaggctt caggggactgg gttttaagaa
139081    gagtaaaaat cctaacattt gttgagcccc ttctgtggag caggcattgg gctacatcct
139141    cttcacactg catctcattt agtcaccaag gaagcccagc gtagtagata taattgctac
139201    attttacaga ggaagaacag agggactaac ttgctgaagg tacacaggtg ggaaacagtg
139261    aaaggggctg tgagctcagc tctttcagct gccagagtct gagctcttgc agcagatggg
139321    agtgtgagtg tcagtttttc aaattccatg atgggaaccc tggaaaaatt cagatgtcta
139381    gtgaatgaag gggaagaatg agttgtagat tgtgactggt cttgtattct gagcaggcaa
139441    agagctgaga ttaagagtt taacctgcgg aaaatttgtt gtgttggcta ctaaccaaat
139501    ctgtttcat tctcctggaa gctctggacc catgttgaaa gcagacttct ggtaagtttt
139561    cctgagttga tgtctgggct ttttcctcaa aggagataga tgtgaagctc ttaatctggt
139621    tccttctagc atggggagca gaaagtcaga agccaagatg ccctggctga tctgttcttc
139681    tgtcttgagg aaagagtata cgttaaacta tttccatctg atgtaaatct gaaacactct
139741    ctgcggtaag ggaagacagg ggaaaaattt cttatcactc caaatgagga acaaagaag
139801    gtaaaataat taccctcagtc caccaaaagg tagagaaatg ggtctgggcc cacctgaaag
139861    tacggtgtgc cttgtgttct ctctccttctt cccctctatt caagtaagac ctggaaactc
139921    ttaaaaacct ccgggggaggt aggtaacaaa cacttctct tagtaactct ctaaggccat
139981    catagttctt aataacccct atgtaaggat gtttcccctc tagagcaaac ataaatcatt
140041    tggctgcagg ttaattctat tttctctctt ctctctagtg aggagaaaga acagctgttt
140101    accatcttcc cagagtcaaa ttgaacacac tggaacacag aggtatcaaa tcaccccag
140161    actttcatca ttcaggcaaa atggcattga catgtcagta gttctcaaag tggttctctg
140221    aacagcagga acagtatccc ctgggaactt gttagacatg caaattctca ggccccacac
```

-continued

```
140281  caggcctgct gaatcagaaa ttcaggaggt ggccccagaa gttggtgttt taacaagcct
140341  tccaggtaat tttcatgcta tctgaagttt gggaactcaa tagttatgaa tgatatcata
140401  tgtagatatt ttgatcagat atggggtgact attactaata atcatttgaa taattcgtaa
140461  tgttttttct acatttgtgt gtatgtctgt atataagaat gtatataatt atgtattgat
140521  ttaagtgaga tttctagttt ggaatcagtt attcttgtaa gatacggtga aaccagtgag
140581  catgagaatt gaacctttgg ctctggcctc atgagtatac gactagagaa agtctaagaa
140641  tttcagttgt gttatgactt gtgttaaaga gttatggtct gcagaaagtt ttgagtttct
140701  tccaaacatt ttaaatactg ttgctgtgca atggtagtcc ttgcacagtt cgtaacatcc
140761  ccgtttcaaa tcttactctt tacagaaact ctcatgatac catgaccaac gagatgctaa
140821  gctgacatga cccatgggcc cgctatagct ttctttctaa ctcttgataa agttgaccta
140881  tattaaagga ccttctcctt gtttttcact caagcttagc tttgggaatc ttgcctatac
140941  taaagtgaga ttaatgtttt gaaacattac ccagacccct taatttgtct tgattattct
141001  cagattgtgt tgcacagtca atataactcc tgttcttccc ccacaagctt taatgaggta
141061  taattgacca ataaaattgt ataaatttaa gatcttccat gtgatgattt gatatactta
141121  tatatcccta ttttttgaag aagctgagaa aacacatcca ggctgcaaga ctaggacaaa
141181  agattttcca ccattttat atggggtgtac ataagccagc aggaaatctt tgtcaaccat
141241  acccttttag gcatagatca tgtctgtttc gttcactgca gcataactgt aactaaccct
141301  gggcttagca caggtatgtt gtcaatgaaa acttgctgaa agaatgaatg aaggaaaaca
141361  tttttatgac tatttcaatg gggcaactag gaattctgct ttaaatgaca cctggaagga
141421  tatatgagaa atcttgtaaa aaacttttata gaaacttttta gaacacattc acccagaagc
141481  cgatatttt aatctttaaa atgagcatgt tcattagtta taaaaatat gtatatatat
141541  gtgctgctaa aatatttgtt ttgggatctc aactcaggtc attaagatgt tccaaaatat
141601  ggtatttatc tgttcaaatc caactttag taataaatat ttgccaaggt agatgtaccc
141661  taaatatcca acagtttatt tagcaaaata acttgtctag aataatcaag agttctcaaa
141721  gaattactgg ttatgactaa gattggctat taagacatga aacacatcat attctttttcc
141781  aaatgttttg aaccctaat gatatactt tcatgttttt cacttacttg caatttttt
141841  gtcatgcata ttcttcaaac aaaatcttct cttatcatgt tacatgttat ctctttttctt
141901  cccctgctgt cagcttaaga tataaagtac tttttcttte aacaaagttg ggggggaaag
141961  atcttatttt taaactaact tggaatggtg taaattttt taaaaatcaa acattggtat
142021  attgatagca tgtactcaac atcagacagt attgtatttc acaaatatta actcatttat
142081  ttttcacaag aattaggtac aaacactatc ctcattttgc aggaaaattt aggcacagaa
142141  aggttaggtg attttcccaa ggtcacacag tcaggaaaaa gaagaactgg gactcaaaca
142201  tagatagttt ggctatagtc catgtacttc ctattgaacc atgaagcctt tctgggatta
142261  tggctctatt taggtcatcc tagggtattg cctttcaatcg tgggtttggg gtggagaggt
142321  tcatgttgag gatttatgga ttaggagctg tagcagctgc ccagattttc aattttttctg
142381  atattaaagt ggtgagttta aaaagctgac atttgtaaaa gataatcatt tctgaattgg
142441  gaggggggat ttttccacta tttaaatggg attttttacaa gcataaataa atctactgag
142501  aaaaatgtga tgtttttacct gaattgcaat tactttattt ttaaaataga agttaaaagt
142561  ctcagagaga gttgtcaata agggcttcgg ctggaactag tatgtttgca cacacctccc
142621  tctccttcgg ctcttttcct tcacccaacc ctgtggaaag taaaaatgcc aagaagaaaa
142681  atggggaaag tgatgctatt aaatatagca caggtgctgt tttcataggt ggtgggaagt
142741  tttagctttt ctatctttta cattctctgt ggagctttat taccattttct cagagataca
142801  catactgaaa gagagtccag gattactggg gaattgggtt ttattcactt cacttgtttc
142861  aggtaggggg ggaaattgtg aaagagtgag aaaacagcaa gagcctacta gatcagtatc
142921  tgtttttaaa gtggcattca attgaataaa atttttagag tgcaggagta gagtttctg
142981  attttactta tttattatgg caaatcttat tcaacttttgt tatagaaaaa tcgaaaaag
143041  ataactgtca tgagtttcag ctttcttaaa tcagaactta atttgggaac tgccccccaaa
143101  aaatcccctc aagaaaaatc taccaatacg attttcaact aaaattggta aggaaagata
143161  ttataaagta ttaaaatcat aaggaatgcc tttttattt gagagaaagt aaggttttat
143221  ataattcacc ttgcagagtt caacattttg caaattaagg cagcaacatg ttggagcctt
143281  tccactcaag tcaatggata aagtcttgac cctaatatg taatgaacat atgcaaataa
143341  tggaaaatat tttccaacca ctgattcctt tgctgatgtt accaaaggtc atttcatgt
143401  ttcaatcatt aaagttagtt ttgcttcctt ctcttacctt agtaaaaata ttctaaattt
143461  gtattcaaaa tctccatatc ctcttggctt ccaaccgaga gctgacgaat attacaaaga
143521  agcagttaaa acctgtccat taaaacttat gacacttaga ctatttgtat acacatgacc
143581  ttcaaggtta tatgaaggta gtccattaat ccctctgtct ggtctttatg ttttcccttt
143641  actcttaaaa tgaatgaagt tgataaggaa taaatatcac tagaaccatc atgatttttgg
143701  accaagttac ctgaatttcc tgtttgataa tattctgttg aagaaccatt tactggagga
143761  gccaaatgca catgttcatg gtggtggtga ggaggaggtg gtcagggatg gggaaggaag
143821  gtgggggtgg gtggggtgga gagcagtaca aaaagagacc acagtgttct accccgcgct
143881  gctggtgttt tcagattaag atggggggatt aaggaatttt actcagcaat ttgagatgct
143941  ttgttaggga ctgaggagat ttgagctgct ttgttctcaa accacatgtt agtgaaaaag
144001  caaacaggca cttaatcctg acagacagca gaacttgaca tcaatttgcc ccttgggagg
144061  tgaccaggag ttctctatga agggctaaaa tggccagccc ttgttttcct ggagcctaat
144121  gccaacattc catcctaaac tgtattcctc agcagtgggg ctataactta tttggtttga
144181  ctaaccaaga gtttctagag actatggact tttacattat tttaaaaac aaaacaaaag
144241  acctttaaa ggcaaataac ctacaaggtg ccaaatattc aaagagtttt caaacatgtc
144301  taatattttg gtcactcagt cttgaagtga aatatagaaa ggctgagatt cttttttttt
144361  ccttttgaaa ataatggttt cctctaacaa taaaatcaca gggcaacata tcaatttttgg
144421  agcccatggt tatgaaataa acatcaattc ttatgtagat gtttgaagga gattctactg
144481  aataaccagt tatattctaa ggtcatgtcc ttccaagtca ctgaagtagg acaaaagcaa
144541  acaaaatgaa taggaaagaa attaatggct tcttcaattg aattttatac attataaaac
144601  ttaagtatac atagttagat agtctggcac acaatctgaa attgtgggat aaaggctcac
144661  ttttccatct tgagtttgtg ccaccctaat ccgttgacca aaagtgaact tttagtggcc
144721  tattgattta ctaaacgttg gcatgcatag ggaagccatt tttaaaatc agaattgaag
144781  cagcaaattt ataaaacaca tttcagagca aatccttaca ttctaaagag tttctagttg
144841  aatattcagc ttgaatcaat agttactgta ctctggtagg atgtaaaat ctgctatatc
144901  ttaataatta aaaagcaagt tttgtcacaa ttgcaaaatt gctacatatt gcactattta
144961  aacacagaac tttgagtcaa gtcaagcctc tgctcctgct cacccttatc tctccctgt
```

-continued

```
145021  aaactcaaag gaaaacttat ctctttatat cgactctata ggtgattttc tccattctgc
145081  tataaactca acattttatt cttaaataac catagagttg ttcaaataat cttttctttc
145141  aggattggtg cagccctctt tatgtttaca tggcactaaa ctaatttta aatgaccatg
145201  aacacatgat gatagaatat ctttataaga aagttaatgt cagctgagcc tggcagctca
145261  cagctataat cccagcagtt gggaggatga ggaaggaaaa tcacttgagc ccaggagttt
145321  gagaccagcc tagacaacat ggcaaaacct catctgtaca aagaatacaa aaattagctg
145381  ggtgtggtgg catgcaactg tagtcccagc tactcaggag gctgagttag gaggatcacc
145441  tgagcccggg aggttgaggg tgcagtgagg tgagcagaga tgacccaact gcatcccagc
145501  atgagcaaca aagtgagaaa ttgtcttaaa aaaatttatg tcactttata tttccaaaga
145561  aaaatggttg ttttctatgt tgaagcttta atttgaggaa aaaataccct tgcacagggc
145621  aatggaatga gcataaaaaa gtgtttgtat tattagttgc caatttggga gatgagacaa
145681  tttccaatat tttgtatatc cttaattatt tattataaaa accagtggga cagaaatctg
145741  aaatttaaaa tattataaag agatactttc attaatttta tttaaaacat tatatgcttg
145801  gctttagatg acttctgagt tgtgttgttt ctctctcctt tatgaaggtt taccaggcat
145861  attaaaagga tcaaatacaa ggtgaagtaa aagcagaaac acaatattca tttatttaac
145921  tctggtacag tagagcaaat tcagggtgac tcaagggaca cagtgtcttg taaaacatat
145981  gtacttaata taagggtcat aaaacttatt aaattaaaag ctaggttaaa aataggaaga
146041  aaatttatgc tgctgtctaa aatagcaata atttcccttt ggcctttccc tttccaagta
146101  atatgggttc tggtcaggag gaaaaaaaaa aggcaactta taaaatcttc attttggagg
146161  accaaatgca aatctttgtt aactacacca tgcatttaa caggcaagtg atacggctga
146221  aaatagagta gtaagaagat aaaatgttta gccttaaaaa gtgtacttgt gatgaggatt
146281  caaggatata ggtggcatta ttcctgagtg caaacaataa actccattct tgttagctgg
146341  tatccaggaa gaatagcttt agggtatggg gacagtagaa aaaatattaa aaaatagttg
146401  atttggcttt gtggcagcag gacagtgagt agggagcaca aagtgtgcat tgctgttcag
146461  tcagggcaca gcagtgcttc cctgacaaa accttccacc cttgtcccag caaaatttgg
146521  gctgtaacaa aatctatgta agccagaaaa tttgaagtga agattgacct cctatttgtg
146581  tctcactctg ctgcctgtgg gccactggtg taggaaagga cacattaccc ttataaacaa
146641  cttcagggtt tgagagtaag tgtggcctca actttgtaag cacttgtatt tttttttaat
146701  ccatgcagct aaaatatatt gggcttgctt aaatgtttat tctcaacatg atagccattt
146761  tcctacctgg ggttcctagg tataacacct tagtaatttg aaaccaaaat aaatatcaat
146821  ttccttctac tgtagtcaca tggggggttg tttggaattt tatcttcaca cgaaagtctt
146881  acggctgttg agaagggctg tgccggtcat ttatctgttt actctcagac tcactctcat
146941  ccttccttg ctctttttgtc ttccaggcgg cttaccctg caaagtacat taccatctgg
147001  cttccacaaa ggctctgcaa agggagatgc tttttaggg agtaggagag aggctaggat
147061  agccattctc ccactctccc acctgcattg aaagtgcttc tgcaatgcct acctctcccc
147121  tgaggtctca gacctgcctt cttctctttg tccttctagt caagggggtgg cagtggcttt
147181  acgtctttgc caaactcttg ttgatctcat catccccatt tggacttca gttcttccaa
147241  cacttttgta actacctccc tagattaaat ctctaggttg aactacttgg tagtgattct
147301  gtttttcctg actaatgcca ggaccaactg ctttaaaaaa attatttcta ggttattagt
147361  ttgaaagata agagattctg cttgacgtct tgaggggtct ttgcctgttg gccagtgggt
147421  aggctgtttga gtcataatag tcactttggc aaggttctct ttttggttga agtgaagcaa
147481  acctgtttga aggtgaaatg agaaagtaag aactagtcaa ggtcttttaca gggtggacat
147541  tttaggaata caagagaagt tgaactgaaa gggccgtgtg gatatgttgt tgatcttggc
147601  gaactctcct gagctgtata gcactgacaa tggagtgcta ttatagcctt tggaaaaact
147661  cagctaaaac ctcataatcc attttctttt catccttgca atctctttt tttttaattc
147721  tgtaatgaac tagcctgata gtgtaaatag cctcatttga gctaagatgg gcaatataaa
147781  cacacacact cagagatcag tagaggaact ctgaaaatca tacaccagtt tctctttctt
147841  tctcttttttc ctctttctct tctcactcac aattgctaac aaagttaaaa gttggttctc
147901  atgatgaaac ttcataggct gctgtctgga atgaattttc ctgaaagagc tctaactgct
147961  gggggaggga gggaatgtag ggtggggtgg gggagaatcc agacctcaaa cccaatagcc
148021  ttgccattca aaataccagc ttgaaggttg acatttgcag ggacctggg agtatagcac
148081  gtgggactt ttatcctgct acttcagtga cagctgggcc tggtccaaac aacactgcca
148141  gtaacattgt catcgagtag gttaagcgga gctggagggg aacttccttt tagctttaga
148201  ctttagacta caaagtctca gagcctttgg gtattcattc accattcagt gaacttagac
148261  tggcctgaag tttattttca tcaggatgtt agtagggctt gggaaacctt gaaaatggaa
148321  tgctcagttt ttgtgaagac tttcttttaa acctacagat ttaatgaagt ttaaacacat
148381  tgttcattgt gtaattatag atgaaaatatt agagaagtgg actaattata cacaatgcac
148441  tcaaacccaa ttaaattaac atctgtggtg aatgtaagga tattctcttt tactaataag
148501  aaatattttc taaacaacag agaataaaat cattaaattg gatatgctgt agagattata
148561  aaatatcctat tagcatataa aatgaggatt aaccttattt aatcactgca tgtcagatca
148621  tcaaaagtca tgttgcaccc ccataatgtt gctgtattaa ttctacagaa ataacaataa
148681  aaaaccctac tattaatcaa catagctctc aatgaatgct gttcttgtct actaaattaa
148741  actgttggag aaattcaagt attcccataa ttgcttaaca aaatagcaaa aatacttttta
148801  cctattcatt gtggtattat ggctgattca gatttacgtc atctactggc tgaagaggtg
148861  tgtcttcctg gctaggcaaa ttagcctacc tcaaaataaa taaatatac tatccattcc
148921  agctagcacc acaagtgacc ttttgaaaat gtaaattaag tgattgcaaa taccaagagt
148981  gtattcaaaa tgaaaacgta tggacttgag acatagtgcc accattgctc cagggattaa
149041  ttgcagact atgaatccag ggatttctac ctttcaatct ggggcattca atattccatt
149101  ggaagatact catgaccatt gttactgtga ttaaataatc aaatctgggt ggagcgacaa
149161  caaagtggac ttggggtttat ccagattcat gttatagctt attatgaata ttgattggat
149221  gcagtaacaa aaaacaaatg acagcaaagt tgaaggtagc catttcatat atcatgttca
149281  tagattgccg ttttcacag ctgagggaca gaaatcagtc aacagggatg gttgattcga
149341  gggagtcttt gtcagaagag agtgaaaagag ctaaaatcaa tctttcttgc tttttctttc
149401  ttccctgttt ctctttcatc tctccttccc tccctccctt cctttgtttt ttccttcctt
149461  ccaaagagtt cttcttttata tttcttccaa aatttgaagg gcgttttttt ctttcattct
149521  tgtgaaaacc ataattacag ggcctggaat ataaatgtac ttataaatat tgagaataat
149581  tatggctatt acaactttgt atttctaatt tggtgaatta aaaaaaaatc aacacataca
149641  attcttttc agttgaaccc ttccacttag tttgcctact catccttatc tgaggaagta
149701  agttcagttt aaaatgtaaa aattcagatg taattggaaa gaaatttaga ataaactgga
```

```
149761  ggtaacctgt ctgcgggggc atggtagggc acactgtgat gggcccacgg gcagggactg
149821  aatccaggaa tacatgtgga gggcagaaaa gtctacctgg gaaactgaaa tttaataaac
149881  acatcaaaca catgaaagaa aatgtgattt tatcacacta gaagtatatc tctcagaaag
149941  ccacttcaaa gaaagcaagc agaatgcatg cgcaagtcaa agtccttttc cgtcctcagg
150001  accaaagctg cttagccaag aagtttttct ttctgtccag gtgccataca ccatttaagt
150061  ttttttccag tttccttaag attttaaagc cacttgcact acatatatgt agtgcaaaaa
150121  gaatatatat atatatattt tttttttttt tttttttttg agatggagtc tcgctctgtt
150181  gccctggctg gagtgcagtg gcacgatctc agctcactgc aactttttgca tcccgtgttc
150241  aagtgattct cctgcctcag cctcctgagt agctgggatt acagacgtgt ggcaccatgc
150301  ccggataatt tttgtatttt tagtagagac ggggcttcac catgttggcc agcctagtct
150361  cgaactactg acctcaagtg atccaccctc ctcggcctcc caaagtgtta ggattacagg
150421  agtgagccca gtgggcccgg tcaatatatg tatatttaga aaatcttctg tggcttcttt
150481  attctataga gagagcaata tgttgtgaat acagtgttaa taataactac tattttttgcc
150541  cttttttgaac aaaccaacaa ttgtgagttt tagctttat ttttgttctc tttaagctca
150601  attaaaaagt acttttgcct tccaggagcc attttacaa tttatttgaa gtgctgggtg
150661  aattaaagaa aatcctatgc cttcaaattt tagttgaact tatagatttt ccataacaat
150721  attactttaa aagactcttt ttcttccccc ttcttccagg tctcactggc ccagcaattt
150781  agccttgcct cagaattgtt acattacggt caaatggttt ggttgtgaca caggatggtt
150841  ttcagaaaag cagcagacag tgtctagaag tgggaaaaaa ggtctttatt gagaaggtca
150901  aaagggacat aaaggcaaaa actgactttc accgaaacag aactggagac caggcctcca
150961  gtgtccttt tgtaattcat tgcttgtttt caggtcccgt gatagaattc ttccataaca
151021  gaaggagact tgttaaatt gtaaatgagt attacttcaa gcactctgtg gaaatatatt
151081  ctccccctat agcccataca ttatttctgc ttagttatag tggctcacct ttcctgtaac
151141  tatcaaagag aacttaattc aactcacacc acatcacttt acaattgtgc agctctctta
151201  atcaaccttt gtgtcagcca cgaatgtgca gtatgaccta atttgaaaat gtctcaaagt
151261  gctgactcaa actgttagtg aataaaggct ggtcattacc attatgacac taatgtgatg
151321  caaaatataaaa ttgagttgca tcagctgaac attagttttgc aaaaatatca gtgattgaat
151381  ccatttttctg ttcatatttt atttatactt agatatgtat acatatatac ataggcacat
151441  attttttgtt tgtttgaaac aggcttgcgg caaaattttt gagggtagag gaaggaagcc
151501  acattttaac actggaaaaa gacacagggt taaaggctga tcatatgtgt atcatgatct
151561  cctctctata acatgaagac atgttgttga aatcttatta ggatattttat atgcacataa
151621  gcaataacat atgaaaatta tcatcttgtc gtgtactttg gtgctagatt ccaaggtttc
151681  taacagccct ggcacttctt actacttcgt attactccaa aattctgact ttgtattcgc
151741  aagtaacaaa aatttgagat ttttttctttt catgggactt ctttccttct tctttacttg
151801  acaaaaagtt actttgatt ggaaatacct ttaatacaca ctgtcgttaa ttacttgtga
151861  acaaaaagaaa gtgagatata aaactagaca ttatttagcc tcatccctac tgataatact
151921  ttgtggaaag caacatcaat gatcttttttc ttacacaatt cagatggttt tgaggaaaaaa
151981  ctcatgggct taattaatac ctgtgcatcc taaaactagc attggtttca aanctaagc
152041  tgataagtag tcattgaaaa taaatcagca ggaaactttc ttaatttaga gaaattttcc
152101  taatggtaaa tgagaaactc caccctgtat ctcatttttgg gtctccagaa ttctgaaaat
152161  cctgaacata aaagtgaggt attagtgata aaatactttctt gatttttatt ctttaatggt
152221  tctaacaaac ctagcacaca aatgcaaagg agatatgttg tccttttaaaa tggtcaagga
152281  caagaagttt tggctatcag gaaattattt aacctgcttc caattgagag agtatatgtc
152341  ttcataatat atcaccataa gcgatcagta gagaatacag ctaaattaaa atgctggcaa
152401  gctcagttca ttcactttt agaaaagcaa gtaaaaccctt ccagcaagat gtgtagaaat
152461  tttctattac gtgatgactt tcatatttga atccattttta cattgtgtaa tatgtgactt
152521  gggctgtttt tatgacctgt gcttattac cacattaaga caatcgacat ttcaaaaaag
152581  aaaaagtttg aataatttca aagtgaactt gccaaaatca gcattcagaa gcatgggtgc
152641  tcgcgcgctc aaacacaggc acactttcaa tttacctaaa aacgggggatc accctttgta
152701  gctaaaatgc aatctttctt attttttaggt taccctgaga aaaggtatgt gggtgtgatt
152761  cctgcaaatg gattgccagt ttcttaacag ttcatcattc ttaaatgata gaagtatagc
152821  agcacccttc tgagaaacat ctttttctgta gattttactt tgtccatgcc aggacaaatt
152881  gcgtgctaag ttgaataatt ctgagatgtg agacacctcc ataactgtcc ttggactacc
152941  aaggagctgg catttctctt tggaagatga ggggagaatg ctccctgctc tcttaattga
153001  tgatttactg tgctttccct tgggaccaca accgatgatc tgtaagctg ttgaattttg
153061  aggtagatac taaatataat caatatataa aaatatttaa aaaggagag aaaaaatgca
153121  atgaaaattt atgaccttaa cattccttca gggtcaagca atttatcaaa ttctctcact
153181  ttctggtttc aattacacag ccattgtgga aggaacttat tttagcaggt tcatttgcct
153241  cagtggggaa tacaggactt tggcctaatg cttcaccttt agtgcaggcc atttgagcct
153301  tagaacaaat accaatcatc actctttggg aaaaaagaat ctgcatcggc gtggcctatt
153361  ggaatggggt ttctgtcaag gtaaacggtt gtcggcaatg actgtggtag agtggcgata
153421  aatcccattt tattgctgaa aaattccagc ttctctccat gcctgacagc tccccacatt
153481  ctcatacccca ttttgggcaat ttctgcacta tgtctccatctg gtctcatta cctctcaacc
153541  tccctgcgtc tgatccagaa aaagagcagg tcagaaatgg ggctgggggt gacgaaacca
153601  aggtgatgaa caaaacagaa agcagggggga tggcccatgg ggttcgggga agagttgagg
153661  ttgggtggag tagggattcc agctaagaat ctgagtggtt ttgagaaggg gccatgtcaa
153721  ttattaaaaa tgatcatgac agagctggag ccagaagcca gagaacctg tatctttaga
153781  ctcaggcatt aaaaagacac ctgttttaag gtgaaagaga gagtagagag agagaatgtg
153841  gtaggtagag gagggtggga aggcatctct attaagggca ctgccagctg gattatcaga
153901  gtagcggacc tgttctagaa aagcacggag ccctgtgtac acagttggca ggctctcaaa
153961  tatgctgatc aaactctgct ggagattaga ttttggttca aaaacatatg tttttgagga
154021  caaagaaaac ttttggccct ccaaccttat tgtctccatc tttcgaagaa gaataatatt
154081  taaaaactaa cttgtcttaa ttagggcatt tagaatgaca ggactagcac tgactcactt
154141  gggaattcat aaccctacat ataatcactt ttggaatgga gtgcatttat gccttcaaaa
154201  agttggcctc attttctgaa gctgaaatcc ttttgatcat aattactct gacctaaaat
154261  tacccacagt caccacacaa tgccacgctg ggacaaaaaaa gaaatacata ttgtaagtat
154321  ctgataacagt atataaacta tcggccaact taaatagtat cattaattag actaggatga
154381  aactatacaa ctatatattt ctgaatataa catttaatca ttattattat tctttggtg
154441  cagtggttgg ggccgttgtc ataaatgcta aaataagagt tgttaaagta tattgaagta
```

-continued

```
154501  taaatgataa agacctgaga actttgcata aaaatgagaa tcagatgaat gactgcattg
154561  atgtagttat ttcaccacct gttttgaagt caaattttat atgcaaatgt cttaaaacca
154621  gatatgattg tgtattctta aatacgttgg agagctgtgg cattattatg atttgtagac
154681  agaatctctc atgttagata tgtttggatg gacatattga atggtctctt agtgccttct
154741  ggatcccagg gatccagagt gtatttcagg tcctaaaaat ggacattttt gacagtcaga
154801  accccccagta ctgcactgaa tatctgtttt tttatgggtt gaattcccaa tatcgaaatt
154861  acgttaaatt ttagttgctg agccagatcc tttagacaag aaatactggc ttccagtaat
154921  caggatttaa tttctaaatt ttcaagtcat gaatgctcaa aggaggtttt atgaaatgta
154981  cctgaaattg taaatgaatc ccacgtagac acttaaattg agaaattgtt gctaaaaatt
155041  ttaaattaaa acgacaagat aatttggact gacgtacatt agaaatcata aaaatggaag
155101  tttgttaact ttaaaatgaa tattttagtc aacaaataaa attctaaaac agacgttttc
155161  acatgcacat attaaaaggc ataaacctt agctagggtc acgtatctat taaaacggtc
155221  ttgatttaa tggtgtctct aatttggaaa gtaatttcag attcttagcc aagaagaatc
155281  ttgcttgaac tttacttttc taggctgtac ataccaga gaaacatgat catttaaatt
155341  ctaaaggatg tttgtttctt ttaatagcat agcagagaat taatggcatg ggggaggggg
155401  acgtgacaac ttaacctgat gtttgatagc tgtttactta tgaatgtgtg ccacagattt
155461  cagtgtctgt aaaagaaggg gaaataaaca aaccgatggc ttttagggaa cttaagacac
155521  atggaagaaa gtgcttagaa ggctattgaa atatttacaa aacaaatcat ttacattaac
155581  tttcttatgt gtagaaactg gagtgcccat gaaaagacag agccaatttt ggctatgaga
155641  agtatttcag catcaaaatg gttaacagta ttatagcttc aaaagagcct attggctcac
155701  cctcaaggat gccctgcagt tgttgttaaa gtcatcagat gaagctagcc ttctcagcta
155761  gccttcagat ttgtctgcta acagtaaaaa tactataata aatcggtaac atatgttgcc
155821  aggcaaggaa aagtgatata aataaagaga ctgggagacc caaccaagt acatgtgaa
155881  aagaatttaa atttcaatct atttgctggc taattaccat ttgaaaagta atttgaaagt
155941  tttactgtta tttgctgata ttcttcctca ttttttcttt tttcctcttc agattgcatt
156001  cttacccaaa tactcttcgt gattgcctgc tttgcggctt tgggtaagt cccagttttc
156061  cacaaccta agaaaaaaat gcataacata aaagatgcca gaaagactta tgtgtcctga
156121  tagtcggggt ctgtgaaata tacatgggtt tgttacgggg gtgggaggca taatgaaata
156181  aagaaaagcg atttgtttct gcaaggatca aaagtgtgcg aaagtgtgca tatgcaaacg
156241  aggctcccat caggaaagcc acctctgaa tgtaaatgac aaagcttgga acacacacaa
156301  tcaattattt tcaccagcat ttaaaatata gaaaacaaaa tctgctttgg gaattgactg
156361  aatattttat ttagcttttt ttattgagac atcctttgaa aaatggcata atataaatag
156421  ttttacaaag caacaatata atcaatctct aaactagaat ataaatcaag gatttcatta
156481  actgctggta gccagtttaa attgtagtct tgtccataat gtctatctat ctatgtatgt
156541  ccaagttata ttaaaaacct ttaaatggct ttgtaatatc agctacatct agctattata
156601  ataattaatg gtactgtttt ataaatcaat acatgtattc ttgataaatt catatccagt
156661  taatgtgta atttaaataa aaaattaatg taataaagga catacagaag cgggcaggaa
156721  atctttaaag gttaagagcc aaatttgtct aaattcattt ttaacctgtt ttggaaaagt
156781  ttatatttaa aatcagctga gacttacctt gtttctgtaa aactaatctt gccattctg
156841  gtggtatcta gtattaaatt tgtaaggtgt tttctgacgt tgtttttaatt acgtagttac
156901  aatactgtgg aatattttac tgtcgttgca ctattttgtg actattgcat attctttagt
156961  aaaatagaac aaaacaaact aaaaacatca caccagcaat ttattttaa tacacaaatg
157021  catgtaaatg atttatttt tgaaaatctc caaaactata cacacattt atttaagggg
157081  aaaaatgact gactagttca ataatttgc atgtggaaga gccgagcatt ttcactgctt
157141  ccgctgagtg aacattccaa gaattttaga aagaaaagaa aaatgcatga aagagtctga
157201  aatgtatttt aacgctgcac ccgggtacga gaacattcta ccaaaagatg agtgtattac
157261  agttctaatg taaagaatac ataccaaaga catatttaaa aaataacaag atttagaaaa
157321  acaactgaag gttgtatgtt atcaaataca atatcaaatc tttccaaata aatttcatt
157381  tggttcataa gagtacgcgt tttacaaaaa atatctttca aaattatgca gaccagtctg
157441  ccctgccatc ctccttgaca tgatgcagaa atgttccttt aatccactga gcttttttctg
157501  acatttttct taacattgct gagccttatt tagagcacca aaggaggcgt gtgcagtttt
157561  ctttgacact gatgggtatt tcaaatgtt acagagagag gggggaaaaa aagaaagaa
157621  aagatttgct gccagtcact tcatcaatag agctacagaa gcaattacta tttgttaaaa
157681  gtttacattt caaatgaagc taaattttaa agaagtctca tcctttttaga aggactggtg
157741  cttggaagag agaggaagag aatgcacatt agtgattaca tgttaaagtg cactcaagta
157801  ctggaaccat ttaaaatgta ttgtgttttt agttgaaacc tgcagcaaaa ccactcctaa
157861  gaggcttaat ttaggtttta taggaggaac ataaaaaaga ccaggttaca gcaacatgct
157921  gaaatatggg gtacatttta aatatcttca tttaaaaacg tatgttttatt tccctctctg
157981  ggatcactaa cgtgtgtctc cacagagaaa gcaaggacat gcattcttaa aaattatctg
158041  ttaaagggat cacattccaa gacaggtttg agcattttta ttactacaga taacctctta
158101  attgtgtcac tgccttccac ttgttaatca gggacattca acatagttaa ccatgcagtg
158161  gttgtcttta gaagaataca ttatcattaa ggattagaaa cacattttat tcctataatc
158221  atattgcatg tatggtttta gcactgctaa aaccctattt acctgcttta aatacataac
158281  acctaagaaa ggattgagat gcctataaca atgttgttca ctacttcaaa ctatgcagtc
158341  catgaaaagc tttaagagac agataatttt acttttcttg tccccctcct ccacctcccc
158401  catgtcccac gcaattccta tttgaattga ttttaggttt cttgtgtagc caccagcatc
158461  tgagatactc aggtactctt tcagagacca aggtgtaagt gtgaagtaaa taaaatcatg
158521  ttcactgtt gctttatcaa ccctcctagg tagtttttct gccagccaac ctgcgctgtt
158581  aagacccata aaattatgca atagtgactt ctttggaggt tctctaatca gataatggct
158641  ggtgttggga ggcaaggggcc caaggcaatg ttgctggtac ttaacactgt ggttggtcat
158701  tacttgtcta gtagagacca ataaacagct gattactgtc ctatatggag ccaatatttt
158761  acatttatcc tagttattt ttccttttct ttttaagttc ttataacagg aagtatttgt
158821  caagaagata tatgagtaat agcctcccag gcaccttaaa aataagaatt ttcctaccat
158881  gaaatgatgc cttttgtgga aaggtgggaa tgattctggt ttttacaaga gcaaaggttt
158941  gattcgtttc aagcccactt ctttcagaca gggacactcc acgacaccat ccctgctgct
159001  cctgtccct ttcccctct atgacaggtt cacaggctgc aaccaaggga ttttaaaatg
159061  caaaggttta cattcatatt tgcactctgg caataacagg cccattttgc ttcctctgta
159121  agcctgtgat aattgatgct tcatacctgg aactatgttt catttatctc tttactcatg
159181  aagatagtat ataaataaaa ggtaatgtat ggaaaggaac caaccatctg aaataatagt
```

-continued

```
159241  cctaaatcca actagataat cttttaaagc tgtaagagtc agagatggag atttctaaac
159301  tttcaaagaa aacttgattg caaatgagaa acctgtgcat ttttgaatgc ttattgaatt
159361  tgaatgtctg tgtgggccaa aaagaatcag agggacaaat ggaaggcagg aaagaaaagg
159421  tgtaaatttt agatgtgttt taaattaatg tatttaatga catattagac tcattacaat
159481  tttattgact ttccctttac atttgaatgt aattttttac tagccgatgc aagctgcaaa
159541  atggcgagtc ttcttaaggtg cctttccttc cctgggatcc tcatcttaga atgagcagag
159601  gcacatcgat aagaactgga ccttgatttc acaacctcat acaaagccag gcaattcttg
159661  agccaaacaa aggggggtgta agctatttca tttatttttga taatcctcct cttgcacggg
159721  agcattttgc tgtctttgtc aaagtgaatg acaacaattt ggccaactct ctctgagctg
159781  cactcaacag tgacaggcaa attatcagag gccctgcact tcttattatc agaggagaag
159841  ccatcagggg gacgcatgga ggataccctct cctttgtcac tatttgtcag tgggacaagg
159901  gccactgcta tgggtagctg acaggtaatt tcaacaataa caattactcc tattactggt
159961  gtcataaaca attcgcccaa ggcatgacaa tagcaaagct ttataattca atgccatata
160021  aataaatgcc agcaggtaac aagtaattta gctccaatca agctttcacc ccggcattaa
160081  tattgttatt gcaagaaaat ggaaaattga aaaaattcaa tatgttaatg aattaagaga
160141  ggttcaaggg ctagacaaga cgagttggaa aaaggaaaca aaaattattg tggtatcata
160201  ttttggtgcca tcctggaggc caaacatcag tataattact ttaagacaag aaggggaact
160261  ggagtgcctt agatctcaga gcagggaaaa atgtgacatg agctttcaaa aaatccacct
160321  aactccaatt tctgaagaat ataaggagaa atatgagagt gtatatatat aatgtagcat
160381  ttcactggct ttctttttct acctgaaata tttcatatga agcagaagca tgagtatcaa
160441  agaaacgttt ccatctgttt aagaaaattg tatcagcacc tgcttccttt acattaagtc
160501  tcataatgaa actatttttaa taatcctttt tttttaatc tgggggtgaag gtaaagctga
160561  aagtcatctt tgctctccag ctgtccacct tttggaagtg gactagagga tacagtgtta
160621  tcttcatacg taaaacttcc tgatcaagcc aatttgcaat ttagtattt gtccagcaag
160681  acaatgtgcc atcatggtga cagcataaa agaatttgaa aatctctaat taggagagct
160741  gcacaccaat taacgcatgt caaatttcac ttcatcaagt gccactctaa tttcctct
160801  aaaaattaat ggattttttt tcttttggta tgtgtgtgtg tcccttaag gcaatgttga
160861  ttcaaatctg ctcgagatgc agtgttgcac agctaagcat cttcttgatt acaatccgcc
160921  acacttctaa ctgcgctcat tcgcactgcc acggatactt tgtcaacagt caaattacac
160981  cacgctgata acaatgcata atggtgttcc tcctccagte ccctgtcagg agaggggctt
161041  cataaaaatg tgatgttttc ttctcaactg tatctaaagg aagtttgtat gaccaggtcc
161101  ccagtcaggt gttgattttt aaaattagtt tgttaatttc aaaaaaaaaa aaaaaaagaa
161161  gaagaagaag aagaagcaaa ctgatggcat ataaaaagtc ctcattgaaa aaaaaatcag
161221  caaagaatga ggaatggaga atatctatgg ccaaagtttt gcttaaacac tttgttctga
161281  gacattttca agagcactat tcttggttaa ataccagatt ttttttttct ttacttatgg
161341  tctataaaca ttggaagcct ctcttgaaca gactgtattt agattgtgct agaagtttgt
161401  ttaactgcca tatttgccag aatcctcaaa acatcacagg acatagaaga caaatgactt
161461  tgtgtgttgc ggggagggg gtggggggga gtgcgtaagg gggtcaggac tgtatattcc
161521  agataaatgt tgattcactt ttaactattt tttatcctag ttgcttgttg cagattggtg
161581  tgtctgaggc atcagcacgc gtggtaatat ttctcactga aaaatgaaag aaagaaatgt
161641  agtgattaga agatgatttt acatttagtc ttttagagaa ttatttagat ttcttattt
161701  tcaaaaacaa tcagaaccag aacaaaaaca aggaaattaa acaaaatttt aaatatattc
161761  tctcatagat tcttcaggga gtagagaaca ttcacacggg ttgacatccc agttttctca
161821  gcatgtaagc atattgtaat cctatttatt cactaaaaat ttaaattcat gagatctaca
161881  ctttattttc tttaatctgc aggccgaata cagctctcta ttcactgatg actaactcaa
161941  aattttaaaa cgatattttt aggtttgtat ttccgaatat taaaagtgtc ttccttatct
162001  tatggccccca cccccagcatg ttcttaagtg gtcatattttca aacaaaagaa aatgacatcc
162061  cccttttcaac tagccaaaca ttagattctc tcagaactga ttggggggttc actagaagtt
162121  ttgcaattag attcatacaa attgaattat tttcttttt tccaaacatc gttcttagaa
162181  cttttataaat atagcaaatac tggcttcaca gtttcatgtg gctcgtttac aaataaaggt
162241  attttaataa aaccaagttc tgtgtacctt tgaaaaacaa aaagctggaa caatctcaca
162301  ttaaaacatt acaaaaggat tgtaaaggga aatttaaagg gagaaaactt gatcatataa
162361  tgcaatccag cagtaatcaa tttacccttc aatatcttgc ttttgttttc aaaatgctaa
162421  ataaacaata cataatgcat ccctcatcag ccaaaccatg gaggctctgt gctcaaataa
162481  caggaaacat attcaatttt cctaacagaa gacagttcat taagctgtgc cacatcaaat
162541  aaaactttaa tttctccagc atcagagtcg caatgaaagc aattgaagaa gatgagccat
162601  atggtacttc tatcagcaaa cacatattgc tcattccccc aaagttttct aattctgctc
162661  cccagacctg tgtaatatag ataatgtgct ccgagagcag caaccatgag ctatctagtg
162721  tacacttcca atactgtatt taatgggaaa taatgaatca taaaagccta gagaagacgg
162781  cttttgctaa cctaaatctc agctgtaatt tcattgttct gtgcctaaga tgctgtttgc
162841  cctttccaaa caacagcagt tgaacataat tatgctgctt cgaagctggg tttgaaaaag
162901  catccctaat ataaccaact ttctattaac tcctgaaatt ctgaatttaa tgatgcactg
162961  atacaggcat tgagataacc aagcatgtgt catttaaaaa tccaaacagc atttttctcc
163021  ttcttctctt tggtcagact gctcaatgct tttacgcttc ctcctccgcc ccctgcttgc
163081  gtccatcccc caccccacac cccaccccat gcaacaggag tggcatgatt aaaaatgatg
163141  agattttctt gttattagca aatttgacat ttgcctgatg aaatgcacat aaaatgtgaa
163201  agctacacag tactcagaag aatgtctcca ctccaatcct agctaccaag atgaaataat
163261  ttaggtaaag gaaatgtaaa ggtccttgta catctcttgc tgcagaatgc tagggttgcg
163321  ttataaatga aagaaccaaa tattgctgag cttttagagt gatagtattt tgacacatgt
163381  gaagcacata gtgtttcttc tctcaccttta gctgctttga caatttactt aaacataata
163441  cacatgctca aaagcagcaa tttacatgtc gtgagcccaa cctttctctg gtttgagatc
163501  ttggggctgg ggcttttgttc atttttagga aaaaatgttg ctttttcctc taactaggtc
163561  aataattcca gcttttccat ttttaaagct tatcaaatca ttattttacc aacatgatgc
163621  taatttagaa catcatcaga taacaccgtg gatacatatt gaaaacatat tttaatggtt
163681  ttgtttgttt tggcatcata tgaaccaaga acaattaaat taaaagaga ctttaaaag
163741  ttagagattg ccttttttaaa gcttattaaa atcagcatgt taacatgcct gtctctgaat
163801  tagctctcac acttgattgc catcattaaa acgagttgtt cgggtgctgc tcaaagccga
163861  ttcttactag ttattaactt gaaatctctt tccattgaaa tgtaaaaaaa aaaaaaaaa
163921  tcattctcac tagtggaaga aacagtcacc aaaacatgaa ctagcacagc aagccagcaa
```

```
163981  cattaaacca cgaaaagacc aacaggtaaa ataactacag taacatctaa aacacactca
164041  gggaaaaaaa aaaatcacaa caacaacaaa gaagcagttc attgattata tttcatgaat
164101  gccttaaaac aaatgtttaa acagttttct gaaacagtgc agaaaacctc tgcatgctcc
164161  actgggttgc aatgacaatg gtctattgca atgtaaaaca cgctggagga taaaaggtg
164221  ctttttgtta ccattttatc aaagctgttc atcttcgagc tgcaggcagc attttgctgg
164281  aattgcagat atttctctgt ccaggcttct ttgtttgtgc atctcatttg catatattta
164341  tctccagctg agggtgcgtt ctgctcatta aggcctccct tcacattatt tcataagcca
164401  gctgctgaga gggatttcac ctgtggtgac tgagaaaaga ggggtgaaaa actaaattct
164461  tcataaaaag gaaatcttca gagtctcttc ccctataaat gggcaccatt tgtgttaaac
164521  agcctcttgt catgatagat gcct9cagag gtcagggggtt aaagttgatt tgaaggtcag
164581  cagtaaaaca acagacaaac cagacgccaa actggttcct tagctgtcgg tgggagctgt
164641  ggtacaacca ggtcttgaac cttttcaac ctctaataaa acaggggatg aatctgaagt
164701  ggatcaacca ggcccctgag gaagcagcac agaaaaacac aaataatatc aatatcaggc
164761  agccacaggg aaacaatggg gcatttctcc gtgctacatg catgctgcta ttgtttcaag
164821  ggctggggaa ttaattccac ttatttattt aaggcgtgtc aactcactgc ctaaacctgt
164881  ttcagtgtca agatggataa aacttttatg gctcataaaa tagagccatt catctcaatg
164941  ttctttgtgg tgggttttct tttctttct tttctttct ttttctttt tttttttct
165001  ggcatactga gctagacctc tgctctgaaa cggttacatc tgaacccatt gctgctatga
165061  tccacaccat ttaaaaaaaa aaaaattatt tcactggcaa atggatctca acagaaatga
165121  cacagggaag cattttagct acgatgtaat agctccaaaa attcttctaa acagtctgca
165181  tgcagttgca tctgttttga gcatgcatta tttacaaagc agaagtttta ctattttaga
165241  ggaaaagttc aaaagagata gcagtaaaga tattagtttt ctagaatact atgtcacata
165301  tttcatttta ctttagaaat gcaaccttgt taggatagct ctttcccatt catcattttt
165361  tgcccaagtt tccactgttc cgtagtcagc ttatactgat gtaataatca aatgccttct
165421  ttaacttgac tgctcagaat tttatgtttta attttctgca taaaatagca cacataaatg
165481  gaaaagaaaa tgcatttata tgctttttgt attatacatt ttttaaagt tcagttatag
165541  aattaatttt acttttgatt ttctgacaaa tgactttaat aataatataa ataaacaggt
165601  taacatttct aaagtgccac acacaatgtg aagcacatgt attttctcat gcaattatta
165661  attcaatcta agtcacacag gtccacttag aatggactgt aataacactc tttattatcc
165721  acaacatatt ttagttgaaa caaaatgttc cagtcacaca atatcatcac cgtagtagat
165781  cattatagct ttaacagatg acatcatggg aacacagttg ctttatattg aaatgagtaa
165841  aaagaagcaa tttgatgata tttcacaaat tttctaatca cagcctcagc catgtatatt
165901  acacgttttt gctccattgt aatgtaaatt gatttgtgga ggattcactt actgtcttat
165961  cctagttgct ttgttttttga gttctctatt gaatattgta gactttacat atgatgctag
166021  attatttctg atgtagtcag ttggtaggta agggttttcc cacatgaact caagtttttc
166081  cagtaagtag atcatttgag aatggctcca aataaaagtg gtgctttcac attttgctgg
166141  tacacaaaca tatggccctg aggaagacgg attcatttttg gggtgctaag cactgctcaa
166201  gatgtaagtg ctttttattt cccatttgaa ctggtgcatg caccttacag atggaccagt
166261  tgctttacat actggtggcc catttacaaa gcagcccctgt ttgaaaacag atgctttcaa
166321  gtgggtcacc aggctctaag aaaaatattt aaaccccttaa ttattggctt ttggtcgtct
166381  atggcaatgt gttctcattt aaacatagag caggggattt ttcttctata accaattaca
166441  gtttaaaaaa tgcaacgaat cttgcttcac acaaggagct taactctgtgg ttgagaaat
166501  tttccaactt attaaatgtt gtttatatcc tcattttgt cttcccaaag cattttataa
166561  ctccctctgt aactgactta tcaattttct ttctgacctt tcatatataaa tttaaccaca
166621  cccccacccc caaacccaga gcctccaagc aactagccta gagcaaaat atacaattta
166681  ctctctccat atctccaccg acgtctttcg tttttcttgt actctaatct aatcggtaat
166741  tcgtaagctt tggccaaata gttaaaaatg ttaagtgcta gcaaagcctt ttacctcccc
166801  ctcagatctg tctctgttta tggaatgggt cccagtttcc tcctcttctc cttcagcctg
166861  gggtcttcag gtcagaacac agtaaataca cacagcccctt gctggaccca taaatctgag
166921  caaagggcag gcctatatat tcagataagc aggggcagag atagggggctt gaaaggaggg
166981  agaactagcg gagtctgagg ctctgcagcc ctgttcagag aactgaactc aaaagaccaa
167041  gaatccttag tgcagaagga ggaattttgc cttgaaacat ctccccttat ttctaatgga
167101  tgagattggc actgcttcct cucgtttat tttatttttt ccacgttgct tatattcaca
167161  tccttaccaa atgtattatc ttaaaggcaa tcaagttaaa caataaattt aatttatttc
167221  caatgtctttt ttttcttaag tgtgtttgtg ttttgacctg tgtgtgtgtg tgtatatcag
167281  tgatatgaac tgaagtcatt ttactagaaa gtcttctcta ctgtaattt tcagtcccaa
167341  agttttttgac tgtataactg tattcttact gaccacattg aatccccaag aaaaataccct
167401  ctaaaggagg aatgacaaag tgacaaataa atgcttacat atccttcagt cttccaggct
167461  tctattttat tcctggggttc aaatattttc tgttggattt tcacttcttg aaattttcag
167521  tgactcctgg aagaccaccc ttcttggggg atgtacccat tgtgaccaca gataatgtca
167581  ccatgaaaa tcctgggcaa gatgaccatg gctgagaagg tccttctat cacacttgac
167641  agaatcactg cctgattctt ctttagatgc aatgagtcac accacagatt cgtctgggtc
167701  atttcagact ccaggaaaat gtgtcactcg atttgtttcc gagcaatgtt ttgtatttta
167761  ttgtatacat gtatatctaa ttgtaatctg atttctctag gttattcttt ttggctaata
167821  gagaatagat ttttaaaaaa tgctaattca tgttcctcaa aagggggcttc tttttttctt
167881  ttcctcggtt gaaaagttag tgataattcc aggtaattaa gaacattta tggaaaaaaaa
167941  ttgccaagaa agtaattggg ctgggagccc agtgtgttac acctacacta gagcctccatt
168001  tttgacaaat ctctgaaatg ataacaataa tgataataat cattatgtat cgttttatcaa
168061  gcacttactt ttggtaagca atgtactagg aacttaagat atatattaat ttttgtcttt
168121  acaagtggta agtgatgtac tactctatag tctcaatctt ataatgaaa aaaaccctcc
168181  gatttgaaaa gtaaagaaac ttaatccaga acacacatgg aagcccagaa tttgaaagtg
168241  gttttggctg cagagggctg tcttctgagc tgcctctcca tagcctcagg ttctgcatct
168301  tcaggatgag tgtcttgggt gggagggtgt ctatgtagtg gtgatcttcc atggccagtt
168361  gattttctcc cgccccctact ctcctgagcc tagccttggc attttcaata gctctctgag
168421  atcggggcct gtctctcaaa gaccttctgg accacatgtc tgaaacggaa ctcactgatt
168481  ctctagctgc catgtctcta ctctgtgatc catgtgatgt ttaatgggag ggagtaccct
168541  cgattctgta gtccgaactt aaggctctct aactacctac ctttttcac ctgtcatgat
168601  tattatccaa cctggcagag aagtgacctg tcaggaggc attacagtct gaccacctgg
168661  gtttgaaccc tgacttccct gtttaccagc tgtgcagtgc tggacaagtt actttactcc
```

```
168721  tctgcgcctt gattttttt catctgtaaa atggagtcta aaatattatt tattttataa
168781  ggttgtctag ttcagattgt tggtaatgtt tgacagaact attaaaatag ccttcaggct
168841  gctgtttctg cagtgaggct cctccttcca taatccagcc cctctggatt acagaataaa
168901  ataaataata aacatgataa tttcctgctt aaaaatcttt aagactccct attgccctca
168961  ggtcgaacta ttgaatcagg aaaaggcttt cattattttc ctccaactgc cctttccaga
169021  gtcattttcc accatgaccc tctaagcaat ttccactcta gcagcaaaaa attatacata
169081  tgatgttctt ttatttctcc agactttga ctgtgctgtg ctctctctat caggaatgcc
169141  cttcctttca atttccatgt agcaaaagta catttatctt gcatggctca gttcaaaaga
169201  cactttttt ttaaaggcag cataaattga gacagtcact tctagaatgc attcctctgt
169261  tttagaacct agtatgttga taacaatcat atgcatggta attatttgtc taccactagg
169321  ctgtggactg ctgtggggag ggactatgtt tttttaaact taatatcttt tgttctaggg
169381  cctcacatgt agtgggagcc tcccaaattt agattaatat ataaatatc tttcctcact
169441  cctaaaaatg acttagagca aatgtgaatc aaatgactgt aatgtgttta actagttgaa
169501  ttaactcctg ttagcttaag ataataaagg cagtgaactt gtaacaaaat taaattaaaa
169561  actgaagtgc aattatagtg ttcttactgt ctccaagata aaaccatgat acattttttt
169621  cctagcacac gttacattt ttctgacatc ataagaaaat ctgagaacag aaatccttc
169681  aagcatttcg tttgatagag aacatctata ttccatacag cattccatta ggaaaggagc
169741  ctgctttct cttatctgtc cttactctaa acgtaatatc ttatgggaga cagtatatta
169801  gcggttaaga tcataagctc tggatctgga atgtctgggt ttaaatgctg gtgctgccat
169861  ttataagatg tgtaatggct ggaaacagtt ttcttgggac ctgctatctc atctgtaaaa
169921  tgggtaccat agtaacattc agtgtagtga gtggttatga ggatcaaatg agttaatgca
169981  tctagcactt agatgagagt tcatgtatct tgcacttaga tgagagcctg gcttatacta
170041  ggtgctctaa aaatgtgtct tcttatttgg ttggtgttta taagagaggc acctgaaatc
170101  ctgatagaaa ggtgaggagg atttcatcat cagggaacag tggaaagaga tggagaagtc
170161  ttgagagctt gtgagaatgt ccattcacct gtgcaaggac cagtttatct atttcagata
170221  taattccaac acttccatga ttcagtgctt catttcatca ttttacacat ggaattacgt
170281  gtaggaacga acccaagtgt aaacttagcc atcaggaaag ttagctccag aactatcttg
170341  cctgagtttg aatcccagct ccatgacatg ctggctgtct caccctgggc aagtgtttc
170401  atttattaaa gattaaatt tttcatctgg caaatgagga aaaaagagt aatttttgcc
170461  ttttacctgt ggtgagaatt aaatgaaaaa ccatcactca acatgcttat cacagtgcct
170521  gtcgtatagt aagtgcttaa tgtgttgact actattttca tgttgcaaat attattgaat
170581  attttacca catggtgtgg tttttcaag tagttattga agagagtaaa aacatttatt
170641  tatgtagact taaaaatgta aggtgagcac ctctatactc accatcccag gttataaaat
170701  gaaaggttgc cactttctta gaagtctctg caggcctttc tgggcacatt cccatctctc
170761  tctccagcgc gttactgttc tcctggcctt tgaatcatcg tacttgct ttactttata
170821  atttagttc ttataatgt accactaaac agtatgttat ttggtttgt cttttatgaa
170881  tattatagta atgtaattga tatatatttt atattctgtg ttttgcactc agcagatgca
170941  gctggattga tgcatgcact gtagttcatt cagtgtcatg ctgaatagta tttatgata
171001  tcaacatcct acaatttact ttgctattat tttttcatt gatggacatc tggactgtta
171061  tttatttatt gctatcacaa agcctgctat atagaacatt cttgtacatg tgcccctata
171121  ggagactttc tatatataca ccccggtgtc tatataaaga ctttctttag gaagttagac
171181  ctaggagtgg agttactcac ttgtaagatg tgggaatatt caaatttact tggtaatggt
171241  aaactctttt ctaagtggca gcacatgaag gagtttcag cagaagatta ttaggtacat
171301  atttcagatc ctcataaaaa ttatatatgt ggtagttagt ctccaagatt ccacagtttc
171361  aacataaat ccaaatcatc cacttctctt ggtgttcata cccttgtgtg gtccctccc
171421  acatatgcc aaggctggtc tgtgtgacca gtataattca ggaagagtga tggtattgtt
171481  gcttctgttt tggacatctt tcttcttgtc tcttttgcat ctctcactct gggggacaca
171541  gcttccctgt tggaagcaat tctatggaga ggcccatgag gtgaggagca gaggcctcca
171601  gcaaacagcc agtgaggagc tgtggcatgc caccagccat gtgactgagc ataggagcca
171661  atttctagct ccttggatct tgagatgact gcaatttgag agcttgacta taatctcatg
171721  aaagatcctg aaccagaatt gccctgctaa gctgcacctg gtcatgagtc ccccccgccc
171781  cccccccca cacacaaatg tgagattata agtatttgtt gtcttgagct aagctttgag
171841  gtaatttttt atgcagcaaa gataactaat acatattcta ttaaaaaggt gaaaaattcc
171901  aagttcccctt aaggaatatg tgaaataaag caggatatta aaacaaatag atttgaaaat
171961  ggataacatt aaaagttgat gcacctgtaa ttcaggtgc tattaagtta gttagccatg
172021  taaaaaaaa cccatagaga tgggagacca aggataattt gtgattcata acctgtaaca
172081  acgcatgtca agcgtgttca cgtttttta gttgatcttg atttatcatt attagagtcc
172141  tttagatgtc tttataagtt attcttgatg caaaaacatt cattataaca taatagcaaa
172201  aaagaagcca tttagttata cagaaataag agaaaagtta aatatgtcat atatctacta
172261  aagagaatat tataagtca tgacaaatat atacatattt tttaagtgac atattccaag
172321  cataatgtta agtgacaaca gcgggatatc ctatacaaac agtataaaac caactattca
172381  gtgacttaag ggtgaaaatg gcatctctta gttgtgagat tatgtgggaa tttgttttct
172441  tcattaaact tctggacttt caaagtctaa taaacatacg ttaagactac tattgttaga
172501  aaaaagtgta tttagcattg aagaaattac ttttaattca ttttagtaa tacaaagaaa
172561  tgcggacagc aaactttgcc ttcagattgg gcagaaaatc cctatcaaat atatatcaac
172621  aatgagcatc tggaaaggtt ccggttgcta tttcgagttg gcttccttc aaattatctt
172681  gatctttgga tctaatcata gtcctctatc ttgttataat tgctggtcct tttgattct
172741  cttacagaag tgaagatata ttctaagaag tgtatcctta gatgatttcg tggttgtgta
172801  aacattatag catgtatttta caccaaccta aatattatag tatagcctac tacacaccta
172861  ggctgtggtg gtctagcctt ttgcttctag gctacaaacc catacagtat gttactattc
172921  tgaatactgt aggcaattgg aacacaatgg taagaatttg tatatttaaa cataaatgta
172981  taagaattgg tacatccaaa catgcaaaag gaatatttt atgataaatat cttattatgg
173041  cttcaatgtc actaggccat agagaggaat ttttcagctc tattatactc ttatgggacc
173101  accatcatat acgtaatcca ctgttggtgg aaatgtcatt ggaaggcatg acttttttat
173161  tcatcgtttt gtggacttca gagctattgg agaatcagag ggtaaattca cagaatactc
173221  taaatttaaa tgtgactaaa gtttatattc ttcagtttct gctcatgaag ttgagaagaa
173281  taagataaat gcgatttcac ggaggcattg tggaggcaag ggttgcctaa taccttttta
173341  tatcagaaag gatttttatc taaggcagcc aatgctggca taattgaaga aggaatttaa
173401  gttgaatagg agctggagtc attgcctgca cagtgacact tcatggcata ataagtatag
```

-continued

```
173461  aaattttga tattagttta aaaagaaaaa ttctcaaaac ttagtgtttg aatagactga
173521  aagtgttctt tttttgtttt aaaaatgctc tttataacca tatttttgcc cattaaatta
173581  agcttggaaa agaccttaaa atagagtatt taatttggaa gaattaagca aagttccatc
173641  acgcaggaac tgcttcaaca tgttggtgta tttcttctga tatttatatt tcctttctgc
173701  atttccatta caccctgtac ttttagcttg catgctttgt tattactgaa tatttccttc
173761  tagactgtca gttccctgag gacagaggct atgcctttct ggcttatcat cttttcctca
173821  cctagagtt tagtaggtgc ttaataaaaa catgttgaat gagtaacttg gttggacaat
173881  tacacggaaa agaggaaatc catgagtaga aaaataagtg aaagtaaagc tctatgccag
173941  ttgagactat tggcaatttg aagtgtcagt gtcctctgt tcttggtccc aggtgccatc
174001  aaaggtaggt ggaaccaagg ccaggtacca ggtgccacct gagtgctcca gggccagtgc
174061  caagtggaag ttctgggaag gtttctgtga gggtgctcag tcagtgccaa ggaaagagat
174121  cacacctggg tttctgaact ccaaaaggc aaagcagaag aaggagcttt gggtttagca
174181  ggaaaatatc atggctttg gctttatttg aaacctcgaa cactgaatca tatttgcttc
174241  tcaaagcagt gagctatttt gttttatcat gtacaaaata ctgatctcag gtatttcaag
174301  caataggaaa acattaccag ttatggcaag cactggaatt tataatttgg tgactctgca
174361  aagatctaat cattccaaca tcattattcc aagcgttatt tgattaatca ttgcatttat
174421  agagaatctc ttaccagtat ttattgttta gattttttcca atgccctcat cactgaggtc
174481  tctggttgca tgtgtagaag attaagagat acaataagct aggaagaata gatcaagcaa
174541  cacacactag acctaggcca aactaaataa atatgtctat ttctaaggcc tggaattcag
174601  caagacaga cacaaattct tgcatatata aaaagtaaa attttacaa gaaagagatt
174661  tcagccttaa tttgatctga tttgcttaa gttaagcagt ttttatcta taagccagtg
174721  ttcataatta ttttttcgta ttattttttcc aatcatggtt tgaagataat aggagccatg
174781  aggaagcaga accaagaaat taaaaataaa attctccaag ttgtgaattg aggacaaagc
174841  atgtgtttcc aactcaaaac aaatagttta aaatcctttt tgaatctggt gttaataaaa
174901  tcaaccagaa caattacag ctaaacgcag ttcttcctag tgtcagttac aagccaaatc
174961  ccctagttta gattctgaat tttaatttct gatcatgggt gaattactca cctccctgtg
175021  cctcggtttc ctctcctata aactagggac aataacagta tccatctcat aggattgctg
175081  tgaggatccc acaaggtaat atgtgttaag ttctgagaat aatgatggac aaataataag
175141  tgctatataa atagctataa ttacgattaa acaatgaagc aaaacacttg cctatcgttc
175201  tagatcattt catctttttt tcttacaag agaatgcatt tgttactctt tatagcttta
175261  tagttcattt tatactcatt cttatccttc tatacaagac tgcttctctt gttcttctgt
175321  tggtaagtct gatttctttt aactagcctc ttataaggta gaatgctaca atatgctggg
175381  gccagaaagg tgtctttgtg tttttgaca ttctagaatc agccacagca tgtgatccac
175441  attagaaatc tgtaggaaa taagagcaat ttcttaaaat cctttgtgt tcttatttt
175501  atttttaag acaggttctc actctgtcac tcaagttgga gtgcagtggc aaaatcacac
175561  ctcactgtag cagttatcaa cctcgctggc tcaagcaatc ctctcatgtc agcctcccaa
175621  gtagctgaga ccacaggtcc catcatgcct ggctaatttt ttaattttt cttagaatg
175681  ggtgtctcct tatgttgccc tggctaaact cctaggctca agcaatcctc ccacctcagc
175741  cttccaaagt gctaagatta caggcctgag ccactgtgac cagcctttct ctgctcctaa
175801  aatacatttc tttatatatt tgtgtcctgg aatgcaggtg attgaatacc tcatttgct
175861  actatttaaa aatggagaat aagagagaaa ttttttatg tgagtatcat tattgacatg
175921  actgtgcata agaaagctgt atatactggt tcttttcctgg gagatccgaa gtgagaaacc
175981  agttgtccat ttcactggct cttcacttgg ccatctcctc catggtgaag ctgtgcagtg
176041  gacagaggtc tctggacagc agaagctgca ccctgatgct ctacctatta ttgcaggctc
176101  tattacatgg atggttattt cagttcccaa gcctcagtta ccctggctat cctatgtgag
176161  ctgtacatcc ctgcctacat caaagcaaga acttggccca ggaggcagtg gaccaagtgg
176221  tccaggaccc aactcttagg tctatgactc agtttactgg aaaagccttg taattcttcc
176281  tacctataga aacatcttta aaatccagca gtcaagcaag gatatctctt gccacggact
176341  ttttctaaat ctatttgcct tcagctatgg aactgggaag gctcttcaa agggacattt
176401  ttctcctccc acccaaggtg atggtaacat tgctaaatgc catttggatc atgtcgcttc
176461  ccctcgagaa atcctccagt tgcttttcct tgagtatggg gtaacatatc agtatctaca
176521  tgtcattcac agcccttgt actggacctc tgggtctac tttcccacaa gtatcttggc
176581  tttgacccta ataagtgtga cactttcctt catttgctgt cttttctctt cctcatgcct
176641  tgcctttggc tggattattt tttctgttgt tgagatattt ctttgatttt ttgctaggct
176701  aaatcctccc cttcctatac attaaactca ggtgtctgtt cctctgagaa gtctgtcctg
176761  aactctaggc tgagctggat gacgccctct gtacccatcc agtgctcaca gcattagcta
176821  cactgtgttg tacctgcctt ttggtgttca tgttgttcat tggtctggaa gcttctgagg
176881  acagggactg aaactttgt tttggcaact cttgcatgca gcccagagcc tggcagatgg
176941  taagaaggtc aataaatgtt tattgaataa ataaaagaat gaagcctaaa tttgataagt
177001  tctcccatat gataattaga gacaccataa acctagagga cattatgatt ttaggcagat
177061  ttatagctag aggaaaactg ttcccaaaga atttagagaa gggagaacta gatcagacga
177121  taaatgcatg atggttata agaattagaa agaatataag gtaagatgta ggggctcctg
177181  aacctgggga ggagttttca gtaggtaaca tattcaaatg agttagcttt gaaacagatg
177241  aagtgaacag ttctgatttt agggattaaa aagttcatta aattaataca aattgttgga
177301  gaagaacttg tttgaaagtg ctcaaaatga gctaagagtg taatagaagc tctctaaact
177361  ttattatta ttaacggcat attgagcacc cagtacctac tgagcatttt caataagtgc
177421  tttaaaggca taaactcata ggatttagcc ctcatcacat ctctatgaag taggtcattg
177481  gtaatattag ccctgttttgt ggatgaggag gctgaggctg aagtattgta acccacatgc
177541  cgaagcttac agggttggaa aatgtgggtc tgactgagtg agtccaaaag ccatggattg
177601  caggagggac ggtctcactt cattctgcat tgtcagatca tggggaaaga ttggttctat
177661  tttgagtgcc cattttaaga tggttacaga caaactagag tgcattctgt aggggggaagc
177721  tgttgtgaat ttaggaatga ccattaatca catcttgttc ttttactcag atttctgaac
177781  caacttacgg atacatgaag aagtcagaca aggccgggtg cggtggctca cgcctgtaat
177841  tccagcactt tgggaggccg aggtgggcag atcaggaggt caggagattg agaccatcct
177901  ggctaacacg gtgaaacccc gtctctacta aaaatacaaa aaaattagcc aggtgtggtg
177961  gtggatgcct gtagtcccag ctactcagga ggctgaggca ggagaatggc atgaacctgg
178021  gaggccgagc ttgcagtgag ccaagatcac gccactgcac tccagcccgg gctacagagc
178081  aagactccat ctcaaaaaaa aaaaaaaaa aagtcagaca aatagaaatc tagaaatcca
178141  aatgtcagct ttttcagagg aaacttgtgt tatggttaaa tagatgggct actcctgtac
```

-continued

```
178201   ccctagcccc acattaagtg tagccatcag aagtgcagat tcaccctgta agggcctaag
178261   cctgcctgct aaactcacca caggcaggga gaaaattgaa ctctgcaggc aggtccaaag
178321   cagcaggcgc cgtagaccta taaggactta gccagccatg cccagggatg tccctcagat
178381   tcaacaatca ggcaagctat tccttttctt atgggcagga aggaatcaga gagaggtcaa
178441   aagtgtgact ctaaatcttc gtagagacac ataaatccca ggataaaagt cctcatcctt
178501   agccatggcc aggatgctaa ttgtcacatc agtgggacca aggggtggaa agactgttgt
178561   aagggttaaa tttatgtgtc caattgactg ggctgtggta cccagatttg gggtaaaaca
178621   tcaattgaat tgctgtgaag gtgttttgta gatgtgttta acactcgaat tagtagactt
178681   tgagtaaagt agatgtgaactt ccatgatatg tgtgggccat atccaatcag ttgaaggtct
178741   caggggctag gagaaatact cctcaagact acaatatcaa ctctttcttg aatttccagc
178801   ctgcctgcct gccctacaga tttcagagct gccagtcccc aaaattctgt gagccattct
178861   ttaaagccag tctctctctc tctcactctc tgtctctctc tagacatagg tatacatata
178921   tatatatata tggatggatg gatatataca catatacaca catatatatg tggatggatg
178981   tatacacata catatatatg agtatctcct attggttctg tttctctgaa gagttctgat
179041   taatacaatg tggaatgtgg gaatgtggaa tctgtagctg aggagtcaag atggtgatca
179101   tggaagctgt tttcacattt ctgaggggtt cccacaggac aagctatgta gcatctgaga
179161   tggtttaaat ggagtgtgat aactttgttg gtcgtactat agaagaagtg ctcatgttat
179221   gagaaggctg actcatggct ggctgttagg gtcactttga actcttttaa gagtagtgaa
179281   gctattttat gcttctgtta aataatctaa tgccacaggt tttttttttc acatttcatt
179341   gtttgtgaat ttctttcaca tctcttagtt tattggtttt cccgtagtgc atagcacaca
179401   agtaggcaat tatggaattg aattaagagt ttaataatgg ctcattagga accaaatttc
179461   aactttaaat gagcacatat ttctctattt tttgtgttgc tttgttccta tatgtatttc
179521   ttttaaagta ttcatttgta aaaaataacc agcatattgg taatgtccag tattacttgg
179581   ttatttaatt ataaattaaa ctacatagct cacaggattt ttgaccagaa caaagcaaga
179641   aattaaaata ctaacaagaa aataacctaa tttgtaaaat aacgttctct gaaatcaatt
179701   atcttatttt cacaggaaat aaaattagga gaaatctgct aaattcatcc aaaataatac
179761   aagagtttgg gaatatataaaa aaagtactac ttctttaaat gctaatgaac accagcttta
179821   tcatttctaa agaagaggat tttggtgtta tttttcttct cccagtgaaa aatttactgc
179881   tcctacctgg caaagggaca tgggcttgag cctgatattt gagactgtat aaatagctga
179941   tctggaaatt tcaagccaat tttatcctct ttccttcaac tgcagtttca tgctctcccc
180001   tctactcctt gaattatccc atcaacattc ttggtcattc agggttgatg aagccatcat
180061   gccatgatca gctgcttaac ttggcactct gtgagggagg gggatcttt ttgaagcccct
180121   gacaccattc ccctgtccag ctcgtcttgc agggcagtga acaagaggct gagcagaagg
180181   tatcagaatc tttggaaatg ggacccatca gatgtttcac aagtcaaagt attctgatgc
180241   atactcaagt ttgagagcta ctggtttata gcagttcagc tcctcacaaa cacaaatata
180301   tgcacatttg tggtattcct tcagtgaaga tggctctggt cacattgaaa cagtgaatat
180361   gtgcctttgt gtgtgtgtgc gtgtgtgtgt gtgtgtgtgt ctgtgtgtgt gtctggtgtt
180421   tgggggtaga agtgataacc aggaaatgtc ccatgaaatg tctcatgaag caaaggcagg
180481   ggtatttct atgaactatc tccattaatc tgtgggcctg cattcctgga aaatcttcac
180541   tcaggatccc taaggcttcc tagagcaaag gtggcccagc ctgggtcttg gcatagtatg
180601   acctcagggt gtccaggctg aggacaaggt gaatgtcctg cctctgctgc gctgggtctg
180661   ggtgccctgg tgtgctcctg ccctctcctt gtcagggaac cttggactgg gtctggggcc
180721   tgagctcaat tcccagaccc acctctattg agctatgtga ccttgggtcc tatgctccct
180781   gggccatctg tggtgagtgg gccatatgac aggccatctc agggaggtgg gcagggatgg
180841   tgctcaccat acaggcctcc ctcacttctc ttcacctcca attgtatgca gaagacttca
180901   gtattacaca tccttccatg aaggacctct cctaccagaa aaaaaaaaaa ataaaagcaa
180961   aaggaaatga tttctcgttc actttcagct cggaaactcg acaggcaggc cttggcttgg
181021   tgtcttaact cggcagccct gtggtgctag gttttataca ttatttcaaa gggctagagt
181081   tccctctga agatttgttt tctggtggtg ggcttagcaa ctctattttt ttctccttaa
181141   tctatttct tacacaaaga acaaatgcct ccaagtacaa ttgcacccag attactagac
181201   tctccttaaa cattaccaaa agctataatt ttgaaattct tttatctatc ccaagctaat
181261   agcagttttg catgtcttta tattgtttc atctgtttct tagctgcccc ctcctcttgg
181321   gttattgtct ctggaatatg tgcgggcttg tttaatttta gtgctgaatt tgggatatgg
181381   aaaagattat tccaattat attacttatt tgttgaaaca taatatattt atatggacct
181441   tctgtgctcc agaagcagtg tgttcttttg tgaagacatt gctggagttg ccaaggcggg
181501   gatctgaatt gaacaggatc tgaatctaaa gcaatctagg agtagatcta tccttcagca
181561   tcttcaaacc aacttatcaa atatttcttt caacatgaaa cattcacccc agccctgtag
181621   ccaactagtt cagtgctatt ttttctacaa ttcaatgaac ccgtgaggcc ccatctaaaa
181681   caatcaccac agcagaacct tggggtctaa caaagatttc cctcccaggg agaataaggc
181741   atgttgaatt ggtttgaatc aatggggcat ttttttctctt gttggcctgg tgattacaac
181801   cctgtctctt aaactgcact caactcaaat gactttttt aaatgatata atgctactaa
181861   agaatagaaa atacattctt ggtcaagcta ttaccaagca gaaaagaaaa aaaactccat
181921   cactttgaat ttctcacttt gtcaataaaa ttatcaacct cgacttcctt tatgtttctt
181981   ggtgcctgct gttaagccat gagtcagaaa cccccagctt tggatgttgt catagagccc
182041   agacaccata tgctcctctg tcatgagagc aggaccagct atatgatttg tggggagcc
182101   caatgcaaaa tgaaagtgtg aggccccctg ctcaaaaatt atgtaggatt tcaagacggc
182161   gacagcagag cattaaagga agtgctgggc ccttcggaac cacacaggac acatgtgcat
182221   gaagctagcc cttgttcaaa gacagaccta gttgaggagg aggaagagtc catttccttc
182281   tctcctgctt gtcagcccaa gttatttagg tttatctcag aggtctgcat tcaattctcc
182341   caactcaatg aactgcctct ctcctttcca aatttgctct gcatttggga ctctctctaa
182401   acaaggtgtg cagcttcgtg caaagttaag tcacactgcc aagtcctcta aggcctgatg
182461   aaagccttgg ggcaccagga ggggcagaga ggcagccctc gtgcctcacc acgctgctct
182521   gctctgccag aggtaatcgc tttgcagatt ctcaactaca tctccaactg tggtgttttc
182581   tctccttgt ccttctgaca aagactttta taattctctt taaatgttcc agggattttt
182641   ttgctcttc aaataattgt tatcaatccc taccaaatgc cttagatctt ctcctcctcc
182701   ttgtctttac tgtaaatatt ttcccttctc ttcagcagca acgttatgcc tatacatagt
182761   aacaaaatct ctacagctat cttagtttct ttattcttgt gtcttcaaag actcccaaat
182821   cttgctctgt tggtgtttgt tgaacttttc taataagatg acttttaaaa gaaagctaaa
182881   tacatatatt tttttatga tactttaagt tttagggtac atgtgcacat tgtgcaggtt
```

-continued

```
182941   agttacatat gtatacatgt gccatgctgg tgcgctgcac ccactaactc atcatctagc
183001   attaggtata tctcccaatg ctatccctcc ccctcccc caccccacca cagtccccag
183061   agtgtgatat tcccttcct gtgtccatgt gatctcattg ttcaattccc acctatgagt
183121   gagaatatgc ggtgtttggt tttttgttct tgcgatagtt tactgaagat gatgatttcc
183181   aatttcatcc atgtccctac aaaggacatg aactcatcat ttttatggc tgcatagtat
183241   tccatggtgt atatgtgcca cattttctta atccagtcta tcattgttgg acatttgggt
183301   tggttccaag tcttttgctat tgtgaataat gccacaataa acatacgtgt gcatctgtct
183361   ttatagcagc atgatttata gtcatttggg tatataccca gtaatggggt ggctgggtca
183421   aatggtattt ctagttctag atccctgagg aatgccaca ctgacttcca caatggttga
183481   actagtttac aatcccacca acagtgtaaa agtgttccta tttctccaca tcctctccag
183541   cacctgttgt ttcctgactt tttaatgatt gccattctaa ctggtgtgag atggtatctc
183601   attgtggttt tgatttgcat ttctctgatg gccagtgatg gtgagcattt tttcatgtgt
183661   tttttgtctg cataaatgtc ttcttttgag aagtgtctgt tcatgtcctt cgcccacttt
183721   ttgatggggt tgtttgtttt tttcttgtaa atttgtttga gttctttgta gattctggat
183781   attagcccctt tgtcagatga gtaggttgca aaaattttct cccattttgt aggttgcctg
183841   ttcactctga tggtagtttc ttttgctatg cagaagctct ttagtttaat tagatgccat
183901   ttgtcaattt tggcttttgt tgccattgct tttggtgttt tggacatgaa gtccttgccc
183961   atgcctatgt cctgaatggt aatgcctagg ttttcttcta gggtttttat ggttttaggt
184021   ctaacattta aatctttaat ccatcttgaa ttgattttg tataagggt tgcaatccta
184081   gtctctgata aaacagactt taaaccaaca aagatcaaaa gagacaaaga aggccattac
184141   ataatggtaa agggatcaat tcaacaagaa gagctaacta tcctaaatat atatgcaccc
184201   aatacaggag cacccagatt cataaagcaa gtcctgaatg acctacaaag agacttagac
184261   tcccacacat taataatggg agactttaac accccactgt caacattaga cagatcaatg
184321   agacagaaag tcaacaagga tacccaggaa ttgaactcag ctctgcacca agtggaccta
184381   atagacatct acagaaagct aaatatgtat ttataactct tccatgaaag tctgcctgct
184441   ctccccactc ctaaatatat tagtgattc tgagcataaa aaatagattg attttgtgac
184501   attatgaact ggtagtcata gtttgcctac tgataacttt gccaaacaca ggagcatgtg
184561   gacattgttg cctctaaacc cagctgcatt ccctgcaaac tggatgccct cagaggagaa
184621   gggtgagagg gtcctttata gaatatttt gctgatagtg gttgccacta ggcaatgaca
184681   ttcacagatg ttcgcaaatg ggtagttcaa ttaaaagttt tcataaatca agttcaggac
184741   ctctgaatca ccctaccaca gaaaattgac agatgcattg aaaatgaaaa ttaatgcca
184801   gggctgcatg aaccatttct tcctgttctg ttcaatgtta ctacttgttt gcggagggga
184861   acacttggaa tttccacttc tgcaagtggg acccattct ctctgggcct taattcctcc
184921   tgatgacagg ctgaaatatgg tagtgactat agtctcagga agatacatca gaagccatgc
184981   agtcagcttc tccaatactt tctttgccta ttaatttcta catgactttg gtcagatcac
185041   cagatgcctt gatttccaca ttttaaaaat gataattgta cctgtgatca tggataattt
185101   ttttctttgc agggaggtga gtaatgtgga taaaagaaat acctgtgaga gaatttagaa
185161   atatttgaaa gggaagaactc ttccttcaaa tgtgttttgt tttagagat ggggtcttgc
185221   tatgttgtct aggcaggact tgaactcctg ggcttggacc atcctatcac ctgagcttcc
185281   agagtaactg agactacagg tgcatgccac catgcccaac tcacatgtga cttttttttt
185341   ctctctagat cttattatgg gatttcccac tcatttctta gttattttga aagacaagac
185401   agtgaggttc acacctctga atgttttctc attatgtaag caaatttgga cttagctttt
185461   gcatccatgg cttcttgaaa agaaagtctc cttgagcctc tgaggctgaa ttcttagtac
185521   attaaccctc ctcttctgtg ttgcaactgt gatataggaa agtctagtta gcatcctgat
185581   ttatttggtt ttgttgagtg tgtgtgtctc tgtgtttgtg tgtgtgtgtt ttccttgaag
185641   tattcttggc gtgggcatgt gtgtctaatt aaaaaagtaa attgacagag ttgaggccac
185701   tgggctctta catagattgt tttcccattc ccagtccagg catacctcat tttatcgtgc
185761   tttgctttat tgtacttcac agatattgag cttttgagaa attgtatatt tgtgtaaccc
185821   tgctttgaac aagtctatca gtaccatttt ttcaacaaca tgtgctcact tcatgtcact
185881   acgtcacatt ttggtaattc tcacagtatt tccaactttt tcattacaat tatatctgtt
185941   atggttgtct gtcatcagca attttaatg ttactgttat acttgtttta ggacatcaca
186001   aactgtaccc ataaagatg acagactaa ctgataaatg ctgctttgt tctgactgct
186061   ccactgacta gcaagtccct catctctctt cttctccttg ggcctcccta ttccctgaga
186121   cacaacaata ctgaatttag gccaattaat aaccccttcaa tgatctctaa gtgttcaagt
186181   gaaagagtca catgtctctc acttttaaatc aaaagctaca aatgattaag tgaggaggga
186241   agttgaaagt caagataggc tgaaggctag gcctcttgtg ccaaatagtc aagttgtgaa
186301   tgtaaaggaa atgttcttgc aggaaattaa aagttctact ccaatgaaca catgaatcat
186361   aagaaagcaa aacagcctta ttgttgatat ggagaaagtt tgaatgattt ggatagaaga
186421   tcaaaccaac cacgacactc ccttaagcca aagcctattc cagagcaagg ctctaactct
186481   cttcaattct gtgaaggctg agagaggtga ggacactgcg gaagaaaatt tcaaagctgg
186541   cagaggttgg ttgatgaggc ttaaggaaag acaccatctt cataacataa aagtgcaagg
186601   tgaagcagca agtgctgata tagaagtggc aacaggttat ccaggagatc tagctaagat
186661   cattgatgac ggtggttaca ctaaacaaca gcttttcaat gtagacagaa gagccttcta
186721   ttggaagatg ccatctagga cttttcttagc tagagagaag ccaatgccta gcttcaaagg
186781   acaggctgac tctcttgtta ggggataatg cagatggaga ctttcagttg aagccaattc
186841   tcatttacca ttttgaaaat cctatcgccc ttcagaatta tgctaaatct actctgcctg
186901   ttctctataa atggaaccac aaagtctata ttacagcaca tctgctggtc atccaagagc
186961   tctgatgggg atgtacaagg agattaatgt tgttttcatg cctgttacca caacatctat
187021   tctgtagccc atggatcaag gagtaatttt aactttcaag tctttttatt taagaaatac
187081   atttcataaa gctatcgctg ccttagatag tgattcctct gatggatctg ggcaaagtaa
187141   actaaaaatc tactggaaat gacttaccat tctaaatgcc gtaaagaaca tttgtgattc
187201   ataggtagag gtcaaaatat caatattaac aggaatttgg aagaagttga tttcaagctt
187261   catgaatgac tttgaggaat tcaagacttc agtggaggaa gtaactgcag atgtggtgga
187321   aatagcaagt gtgctagaat tagaattgga gcctgaagat gtgattgaat tcctgcaatc
187381   tcctgatgaa acttgagtgg atgagaaatt gcttccttga gatagaatct attcctggtt
187441   aaaattctgc gaatattgtt gaaatggtaa caaggatttt acatatcac ataaacttag
187501   ttgataaagc agttgcaggg tttcaaagga ttgactccaa ttttgaaaga agttctgctg
187561   tgggtaaaat gctactaaac agctttgcat gctagagaca tctttcctga aaggaagaat
187621   cattcaatgt ggcaaacttc ctttattgtc atatttgctt tattgcagtg gtctggaact
```

-continued

| | |
|---|---|
| 187681 | caacctaaaa tatctcagag gtatgcctat acatcagctc cttgaagagt gacactttat |
| 187741 | taaatgtcct tttgttataa cgttgatgaa aaaaacactt cctggctgga gccacagttc |
| 187801 | ttgtcaagtt tgcatgtttt ctctatgtct acatgggttt tctctgggtg tactcagctt |
| 187861 | cctcccacat ctcagagatg tgcatgtcag gtgaatgggc gtgtctacat ggtcccagtg |
| 187921 | taagggagtg tggagatgtg tgtgtgtgtg agtgcacttt gagatgggat ggcggctttt |
| 187981 | ccaggaccga tttctgccct gcctcctgag ctgctgggat aggctccagc cactggcgat |
| 188041 | gctgaactga aatgagaggg ttggaaaata agtgaatgaa gaatgattga atgaatacac |
| 188101 | attattgtaa aataacagtt caaaacttct acaacaataa tgcaaatgca ccacagtaaa |
| 188161 | caatgcattc tgaacgcgct cagtaagcct gccagatttg ttcttgtttg tttgtaaact |
| 188221 | gcatggtggt ggtaggtact ccttacaatt tttcctttgc aaacatttac tgcttggttc |
| 188281 | aatccaccat cactaggact gctgtcactc actgattcac caaaaaaatt gggtaattat |
| 188341 | cttgtttcta ttaatctttt ttaagtatct atatctcacg tgtatttcac tgtttaacat |
| 188401 | tagaagtgtt ttggtttgga cttttttaga agtttggtga tattttggg accagacata |
| 188461 | ggccgtagga acttaattct tgtttatatc aattagctca tagtaaaatt ggttttgctt |
| 188521 | aatgtggcag tttccaaaaa catatgaata ttgttaagtg aggacttact gtaattgtta |
| 188581 | tgcaacttct gttctgataa caacccagtt gttgttcttt ttaatgaaat gatactggaa |
| 188641 | ggaaatagca ctttgcattg ctgtaaacta acaaggcgtc ctcctatccg tggcttactt |
| 188701 | atgattcctc agcactttgc tgctcttcgg cactgtgggc agcagatctc attctgctgg |
| 188761 | tgtttttcct tcactttgtc atgccgtcaa gtacttcttg ctaatatggc tcagtttcag |
| 188821 | tttgtttcac cagaaaataa attttatttc acagcttcac agcttttcat ccttcccatg |
| 188881 | ttactccaaa cacatgctca ctgggtttcc ataactcatc gagtaatctc ttacagactc |
| 188941 | tttctacgtt ataagaacat tccctgtttg ccttccttga catctctttc ttaaactctt |
| 189001 | ttccaacatc aaaatcctca cttcctggga gaaaagagtt gtgttgtgaa aagagcatac |
| 189061 | atgggattca gagttttcag attccagtat tacctcctc tgcaactccc tagctgtgaa |
| 189121 | aatttaagcg attgctcggt ctcagtttcc ttagttgcaa atgggaatga caaacaggac |
| 189181 | ttttccccaca gaggcactgt gaggattact tgagatagta catgtcaaaa gctgttccta |
| 189241 | gagatttcaa aatgtgttca ttgttatttc agcaggtcga ttttcttcta atttttactt |
| 189301 | tgatagactc tcaattcatg caaataaatac atggcctatt tgcagtttaa atttaattac |
| 189361 | tgattcacaa aatatgtatt tactttctcc taacattaat cattggta,cc aagccaggtt |
| 189421 | ttgacctttt ttaacctgagg aatttagagt tggaaataaa aggcaaaatt ataaggagga |
| 189481 | gaacgaagta tagttcaagt cctaaagtat gctgattaac acatttgttt gcctttggaa |
| 189541 | catctgggaa agcaactata tactaattct cttaaaaatg attattttaa acatttgtgg |
| 189601 | aagattcagg tgtgtgattt taattgcaca attaattaat tattggtgag gtcctttat |
| 189661 | ttcttcctag taatcaacat aataaaacgc tgtagtataa attatggcag aaaagaaaat |
| 189721 | taataaaatgt agttgcagct tttaattttt attctgaaag tatgtttaaa caattgatta |
| 189781 | ttaatttta gctagatttt tcttcttcct tgctctttcc tttccccctt ctccctcttt |
| 189841 | ttgctgatta attcattcct ttcttcttc cttcagttta cacaaacaaa acacaataat |
| 189901 | gagaacaatg ctatatgaaa ggcctttcct aaaaatattt aagctgtgaa aaaatgaaaa |
| 189961 | caaaggaatg gacagcaata gctaatctga tatttgtcta tgaattaaca ggtaagaagg |
| 190021 | aaaaaaggtt gctgagtgtg tgtatgtgtg tgtgtgtgtg tgtgtgtgtg tgtgtattta |
| 190081 | tgtttgtttg tttataaaca atccggcgca ttcatgccca gtgaagggtt aattactttt |
| 190141 | gacgtttgt taatggcaat gtcgttctct tacttattat tgctatctt tttagatcag |
| 190201 | ctatttttaa acttctatca gactttgaat gaacttatca attttcagtt aataaaacgt |
| 190261 | tgaatttgat atccttacaa acttaccagt ggtaaatatt atctcctaag tagtactgtt |
| 190321 | tgaaaatcac atctactcgt cttccagtcgt atctggtacc tggactatct aactggtacc |
| 190381 | tggaccgttc tccacttatg tttcctttgg gtgaagattt caaagatttc tggtaaaacc |
| 190441 | aatgtgctc ttggggaaag tatatcatga aaacgtattt accagtcatg actgaaggat |
| 190501 | gtagatggtt ttaagcaagt tttttggaac catgcaattc taccctcccct gctgattagc |
| 190561 | tgcacagcct gaatagttgc taaaatttct gaagctgttt tctcatctgc cagatgtgta |
| 190621 | tggtggtatc ttttttttctg ggttatgata atgattaaaa gtagtcatgt ttataaagta |
| 190681 | catagcacag taccccagcct gtactcaata aacatcaata aactgtatat tcacataaat |
| 190741 | actatatcga tagctaattc tgtgcctctt aatatgtctt gaattgcctg taacaggaaa |
| 190801 | atctgattca aacttacta taaaggctga aaccatacag agactcattg gctcacataa |
| 190861 | gtggtaagca gagttagtca ggcctccagg ttggtttgct tcagtggtgt ggtaaggtaa |
| 190921 | tatcatcaag gcccactcac catctttctc tccccactt acttctgctg ttagctttat |
| 190981 | cctaaggctg gcttctcttt gcggttggga ggtggccgtg aacacttcct gggtctacat |
| 191041 | gtttccccct ccaggagcct ctcgaaaacg ttaagaactc tcctttccta gaagctcct |
| 191101 | gtgtctcttt gatccaactt ggcctatata tttagcctat atattcatcc caggccccaa |
| 191161 | agctataact agaagtagga ataaaattga taagttaag cctagtcac cagctctaac |
| 191221 | ttgatgtcag cttctctcaa aacacagggg ttacaaagga gaatgtggat atcctgggaa |
| 191281 | gcagggcatg aataatgagg aggagaccac agcatcaatt acagtgttaa ttacacctaa |
| 191341 | agcaccacca gcaaatctgt gtatctctat gggacgtgag ttctgacaag gcagggcact |
| 191401 | agagctcaaac gttaccccttc ccagtgtagc ttaggacttg tgatttcccc tgtagaatgt |
| 191461 | tttggaagag gtaggggtct tagaggtcac ctagactttta agaggctgtc ttaaatctgg |
| 191521 | tatcacagag cttgttattg gtacacttag gagcagaaca tagttgtcct gatggtatat |
| 191581 | tggatctctt ttccccatte agcgcagctc tgcctcttaa gctcttcctc tattttctga |
| 191641 | tattacatct ggaaaagtca cacagctagt gtgtggcagt cttggaactg gacctgccac |
| 191701 | ttcagcccca tgcttcattt aaggcaccag tggaacatgg cgtatttgg aaaatatgtc |
| 191761 | cagaatgtgt atatactaac ctgggcaggc aagaactttg ttcttatatt acatggaga |
| 191821 | ccgggaatgg tggctcacac ctgtaatccc acactttgg gaggctgagg cagaagaatc |
| 191881 | atctgagatc aggagttgga gactagcctg gctacatggt gaaaacctgt ctctaccaaa |
| 191941 | aaatacaaaa attagctagg catgtggta gcacctgtag tcccagctac tggggaggct |
| 192001 | gagctgggag aatcgcttga gcccaggagg tggaggttgc agtgagcaga gatcacatga |
| 192061 | ctgtactcca gcctgggcaa cagactgaga ccctgtctca aacaaaacaa aacaaaacaa |
| 192121 | aacaaaacaa aacaaaacaa aacaaaacac accaatggag aactagaagc tggccattcac |
| 192181 | agggtattct tgtgactgta gccattggat ttagtggctc ttacaagagc cctaatcagt |
| 192241 | tattaggact cttgtaagaa aatagtgtca tgtacatgga tattcatttc agcattcttt |
| 192301 | ataatgacag atccctagaa acaactaaa cacctaccaa tgaggaaatg gtaaaatcca |
| 192361 | ttatattgca acattaggac aatggcatag ctccatttgc gatggaaatg tttacataaa |

-continued

```
192421  tgttcatcaa gctacaggtt atgtgaagaa agctttgctt agaagaacat ggtattatgc
192481  ccctaatcat tgtgtgtgtg tgtgtgtgtg tgtgtgtgtg tgtgtgtgtg tatgtatgtt
192541  tatatgtagc taagcttata tttctttaag agtattagag aatctgtaga cagtaattac
192601  ctggggaagg aaattagagg tctgattgag acaaagacat tttcactaat tgattttaa
192661  aaaaacaagc atatatacta cattttcact taaaatacta cttataaaag aacttattct
192721  tggtttcaga acttgagtat caatctaggg tctatcattt cttggcatca tgatcttaag
192781  caagacattt tatttctcag ttttctcacc tgtaaaatga agacgatgat gtttgtcaca
192841  cgagtgttat gcaaattaac tctctgtgaa agtgctitct aagctctcaa ggggtgattc
192901  ctatggggga cttttcttga taatcacctt cttcctccta ttccacacag ttcccccaca
192961  gcccactgcc tcagggaaga tgtctgtcat taaagggcaa ataatctcat tggaatttct
193021  ggttggccgg gagcactgac tgagaaggaa ggctgaggaa ttcagggaag gtttaagttg
193081  gattccacca accttttccc acaatttgat gagcatttta attctgtgca actggactca
193141  gtgttcccag gtcctaactc aactctgaaa tgggattcag aaatcctcac tgcattctca
193201  cctgtccaga caagatggaa aagtctaatt ccatttcaat tcattatttg ttcaaccagt
193261  agttattgaa caccaactgt atgctaggtg ctcaggggaa ttc
  2341  actaacaggg gcggagacaa aagggaagaa atctctcctt tccagcttgg gcgataagtg
  2401  tccctgctg gccactgctc atcagttctc cagcaggaaa gtaaagtat acctgggtgg
  2461  gagcttttat ctcagggcta ggaggactgt gcagcagtct gggaaacatg cagcttggtt
  2521  aaagg(aaat tttgacctgg gtcactggca tctagagaca atgcatttga gagagcccac
  2581  aacaacaatc aaaatagcag ttgtaaagca ctaatgtgcc aagcactatt ctaacacttc
  2641  gtaaactcat ttaatctaca ttgggttggt actattatcc ttgtcatttt acataggagg
  2701  aaactgaggg acgagaggtt aaatcccttg cccaaagtca cttagctagt aaactgagat
  2761  tcgaaccatg gcaatccgtc tctagaatcc aggttcttaa accctatctc aggaataagt
  2821  agggaatttg gccagaggaa gctgcagagt ccctaaactg cctcaatctt tatcagggat
  2881  gaaatgagga gacatctact cctaaattcg ttactgaagt aggcagaact aaggcactag
  2941  atcaaaacac taagatatgc ccactaagct tgaagaggag taatgatgat gtaatcataa
  3001  atcaaaagta acaaatggct tccactatgg agcccttctt gggacttcca ggagcaggcc
  3061  aactgggctt aggaaaatga ctggcaggag caaacagaca tataccctag agattaactt
  3121  gaactatgat aggtgaaagc tctgggagcc ttgactgatg ggtttctgac acctaaatgg
  3181  tgttttaac gtgtatgaag agaatcaact gtctcttcaa gagatgaaat caagggaaaa
  3241  ctgctggctc taaatgatgg tctttacaatg taagctaggg ggctaatcaa ctgaaaagtt
  3301  taaaacactt atcatagttg gcttgtcaa catcaaatta tatacatgag gtcatatata
  3361  tgtaaaatac aaattacaac acaaaaatat tcatacatac ttttacaca tttatatata
  3421  tatgtagaaa tactatacaa gtaaaaaata atgtgtgagg actccttacc aaacgcacac
  3481  agaacgtttg agaggggagag gatccaaaga aattccaata aaatgagctg ctgtagtgac
  3541  tgtggtatat aacttttcgg tttaaaggat aaaagttggg aagagattca attaaaggct
  3601  atcgaatgat tatgtctagg ttgaacaaca agcatttgct caaattctgg ccttgtggag
  3661  ttaggagggt caccatttga actgtaaat tggtaagtct taagcaaaga aaaatatcat
  3721  atatcacata tatgtgtgtg tgtgcatttt taaatccaag aagtatcttc taatataaaa
  3781  tcacttttga aaactggcat taaagataga tccataatgg gttatcaaca cttggggaca
  3841  aatcttaaa tctttctgta ttaaattaga cagccaaata ttccttattc tgtgagaata
  3901  atgcagagtg atttatcatt ctaagaaggg tgatcttttc atataaagag cccattttta
  3961  aagtggaatg tctcctgtga caccctcact gtgcaggcaa caagaagtag agctgtttat
  4021  gctggccaaa cctcatccaa gatttggtat gcagagggg tgataatatt attacctgag
  4081  gtgtttggac tccaggactt tctgaatcat tttcagaat aatgactgga gataaaaagt
  4141  ttttacagat aattactcaa gacactgaat taccactgca acacatggtt tgttcaactg
  4201  aaataaagag aggaagtgta tcacagaggt taaaagtgtg aactctggaa ctgggctgct
  4261  tgggttcaaa tcttggcctg accacatact aacttcggga ccttgagcag ctttagatta
  4321  tctatttcag tttccccagc tgaaagtgaa atgttgtaag taaagcattt agtaatgtct
  4381  ggcccttagt aagcagctaa taagtgtgcg gtattgtcat taataaatcc ttttctcaat
  4441  tccaaaagat ggccaataag aacagctttg ttttgactat aacaactcta caaataatct
  4501  gtatattaac aaaagtggct acttctgtac tgaatacagg aatgcagact tgtctaagtt
  4561  cttctatctt agaggtctct acaaccaacc tcattataca gttgagatgt ctcaatttg
  4621  agccctgctc aatcccactg tctttcctca ttagcttcat ctcgtacctc aaactctggc
  4681  aacctcttaa tacaattat ttttggaagg agggcccat tcttttttcc tctgcagtca
  4741  cttcccactg cactctctgg aatcagtttg attgtcaggt tacgttttca ttcatagccc
  4801  gtgttgaaac tcacctcact tttcattact ttagaaactt ggctcttccc caacctctcc
  4861  atgcttttg ccttaaacac ttaatgtctt gtttaccttg aatcaattag aaaagacaag
  4921  ccagtcaatc ttattcttat tcttaatatt atttgcaagc tttatgattc attcaagttt
  4981  tacaacagat acttctatct ggccattgtt actacaattg atgaccgtta tttctaccct
  5041  ggacctgctt cgcttttata ttcttcgttt ccatcccacc ccgttattgt tatttcaaaa
  5101  tccacataca taaaatgctt cagaggtttc tggtttccta ggatcttgtc actgtcacac
  5161  cacatctata tgttatccac aaaatgtact cctgacttca tcacaaagca ttctctcttc
  5221  actgcattcc ctaatgtagc actcctattc catatctaac atgtcacatc ctccatttgc
  5281  ccctcagggc cttcaatttg cctatattgc caatttagct ccaattagta gccttattct
  5341  actatatttc ctctttatcc tggaaagcta gtttaatcct ctttgatgcc tacctggaaa
  5401  ttccatgtca ctccacctt ttttggtact acaactgtat ttaagcatga gaataaacca
  5461  gaacaaaacc cccacgtgta tttttatttt tattttaatt tttgttgaga tggagtcttg
  5521  ctctgtcacc aggcgggaga gcagtggtgc catctcagct cactgcaacc tccacctccc
  5581  ggattcaagc gattctcctg cctcagccct ctcgagtagct gggattacag gcatgtgcca
  5641  ccacgcctgg ttaattttg tattttagt gggagatgggg tttcaccaca ttgtcaagat
  5701  ggtctcaacc tcctgacctc gtgatccgcc cacctcggcc tcccaaagtg ctgggattat
  5761  aagtgtgagc cactgcaccc agcctccaca tttatttta aacaagtatg aactgtaccc
  5821  tcctataata ggcatattcc attgttctga gtctttgttt atggtccctt tataatatta
  5881  ggtatataag aaagattaag tagtgtgcag aaaggcaaat ggaggaatgt gcgcaatgac
  5941  agaacatatt aagcagaaaa tgaactggaa agaccccaag taaaggcact cagaggagta
  6001  gaaggcaagt ttaaaacaac gattgcattc cagcgagcag tcagattaaa agagaggctc
  6061  tgaagttact atgaacagta atttcagttt ggataacaag tctataaaat cagattagat
  6121  aaggagtatg catagcatgt ttggtaagga gaacattctc acacaggttc tcatcactaa
```

-continued

```
6181   gtaaagtccc ctccactgag aagagtttct aacagtgaaa cagcaaaaga actaccataa
6241   ctaactccat ttttgtttaa ggacccttta cctattcctc catgtaggct aattttagag
6301   cagagataat atgcaaaaac agcaatcatg tagttttaaa aactaactct gggattaaag
6361   aagtatgtat aacaattatg ttttgttgaa gatttgcagg agcattgtga cccaaccaat
6421   gacaaagaag ttcccaacct ccttggactc ttgctggcgc ccagatgtct gtggtcatag
6481   gtcacctctt catcccaact ctgtcctctt ccctttgccc ttaacataaa aagagccgag
6541   cccaacattt gtactgactt aagatggtac tttaggacag tagtctacca tcgtctcagt
6601   ttgctggctc tccgaataaa tctgctttc ctcgcaccaa ttttcttctc tcccgagttt
6661   tggctttgga gccgcaagca gctgaacctt ggtttggtta caagtttgca ttctcattat
6721   gtgagaaatg ggaggcaggg taaacttagg tagagcacag gcctcacata cttagagcta
6781   cagagctccc agactcactc tgggttcctt gtttcctgga ggaaaaaaac taggtttcca
6841   atcccagttg cctcagtgcc tcatgtgtgc aactccaatg ctggggttat gaaaaaagcc
6901   taactaagca gtcctcaact tatgagtaag ttgtttttca actgttcatt tgcctttctc
6961   tcttgtgaac tcaagaaggt ttttccacac agaaagtcat gtaagttcca atcccagaag
7021   ccaatttgac acctaatata cctgaattat aatacttata ccattatgac ttctatggga
7081   atatgtgttc atatttacaa cttagctaga aacataatat tcctatagga ccagagacgc
7141   ttctagttcc aacccaggga tgaaattcta tacagggttt atggctagag aggcaagaga
7201   caggggcact aagaaaatgg ggctggggag tatattacag gagtgaagag aagatgggac
7261   aaagacacag ggctgtgtag aaaggtaatt aggagtggga cttactaagg aagaatgcag
7321   attaccctc ttttattttt cccctcccc ttttgtcact gtctcaccac ttcaaaccca
7381   ctaaccagct agaagtgtga agagaagaga ggactggagt tgtgttgggg tgtagtagga
7441   agttagtccc agaaactgtg gagtttgctg tggcagggta gaaaaggaag gaaataacag
7501   gccatctcag tagagattaa gaatgatttc tgtaaataaa aagcagatc aggagccatg
7561   tgtacttcca tgtggcttat ctgttgtcca ctaaaataat caagacaggt tctcatccaa
7621   agcagaattt ttactcagca aggcaaggtt agagtcaacc agttttggtt gattcatttt
7681   tcagaagccc aaggggatagt atctctaatt tggggtcctt ttatgtgctc aagaagtaaa
7741   caaaccaaca aaatgtaaat cagttctcaa gagccattat tagggaattc agaactatgt
7801   gctaacatga gatctgagaa ataaaagaag gtaaagcata aaacagagaa gagcaccagg
7861   ccctccccta aataaacaaa caacacaagg cctgcactc agaagaccct tggaatgtag
7921   gtctgtctct cttcttga atacttaaat ctgaagggat ggaaagacca cctaaaaatc
7981   ctagttttt ggcatgatgg gggtctaatt ccttgttcac tccaaagagc tgatggcaca
8041   tgttccctgt aaggatctcc ttgtgctaaa agtctgcagt ggcctttagt ttataggact
8101   gtgttcaggc ttccccactt cgcagacagc catgaagtca gctgtcattc aactcaacgc
8161   ttctcaaatt ttaagtata ttaagtaact gtggagctat aaaaatgaag attctcaact
8221   cccatcctag gcctaatgaa gcagaatgtg agtgggattc agggatgtta aacaagctcc
8281   aaacatgatt ttgatgttca tcaaagttgg aggatcacta gagtaatggc caggactaga
8341   agtcaaaaga cctgcactta ggttactggt ctttttcttt gtgtggggatt atagctatgt
8401   tgccatctcc ataggcaaga gtattctcat ttttaaaatg gagaatgctt ttgatttacc
8461   aaggtatttt aggaattgag aaaagtgctc tgtaaatgtc caagtgctat aaagtattag
8521   atgaaattat tcacactctg gccctcttat gtgtctgtcc ccaagctgtt tccaacttaa
8581   tgctattgat tgcccaattt gcacgaacct tttacttcag gttggctagt cttttccctg
8641   atgcttccaa accacatgca ctcttatgat ggcttacatt tgttttaccc gctttctccc
8701   ttttgactgc taagtctgcc cgtcaaatcc ttattttaaa taaaatcttt cttgaccact
8761   ccaggcaaaa gtaacctgtc cttagaatt tacagcactt atagtctgtt acaaagtacc
8821   actttcattc gacaccatct ggtgcatcaa ttctactctc ctgtagtctt atatgactaa
8881   atatgtggat cttatctatc ccaaactagg ctacaaactc tctgagaaaa gagtttgggg
8941   ttatcttctt gttctccaca gcacgtagta caatgggcag cacacagtga attcttatta
9001   aatatctgag gtttccttat aacaatggtg actgaagttt tgccccaata attgtaaagc
9061   taaatagtat ttctcaccgg cctgaactct gtgagataac ttccctgtag tcatcacaca
9121   gaaacagatt tttctccttt gtgggatagtc tgatgttgag taagagctga gttctgcctg
9181   aatgatttcc cacactcttt acatacatag gtaccacgtc tattatggat tctctggtgt
9241   ttactaagat ctgacctctg tctgaaggct tttccacact catcacattg gtagggcttc
9301   tccccagtgt ggattctctg atgctgaatg aggctggtga ttcctcggaa ggcattccca
9361   cactcatcac acttgtaggg cctctctcca gtgtggattc tctgatgttc cgtgaggact
9421   gatctttgag taaacgcctt cccacactta tcacatttat agggtctttc tccagtgtga
9481   attcgctgat gttctgtaag acttgtcctt tgaataaagg ctttttcaca tacgtcacat
9541   ttgtagggtt ttccccagt gtgaattctc tgatgctgaa taaggccact ctgactgaag
9601   gatttcccac attccttaca ctgatagcat ttttctttgt ggtggatttc ctgatgggaa
9661   acaagggatg agttataaac aaaggctttt ccacactcgt tgcactcata cggcttggcg
9721   ccggtatgaa ctccttgatg ctgagtaagt atggaacgcc gactaaaact tttattcac
9781   tgagtgcact gataaggttt gtctcttgtg tggatcttga tatggtgaaa gaggcctgct
9841   ttctgactaa aggctttgcc acagtcatta cagtgatagt gttttctcc tgtgtgaagt
9901   ctctgatgtt ggttaagagc tgaccaccgg ccaaaggctt tgccacattc attacactta
9961   tacggtttct ctccagtgtg tattattttg tgtcgaataa gcacagttct cccacggaaa
10021  gcttttccac attcttcgca tttgtagggt ctatctccag tatggatcct ctgatgttct
10081  atgaggtgtg agtgctgact aaaagctttt ccacagtcat cacatccgta agattcttct
10141  cctggacaga ttctctgatg ttcagtatgg tcagagttct cagtcaggct tactccattt
10201  tcatcacagg taggttgttt atcttctctg gagcaagcag agggctcttc tgttatttct
10261  tcaggttcac gagtttctcc acacctagca gacttggaca tatcatttc aaatttactg
10321  gatgtcttcc catgtggttc catttcttca gaaacttctt gctttaaatt cccatactca
10381  tttccagtct caacatctaa aactaagaag ggatcataaa tgttacctct ttctaccttt
10441  aaaatgtatc catacatttt aatattaagc agctgtttag aaataaaaaa tgcaagagtc
10501  taccatctta gtgatgaaaga gagcaaaata tatttgtttc aatatggaaa acatatgcat
10561  caaaaaaata tctggaagga cacacgaaaa attagtaaca gttacaacct atttcagagt
10621  aggaggaaga gactaggtgg ctgggaaaat cgagtagaat agaaactttt cattaaataa
10681  cttaaaaaat ttttgttttt gagccatgta catttttacc tacttaaaaa attaaatgaa
10741  aatgaaaagg atgcagagaa agtagaaata aggtagcgga tctttcacac attcaccaac
10801  ttttaatatt ttgcaacatt tgtttttatta ttttttcttt ttcttttttt tttttttgag
10861  acagtcttgc tctgttgctc aggctggagt gcagtggggt gatgtcagct cactgcaacc
```

```
10921  tccgcctcct aggttcaagc gattctcctg cctcagcctc ctgagtagct gggattacag
10981  gcacgcgcca ccatgcccag ctaattttg tattttagt agacacgggg tttcaccatg
11041  ttggtcaggc tggtctcgaa ctcctgacct cgtgatccac ccaccttggc ctcccaaagt
11101  gttgggatta taggcgtgag ccaccgcacc cagcctgtta ctccttttct ttgtaagtat
11161  acaaattttt tttttcttga accatctgaa agttagttgc agacataatg gagcaaaggc
11221  ttatttagtg aagcagaaag gatatagtgc aagtggaaga tagaggtatt gtctgatagg
11281  ataaaggcta aaaatagcaa ggaggtcagt ataaagagag ataaatatca gaaggactaa
11341  attaagtggt aaagccagaa tttagaagaa tatgaatata caaaaaagta agggttgaag
11401  agtgacaaac taggctgtct gagagtctat atatgagcca tcagattctg agacggcctt
11461  tttgacttta atgatcagaa acagtagcaa gtacaaaaaa gccccaatgt cctatgttac
11521  ccatcttccc cttcctccca agatggtct ttcttcttta ccttgctcct gttgggattc
11581  aagttctgga gattcatact ttggctgggc tttcatggac tggagggaca tactgggttc
11641  tccttctttt cgtagacgta ccgtctcctg caagaacatt tcctgttccc cagtgtggac
11701  tgagacctga ggaaaatgag atgtagctga cagactcact ctgataacag aaaacaaaaa
11761  gtatactatt tgtggcagtg gctgaaccct gaaatgacct tttttcccaga tataagcctg
11821  ccataaccct acccattctt caaggccaat ataaatgtcg cctcctctgg ggaatcttcc
11881  cttctccacc cagatgtaat ttctcctgtt gttaccgcta aagtatgttg gttgtgccac
11941  tgttacctct ttatcttatg cttaagaag tggagaaagg aaagggagaa agacaaaaca
12001  aaggagagaa gaaaaaggtg aaaagaggca gaaaggagga aataagatag aacttagggt
12061  aaaataaaac attaagagag aaagaggaaa aggaaagggg atatgtaaag gtaaataatg
12121  tagagaaatg ataaaaaaaa aaaaaaaaag gcaccctgg gatgccatgg tgggaggatt
12181  gcttgaggcc aggagtttga gaccagccta ggcaatatag caagaccccca tctctccaaa
12241  aaaattaaaa atgatctggg catggtggtg cacatctgta gtcctaacta ctcaggggac
12301  taaggcagga ggactgcttg agcccagttc aaggttatag tgaactatga ttacactact
12361  gaactccagc ctgggtgaca gagacactgt agctccaaaa aaaaaaaaaa aaaaggttga
12421  agggaacaaa tgaggagaaa gaaagggaaa agaagggaag gagagaaatc tcttccatat
12481  tcattcccta agctgttccc aatagtctct gctcttctga ggtgcccgtc ccacttctct
12541  ctgggaagat tatcttattt tctatttatc caagatcaca atcatctcaa aaatcatcta
12601  ctcttcattt tatctatctc caccctcata ctcctctcca tttcttctat cttaggatga
12661  tgtcttctct ttttcaaggc ttacgtctct actttgcct tcaatcccat cacttttggc
12721  ttctctctga cccttgctcc ctcagttaac tcatttattc aattcagcc actgggtggc
12781  tcccattctt ccatgggctt atttcctctt gcatttaaaa ataacaggtt tcttcagcaa
12841  ggtattgtaa aaagcaggga tttggaatca catggattac ttactctctc tcttagtcta
12901  gtagctctgt gacctgggc tagttactta ctctctctga gattataaat aacatttgta
12961  taaaccacct tgcacaggga ttggcataca acaggttctc aaattactcc cccattctct
13021  tcaaaggtta aattttataa ctaagaaatc accatatact gcctctattt ccctgataca
13081  ttttcatttt gtagcctcag tcttcagaat aaaagcgaga gtcagcaaaa tgctatctca
13141  gatgtataga aaacggtgtt ttgatatctc atattttgaa aaaagaaagc cggggggaaaa
13201  ggccagtact gcgagctgtg cctctattc tgggatctct ggtcaggcct cagaaatcaa
13261  gctgtaaact ccattatatg cccctgcagt gctttcagag aaagaactgg ttggcaatac
13321  aaattcagca catttaaaac caaattactt ttgtctgcat ctaagaatcc cattctttgt
13381  acctccctag ctactctgtt tctactgctc attacctccc tcatgatctc atcctatctc
13441  gtggctttaa atactatgcg tattctgaaa agccccaatt ctgtagttct agcacagacc
13501  cttccactga attccagttt attatatcta gttgtttgct caacttttct gcttggattc
13561  taataggaat ctcaaaatta acatgtccaa accctgtttt ttttgttttt ttgaggcaga
13621  gtctcactct gtcgtccagg ctggagtgca gtggcaagat cttggttcac tgcaacttcc
13681  gactcctggg ttcaagcgat tctcctgcct cagcctcctg agtagctggg attataggtg
13741  cctgccacca cacccagcta attttgtat tttagtaga gacaggcttt catcatgttg
13801  gccaggctgc tcttgaactc ctgacctcag gtgatctgcc cacattggcc tcccaaagtg
13861  ctaggattgc aggcttgagc caccgtgcct ggcccaaacc ctaagttttg attcctgtct
13921  ttccacccca aacccacttc tctcccagtc tttaccatct ctatgaatga caaatccact
13981  ctatctgatg ttcagaccaa atacttcggc ataatcctta acttactttc tctcatattc
14041  cacattctat ataaaaacaa accctgtcaa gctctagctc caaaatatat ccagaatcca
14101  atcacattt accactccca ctgctactat tctagtccaa gtcaccaata tctcttgcct
14161  ggattattgc ttattattat tgctcctaaa atggtttcgt tgcctctacc ttttactcct
14221  atggctaccc cagcccccatt gtggaacttt ctcacagtag ccagagtgac tattttaaaa
14281  ttcaagtcag attatatctc gcttctgttc aaaattctcc aatgactttc catctcagaa
14341  tacaattcga aattcttata atggcctaca agttctgaca taatatatat ttataagcat
14401  ttttatttcat ctcctccttg acaaccacat ctccaccatg ataagtacat tctcactta
14461  agaccctctg cctgaatgct gttatccctg atagcttatg gcttgctctt ttcattcaga
14521  tttctcctgt aaatgtcacc tatctgaaaa accttctctg acaagtctac agaaaacagc
14581  acaatcccca cttatttcac tattccttt tctctgctttt attgttgttg ttgtttgaac
14641  agaattttatt accacctaca tcttgtaggt gtttgttgat ttttttttt tttttggag
14701  atagggtctc actgtgtcgc ccaggctgga gtgcagtggt atgatcgtgg ttcactgcag
14761  cctcgatctc ctgggctcaa gcaatcctcc cactttagcc tctcaagtag ctaggactac
14821  acacacctgc ctggctaatt tttgtatttt ttatagagat gggggtctca ctatgttgcc
14881  caggctggtt tgttgatttt taatttacta tctgtctcag tggaccagaa cctacatgag
14941  agcagcaacc cctgtgtttt gttcgctgtt gcattcacag tgcctaaaac agtacctagt
15001  ccaaacagac attcggtaaa tatgtgctta attgtttcct gcagtctta actttgttag
15061  gagtgtctcc attatactag tctttcaagc ttaaaatccc tagtgtttag cttagaatac
15121  attgctctgt aaagagttct ccattggttc ttccttctt atttaataga gctaatctgt
15181  catcacttcc aaacagttct tacctaagac atgcctcatc cttggtaatc acactttcac
15241  gatcctattt cttttttctg tttgtttgtt tgttttgtt tttaaacgga gtctcactct
15301  gttgcccagg ctgggtaca gtggcacaat ctcggctcac tgcaacctct gcctcctagg
15361  ttcaagtgat tctcctgctt cagcctacca agtacctggg attacaggca tgtcctgcca
15421  caccggctg actttgtat tttagtaga gacggggttt caccatgttg cccaggctgg
15481  cgttgaactc ctgacctcag gtgatccacc tccttggcc tccaagcgc taggattaca
15541  ggcatgagtc accgtgcctg gcctcatgat cctatttcaa acttagatat tttgccaca
15601  tgttcctacc ctctctattg catttgtgat cacagtgcta gattatactt ctgtttcatt
```

-continued

```
15661  atttccctaa gtttcaaact ctttataccg gggtttccca gcattggctc tactgacatg
15721  ttcctagcat tggctctact gactttgttg tctggggctg tcctgtgtgt tttaagaggt
15781  ttagcattag ccttgccctc tctacccact agatactagc agcacctccc cgagtgatcc
15841  actagatact agcagcacct cccccaagtta taacaaccaa aaatgtccca agacattgcc
15901  aaatgccctc tggtgcacaa aattggcact ggttgagaac cactgtctca ttttagtatt
15961  aaaaacaaaa caaaaacgtt ctacataatt tggttctctt ttacatctta caattagtaa
16021  agctcatttg gactcaagga gaaaaggtta ggggcatctg tcctacagaa taaaatctca
16081  attccagagg ttgagattca aggtcctgga cactatctca actctgctat ttggaattca
16141  cctttccaac ctaactgggc ttttctgctac tcaaagaaac acagattccc caccctgctc
16201  tcctcactaa ctttccattg tactcccaca tctcattccc ctgaaatagt taatgtcttc
16261  attttaaaac cctgtaatgg agtcagagca atggatatat ctgcaaaacc ttaattctta
16321  attatttgta ttgtgcaaca gagtgatgcc cctccaagag actgcttccc atcctgctac
16381  tgtcatctct ttgatacttt ctcttgtctt agaagttttc taagatgagc agcatgttta
16441  tcaaacagaa ttttgtagct taatagagaa atataaaatc cttccacaga aaagttataa
16501  ataagttggg accacattag ccaactttcc gtgaaactca tgccccttc tgatgcacca
16561  aactgtcaaa aacatgctt gtgaaaaaat ggctgttctt cactctggcc tagaaatcca
16621  caatttatgt tttctcaagc agaagtcaca tcttttct cacctgctct cctggttcat
16681  ccagttctct ctctaaatcc tccagcacag tcaccacctc ctccccactc tctggatgct
16741  gctcctgcac ccaggcctgg agctcctcag gtaggatggt caggaactgc tccagcacca
16801  gcagctccag aatctgttct ttggtgtggg tctctggcct cagccactga tggcaaagtt
16861  ctcggagtcg gctcaaagcc tcacggggac cagatgtctc ctggtagcag aactgtctga
16921  agtactgacg gaagacctct ctgctatggg tgttgttttt acgcaggtcc caatcctgtc
16981  tggtggtata tttctcttcc tctatcttta cttccaaagg ttcatcctgg tccatgtggg
17041  cctggatagc ccaagtagat gccattttag ctgtgctaga actaccggtg tttcaagtaa
17101  gatctcacct ggaaactgta ttcctggaca gtcctgaaga ataagccatc attattaata
17161  caaactccac cataaagtaa aactgcaaat tctgagaact taactatgac ctttgaaatc
17221  tgacctccgg attaatgtac aatacttact cagaaaaata ctctgataga aaagacttaa
17281  gattagaccg attaggccg ggcacagtgg ctcacgcctg taatcccagc actttgggag
17341  gccgagtcgg gcggatcacg aggtcaggag atcgagacca tcctggctaa catggtgaaa
17401  ccccgtctct actaaaaata caaaaaaaaa aaaaaaaaaa aaattagccg ggcgtgacgg
17461  cgggcgcctg tagtcccagc tactcaggag gctgaggcag gggaatggcg tgaacccggg
17521  aggcggagct tgcagtgagc cgagatcgcg ccactgcact ccagcctggg cgacagagcg
17581  agactccgtc tcaaaaaaaa aaaaaaagat tagactaatt taaagagaaa gactgaggaa
17641  aggtgccaag ttgtttcagg acttaagagt aagacttgtt ggtaaactta ttctcatttg
17701  gtcctaaatg aaagacaaat ggaataaaac taacatttag atcaagtaaa taataataac
17761  aaaaggttag gacatccttg attagttact tttatctttt gaatgtccag atgtctggtg
17821  gaaaccatga aatcacaaaa gctacagtca tgtaaattta ttcttcagg gacttaatct
17881  ttctgctcct cattcttcat ttataaagtg agaaggctga agaggttact ctttaaggct
17941  tccctctaac ctcgtggtct gtgattataa tctgaagtga ggaaggccca ggaaagggtc
18001  cctaggacgc cggcgagcgt ctgtgaccca ccactgtcca gaaatgtcgg taagcgctga
18061  acccaaggat acacagcccg aagcaaacgc ggaaggtatg ggccttacag cctggaattg
18121  ctgcagagac tgggagccaa accctcatcc taatgtccca acgcactttg gggagggaga
18181  gcttcccgcg gatccgcctg ggtttgggag gaccggggtc cactctgcac cggccagggc
18241  ctgaggggcc cagcagctgg aatacagcaa tctcccgccc acctgctcgc agcgtacaga
18301  gcacaacatc gctcacctgc ggccccagg gccagaaag aactccctcc tacggagcga
18361  aggcaagagg cctcgaaccc tttgggacc cggaacccat caaaagtgac ccacaaaggc
18421  cggaagcggc cacgggggt ctaagaacca gcccgcgcgg ggcgcacttc cgcggccgct
18481  ctaggaaggg agcgaaaggg gctttcaact cggtagtgtt tccgcgcgtc tacgtgagag
18541  gaaggttgat ggctttcagg cccgctggta aatggaacgg gtttatcttc tcctcttctt
18601  tacccagcca ttgtccacac ttccccgac ccgatgggtg gtcgaggctt gtagaactga
18661  tcttaagaca gggaaatccc ttgcgtctcc attcactttg ggattctgtg tctctgaggt
18721  tagagatgcc tcaaagggat gttctccggg ggaccttccc aaatccgcgc ttagcggtgg
18781  cgaagggact tcttccacac agacttctca agggccagcc ggctggtttc tgccggctct
18841  ttcgccatcc acgattcttt tgatgttctc ttttatgtgc tgatgtatga ttatatgtca
18901  gaaaacccgg ttcaatggaa aaactataaa aaaaggataa tttagtaaaa tagcaagata
18961  taaagttaac acactaaaat caacgaccct catatatgtg aataatcaat gataacgagt
19021  tacgagatat aatggaagag aagaccatat ttacaagagc agcaaaaaag tgaaactagg
19081  aataaactta acaagaaatg aacaaaactt ctatgcggga agctttaaaa cattcctaaa
19141  aggccaagta tacatttaaa caaacagaaa gcgatatgag gttcttggaa agactcaaag
19201  aggtcagtcc tccctaaata cgtatgcaac tgtagtattc caacaaaaat atcaacaaat
19261  attgttctgg aattagataa actgattata aaattcatgt ggggaaataa gaatagccag
19321  gaaacccatg aaaaagaaaa atggtgaggg tcaacccttat cagatactgg aacataccca
19381  tataattta gtgtattaac agagagaaag aatgaccag aaatggatcc aggtatgtaa
19441  ggatattgag taaatgatga aggtgacacc acatatcaac agggaaatga agaacttaga
19501  agttgtgctg ggatgataac cgtttggcaa aggtaaaact ggattttgtat ttcccaccac
19561  acatcacaat agagataaat tctaaatgga tctgagatct aaatataaaa aatccaccta
19621  tacatgtatt agaagaaaac atgaataata attctaacac gtgggaatag ggaaacatta
19681  tctaaccata tgactcaaaa tctaaaaccc ataaaaataa taaatctggc tacatgaaaa
19741  taaaatgtat tgcttgtcaa aaaaaaataa ggaagaaaa aggcttgcaa catatcacag
19801  gcaagggcta gtttccaaa tacctaaaga gctcctaaaa gttgagaata accaataacc
19861  caatagagaa aatggccaaa agaaataaat agttgacaga ataagaaatg ctagcagccc
19921  tcaaacatct gtaaatatgt tcaacttcac tcaaaatatg aacatacaaa ttaaaaacta
19981  tgctgactga ggcaccgtta gtcatcagat tggcaatggt acaaaagttt gacagcatgc
20041  tctactcatg aggaaggaga aactccttaac attctagtgg gaatgcaaaa tggtacaacc
20101  cataggtatg aaagataata ctatacagca aaattatata tgtaagttta cccttttgttc
20161  ctgcaatacc acttctagaa atccatctca aagtactttt gacaaaaata tgaagtgaca
20221  cacacacaag attaaatgag atcaggagag gcctgatttt taaaatgcca aatatgaggg
20281  gatgaaattg agaaattctc aggaggaaaa atggatcagg gcttcatcat tgattatgtg
20341  ggggataaga gaaccaaaaa aaaaaaaaaaa aaaagcctgg tatcgtcaga ggatggtggt
```

-continued

```
20401  ccctccacca agacagggga cactaaatga caagtagcat tttgagaaga aatttatgag
20461  cacagcttgg ccatgttaag ttcgaaatcc taggaagcat tacactgtag atgttgctat
20521  ttgttaatgg attggtttag ggatttgtgg gtctaggagt catgagaaga gagttagctt
20581  gagatccata ttttggagcc ttccacctttt cagtaatggt taaaatgatt aagatatctc
20641  atgaagtgtg tggtgctaaa aaacagccta ggacagattt ctggagtgcc ctttgccccc
20701  tactgccagc cctatagatt cttctttcag ggcgtctgcg gagaagggag agagagatcc
20761  ctcctcacac cgtgccaggg ctcaaatctc acctgaagcc gtagaacatc tcagaaaaca
20821  acagacagag aaattattgg acaacaactt gaattcaacc tggaagtgtc cctcaagctc
20881  actttggggt ccttttccag gcatcttgaa ggatttttgc aatgcagttg ttttccaagt
20941  tccacttggc atgacttact gtaagaagct gatatgaaag tctcacttaa aaagtcagct
21001  tgcaccaagg atgattgact tggcatagtt cccagggacc taggtgaaac agtcaacttt
21061  ttgtcacaga tgcaatgtag ccagaagaaa agagccatcta agcacaaaga gagcttaaga
21121  cagaactccg agtaaaacca atctccgtct tttgacacta gagaaacaca aggatataga
21181  gacaaagagc agacaaaatg gatctccaga ataccttttat tttaaacaat ttttgtctaa
21241  cattattact aacacttttt ggccattta ctaacaaaat aactctaaca tttaaaaagg
21301  agaaagcttc ctgtgatata ttgataagcc ttctaactgc acttaaaagg gaaaaaaagc
21361  agatgttgag atctaggact caaagactaa gagaaaaggt aaaactgtaa tattggaagc
21421  tcactttgtt actttgtgaa aatgaaagca tgtataaact tgattagctc ataattgtgc
21481  caggttttatt tagtgaggtt gaaaggggat ggagacaatt gagaaaaaag ttatttggga
21541  aaagatttca aaaaaaggct tattttcct tcagacttta aatctgaggt ggataaaggt
21601  attgtggaaa attaaagatg actacaaatt atttggcatt tctcatcaag atgtggggtc
21661  tatgtcactt tcccttgaat ctgagtgggg ttaatcatta atttgaccaa taaaatactg
21721  caaaagtgat gctgtggttt ctggcctgag cctttggaga gcagcagctt tcacttttttg
21781  tcttttagaa caattgctct tgaagtcctg agccaccatg gaagaagtct gccaaccctg
21841  ctttccagtg actgagttgc aagaatcctt caagatgcca aaaagatgac cccaaagtga
21901  gctttgtgtg tctccgagac cacataaaga agctctgaga ccacatggag aagatcagcc
21961  cggctaagcc cacttttctg gctgtccctg ccaaggcact tggcatggca gtgaagctgt
22021  cttggattttt ccagacaaat tatactgcca gatgaatacc agcatgtgat cttagttgac
22081  accacatgaa acagaagaat ttctcagcta agtcctcccc aaattcctgg cccaaaacat
22141  gatggtgtgt ttttgtccac tgttttggag taactattta tgcagcaata gataacaaga
22201  tcagatgttt accagattgt aacagtttga ttagacatt tcctaagaat attaactttc
22261  cttcgtttca atgacatagt caacatgcaa ttttcaattt gtagttgata tttaaatttc
22321  cagttaggaa aaagcttgat gttggaggact tgcactaaat tttaggccag gtatagctcc
22381  aattttttatg gaaattatta tgtatacagt ataaggtaat tttttatagg ctatagttaa
22441  caatttcttt tttatctttt tttattattt atttatttt tattatactt taagttctag
22501  ggtacatgtg cacaacgtgc aggtttgtta catatgtata catgtgccat gttggtttgc
22561  tgcacccact aattcatcat ttacattagg tattttctct aatgctttcc cctatccccc
22621  caccccacga caggccccgg tgtgtgatgt accccgccct gtgtccaagt gttctcgttg
22681  ttcagttccc acctatgagt gagaacatgt ggtgtttgat tttctgtcct tgccatagtt
22741  tgctcagaat gatggtttcc tgcttcatcc atgtcactac aaaggacatg aactcatcct
22801  tttttatggc tgcatagtat tccatggtat atatgtgcca catttctttt atctagtcta
22861  tcactgatgg acatttgggt tggttccaag tctttgctat tgtgaatagt gctacaataa
22921  acatacgtgt gcatgtgtct ttatagtagc atgatttata atcctttggg tatatacccca
22981  gtaatgggat cactgggtca aatggtattt gtagttctag atccttgagg aatcgccaca
23041  ctgtcttcca caatggttga actagtttac actcccacca acagtgtaaa agtgttccta
23101  ttctccacca tcctctccag cacctgttgt ttcctgacat tttaatgatt gccattctaa
23161  ttggtgtgag atggccatctc atggtggttt tgatttgcat ttctctgatg accagtgatg
23221  atgagcattt ttctcattttgt ctgttgtctg cataaatgtc ttcttttgaa aaatgtctgt
23281  tcctatcctt tgcccactt ttgatggggt cgtttgattt ttcttgtaa atttgtttaa
23341  gttctttgta gattctggat attagcccct tgtctgatgg gtagattgca aaattttttct
23401  cccattctgt aggttgcctg ttcactctga tggtagtttc ttttgctgtg cagaagctct
23461  ttagtttaat tagatcccct tcatctgttt tggcttttgt tgccattgct tttggtgttt
23521  tagtcatgaa gtccttgccc ataccatgt cctgaatggt attgcctagg ttttcttcta
23581  gggttttatt agttttaggt ctaacattta agtgttaat ccatcttgaa ttaattttg
23641  tataaggtgt aaggaaggga tccagtttca gctttctaca tatggctagc cagttttccc
23701  agcaccattt attaaatagg gaatccttcc cccatttctt gttactaacc aatttcttaa
23761  tcacattaga cactaaacca aatcagggtt agacctgaaa ccttttttaaa aaatcaaact
23821  gtgggatcct gtggtaacta tactaaaaca gttgttgtca aatcacattt ttgtatttta
23881  aatccatatt tctcacctgg aaaaatgtta gtatttaaac tcaatatata aacatttaac
23941  atattgccaa attttaaatt ctcatatta ttaaaaaata ctaatttctg gccaggcgtg
24001  gtggctcatg cgtgtaatcc cagcacttta ggaggctgac aggggaggat cacctgaggt
24061  caggagttca agaccagcct ggccaatatg gtaaaaccct gtctctacta aaaatacaaa
24121  aattagctgg gcatggtggt gggccacctgt aattccagct actgggaggg ctgaggcagg
24181  agaactgctt gaacctggga ggcggaggtt gcagtgagcc aagatcacgc cactgcactc
24241  cagcctgggc gacagagtga gactccatct caaaaacaaa acaaaacaaa acaaaacaaa
24301  aaactaatttt cttaactcta aatcatcatt agtgataata aaggaagtat ttcatttaca
24361  gatttgaaaa cagaagccaa aagcaaaaca aagttttgtg atgtgaattc tgtgagcttc
24421  agaagtata tagttgagaa aacaggtact tcagagaaag catatagtta agaacacagg
24481  taaatatgtc aataaaggaa gaactttcag ggttcacatg gatataatag aatgttttgt
24541  ttcctatcta cagctctaat gggagagtcc ataactagct gtttaaaaaa aatcaaattg
24601  tatctaattg atgaaccatt gataccattt gttttttgct ggtcatctct catctaccttt
24661  taagaaatgt gcgacagatt gagaagaagt ctgaaaacta tttcaatagg tccatgctgg
24721  taagcagata ctgagccata taactgggca taaattgaat aaaaccttgt tttaaaaagt
24781  gagtgagtaa aaaagtaaaa agtgagtaaa aatttaagct gcccttcatc ccaaggagac
24841  aaaagtagaa actgagaata gtaaccataat catatattga agattgtgac ttaagttcta
24901  attgaacata gcaaatattc aataggcagt gttaagagta aataaacaaa attaacaaca
24961  acaagtaata gaactaaatt gcttagtgat atggaggtga ccattaggag aaccagagat
25021  agaaaaggta cccctcagga ctaccaggga gtgtgtcaaa tgataaagta ggtctgctgc
25081  ttttcatcat aaaacctggt ttgctgtttg attttttaaa tattataaac ctttcagtgc
```

-continued

```
25141  aaagtggtcg ataaaaatta taagcctatc taactttgat taaagaaaaa gacaacagca
25201  tgttggcagt tttcatgttt taaaaaaaaa gagagaagaa aaagacaaca gcaaaagaaa
25261  aattaaaggg cagtggtgca tgcctgtaat cccagcactt tgggaggccg aggtgataag
25321  atcacttgag gccaggaagt tgaggcttgc agtaagccat gactgcacca ctgcactgca
25381  gcctgggtga cagaatgaga ctccatcccc gaaaaaggaa aattaacatt ttgagtattt
25441  gtcaaaatgc ggatgctact gcccaaggcg aacaataccc aaggtgaaca atatgaacat
25501  attaacaaaa tagtaaaatg tacctatcct agaagcatca tctaggcagt tctgttgttt
25561  aatacaaatg gtttctttgg gagggctaga ttgtcctctg agttacaggt cctlaggttt
25621  tgaaattcac agatcactaa gatatcatgg cccatctaca atatctgctg cgtgtgtgtg
25681  tatgtgtaac atagactttg atctttgat aaaactgata tttttgtatg acctcttaga
25741  gaccctgtag gaaattactc ccacattgaa gactgttgag ttccatctag gattgaatca
25801  aagcattaag aatatgagta tgaataaagg aaaagaggaa ggctgcaatc tatatcttcc
25861  acaaacacta aaagaaacac tgttgggagc tgcaacagta ggtaattttg atagcacgag
25921  gagagagtca gtgtgacaca gaagcagagc atcaatttaa gagaaagagt ctgaatctaa
25981  gagattttga tataggtctg aacctcactt ctggcactta ataaccgagt gactgtttta
26041  taaaatttaa agattggttg atgaagggac acaacatact gatgatgaaa attagaactt
26101  tgttacttac aactccaaaa gagagaagct gccatgcagg gctacacaga gttggaccca
26161  gggacagagt aacggcaagc tggagttgca gaaggcagtg tatatatggc aaggaggtgg
26221  agttagctcg gtttcagggg ctccatgtgg actggttaat ttcatagcct ctgggtcata
26281  ggggctgtcc ctagttgtct agtacctgtc ctcagagaat gaggccctaa taagggaggc
26341  agctgtggtg tgtgcacagt ggcttcagag agtggaggac caataagtaa agagactggg
26401  atagggtta gcaaactatc tgcaaagggg aattgaagat ttgttagcca taacttacaa
26461  actgggtcaa gacagcattt gtgaaatatg tcacagtgac cttgagcaca cgaccactcc
26521  attgagcttc agttgcctca cctctaaaaa atttccatgt gtgaagtatc ttctactact
26581  agtacctagt tataatacat tcacaataaa tggaatttac aataatatag acaacttgct
26641  ttgatgtctg acaccagttt attccatttc tttgtcaata atctgggaga taaataaggt
26701  atttacagta aaggcagatt tcccactta aaagcaatca taaaatctgt cctgatgttt
26761  aatcaatatt gtttactatg ctgtttttatg atagtctcaa attaaaagat agtttactaa
26821  acttactaca tagtttacac tgaaaagggt tttcctccag tttgtactca gagatggtaa
26881  aacaggcctg tgttctgaaa tgttcgccac actcattgca ataacagtgc tcctctccag
26941  catggaaaaa ctggtgctgg ttaagggcta acaactggca ggatgctttc tgacattcat
27001  tacatttgta gggcctctct ccagtgtgtt tttttaaaaa aatgtctaat acagctacca
27061  tttgcactta aagtcttttt acattcttca tgtaaaatga agattgtagg attggtctcc
27121  tgcataagtt ttctaaagtt cagtaaaccc tgggcttaag tgcttcccac agtcagtacc
27181  ttcgaggtat ttctcccctg aagagtgtat gttctgatgt ttcacaagac ttttactgag
27241  tcactagtct caatctcatt atgctcacag agcttgtttt tcagaaaatc atttccagga
27301  aggcctccat tgtgactctc actttcctac tgggtatctt cttttctcctc tgagtgagca
27361  ttcttagtac agatgttggg ttgcccatgc cggtcctatt cgcaggagaa atcctgcaaa
27421  taggacctca taatggatct tcgtagtgga tctctgctgc tgagtgtggc ctgctctcta
27481  actgaaggct aacactgaat acatttaaag aatgttttca tctagtggat ctcctgaaga
27541  gggataagtt gtgtacagaa gcttttctgc cgtcatggca cttacaagtt ttctctgcta
27601  tataaactac ctgatgctga atcaaggcag accgatgaat caaggtttta ctacactgat
27661  tccagccaaa gcatttctct tccgaatgtt tttcaagatc atcaaaaact cttgcattct
27721  gagtaaagcc ttttcaacaa gtgtttttca cttgtattaa gtctccaatg tcgactaaaa
27781  actgatcttt aacagttttt ccacacccat cacattacag ggttttttctt tccacctgga
27841  ttcccacttg acgaataagg ccatttttg atctaaggggt cttccacac tcttcacata
27901  acagtgggtg ggctcagagt ttgctttctt tgctgctcag cgaggtctgt atttggagta
27961  aaggctcccc catgtacccc atgctgcaag actttctgtg ttcagatgag cctctgatgc
28021  tgattatgta ctaaattctg gataacgttc gttttggagt cattgagttt gacttgtttc
28081  ttaatcgtgg agtgtaccta actgctcctt gagattctgc aaaattttcc tttgggtctg
28141  ccagatagtt ccctatgtgg ttcccttct tcatgtttct tgctttggac acatatttct
28201  gtattttgtt ctagaatcac catctgaagc tacaaataga cgaactatcc aaggaagaac
28261  ataaattcaa tgagtacaat tcagatttat gaggcaagta tttaggatg agggtaacag
28321  ggcttctgca tgtaggagag ggaagtagtt agcaagaaga ctgatgaagg tcactgaaaa
28381  aatgcaaagc acaataggaa gccaatcaag atgtgtagaa gggacaatat ttgagagtaa
28441  ggagacattg tctgaaactt ttgcagtggt aaagtgatgc atatgggtaa gtgtagaaat
28501  atggactaag tgtataaaat cttttggaaaa gtagccagtg gtaagagca ggaaaggacc
28561  gttaaagatg atgattctga ggttgattta tactcactaa taatggacaa ccataaaaag
28621  gggatcacag taaatatgag agtatgtgac agagacactc tagaaataag caagtcaagg
28681  tttagtggaa gtcttgctcc atttgggata cttattatcc taagtcaaca actgatggtg
28741  ccctggagtc tctttttatc taagacttct taaatagatc cttctctgct acttagtata
28801  agaaaggaag ttaaatatgt ccaataaaag tatactgtgg ttttggcatt tatttaaatg
28861  tataaaaaca tgtacacatt tatttaaatg tataaaaaca tgtacacatt tatttaaatg
28921  tataaaaaca ttgcttctcg gccttttggc taagatcaag tgtaaatgta taaaaacatt
28981  tacacattta tttaaatgta taaaaaacat aaagaatatg taatttggcc aggggcagtg
29041  gttcattcct gtaatcctag cccttttggga ggccatggtg ggcagatcgc ttgaacccag
29101  gagttcgaga ccaacctggg caatatagcg agacctcgtc tctacaaaaa atacaaaaaa
29161  attagccagg cgtggtggcg cctacctgta ttccacagtg tatatttgcc acatttctt
29221  tattccacca ctgatggcca tctaggttga ttccatggag catggggtac atgggggagc
29281  ctttacttcc attttttgcta ttgtgtatag tgctgtgatg aacatgtaag tgcatatata
29341  ttttggtag aatgctttat tttcctctgg gtacataacc cagtagtggg attgctgggt
29401  tgaatggtag ttctttgaga agtcgccaaa ctgcttcca cagtggccga actgtgtata
29461  agcattcctt tttctcctca gcctcaccag catctcttat tgtttgactt tttaataaca
29521  accattctga ctggtgtaag atggttctca ttgtggtttt tatttgcact tctctgatga
29581  ttagtgatgt tgcacatttt ttcatatgtt tgttggatgc ttgtatgtct tcttttgaga
29641  tgcgtctgtt catgtgatt gcccatttt taatgggggt gtttttttgca tgttgaattg
29701  tttgtttcc ttataaattc tggatatcag atctttgctg gatgcagatt gcaagtattt
29761  ttttttcatt ttgtagtcta tttacctgtt aataatttct tttactgtga agaagctttt
29821  tagtttaatt aggtcccact tatcaatttt catttttgtt gagattgctt ttaaggactt
```

-continued

```
29881  tatcataaat tctttcccaa ggctgatgtc cagaatgcca tttcctaggt tttcttctag
29941  gattttttt ttttttttt ttttgagat ggagtctcgc tgtgtcaccc aggctggagt
30001  gcagtggtgc aatcttggct cactgcaagc tctgcctccc gggttcatgc ttttctagga
30061  ttcttatagt ttgtggtctt acttttaaat cttaatcca tcttgagtta attttctat
30121  atggtgaaag gtaggaatcc agtttcattc ttctgcatat ggctggccag ctatctcagc
30181  accattatt gaatagggag cccctttccc tgttgcttgt ttttgttctt tgtcaaagat
30241  caattgactg taggtatgca gccttatttc tgggctattt tgatccattg gtctctgcgt
30301  ctgtttttgt atcagtaccg tttggttact gtagtcttac agcatagttt gaagtcaact
30361  aatgtgatgc cctcaggttt gctcttttg cttaaggttg ctttggctat ttgggttatt
30421  tttggttcca tatgaatttt agaatagttt tttctaattg tgtgaaaatg acattggtaa
30481  tttgatagga atagtgttga atctatagat tgctttgtcc agtatggtca ttttagtgat
30541  attgactctt ccaatccatg agcaggaaat gcttttccct ttgtttgtgt catctatgat
30601  ttctttcagc agtgttttgt agttctttt gtagaggtct ttgaagcttg gttagatata
30661  ttcctaggta ttttattttt ttgtatctat tgtaaatggg attgcataca acttgctttt
30721  agatggttca gttgaaaaag gaagaaagaa aggaggaagg aaaggaggaa tgaaagcaaa
30781  gtatacatgt ggctgggtgt ggtggctcat gcctatagtc tgagtacttt gggaggccaa
30841  ggaggagga tcgtttgagg ccaggagttc aaaaccagcc tgggcaatat agtcagatcc
30901  tgtctctaca aaaaatttaa aagttagctg ggcatgttga cacatgtctg tagttttagc
30961  tactcaggag gctgaggtgg gaggatccct tgagccttga actcaggagt ctgaagctgc
31021  aatgcagctat ggttgcactg ctgcactcca gcctgggcaa cagagtgaga ccctgtctct
31081  taaaaaaagg aagagagaaa aaagtgtaca tgtgtcttca tctgttcagt atattataac
31141  aaaaacacca taaactcggt gatgtataaa caacaaacat ttatttctca cagttctgga
31201  agttgagaag tacaagatga aggcaccagc agatctggtg tctggtgagg gtcaatgatg
31261  gtgacttctt gctatgtcgt cacacagtgg aagggtatgg cagctctctg tggccatttt
31321  tttataaggg cactaatctt atataagagg gtatctccaa agggcctcac ttcctaatac
31381  catcacagtg atgactgatt aggtttcaat atatgaattc tggggacaca caaacattca
31441  gaccatagca gcagtataca ttctgataaa gcaaattttt tttaaaaaag tagtaatttc
31501  accgaaataa ggaattttta aggaaaagga agtgaaataa tatatgaaag gcaatggaaa
31561  cctggctggg tgctgtggct catgcctgta tcccagcact ttgggtggcc tcggagtttg
31621  agaccagcct agccaacatg ggtgaaaccg tgtctctact aaaaatacaa aaattagctg
31681  ggcatgctgg tacttgcctg taatcccagc tactgggag gctgaggcag gaggatcact
31741  tgaacctggg agatggaggt tgcagtgagc agagattgct cgactgcact ccagcctggg
31801  tgagagagta agactccgtc tttaaaaaa aaaaaaaaa aaaaaaaaa aaagacaata
31861  gaaacccaat caggctcaaa aatgagaaga ctcactagcc atggttgata aatatggaga
31921  cagggttgcc aaggaatatg caccagactg gggtctcaat tattttggcc tcattttgtc
31981  tccaactaaa aaattgacct cgagcaagta acataaactc tgcgtctatt ttgtaaccta
32041  tgaacaaga aattaggcca ttagatttta atcccattcc ccttccttt ttacagacca
32101  gtaaaaggaa ttttttttt cttttttctt ttttcttttt tttttaaata ggaatttgct
32161  ctgtcaccca ggctggagtg cagtggtacg atcacagctt actgcagcct cacctctgg
32221  gctccagtga tcccacctaa acctgcagag tagctgggac tatagacatg cgccaccatg
32281  accagctaat ttttaaattt tcttagaga cgaggtctta ctatgttgca acactggtct
32341  agaacttcta gactcaagtg atccttctgt cttggcctcc caaaatgcca ggatcacagg
32401  tgtgagctac tgcatttggc aaaaaccagt tttaggaatt tgaataaatt cctaaaaata
32461  aagcagagcc ttttctcagg tgaagcaaag ggggctggat gccagaaccc tgcttgactg
32521  acctgatcct gcccatggct gactgccaag taacatctga ggagtcacct aaggttctgg
32581  agaacagttt gaaagccaat gattgtgctg attttttaaag gcctttttata ggccttttaat
32641  atgcttaaag tgtctgtagg ttaaaaaata aacttgctta tcattgtctg ggaacattaa
32701  aaaaataaat ttgtgaggtt taaaaacagt atacagtcaa ttattaagct cttaatagag
32761  gccttcctg attacggtag agtagccttt aaccacactc cagtcaccat gacaacatcc
32821  tattttattt tctttatagc atttatcagt acctaaaatt atcaatactt ctgtgtttgt
32881  cggttctctg tccctagaat gtgtattcct tgaggaaagg gattccctaa tctaaaaggg
32941  attaataatg agatgatggc atccaatatg tgctcaatat atttgtcacc taaggatttc
33001  agaaacataa gtttccatgt ggattttac acttcacatg ttaaaacttg gtcatcttat
33061  gggtggtttc tactttctct tgaaaattaa ccacaattta ctaattttaa taaactaatt
33121  ttgatgcag ccctggaaaa gggactatgt tgtaggctct ctggattctg ttatgttctt
33181  ccaaagtatt gagttttgta ttttaagca gtagataact ttattattta ttattattt
33241  tattttttga gacggagtct tgctcttgtt tcccaggctg gagtgcagtg gtgtaatctc
33301  agctcaccac aacctctgcc tcccgggttc aagctgttct cctgcctcag cctcctgagt
33361  agctgggatt acaggcacct ggctaattt tgtagtttta gtagaaacag ggtttcacca
33421  tgttggccag gctggtctcg aactcctgac ccaggtgatc cgcccgcctc ggcctcccaa
33481  agtgctggga ttataggcgt gagccaccgc gactggccgc aggtagataa cttttaaattg
33541  tcactcccgt actggatggc aactgaaacc taagttgaca ttttagccat agctgaacta
33601  cttgaaatct actctgtgat gcatggttca ggaaccatgg ggaaattggg gtggatttta
33661  tatatagaac ttggggctgc ccttatctgt tttttgcctt cctaggattc ccacccccact
33721  cccttacag ttgctgggat cccctaaact ctgtcctttg gttctttcaaa ccagtaagac
33781  tgcggatttt ccagtcctt ttcagtcatc ccacgtggca tagactgaga cctactccta
33841  ggctaggaga tataactacc aatgcactgt catgacagat cggattagtt aatataattg
33901  aaaggacttt caaagcaaat gtaattatta atattgactc tcatatacta taacttagat
33961  ttcctgaaat gcaggcatga caccatgttt atctttgcaa tcctgtagca gcttacattg
34021  tactacacat aggtgttcaa atcattttca tttaactcaa atgagtagta cctaattagg
34081  tgtggaagta acaggaaaag tggtagtttg gagaattact ctagaaggca aaacgttttc
34141  atcaattaac aagaactttg aaatgcacaa ctaataaaac aacttgggag atacagaaat
34201  actcaaatat gaatagaaat tagtcaattt aatcataaat caatcacttt attctagtca
34261  gtaactgatt aaataaaaca aagttcaac ttcctgtgct acttatcagt gttcactcag
34321  taggtaaaat gtatacactc tcatgattct gggaggaaaa atccacttta aatggcaaga
34381  gaaaccaaat tatttggtgc ccctccttca tggctttgaa atacccaatt cacattgctt
34441  tcaaaattta gcaagatatt attgcatttt gcgtagtatt gtgcatacaa taggcactca
34501  acttttttta catgtcttca gttgctcaca gcctatgttc taggaattta tagacgctgc
34561  tgaattgttt gatctggact gcagaacact gacctggaat ccactgaact taaaccagtt
```

-continued

```
34621  ctctggctta ttactttcta acattaaata aatctttacc tttcttagcc tctttatctg
34681  tagaaaacag acaataacta gttcacagag ttgtaatgat taatggagaa catctgaaaa
34741  cattttataa gctttagaaa aaacgataaa gatgtaaatt ccaaattgtt cacaataggt
34801  tttagtgcta ggcacgtttg ttattgggaa ctaacttgat aaacttttc tccctgtgcc
34861  tcaaaaaaag tttcatgaaa tagaacaatt tatttgttct ttaaccaacc taagaggttt
34921  tgttcaatag ttcacatact tttggcaatt aaaaacagta tatttgtgag gtttttcatg
34981  gggaaatctg gaaaataggg ctgagcagtg ttttccaagg tttaaggtat ataacaatca
35041  actggggatc ttgttaaaat gcagattctg attcagttgg tctggggtga tgccaaggct
35101  gctgatcttc tgaccacttt gagtaaagag tctaaaccta ttgaagaaag atagtaaaca
35161  atcatcttgt tcatgcttat gattaaagat agcatccaag taagctgttt tcctacgcag
35221  ataactagta ggtaggctag gtaattttta aaaactctac gttcagttgt gaattcatga
35281  cacttggaac aattgctgaa aatgtaacaa tttttctaag agttggaggc taaaagctta
35341  agaaggaagc acttctgagg gcttgtaaga gataattttc ttccctgtgc aactcctgaa
35401  agggaaaaca attgctttaa gataaagttg tttttttttt tttttttttt gagacggagt
35461  ctcgctctgt cgcccaggct agagtgcagt ggcgcgatct cggctcactg caagctccgc
35521  ctcccgggtt cacgccattc tcctgcccca gcctcccgaa tagctgggac tacaggcgcc
35581  tgccaccgcg cccggctaat ttttttgtat ttttagtaga gacggggttt caccgtgtta
35641  gggatggtct cggtctcctg acctcgtgat ccacccgcct tggccttcca aagtgctggg
35701  attacaggct tgagccaccg cgcccggcta agataaagtt tacataggag ccagatcatc
35761  ttaatctggg ggcttctgat attgaagtcc atggacatct agtggaaaga acaatggact
35821  gggatacaga gccctagtat ttattaattt gcttcctagc attgggtatg tacgtacata
35881  ttttgttttt aactgtctca acttcctatc agcaaaacgg gaataactgg tcctgacaac
35941  ttcatagggt gactatgtga atcaaaaggt aatatatgta aaaatatttc ttcaaggctg
36001  ttagaagtgt gaggtggtat aatggtaaag aatgcagact ctggagtcag accagctca
36061  cttcttata gctgtgtatt atttaccttc ttctggtttc atttcaaaac tagactgagg
36121  aataaacaaa tgcctctgga ggaatttata ctgatgacca ttcaggaaaa tttcttacta
36181  agtgattttg agtatcaaag ataaaagaca aattatttct ccagagcttc ccatttatta
36241  ttttgcattc acataagaat acagattata ttcatgataa agaatattaa ggccaggtgc
36301  agtggctcat gcctgtaatc ccagcattt gggaagccaa aatgggtgga tagtttgagg
36361  caggagtttg agatcagcct aggcaacaca gtaagacccc tgtgaagttg acttcaagtt
36421  gtgaaacact gtatgattat gttatttatt tttaattttt taatttttgt gagtacactg
36481  taggtatata tatttataag gtacatgaga tctttgata caggcatgca atgtgaaata
36541  agcacataat ggagaatggg atatccataa tttattttatt tatttatttt tttgagatag
36601  agtttcactc tgtctcccag gctagagtgc agtggagcca tctcggctca ctgcaagctc
36661  tgcctcccgg gttcacgcca ttctcctgcc tcagcctgcc gagtagctgg gactacaggt
36721  gcccgccacc acacccagct aatttttttgt attttttagta gagacggggt ttcaccgtgt
36781  tagccaggat ggtctcaatc tcctgacctt gtgatctgcc tgcctggcc tcccaaagtg
36841  ctgggattac aggcatgagc caccatgccc ggccaattta tttattatt tttagataca
36901  ggatctcact ctgtcaccca ggctggagtg cagcagcaca aatgtagctc actgcagcct
36961  ctaactcctg accttaagcg accctcccac atcagccttc gaagtagctg ggattacagg
37021  catgagccac cacatctgga tacatatgac ataatttaca gactggtatt aaaattaatg
37081  atggttcaaa gactattagt tgattattta aatgattcag cagtaaaacg tagtaagctt
37141  ttctacacta tactcaaaag tataaaaga tcattatgtt tatggtggtc aaaatgaaca
37201  attaacttga tcatctttct cctgcagtag aactcaaaat caataaggag gattttggca
37261  attttcctga accccctaata aaatgtatta ataataataa taaatcaata aaacttgttt
37321  tgtttttcact tttttttttt tttgactct aggactactt tactcattta cctgcctggc
37381  ccataaacaa aatctgagtc tgcttattcc cttcctttga agaccagctt gggtatctcc
37441  agtgttttcc taatgcaaat taaaattaac acacctctat taaaaaaaaa aaaaagatgc
37501  agctaggtgc agtgactcat gcctataata ccagagcttt gggaggctga ggtgagagga
37561  ttgcttgagg ccaggagttc aagaccagcc tgggcaacac agtgagtttc catctaaaaa
37621  aatttttttta aattagctgg gcatgttggc atacacttgt agtcctacct agtcaagagg
37681  ctgaggaagg agaactgctt gagctcagga gttcgaggtt acactgagct atatgattgt
37741  accactgcac tgtagcctgg gtgacataac aagatcctgt ctctaagaga gagagagagg
37801  aaaaaaaaaa gcatctttct tgtttggagt cttggctggg aggtacatgt tatacatcag
37816  aacttaggta ggaatggaag gcccaagaat tcactgtgct gtccgtaaaa ggatgctaaa
37921  catgtttgac ttgacaaatt atcaccactg cagctacatt taaaatacat taatcatcta
37981  atattcttat ttgcatttta tgtacaactt aagttttcac taaaagtat tattaaacaa
38041  cagtctaagc tttgtgaga actgtaattt ggaacaacta gtaaacatc tggaaactga
38101  actggtggtc cacaggccac tctgaatcac aaaagtgttt tatttgatta gcggttaggg
38161  gaaaagtaag tggccttgttc tgttaaatga caggattttg gtggggacca ttttgaaggg
38221  ccagttctca tccaaaccaa gttcaaggtc tggtgggaag aaattctgcc ttgccaattt
38281  cagatgctgg acactcacaa aatttcaatg tcaggtgaga agctattatg caaagccttt
38341  tccatccata tttatcaact tcctaagttc tcttttgagt ggattctctg gtgttgaata
38401  aggaatgaac gttaaagaga aattttacta tactgattac actgaaaggg tttcttttcca
38461  acatggattc tgatatgatg aaaaagctga attctgactg tgaactttac cacacttgtt
38521  acactggtag taacatatct ccctggtgtg aagcctctgg tgctggttga ggactgacca
38581  ctgccaaag gctttgttgc acttgtcaca tttattatag ggtctctctc cagtatggat
38641  tctcttaacg atgaatgagt ccagtgtttg cactgaaagc tttcccatat tcttctcatt
38701  tatatatcta actccagtgt gaattatctt atttgcatga agcctacact cctgagtaaa
38761  ggctttccca tacttgttac atcatagga atctccacca gtgtgaattt ctgatgctga
38821  attaggacag agttctgagc aaaaattatt ccacattcat cactgtggta ttttctggat
38881  attttcctag tcttttcctca tacatttgga catctcacaca aagttctcag gaatactgcc
38941  atcaaatctg acagtgtttt cctgttggca tgttatttca tttcttttgt ttgggaagaa
39001  cattctcatt cttcattttg atcaaatcat ctgaaagaag agactgaaaa tgtcagcata
39061  attcactcat tcacatatac tttactcaat cacttgctca cgaaataagc acttttaga
39121  actacatgcc agaagagata acagaaggaa cttactgtgta tatccactgg tggcataacc
39181  atataaaaga ataattattt catatgtcct taaagcagta aattttttt ttgtatagcc
39241  caagtgagat atatcttaag aacaaaaaga acagaaaaca tgtgtataca cacacacgcc
39301  accattaagc tatttacagt aatcatattt gtgggtaatg cgatgttttt tattatgagg
```

-continued

```
39361  ctattgtgta tatattgtgg gacagcaaat gagtaattat ttgatgttct atcattcctg
39421  gtgtctttga gaatcctcta aaaggagata cagatgaaga taagagatta agaccccgaa
39481  gtagtaaatg tgaattagaa ctatcaatgt gaactcatga tacacacttt cttttaaatt
39541  ttttcctaac tctgagtact ggaaaggcct aggaccaatg actaagccat aagcactcct
39601  aatgccctat ttttggtttt gaaataccat ttcccattag gcagaatggg gggtccttgg
39661  aaaaagtatt aattctagga ctatgtaagg aaaactataa gatgggcctc gtacatctta
39721  tcatacaggt cagcaagaaa actatcaaag atgactaggt tcatgtcata aggattcaca
39781  tgccaaactg aaaaggtttc tactgctcaa agaggagaca aatgagcttt agtaaggata
39841  gtattatgga ctgaaaaaca tcaataacg cttcaatcca aaagttccta atgatactat
39901  tactaacaac tggtcactgt tttaaaggat gactacaaac taattcattg ttttgaaaac
39961  tgatttaaaa agcaaagtag tggggagtga cttaagcaat tatcttgcct ttcctaaaca
40021  aaccattgaa taactaaaca aaaaatcagg ggaaatgtct ctttatataa ctattccagc
40081  tttattaaat gaagaaagaa ggatgcaatt agaatgtcac cattttggga cccgtaatgg
40141  attactggct ataggtattg aggatcaata gctgctaaca ccacagaaaa agagacaaac
40201  agaaaataat aggcttcaaa tagaacacac catcttgcca aaatcattaa atttatctgg
40261  tcaaaaaaac ttaaaacttg atttttgatca agcctgtaca ttactacaat ttacagaaaa
40321  tacagaggac aacagaacat cttagactat agcacatgat gcagacagca aaacccatgc
40381  tgtgtgcaac tctacaggac aaacaacttc atttctttta acaagtgagt tggaagagaa
40441  aacaggagag ggtacccata tattaaaaga aacttaggag acatatcaac ccatcacaat
40501  gtgtttttctt ccttggatct tgattcaaat aagttaaaaa acaaaatgaa caaaaaaaag
40561  tttatgacat ctttgagaaa actggaaaat tgatattaag gaattactgt taattgttta
40621  ggtatgaaaa tagtatattg tttacattt taaaattcat atctttaca gcaaatattg
40681  aaatatttac atttgaaaga ctatgctagc tcagatatgc tttaaaatta tatatatata
40741  aaagcatggg atatgagtag agttgtaagt gaaacaagtt tggccataat ctgataatgt
40801  tgaagctggg tgacaggttt gtggggattt attagaagta gtacaattgt acttttatat
40861  atgcttaaac ttttttcata gtacagagtg aagaaaaaaa gaaaaagaaa agagtttatg
40921  gcttttagtt ggtagtattt aaaaaagaaa aaaagcagca atgtaaaaac cctctaaggc
40981  cagttacaaa ataattcaat acccttgcag tgaaatgtat gtcagctaca tataggtatt
41041  atatgtaact tgaaaagata tccataatgt aatattaaac taaaaaacaa gtggtaaaca
41101  atatgtactg tacaatgaca ttttagcatg catgcgtgct ttcccagtaa gcatgcacct
41161  actaaagttt tatgtttcct cacactcattt aaaaaaatgta catttaaaaa tttactaatt
41221  gcatgtagcc ttttagtagt tttctattgg cttcaatata gaaaaacatt ctcctgtctt
41281  tgcgataaga ggtctgggtt aaggaagttg gcagttattag aagggagaaa ctgaaccatg
41341  caaggtaaca tgagtagcag gatttttttaa aaaaaacaat tttaaggcaa agaagtgaag
41401  aaagaaaaga atcataatcc aggctaaagt ggtatgctta gaggaacagg ttaaaagtgg
41461  aataggcaat agagattaaa tgaaaggtat gcagagattt tagtgacaag gttcatttgg
41521  aaaaatgcaa aaagcacacca acatttccta acttcttctt tgctatctcc tcctcagcgt
41581  tctccttaac agtgtgaaac tcccaacatt cagagctgag ttgaccctt actggctgga
41641  gccggactcc agttgagtcc tatgaggctg ccagatacac tatttgcgtt gggacacttc
41701  ttgtccctg taggagggtg gggaactggg cacaattaga tggagtttaa tgagggtgac
41761  atttgctgaa agttagagct taaaatccca ttattactgt ggaacacacg atgggagggc
41821  agaaagcagt tttctgtcat ctgcaagggc agggatacac agacaaagag gggaaaatac
41881  acagggccta caagttaaaa aaaactcacc aaactagaac aaaaataaat aactctggcc
41941  aataacatgt tagccatttt ctctaactac gctagagaag ttatctcaac tctcttatct
42001  ctctctggag ataatatctg ctatctgata agacatttct tcattttacc tttcctctca
42061  gatcattcag cttcctctcc aagttcttca gtacagacag cctctttcct atactctggg
42121  atgctcctat acccaggcct ggagttcttg ggcaggatgg tcaggatcag tagttccaag
42181  acgtgttcct tgctgtgtat cactggtctc caccactgat ggcaaagaac ctgaagctgg
42241  accccttgagg cccaagtaaa taccaccat atcctctctg aagaactcct gaccagaagc
42301  tcccttttctg tgtgggctag attcttttaac tatttgacac ttctttcatt cttctgcagt
42361  tggtctgaat gcattcctgg gtgaaacagc tcagaagact ggctcactgc agcagtgcgt
42421  atgcttcagg ctgatgctaa ggcataacac atcattgttg agatcagctc caaactggaa
42481  catatttact gagtgaatgg ctgtatcaag gcaaaaagtg tgaaggtaaa aaaaaaaatt
42541  tctgtgaaag ataaataagc aaaaaatgac ataaaattaa ctaaaagaca tttcagttac
42601  ttcaagagtg aagaataaga cactattagc ttttagatct agaaaattca gtgaaatatt
42661  cagatgatta tcaaaaacaa taggtgcaaa aagtaatgca cacaacttgg tatgcttata
42721  ttgcatgtca gatgggtcaa ttaacattta caggcataca ttggacatat tgcagatttg
42781  gttctagacc actgcaaaaa agcaaatatt gcaataaagt gagttacaca atttttttgc
42841  ctttccagtg catataaaag ttatgtttat actacatgac agtctattaa gtgtgcagta
42901  gcatgtctaa aaaatgcata taccttaatt aaaaagatact ttattgctaa aaaatgcagg
42961  actcttcact gagtcataat ctttgaggct gcagagtctt acctaatgt ctgctgactc
43021  atggctgatt agggtgataa ctgctgaagg ctcaggtggc tgtggcaatt tcttaaaaca
43081  tgacaacact gaagtttgct gcatcagttg attcttcctt tcatgaacta tttctctgtg
43141  gtatgtgatg ctgtttaata gcattttacc cacagaactc tcaaagttgg agtcaatcct
43201  ctcaaactct gccactgctt tatcagtcaa gtttatgtga cattctaaat tctttgctgt
43261  tatttcaaca atttcacagc atcttcccca ggagtagatt tcatcctaag aaaccacttt
43321  ctttactcat ccataagaag caacttctca tccattcaaa ttttatcata agaatgcagc
43381  aattctgtca catcttcagg ctacacttct aattctagtt ctcttgctat ttccactata
43441  tctacagtta tttcctccac tgaagtcttg aacctgtgaa agtcatccat gaggatggga
43501  atcaacttct tccaaactcc tgttcatgtt gatattttga tctcctccca tgaatcacaa
43561  atgttcttaa ttgcatctag aatgtgaatc ctctccagaa ggtttttcaat gtactttgct
43621  cagatccatc agaggaatca ctatctatgg cagctatacc cttacaaaat gtatttctta
43681  aataataaga cttgaaagtt gaaattactc cttgatctgt gggctgtgga atggttagct
43741  gtgttagcag gcatgaaaac aatattaacc tttttgcaca tctccctcag agctcttcag
43801  tgactcggtg cattgtcaat gagcagtaat atttcgaaag gaatctttt ttcttctgag
43861  cagtaggtct caacagtggg cttaaaatat tcagtaaacc atgctgtaaa taaatgtgct
43921  atcgtccagg ctttgttgtt ccatttctag agcacaggca gagtagatt agcatgattc
43981  ttttttgtttg tttgtgtgtt tgtttgagac agggtcttttc tctgttaccc aggctggagt
44041  gcagtggcac aatcttggct cactgcaacc tctgcttccc aggctcaagc aatctaccca
```

-continued

```
44101  ccttagcctc cctagtagct gggaccacag gtgtgtacca ccacacccag ctaattttg
44161  tattttttg tagagacagg gtttttccat gttgcccagg ctagtctcaa actcctgggc
44221  tcagcaatcc tcctgacttg gcctctcaat gtgctaggat tacagcatgc ccagccagca
44281  tgatccttaa ggactctagg attttcagct tagtaaatga gcattggctt caacttcaag
44341  tcaccagctc cattagctcc tatcaagaaa ggcagactgt cctttgaagc caggcactga
44401  cttctctcta gttatggaag tccaagatgg tatcttcttc caatataaag tgtttcatct
44461  acattaaaaa tatgttgttt agtatagcca ccttcatcca ctatcttagc taggttttct
44521  gaataacttg ctgcagtgtc tacactaaca tttgctgctt cactttgcac tgttatgttg
44581  tggagacagc ttctttcctt aaacctcatg aagcaacctc tgctagcttc taactttct
44641  tctgcagctt cctcatctct ctcagccgtc acagaattga agaaagttag gaccctgctg
44701  tggattaggc tgtggcttaa aggcatgttg tggctggttt gatcttcttt ccagatcact
44761  caaactttct ccgtatcagc aataaagctg ttttggtttc ttatcactca tgtgttcagt
44821  ggagtggttt tacttccttc aagaactttt cctttgcatt cacaactggc tgtttggtac
44881  aagaggccta gctttcaacc tatctcagct ttcaacatgt cttcctcact aagcttaatc
44941  atttctagct tttaatttaa agagagagat gtgagactct tcctttcacg tgaacactga
45001  gaggccactg tagtgttatt aactggtttc atttcaacac tgtgtgtctc agggaatagg
45061  gaggcctgag gagagagaaa tgggggaatg gttggttggt ggaagagtca gaacacacac
45121  cacatttatc agttaagtta ggcatcttat atgggtgtgg ttagcggtgc cccaaaacaa
45181  ttgcaaatta catcaaagat cactgatcac agatcaccat aatagatata ataataattt
45241  taaattttga aatactcatt taccaaaatg tgacacagaa acacgaagtg tgcacatgat
45301  gttggaaaaa tggtgttgac agacttgctt gatgcagggt tgccacaaac tttcaatttg
45361  cagaaaacac agtatctgtg aagtgcaata aagcaaagtg caagtaaaat gacatatgcc
45421  tgtataagtc aacttctctg tgccaagaat tgtgctagat gatttcaaaa gtttgtctgt
45481  ttgtttgaga cagagttttt tctctcattg cccaggctgg aatgcaatgg cgcgatctcg
45541  gctcactgca gcctctgcct cccgggttca agcctcccaa gtagctgaga ttacaggcat
45601  gtgccaccac actcagctaa tttttgtattt ttagtagaga cggggtttca ccatgttggt
45661  caggctggtc tcaaactcct gacctcaggt gatccacccg cctcggcctc ccaaagtgct
45721  gggattacag gcatgagcca ccgcgcctgg cccaaaagta ttttaattt tagaatagtg
45781  tgcatgtcag tcaggggacc tcacatctga cttatcagtc ccaagttaaa caaacagggc
45841  ccccttggta cacaaaccca gtgggtattt ttcaatcctt ttcctaccag atgcccctgc
45901  agcacctaac actgctaact actcccaatc ttctaagaaa cactatactc ttctggttgt
45961  tcttccataa gttggttttt gtagcgttta gcctaatgct tggcactcag gaagaacagt
46021  tatgcattgc ttaatcacat ggttatgttc tgagaaatgt gtctttaggc aatttcatca
46081  ttgtgagaat atcatagact gtacttccac aaacctagat ggtagagcct actatacacc
46141  taggctatag tgtataacct aatgctccta ggctacaaac ctgtacagca cgtttctgta
46201  ttgaatattg taggcagcta taacacaaag ccaagtattt gtatatctaa acatatctaa
46261  acacagaaaa ggtatagtaa aaatatgtta ttataatctt atggaactat tattgtacac
46321  gtggtctgct gtttactgaa acatcgctat atggcacatg actgtattat acaagtacct
46381  gttaaatacg tttctaatga ctattattta gtctacttcg tagctctat tctgcctgtc
46441  aaaaatgtct agtatccagc tgggcacggt ggctccaacc tgtaatccca cactttggg
46501  aggctgaggc gggtggatca cctgaggtca ggagttcgac accagcttga ccaacatgga
46561  gaaaccccat ctctactaaa aatacaaaat tagccgggtg tgatgcgcg tgcctgtaat
46621  cctagctatt tgggaggctg aggcagaatt acttgaaccc aggaggcgga ggttgtggtg
46681  agctgaggtt gagccattgc actccagcat gggcaacaag agcaaaactc catcaaaaaa
46741  aaatgtttag tatcctaaat tgaaatccag ccttattctc atcccatatt tattctgggc
46801  aatctcaacc atttgatgac atcagctttc acctgaaaac tcctaagcct gattctctca
46861  taccaatctt tctttggagc tccaggcct tacagtccag tggtgcatta gaccttttca
46921  cttgtatgtc ttacaagcat cttcaactca ccaccaaaaa ttcatcattt tcccttgtg
46981  accaatttat tctccaatat tagccatctc ttataaaatt gtgccacact tacctaataa
47041  tttaatccaa aaacctgcct atttatccct ggctacatt attttattta aagaatacac
47101  ttagtgtgtg acaggcagtt ctctcagtac ctttcttc tcactttcat caatctaatt
47161  agttatcagg tctagttaaa tctgtaatct ttaacacagt tccacttggt gccctcttta
47221  tttctatagc cagtgactta ctttcaccaa cttatggttt tggttcttc tttaacaact
47281  acaagtctct tatctccctt gcttcagtt ttgccccttt ccaattcatt caccacacca
47341  cttctagaat attttctagaa agctagtaag attacattac tcctctgctt aaatccagac
47401  agagcatata actgcccaac tactgtgcat tgccacagtt tactgggtgc ttcaaatggc
47461  ttataggagt accaccagca tactgatctc ttcagctacc ggggtggcca ggaagtgtgc
47521  atacaaattt tctttatgtg ctgtgacatt aagaaaatgg aaaagcacac caccctataa
47581  actttaaatt cctcagcata tttcagttac tctctactct ctttgcccca cctctgccac
47641  tcttgttgcc caggctggaa tgcacccacc ttcatttact tgtggtttc tgaaatggtt
47701  ttctgatccc tccttcacat actataacta tccctcaagg tccatttcct ctttgctatc
47761  caacttctga gagtccacag agacagctct gctattgcct actcagggaa gttatcttta
47821  acgttccacc tccaaagtcc ctatgtacga agtttatttt cctcaaggca acatgtcttt
47881  cccattacac tatacagtaa gaaatgcctt ttatctggct tattcccatt tttgcaacat
47941  aaagcctggc ccattatgtg gcactcaata aatgcttgct tgaatgttct aacttctgaa
48001  tgttttctta cccagagaaa ttcacgtacc acttccctct gttttgcaga attgtgggga
48061  ccatgtaaag tattttctt taagtactaa gccttacag atacacaata tcgtgaccat
48121  tagcatagg gatttttatg aaaactctga aaaactgtt caggttaaaa cggccgtagg
48181  attcagaaaa cgtatacgga agccagcttt tggccataag gacctgtcag ctgatggatt
48241  ccggtgaggc ctccttgctg gtaagtctgt gccctcatct cagaaggggg tgatccatac
48301  agacctagct ctgtacagcg ctttgttcag ttctctgtat ctctgaaatg tctgatggag
48361  taaaagaggg acacaaaatc ctgatcctga gagatctacg taaaagaggg gaactcgagc
48421  aagccctgga aaaggggggca acagcacccc ctccgagtac cgttatctct ggatcgctga
48481  gaaagtataa agcatcttgc atgggtagaa gagaccagga caccgcctac acacacagtc
48541  ccaggacact aaaacctgaa cacctctcta ggagaaagga cgcacttcgg ccggctcctc
48601  tgccgcctct ctaggattct tggaggatcc atcaatctca gtggttcatt tgtgcacacc
48661  acctggctca cctttgtgag cgcagaagcc gcctcaaaaa ggctgaggcc gacaggggtc
48721  gtaacctctt gtgtccagca gccactcagt ctgggctgac ttctctctct cccctgctga
48781  agacacttga ctgctcgcac tggatcctcc gtgtcctccg ttccctaggt cccgggtcct
```

-continued

```
48841  ccagggtctc aggcatcagg gtctttccct ctatcctcag ggagattcct caattcggcc
48901  ccaacgagca ccttagagcc caaccaagat cctgggatgg ctgatggggg tgtaggagtc
48961  taggcacagg cacactcaga gctcctccca cagccctagt catgtctctc agaagataaa
49021  gggctttcca aacaaaacaa ccaaccaacc aaccaacccc aggtctggta ttatctgtac
49081  cacacaaatt gtccaattac cttcactctg cccccaaggg tcaatgcaa taatcaacac
49141  ccacctgagg aaaacgggga agatgttggc ttgttctcca ttgttttaaa cctgtttaaa
49201  taaatcaggt cccccccgagt aacttaacca ctagcaagtt tggggcttat agatccctga
49261  ctacataccc ctctacaatg aattagcaga agtcagggggt gatgagggga ggccaccacc
49321  accccccaccc ctgcagtcaa tgatcttgag tcaattgctg aatagcatg aagatctatt
49381  gacacactta aggcagggtc agctgtcttt ggtaccatca agtggcaaga ggactcctcc
49441  acagccaaca aatgatgtgg agtgaatgtg ataaattatg aaactacttg gtacaatatc
49501  tgccccccttc cccttcatcc gactacctgc ttaaaatggc tcactgtttg ccttaacact
49561  gcaagctctg atccagtact ctatctctc actttcttct acagtataag gttgaacact
49621  gtactccatc ggtccctata ccactgaaac actcctgtgc ttccaggatg ttgtccatct
49681  tgtctggtaa accattcact caataggtta atcttaggta actagttatg ttaacaatgg
49741  gtttgtctta attagggggcg ggatgggggg gccctctgtt ttgtttgtgc agacatatta
49801  tccccatcctt tcttttcctaa tccaatagat ctattactgg gggttaccag gctaggtggc
49861  tacacctaag tctccaacag ccttttttcat atatattctg ccttagcttt catgacagaa
49921  cattgtaatc tttctgattc tctgtctttt ctatatgctt ggttgaaaaa atactgccta
49981  ttgcaaaaat tattagtatg gggaccgtac ctcctggttt atacctgttg tcttggtgta
50041  attattaaca gcactcctt tcattttcaa gtgtccaga ttggacaata aattatatag
50101  ttaccttatg tgtgtggacc actaatatgc taattagata cagattttca ggctctgcct
50161  cagaaactga ttcagtaggt ctggggtggg gctgagaaaa ctgcacttca aaccaacaac
50221  ccaggtgatt ctagtgcagc tatcatcaag aaatagtgct ttcaacactg cccattggca
50281  gttggcatag aaaaatgggg ataggttcaa ggagatctaa aaatcacagt ggtttataga
50341  ctgcttttct ccctgtcctc catttttatgg aaagtaataa aaagtgtgag gagtaaaagg
50401  cagtgagatt ttcactgctt aagacaatag tatctaaaaa cttggaccag ttgataaata
50461  agagagattt ctaataatta ttatgaagat gaagcatgtt tcttggcaac actctgtctc
50521  tgcatctatc ttttttatttt tccttttggtc aacatttttt gcccaatcta gagtttttagc
50581  atctaatttt accttctgtc tgattcttt ttatgttctt atattttgtt ctttttctt
50641  tccatcccac tttgttgttg ctgtgtttg cagatgccta cagtgggtct cagggctcca
50701  agtgtaagtg tctatgaaac catatataat tcacaattat ctttgttcat aattggtttc
50761  ctttacaaaa tttttaaggc aataaaaagac agaaagatta ctacaagtgc ttaagcactt
50821  tggacttcac ttttctcatt atcttaaatg gagaagcatt taagatattt ataaactcag
50881  aatactatag aatatgtatt acatcacttt atggaataca tatttactta agaagttgat
50941  tttacttcaa aatcgagtct actatatttt tcttaacttc actcaaaaat ctgtagctat
51001  ttatcttgga aataatttaa cctcaagaca caataaaaaa tactttttcag gaaatataag
51061  ttttttatataa tacccgcaat aagccttaag tagtgacaca aacagtttga tatgtaaggt
51121  gtaagaatat gtgatagaac taaatacact aaactgaaaa ataccacccca tcacttctcc
51181  atttctctgt agaagaatta tgtgcaattc tggttgccca cgccttgttt cctagctcat
51241  atgaaagctg ttagcttttg aacagaagga attaacttg gactaaactg gggaaaagaa
51301  tgaaacagaa tatgtaacat ttaaaatag tgagatttt catctataagg agtttgttaa
51361  actatggagt atgaacaaat aaaattctat tcacttataa aagaatgaa gaagttctgt
51421  tatgatgtgg acatctctaa agattatatt ctttcatgaa aacagcaagg tattagaaga
51481  gtataaataa tatgccatct tcctgagtaa tggaagaaat aagattatac attcatattt
51541  gcctatatttt acataaagaa acactgaaag atacataaga aactagtaca atggctactt
51601  ataaagggaa agtagaccctt tttgtattat tttgatttt gaaccaggtg aagaatgaat
51661  tatcttttta aaaaagtcct actgagtaaa ttaaatttta aaagctaaaa ataataatta
51721  caaaaataaa atgctttcaa tgaggaataa atgagaagag tcttttcctgg actccactgt
51781  aaattaaata gaggagttgt gcttattga aacatataaa tgggtgggtt tgttgagcaa
51841  cttcagtgac ttataaatcc tataaattcc atatactgt aatttttatt tggtgatata
51901  atgcctccag tggcttaata gaatgttaca ctaggaagta ggagacaggg ttcagttcc
51961  agctctgctt ttaactggct gtatgatctt agttacttcc cagaacttcc ttttctctta
52021  tctgtcaaat aagagcaagc agaagtgatc tctaaggtcc cttagagtga ttctgttatt
52081  ctaaagttac ttgctatgta ttgggtattt gggtgtattc caaaccagat tgttttcacc
52141  ataggttttc catttctttg tctcctggac cttgtgtaaa gctttgtaaa gagttactaa
52201  gtcaatgtta agggaaataa atttttttat ttatgatctt ggtggtaatc aatagtaaat
52261  gctgagaaaa tgtggaggtt ataaaaacaa tcaactgaa agagtgatca tactcttctc
52321  ttcaatcttg aaatatgtttc aaattttcca tacaaaatat tgaataaagg agaaaaaggc
52381  aaaaacaaaa aaatgctcat tatatgttac gggaaaaata caaagaggcc tgtattttcc
52441  aataagaaat ctgaggtgag atatcagatt tttagctaag tttcttagcc tctgcgtaaa
52501  tttaaaatca tgagcaatat ttgttatgag gagccactga gctgctaata acatatggct
52561  gcttcagttc cttggttcct aaaggctaac taaaaaatct atagaaatct aacttactat
52621  aaatctacat ttatatagga ggattcatct gcccctttt gtaggttaca aaacaaatta
52681  tcatattttta tgtgaatgga aagaagtcag gaaacctata ttatgaattt tattacaatt
52741  attttttaagt taattttttaa atactcggtg aactgcattt gagattattt tgtactcagc
52801  ctacatataa ctatttttaaa cttttaaaaa aagttttttaa aaactaggat gaagaagttt
52861  tcctgaaata gaaaacttct tgcacagatg tgtgtgaaac taggtctaca gcatacatga
52921  tgaatcaac acaagaggca acattcagta ttgcaaagct gtggatgtca ctgatcagag
52981  aactcggcag atgtatttaa gatattatgc ttctctctgc ataaaagtaa gggaattttt
53041  actggctttc ccttgaactt ttctatgcta gaggacacag cagggacaaa gtaagaaata
53101  ttatccccta cctgttccaa ggagctagct tgattcagcc actgggtgga cttttccgatg
53161  ctggattagg ttgcaatggt aaatgaagtt cttgccacat tcttcacatt cataaggtct
53221  ctctccagtg tgaattctct gatgcttaat gaggactgaa cgtcgactaa aactcttatt
53281  gcactgattg cactggtaag gcttctcccc agtgtgaatt ctgaggtgat ggaaaagccc
53341  ggcattctgg ctgaaggctt tgccacaaac actgcactgg tagcgcttct ccccagtgtg
53401  gagtctctgg tgctggaata ggcctgacct ctggctgaag gcccgcccac actcatcaca
53461  ttcataaggc ttctcacctg tgtgtgttct ctggtgctcg ataaggatgg aattctgggt
53521  gaagcttttt ccacattcac tacagatata gggtctctcc actgaagagc tcacccttg
```

-continued

```
53581  cttttccaat ctgccctcac ggtcacaggt atctccatac tcaggaatct gagtaatatt
53641  accattctgt tttccaagaa cttgtataag agatttcact tcctgagaaa tctccctctt
53701  tggggctaac tccacattcc aagtcccagc cttgccatct aaaataacga taacatgaaa
53761  gataacatga agtatgaaaa ataacagatt atctttccaa agacaaaaga aaaaaagtgg
53821  ccaggagaat gggtggaagg ggacaagtag ccactttttc tgtttatttt tccactctaa
53881  agctattata cccagacctc agggaaaaga tgcatggtat tataactgct tacttaattg
53941  tctgcctctc ccactagact gtaaacttcg tgagagtggg gaccacatct gccttgttta
54001  tcactgtatc cctggtacct ggcacagtgc ctggcataca gcagacacta aataaatggg
54061  ttgaattgat aaatattcag ggaatgaggt aggctgtctg aggaaatcct gatcctcacc
54121  aatctcttga actgggcaca cctctcgcaa attataccca agttgctctt ccaaggtttg
54181  gaattggtca tttgatgact cctgagctgc tcctggagtt gccttctcct ttacaaactc
54241  ttcctgttca tgagcatggc tcaggacctg gtggaaatca aggacagttg ggaacccaat
54301  atcagagaga acatggcaag gaggcctcct cagggccgct ggatagaaaa gaaggaccaa
54361  gaagctggca aagaaaaaac agaggcagag agactaaaag cctacagaag atcaagtctg
54421  gcataaaaaa aaaatcctcc tcctctacct tttcttgttg cactgaaacc ccatacttgt
54481  tctataggt acaaatccct gttctcccat cttctcacct gctctcctgg gtcatccagc
54541  tctctctcca aatcctccag cacagtcact gcctcctctc cactcacagg acggtgctgt
54601  ctgacccagg cctggagctc ctcaggcagg atagtcagga actgctccag caccagcagc
54661  tctaggatct gctccttggt gtgcatctct ggtctcagcc actgatggca gagctcctgg
54721  agtctttgaa gagcctcccg gggcccaggg gactcctgat agcagaactg cctgaagcgt
54781  ctacgaaaga tctctctggt atgagggtta tttcttgaca ggcctgattc tggcccacag
54841  gaatgttcct cctcttcctc ctttaccttc actgccagaa gtccttcctg catctctgca
54901  gtctgaaggg tcaaggttat ggccatcaaa ggtttaacta ttcagaaaaa taatctattc
54961  ttgataattc tcccttgatc ttttcttctg gaaaccccga gatctagaca ataatttacg
55021  aagaaaaaaa taaaaaaatg cagaaaacct caggacaagg agggactgga gtatttacac
55081  taaaatcagt cactctgtct catgaaggaa caccaaaacc tgattaatga tagatacttt
55141  agaaatacaa atccagataa tataggaaga aaaaagaaat ggaacaaaaa cgcctacagt
55201  tttctgaagg aaggtactgt ttcaatcatc ctgaccgaaa cagctcaaat cagcttgagt
55261  atattgggtt tccatttgaa tagcaagata ctaaattcag ggtaaatttt agctgtatga
55321  aggtaaaaaa acactttggg cccaagtggt cacagatgac accagaatc aagaagaaaa
55381  gggaaacaaa tggaggatgg agggaaagta aagaatataa aagaataag aaccgtaaga
55441  aatgcacttg gagagaggag gcagagtccc tccagccata gaaggtagag tccctccagc
55501  cataggaggt atggaggagg gagatctagg tttaaggtct gtaaggtctt ggactgagac
55561  atcaacctgc aggtattccc tccagagtct tgggctttcat gttttgagcc ttggtctctt
55621  caatctataa aacaggaatc ctaaaaccaa cactgcctat ctttctaggt tgatacaaag
55681  ataaaacgag gataatgagc acaaagaagt tggctactta gtaaactcca aagtggtaac
55741  acttatttt cttatgttat tgtatgatta aatgaatatc ctagtggttt aaggctaagg
55801  caaagaatc agaaagtagt tgactcagt ggtctaggct cagagatact aaaatgacgg
55861  aaatattggt tccagtactt taaaacagga gtagaatttg accttctct tgcccttaa
55921  tttcttttgaa acttttctc tttgaagcta cttgaaggtg gagagtaggc aattttatgt
55981  aaaataaaat tactgctaat aaaaagacaa atgtctatga ctcctgaggt caggagttcg
56041  agaatagcct ggccaacatg atgaaacccc gtctctgcta aaaaatacaa aaattagctg
56101  ggcttggtgg cacacgcctg ttatcccagc tactccagag gctgaggctg gagaatcgct
56161  tgaacccggg aggcagaggt tgcagtggac tgagatcaca ctactgcact ctagcctggg
56221  cgacagagca agactctgtc tcaaaaaaac aaaaacaaaa acaaacaaac ttatgagcaa
56281  tctttaccag gatagtaatt aatgaagaaa attttctgaa agaaaaacaa ttatatgacc
56341  cagtgatttc taagcaccat cttcgagtag agactttcaa acttttttga ccaggactct
56401  tattaagaaa tattttatat tataacccag aacacacatg catatgtata tatgtttgtg
56461  catttatgag atacacaaat acctaaaata ataatttcac aaaacactat gtatcctgc
56521  tctatatagt gacatacaat tattttaaa cctatttcat taaaagacaa aacaaaaaag
56581  cctgggaaca gattttgtgg gttataaaat ctatgtggtg ggttgtgaca caccacatag
56641  attttatgac ccacaaatga aaataacct gtagaataaa atattttgt tttaagtaaa
56701  attgttgtaa tccattgcaa aaataaccct actctattct gtttgttgtt ttttgttttt
56761  gtttttgtt ttttgagaag gagtccttgct ctgttgccca ggctggagta cagtggcaca
56821  atctcagctc actgcaacct ccgcctcctg ggttcaagca attccctgc ctcagcctcc
56881  tgagtagctg gtattacagg cacccactac catgccaggc taattttttgt attttagta
56941  gagacagggt tgtaccatgt tggccaggct ggtctcgaac tcctgaccgc agatgatcca
57001  cccgccttgg cctcccaatg tgctgggatt acaggcatta gccaccgcgc ccagcaaccc
57061  tacactattc ttaaggtgtt gacatgcatt gtgaaattaa ataactaaga atagggtatt
57121  ttattagtct gttctcaagc tgctactaaa gacataccca agactgggta atttataaag
57181  gaaagaggtt taattgaccc acagttcagc atggctgggg aggcctcagg aaacttacaa
57241  tcatggtgga aggggaagca aacatgtcct tcttcacatg cagcagcagg agaagtgccg
57301  agcaaaaggg ggaaaagccc cttataaaac cgtcagatct catgagaacg cactgtcacc
57361  agaatagcat gaaggtacct gccccccataa ttaaattgtc tcctaccggg tccctcccac
57421  gacacatggg gattatgaga aattgggaac tataattcaa gatgagattt ggatggggac
57481  acagccaaac catatcaggt attttaaatta caagtgaaca ctgatcacat tacaacccga
57541  agaaaaatta gattcatatt gtgattattg gttatattta tcaaaggggga aacaaactac
57601  tggcatggga cagcatcctt ccggataacc tgcacacata atcctctcca taaagttctg
57661  acatctttgg tttggttacc ttctgtaatc actaccccag gaaatgtaca gaggatttt
57721  ttcctctaaa gacagaatct gcaaattcat gtttttccccc acttttttt tttttgagac
57781  ggaatctcac cctgtcgccc aggctggagt gcaacagcac gatctcagct cactgcttcc
57841  caggttcaaa tgattctccc ctcagcctcc tgagtagctg ggattacagg caccccgctac
57901  catgcctagc taatttttgt atttttttgg tagagacagg gtttcaccat gttggccagg
57961  ctggtttcga actcctgacc tcgtgatctg cctgcctcag cctcccaaac tgctgggatt
58021  acaggtgtga gccaccacgc ccagcctcc tccactttc ttggtgcgac tcaccaccac
58081  tgtgactacc atactatctt tttctgtcat aactttcat acaccattca ttcacttggc
58141  agatatttat tcagagccta ccagcaaata tatattcaga gcctaccata ttccatgtac
58201  tgttctaggc actgggggata cagctgcaat tataacgaag tccctagtct catggaattt
58261  acatcctaat aacagtatta ataatagcgg acatttatag tgcttttaac gtgccaggta
```

-continued

```
58321   ttgttacaga tgctttatat atattaaccc atttaatcct caaaacaacc atgaataagg
58381   tgctattatt accccatat cacagatgag aaaactgaga tatgaaaagt ttaagttact
58441   agtccaaagt tcaagtcagt tacagatagt aagcagtgaa gctgcaattc aaacccaaca
58501   aatctgacat cagaatttac agtctccact gctacaacac taacttctgt tggggaaaag
58561   aggggccagg atgaggaaaa cgggtcagag gaaacagata ataattaagt atttgtgaag
58621   tagtgataaa tgctatagag aaaataaagg taaggagaga gagagtaagg ggaagaaag
58681   gttgctattt tatagagtca gggaaggcct tgataaggta atggttgaac agacctgaag
58741   gaagtgagga gcaagtcaca tggctatctg gagaaagact gttccatgca aaggtaactg
58801   ccaagtgcaa attttgcag gtgggaacac acctggattc ttcaggtaat agctagttga
58861   acaatggctg gaacaaagaa aacaaaaggg aaagtaacag gagataaagc agggagcttg
58921   ggaactgatc atgaaaggca gtggtaaggg ctctaacttg tattctatga gatatggaaa
58981   ccactgggga ttttgagcc aaggggtaac aaaatttttac ttccatttaa cacaaaagca
59041   taactctagc cgctgtgtca atgaccttgg ggttaagtgg aggcagagag ggatgctatg
59101   ataatcatcc agggaagaga tcatcatggc ttgaaacatg atctgctgaa ttggttctag
59161   ggtaagaaag ttttgtggta gaaatatcaa atagctaaat ccagaatatg tactctcaca
59221   ttactcaata aacgtaccat ggattcaaag gatgaaacag ccacttatgc tttcttgttt
59281   tttcaatctt ttagggtccg aaaatgtctt tttcttattt accacctgtg ccgcttggtt
59341   tcaagtcaaa gttttctat tcaaaggcaa tgcagctgaa gcttagagct ctgcccagaa
59401   aaattcattt ctgggatgtg gtgtttcaaa tctttataca gtttcccaaa tacaaatttc
59461   cctattttct ctgtatactc tgggttcatt tttgcttttcc ttcacctgat tttgctttta
59521   tctggtggcc ttaataccca gatccttgca ccagcatacc tgagttcttc tttgaacctg
59581   gtgtctccaa aaggcttccc cagttttttg taatactgcc ctcctcgtca caaacataga
59641   gttcctaatc ttccattcag gatcacaacc tcaatgtata tgccaggtat ataattagca
59701   taataagtct taccttaaaa aatacatctg cattttaaag ttggttcctc ctagagcctc
59761   agcaagctga acacccccaa atctaccatc atcctcatgg aaggatgctg ttaaccaagg
59821   acatgcacgt aggtgaagac taagcagcat gtaatacaaa tgtgccttta tcatcatata
59881   tcccacgacc ctcacctccg ctgacaccat ctatggctcc tcactaattg gatgaattcc
59941   caaactctca agcacagttt aaaaccagtc agacctttag cttctgttgt ctggctccac
60001   tcttggtttc ctctattcca caagcaaaaa ctctcagctc cagtcaggtt tttcttctca
60061   ttattctaat caggcgtttc tcatccctgc gccatgagct tggtcttgcc ttcttccctt
60121   attcgaacct tacccaatct ctgcagcttg attcaaatct cacatcctct ctgaagtctt
60181   ctttacccat ttcagctcac cctcttccaa ctgcccactc atatgtcatg tactgtatga
60241   gtcccaccctt tcaccctcag tcacaattta tcttgtacca ttacttctct tcagaacctt
60301   ttttaaatcc aaaaagtaga gaggaatata gaattctttc accaagttct attaccctga
60361   aataaacagt cttaaatact ggaatgtgtc cttttctatg catttgcaat cgtatataca
60421   catgtataca catgtgcaca catagagttg atataagccc atatattta tttaccttag
60481   acaagcagaa ggtagtatga gatagcagag aacacaggca gatctggttg ttaatttttt
60541   ttttttttt tttgagacag agtcttgctt ttgttgccca ggcgggagtg cagtggtgcg
60601   atctcggctc acttgcaacc tctgcctccc aggttcaagc aatcctcctg cctcagcttc
60661   cggagtagct gggattacag ggacccacca ccactcctgg ctcattttg cattttttagt
60721   aggatggagt ttcaccatat gggtcaggct ggtctcgaac tcccgacctc acgtgatctg
60781   cccacctcgg cctcccaaag tgctgggatt acaggcatga accatagtgc caggccatct
60841   gtgaattta acgcagtgat cttgggcaag ttagttgatt tttctaagcc tcaagctcat
60901   atatgaaatg aggtcaacaa ctgccttgcc aacttgttga gaatattaaa tgagataatg
60961   catacaaagt gttttgcac aaaacctggc atataacat gcaaattaat cttttaataa
61021   gataatgtac aattttggta caatggtagt ttaattaata gttgctactt tcccttaggg
61081   ccaagactgt aatcttttc tattgctcaa agaacaagat gagtgggtga aaacatgcac
61141   acaaaccaat aaaacggctg tttcatcagg tttgcagaaa cactgaaaga tatacgtctt
61201   cagatatatt ctctccaatc aaatcctaac tagaagccca ggactactga ggtacaaaag
61261   aaggacggga ttcaaatgag cgaagtaact tcccgggtta tagctgtaaa gctaatatag
61321   gaacagagtg gagttagcat agcaaaggtt ttaagaaaat ggagtctgga gccaaattgc
61381   ctgtatttga atctgccta caccccttac tcgctctacg accttgggca agttactaac
61441   ttcattttct tcttgtatgt taattttaaa aagggcggg acagagaggt ggggtgtagt
61501   ctacataata atagtgtcta tctcatagag ttatgagaag cagataatat ttgtaaagtg
61561   cttagaacag tgctgggctg gcacatagta gatgctattt attcttttaa aaaattcgat
61621   agcagcaaga gcctttatac tatgtgagtt agactaagaa aggctgtggc atagtttaaa
61681   actatccctg ctcattcttt aaaataagtc cacagtagag aataagacat cggaaaatac
61741   aaacatttct tcatatccga atctatttga atcctaagat gcagatacgg agagttcaga
61801   gtgccatcag tacagggcag agaggttgaa gagctcagga acagacatag ggtggggaa
61861   aggggtaggg gcaacgacgc tgactttttgg ttaacaaagc ccttccaggc tgcggagcaa
61921   cctcctctgc ccttcacctg cccggcccat ctctggccaa gaagaccctg ccgccaaatc
61981   cccacaccca gtccaggtcg cagtgcacag actggcccctt ccgaagcccc tcagcggtag
62041   cccgactccg aagctcaccg aggcatccgt gagaggagat gccacctagc gcagatcaca
62101   tctgctctga atccttgaca accgcagccc aaagaatgat aaactacaaa ggccggaaat
62161   gcgtcaccgc ggcccgctct ccgcgaaaca gcggttccgg ctgtgttcct tctaggaagg
62221   ccggaggttt ccacacctct gtggtcgtca ctctgaatcc cgtctgtagt cttaagtgag
62281   atactaggtg acacattgtc ttccacgcgg caatataata acgccaaca tagtgtttta
62341   acacgtatta attcattacc ccgcataaca accctgtgag ttaggtacaa ttatctccat
62401   ttaacaggtg aggaaactga agcacatttc tacatttatt agttgccatt tcctgcaaag
62461   aatacccttt cttttccctg ccgtctcatt ttatcacgat gaactcatgg attcctttac
62521   aaataattac tgttattatt atgttgatgc tcaaattatt taaaatttgg tcagttggag
62581   ccctttcaca ctgctccctc tcttttcttt ttttgacaaa gtctccaggc tggagtgcag
62641   tggatgcgat ctcagctcac tgcaacctcc gcattccggg ttcaagtgat cctcctgtct
62701   cggcctcctg agtatctggg attacaagaa cacaccacta tgccttagtg aggctggtct
62761   tgaactcctg tccctcaagt gatccgctcc ctcggcctcc gaaagggctg ggattacaga
62821   agtgagccac cgcacccggc cacaaacagg tttctatgtc ctttgataag ttcccaacag
62881   ttttgtgca cttcactttc tcacaaaaga tatttcagtc ccattttata ctattcctac
62941   cctaaaccta gaatcaccat tgcttcatga agctacagta catcagtgaa aaatggtata
63001   tagaaaccaa gatctggatt tcgggcaatg aataacctca ttgctactgt gtctggcatt
```

-continued

```
63061  ggttcctgcc agtctactgt gtccagaatt ggctccttcc agtgggttcc tgctctgact
63121  tcaagaatga agccgcggat actcacggtg agcattacag ttcttaaaga tggtgtgtct
63181  ggactttgtt cctctgctg ttcagatgcg tccagagttt cttccttccg gtgggttcgt
63241  ggtctcactt gacttcagga gtgaggtcgt aaaccttgc agtgagtgtt acaactccta
63301  agggtggcgt gcctgcagtt gcttcttcct tctggtgggt tcgtggtctc gctgacttaa
63361  ggactgaagc tgcagaccat cgtagtgagc attacaatgc ttaaaagtag tgcagaccca
63421  aaaactgaaa agtggtaagg tttattgtg aaaagggaaa gaacaaagat cccacagcac
63481  aaaaatcaat gctagcaggt tgtcactgct gactggggcg ggggtggtag ccagcttta
63541  ttcccttatt cagccccgcc cacatcctgc tgattggccc attttacaga gtgctgattg
63601  gtccatcttt acagagtgcc gcttggtgtg tttacaaacc tttagctaga cacagagtgc
63661  tgattggtgc attttacag agtgctgatt ggtgcattta caaatcttca gctagacaca
63721  gagtgctgat tggtgcattt acaaatcttc agctagacac agtgctgatt ggtgtgttta
63781  caatccttta gctagacaga aaagttctcc atgtccccac cctaaccgga agcccagcca
63841  gcttcacctc tcactactag gacatattat tgcctctagg ctccttcagt gtacaagagc
63901  tagaatatat gaatatgtta tatatataat atattatata taatacgtat tatatattat
63961  cctatatatc atatattata tattatatat aatacatatt acatattatc ctatatatta
64021  tatattatat acggaggatt ttaattata tatatgtgta ttatatataa catatataat
64081  atattatata ctatatatta tgtacataat atatattata tacagataat aaatcctcca
64141  tatacatata taatatatat atggaggatt ttataagata cttctgttc aaaaacaact
64201  ccacagaatt cttttacatt tttcaccgtt gcacatttgt tttttttctt ttcacccaca
64261  gtgaaaactc tggctcccaa cagcataaat aaattcactc aaacaaaata gtttcttata
64321  aacaaaatag tttcaagatt ataataccaa tacatcacta gcaataacat atctactatg
64381  tagaattcaa aatttctttg cttgttttgt ttttgaatta tatcccatta agggagtata
64441  gctgtataaa taccttattt gaattaatta ttttctctgt ggttatattt taaacgatat
64501  atggttagga gcatttgttt ctgtttatat tccatttcag ggtttgcttt catccctttt
64561  taattttttt gacaattcaa aacatttact tagttcaaaa tccacactat ataaaaggt
64621  atgtttagag gagttctgct tccatcccca gtcccttac cacatatact catacccaat
64681  tttcattatt tatttatcct ctccttcctt ccttcttcat tccctcctcc cttccctact
64741  ttttctcttt tttcttgcaa aaatgagtat ttatcttctg taccccataa gttatgttat
64801  atacattctt tcatgccttg ctttatcatc taacagaaaa gcctagaaat gtcctgtttt
64861  tgaagtagtc ctcttttttc acacctgcat aataactcat tctgtggatg taccataatt
64921  tttttaacca gtttcttggg ggtgggtatt tggattactt ccaatatttt gctttaacaa
64981  ataatgctgc aatgaacaat aagagagaga cttttgtaga ggttgtgtta ttttgtactc
65041  tcaacagcaa agtgtgagag tgcctgtctt cacacagcct catgatctgt atgttttcag
65101  gcttttacat attgccagta tgataggtcc tttgatattt cttaaggaat cacaaacgca
65161  atgctgaaat ccctgctaga aatggattca cagtgccaaa tttcagcaag gattatggaa
65221  caatgggaat tttcacatat ttttcatgag agtgtacatt ggtgaaacca ttttgggaa
65281  actctggcat atctactaaa gttgaatgta tgcgtattct gtgacccagc caccagaaac
65341  gcatatgtgc ttgcatctaa agacatgtct tagaagcatt ttttggtgat tgctttaaac
65401  tggaaacaac cctaatgtcc attaacagta ggatgggttt taaaaaaaag tttattcaga
65461  caactgaata ctatgtaaca acgaaaatga atgaactaca gctacaaacc acgttgataa
65521  atttcacaaa cataatagta aaaggagcca gaatatgtgag taaagaaga caaaaacac
65581  gacatttgac ctctcgtccc tgagaggcgg gtggttgtta gttcagggg ttatgggagg
65641  gctctggcat ccgggatgga ggcgcgtcgc tttctgtggc tggcgctgga tccacccgg
65701  gtctccagcc acggctgcag agagggtagc gcggttttctt aggccagagt ggagtgggac
65761  aggaggtgcc cagagacgac tgtggtggct tgagacatgg aagcgctgca gcctttgagc
65821  ccagtatcca gcattgcagc cgccgcggcg gtcaagagc tcaaaccctt tcaggcgcgc
65881  gcaggaggag gagcggcggg ggcggcggaa caagacgacc ctcacttaac gtggccgctg
65941  tcgccgtggg catgctgggg gcgtcctacg ctgccgttcc cctttatcgg ctctattgcc
66001  agactactgg acttggagga tcagcagttt caggtcatgc ctcagaccag attgaaaaca
66061  tggtgcctgt taaggatcga atcattaaaa ttaactttga tgcagatgtg catgcaagtc
66121  ttcagtggaa cttagactt cagcaaacag aaatatatgt ggtgccagga gacactgcac
66181  tggggttta cagagctaag aatcctgctg acaaaccact aattggaatt tctacataca
66241  atgttgttcc atttgaagct ggacagtatt tcaataaaat acagtgcttc tgttttgaag
66301  aacaaaggct taatccccaa gaggaagtag atatgccagt gttttctac attgatcctg
66361  aatttgctaa agacccaaga atgattaatg ttgatcttat cactctttct tacactttt
66421  ttgaagcaaa ggaagggcac aatttgccag ttccaggata taactgaagt cagcaactaa
66481  gtcttccttc aaagttgtga ttttgggaa aatcatgtat cctatcttct caaaggagaa
66541  atattgtaca ataatatgaa gacttatat ttaaataatt attttttctc aactaattta
66601  tttcacttaa aattgagaga acaagttcag cttttatcat aacaaaccca catgcctagc
66661  tagaatatat gagtgactat tcaataccat actgaagagt ttgatagcat taaaataagc
66721  cgctttgttt tttaaatatg caggcatggg ttcagcttaa ttctataatt cccttccaga
66781  ttattaactc ttcatactta tagcaaagaa tctgacaatg tttttcaaaa atgaatgctc
66841  agggttattt gtttcaagtc ataggccaga acttctgacc atgtttatta tgtctaaaag
66901  agttggttgc tatttttcctt cattataaac agtcagtatt ttaaaagctc aaagtagaag
66961  aggagtcacc aagccctaac agcttgtcca aagatttaaa ttcttatttc aaatttgatt
67021  tgtccttaa gatttagggc tatttttatat tcagagttct gaataattac tttgaaattg
67081  tagtatcatg aaattgaaat aaaatacatc tactaggctg ctagccaaag catcatcatt
67141  acaagtccat gaatgctaaa atgtacaagt gggattgtga agatttactg acatcaaaag
67201  ttcttctgga aacaaacctt tgtaaaaaaa aaagtgtaaa ttatttaat agtgatttat
67261  ttgtcatcaa atgtacaact tattctgaat attttcattt tctgtgttcc aaacagaaat
67321  gttaagttgc agtaaaaaga gaaaaaaaga ctatttagaa ttacaaagaa tcatatttaa
67381  aggctgccca atgtagagtc tagtgacctg ttcaggacac ctgaaatata attaaatgac
67441  aacatcaagg ttttaacaat ttataattcc aaaccagagg attataaaga agtgcaaatt
67501  gacttttaca ttcaacttta gttaaatgaa ggcactcaat attcttcctg aataatacat
67561  tcagtttctc acatttatg ttttcatctg ttccaattat tttgtagtaa aataatctac
67621  tcttatcaca gctgtgtgac gatttctaaa tgtaggaagg cctgtgaaac atatgacact
67681  gcagttaaat ttgttggcct aaggactaag taattttct tctgctgaag tttaagtga
67741  gtatttgttc caaacaagtt ctgttgaaat ctcacgctgt tgtcaggaat caatgttatc
```

-continued

```
67801  ctggaactgt tattcttcta tttaatcttc atcatagcag aaatgctcca ctgtggcttt
67861  gacatgttgg taggtattgt cttccaggct tcaaagctgc acagagtcta ccctttagag
67921  aattggcacc tttgatgtgg ctagtgagct gatcatctac tttcttctaa aataaagaga
67981  agaaaatgaa aaaaaaaaaa aaagatgaaa aacacaccct tcatgatttc atttctataa
68041  ggttcagaac agaataaacc aatatctgat gttagaagtc acaacaggga gaaggaaagg
68101  aacaaagttt agcagggagc acaactgggc cttgtggggc acaggtaacg gttctatttc
68161  ttgaccttgg tagtggttat atgaatggtt ttacttttgca gtatttcatt tcactgtgca
68221  catattgcta tgtatttcta agtatatgca tatttcaata attttttttaa aaatatgcaa
68281  actactcatt ttaaagctga aagaaccaga gctcagatac atgaagtgtg ttgctgagct
68341  caacagaccc aggactcata tccagttttc ctgatccgct agctcccttg gctttgaggg
68401  gttagttaac taggtacccct tacatgtgga tcttttttt tttttttttt ttttctgaga
68461  tggagtcttg ctcttgttgc ccaggctgga gcgcaatggc ataatctcaa ctcgccgcaa
68521  cctccacctc ccaggttcaa gcgattctcc tgcctcagcc tcccgatagc taggattaca
68581  ggcgcccacc accatgcctg gcgaattttt gtgtttttat tagagacgag gtttcgccat
68641  gttagccagg ctggtttcga actcctgacc tcgggtgatc cacccacctt ggcctcccaa
68701  agtgttggga ttacaggtgt gagccaccgc acctggccat attttcttta tacctctaga
68761  atcctactag aaagtgttgt gagtcatctg gaatgattat taagcattat ttaaaatggc
68821  cccaacgtgt ttatttaat agctaattta ttaacagtca tactattcca gtttgtatca
68881  tcatgaacaa gttagcaata tacactttt tttttttgag atggagtctc gctctgtcac
68941  ccaggctgga gtgcagtggt gcaagctccg cctcccgggt tcacgccatt ctcctgcctc
69001  aacctcccaa gtagctggga ctacaggcac ctgccaccgc acccggctaa ttttttgtat
69061  ttttagtaga gactaaaata caaatagtt tcaccatgtt agccaggatg gtctccatct
69121  cctaacctcg ttatccagca atatacattc ttatgcacgc ctgttttgca cagacaattt
69181  tatttatagg acataggttc tcataaatag tattgataga tggaaaaaca tatgtatttt
69241  tagcaataga tgctgttagt ttgctttcca aaaggctgta accacctcac acttcaaaga
69301  gcaacaagtg ttacaacttt tctaaatttt tggtcagttt actggtatct cattttattt
69361  gtggatgtgt ctcaaattca catctccaga tttgatttga atccatgatt gaatgtcatg
69421  attgttttc cttctatgtt taagtgcctt aaaggcatct caaacaaaac atgttcaaag
69481  ccaaacttgt aatctctgca cccaaatctg atcttcttcc aacatccctt ttgttcactt
69541  gtccaaatca gaaacttggg catttctgtt ttttaaccct cacataaaat ccatcaaact
69601  cctatcaaat ttatcttcaa aatatttatg tacttattta tttattgat gcataatatt
69661  tgtacgtatt tatggggtac aggtgatatt ttgttgcatg catagaatgt gtaatgctca
69721  agtcagggta tttaggatat ccatcactac aagcatttat cacttctatc tgttgagaac
69781  atttcaagtc ctcacttcta gctatttaa aatgtatgat aaatcgttaa ctatagtcac
69841  cctactcaac taacattaga atttattcct ttaatgtaac cgtatgtttg tatccattaa
69901  ccaacctctc ttcaccccca cacctcatc cttcccagcc tctaataact atcattctac
69961  tgtctgcctt cattagatca acttttttag ttcccgcatg tgagtatatg tgatacttgt
70021  ctttctgtgt ctggcttatt tcacgtagca taataatctc cagttctatt cacgttgctg
70081  caaatgatat gattttcttc tttttaatg gtggaataat atttcattac ttaaatgtac
70141  cacattttct ttatccattc atccactgat ggacatgtac attgatctgg tatctttgct
70201  attgtgaata atactgcaat aaacatgggg gtccatggac ctctttgata aattgatttc
70261  ctttccttt gataaatacc aggagtggga ttgttggatt gatagttcta ttttagttt
70321  gtgagaaact ccatagtgtt ttccataatg gctatacaat ttacactccc accaacagtg
70381  tatgaaagtt cccctttctc tgcatccctca ttagcatgtt ttttttcat cttttgataa
70441  tagccattct aactggaatc atatgatacc tcattgtagt ttgatttgca ttccctgat
70501  gattagtaat gttgaggtgg tgcatgcctg cagtcccagc tactcaggag gctgagatgg
70561  gaggatcgct tgaggccagg aagtagaggc ctcagtgagc tgtgattgtg ccactgcact
70621  ccactccagc tgagcaacag aataagaccc tgtctgaaaa agtaaagaaa agaagagag
70681  aaagacaaaa aagaaatggc aaccatcatc ccagaatttg atggctttca ttttgtgca
70741  ttttagattg tgcatctatc tataacttta aaaatatccg taagtggtgt gtgtgtgt
70801  gtgtctatat atatatatat tttaaaacta tttctttact aatctgtttt gcttaacgct
70861  ttacatgttt tgtgttttgt tttgtttgt ttgagaagga gtctcgctgt gtcacccagg
70921  ctggagtgca gtggcgcaat cttggctcac tgtgaccccc gcctcctggg ttcaagcgat
70981  tctactgcct cagcctcctg agtagctggg attacaggca tgtgccacca tgcccagcta
71041  attttttgtat ttcagtagag acggggggttt caccattttg gtcaggctgg tctcgaactc
71101  cttcctggct ttgtgatctg cccaccttgg cctcccaaag tgctgggatt ataggcgtga
71161  gccaccacgc ctggtcgttt tcactactgt acactattcc agattataaa tgtaccccaa
71221  tttactcatc attctcctat tggtgtgaat taaattgttt acaaacaatg ttgtcatgaa
71281  cattcttgta catcttcttt tgtgcatgtg tgaggacatc actagtgcat ttagcttttt
71341  taaaatgaca tttacccaat agtgaaattg ctgaaggggga tatgtttctc tttattgtat
71401  tggatgttgt gaatatttga catatttgtg gctacccaga atacttggag cacccttcct
71461  atagctatga ctttccccca ttataacttc tacctttta aggtaggtgc tagaaaaacc
71521  catttttaa cttcttctgc aggtagtgag caggcatgta acataggttt tgccaataag
71581  atgcattcat gaaaaacttc aatttagaag agagcactgt gaggaagggg atgctatgcc
71641  gaattctgta aatgaggtag cagtgtggtc atgttaagaa cttttagaag caaaagtgac
71701  caagatccat gctgtagtgt cctgtgtttc gtgttcatat tgaaagtgat gataattatc
71761  cactgttgtg ggattgcttg tatgagcagt ctgggagtga aatttgggca tttttttcc
71821  tgactgcata attctagtgt ttctctggcc tttcaggaga ctctaagtca actgatattc
71881  ttaataaatt cttatactat ttcatctgta gagtggattc tgatgcttgc aactaagaat
71941  tctaacagaa acagttattc tcaacccttc ttctctcatg gtacataagt aagtgacaat
72001  tgtataacaa actggaagtg atgtataaag ctgcttgtgg ctagaagcaa ccagaactat
72061  agttattaat ttcctatggt cttgcctggc ctctgtaagg agatccgtat ctcaacagca
72121  cacctgtcac acattcatag cccaactatg tgccacagtg ggctagctgg aaatctgtgc
72181  actagatatt gctaacttat tctcagttta tactccttct aatagtgtgt gagagttctt
72241  gctggtcaac gtcctctttg accttttttt ttttttttt gagacagagt ctggctctgt
72301  cgcctatgga gtacagtggc ttcttcgact tttgatatcc ctggacttta aaacttattc
72361  cggttttatt ggtataattt tatatatgat ttttaaaatt tgcattttc tattactagt
72421  gagaatcttc taatttgtat ttccttattc gttaattact ggttcatat cattttatgc
72481  tttcctcttt gactgctggt cttttttatta ctgatttata aaaagctctt tacacgtctt
```

-continued

```
72541  tgatatttag gattcttcac ttgcctgggt tgctttgaag gctgcaagag catttgtagt
72601  aattatacat tcataatttt gtattctact tttgaaaagg gtcccccaga ttatacagga
72661  ttcaggttct acaaaacctg gatccatctc tgacatccca attggaggcc tatctctctg
72721  ttttgcttat tggtgtcttc tgaggcacag aagattttat ggttaattta gttaaattta
72781  tttttattt tatatggatt gtactatttg gatattgttt aagaaaaatt tttctaaccc
72841  tataagatta aaatatgatc ttatattttt ttcaaatgat ataaaatttt gttttataa
72901  agtaatattt tacatttagg atacattttg gaggggtatg atatgagtca gtgattccat
72961  tttatttgta tttttctgca tgaatactca attgtctcac acttgttatt gaataattca
73021  tttttcttca ctaatcctca ggcccattta tttatgaata aaagtattt tttctcttgg
73081  tttttttgttc tgttctgttt gtctagttgt ccatctatga ctacagttga acaagggtat
73141  atcaagaggc aactaagtga accatctgag cttcatatgt attccaccct gatctcacta
73201  tgtaaaaaca gctctacctt ctcttctctt ctcttctctt ctcttctctt ctcttctgat
73261  ccctggacac aaagatctca aaatgcctag gtggcagttg tagctttttac ttcaatgggc
73321  ttcttgctat atcccctggc aagagtggac tgtctttgag actaggagtc taattttgcc
73381  aagctcagaa ttgtgggaat gggaaataca aatccccaag tggtctactg gaagtaatga
73441  ttaatggggc cactcctgct tccatgtttt ggttcctgga ctcacgtttt cttcctttg
73501  gagacacagc accatttagg agctctaatt cagtagtaca tacattgcat cctggagaat
73561  gccgtattac ctctgagctg gtgctgcagc tgtgccttca gcaagccagt tcaactctct
73621  gtcagatcag gtgcttctag ataatgtggt ttggaatagg accagtgagt cccatcatta
73681  tgggcttact ggaagcgggt ctcctcacca gtttgtatgg tcacacacta gcttttgtga
73741  gattccatgc atatgaaccc aaatatccct atatagtggt cttgactggg gctatatgaa
73801  caagaatgtt aaacccatac caagaatagc taagacattg aaagtcttag cattggtatc
73861  tattgctgga actttggacc tttacaggca gcatctgtta tttctgcttt agtaaatggg
73921  agtttattct attgcactct tgtgtagtct ttatctctgc caccttggcc actccattca
73981  catgctcatt gtgctagtta tgtgtctgct ggttgttatg ataattgcag tcccttggtt
74041  gctggtgttt aagctctacc ttcttacttc acgtccccat tgccagccaa tggggagctc
74101  tagaataaag gtttctcact agagaagtcc caggtatgcg agaaattggc aggccctggt
74161  atcttcacca tcttcaatct ttggtttgga gctccccagc atgaagttgg cctcagatag
74221  aatgctgtag cagatctcaa aggttgttac agttagagac tgttaggtga cagactctaa
74281  ctaaaggaag atctgagcta tacacctcta caggggcaac tgaattgtga ttgttgactg
74341  cagcagtgaa ttggccagac caattagcca agcagtgctg gacaggtgca ggcagacctt
74401  atggtctatg attatagtgt accttggagg cttacagaca gccacatagc agtctaaggc
74461  cacgatgcca agaaggacac attcaataca ggctagccag tgaaatacat aggcctgggc
74521  catacagcct atttaagtga tgttcttgtt ggggccccta aattgaacag catttgaggt
74581  actgttgtgg tggtgaaaca gagatataag acggaaagac tggtgagaag gaaatacata
74641  ggactatgaa gttgggaatc tagttgagag accagaataa tagcactatt tcccaacaat
74701  gtgaacatgt agaaggtcaa gaggacacag aagagaagaa aatccagcca tggatatttg
74761  acaaagccca tgagaatgaa atcctctggg aaacttttcat tcaagtactt cactgaatct
74821  cagtgacacc aacctgctaa aatcaggtaa gataagagtg attttttaaaa tgttctgagt
74881  tggtagaagt tctgaagaca gaacttttc taggaaaaaa tagttttagt agggagagat
74941  gggacacacc ctaaatagaa atcataacaa taataatgaa taatgaatca gtgaatgaat
75001  gaatgaatat aataattact ataattaaca ttatgaagta atatttgaaa agctctttca
75061  gtaaagaaag tggtttcaca tttttccccc aactcaaaac catgtgtgat aggttagtag
75121  actttagttg ttatggcttt tatgtctgac taaggaaacc agtggaaggt gggctgcata
75181  ttctcccaga tgcctggcag caaagggagt atgtcacctc agtttggtta atcacatgat
75241  tctaccccctg acttgagtct gggtagaaat tatgcaaaag aatgaagaag gagaaaggga
75301  ttgtcaaaag tacagagaag ctgccttcct ggattgatgt cccataatga caacttcaaa
75361  cgatgtgtcc tatatgcttt cttccagggg tggcatcttg gttgttttgc ttctcctcat
75421  ttctgccttt tgtgtgtgtg ccaagttta ttcttaccc ttcttattga ttctatgaac
75481  tactactctt ctaatatttt ctttttgctt atctttttgt tatcagactt gcttttcttg
75541  tttacaactg actgatacag aaaatggcac cagataataa attgaaaata ttctgcaggt
75601  ctcttctaag tcagagcact gatgataaag agtaggaccc aagaattaga atgagggtat
75661  atggtacata cacagtgttc atgatacccc acccccacct tcctattcta gacaagatgg
75721  tcttcctctt ttgtctgata aagttgcctt gcttgaaaat cccataccat caagagaatg
75781  aaaagaaaat ccatagactg aaagaaaaag tatttgcgga agacatattt gataaaagac
75841  tgttaaaaat acatcaaaaa cgccaaaaaa aatcaatgat aagtgaaaca gacaacccaa
75901  ctaaaacatg ggccaaggtt ttaacagaca gctcaccaaa aaaaatatac agatggcaaa
75961  taagcatata aaaagatgtt ccacatcgta tgtcatcagg gacatgcaaa ttgaaagaat
76021  gagataccac tacacaccta aaatgtttga aattcagaac actgatgaca ccaaatacca
76081  gttcaggtgt ggagcaccag gaattctcat tcattgctgg tagagaatgc aagatgatac
76141  agtcacttgg aagacacttt ggtgatttct cacaaaacta aacataatct taccatatga
76201  cctagaagtt gcagtctttg gtatttattc aaaggagtta aaaccttacg tccacacaaa
76261  aatgtgcaca cagatgttta tagctgcttt attcataatt gccaaaactt ggaagcaacc
76321  aagatatcct tcagtaggta aatagataac tatggaacac ccagacaatg agatatatt
76381  caatgctaaa gataaatgaa ctatgaagtc ataaaaagac atgcaggaaa cttaaatgca
76441  tattgctaag tgaaagaaga caataagaaa aggttacgta acatatgatt tcaactatat
76501  gacattctgg aaaaggcaaa actacacaga caataaaaag atcagtggtc accagggatt
76561  aaggggggagg gaggaataaa caggtggagc acagaggatt tttagaaggc accgaaacta
76621  ctctgtaaga tactataacg gtgaacacat gtcattatat ctttgtacaa actcataaaa
76681  tgtgtaacac caagagtgaa tcccaatgtg aactatggac tttggttaat aatgatgtgt
76741  caatgtgggt tcatcagttg tagccaatga actaccctag tggggatgtt gataatgagg
76801  aagactatgc atttgtgggg gcagagggtt atgaacctaa aattgctcta aaaaatgaaa
76861  tatttacaaa atgctgtacc tccttactga gacggacaca gggtaaaagg aagccaagtc
76921  tcctcatggc cctctcccata cctatcaagt aaacagggtt agatcccagc aggctcttcc
76981  aaggctaatt aaaagacaat gctgagcaaa aggataatac ataagaaaca ttgtaggagt
77041  ttgctagttt ggagcagaga tttggagatt agatgtgaga atgaattctg agagtgcttt
77101  accaaagaaa gtacatattt atttatcata atgattacct ctaccagaca gacttgtttc
77161  agtctgctgg ctggatctgt aagtgtgatt ttaatttctt tctctgctgg gtgactaaaa
77221  tctggtttta aagtgatcca cctaaacaat gttgatttat gagaattccc ttagtgtgtg
```

-continued

```
77281   gtctatgaac cctgaaggga ttgtgggtgt atgtaacaca tgagttaagt caataaataa
77341   gaacagactg gttatgaaga caagatcatt attgcacatg gctcagttgg tttcaaaggg
77401   aaaggaccat atctacaatc agactacacc cttattctaa gctattttaa atgagtgaca
77461   tcatgtgatg atgggtcagc acaaagtaac ccctctcctt aaaaagcaac tcaaagtaca
77521   agaaaccttg acttttatca attctatctt tatagtatat gaaggagaat gttttgtatg
77581   aaatgtgagt aatagtgata catgcttgtg tcacgtaaaa caagagatag gcatctaatt
77641   catgattaac taaatttttt tttcagagac aagttctcac tatgttgccc aggctggtct
77701   caaattcctg gactcaagta atcctcctcc caccttggcc tcccaaagtg ctgggattac
77761   aggtgtaagc cactgcaccc agtgaagtta actacattta tgtgcaagta taattagaaa
77821   gaattcttga aatgaataca ctgagagagg tttctgcttg atctagattt gcgtctcttc
77881   ttatcttgca cttgtacttg aagctggagc agtttttctt atagaaatca catactcctt
77941   acccagctgg tctgcctttc atccagctcc aagccaataa ttcattatt tatgccactt
78001   tggataacta tgccaaaccc aagaaattct tctgattaat tctatgcaaa tctgcttatt
78061   cttttattt ttcttgtttt atccacctat gaaccaatgt atctactctt tattatgtta
78121   gtttgttctt actgggtttt ggattatgca tttaattagg ccattttatc tttgtgttgt
78181   aattgtttaa tgtaaatgtt caaaatatat attcatgcct tgcatcttca tagatattga
78241   ttctgtaagt cattggtgga cccaggaatt tgtattttca accattactt cagatgatgc
78301   aagtggtctt tggaccatgc tttagaaata tttatacttt aggaaattat ttattcgata
78361   agaattattt gagcacctat taaggattat tcgctattct aggtgctagg ggtacacaat
78421   tggaaaaaat agatattgcc cttccagatc ttacagtgca gttggaggga acagacgcca
78481   gacacataga taaataacta atgggtcatg tagtgataag tactagagag aataataact
78541   cagcacaaag ggatataagg catgctaaaa ggattttat tatataaaga agttgacgaa
78601   gtcctcactg ataaagtgac attttgagta aagacctgaa taaagagaag gaaggagatg
78661   tgaaatttgg ggaaagagca ttcaggtaga aggtacagca taaatcttga aacagaggtg
78721   tactgggtgt gactgagtag aagcaaaaat atactgcaat aagagctcag taattgtgga
78781   ctgcttgtca gaaaaagtaa aattttagct gtctgtttag agaggaaaat gagaatagaa
78841   agaatggata aaaggtcata ggtaattta tatttcttct aaatcataag ccttactcac
78901   caagagtaag ttcatgtctc caaatccagt tttcagatgg tgcaggtatc cctcaagatc
78961   acccctttgaa tgggagagct aaatttgccc tgcatctcct ctgccgccca ctcagaagga
79021   attaattctg agcattttgt atctaaaggg caaagtagta actgcaagaa atgatatgaa
79081   atacatggct cctccattta aagaccttat aaactaattt tagagacaaa tatttcataa
79141   gatgaaatac attcaaaaga aaattatcat acttacaatt cccaaaacat agaatgtagt
79201   cttaatgttt aagttcagag aatatattg ttgattattc agtcatttat ttatacattc
79261   actcattaaa ttaatattac ttatgtgcct accaagcatg gggcaccata ttatgcagtg
79321   tgggatagga aaaaccaacc atacccaccc tctgttccaa gaaatctata caccaggacc
79381   tttctacatg tgcataaata actaacaaca accaagaatg tgctaagtgt catcctcgat
79441   gacaaggaca gtttgaaaat gaaataaatt acttgtaagt aggaatccag ccgatggtgg
79501   gatcatgaat gtgaatgcta tttgtttttt tttttcagat agtgtcttgc tctgtctcca
79561   ggctggagtg cagtggcgcg atctcagctc actgcaacat ctgcctcccg ggttcaagtg
79621   attcttctgc ctcagcctcc caagtagctg ggactacagg tgctcgccac catgctcgac
79681   taattttgt attttaata gagacgggt ttccccatgt tggccaggat ggtctcgatc
79741   gcttgacctc gtgatctgcc cgtctcggcc tcccaaagtg ctgggattac aggcgtgagc
79801   caccgtgacc ggcctgtgag tgctattaa ctagatcttg aagatacaga ttccaggcta
79861   aacatggcat atataacata tgcatttgtc tatacctact aaaatgggggg taaaagaata
79921   aaaaagtgta aactcctaaa aagaggatga gaaaggagat cacagcagaa acacaatgtc
79981   aacaactttg tagaagctga taattaggtg gtttagtggt aattgtctta gaagacctga
80041   gaaagcagaa aacttactca gcaatgctgg gagtcaacaa gcaaatagat tcatatggga
80101   gaaacccata aaggcataag aattggagga accagatcac tgaaggtgag gggtgtggca
80161   tggacttgaa agcaaaagca ttgtctgaga gactgtatta aaaacagcta gagccctgga
80221   tgcccaactt cttcaatgat agcaaatacc tgtttctccc ctaccctggc acaaggcagc
80281   aggtttgctc ctttgtaagg gtgaactaaa ggcaccctag gcttggggac accagcaaac
80341   ctgagaacag gagtaacgga gccgaattaa aatgggggcaa ctaaattaca gtctgcctgc
80401   tgacttatga gaccccccaac tcttaacccc tttcaataac cagaacattg gtagtcatgc
80461   ctatacagtc taaataagaa ttttgaggat ttatcatttg agaaacagtt ctggaaacac
80521   ctacattttc aaatgaagat tttaaaatga aaatctgcat ctgcacttga tcacccaaca
80581   gcaaaaccca cacatcgcca agctccacat attaacacag agctgtcaat tagcatggta
80641   gcgtctcact cttaagtagg aatggaccag gataactgaa tgtcctagga aagcttctga
80701   ttagagatac aaaaatataat acataattaa aaaaataaac agaatgaaaa cagtgtaggg
80761   aggagaggtt ctcagataac atataaaaga tattgcacc ttgaaacatg aacaggatta
80821   ctggaaaagg gagggtacaa agtacatgaa atagcagttg aaacttaaga atatggtata
80881   aattaaaaaa tttaaaaggc tgaaaggttg tggaaatttt tcagaaagta gaacaaaaat
80941   atatagaaat gaataaaaat atattaaaaa ggattatgta catgacttgt cagagtttag
81001   gggaattaat taataacaca tctgccttct cttcctgaat ttagaacaaa atgaaaaatg
81061   gacattgatg ccagaaagac ttaggtcaaa atgttcacct tgttgttagt gctgtttgaa
81121   gatcatggtt ttagttatgc aatcaaatca tcttgctttt tctgcatccc tgagaggatg
81181   tacctgtcag tcattgactc aattggacag ccacccactc aacacatgca cacacacaca
81241   cacccacaca cacacacaca cacagaaaat ggatctgtgc gtaggtcggg gtatggagaa
81301   gcagagcaga atgaatcttg aagacagact ggattcaacc agacagaagg gaagtggctg
81361   agtcaaacat gcttagttgc atctgtcaga tttaccaatc tgataaattc ctcttcctt
81421   ctcaaaactg aatgacagag ttgagaaaaa ctagaaacat tgttcccaga catttcctcc
81481   ctggtgaatg taataaaaat gcttgtactc tgtgaaaaat gcacattaga gaatcagtgt
81541   tccctcctcc ctcatcaaag ttcaaatctg aatagtggag ttctaccaag aaagaatttt
81601   aaagatagg cagggaatta gcaaagaaat tcacagtaaa aaaatattcc caaactaagg
81661   acaaactaag gacctggtga gtggccaggt attcagcaca atgaaaggca aagactaac
81721   gtctagttgt gttattcttg aattttcaga ctaatcagga taagatccca aagacttcca
81781   ganggggtgt gtgtgtgtgt gtgtgtgtgt gtgtgtaaat taaaattata ttggactagc
81841   agcaacacta gatgttaaaa ggtaaggggt aatgattgaa aaattctgaa gaaaaataat
81901   ttccaaccta gaattctatc tgcaaaaaat caatcaaatt agaataagac atttttgggt
81961   agttttatt ttccagaaac agcttcttag gaagctatta gagacaccag cttggggaca
```

-continued

```
82021  ccagctgggt agctggacaa attgacatag aggtgtctgg aagaagcggg aatccagcct
82081  atgataaata aatcctcaag ctaatcctca tatgccaagc ttagaattta tcactttta
82141  ggaggtcttt cttgattaaa ttgtctattt caatcaatct tcacatatag gctcctttct
82201  gtttattgca tttctaatct cccagcatct cagattaaag cttcgattac ttttaactcc
82261  ttcatctgtc ttatacccat gacttgtcct tgatttccac tgccacaatc ctctctccag
82321  tagccttcca gatgacccct caacttccaa ctcttctaat ctttaacccc tcattatcct
82381  gccataatat ttttattatg aatctctttg ctaattttct gccctatttt ttttattctt
82441  tcttgctgga actccactat tcagaggtta tgtgtcacca aaataagggga ttaagtagaa
82501  aaagaggaaa acatacaaga aacagaaaac ccacacaaga ggatgacagg aacttccaag
82561  gcaatggtga aggcagggct ctggatactg ctagaaaaca accaggattg aacaggcacc
82621  aggagccatg tctccaagaa aagagtaaga atgaaattgg taacatctgt cacacttagt
82681  atgacacaac tcactgagag gagatttta ggtaactata ggtcattaca tgattccacc
82741  atggctaatg tttatgcatt ttgaaagtgt agggccgggc acagtggctc acacctataa
82801  tccgagcatt ttgggaggcc aaggcagaaa gatcacttga gtccaggagt ttgagacctg
82861  cctgggcaac atagcaagac gtcatctcta caagaaatac aaaaaattag ccggctgagg
82921  tggcatctgc ctatagtccc agctactctg gcgactgaag tgggaggatc acctgaacct
82981  gggaggtcga ggctgcagtg agctgtgatc acaccactgc ataccagcct aggcaacaga
83041  atgagacact atctcaacaa caacaacaaa aaaagtgtaa accttgaatg ctgatctagc
83101  ccaaagtgtg atatgtgagt atctgaaagg tgaggcatac gtttttctct tttgctcact
83161  tgcttgctct ctgttattaa gggttaaaaa gatcttattt tcttatgata agtaagaaat
83221  aatatttaaa actgaaaaat tcaaatagag taaagctcat tattagaaaa atgggcaaat
83281  aggtcaggca tggtggctca tgcctgtaat cccagcattt tgggaggcca aggtgccgga
83341  tcacttgagg tcaggagttt aagaccagcc tgggcaacat ggcaaaactc catctctaca
83401  aaaaatacaa aaaaaaaaaa aaaaaaagaa agaaaaatag ctgggcgtgg tggcgggcgc
83461  ctgtaatctc acctacttgg gaggctgagg tgggagaatc gcttaactg gggaggtgga
83521  gtttgcagtg agttgagatg tgccactgt attccagcct gggcgacaga gtgagactct
83581  gtctttaaaa aaaaaaagaa aagaaaagaa aataaaagaa aaagaaaaaa aaacaatgaa
83641  aaatgggcaa atagaagaaa acattgaaat attaagagcc tgttgcttca ggagaacagg
83701  aattgagggt gaggagtgat gaggaagaca actgctattt cacattgcaa actcatagta
83761  ttatttact ttttaaccctt gaacatatat gtatttaata aaaataaaaa ataaagaata
83821  gaaggtatct taatatttat aaatgattat gaagaacatt agagggtat gcattgtttg
83881  aaaggtgaaa aacacacatc attgattatt gcagcacagc atgcataaag tggtgtaatg
83941  gcaaatcagg ctgtaaaagt aacttggatt caggatatgg aaatcttaaa tactaggtta
84001  agaagtctga tcaaacaaag attttttagg agggatgtgc aatgattgga gcagcactt
84061  agaacatttc ttatggcgac aaaatgggga attaaaaaag agcctggtac ttgcagatgt
84121  tttcttgtgg aaaaataaat aaataaataa ataaaagcca cgaagttagg aggtcatctg
84181  gaagtctgga aggctactgg agagaggctg agaggatcag ctgtttagtg acagtggaaa
84241  tcaagaacaa ggcatgggta taaaaggaaa gagttaaaag aaactgaagc tttcatctga
84301  gatgctggga gattagaaat gcaattaaca gaaaggggcc cctatgtgtg gactgattga
84361  aatagatgat ttaattaaga aagacctcct aaacatggta aattttaagc ttggcttgta
84421  aggattagct tgaggattta ttcatcctag gctggattcc tgcctcttcc agtcacctct
84481  aggtcaattt gaccagccac tcatctgcaa aatgtcatac aactacctga attcatggct
84541  aggaatggtt tgttgccgct ggtgaatgac caagggcagg gaccaggaca aatatagagg
84601  cagaggcagt ggcaaaggaa tatgcctcca caaacagaga agacaataag ctacatttga
84661  cagaaagtaa atgcattaac atatagaatg gcagaggaga aaagcaaaac aagatccttc
84721  ccgctcaaaa atattctcca tattttgctt attattcatt gtttatattg tttgattctc
84781  agattgacct tcagagtgtt ggctttttaga gaattgatgt ttagtgactt gacttgctct
84841  ctcatgcctt ccttttttcct agacaactgg atcttttgga cataacttgg gattgagatg
84901  aacaagtgac agtcattgat ttggcataat gcttcactga ggcatcttac ctttgctgat
84961  tttatccagc attcagaacc ttcattttct ctctcaaaat aaaataaaat aaaataaaac
85021  taaatccaag gctatttagg ctgtgtgtgag tagaaagaga catcactaga gcataccctct
85081  tccatttgag cttgtattaa gcaggcattg tcggctattg aagtctagat aggagaaaag
85141  tctcaggaga aagtcctgag agatgggagc aggtacgatc aggccaaggc ttaaataaga
85201  gccacaaaag gtcttaatac agcaggtagg gtgaatgtaa ttctgaaggc agagaacatt
85261  ctctcactcc aagtctgatt aaaggcagtt aaaaccagtt cttacccagt atataagtga
85321  tcccttagag actgtcactg tgagtgaatc tccctggaga aacatttaac ccagtcttga
85381  atttaccatt ttggttatga ttatagattg catcagtttt tccactcatt aatctcatct
85441  taatagcaag ggaaggcaga tttgccccat caatttcag aaagcaaata aatattgtgt
85501  taataataat aatgataata atagcttaat atatcctaga cactttacat gaattatgta
85561  atgctttcta acaactcctt gaggtggaca ctattaattg tctttttcat tgaggtattt
85621  gaaacttaaa gaaggtaagt aatttgtcca aggtttgcaa ggctcacaca tttccagaat
85681  tcaaacactg agtgctttgc acacgttatg agtaaacaat tgtttttctt atgtctatag
85741  tatttgggt atgtgcttat ttggtctttt caatcatatt aaaagcttct tgaggacaag
85801  attcatgttc ttttggtcag gtgcaatggc tcatgcctgt aatcccagaa ctttgggaag
85861  ccacagcagg tggatcactt gagatcagga atttgagacc agcctggcca acatagtgaa
85921  ctccatctct actaaaaata caaaaaaatt aactgggcgt ggtgttattt gcctgtagtc
85981  ccagatactt gggaggctga ggcagaagaa tagcttgaac ccgggaggcg gaggttgcag
86041  tgagctgaga tcacgcact ccagcctggg cgacagaaca agactgtctc caaaaaaaa
86101  aaaaaaaga ttcatgatct ttttcaactg gcttatgcac aatgccaatc aaattaaggt
86161  cctactttta tttcttaagc aggctggttt aattttaact cattccatca catgaagaat
86221  atctcaaagt gaatcactcc tttggacaag gtagaacaga agcaatttaa acagtgcttt
86281  aaaggccaaa tccttgttta attgacaata cttttacctc aacattttc atccacaaag
86341  ctcccttct aagttgccct tcagaagctg ttagatgctg tcactaagtt gttcagagct
86401  atgtcacaca gttcccccctt cttcctactt gtaaatctaa acaatcaaga tgaacggagt
86461  atgaatccaa aacagaagca gatatacaca gcccaagaga tagacaagat gcatatacag
86521  cttgttcgta tggcctgttc attcttcatg gagaacctcc tacatagata tctaacattt
86581  tatttctat ttaacttctc caatactaaa atggctaaat agctgtttat taggctgcta
86641  acttctcctc acagaaaatg gaaagttaac tcaggtttcc taacccacag ggctaaggtt
86701  tgagagcagt ctaaatagct taattttgtt tagctgtgtg gccagaaact tcactcttga
```

-continued

```
86761  ctctagtaaa atagcaggct ttatacgggt ggctcacact tgtaatccca gcactttggg
86821  aagtcgaggt gggagtttga gaccaacgtt gacaacatag caaaacccca tctctaaacg
86881  caattaaaaa atacactaaa cataaaagtc acaaattctg actggtgaaa tacagagcgc
86941  tacggaagca gtcatatttc agaaaaaaac ctaaacatg ccagggcttt ccatgttctg
87001  ggaatacaat aaacaaaaac aagttcctat cctcagaggt attttgctga gagttgtttt
87061  cctgggaaaa atatcattta tctaatacta aagaatatga acgaagtaca taacagcaga
87121  gcatatgtga aggtatgagg tggaatgcta ttgggtctgg aattttaaga gttcttggtc
87181  tcactgactt caagaaggaa gccacagacc ctcatggtga gtgttacacc tcctaaggtg
87241  gcacatctgg agtttgttcc ttcttatact caaatgtgtc cagagtttct ttctggtggg
87301  tttgtggtct tgctggttca ggagtgaagc tgcagacctt cgcggtgagt gttacagctc
87361  ttaaggctgc gcattgggcg ttgtttgttc ctccctggtgg gctcgtggtc tcactggctt
87421  caggagtgaa cttgcagacc ttcccccgtga gtgttacagc tcataaagat agtgtggact
87481  caagaaacga acaacaagat ttatcgcaaa aaacaaaaca acaagactcc cacgtagcgg
87541  aaggagacct gagcggttg ccactgttgg ctcgggcagc ctgctttat tgtcttatct
87601  ggctccaccc acatcctgct gattggtaga gccgagtggt ctgttttgac agggcgctga
87661  ttggtgcgtt tacaatccct gagctagaca caaaggttct ccatgtcccc acttagatta
87721  gctagataca gagtattcac acaaaggttc tccaaggccc caccagagta gctagataca
87781  gagtgtcgat tggtgcattc acaaaccctg agctagacac agggtgctga ttggtgtgtt
87841  tacaaaccctt gagctagata cagagtgccg attggtgtat ttacaatccc tgagctagac
87901  ataaaggttc tccacgtccc caccagactc aggagtccaa ctggcttcac ccagtggatc
87961  ccgcactggg gctgcaggtg gagttgcctg ccagtcccgc gccatgcgct cgcacttctc
88021  agcctttggg tgatggatgg gactgggcgc cgtggagcag cgggcggcgc tcgtcgggga
88081  ggctcgggct gcacaggagc ccacggaggc gggggaaggc tcaggcatgg cgggctgcag
88141  tcccgaggcc tgtcccgcgg gaaggcagct aaggcccggc gagaaatcga gcgcagcacc
88201  ggtgagctgg cactgctggg gaacccagta cacctccgc agccgctggc ccggtgcta
88261  agtccctcat tgtccgggc cggcagggcc ggccggttgc tccgagtgcg gggccccgcca
88321  agcccacgtc tccccggaac tccagctggc ccgcaagcgc cgcacgcagc cccggttccc
88381  gctcacgcct ctccctccac acctccctgc aagctgaggg agtgggctcc ggccttggcc
88441  agccccgaaa gggctccca cagtgcagcg gtgggctgaa gggctcgtca agtgccgcca
88501  aagtgggagc ccaggcagag gcggcgccga gagcgagcga gggctctgag gactgccagc
88561  acgctgtcac ctctcactat atctggttga agtgactgct atgagcttgt gagctcgttt
88621  cagagacttg actggatcaa gcaggagagg agctcagaat aagtgatttg aagaggaaac
88681  actatagaca ctaactctgg aagacaagca gatttcttct gtgatacttg gaatgagtga
88741  tatgattgtc cacattaaaa cagtagaaaa taatcctgcc ttttaaaaac atacacttaa
88801  atatgttgat taggaagaaa gagtactttg gttaagtata aaataataga aagattttgtgg
88861  caagatgatt gctgtaatat acctgctgag tcttctgaa tcactccatt aaaaaagcat
88921  aacaattagg atagaaaacc aaccaaacaa aatcccatca gcaatatcct caacaaaatg
88981  aggtaattaa gtattctcac aaactgtcaa atatgactga gtaggaacta ctcaccaaca
89041  aatgcaaggt acaacaactg taagagagga aatgaggaga aaggaaatga acgtctgatg
89101  gccctcagaa ctggaaaatc cagaaattcg cctgctaaaa ggaggagagg gctccaccta
89161  agaatagaag ctcagcaaat tgatctaatt acagtgtctg aaagggagag tctttacagg
89221  ttctgattca taagtaagtg caaggagccc aggttgtctg ggccctgtga acccttgaaa
89281  tgaaggaatt ttctgtagta aaaacccaca ccatggcagg gcacaggggc tcaggcctgt
89341  aatcccagca ctttgggagg ctgaggtggg cagatcactt gaggtaggag ttctagacca
89401  gcctggccaa catggtgaaa ccccgtctct actaaaatac aaaaattagc caggagtggt
89461  ggtgcgcacc tgtaatccca gctactcggg aggctgaggc aggagaagca cttgaaccag
89521  agaggcagag gctgcagtga gccgagacag cgccactgca ctccagcctg ggcaacagag
89581  agagactcca tctcaaaaaa caaaacaatc ccacattcac attaaacaac taagaacaaa
89641  gaaaaaagac gtaaaagtag acctaaataa atggacattc attctatgct cttggattgg
89701  tcatcataaa tatatcactt ttctttataa attaatataa attatattaa atttataaat
89761  ttaatccagt atcagtaaat aaaaagtact actcatttag tcacaggaac ctaaacagag
89821  cccaactatc ttctagagtt ggggagttag cattcaagga agccaaagta actaaaattc
89881  acgggcaaag taccaaggag aagagggcta cagagaggga gagttctgaa gatctgcaga
89941  ggttctttgg caattagaaa gactttttagt tgagttctat gtcccttgac ataccctcat
90001  catcgtgttg tttctgagca cttttcactt ttctggcact acaagattct ccaggctcat
90061  cttgtatatt tcctacccag tcctacaatt caccacttct ccaaggagcc ctggttcctt
90121  ttattggaaa acagttttag aaaccaagat ctgggcaata gatgtcctta ttggtaatgg
90181  gatattgttg cctttaggcc ctctcagctg acagaccaac aaaatacatg catgtgtgtt
90241  tcatgtgtac atacataata tgtatacata ttatatacac acaaatatct ataaatatat
90301  atccattgt atctatatta agctaaattt gagttcatac tgatatctcc aattttaatc
90361  cattaccacc tgtatcattc tagcctttctt cccttgcttg tctataaaat ttccctccca
90421  aagtgagaag cctggctctc accatctagc attcatttat ttagttgttc aattccagta
90481  cccatgtaga ggggtttcag aattttttaat ccatactccc ctggtaaacg acttaatcaa
90541  ctagagtaca atgttatata cagttctttt tgactttagt cttgcagact ctactatatt
90601  tccaaattta cttagttcag cagcttcta ctctacttcc ttcaatgaag ttgttttata
90661  gatttgtaac acaggtatat tcttttgtca cagtatgagt tccatcctgg gatgctgata
90721  ggagaatctt tttaataggt gatgtataag aaaaccgttt gctcccaagg cctattattt
90781  tggttacttt ttcagcaagt tccagcatat gtctagtttt ggggcaaata atttgtgatt
90841  atcagtaagt tttgaagtat tgagactatc ggatgcaact tttaaaatat gttaggtcaa
90901  ctattccata gtatgtaaaa tcattacaac tgtataagaa aacagctgtg gccgggcgca
90961  gtgtctcatg cctgtaatcc cagcactttg ggaggccgag gcgggtggat cacgaggtca
91021  ggagattgag accatcctgg ctaacacggt gagacccat ctctactaaa aaacaaaaa
91081  aaagtacaaa aaaagaaaa cagttgcaaa atcgtgtgga ttgtcactg cgttttgaa
91141  taaataaaaa taatgaaatt ggccactatg atcatatgca gccagaatct attacattat
91201  gatgtgctac aattattttc tgaatacaca gtgttccact gtcaatgaca gttgtttgat
91261  gttttcttca ttgttttttct attctacaaa taatttata tccagatgta gtctttgat
91321  agcagtttga gattcagaaa tttcacaaaa agcaaataaa acagaagcat aattctatct
91381  gttaaacaga tatgttgcta aacttagaaa tgctttgagg tgtttctaca tatccaaata
91441  cttggtggcc ataatcaaaa gcacactgaa tgcaccaaaa tgcatattta tgaaccaaat
```

-continued

```
91501  tttttgtgca tagcataatt taattcagag aagagctttt aggcatgtaa tttaatcatg
91561  atgatcctga tttttattat tgtgtaaatt tctatatatg tttgctacct aattagaatt
91621  atatgaggct aacattttta tgcactctct taaatatttt atttaactgt tgatctattt
91681  ccctaattat tttaaaattc tgtattgtt ctgtacatat atgaatagaa aaaaagatag
91741  ttttttttta cttgctagta gaagttagta aattgttaag cttttgggatt tttatcataa
91801  aatgaaataa gagcttaaag tgtggtttaa agaacgaaac acttggcccc aaaaaagttt
91861  gttcaaataa taataataat gctgaccctt attgaaagca tttttgttaa aaagtaattt
91921  atttgtattt attcttgaaa acattcttat aacaattcca ttatcattaa acaaacaagg
91981  gaagtgaagc ccagtgaagt tatgtagttt gccaaaacta catagttatt aaagaggaca
92041  gctgagggat gtacgcaggc attctgatat gacttcgaat ggatccctgt ccagggtcgg
92101  gatctaatga ggggcagcat gtaatagggt gcagcaaagg taaagttgaa agtcaattca
92161  ctgtttaagg atgttaccta gggttgttag aataacatgg cgatcagagt catcctaaga
92221  tcactctca taaaagataa aggaaaacaa aaaatagatc tgctagtgcc ttataagaag
92281  ggcatagaaa tcttggtttc tactcataca ctcctcgtct tctttgtttg cttaattttt
92341  ctccatagaa ttcaccacaa tctgacataa tatttattt atgtttttat ctattcatta
92401  tcttccatac tcttctagat aataaggtcc atgagggtaa gattttttg gggtggaggg
92461  atggtgaggg gttggcattt attaaactgc cttaccccctg gcacttggag cagtaccttg
92521  cacatagaag gcagtcaata cgtctgtgtt gaattaacgg tcaaaataat gagatatgca
92581  aacacatgca aatgaaacta atcaagtaag gttggcccct attagctttg gatgtttgaa
92641  aattttcttt gatttgctct attccttcag cacttttgtt ccagccccag agatgcacca
92701  gcctctggca aatatagctt ctaactggct gtcactataa agtgttccta gttcatttta
92761  taagagggtt aacagggttt taaaaattat tttcctcctg ttctcttcaa aaggcaagta
92821  ggaccctgca aatatgctaa tttcccatct gttttatggt agacttatta atttatggta
92881  gtatattaat ttatatgaac tcttctgaaa tcagccaaag agctggacat tattggattc
92941  tagggatgac ataatctaca tctacatagg ttttgaatct gtgcatacac agagaagctc
93001  aataaatatt tgttggaaaa aaagatctgc tgccagaatt taattcaaaa cttcacaaag
93061  ttctcatttt cttctttgag cctgggaatt ttgccttcac ataacctata attgattgca
93121  ttagaacttg cagtatagtg aatacagtgg aagatttagg tacagtcgag gttaatgaag
93181  aactggcttt ctagtgaaaa tgaaaacctt aaggctctac tgggattcga acccaggatc
93241  tcctgtttac aagacaggcg ctttaaccaa ctaagccata gagcctacat gtgcagtgaa
93301  gttgcctatt gaatctattc ctgcttttaa gtaaaagatt cttggcatag cgtctctaca
93361  gtctgcaaca gtttgccgtg agagaagggg caaactccaa aaatacgttt tgcttactta
93421  gatgcactgc ggaactaata caaacgaaaa aattttcggg cagcttaaat gttaggacca
93481  ttaatgcttc agctagtcca aggataacca caagtaaaag tcaaggctac ttagtttgtc
93541  caaatgtgat aaagtttcct aaaattaaat tttgcaggtg ctactcttta tcattttaat
93601  gattcgtcgt tccaatgtcc taagggaaaa cctctaacaa aagaagtcca caagagactc
93661  gtaggctacc gagttgggcg tatggtgttc tgacagtcat ttgcactcag gaggcagcta
93721  tttggaggac cggagcgtca accccttccc aatgtgagca tcgctctaga gattgtcttc
93781  tgggcttatt tttcttaga cttgatctca gctcgctctc aggaccagtc aggttctatt
93841  ttataatatc ttacttctct gggctgcact tggcaagaca ggggaatcgg tttgaatgtg
93901  tctctgggtt aggaaaggtt aatacattta gagctgatta aaggaaactt ccgaacgttc
93961  tctggaatct cagtcttgtt tccaaaatga attatttgag caattaattc tgaagtttct
94021  accaagattt ataattacag agctcagggc gaaaatcaga aatcaccttc atttctttgc
94081  cacaaaagca ataaggaaaa ttatcctggg attagatgg gaattccttt ggattgctag
94141  ataaatttta gggagaactg ataaactttt aatccataca tatggcataa cattcaattt
94201  attcttttat taaatttatt cctataaatt tgatgttttat gttattataa attatactttt
94261  aaaatttttt atttctactt tttttttttt ttttggagac aagatcttac tctgtcaccc
94321  aggctggagt gcaatagcgc gatctcggct cactgcaacc tctgcctccc aggtcaaga
94381  gattcttgtg cctcagcctc ccgagtagct gggattacag gcacatgcca ccacgcccag
94441  ctaattttt tgtattttt ggtagagacg gagtttcacc atgctgctca ggccggtctc
94501  gaactcctga cctcaagtga tccgcccgcc ttggcctccc atagtgctag gattacaggc
94561  gtgagccacc gcgcccagcc cttgtttaca gctggtgtt aaaagtacaa ttcatttta
94621  tatttaccct gcataaagac accttattaa atttagttat taattctaat agtttgtaga
94681  ttttgaatct tccacagaca caattttaat aaaggattac attttattaga ttttaaaaat
94741  aaaggaaatc accttcattt ctatctatgc ctgaaatgag gttgacagca gacacaataa
94801  aatctgttgt caccagtcag tgcaactaat ttaataataa aagcttaaat tagttacaac
94861  tttgtattac ttttagaaaa ttaaaaataa caaatatttg tatttataaa aacattaaca
94921  gggattgcta atatgtttga ggctgactct gctgcttcat aaatagaata gtaaacaaca
94981  gacatactga attcccacac ttgaatcttc tgtcaatgta tgccttgagt aaatgacatg
95041  ctcaggtatt atgagagagt gaacaaacca ttgttaggcc accaaaatag ttttttttct
95101  ccaatggaaa cactcaaaag ttgagagaaa aaaatggtta agactgtaat cattggcaac
95161  ttaaatcaat agaaatggc agattattca aaacatgtgt tgggctaatt ggacagccac
95221  ttaggaaaag aaaagcttaa agctcatgaga ctaaaataaa ttccaaatac aagcaaattg
95281  taaaagtaaa gaatgaaaca aacccacagt tataattact agaaattcca agacagaaat
95341  tttatataac tttggtacag aaaactaatt tttacacaa aattcagaga caatgagagt
95401  ttaacataat tcactgcatt aaacaacatt taaaaaattc cactgggatg taccctcatc
95461  ccctcaaaaa aggcataaac acagtgacaa aacatcaagt aaaactgggg gggaaaatat
95521  ttgtaactta tgtttaaag agttaattt attcatttct atctgttgcc tgagataagg
95581  ttgatagcag acacaataaa atctgttgtt cccagttggt gcaaccaatt taataataaa
95641  agcaatatag aagtaagaag taaaagaagt ttaaaaaatg aaactataga aatacagtga
95701  gataatgtct ttaacatatc agattggcaa acaacagcaa aacaaaaaca gttgttttgtg
95761  gtagtgtgcc gaatagcact taaagatgtt gaattagttc tctgtagctt ctgtaacaaa
95821  ttacagtacc acaaacttga tggcctaaaa taagtgactt cttttctcac agttctggag
95881  gccaaaagtc caaactcagt atcactggtt tgaaatcaag gtgttggcag ggctatgctc
95941  cctccggagg ctctagggaa gaatatgtcc ttaccttttc ccagcctctg gtggctgctc
96001  gcattccttg gctggtggtg gcattgcttc tatctgtgtc cgtgtggtca cattgtcttc
96061  ttctcttctg taactgtata atctccctgt gcctctccct attaaaggca cttgtgatgg
96121  tatttgagct ccacttggat aatccaggat aatttcttca tctttaactt tttctccgaa
96181  gacccccctt ttgggggtct gtgcaaagta aggtaatatt cagagattcc aagaattaga
```

-continued

```
 96241   gcatggatat cttttggggc attttcatt caatcacagg cactgacatt cttattcctc
 96301   catctacaat ctatgtgatt tagacgactg tgattatgtg attaatcggt cacaactcca
 96361   attttctttt ctgtaaaatg tggattatat gaacatcctt atatattatt gagattattc
 96421   tatgactcaa tatatgtaaa gaatttatga caatatctgg ggcttagttg gagctaaatg
 96481   actgataatt gtcattatta caatgttctg tgctggtcag ggtgttgagg aaacaggtcc
 96541   tttctgggcc ctataggaga ataaattagt aatatttagg gaaggagaat aaggcaagag
 96601   ccaccaaaat catcatcaca tacatatgat ttgatttagc gattgcattc ttagaacgtt
 96661   ttctaatccc aggcacttat taaatgcgga tatacaagtt aatttattgc aacattattt
 96721   atattgttaa aaatggctgc tgaaataaat tcagatacat ttataaaact aaatgctata
 96781   cagacaaaac aaagagggaa gaggctcttt ctttgttgac atggaaattg ctgcaacata
 96841   cataaagtga aaaaggcaag gtgtaataga atgggtttgg aaagcgtatt tatagtgaaa
 96901   aaactatatg caaagaatat gcctttaata gaactccaga ttttaatatg gttggttgcc
 96961   tgagggtcca gaattgggtg tccggcagga tggggtgggg gcacaaatag actgtcatta
 97021   tgtatgtatt cttgaatttt tgtaattttg aatcatgtga gttgtacttt ttgtatgagc
 97081   atttttaaaa cataaaaagg aacatactcc cttggagagg aggtcttaga aataactgat
 97141   ggcagtctga ttttgcagct gctatttggt tttcaaccta ccattatcag gattaaatac
 97201   ctaccttgtg ctcgcagtgg aaaatgtttt tcttgcaaat ctcaatgagc tttagatatc
 97261   cctactaatt ttgcaataaa cctggcagcg gtgggattca aacccacgcc cccgaagaga
 97321   ctggagcctt aatccagcgt cttagaccac tcggccacgc taccacgcta gtccagtatt
 97381   aggactcatc ttaatgattt aaaagcacaca agattattct gcgtcttact attttttttt
 97441   ctcagagcat ttctacacaa atgattccgt agccggtctca actaccgata aaatctacaa
 97501   ataggttcct agtcccagtc ctttgtcctg cagctgagat ttgcatttgt ctcccatgct
 97561   gtttctaata cctgagagta aagggacagg aagccagtac ctaatatcca acaaatccca
 97621   agagaatcgg ttcttaagaa catgattaga aatcccacgc ctaggccgac gcagcacggg
 97681   gactctgagg actctgagat cgagtctcca gtttgtcagc tgccgtttggg ggtctggagc
 97741   aagatgttat ttttgatgtt tgcaaccaga aaacagagga gctgtcatcc ccatccaccc
 97801   ggaactcgcg tcttggttta tgtgtctgtg cgtgattccc tcttgtgaaa gaggtggaaa
 97861   gaactatgca aacagacctg cttttttagc tgaatgtgtt catgacctta gtttttaaag
 97921   ttcagggcga ggaccagttt gtatttggtg cggagtatca catcctctcc ggaccctaac
 97981   aggatgtgtc gcctgctcgc tccaacccca caaacgccgt ctgggctggc actccgactt
 98041   cttcttccct gttgcagccc caacgccgct catcttctta tttagtccca cctgtcccat
 98101   tagatgctga ccctttttaa aagagccaca gttggaatat ttcaaatgcc agcagctcca
 98161   cttaatagct gcagggtcat tggcaagtca cttaagctca ctgatctcta ctttcctcat
 98221   atgtaaaacc gagacaataa aacttgcctt taaaaattac agcagaatgt tttgatacaa
 98281   tggattttgg ggactcgggg gaaagggtgg gggagggttg agggataaaa gactacacat
 98341   tgggtacaat gtacactgct ctggtgacag atgcaccaaa gtctcagcaa tcaccgctaa
 98401   ataacctact catgtaacca aacaccaccg ttcccccaa aacctattga aataaaagag
 98461   ttaaaaaact atagcagaat ttttattttt agcaaatgca tgtaaattgc ttaaaacagc
 98521   acctggctca taatagcac tcagtgaagt ttactatcag tattggtatc atttattagc
 98581   atttactgaa cttttatat caagtgctca gtctcatgaa tgacagtgag atctctcatt
 98641   ttacagttag tgaagtttt taaagtaaca tatttacaag acagtcgagt gaattatttt
 98701   tcttaagtta agatggcacg tggaaaattt acacctcaac cctacaattt caaacgtcgg
 98761   acaattttca ctttgtcaga tcgctttacc ttgtatattg tttctcccct ctcaatcatt
 98821   tcacctcatc tcttcccccct tgtctcacct ctatttacac tattctgggg ctctagacct
 98881   gtaaagatcc ttcaggtgac atggttaggg acactgattt taaggagaac tttggcaggc
 98941   aaggaggtgt agcttcagac ccaggtaaac ctgcagctat gatctcatta gaacttatct
 99001   gctttctgcg tctgtcattg cttccggctg cgaatcttca ggctgtggac ccagctcagt
 99061   cccttgcgt ctatatgtca ccttctagtt acataattta cacatgttgt gctgggggt
 99121   agtgtgcaat ctaatgaagt ctaacatctc ccaggagaaa gtggtgttta aggcacagtg
 99181   ggaaaatcca ctgtgttgta catttattta aacaaggggga aagtcccgag atgattttg
 99241   caagtcatac gacatactg gaaggacagt aaacacatga catgccatac attctcattt
 99301   tacactctat ttttaaaatc taacttttca gaaagttcac ataaacttga aagagtataa
 99361   ttaacggatt tgctaagaca gcagtgcctt cttagccctg gaggcagcac atcagtctca
 99421   taatctgaag gtcccgagct tgaacctcag agagggcatg gtgattttgt actttccata
 99481   tacttttgct tgagaaagaa atatcccacc cattaaactt ttcggtatga aatctggatt
 99541   cctggatcac tgacagacaa cacaactgaa aaatgaggct gcagtccctc aagaaccta
 99601   ccaacttcct ttgtgagcta gatgctattt taatgccctg actgcagtat tatacaatac
 99661   cacaatctac accaaatacc ataaatctgt atcagttgcc tatggcagct tttgaaaatt
 99721   accatgaatt ttgtggctta aaataataca aatgcattat cttaaattt tggggacag
 99781   aagtttaaaa tggtgtcttag ggagctataa tcaacatgtg gcagagctga tttccttctg
 99841   gaggtctag ggaagaatcc atccttgcc acattgctcg gctcatggct gcatcattga
 99901   tctctgcttc tgctgttaca tcttctccaa ctctggggag tctcatgcag cctggttgat
 99961   gcatctgttt ggtgacgggg agtgcaaact caatgtcacc cgactggccg agtttgagaa
100021   aactgaccat aactctggtg ttgcagctct agttttgcct tcacccaatg acagaaccag
100081   caggacaggg atcgagataa acctatccca ttcttagttt gtgttgatag gaacaagagg
100141   gctgtattcc ctactgcagg aggcttccc aagaggaaga accctctaga aaactgtcca
100201   tgaagtcata actgtcttgc gtgggaaggc aatagacagg tagaaatagg atcctgctcc
100261   ccgacaagat gtggacaacg tggtcccgtc ccagtgacct tggaggcttt tatgagacaa
100321   gatcctcctc aaaggcaggt cctcctgccc cgtcagaaat ggaccaaagg gcccaccca
100381   tagcgcatga gcacctgcct gccatggatc atggtgtcac tcctgaagcc ctccaatgct
100441   atcggcttac ctctaccctt gcgagaaatc aggattcttg tcttttaaac ctcagtgtcc
100501   aaaaacccca tacacatctg aaccccccact cctttctccc cttctaccct tgctggtatg
100561   tagggtcact tgaccatagc aaaaaccagg agaccgtggc cctaccccta attgttcttt
100621   ctgagggag taaagtcagg acacatgcaa gaagagtggt cctccacccc aagggtggcc
100681   acgctttgac taagagtgga tgaggaccct ctgcccaatg tgctgaactc tgtgaggtac
100741   tgatggccgt gcaggtact ccaacagcaa ctccctgcta tttattttata gactcatggg
100801   ctgttataaa tgggctagcc atatggtcca gtgactgttg gacagataat taagcagcca
100861   ggccaacatg gtgaaatcaa aggaaatata ctaatagaga gatattccct ttgcatggtt
100921   aggaggactc aatattatca agatgtcaat ttttcccaat ttgatctata gatacaacat
```

-continued

```
100981  aatcccaatc aacatctcag ccagttattt gtggatattg acaaatagat cctgaagtat
101041  atatggaaag gcaaaagatg cagaataact acacaacatt aaagaagaac aaaattgaaa
101101  tactggagaa acacctctgc catgtgttca gatatctatt cagactctaa tctgaccaag
101161  gcaccttctt cacagcccag ataatgcagc aatgggcatg ttcctatggc gtacaatgac
101221  cttgatttgc tccatcactt ccaggcaccc agagtgggag gggtggtgtt aaagcactag
101281  aatgaataac tcaagcaaca actacaaaaa ggaccatcag gaaggacaac tcaacgaagg
101341  gtggtactcc tgcttaatga aagtatttgg accttaaatt gtgccctcca gtgaaaggga
101401  aacatggcat tgcaatgcct gctgggcaat gctgactttg gaagcatggt tgcctgacgt
101461  gtctacgcct gaggaatccc tatctcagta tatccaacca cagtgtttgg aggtcaaggc
101521  tgtagggagc cacaattgag ccactgcact ccagcctggg tgacagagcg agaccctgtc
101581  tcaaaaaaaa caagcaagca acaacaacaa aaacaaacaa acaaaaaact aaacaatct
101641  atgcagtagg ttgacatcct ggactattgc ttctggtggt agactgtgtt acactcttg
101701  ttatcctcca cccagtgaca atggtatttc tctcatttgt ttaagtcttc tttacttcct
101761  ctcagttatc ttttgtagtt tttcagtgtg caggtcttgc acacatttt taacttacct
101821  ttaagtattt gatagttttg aagctcttgt aaacggtatc tttttgttt aaacatccaa
101881  tttgtcttc ctttgaatgt ttcactaact ttggattctt ggagtttaat cccaggaatg
101941  tcctgctttg tcatgatgtg ttatcatttt ataaatggtt gaatttgatt tgctgaattt
102001  ttaaggattt tttttcttct taggaggaac actggtttgc agtttcgttc cttgtatggc
102061  tttgtctggt tttggtatta gggtaatgct ggcctgataa gtgagttcag atgtgtggcc
102121  tcctttttg ctttctgaaa taatttgtgt aaaattgata ttatttattg cttaaaagt
102181  tggtagaatt tactttggag ccatctgggc cagatttgt ttctttgtaa gaatgttata
102241  aagcatggat ttaatttagt taatcgatgt aggtctattt aggttatcta tttcttcttg
102301  aatacacttt ttgtgtcttt caaggagttt ttccatttca tctatgatgt caaagttatt
102361  ggtaaaatac attcataaca tttccttgtg tccttttgtt atttgtagaa gctctagtga
102421  tatctactcc ttcattttgtt tcttttgttt ttctctgtta atatatttt tattttaa
102481  atatagagat ggggtctcgg tatgttctc aggaattagt tcgtgagcca ccatgcccag
102541  gctactgtca tttgtgatat ttgtgtctct tctctcttt tttcctgaag agtatggcta
102601  gaaatgtatc aattttgtta atcttttcaa agaaccagct tttgacgtta ttgttttcc
102661  ttattgttt tcagttttct atttcattgg catttactct agtattttcc tcttctgcct
102721  gctttggatt taatttgctt atcttttta ctaagtttct aaggcagaag atgagaacat
102781  tgattagaga catttcttcc tttctaatat aaatgtttaa tgctaaaatt atcccactaa
102841  gtatggtttt tgttgcatcc cacaaattt gatatgttgt attttcagtt ttattcagtt
102901  taaagtgttt tctaatttct ctgtgatttc ttctttgact tatgggttat tagaactcca
102961  tggtttaatc tccagatatg tgtggctttc tcaaatatct ccaaatgtta ttgatgttca
103021  ggttattttg ctgtgtacaa gaaaaaactc tctgtgattt taatcctttc aatgattatg
103081  catatatata tatatacaca cacatacaca cattgaaaga atgtgtatat atatatattg
103141  tcttctatgt tatcatatat gtgtgcagtc actcagataa agatgtggac ttcatagttt
103201  taaaacatgc ctgaactttt tctttttt tttttgaga cggagtctcg ctctgtcgcc
103261  caggctggag tgcagtggcg ggatctcggc tcactgcaag ctccgcctcc cgggttcacg
103321  ccattctcct gcctcagcct cccaagtagc tgggactaca ggcgcccgcc actacgcccg
103381  gctaattttt tgtatttta gtagagacgg ggtttcaccg tttagccgg gatggtctcg
103441  atctcctgac ctcgtgatcc gcccgcctcg gcctccaaa gtgctgggat tacaggcgtg
103501  agccactatg cctgcccaga aatttacttt gaaagtcttt ttaggccgga cttgttggct
103561  ggacatggtg tcctgcgtct atagtcccca gttacttggg aggctgaggt gggaggatcg
103621  cttgaggctg gggggtggag gttgctgtga gctgagatca caccactgca ctccagcctg
103681  ggaagcaaag tcagactctc taaagcatac cccaagcaca aggatgtgcc ttaatgagta
103741  tgtgatttat tgaggaaatg atcctctgga tggggaagaa caagtaacaa aacaaagatg
103801  tggtctcaca taaagtctag cttttggcctg acccatgaga caggggctct ggaatataaa
103861  ttgcatagca gagtggtcac tgagtcaagg gacttgactt ttatactcct tccccccatcc
103921  gtcagttatt agctgctggg aatggaatgg tggtgtaatc tactagatgt ctccaaacag
103981  ccaagggcga ttcatgggac aacttcacag agttacacca ttgtggggat aggtgtgtaa
104041  cttcccaagg agtccttcct gtccactgca cccagaaaga ccacaacatt gcagtaaaga
104101  aagagtttaa tagacacgag gtcggccatg cccatgggga gatggcgtta gtactcaaat
104161  tatctccctg aaggcatgga ggttatgggt ttttcaaaga cagtttggtg ggcaggggac
104221  cagggtaggg ggcaagctga ttggttgggt tggagatgaa atcatgggga attgaggctg
104281  tcctctcatg ctgagtcagt tcctgggtgg aggccacagg atgggttggc gggtccaggt
104341  gaggacacgt ggttgtcaga aatgcaaaaa cctgaaaaga catcaccata ttgtaggttg
104401  tgcaatagtg atgttatctg caagagtaat tggggaagtt gcaaatcata ttacctccag
104461  aataatggct ggtagttatt tagaattcag acccttctca tcctctaact tggtggcctt
104521  tcattagttt tataagaaca gtttagtctt tgggaagggg tattaccatt taaattataa
104581  actaaatttc tccaaaaatt agtttggccc atgcccagga atgagcaaag acaaccaacc
104641  agtgaggctg ggaacaagat gaagtcagca tgccagattt ctcttactgt cataattttg
104701  caatggctgt ttcaggtgta gtggcctgta aaaacaaac taggaagaag aaaagaatt
104761  gagagggttt ccaagattct gtgctactgt aaaacaacta aagaagtgga atacccctagg
104821  tttgtaattt taagttgagg tgtgaatatc ccagatgtca tctgttattt aggaaaaata
104881  atagatttca tttacttgct agtataaatc actaattttg tttttaatgtt ttgtgttagt
104941  ttcctagggt tgtcataaca aattaccaca aactgggtgg cttaaagtga taggaaatta
105001  ctttctcaca gttctggaag ccagaagtct aaaatcaaga tgtggacagc gtcatgctcc
105061  tttaaaagct cttgggaaga cccttttctt gcctctttca actgtgatga ttgccagaga
105121  tccttggtgt tcctgtaacc acctaacagg ttcccctgc ctgctgccta gacacaacca
105181  acttatcaag acagggaac tgcaatagag aaagagttta attcatgcag aggagtacag
105241  gagactggag ttttattatt ccttaaatca gtctcccccca aaacatgggg attggggttt
105301  ttaaggataa tttggtgggt agggtttagt gagttgggag tgctgattgg ttgggtcaga
105361  gatgaaagca tagtgagttg aagctgtctt cttgtgctga gtcagttcct aggtggggcc
105421  acaagatcag atgagccagt ttactgacct gggtggtaca gctgatccat tgagtgtagg
105481  gtttacaata gaatagtgat gttatcccca gtagcaattt gggagtgtc agaatcttgt
105541  agcctccagc cgcatgactc ctaaaccata atttctaatc ttgtggctaa tttgttagtc
105601  ctacaaaagc agtctagtcc ctaggcagga aggggtttg cttgggaaa gggctgttat
105661  catcctgttt caaagttaaa ctataaacta agttcctccc aaagttactg cagcttacac
```

-continued

```
105721  ccaggaatga acaaggacag cttggaggtt agaagcaaga tggagtcagt taggtcagat
105781  ctcttttact gtaataattt tctcagttat aattttgcaa tggcagtctc actccttggc
105841  ttgtggccag taactgcaat ctctgcctcc atcttcacag ggccgtcttc ccactatgtc
105901  tgtgtctctg tgtccaaacc tccctctctt cgagtaaaga tcccagtcac tggattatgc
105961  cccaccctaa tccagaatga cctcatcata acttgattac ttctgcaaag accctagaaa
106021  ggcagattta ttagagaaag tatgaaaata ggttgcaaga aagcaatggc taaatcagca
106081  tgagagaagc tgactgcaaa gaaacaaagg cttgctggag acttacaga atagggttta
106141  tgctgtaaac tgaagagggc tttgtgcagt actgataatg ccaagttga aatgaactgc
106201  cttgcaggtg tgtggtgata gttgagcaca ggaagattgt gagttgtttg tacaagaggg
106261  ctatgtgtcc tggaccatga agaaaggcag acttatagct tatctgcttt ctgttcttgc
106321  tttccctcttgg tcccgccagt ctgactcctt ttcccaatta ggactccaca gttaacttgg
106381  tccatgccca gaaatgagag aagacagcca gcccatgagg ctagaagcaa gatggagtca
106441  gccacagcca tgtcagattt atgctactgt cataggtttg caaaggcagt ttcagagtaa
106501  aaggattaaa cacttgtccc taattgttca ataataaga aaaattataa aaagcaacaa
106561  tatagtgaac tttattgctt gtttaggtgc caaatatcct tctaaaatat tttgtatact
106621  tactcaacaa gctctcccat caactatatt aggtaggctt attactattt ccattccaca
106681  tgtgaagaaa gtgatgccca tggagctaga gcaatttgct aaaggtccct tagccatcaa
106741  atgtagcagc tgaggtttga atacagccga tgtgacctag ttcaacaagg tcccaatcaa
106801  aatgaacagc agtgaggtcc aaacataggg acaattttcc aatgttttac gttgctactt
106861  atgatactta gagtaacata gtagccacat tgtgaatatt tctcattaaa aagtaaaaaa
106921  acaggccacc cgcggtggct cacacctgta atcccagcac tttgggaggc tgaggcaggc
106981  ggatcacttg aggcaggaat tggagaccag ccgggccaac atggtgaaac cctgtctcta
107041  atgaaaatac aaaaattagc tgggcgtggt ggtgcacacc tgtaatccca gcaattctgg
107101  aggctgaggc atgagaatcg ctactgcact ggagcctggg tgacagagcg agattccatc
107161  tcaaaaaaaa aaaaaaaaa ggcaagcatg ccctgcaaa tgtcctaatt tttgtttgta
107221  gctactaatg ggtttgttgt tcattaattt cttatcttat gaattcaatt atagagctgg
107281  agatttttag aatctagaga gattttattt atctgcatgc ctacaacagt tatctacatg
107341  cttaaactg taacacattg taagtgctca aaaacatttt accacagttt aaagcaagac
107401  atacgaaatt gattgaggtg ggtcacatgc attattcttt cgcacttttt gcatttgcat
107461  tgtcttcctc ctaaaaattt acttttaaa agtaaggaat ctgagcagga tgcagttaaa
107521  caacttggga tttatccagt tgtgttctac tgctgttaag tttggtgaga atgtttggca
107581  attagtggga ggacgcagtt cttcgtcaag aaaacaattt tcagaaacag ctgattttct
107641  ctggaaaaca tcaggcccca ctgggagtcg aacccaggat ctcctgttta cgagacaggc
107701  gctttaacca actaagccat agagccacgc ggaagcactc tttagaggtg aatctatctc
107761  attttacttt gacaaaatga gtttagttag ttatctgctg tcttcaaaaa atatgtcaac
107821  tcgagaaaca cttcatttcc tcagtatctt ttgaagacat acgaatacac ggggaaacgt
107881  attcggcagt ctacagtgtc aaaggatttt tctattaatc caagaaagag cattacagaa
107941  agctatacaa tacgtgaaga cgattaaaag gaatatatct atacataatt ttaaaaaacc
108001  tttgaatctt gaaagtcact cacttagggt acgtgaagct gccaaattta tcagagaagg
108061  aacaggcatc tctcgcatgg agccgtgggc ctcggcgtta aggcactctt cagctacagg
108121  tggcagcccg tttagctctt cttaaggtct tgtgatgtca ttttcaagag gccagtaag
108181  ttctgtgtca cgtggggcct ctcaggaggg gtgcggaggt gggggaggg cggggagcag
108241  gactccactg ctttggcctc aaggagtttg gtcgacactt gaagactgac caagaaaaag
108301  taatttgtcc cagtttctc ccaccctttg tttctctg ctcctctgg gcttgttttt
108361  tttttggggg gggggttct ttcttttttc tttctttt tttttttt tcccgcagta
108421  agttctgaaa atcgcctccc agaggagata acgcgttctc ctctgtaacc cgtccttcca
108481  cgtcccggtg gtggggggg gggtcccgt tctcattctt tcggggacct gcaaggagcc
108541  ccgcccgcag gctttgaacc gatttcggct ccgcgtccag gagcaggccc tacgtagggc
108601  cggggaaatt caggtgcgtc tgcggggccc agggcaccca gggcaggcgg ggactgagac
108661  gactgaggt tgagggacaa ggaggttggg actggggagg ggagacccgg gacccgccca
108721  gaacgctttc gtggggttgg agagggcagg acacagcctc tctgggcccg gtagtatgcg
108781  aagacacgca taacgcaaaa ggattcccgt cctggacttt gggaattaag gccctgaaca
108841  cattgagcaa aaagtagatc tgtctgtaca gacgtttctt tccacgtctt tcatagtaag
108901  gactttatta aaagcaggc actcgaatcc taggtgggta gatgggaggc tggggctggg
108961  gatggggacg tcctctgttt tctggttgtg cacattaaaa ataactctct gctgcctact
109021  cctaaacgca gccggcaaaa atgagacgtc aactaagcgc cgtttcagtc ccagagccag
109081  gtcgtccatg gggttttca agcgttttct cgatgactga ttttctaga agcgaatgga
109141  ttttattctc ccaggtgtaa aggctacctc ctgcttcaca cccgggtaac ataaaagaca
109201  gcgctgggac cgaaactcgg gtctcctggg tcctggttgg ctggagagag gggcaatgaa
109261  cgtcccgaaa agaattctgt cttttctcaa tatctgggag gactcataac agggtagata
109321  atcaggatgg atgtttggca ggtgggaatc tttgagacgg tctgtgcaca caattttaac
109381  tctactttg ccagtttgga ggacatgaaa ttcctgatga gtgtatgtta aaagggaata
109441  gagaaggtaa tatacacaac gttctaaaat aattgctttt cgtggaggca aagtggctaa
109501  gcagtccaaa gcgctggatg aaggctctaa tctcttgggg tgtggaggtt ctagcctgtt
109561  tagccacaga agtcatgaaa ccactatgtg gtatttgtta aataatgagt tttgatactt
109621  aaaataaaat ggaattattg gagtgaattt tgtttggttc tgttgaattt gttattctta
109681  cacacactag ccagattcta cttatttgtg ggcggcaagc cacccaggca ccgaggcaag
109741  agacagagga cacgagctgt tccagtataa taaaatataa aacaagaata gttataccaa
109801  atatagatct tagatatgat tatatatgaa aatcattaat cattagttttg tagcaattac
109861  tttttattcc aatattataa taatcctcgc tctataatca tagcctagga aaaaccaggc
109921  cttacagaga taggagttga gggaacatag tgaggtgtga ccaagagaca agagtgcgag
109981  cctctcgtta tgcccggaca gggccagcag aagggctcct tggtctagcg gtaacgccag
110041  cgtctgggaa gacgcccgtt gccgagcgga cggtggtcta gcagaagcct cagtgtcaag
110101  aaaaaacacc ggctgcttag cagacggaa aagggagtct ccctctcccc ggggagttt
110161  agagaagact ctgctcttcc acttcttgtg gagggcctga cattagtcag gctcgcccgc
110221  agttatccgg aggcctaacc gtctccctgt gatgctgtgc ttcagtggtc acactcctag
110281  tccgccttca tgttccatcc tgtacacctg gctctgcctt ctagatagca gaagtaaatt
110341  agtgaaagta ctaatagtcc ctgatatgca gaaataatgg cgtaagctgt ctttctctct
110401  gtctcctctc cctctttgcc tcagctgcca ggcagggaag ggcccctgt ccagtggaca
```

-continued

| | |
|---|---|
| 110461 | cgtgacccac gtgaccttac ctatcattgg agatgactca cattctttac cctgccccctt |
| 110521 | ctgccttgta tccaataagt aacagcgcag ccagacattc ggggccacta ccggtctccg |
| 110581 | cgcattggtg gtagtggtcc tccgggccca gctgtctttt cttttatctg tcttgcgtct |
| 110641 | ttatttctac actttctcgt cgctgcacac agggagagac ccactgaccc tgtggggctg |
| 110701 | gtccgtacac ttattaacat tttatttgat atgttgatct ttgatgtat gaatttgatt |
| 110761 | gttctcattt gatttgtttt gtttttactt tgggttctat ttatgtcagg ttttggtaac |
| 110821 | cttaatgaat ggattaggca gttttccact tcttatgccc tgaaacttttt caacccagaa |
| 110881 | gagttacctg atccttgaca atttgacagc acttggccta agagaatggg gccttttcat |
| 110941 | ggggcttaga aatggaaaga gactttgac agcctcttca tctattaccg tggttattat |
| 111001 | tctgtgagga tgtgtcattt gagtgtgtca tatagtgcct ctgattctca gttgcttatt |
| 111061 | tgttgagaga taatgatact gaatattaaa tgacttactg cttttaaaat tctagtatga |
| 111121 | tgcctgggcc atgcaagcct tcaatcaatg ttatttatta ttatcacatc aatattggta |
| 111181 | atttatattg tcctaaaatcc tatctcattc actatgctta gattatcagg gattatcaga |
| 111241 | tacagaggta gaaagttgta aaaaaatgct ttttatttga gatacacatc tcatctctat |
| 111301 | ttgtaaatgt gtcttcttca ctaattttga attctaagtt tatattttcc cttagacatt |
| 111361 | ccacagattt gtatttcagt tttatttaca aaaaaaactt tcttagctct cctagcatgt |
| 111421 | aaacagattt tctctgttga ttccttttctt ctgcttttcat ttggtatgtt ttgttggtct |
| 111481 | tttacttgct tctgaagaga aatactcacc agcatttcag tcatttaaag tctttctcat |
| 111541 | ttacttaaaa aatgcactta agttacaaat gttcccctct gacctgcttt tgtagcattc |
| 111601 | cacagtaatg atatatgttg tcttattgac attctattat acctggcctg taattttagt |
| 111661 | tttgatttc tctttgagca aagtatttt tagaagcatt tgacattaag tataacattt |
| 111721 | tatacttttc tgattatatt ttgatgctga tttctatctc tattttctag cacagttatta |
| 111781 | attttctaaa ttaaaaagta ttttgatatt ttcttattag atcattgtat agtcaattct |
| 111841 | ttaatttctt tgggcaattt aaaaattgtg ttttctctat aaagaatttt atgatatcta |
| 111901 | tcaggtcaat gttttattct tatttgtctt ttataatatt acttatttct ttgtccactg |
| 111961 | atatttcttg aactagagc aataaattga agtcaattac taaattgtct ctgcctttct |
| 112021 | acttgtgtct ccactgaatt tctgctgaat gaaagttgct gctttatttt gagcatgaat |
| 112081 | atcaaaaaaa ccaaaaatct ttacctccac ttaaactgta attttagca ttttgcagta |
| 112141 | ccctctttg ttttatttaa tgagtgttgt ccaaaaatccc acctcacatg attttaaatc |
| 112201 | cttgagtcct ttcttttgt gagttgcct gatattttttg tctgttctt attttcaaac |
| 112261 | ttcctgattg tttccaagcc tgtgggtaag tagcaagctg tggggaggca gtgtgacaag |
| 112321 | gtatatgcag gaaacaaaga gctcagagag actagtttt ttattttcac agcattttaa |
| 112381 | aagccaatga ccctaattaa gagatactta atcttccact ggttatgtg gtcatagtga |
| 112441 | aaattacagt tgagatattg aatatagcaa atgtgtagct ctgtggagaa attgtggcac |
| 112501 | tggaatctct gattctagcc aagaacttcc cagaggcatg agtaaaatgt tcccaacttg |
| 112561 | aaaatctagt gcaagtagaa gattcaatct tttaatgttg atgttttcta ggttccatat |
| 112621 | ttggttgccc tttttttctga gatggtattc aaaggaatat tccacacact catatctttg |
| 112681 | aaccttttcaa aatacttcca aatatcttgc atatttggaa tactgataac ttccaaatat |
| 112741 | cttgcataaa acttttttaga atgccatatg attatagcca actgcctaca agacatttcc |
| 112801 | accttagtat ctcatagaca ccgtggactc atcaagttcc tcctattatt gctttttctt |
| 112861 | ttgagtagca ccacaaccta gtctgttaaa gtgaaaactg tgtgattact gtagatgact |
| 112921 | ctctttgtcc cctcatgcat tttttcatc aggtgaatat gatgtaactg ctgttttagat |
| 112981 | tcaaatagtg atccttccct aactagccat ggcaattagt atgatattct aagcagaacc |
| 113041 | tgctgttgtg aaaacataat ttgatggaat tgagagttt tgctattcag ttaaactctt |
| 113101 | agtgagtcaa atatgccaaa tgtaaagttc tattttaat ttaatatttg ttttgtctct |
| 113161 | cgagaagctt ttattctaaa cagagagata caaatctgat gttttgatgc acacattaaa |
| 113221 | aaatctgaat caagtttggc ataagagat acttaaattt gccaaaatac ttatgagaaa |
| 113281 | taatcataaa tgatggcata tattatgcca aatttattt tttttgcatg aagggaattg |
| 113341 | tggaaattga cctgattagt ttggactgtc aagagcagag ttgaaccata atccccacag |
| 113401 | cacctcaaaa tcctgagaca agctttcat cccccacatg aatactgttt tctgtccctt |
| 113461 | ctgtccccca actaatgggg ccccttaaaa tgtaggatgg gtttgagctt tggttcttaa |
| 113521 | caaaggaccc agttatggag gatctggaag tctttttttc cccctgggcc ttatacccca |
| 113581 | tacatataat gcaaggccca catcagttat ccattcactc ttaaattgag agaagacaag |
| 113641 | ttagaaaaaa gcgttgaaag tttgtttata tttgggactt agatagggtc tgtgaaaatg |
| 113701 | cagtgctggt ttaggaaggc atgaagtggc tggtttcaga attcctgac agcagacatt |
| 113761 | gagagcttgg ttttacata atgttgcaaa ttatgaatat agattgaagc cagaaggtac |
| 113821 | tcatgtgccc ttataactct taaaatacag tgatttatgc aaatttactt tttcaacttt |
| 113881 | tttttttttt tttaacagag tctcgctctg tcagccaggc tggagtgcag tggcgcaatc |
| 113941 | tcggctcact gcaacctcca cctcccgagt tcaagagagt ctcctgcctc agcttcccaa |
| 114001 | gtagcaggga ttacaggcac ctgccaacat acctggctaa tttttgtatt ttttagtgga |
| 114061 | gacggggttt cgccatgttg gccaggctgg tctcaaactc ctgacctcag gtgatctgcc |
| 114121 | tgccccggcc tcctaaagcg ctgggattgc aggcatgagc caccatgcct ggccaattt |
| 114181 | ttaaacttta tattaggctt ttaaaataga ttattaaagc cattaataat tcctctcctc |
| 114241 | ctttggtggg aagttacagt ctgaggactc aatttttctc taataagagg atagaaaaat |
| 114301 | tgaatgtcat ttagtttga ttaccattca tcttctgct ccttccaaa taacactatt |
| 114361 | gtttgttcca tcatatattc tatttattct atctgtaaca tatcttccat gttactaatg |
| 114421 | tacttgtatg tgtatttaac acaacttagt aattctgctt ctgtctcaca agctacttat |
| 114481 | taatttatgt atagttaaca catcttctga attttgcctt atcttgtaag ctattagctt |
| 114541 | acgtactatc tatattggtt ttatccatcc aatttgtttt cctatttcct atatctgaat |
| 114601 | ataataaaat catcacagcaa ttcatatttt caggagccat tgaacttaga actctttgtt |
| 114661 | tttggaaggg gagccctaga aagtcagtat tctgaataga aatgactctg aggctctaca |
| 114721 | gataaagata aagctctctt tgccaggtgt agagtgtctt caaacataac ttattaggtg |
| 114781 | ataattccat ttctattaac ttgtctggct ggaggcaaag aaatacagag gaaattggaa |
| 114841 | agagagaaaa gaataaagac ctggaaaaag ggaagatcct tgagttatct ttgccttagt |
| 114901 | tcctctgaag ttataatcta aaaattggta taagctctac atacactcta ggtggcactc |
| 114961 | tgaggttata aaatggttca tatggtgagt tgaggccact gtgttttgtt tcattttatt |
| 115021 | ttatttttatt ttgagacagg gtctcactct gtcacccagg ctggagtaca tggtgcaatc |
| 115081 | tctggtcaat ggagcctcga cctcctgagt tcaagtaatc ctcccacctc agcctcctta |
| 115141 | gtagctggga ctataggtgt gtgccaccac acctggctaa tttattttt tgtagggatg |

-continued

```
115201  gggtctcact atgttgctca gtctcaaact cctgccttgg cctcccaacg tgttgggata
115261  acaggcatga gccaccactc ctgaccccac tgtatttcaa aggccaaaag gagtccaaaa
115321  gaattaaaac tggttttctt ttccctttac aaggaatcaa gaaaaggtag acagtcaata
115381  tggtttcata aggaaaattt tagagggggca tggaatccct atccaggaac ttcacagaga
115441  ttcaaagaaa agaaagtttg taaactaaca cttgaaagag caagagaaaa cttgcaatca
115501  gagcaatgcc agctggaggt caggaaggga agcggtaaag aaagaagaga aaatgagaac
115561  ttttttatttt actccaaatc acaatgtatt tgaaaatata tattaaagaa agattatttt
115621  ggcacttgat aaagtgctag taaagactaa gactactgca attagcgaga gagactgaac
115681  tcaatgggga caaatgggga tttaaagcca acaggcagag tgaaggtgtc gtagatgatg
115741  gaaaattact aagcacagat atcaaaagga ggaagagtct tgctaaactg gcctaacagg
115801  attcttgcta atggtaggct aaggacttag aaattaaggg tagaggatta ataatctgtg
115861  cagataccag acttggggag attctcagta aactgataga aggagtcttg ctgaaggtag
115921  tcaaaagcca aggcctactt gagaaggcta aaagaaaaga ctgtgttttct atactctcac
115981  aatacttctg acaccatatg tgtgggtttt ccactccaag caattctcca attctgcaga
116041  cacaaactgg gtgttgacac tgcaactcaa ttctgcacct aactacctgt aattagtgca
116101  gacccctatag gtgaagggct cagttccaca agactgcccc ccacttcaca tgtcaatcat
116161  aagtcccagg ttgtcactca tatttctgac caactgctgt aaattgaggg ttcctatgac
116221  ctcccctga agtttgacaa tttgttataa caactcacaa gactcaggga aacatttact
116281  tacgttcatc agtttattat aaaggatatg acaaaggata tagatgaaga gatacacttg
116341  gcaaggtatg gggaggaata tagagctttc gtgtcttctc tgggggcacc acactcccaa
116401  taactccgtg tgttcactag cccagaagct ctatgagttc tgttgtttag gagtttatg
116461  gagatttcat tacacaagca tgatggatta aatcattggc ttttgatgac tgggtcaatt
116521  atcagctcct ctgccctcct cagaagtggg ctggggtgct gaaagttcca aatctttaat
116581  cgccatggat ggtttctctg gcaaccagac ctcactctga agctatctgg ggacttcag
116641  ccaccagtca tctcttaac atacacaaag acagttatta tttaggagat tccacgggtc
116701  ttaaaagctc ttgtgttggg aaccagggac taagaccaaa tgtaacaaaa gaacctctta
116761  tcatccctat cactcaggaa gttacaagga ttttagaagc tctgtgccac gagttgggag
116821  gaaagaccaa ataaacatat ttcttatgat gtcacaaagg ctcagagaac cctgactaca
116881  gttgggtcaa ggagggagtc tttgtcagat aacacatatt gaatttggac ctaaatgaag
116941  atgatgtgga tcagagactg aggaaactaa taaaccaagg gcatggctgg attgtccatg
117001  ttaaccctgg gggcacctaa ggactgagtg ggaggcagtg tggcttgatt gtgcagagca
117061  gtcagtagcc acatgaagta caagagaagt tctccttact catcctatgt caaaatgaca
117121  atattttctg caaattctcc attccttaga gcagtggtcc tcaaacttta gcatgtatta
117181  ggatcaactg gaagcctttt gaaaacagac tgctggacct accccagggc ttctgggtca
117241  gtgagcccag gagagatatg aaaactgcat ttctaagttc tcaagtgatg ctactgctgc
117301  tggccagagg actatgcttt gagaatcaat ttcctagaga cagaagtcaa gaaagggaaa
117361  atgatgactg attgtcaagg tccttttctc agggcctcta ctcgagattt ccctcaataa
117421  tgactcattt gtggagggta ataggtggtc tccacagcct tacccagatg ggctttactg
117481  ggctagtgcc tgcatctcca cttgctgtga gttttggctg ctaatggctc agagctgctc
117541  cttctccagg gtattaactc tcagtggcca ccttctccaa agaattttct tcagccaaag
117601  ggagccacct cgcctgggag tttatgcctc tagagttcaa gggtgggccc ataagccaat
117661  gactgactca catgggctac aagaggctat gtctcatcct tcaagatggg actgattata
117721  gtgtgatttt ttctgaagct aagctccagc agaaattgca ttttaattct ctctttttcct
117781  ggccttatcc tgcttcacag attccctttct tctgagacca ttctttcaat aagctatatg
117841  tgcctcaatt cttgtctcag attctgttta tggagaacag aagccaagtc aagaggtgtt
117901  cataagacca cagaagcaat atttgatgtg ctctgggata gactgtgtcc tacttctcat
117961  attttgagaa ttcacctccc agaattaaca cgggtactct ccaaggctaa gagccacctg
118021  tgtccacaca gtccacagaa aatatattac atccacagac taactgccac aggggagacc
118081  acagtggttt attacctcct gctatgggct gctttgcaaa tctgggaata ggttgattag
118141  agagggtctg agtcctggtt ttctaggacc ttagaaccett cccgtcctgc ctgagaactc
118201  tctccaaaag ttttgtgatc agtggagcct taatgattcct agatgcctgg taggttgttt
118261  gtgggggtagt ggatttatgg acccaattag ctctcagtgta cctgatttgc gtaataagtt
118321  gtgggaactt ctggttagaa gaaaaaagtt ccacagcaat aatagtgcct gtgatggtaa
118381  tgatgataat cacctgatag taacctttta actactatga cagactggag ctccttagac
118441  actcctgaga agtcgaccca cttccagaag gttctaagtg taactttcgt tggggactaa
118501  gctctgctat tgggattggt tgaggaggag agaagtggaa atttttatgt cttgatcctc
118561  tcttttataaa gacattttac attattatta tattttacat tattattatt gccatcatta
118621  tcatcattgt catcatttgt gacattctga tctggacttc tggcccccaa acctgccct
118681  cacctatgcc cacctcccac tgcaaggaca tttctgtttc tcatttctat ggtcttggct
118741  ctctccagaa aaatgtttat tttctcttca gggacagcca ctggaaggca ttaggaggat
118801  agaacctgga ttttcagagc agtggcagga tgaagaccctt tccccgcatac tcaggcacaa
118861  agcattcagg ctgaaggctg cagtcctctt tcttcattac tataggaatg ttggtcacct
118921  ggagcaactg caggttcctg ggttaggctg aaccagtaac tggagagaat tttatacatt
118981  gtgtcagctc atcctctcca cctactttct ggaccttggt tatccagatc ttaccaggtc
119041  tggaaccctt ctgaagacta ttaaggtccc agaggtactt aaccacttca gagatttaaa
119101  agaagctaaa aaatgaaaca tatttcttaa caccactggt agctggttct gtaatctcct
119161  cactgctctc acaaccgcca tagcggttag taaaagattt atggaaatct caaatcctat
119221  ggtttacagc caaggaaagc ccgatttttt taactcattt tttcttacta gatgttaagt
119281  ttaagaagag aaaacatcca aatattttga taatatttcc catttttcat gtatcaaata
119341  tccaccattt atgaattta aggtcttaaa aatcattttc ctaacagttt ttggttagt
119401  caattttcat gttgctgaat aaagattaag tcatggatca catttcttct ttcttccttt
119461  tttttttttt tttgagatgg agttttgctc ttgttaccca ggctggagag caatggcgcg
119521  atcttggctc attgcaacct ccacctccag ggaacaagca attctcctgt ctcggtctcc
119581  caagtagctt ggattacagg catatgccat catgccccgc taaattttt gtatttagta
119641  gagacggggt ttcaccatgt tagtcaggct ggtcgcgaac tcctgacctc aggtgatcca
119701  ccctcctgg cctcccaaag tgctggcatt acaggtgtgc accactgtgc ccagcccata
119761  tttctattta ggtacacagc aggattacga tccccataat gtttgaaatt actcactgat
119821  ttaaatttcc tgcatttttt aagtgcaaaa aatattttta agtgctaata cctatgttcc
119881  aagtaatttg taaaagagaa aagaaaaaca gtgattttat tttacttcct catctaattt
```

-continued

```
119941   ctttccttaa tatctggttt tctgaaatct gcttgaatta taaaacactg tatttaact
120001   ataaaacagc acggggcaga tagggcttcc tagcaggtcc tttgcacctc tgattaggag
120061   tgggttttgt tccactttgt tttgttatgc tttttactt ttatgtgctt tcagatttta
120121   acagtgagca tgaattaatt ttataaacag aaatatatgc cctctccctc tccgtctccc
120181   tctccctctc ccccctccacc tcccccctccc cctcccttt gcacggtcct cctctcccct
120241   ttgcactgtc tacctctgat gccgggccga ggctggactg tactgccgcc atctgggctc
120301   actgtagcct ctctgcctga ttctcctgcc tcagcctgcc gagtgcctgg gattgcaggc
120361   gcgggccacc acacctgact ggttttcgta ttttttggtg gagacggggt ttcgccgtgt
120421   tggccgggct ggtctccagc tcctgaccgc gagtggtctg ccagcctcgg cctcctgagg
120481   tgccgggatt gcagacggag tctccctcac tcagtgctca acgtttccca ggctggagtg
120541   cagtggcgtg atctcggatc gctacaacct ccacctccca gccgcctgcc ttggcctccc
120601   aaagtgctga gattgcagcc tctgcccggc cgccacccg tctaggaagt gaggagcgtc
120661   tctgcctggc cgcccatcgt ctgggatgtg aggagcccct ctgcccggcc gccgagtctg
120721   agaagtgagg agcgcctctt cccggccgtc atcccgtcta ggaagtgagg aggtctctgc
120781   ccggccgccc atcatctggg atgtggggag cgcctctgcc ccgccgcccc gtctgagatg
120841   tgaagagtgc ctctgcccgg ccgcgacccc atctgggaac tgaggagtgt ctctgccccg
120901   ccgccacccc gtctgggagg tgaggagcgt ctctgaccgg ccgcccgtc cgagaagtga
120961   ggaccccctc cgcccagcag ccgcctggtc tgggaagtgg ggagcccctc cgcccggcag
121021   ccgccccgtc tgggaagtga ggagtgtctc cgcccggcag ccgccccgtc cgggaggtgg
121081   ggggcagcct ctgcccggcc agccgcccag tccggggaggt gggggggcgcc tctgcccagc
121141   tgcccggtct gggaagtggg gagccccctct gcccggccgc cgcccccgtct gggaggtggg
121201   ggggcccctc tgcccggcag ccctgtctgg gaagtgagga gcccctctgc tcggccgcca
121261   cgccgtctgg gaggtgtacc caacagctca ttgagaacgg gccatgatga caatggcggt
121321   tttgtcgaat agaaaagggg gaaatgtggg gaaaagaaag agagatcaga ttgttattgt
121381   gtctgtgtag acagaagtag acataggaga ctccattttg ttctgtacta ggaaaaattc
121441   ttctgccttg ggatgctgtt aatctataac cttaccccca accctgtgct ctctgaaaca
121501   tgtgctgtgt ccactaaggg ttaaatggat taagggcggt gcacgatgtg ctttgttaaa
121561   cagatgcttg aaggcagcat actggttaag agtcatcacc actcccctaat ctcaactacc
121621   cagcgacaaa aacagtgcag aaggcagcag ggccctctgc ctaggaaaac cagagacctt
121681   tgttcacatg tttgtctgct gaccttccct ccactattgt cctatgaccc tgccaaatcc
121741   ccctctctga gaaacacccca agaatgatca ataaatactt aaaaaaaaaa acaaacatat
121801   gcatatttgt tgtagagaga gagagaggat tctttgagag gcaaggattc ctgtcatgta
121861   ggggcctggt caagagacct gaacgggagg gtgcagaggg acctgacacg aagagatctg
121921   tgctcacggt cacagcagct ctgagcaacc agttccagcc gtgctttat atgtgccaag
121981   gaaagttcta gagcatttt gagaaaaaca aaatactgaa gaacaagaca agggaatcaa
122041   gaaagcaggg acaaagtgac agagaaagaa gaagtatgac tggacataat atgggactgg
122101   gaaaacacca cacagagcca ggttgctgca gaattttaa atttgagaca gtgatcaaaa
122161   taagcttaaa gttgaggagg ctcagggtga ggagaaagcc catcattcag aatacaggga
122221   caccctgcc caggtgccat gacctgaatg cactaaggga caggcaccaa ggaaggctct
122281   ggcagggtgc gacccagagg ggttttggga tccaccatca tggagatgcc cttcccttca
122341   tgtgaggtgg ggtttctgct ctcactctgc cttcagaggt cctacatgag aactactgag
122401   tggcagggga ataaaggaga attaaggaga aaagagttta acaatgcatg cctatcttag
122461   aggagagagg ctatgaagga ggcctagagt cttgcggcca gctcctgctt tctttaaaac
122521   tttcaggaag gggaaggat agatgtcaca acttctcggg attgcttttt tagggacaca
122581   ggatagtctg attcatctac cctaaaatat gattttcctt tggaatagat atttcaggat
122641   cagagagttg gagagatagg tgttctttc cttaatcttc aaacacacac acacacacac
122701   acacacacac catacataca cctatgcata taccacaaa tacaattcta catatccata
122761   cacacacaca cacacacaca cacagctaca cacacatgct aagcaggtgc ttgggtagta
122821   caggatggtt tggtcatcag gaggctgggt aggcacgagt gtggagcaaa gaaggaggaa
122881   gatggatgct ttgttagaca ttcctgcagg tgggagacag ggtagttatt tctgtcagtc
122941   gctagcccct cctagtgggt attgaactgc tttaggtact ccaggatgtc tgacttgact
123001   gtgctgactg gagcctggtg gaaccaatgc atgacaggga ctccatcggg ccccaccaga
123061   aatttctcaa agttccagcg gatatcatgg accttcatgg gctcccagaa gagttgcctt
123121   gatgagccca aagatcaga ggtcggaggg caggagttct ggagcagaga tatagaaagt
123181   agagatatac atttatttct acttatttc tacttctgtg tggtacagtt ttatctccag
123241   actagagagt ctactccacca ttatgtattt taatatatta actactttgc atgcttccaa
123301   tcaaccacag acactgcaat gtatcaatac caatacacca actaccaaat aaccgagagt
123361   tagagagtat aatggtaaat agaaagcatt cctccttccc ctgtcttccc tctatttcca
123421   tggttttatc acgatgattc agtaaaagac tatttctgt ttccttgggc aagtcatatc
123481   atttctacag ttcgtttcct tagcagaaaa aaaaagagat tgatttagag tagtggctcg
123541   cagagttgg ggcttcatag gcttcataag ccagtaaaat ttcaataact atttccttgg
123601   atattaacgt agaatcacta atactcattt tgccaataag aaaaattaaa agtctactgt
123661   aagcacacat ttaaaaatta aggggatttt aaatactcag ttgtaccaca taaaattgat
123721   tatagcacca tttttgagta agtaaagggc aattatatg ggtaaacgta atagtaattt
123781   aatgtcagaa taaatgttgg tcttatattc aataagttga gcttatgaa aaattctgca
123841   ttgtcttttt tcccttgttt gctgtggatg agtgaaaatt tcagcaggac cagcattgtt
123901   ctgcagacca gcatttcggg ctgagtagac aaagagaccc tcgggggtcc ttcatctctg
123961   gtattctgta ttttaccac tctgtgactc taaaagcatt taccacatgg tattctgtat
124021   catccatgtc tgtctcctga ttaaatgtga gttccttcag ggaacagact atgcgctatt
124081   aatgttttgt aactcatata gcacatactg gagatctgat aaatgattgc tgaatgaatg
124141   aatcattcca ttcaataacag gagggtagtc catgtcagag ctattgtcca tcatgggtt
124201   cctctactta aagctaaagc atcacagcag atattgccat gagccttgaa cttatctgag
124261   catctctttt ccaaggagtc caaccacaac cctagacatg agccccactg ctttcagagc
124321   atttctagct aacccatcca tgccaggttt atactcatgc accttcagga aagtaaagac
124381   cttctgttct tttctccat tcacatcccc tttctcaaag agctggaaac tggggacaaa
124441   gccactacct ggacacacat acctgcagtg aaccaaagtt gttcccagca agatacaaat
124501   taagacatgg atggaaaata atggccacca ccaattcact accacaggaa attcaagata
124561   aagggaagag gctgtgcaca gggaagataa gaaaagatag tctgtgggaa gcaggattt
124621   atgcaatagg ctttatggcg ccaatagaga attctaagaa aattggaagg caatattttg
```

-continued

```
124681  agcttaggtt tcctgcttca cttccatttc ttatttctta tactcccttc ttttctctat
124741  gcttcttttc cattcaatct tcccttagcc tcaccatcaa ataattcaaa agtaaagaga
124801  atatttgagc actgtgaata gaatagattg aattcaaaac atcataagga tatgcttcaa
124861  cccatgtatc tatggcctat cccagaagtt tccagaatag gcaggcatct aggtggaatg
124921  aggaatggaa atcccgacag ggcatctgca gggtcccatg caagcactca cttgagacca
124981  agaagtattt ctgagtttgt tcctggttct tgttttccaa actggttgca gggaaaggcc
125041  aacacaatga caccaaaatt cttcagctcc tcctgtagtg cattcagttc tgtaagtgga
125101  caatgaatag caggggtggg ctggtcagga ggcctacctc aagcagtgaa agatcactga
125161  atgtatccat ttatcacatg aataaaccga ggactaagaa gggaaagatt caaggttaca
125221  gagatcaaag gagtagagaa aaaaaaaaa gactagagca cacgtttcca gaaatgcatc
125281  tgaatggctg ctgttttttct tatacagtag ctcccatgcc tggctacact ttaccatcca
125341  atgagaactc ttattttttt tttttaaacac acacacacac acacacacac acacacgttg
125401  gtagccttgt gtgggagtcc tgtttgactc taaagagaag tcagatttga atgccactgt
125461  cttccttagt tgatgaattg atcaaaaaaa attgtaagga aaaagcaaac aaaatggaaa
125521  tcctacccac ctatccctgc atcccccccgg ccccactact acaatgtccc atggtgacac
125581  aaccagacac tccagttcca gtcccattcc caggagtact ccttggtgct ccaccctggg
125641  agtggtagag aaagagaaat tccaaggcta tcctctacag tattctgtac cctctcctca
125701  attccagtga cctaactgat gctgcaacat gccctggaac actccctggg acgccaggcc
125761  ataaactcca aattgctctt tactactgtc aggaaccttc cagcttgtct gtttagactt
125821  gaatcataat ttccatcttc agctattttc aggtaagatt tattcagacc tcagaacttg
125881  tactggccat tgtcattcag attcagctct gcctgctgga atgtcccta agaacctcct
125941  cttaaataga gagtgccttc ctgtttttct atagttcttc ggttgctatc gaaactcatc
126001  tctctcttat ctttggccat caagaatatt tccttctat agcagacaca cttaacagac
126061  cttgattcta ttccttttggc aagtttcttt aattctctca attttctcat ctggagtaaa
126121  atttgaatga ggtgctcttt aaaattctca tgaactaatt taataaatta tatcacagca
126181  acacaatgga atactatgcc ttaaaatgaa tgaggaagct caccatgttt ttttgttttg
126241  ttttttagaca gagtctctct gtcacccagg ctggagtgca gtggcaggat ttcagctcac
126301  tgcaatctcc gcctcccagg ttcaagagat tctcatgctt tagcctcctg agtagttggg
126361  attacaggca tgtgccacca tgcccagcta attttttgta attttagtac agacagggtt
126421  tcaccatgtt ggcaaggctg gtctgaaact cctgatgttc aagagtgatc cggccaccttt
126481  ggtctcccaa agtgctggga ttaccttggt ctcccaaagt gctgggatta taggtgtgag
126541  ccaccactcc tgtccccact gtatgtgata tatgtgaaaa agcaatgtgc ataatcattt
126601  ctgtgtgtat gtttgtgtat gtgtatgtgc ttgagagaaa gaaagtgaga gagaaatgtt
126661  tgcttgtata tgcataacag atttctggaa atatacacca taaactgata ataatggttg
126721  cctaaagaga agggaacatg gcaagtgcca ctgttaaacc tttttatatc tcttgaattt
126781  tgaatgttgg aagtatattg cctattcaat atgtagcaaa tttaagttaa aattaaatta
126841  aattaaaaca aatttaagag cagcttcaca ttccatggaa ctgcgtttac acatcacaac
126901  ttttaaaatt taccatattt ttcaaattta acttttttgaa gggaggagaa ttcttgcctg
126961  ctaaatgata caaaactgtc gtttgggctc taatacctag gtcctgaggt cctatagtag
127021  acacaattgg cagaacttga ttctattcct ttggcaagtt cttttaactt tctcacttac
127081  taaatgatac taaattgttg tttgggctct tataataaaa atttagtctg tagcttttca
127141  ggttttccct agacttgagt gtacataaaa ataaaaaaat tgaggccggg tgtggtggct
127201  catgcctata atcccagcac tttgggagat tgaagcagtt ggatcacttg aggccaggag
127261  ttcgagagca gcctgaccaa catagtgaaa cccagtctct attaaaaaaa aaaaaaatta
127321  gctgggcgag gtgatatgca cctgtagtcc cagctatttg ggaggctgag gcaagagaat
127381  agcttgaatc ccagaggcag aggttacagt gagccaagat tgtgccctg cactccagcc
127441  tgggcgacag agcaagaccc tgtctcaaaa ataatagtaa taacaaaggg accccaaat
127501  tatttttaaat gtgtgattct tatccttaatc tgtactttg agagcatctt ttatgcata
127561  attttaccat taaattggaa aagtattcag ctactcttgg taaatgtgag ccattttgtac
127621  tttggaggag ccggaatttt attagaattt tggcttaaat catgtagcat cctctgaatg
127681  ttaattttaa aatgtcaaaa tttggtgagc cagatctttt agacatgaga ttacaatatg
127741  cttgacttta agtgttactt aaaagggcta aaattctggg attttatta ctgaaaatcc
127801  attaagaaaa attgataggg tttatatatt tttgatcagc tgaacagata atagtgtcaa
127861  tgtgtggaaa attttttctta aaacttgttt ttgtatagac caggtgcggt ggctcatgcc
127921  tgtaatccca gcactttggg aggccaagac ttgtggatca tttgaggtca ggagttcgag
127981  accagcctgg ccaacatggc aaaacactgc ctctgctaaa aatgcaaaaa aaaaaaaaaa
128041  aaaattagct agatatagtg gtgcatgcct gtaatcacag ctactcggga ggctgaggca
128101  caagaatcac ttgaacctga gaggcagagg ttgcagtgag ctgagatcac accactgcac
128161  tccagcctgg gcgacagagc gagactgtct caaaacaaaa caaaatttgt tcatgtatta
128221  ttttgatcca cttcctctgtg gcatttggtg caataaatct tttaaattta tcttgagcca
128281  ttttttaaaa gcataaaata aagttcttgg cccgtccaaa gctgtatcta tctctagtat
128341  aattgatcta aaattttaaa taacctttc tggaccaaca gtaatgcaaa actcttctcc
128401  aataaggcca caaagaaaat ggaaacacac ctcagctacc acagaaggtt aggccaaggt
128461  tggcgagatg gagcattctt ctacattgcc agtcacacta cacagcccct gtaccaatca
128521  aaggctgccc agacagaaaa cttcatttcc ctcttggtca tttgcaggtg cctacagaac
128581  ccaagggcat tttccagaat atcaaagatc actcatctct cctgttttta tcagaagtaa
128641  ccgatgagaa gcataaaatc agtccttgaa agccaggtat ctggcctggg agtcacagct
128701  aggctttagc actctgctag gaaacataaa caacttcata gaacagtttc atacaaacaa
128761  tatcacataa catgtgatc
  2341  gtctcaccttt ctgaagataa aggccatgcc atcatgccat agatatgagg gcaagacaat
  2401  ccaggtatca tcattgcaac tcccagttgg catccagaaa gaaccatgta tttgaaaatt
  2461  gcttcccaaa cattttcctt agctttgctt tactttgctg tgaggctagg tagtagtgct
  2521  gctctctgtt ttacaggagg ggaaagtgat accgagagag attaccaggc cagcataata
  2581  tagcccatcc ctcctgtccg ttcagtgttg gcatcacatt tctccttttt tctcacctga
  2641  gccaaatggc ctccactttt ctgttattcc cactgtcact ggattttgt aataaaaatg
  2701  aatctgtttc aactaaaggt ataattccag accttctgga aggcctgaag ttaagaaac
  2761  aacaaaggcc tactaacact gcgggaaatt actggggttt ccatgcagtg gaggtatcac
  2821  tgacaaatga gatatcttga ctcaaggagt caaaagatta ttagggtttt tttagcataa
  2881  tagttcatca tcagtcatct actaacaaag gatacatcta tttttaccca aaatatcaca
```

-continued

```
2941   tcaccaatct gacaaaccat ttcagagtta aaggcactgt gacaatgtat tccaaagatg
3001   accatccaca atatctatgg ttgcataaga tcttctaaac ctcccatatt aagagtcagt
3061   tcagtctaat tcttctcctt cctggtttcc aataaaatgt aatgccagtg tgtgtgacta
3121   ctgagcctgt cagaaaaaaa gttatatctt ctaccttgct tgatggaaca ttcatactgg
3181   agtcctgagc caccgcataa gcagtcagac tctcctgagg ccaccatgct atgagaaagc
3241   ccaaactagt ccaccaggag agaccacatg gagaagcctg agacaatatg aagtgatac
3301   acagatagat ggataggtag gtaggtgggt ggataaatgg atggatggat agatagatag
3361   atagatagat agatagatag atatagatag atatagataaga tagagataaa tagatgatag gtatagatga
3421   tagaaagata tatagataga tagatagata gatagataga tagatagata gatagatatg
3481   gagatatgcc tggccagcct ccagctcctc taggccactg ctatagtacc agctactatt
3541   tgtctacaac catgtaaaag accccaggcc aaatctacat gagtctgttc caaattctga
3601   tccaagaaac tatgagataa taatgattaa tgttgcttaa agccactaac ttttggggtg
3661   atttgttatg cagcagttaa ccagaaacca ttccctagga catagaaaaa aaaaacagcc
3721   tatggattgt ttccctgaga cttctgtaat cactggcaag ataaaaattg aaggaatgat
3781   ggactgacta ctatgatgct cacttcctt tgctccttta attttgaattg gtttcataga
3841   aagaattgag aagtaataggg gatcaataat ctaccaattg aaccatatta ttttggcata
3901   accttttgcc agcttatgtt cacctgatag catcatcttc aaggtacgca atgctttcaa
3961   tattggatct agagctaatt atgctatatc agttccctct acccataaaa atagtgtcac
4021   tttctggatg caagagcaaa atagcgtcat gccatcttct cactagttag cagtaaactt
4081   tgcaaattat gtttctcttg ttgcccttgc cttatgtctt ttgaaatgta tttatttta
4141   tataaagttg aatgtaccga cacatgctgt accttttccct tagaaaaagt gcatatgctt
4201   gacctggctg tggtgtgttt tactggtgca aaacagataa tgtctacatt ttctagatcc
4261   tgccttctga ctaatttggc aaagtagggg tttggtattg cttcttcttt tttttcttct
4321   ggcactttgc aaagcttggg tgtaggacga gagaggaagc aatactaagt cgatttttgaa
4381   aggacaaaac caagcctgca gacaactgtg caaagaatct gcttttagat gttgtgctgt
4441   actggggtga tggtgctcat tacatgttac atgttgttgc catccaagtt tctggcacgt
4501   aaaaccataa tctatgactt ttacttttac attttcact aagatgagga gaaattgctt
4561   taccatgtca atcagttatg ccctttaaaa agggtggata agagtgagca ttacctactt
4621   gaatatcata ttgttttaaa aatcaaatag gcaactccga ggttaaaaag tttaatgttt
4681   ttctgagtaa taaaaatgta aaattgagta tggccaaatt cattgtaact aacccattca
4741   aagagttcgg gggagtaggaa gaaacttggt tttgtagaaa attctaaaca ctgttcacct
4801   gctttagaat gtggccacgt gattttttgg aaacttggtc acttgttatt atgggctttc
4861   tataggttta ttattattat tattatccac agttcttaaa tatacccca agattcttga
4921   actgttcccc attttttgtta tttgagctgt gtcctttcaa agcagctcac taatttatct
4981   gtacttaata ttctttctta ggtaatgaat gcatagcttc tatcctgagc agggccttat
5041   tcatttcctc ttttgaaaac actatcagta taaactaccc acattcaatc tgcctacagt
5101   tttggcagag cttgaaaacg ttatgattcc aagatacacc attagcttaa tatcttatct
5161   cattaagtta tgttgctttc taagcataat gtaaacaaag taggattatt aacaacttcc
5221   ctgagtcata tgtgtaattt attttttatag cagctagttg ttaatgagt gtgtctgtct
5281   ttacatagtg cttgtatttc attgtggcct atgtctttgc tgttcatgaa aaataaatct
5341   gctttcaagg atatgaaaga aataaagaaa caaactatga aagaaataaa gaaacacact
5401   ataagtaaa aaaccttatt tttactctca tgttgtcaat ggtatgaaca ggttttttt
5461   tttttttaatc cacaggatta tttctcttaa agttattgtc cataaatgtg ctgtgttttt
5521   tatttggcac aaaatagaaa aatataattc aaaattaaat ctcaactatg taaaatatat
5581   cataactaca tatatacata ttacaaactt ctacttaggt aattaacttt tatgacacca
5641   atattaacag caactgagct tgaggtttgt atcaataatt tttttctctt tctttcacta
5701   accaggacaa tacaaaccaa ctcttttttg gatataaccc attttaactt tggttttcca
5761   cagcaaatta ttcttgagtt tgcctttta tattctcta tttttcatta acaaaaccta
5821   aactggggga agttctgtgc tttgcaaaat aaaacaaggc ttattatgaa cagaaaatgt
5851   agctctccct atttagtttt atattttgcat ttagagagta ctaaaagtca acaaaaactt
5941   ttaaaaaaat taaagtgttc ttcatttgtg caccatgctt tgttggttac ttggaaagaa
6001   agacctttaa aaatatttg ttaatcaaaa tgttatagat tttgattcgg tttataatat
6061   ttagatatct aaaattttct gcaggctttg atttcagacc acacatggac tattagaaat
6121   tactgaacct ggcttcccta ggatgggtttc aagtggggta cacctactca gaagcaggcc
6181   ctcctggatg atagctagca aattcagtgg aacaagacta ggaagccctc aataagggac
6241   acttggctca ttttatatca tgcaatgaaa aagaaattaa ataatcttaa aacagacaat
6301   tcctaagaag ggctaaacct ttatatcttt tgccccttt atgacattac taataacata
6361   aattaaatat tgccctccta gaaaaaaaga tattgaggca gttgttattg tgaatattag
6421   aacaggcata cttcagcaac taactgcatt tcttagagca atataggttg cccacccagc
6481   acaaacccca ctaaatgctt tctcaaattg caaataggaa gccacgattc ttaacaatct
6541   gagctcactg tattgttgta tgacaactgt gttaagtttg ttcctgatat tataacaaat
6601   ggagtacatc tcttatctaa caagatgaaa atcttgagat aaatggttta ttttccacat
6661   gtctctacgt gtttccatga acatgtaagt agcttcgcta tttttctaaa ataggggaatt
6721   gcttacagac attttatgca aaattctttg agaaaaattt gtccccctaa gaggttccct
6781   aagttactgc cttctgccca ttttaaatgc tgagtttggc acagaaaacg tttaagaaaa
6841   tgcagaaaaa atgagcgtca tcagcaactt caaagtaagg ccatacaatt cagaatttgt
6901   tactaaaagt cttcaggac taaaccacac atggaggtat ttttccctc attctcaaa
6961   gcagaaaaag ctgtgttgta gatcgcccta gttattaat tttgcaattg attatactga
7021   ttgcatgaag atttccatta cagaaacaga tttttgagga ctaaaaatac agcaattatg
7081   ctggttactc atttaagtca gtaagtaact acaggttgtt aagaatgcag acatttttaaa
7141   cacagggagt catttacttc cttccttgaa gtacctgaaa tttctattca tgttttttt
7201   ttaaaaaaaa gaggggcaac acatgttaaa tgatagcaat caagattttt catgcaatag
7261   tttaaaaatc taaatgaat gatttctgaa agcattatag ataattaaaa tacaacattg
7321   tcttgacaaa atatctctat gaaattaaat agggcctgat cttcagaaga aggaaccaag
7381   aaatcctctt taccagctac aaagccctca aatggtggag gtgaggctca gcagagcatc
7441   ctcctgccgg catgtgtcta cttcagtctc ttcaggggtt ctcaacagga aaaggagggg
7501   atggaggagc tgggacattt tcatttgtcc cagtgaggta gtgctcatgg tattagtgc
7561   caagggtcag ggatgctaaa caaggctcat acaatgaaaa attgcccac ccaaaaagcc
7621   ctggctcctt ctcaaaagat gacctttga aattgctttc atctgctcaa gatgctctta
```

-continued

```
7681   ctgctcacaa caaatttgag tgaaaggatg aaggaaatca cccttggatc ctaattctaa
7741   ctgaattaca gaaaccaatg tcctcacagt ttaatgcagg attgcttaaa ctggcttgat
7801   gtcccacagc agggattctg atctgttttg tttgctgaaa gcaccccagc acctagaaca
7861   gtgactaaca tatattacat gcttcataaa tttatgttca atatatgaat gagtcaaagg
7921   gatccattgg gtcgcttatt aaaaatatga atcactgggc tcagcctagg cagctgagtg
7981   agaaactcca agggtctgca gaagccaagg atctgtattt ctaacaaaga cttcacgtga
8041   atcttggaat caagccatta tttggcttag aagccaaata gatctgggac aatgccttgc
8101   tccaccactt aatagggtgt gaccttgaac aagacacctc atgtttgatt cattcattaa
8161   acaaatagtc taggatgcct actctgtttc agcattgtac tactgctgag aatgctatgc
8221   tgaggacaag aatgcaggat ttgccttcat ggagctcgtg ggtccttatc tttaagatgg
8281   gaataaataa tgccaatgcc tggggttgat gtgcaagtca aatgacataa aaatataaat
8341   gcaaattaga taccaaagcc tttgcatgga tttgtttctt taccaagtcc catttaaatg
8401   gcagcaaagg agcatcgctt ccactcaaca cacagcaaag ttttctgtag accatatttc
8461   cttttctttc tttctttaat ttcaattttt attttagatt tgggggttac atgggcaggt
8521   ttgttatatg ggtgtattgg ataactctga ggtttgggct tcaagtgatc atgtcaccca
8581   ggtagtgagc atagtaccta ataggtagtt tttcagccct tgccccactc cctctctctc
8641   tcttctagtg tctattgttc ccaccttgga aaccacgttt agcatctctc tcacccaggt
8701   gacaccctct gtcagattcc acccaactct tctgtaggtt aagtaatcac accagtgaga
8761   tatttgtgtt ttaaaagctt tcgtccttt cccatttgaa attactatta ctcaagactc
8821   cacatttcaa ctaaagtgtg aaattagtaa ttatcattat caatattaat catgctgctt
8881   ttattttgtg gagttctctc acaggcatct catatgatct tagcaactca tttaaaagag
8941   gtggagttga cattataatc ccattttaa aatgctcaaa agaagctcct ttgcccaagg
9001   cactacatgg agaaggaaga atctaggtta tgcatgggtc ttctttctgt tagacatgac
9061   ctcttaagca tagtcattca gagcaagaac aaggtctcct aaggccttca ctcttatagt
9121   gtgatccacg ggccatcagg atcacctgga gtttgtcaaa aatacagcat cccaggcctc
9181   atcccaacca atggaatcag aaactgcatt ttaccagat gccccagata atgtgtatgc
9241   atgttagagt ttgaaagtac ctttctagga aaaataactg ttacatggag cacaggttga
9301   atcattaat aactcttgaa tttcttgaag tgctaaacta aacttgtaat gaatacattc
9361   tataatacca tctaatatta tttttcatga gtagcttgtg aatgttattt ttcacgagta
9421   gttgagtgaa tgaatgtgtg catgaatttt atagtgtttt cactttttct tgcaaaaaaa
9481   acagaaaagc atcaagattt gactgcagtc agtcaactat tcactcttga atcctccaat
9541   atagtacctg gatgaagagt ttgaaaatac atttcatttc catagcacgc attcaaacac
9601   ctaattattt cctcacaacc ctatatatag gactatctta tagctactag caaggcttga
9661   aggtcagagg ctaaaggaat gctgggacac aataaataat ttatctagca attatttttg
9721   catctctact catgcaaggt tcagattaga tccagagaca actcagagaa ttttagctcc
9781   ttccttgta gtactgcatg taaaccaaag atgaaaaaaa gtattgctac taagtaactg
9841   acatcttaaa atttgaatag ttataaggta taatgtgata aattcaatgg gaaaggaaaa
9901   gatcagtgcc ctggttattc agagaaaggg aagtttctcc tgagttctgt ggtcaggagt
9961   caagaggcca ggcaggtttc aacaggcaat gtattcttca gtagtagagt ttcaagatga
10021  gatggagtcc agatgaggcc ccaggcctag aagaatatca gctgtatcta attgttaggg
10081  aggaggctca aagaccacaa tctgtgtgtg ttttggaggg catggggtac cagggagctt
10141  ggttgataac aactatggct gaagtctgtg ccacaagatc ctggtgcaag ttactgttac
10201  aaagcctccc tcttccacta cagagcttct gctataatcc ctacttcggt gaggatagat
10261  tggggaactg gagtagtgtg gggacaacca tatgctgatg ggaggatttt ctggagaaag
10321  caaagggaga agggaggaga aggggaattg ggttgatact acattctagt taatgtgcac
10381  tttctagaat gcaaattctg taagccccct ggcccacaca cacaaaaaga tcctgagaaa
10441  gctgacctct accaagtcct agtagaggct catacacaca gagcgtgttc aaaaagcact
10501  atcaagtgat aatggttaac agtgtcgagc agttggctct cctaagctcc ttctctgctc
10561  agggaattaa aatagatgca cagccagact agagggactt tcctttctgt gatatgaacc
10621  atcacttaag cgtggctaca gcccagctat ctatctagtc agactctcag actagatagt
10681  cctcattctc ctagaagccg gaagaaactt agaaaagatt agcaggaaaa tctgtactaa
10741  ttcctgtggg tttcccatgt attttatttt tagtttgtta attagggtat atttgtggtt
10801  ttttattctg cttcattttt taaaatacaa tcagactgtg tgacttcttg tttcagatct
10861  ctttcacaca cagtaaaaaa ataatggatt cttgggtact gtgtgtttat gtgtattatt
10921  ttgggttcag ttgggtttct ctgttaggct tgcctgtcac tacttctatc caaatgacta
10981  tttcataaca ctcaggaaga atcagaagga catacctaat aatttctctg ccctcccta
11041  cccttccacc caattccatg ctgggcagcc tcttttatat ccaaaaacct tatacatttc
11101  gccaaaggaa tcagtactaa tgggagcatc tgtaacttgg ttgttctcag gtttgagatc
11161  ttgagagaga aaatggaaaa gttaacactg aagacctcag gtgactggga tttctggagg
11221  tcacaggaac aaattcagtt atgctctact gtccttcctg accaaggcct gctccctaga
11281  tagcactggc tattttcccc aatcacttca gctgaacact aatgttttgg tgatactgat
11341  gtccatagag aacagcagtg ggatttcact aagatgggaa gttactgtgt tcacctgcca
11401  taaacatgaa acaatacagc aggtattcat tcacccatct cttattcaga tcagagacat
11461  tctcacagac catatccaga ctaaagagca ttctgaatat ttatttttct ttttttttt
11521  tttaattta gagacagggt ctcactctgc tgcccaggct ggagtgcaat ggtggaatca
11581  ccactcacct cagcctcaac attctgggct caagcaatcc tctcacatca gccttctgat
11641  tagctgagac tacaggcatc caccccaggc ccagttattt ttttctttt agggatgagg
11701  tgttgctata ttgtccaggc tgtcttgaac tcttggcctc aagagatcct cctgccttgg
11761  cctcccaaag tgctggtatg aaggcatgaa acatcatacc tgactgattc tgaatatttc
11821  aaactgtaca tttaaaatcc aactcaaatg gcatggcaca ccctgctgtg aaagcaacac
11881  actccaggca gaatcctaga aagctctgag cactcagcat aatcctaatt gtcatcaggt
11941  ctgtaaccac tgctgtttct tcacaaagtc actatttgag gcatttact caaagttgac
12001  tgaatttcaa gaaaggtatg agacacaatc actatcactt gtattagttt tcatttgaat
12061  atcatactgt ccataaattg ttagccacag ggtgggagga agtatgtggg ggccagtttg
12121  tgcgcacata gctgccattc gtggttcagt tctccatgct aagaaaagga gaacaaacta
12181  gaactttctg tgctgattcg gttaatactt tctctgtaga tgactcagaa ccttcctgat
12241  aatatttact tataatttc tacaggagct tagaatctgt atctgtttta tgaaaatatc
12301  cattggtttc ataattatcc tgcaacctga taaattatct taaattgatg gcatacccag
12361  ctgtgtttta actcctgacc ccaaaactaa agctaaaatg ttgccatttc aacttaaaa
```

-continued

```
12421  ctaataaatg ccacaaaaaa aatcaatgtc tatctcaagt aaaaaccaag agcaattaat
12481  ggcaattaaa gtgactgtta tatgtttcca taattctttt aaatacatta catgtagaca
12541  ttaagtacat taagaaaatt gtgatttggg tttttactt tcagagaaat ggaaattatc
12601  ctgaccctag cataaagatg ctgtgaattt tctccatctat gtgaaatttc actgactcct
12661  attttatttc ttggctgttg tgttatacaa aaatacattt ttaaaataaa ataaaatttc
12721  attcattcat atgcactcat agaaatctgt acccaaaact ccactgaaaa taacatatct
12781  tcagttcaag ttataccctt ctagatggag aagtgaacag atcagtattt tacataagct
12841  gaatacttaa gcctcaccac acaggtaatt aacctcaagt agtacaagaa ctttcatgtt
12901  tcttttctaa attttgcctc aggtattaac cacccaaaaa gtagcaggct gcctttaaac
12961  atctctggca aatagctggg tagaatttca catggcataa taagaactt actaacataa
13021  cttccaaaaa attaaaagct agtttggatt gctgttgttg ttgggtgctt ggggctattt
13081  ggagtgaaaa ttttctgcag ctaattagaa attcacacg attaggaagc agagtctggc
13141  attgttcccc ttcaagtgtt gggctagagc tagttctaaa gagagaatat gttgaagttt
13201  acaagatatc aatacaaaag tattgatatc catggtttga gtctggctat cttagcctca
13261  acgaagagca ttctaattgt cactgaaatc agatatgacc aggtggaaac aggattttct
13321  tagactgcct ttaaaatgat ctaagtgtgc aaattaccat cctaatctaa ttcctgaata
13381  tgcaaaacta ttctaattaa agaggaagct ctagaagaat taataatgac tgactgtcat
13441  tcttcaatgt cctggaataa agtatcttgt aataaatgga ttttcatatt actttcccct
13501  ttgtgagtac ccatggctga cacatggtgt gaaagaactc tgctcagtaa gaagatagta
13561  tttagcttag tcaattaatc atattagctc cttcctgaat gccaaataaa acatataggg
13621  aaatgctatg gtccaaatat ccaccaaaat ttatgtgtcg aaacttaaat ctccattgtg
13681  atagtattaa taggtggagt tttgggtgaa gtgattaagt catgagggct tatctctcat
13741  ggattaatac ttttcaaag ggctggaggg aactagttag gccatgtgag gatacagagt
13801  tcatcccatc tggaggatgc agcaacaagt cactatcttg gaagcagaca cagggcccta
13861  tccagacaca aaacttgcta gtgcttggt tttgaacttc ccagcctcca gaactatgag
13921  aactaaattt ctgcttttta taaattaccc aggcttgggt attttgttat agcagcacaa
13981  atagaccaag acaggagaac cagactgtca gtagtggcga gagcatgact cagatgcact
14041  gggagagcca gagacaccag gagagagcca ctgggaggga gcaggagagt ttgtttctaa
14101  ggctgcctca gaacctcata attaatgagc tctttatatg ccaggccttg ggttgaacac
14161  ttcacatgca tcattttatt taatcctcac agtcatatga gatagattct cttactgtgc
14221  ctatttctca tataaggata tcgaggttta gaatgggaag tggccagaac tccaaccaaa
14281  tagatctgtg attgcagtgc aaagcctggc tgtgctggtt aagagcacag ccagaacgac
14341  tatggtctac taccctaagc atcatttcct ctggtttcaa agacacaaag tagcattttc
14401  taaagaaagt aagccttctc tgaatcagtg ttaattctac tgatcacgga attgagaagt
14461  atgctattag atggaggtga aagttcttag ttaatggaat tcttatgtgg ctttcagaac
14521  attaacgtgg aaaactgaat acaaatattc tgtggtactt ctccaacatc ctaaaaagca
14581  ctaattattt actccctcct tcaagactac tattgtccaa tgaacgacat cactaagaat
14641  cattagaagt ggcttgtaca tattgagaca atagatacaa agacaaagtc acaagaaatc
14701  taagtcccct tgcctactgg tccccagaca acagtataca ggatactggg actcacagat
14761  agtgacttct aaaaaaaga aaccaaaaaa aaaaaaaaaa gacaggagac agtgggttc
14821  tcactgctcc tgacctcccc agtaagatca tttggctcct ttctctcagc atgtgggaaa
14881  cccaagggtg atgtcaaact catcctggaa gcctctgtac ttcagttaaa tctcctggag
14941  atacattgga tgtaagaaa acttactaga gggcaagaca tgcattgcta atatatgaaa
15001  atctctttct caacctcaag tatctgtggt atctgtgggt gtgtctatac atatagatat
15061  gtgtgtgtgt gtgtgtatgt atatattctc cactctgtgt gtgtgtgtgt gtgtgtgtgt
15121  gtgtgtgtgt gtgtgtgacg ccaaatttca caaaactctc cagtttatag ttcaattccc
15181  cactcaggcc gtcagtgttc ccactgacat gacaggaggg atctttctgc atctctatca
15241  atatgacaag aagagaatct gcttctattg gtatccttac tttgaagtga tgtgaaaccc
15301  caccgcttt atttgttgg taaaaatccc taagaaccct cctatctttg accccatatg
15361  gagtcttata atctagtctc acttggggca ccagaaactt ttaggccatc actgctgaaa
15421  ttggtactgg aaaagggaat aatatctctt agaaaagtca gagagactaa caggaaattg
15481  tgtgaggaga atattagaag gaaaaaagca gagagagatt tttgtgtttg gttttactc
15541  acactttaa agttaactct tcactgttta cagtattctt ggttgcttcg ctttggctca
15601  ttggttttta tgaatcagct ttaggactat tacagagcat tgagaaaaca attatttta
15661  aggagtttct ttgatgctat tattttgtgt ataagacaca ccatccaaga ggcttttgca
15721  tcaatgacta agaaatataa aatgagagat attttttgaga tagatgatag atagatagaa
15781  aacagcactg aggctaataa cagttattga tataaagcag ggaggaaatg tctccatttt
15841  ttattatgt attgtacaga tatcccttat ttcaaagtaa atcctacgta cccattttct
15901  aatgtgtata attaaaatag aaataaatga tcagaaacca agaagaaaga agataaaaat
15961  aatttgtcca gaaagatgcc acacttaatt cctaatatga ctttgagcct ttgaaaatca
16021  gaacaaaacc aaggaaagaa aatggattac attattctta ttatcaagat tactaagcaa
16081  aaaaaaaaat gtttttctg gcaataaatg ctagtagaaa ttggtcccct aaattcttat
16141  gtaaggatca tttgaaagac ccatatgcaa ctttcaataa ctccaattga aattatatcg
16201  cagaaacaga gcttaaagta tgcagaggaa ggaagagtta acatatcttt tttcgatatc
16261  tgttttgtga attggctttt aggagggtgct ggacaacatg cattcaaagt tttaacttcc
16321  caatgaagac ctgaagtggt gaaattgaca ttttgtctgg gaagcttgta tgtgtgccct
16381  aaaagggata tctgtacaat acgtaaataa aaaatggaga ccttcagagg tatcaatgtg
16441  tagggtcaaa agtccttctg tctctatctg gatatagtgc agcaaacact ctaggtattt
16501  ccagtagaaa gagatttaat gcaggaaact aagtgattac acactcagca gaagagctgg
16561  aaaagcctga gtcagggggat tgcaacatgt cttttggctt caaggtctgc tgtgcaccag
16621  atttcagaaa attactgcta ctgttaatac tactgctgcc atgaatatgt ctgccttcca
16681  ctcatgatgc tgctgactag accgagaaac gtggagtcca gaccttggtt gtcagctgcc
16741  actgttgcag gaagacagcc tttaacttc ttccactttt caaatctctt ccaagtgcct
16801  atcacaatat atccagaatc ttagttgcaa aggaatctga gaaatgcaaa ttttatcctt
16861  ccaggctttc agtacagggg agggagagag agagagcaag atataaatgg atgccaaatg
16921  cccaaagaca gtatatagcg tacccctcca aagagattaa attttgctca tgttttggaa
16981  cagatctcca attgagacct ttaagttctg tgtcatagaa tatgaaatat gttatttttgt
17041  ctagaaaatg ttaagtgcta tgtgttgtca cctcttcagt tcctgaatca gtcctgcccg
17101  aagtggaaag tacttgagct actccagccc tcaccatctt tcttcttaag agagaaggag
```

```
17161  gaagatgacc ccagtaagga tgggtcagca tagttcagaa tgaaggatag aacccttggg
17221  agtctctgtg gttcctgagc tgacctgct gtctcctggg cccagaatac aagtaccctg
17281  gaaccagcag acccagttcc agcctctctt gtcaattctg ttgtgctgca agtgagttgt
17341  gtcacgcttt agggatgaat cttaatatat agaaacaatt acttgaatga attcatttaa
17401  ttgcttggtg aataatattg gctaaaagt aatttatttt aatagagctg atattaaact
17461  actgttttct agaataaagg ccaacaagtt aaagccattc ctgagatggc atagatctgc
17521  atcctatgtt tgttatagta gagaggaatt atttctgaat tgagcaagtt tatttagatt
17581  tgtttaaaga aatgacgtgt agatcaagcc ttcttttcca ccatatacag ttggtatttg
17641  attagtcagg gagtcatttt tgcctcttta gttctgacag tagaatttga aaaaggattt
17701  gaagatgctt taatagttta gacagcttag actccataat tgttcctgtc tataataaaa
17761  tagaatgcaa atctattctg catgatctaa aatcacaaat gtaaacatcc acatcagaga
17821  gatggctgac aatacaaggg caagcttcat gttggcaaaa gtcagattta ccatgttgat
17881  aaaaatcaga ctaggcttca aattgttact gtcaaaaatg cttcttggaa gaatttgtca
17941  ttttgaaaag caaggaacaa ctatgtttta tttattttat ttattcctaa tttaacatgt
18001  ttaagcttta ggaatacttt ctcatcaaat aaaatgattg ctaagttgta aaacttatta
18061  gtcacactat taggtcttta gtgtaaggta gcaaacacct gtctctctaa ataatctcca
18121  aagtgggatg tgctaatccc atggagtacc ttggatttct ttttcttgta tcatactttc
18181  ccaatttatt ttctgtgtct tttttataat gtatgtataa atctgaccat atatgtatat
18241  aacttataaa taaatatgca tatattagta gtttgtgctc aattttttaa taatggaggt
18301  gcaaagtcaa taattttgaa gattaccatt ctacacaaat gttggcctgc aaaacctgca
18361  gtaatccacc cttttctcaa acttcattca atcaagagct cagcaagcat cttttcttga
18421  attttttaata ttttaatgga tattggaaga tggtccttga agtcagagaa tcagaacctt
18481  atttctgaaa gggtactaga gataatatta tccaactttc tcattttttt tctgatgagg
18541  aaaatgaaac cagggaaagc tgacaatgtg acctccttt acctatagag gaggaaaaca
18601  tggtgctttt cctgtagcca tcaaatctgc ttatgctcat ccaaatcata acatgagtgc
18661  tgctgatgtc aatgcctgta atcggccata catgttatgg gtagtgatat agacttccag
18721  tcaaatgtta ctgcatgtgt cfgcttcagt ccatggtagt tgcatcatta ctgtcatact
18781  attagtgcag gaaaggtcaa gtaatacttc ttggggctaac agcacataat tttcattcat
18841  cattaacatt tgtattcact attctttcaa actgaagtct ttgagcctat actctctggc
18901  cctaaatctt atattcatgc aaatttacat aactgccttt gctgaatctt ggaaatgtgt
18961  tgatttgttg gattaaaata cacagataaa aatcataaca ctaactatgt gtggttaact
19021  ttatattaca aggccattat gatttctctt ttggttccaa cttttgtgct ctttattttg
19081  cttagtggtg aaaaaatact aaccctatag aattggggggc tttctatctc gattttataa
19141  tgagatggcc atgtttgtca gcccgtttac cacatgatac cccactcttc atggccgccc
19201  atgctagtct cagcttata ctagggtagc attctaagct cttgttctcc cactacccct
19261  gttagagcca attcctccag gacaccaaca taaacaaggt agacccttc tttcaagtat
19321  tctccctggc tgatcggtac tttctccatt gttagataca atggtcctgc tcctgctcga
19381  gttttctgaa gttcctgatg gctgaccatc tgtttattcc tttggattct cttacaaagc
19441  cttcatctgg ttctcctgtt ttatttctca taagctgaac tatctccttt cagggctcct
19501  gtcctctttc catccctttg tgtgagcatg ccacaaggct ccatcctgtc ttctcctctc
19561  ttttagttga aatctctttc attcacagaa cttcggcaat caccactcta tccccacacc
19621  tgcctctttc atgctctgc tataaagcaa cagattcctg ctatacttac ctgaaaagtc
19681  ccattgatat cccaaggtca atatatttca tcccaaaata agtcctcctg cttctctcat
19741  cttattataa gtagcaccat ttctacaatc tcttaagctc aaaaccttc tacagtcttc
19801  taccgccatc taattagtta cagtatccta agttttcatt taaaatgctc cttactttca
19861  actttttctt tccattttag atgctgacag ccctcttcag acctgcactg ccccatcatg
19921  atcaacatca tagaatgaaa tatctaacag catgtctgct gcaagacagt agaggaaatg
19981  tctaacatag aaaaaggcct ggatcgacgg cttgaagtca aacgtgtgag aaaatgtggc
20041  ataactaaat actctttccc aaagtgtttt tctagttttag ctcctcccac attttccagg
20101  gctcctctga ctcaaaaaaa ttaatttgac caatctagaa ttagaaaata gtaccttatt
20161  tcagtaaaga acacgttgat cccagaagta aatgaacgta tttattatta atttacaatg
20221  aaatatgctg acagccaacc cctttccctc taaaagaaaa acatattgct ccgcaacctg
20281  ccccagacct gtccaactta tagaaatatc tgaagtgata ataattgtta ctggttttaa
20341  gttataaact tagccctaat gagagagatt ttattattt tattaacatt tcatatgaca
20401  aacaataaag ttccttttga tttggattta gcacaaagta tcttaaaacg tctgaatgca
20461  aaggcaagtt tgaaattcgc cagttgggtg tgctggcgtc ccccaactag ctgcagcccc
20521  caattcccat cagcacaggt ggctggagcc accatcgaag taaaaaaagc aaacatcagc
20581  cactggcctc tcctctggtg actgtcagaa cccactctcc cacccaaggg caacttcctg
20641  gcagaccttt gtttttctgc ccctcacagt gaccttgaaa cctctcagaa ataaaatgtt
20701  atttcttctc atagcctttc agcttatcaa aaaacaacaa aaaaaaacat tttattgagg
20761  tacaagcgac atacaaaagg ctgtacatat tcaatatata caacttgctg agtttggaga
20821  caagtatata tccatgaaac tcttaacaca atctatgcca taaacatatc catcacttca
20881  gaaagtttcc tcccaccctc ttcatttgtt atcagtaatt tttttgtgat aggaacagaa
20941  tgtaagatct accctcttag caaaatttta agtacacaat gcaatattgt taattatggg
21001  cattatgctg tacagtagat ctccagcact tatttatttg tataactgaa actttgtacc
21061  atttgactaa tacttccatt tccttctcac cccagcacct ggcaaccact attctactct
21121  ctgtctctat gagtttgaat ttttagatt cctcacatac gtggtacatt agcagaatga
21181  aggatacaaa tcacatgatt atctcaatag attggagaaa aagcatttga caaacttcaa
21241  caccctttta tggtaaaaac tctcaacaaa ttaggtacaa aaggaactta cctcaacata
21301  ataaaagcca agtaaataaa aataaagctc ggccgggcac agtggctcat gtctgtaatc
21361  ccagcacttt gggaggctga ggctggtgga tcacctgagg tcgggagttc gagaccagcc
21421  tgacaaacat gggagaaacc gatctctact aaaaatacaa aattagcagg gcatggtggc
21481  gcatacctgt aatcccagct actcaggagg ctgaggcagt agaatcactt caacccagga
21541  ggcagaggtt gcagtgagcc aaaatcatgc cattgcactc cagcctgggt gacaagagca
21601  aaagtccatc tcaatgcata catatataca tacatacata catacataca tacatacata
21661  cataaagdtc acagctaaca tcacactcaa tggtgaaaaa ctgaaaactt ttddtttaag
21721  atctggaaca ctgcaaggat gcccactctc acccccttcta ttcaacatag gadtctaagt
21781  cttagcatta ggtaagaaaa agaaacaaaa ggcatctaaa tcagaaaaag ggaagtaaaa
21841  tgatctctgt ttttagatga cttgatctta catgcagaaa atcctaaaga caccaccaaa
```

-continued

```
21901   aaattgttag aactaataaa tgaattcagt caagttgcag aatacaaaat caacatataa
21961   aaatcagttg tatttttgta cactaataac aaacaacccg aaaataaaga gaacaatcgc
22021   atttacaaca gcatcaaaat aataaaatac ttacgaacaa acttaactag gaggtgaaag
22081   acctgtacac tgaacactat aaaacattga ttaaagaac ttttagcttc ccttaaactc
22141   attatgtaca aactcattat gtaacttcct gagaagttag gaaaccgact tcaggttata
22201   caactatagt tagtggggca gtcaggatta aaacccatgg ttcctgaagt ctggtcctgg
22261   gtgactctgt catgtcacac tgccttccac ccagcttgag tctacaagga gcagccctgg
22321   tcagtcccaa aggggtcggg cttggatagt gattccatgt gggaatgcct tcctagtatt
22381   tcttgggaaa ttgttgtgtt tttcaaaatc ccaagaaaaa aactctcaag aattttaaa
22441   gactgggaaa gtcttacaa tttgcctgca agaattaaaa cattgattgc taaaacacag
22501   caatcaatgt agagatgttg ctgatttgaa gggctccact gacatcaggt ggaaagcaac
22561   cgaaggaaat atgaacacac aaagtggagg ttaaggttga ccagcatgtc taggaattga
22621   gacaggagca caggaaagag aagtggtcac tacattatgg gtcagtcttg tctataactg
22681   ttgcaatgtt ataagtgagc attcatagcc atagctggta ctaacagtaa gtcaagctta
22741   caaatgaaat aatgattagt atgtctatac aaatagaata ttttaaacaa atcctatgag
22801   tggtattcca agaaataaca agttttagaa gcaatacaag tttttaatt ggcaattttg
22861   agacatgatt ctgcatagtg ccaagagatc tgaactgtgg tattaatcaa atactaccca
22921   atagtctggg ctgacatttt acagcatttg aatatttgct atgggaaaaa aaattataaa
22981   tactactaaa agtaaaattt atttgttaaa aaataaaact cttttagat atctatggct
23041   atgatttctt tttttttt tttttgaga tggagtctcg ctctgtcacc caggctggag
23101   tgcagtggtg cgatcttggc tcactgcaag ctcggcctcc ccggttcacg ccattcttct
23161   gcctcaacct cctgagtagc tgggaccaca gctcccgcca ccacacctgg ctaatttttt
23221   gtattttag tagagacggg gtttcactgt gttagccagg atggtctcga tctcctgacc
23281   ttgtgatccg cccgcctcgg cctcccaaag tgctgggatt acaaggcatg agccacagca
23341   cctggcccaa tctatagcta tgatttcaat gtttgttttc tctcaaactt atgttaaaat
23401   ttaattacca ttgtaatagt attaagaggt gaaacctga agaggtgatt aagctctacc
23461   ttcatgaatg aattaatgcc gccattatac aggattgggt ttcttaagag agaattccta
23521   taaaggatg agtttggccc cctcttgctt tctctcaccc tctctttgcc catagaatga
23581   tgcagcaaga aagtgctcac cagatgctag ccccttgaac ctggatttcc caaacttcag
23641   aatcataagc caataaattt ctgtccatta aaaattaccc agtctgtggt attctgtagc
23701   acaaaacaaa ctaagccata caaaataata tttaaagaat atgaagaggg ttggaagtat
23761   tttaaagaca aaaacagctc atgatttaag aaattattga gatttcctgg gaatatggct
23821   ctcttacttt catatcctat agattatgat cagatagaaa tttagaaata ctgggcttag
23881   gtcatgagtg ggacatagtc ccaaccagca tggattattg ttctaattta gaaactttca
23941   taaagagaaa aaagtaaaag tttttcttgt attaagtgaa ctacttaata ctgatttgaa
24001   attttgcata aaatattttg aaggacaaaa agcagaattc actaagaatt caaccaaata
24061   ttctgcagaa aaatagctgg ttaagtgtta cctccccca aatcattcca tgcattttct
24121   ctctctgttc attgtgataa ctaccatttt tgacacaagt tttattggac attctatttc
24181   caaaatgtca tagaatatca gcctttcctc caggttgaaa aaacaaaact gcctatcctt
24241   ggtggtttcc tttgggactt cagatgctgc tcagacacag tgggccttct ataattctaa
24301   cccaaatgtg gacgatggga aagtttaact ttttaaaggt caaaacatgc aatatatccc
24361   tactaataac tattcttact gaaaccacat tcaatctggt aataatttta tttaactgaa
24421   cgattgttca catctagaaa acaagaact aggatggagg agaatattta ttactttaaa
24481   caaattcgta tgaataacaa aaagattgag atgaaatatt tcatttggat gaaaagtaat
24541   agagaaaaat ctgctatctc aaagcctgat gaggaagatt gtgccctaaa atcatctctt
24601   cttatctaca gaaagggccc attattctcc atgggtata gtactacttg ggtatgcatt
24661   cttttttttt tttttttga gacggagatt cgctctgtct cccaggctgg agtgcagtgg
24721   cgcgatctcg gctcactgca agctccgcct cccggggttca cgccattctc ctgcctcagt
24781   ctcccaaatt gctgggacta caggcgtccg ccaccacgcc cagctaatgt ttttgtattt
24841   ttagtagaga cagggtttca ccatgttagc cacaacggtc tcgatctcct gacctcgtga
24901   tccgcccgcc tcggcctccc aaagggctga gattacaggc gtgagccacc gcgcccggcc
24961   ctacttgggt atgcattctt aatccagagc tgcaaataaa tggttctttc caaacctatt
25021   aattatttat catgacaatt tgtttcttaa aaatccaaca aactctggaa ctgtgagaat
25081   atacccttgt caagtagaca tttatttttt aaaaaatatt tttacatgat gccacatggt
25141   accaaaagca ggtatagggg taaaaataaa gtcctttagt tagaaaagga gcagagtcac
25201   attgcttttt ggtattctat atccagatct tcagtttgat aaatcccttt tatggctctc
25261   aatgtacaca ttttcagaag actcagaagc cttcagaaaa aaaccaaagc aacattatat
25321   ttcatgaaag ttctccctctg ctaaacaaga aatggaagaa gtgaaaaaca ataaacaaaa
25381   ggaaaagtta acatctcatg aatatcttta tagtgtggtt aatattttta atatataatg
25441   agttttttaaa aatcaataag aaaaaaataa ctcaagtttt tttaaataag gcagaaactg
25501   tataggcaat tcatgaaaga agaaacaaat gtacaacaaa cacaaagtca tgttcaacac
25561   aactaacaag tcaataaaaa aaaacctaaa ataatgtgtc attttttaca tatcagatta
25621   gcaaaactta taaagaatgg taatactttta taaataaaaa tgtatgggtg gggtgggaaa
25681   ggcactctaa agagtgatac catgtttctg ggcaaaaatt acccaaatat accaaaacct
25741   ttttaaagttg caattttttg ccaggatttt aaaaaaaatt ttttctaagg aaacaattag
25801   acaaggagac aaagaaatag ttacagaacg tttctgcag cctgtttat aatagcaaaa
25861   tattagaaac agccaaagta tctaataata atgaattttt ttaaataaat catggtaatc
25921   catataacaa attggcctaa aaagaagtgt gcaagccaca gtacaataaa gatattctga
25981   tttcattcct gtaaacacat atgtgtggat atgggtatct agatgcaata aaagactcag
26041   gaaataaaat gtatatacca acaaatattt cttgagtgaa tgagtcaatg aatatggtaa
26101   cagtgattat ctccaggtat cagtattatg gatgattgtg tatgtttgc tgatttacat
26161   tttgtttcct tctttccttc cttccttcct tctcttctt tcttcttcc tttcttcctt
26221   ttctttcttt ttctcttctt tctctttctt tcttttctc tcttttctct ccttttgat
26281   cccattcttc cttgttttca acctacactg gcttctcag ccatgtatga acttctctct
26341   cccttcacct acatggtaaa atgtaaaaag tcttatattc tactcaaaag gaagatattg
26401   ctgacttgag tacaacttttt ttgaagcaat atagatgcct tgcattcacc cttaggttgt
26461   atgataacag gaaaaccaaa tgaagccaaa aatccagagc atgtgttaaa aatcagattt
26521   catcattaac aaatatcatc ataactaaaa ttcagataac taaggttttc caccatatgg
26581   ctagagcaaa gtttattcta tacctatcac tgtgcagaac cacaaaaagc actgagaata
```

-continued

```
26641  cagaaaggaa caaaaaacag tttctaaact ctagaaagtc acaatcccaa ggggtaatcg
26701  aatgtgccaa tgttagtctt aatttaaaca aagctcctca tgagtaacca gttctgcctg
26761  aggacacaga aaaggtaggg aagaacttaa aggtggaatt tagaaagtga gtatgcattc
26821  ctcaggtata aaaagactgg aagggcattt caagtaaaca gactagccag caaaaagata
26881  aggaagcaga aaagttcctg caatagtagg tgtggcaaaa gttctagctc tgcagaagaa
26941  tttggaagta aaggtggaaa gtgcatttgg cctgaatgac aattaacagt tacctggata
27001  gttcagtttg catgtggctg agttttacag attcaaagcc ccctacattt aaatgatagt
27061  gtctcaaact attaataggt ccttgttcag ctatagtggc aggcaattgc ctttgttcat
27121  taaagtggaa tattttttgtt ttccttgcca agaaaggagt gatttcactt ttgtcttttt
27181  tcccttctcag ttctttccat ttatgttttt cagacacaga gacacacccg ttaagccagg
27241  gtttcaatga aagaaaacta gccaatccag ttatgatatc gtcactggtg gtgttaatat
27301  ggagacagtt gccttcttgt tactcaatag ggtgagactt tgaaaaaggc ttgggcatgt
27361  gcgtggagcc agtgtgtctg gcttcagcca cctccttctc tcgcattgcc aaagaaatag
27421  aagcaaagaa accatctcct tattgttctc ttgcataaat aggccagctg cccatagggg
27481  gagggtagcg tctaggcatt ttatgtgacc tgctatggaa gggtggggtt accgtctcaa
27541  aattcctgct cctgaaagtg gggggaaaggg ccacttccaa ctaactaaag taaaagtact
27601  gacctgcaag cctgctgact tctgttaata agaaagaatg ctagaacatt tgctgctagc
27661  aaggacaact gcagaaaatg cagttcagac cgtcatagga gacttgaaga ttggcagctc
27721  ctcaccatgc tgttcagcat caaaaggcca ccctctacct tttttttttt ttgaccagat
27781  acacacaatt gagcccttct gaatctggca tcacagacgt tgagacatac ttttgcagag
27841  cagtttatga tgacatttat gagctatgcc tcacagtcat ctctcaaggt gagtgaaggc
27901  aatccaacat acggggaaac tgaagtgttg ggagcccag tgcaggccct ggcaagttga
27961  agcctcaaga gatggagtga caaaccaaca aactgttcaa accaagaaat ttaattcttg
28021  aatggagatt gtctctttt gagtgggaaa gggaaagtat agttagggag acaagttgga
28081  taaagataag tttcagggga ataaatacag ggggcaaatc taattaaac ctatctttgg
28141  tatgcggcca actcaaagca tgaataaggg gatcctagga atattacaaa agagcaatat
28201  cctattccac taaaaaggaa gctgtttctc ccaaaactga aaggcaaaag taatttcaaa
28261  gatactagac acatagacta aattcaatgt cagccaaaga aacagcagaa gttcaaggtt
28321  aaatcatacc atgaaacagc caaatgtgta cctgggggct acatggatga gctatacatt
28381  gtcccggtag gtttaaatgg cggaatcttt gtcaatggcc tgacatcatg gagtctctg
28441  cataaccctt tggctcagaa agcatagata cagaatttac tctctttaaa gtatcatatc
28501  tcattactac catagaagat tctaggtaaa aatctagttt tccatgaaaa acttttaaat
28561  atttattaaa ctccccccagt gaggtgattg ttttttaaaca aattatttc agaggtggaa
28621  taagcaaacc tctgaagcaa aggttaagag gcttcatttt acctttttta taaggacatt
28681  tttaacagca acttttttg ttttaaaat cttagttcaa tcttatttgc catcagtgag
28741  atataaaaag gttgcacagc attgggaaa aaaaaattga ctaccttgtc aaaaaggagg
28801  tcatatctca ccatgctaac tgcagtcaag aactcatttc aagtgctggg attctacttt
28861  tcggatctta gctcatgttg tttctattgt gaatgtagcc tactcaaagc cgttttcttt
28921  ctgtttagct ttattaagtt ttgcttttgt cccgggcttt ggaggcatgg tctgagaagt
28981  cgggctgacc tgaatttgga tcccagctcc caagttacaa gctggagagc tggaactttc
29041  ctcctttct ctctttgatc tctcagagct ttcctatctt tattaaaat ggcataagtg
29101  gccaggcatg ttggcttatg cctgtaatcc cagtgctttg ggaggctgag gtgagagaat
29161  cacttgaggc cagtagttca agattagcct gggcagcaag gcaagaccct atctctacaa
29221  aaaataaaaa ttaaaaaatt acctgggcat ggtggcatgc ctgtagtccc agctactcag
29281  gagggtgagg caggaggatt gcttgagccc aggagtttga ggctacaatg agctatgatc
29341  atgccactgc actccagctt ggtgacagag caagaccctc ctccctaagta gatagataga
29401  tagatggata aatagataga tagatgatag atagatagat agatagatag atagatagat
29461  agatatgata gataaataaa taaggcataa ggttattata aaggcaaaac aaagaactat
29521  cttaaagcaa ataataaatg atgaattgca ccatgattca tccagctgcc aaaaaagaaa
29581  cttggacacc atccttgact tctcctcctt tctcctatac acaaacaact ggtcatcaag
29641  tcttatcaac cccttcctct ctattctcat ttccactgct tcatctcaga ttatcaggct
29701  cccatgtcta gcctcaccct gtcctaatgt gttcccttg ctgccactat attatgcttc
29761  ctcagccaaa aatatgatgc tgtcattgcc tgctttgact ccagtatctc ctgctgcatc
29821  tggggaaaaa gtcaaggcaa cttattacct ggttccagca cacctgcctc tccagtctca
29881  tctttggctc ctccccctat cccgacccct ttctatcctt tctctagctc tctctgccca
29941  accatactac actattttgc agcagtaaat acgagaatca gaattattta agattagtt
30001  taagtgccac ctcttcttgg aaattttgt aaactcaccc tctcatccca cctagtctga
30061  gttgagagct tcttccaaag tctcccaagc acctttcatc atagcacatg tttctctggg
30121  tagtaattat ctgtgggctt cttaaggata aggactgtct tttcagtctt tgtaacctca
30181  acagctagca cagtactttg catgaaggat gtgcttcatg actgaatgaa aaaatgaatg
30241  aactcataca cctagaatag tattagatgc attggaggca ttccataaga gctagttggg
30301  tttcctttcc ttctttctca gatcaagtcc agaatcaaga gatttctgaa atggggctgg
30361  gcacggtggc tcacacctgt aatcccagca ctttgggatg ctgatgcggg tggatcactt
30421  gaggcctgga gtttgagacc agcctagcca acatggtgaa acccccatct ctactaaaaa
30481  tacaaaaagt agtcaggcat ggtggcaggc gcctgtactc ccagctactc agaaagctga
30541  ggcaggagaa tcacttgaac ccaggaggca gaggctgcag tgagcttaga tcgctccatt
30601  gtactccagc ctgggcgaca gagtgacact ctcaaaaaaa aaaaaagaa agaaagaaa
30661  agaaagaagg agagagagag agagagattt ctgaactggt aattgttttg caaggacttc
30721  tgtgaggtgt gaggtgaagt tttatctttc ttctatacat cccaggacat aactgactac
30781  tttccattct tttttcttct cacctcccta cacacacaca cacacacaca cacacacaca
30841  cacacacaac ccacattccc ccctacattc cacagaagta tcactagcat ctcggaaggg
30901  tcccttgaac taatctgccc ttccatggca cctctagaca tttggaccct tggatttatg
30961  tagagtcact tggggagctt tttaagacac agatgtctgt gcctcaccc catccctag
31021  caagtgtagg gtggaacaca atggttatag tttcaaaag caatccccaa agtaatccag
31081  cagatcttcc aggggttggga actactgctc acaggtcaaa ctttttagttc caaaggacaa
31141  aaagaaatac tattcaatct gtgaccccct cccatgagcc agctcaacag taacccaagc
31201  atgctgttgt tgccaggggg agaaaaaaaa aagaaagttt gtatttttat ttatatactg
31261  atttatactt gtgttgctcc ataactgttt agggtgccct agggcaatag tattctctct
31321  gtcaacaaat ggaaaactat gaaacctcac aaaatttata tccatcagat aacaagtcct
```

-continued

```
31381   tcctaattta aagaatttgt ttcctgtgat tttgaagggg gttcttctgc aatattgagt
31441   ctcccttttcc tgacattcct cagaaagctg cgcaactttg gggctcatga tcctccaagg
31501   aaactcgggc atttctcttg ctgtcagttt gcatttccaa tgatgtccct tatactgata
31561   caatgccatt caggcaaaag tactgtggca agaagaggga aaggtactag aactaatagt
31621   tttttttgttg gttttttggca ggttttttgt ttttgttttg ttttgttttg tttgggtttt
31681   tttgtgtgtg ggttttttttt ttaatgtcag ttagatttgg cacctacctg ttcttttag
31741   cttacagcag ctcaaaataa attagtattt atttttttaaa ataactaaaa cagtttgggg
31801   tttctcccac ttgcagtctg aaaatcatct ctaattttct gcctgaacac tcaagaaagg
31861   gttaagtttc tagtattttt catttctcca tttatttcac ttccagggtc tttcttcaag
31921   ggagtaaagg gagaatgtag ttttacttca gttgtattac attcagaaat cccaaacaat
31981   gttggctcct gcctcattat ttctttattt tctctggagg gaacaatttg gaaaaggaaa
32041   agatgagaaa tctccaagaa attaagcttc ttagctcttt tttcttcctt ttgatgctac
32101   cagcctgagt ttgccactgt gattttcaca gttcagtagg aagacctcca cctataccat
32161   cctaccctg actcttctg ggaattccca agtccatggg attttggatt gttcttcttg
32221   cagagtaacc aggaatccta atcacaccac tcgggaaagg agttcatttc ctccatcgct
32281   gcatattaat agagaagcag gagctacatg atgtagaccc tggaaaggcc ttccttggct
32341   tggaaatcct ttattgtaag tgggttcagg actcttttat tttttcccca ttctgacagt
32401   gaccaacagc aatatgcatg agccgatggg actttctca gagcacacca ttcttggtat
32461   aacaaagccc taacaagaaa aataatatac cagttcttga atcttcccca caccagttac
32521   atagctggtg gactgttcag tctaaatcct tccactccta acaataacac tgtagcccta
32581   ggggagaatc cctgtacaac tgcacaaatc aatccctgc agccctcctt aagacacggc
32641   taccagaaga aattcttgga gccactactc tgctattttc ctacgaggcc atttttcctt
32701   gatatgccaa tagttcccaa actgacgtga gtgtgtaggg aaatatcctc ccctgacagc
32761   atcacaccct attattaggc cacaatacag tgctgccttg taacttgatt ttttattagc
32821   cctactattt ttccagccct atctcctagg acacttgcct tggtccaaag tgggaggggt
32881   cagaagcaat aagggtgcca gcttccttg ccgcacttgt tttagacatt tctccccaag
32941   atgagttact ttgtcattta gaacaccgta gcgaggcttg agggtgaccc ttagccccta
33001   gcaatttaag actgggaggc tgaggatcag ctaggtagct ctacccagcc atttctcctc
33061   cccatgaaag agtttttgggt cttaggaaga ctactcatgg gaatatatac agtcacatgc
33121   cgcataacaa tgtttggtc aacaacaggc tgatatatga tggtgggccc ataggactat
33181   aatagagctg aaaaattctt gtcgcctagg gacgtggtag ctgtcgtaat gtctcagcgc
33241   aatgcattac atgcatgttt gtggtgatgc tggtgtaaat aaacctactg tgctgccagt
33301   catagcacat gcaattatgt acagtacata atacttgata atgataataa atgactatgt
33361   tattggttaa tgtatttacc acactgccct ttttattgtt attttagagt gtacttcctc
33421   tacttattaa gaaagaaatc aacagtaaaa tagcctcagg caggcccttc aggaggtatt
33481   ccagaagaag gcatagttgt cttaggcagt aacagctaca tgcatgttat tgcccctgaa
33541   ttccttccag tgggacaaga tgtggaggta gaagacagtg atatttataa tcctgactct
33601   atgcaggcct aggctaatgt gtgtgtatgt gtgtcttcat tttcaacaaa aagtttgaa
33661   aagtaaaaaa aaaaaaatta aaaattttaa aaataaaaaa gtttatggaa taaagatacá
33721   aaaaaatttt ttgcacagtt gtacagtgtg tgtttttaatc tgtgttatta tgaaagagtc
33781   atgcttaaga attgttaaag tttataaagt aaaaatgtta tagtaagcta aggttaattt
33841   attattgaag aaagaaaatt ttataaataa atttagtgta gcttaagtgt acagtatta
33901   caaagtctat agtaatatat aataatgtcc taggccttca cattcactca ccactcattc
33961   accaactcac ccagagcaac ttcaggcctg caagcttcat tcatagtaag tacccatatg
34021   ggtgtaccat tttttatctt ttgtaccata tttttactgt gccttttcta tgtttggata
34081   cacaaatact taccattgtg ttacaatagc ttacagtatt cagtatagtg gcatgctata
34141   taggtttcta gcctaggagc aatagactat ataccatcta gcctaggttt gtagttggct
34201   accccatcta tgttcgtgta agtacaatct atgatgtttg catgcagtg aactcaccag
34261   aggatgcctt tctcagaacg tatcctgatc aataaacaac atatggctgt atctgaattt
34321   gtggtaggca tacagctcag gtcttcatcc tgtggtttcc ttcattctac tccccacttc
34381   accatttaca acaaaaataa taacttcatt cattcattca ttcattcaac aaatattttg
34441   tgagtcctta gtatatgtca accactgttc taggtgctgg ggctgtgtca gagaaccaaa
34501   cattaaaaat ctttgccctc atagagcttc atcctagtga gataaacaat aaaaaaagtg
34561   caaaagtaaa tgacatagta gtttagaatg catgacctg tttgagggg aacaggagtg
34621   agggctgatg tggggagctg ggtgcaattt aaataaaatg gtcagagtag acttactaag
34681   aaggtggcat tccagcagca ctagaatgaa gtgagtgagt tagcctatgg gagaagagca
34741   aaatacttaa gccagtgaaa aatacttaag gaggtatgtt ctataagtgg aaatgagacc
34801   aatatgtatg gagtaagagt ggggaaggca aagagggaac aggagccaga ttagatgggg
34861   cattcgacgc cattaccagg cccagggcat ttgttgtttg caaatatat tcccatcctc
34921   taattgcctc aaccttgtaa aatgaattcc atagtagaaa taatggaata atggactcat
34981   agatgatcca gaactctttt tagccaatag tgtcaatgaa agctatgtcc aaacagtggt
35041   gtataaataa tgctgataaa ggtaatttga catttatctc ttttttccatt ctacccctcc
35101   tatcagaacc ctaaatggcc cactggcaga atgtccaccc catagagcta atgtttcact
35161   ctagttctgg agaattggct gcaattctga ggccatgctg agatgaaatt tcatgggaca
35221   attttgatca tttaaaaaat aaagtttttac atatgtagac ttttagtttg ctatagaaga
35281   ataatgcctc cagagaaaca aaaggcccta gctagcagta gctattaaca gcacttgaca
35341   acttggagaa gccgaaaaga tatgaagcca gagcctacag ccaatccttc ctcaagtcct
35401   gtcagcattt ccctcaaata tatccccagt gtaaccactt tgccccacct caacactact
35461   aatcaagcct tcaattctca ccttgactac taccacagcc tcttcatggg catcttttcca
35521   tgctcctctc actcccttct acggatgagc tgagcatggc agtagaaaga taggcagggg
35581   ctagatgatc ttaggtatcc ttgaaagcca catgaggagt ctggactttt taaaaatggg
35641   atgggaaatg gctgtaaagc tgtgatctgg gaataatgt gatctaagtt ttttgagttt
35701   gttttttttaa agccctctgg ttgctgcttg gggagttgac cacagtaagg tgcaaagcaa
35761   ggagatcagt taggaagctg ctatggcaat agaggtgaac aaaaaccttg agaatctctt
35821   cctttcctc aaaaattcaa aggtcctttt ctacctgaag aactttgatg ttactctagc
35881   cttggtcttg aacactgatt atcaatgcc tgtctccctc tatttattct agtcttgatc
35941   taaataccac ttgcgtggag gctttcccta gctactctaa cagagtgaga caaatcccca
36001   tctttaccat cctctatcct cacttttct ctgatcattt attatttcct tatattatat
36061   atctctttt tgttgtttag tctgtctctt tcacaagagt ttacattgta tgggagcaaa
```

-continued

```
36121    aacctttct ggtgtctttg tagttgtagc tctagcacca ggaactatgc ctgacacaga
36181    ataaacataa gagggactca gtaaatattt gttgcatgga tgaatgtatt tatctgctca
36241    tagcatggtc taagacaatt taaatgatac caagttcaat ttcttagaaa acatttatat
36301    ttccagaaaa aggagacaat gtattagaag caccaaatac atctgacaaa ggtctaatat
36361    ccagagtcca caaggaacac aaataaattt acaagaaaaa aacaaacaac cccattaaaa
36421    agtgagaaaa ggacataagc agacacttct taaaataaga catttatgca gccaacaaat
36481    gtatgaaaaa aagctcaaca tcattgatca ttagagaaat gcaaatcaaa cccacaatga
36541    gataccatct catgccagtc agaattgcaa ctattaagtc tagaaacaac agatgctgac
36601    aaggttgcgg agaaaaagga atgctttttac actgttggtg gaagtgtaaa ttagtccaac
36661    cattgtggaa gacagtgtgg tgattcctca aagatctaga ggcagaaata ccatttgact
36721    cggcaatccc attactgggt atatacccaa aggaatataa atcattctgt tataaagata
36781    catgcacatg tgtgttcatt gcagcactat tcacaatagc aaagacatgg agtcaaccca
36841    aatgcccatc aatgatagac tgaataaaga aaatgtggta catatacacc ttggaatact
36901    aggcagccaa aaagggaatg agatcgtgtc ctttgcaggg acatggatgg agctggaagc
36961    cattatcctc agcaaactaa cacaggaaca gaaaaccaga cattgcatgt tctctcttca
37021    actgggagct gaacaatgag aacacatgga cacatgatgg ggaacaacac acactggggt
37081    aggggagggg aaagcctcag gaagaatagc taatggatgt tgggcttaat acctaggtga
37141    tgggttgatc tgcgcagcaa accagcatgg cacacattta cctatgtaat aaacctgcac
37201    atcctgcaca tgtaccccag aactaaaaat aaaagttgaa ggaaaaattt ttttaaaaag
37261    caccaaatat tcctggtacc taataatcac ttatttttat tgaaggttca ctatatccta
37321    gactgtatta tgagttttttc ttatctgaat ccatcagcaa ccctaagaag tagatattac
37381    tatcctgatt ttacaagcaa ggaaactgaa acttgaatac atacccactg cgaactctta
37441    ggaacacttg aaagttcatt gccttctaac gctgagatgc cttctaatgc tgagaagccc
37501    ttgaaaaggt ggttttagcc ttgagaaaaa aaaagttgct gataggcttg ttttaaaagcc
37561    aagaagttgt tatagttttta aagcctaaat tgggcctggt gtcagctgat ccaatgacct
37621    tcccttttttt atccctagta atccggtaat ctcccattga tgagcaaagc atgtgtactc
37681    tattaaatac tgggtgcagt ttaggcaacg ctgcctccag cctcaggtgc ccagcaggaa
37741    gtcataattg acaatacaga gctgagtagg gcagcatggt ggcagcccag gtcacccttcc
37801    ccatccatcc ctcctcatgg agcttgctgc actcattttac tgctcagctc ctctttgacc
37861    aatggctaag gccctggact ggacattgcc aagtccaatt ctgttcctaa cacagatgat
37921    tgctgcagtg agtcataaac acctcactga atctcacctg aaaagttaaa tggaatgccc
37981    tcttcattct tgactcccag gatgtgctaa taccccacaa atatgtgacg ttcctcatag
38041    gaaggacatg tatataattc aaagtgctat tgtgagttcc aaactcaaaa tctaaaaagg
38101    cactgagaga agtaaatatt tgtagagaag ctatatccct aacaataaa tcaaaatata
38161    ataaacttaa ttttcatcaa aactatttttt tgtttccaag catagagaca agaaagatgg
38221    gccaggcctg gtggctcacg cctgtaatcc cagcacattg ggatgccgag gtgggtagat
38281    cacaaggtca ggagttcaag accagcctag ccaacatggt gaaaccccgt ctctactaaa
38341    aatacaaaaa aattagctgg gcgtggtggc acgcacctgt aatcccagct acccaggagg
38401    ctgaggcaga gaattgcttg aaccaggaag gcggaggttg cagtgagccg agacggcgcc
38461    actgcactcc agactgggca acagagcaag actgtctcaa aaaaaaaaaa aaaaagaaa
38521    gaaagaaaaa aaaaaaaaga aagatgccct tcctgaaata tcgactatac atggctatat
38581    tttagatttt tcacagttgg aatttggtgt tcatgttttat ccttttgaat atcaatgaga
38641    aagtttatat ttgtgtctac tgccatgata acattagcat gtccccttttt tgtgagtgag
38701    agagatcaga tgatttacct cttctcatct ttagggctta ttttctaaat attttatcat
38761    gaaggagtta tttttttataa agatttgaca tgtcttttat ttttatttttg cttttcttta
38821    tttaggaaaa agcaaaacaa caatgtgttc ttttctgaga tgcacattga cttgtaggaa
38881    ggaagtctga gaagcaattt gtccacaaac agagattatg gtccgtgcag aaaaatgtac
38941    caagatatct ttccagggta agctgtggag gatatgtggg cctgatcctg cacagtctaa
39001    tgggcacaag gctttctttt acgtcagagc ctgaggctgt ttacaaataa acacagacca
39061    acgtgaccatt ctgcccaaga taggcaccat gagggggaact acggaatcct tccattaatg
39121    acctatctga aataatacac caccccttgat tcaggggcag aaattccgct gatgcaatgc
39181    cgagttgggt gggccagcac tgagtgctat gatgaaagcc cttcacaatg gtttccaaag
39241    aatgggagcc agaaacacta aaacaaagtc atactttcac agagcagcaa gagaaaggac
39301    ttccagcgat gagcccctat ggaaaaatct gccctggctt caaggcccca agcacagccc
39361    tgggaaccat taaagagagg ctctggcaga tctcaactga cacataggct aatggcagga
39421    ggcaagggaa ggaagctggg gcccacccca agtcagactt cagagatgca agatcatcac
39481    acacatacgt gcgcacacac agatattcac tgtcttagga aggcatattt tacgtttttaa
39541    tgataagcaa accttgtaac agtaaattgt ctcctcttct tctagagatg ggaaagatga
39601    aaactctttg gaaggaacaa agaagaataa agacctggat tcccaggtct gaaggtgctc
39661    tgtgaatgat caggtgatgg ccacggccag ctttcccagc tttttggttttc actatatttg
39721    ttgtgcttca agaagctctg agcatgttac ttagcctgcc tctacaggaa aaggtatatc
39781    agtaccttaa aaatcacccc ttctctaccc tactcccatc cccacacacc cccaccatcc
39841    cctcagcatc agtcatcctg ggtggtctcc tggaactctc tgtctgctca gtcacctgtg
39901    gcttcattac atttgcccctt cacatggggtg gtttttctatg taacagtgct ctttccctga
39961    atgcctttac ggctggatct ttcctgtcat ccaataggag ctaaaatgtc acctcctaat
40021    agagactctt cctggccaca ctgtctaaag tattgcttgc ctctctttg tagtctgtac
40081    atttttttatt tccctcattg cccttttcct aatctgtaac tgtttttaat tgtttaatgt
40141    ctctctccct catgtgaaca caagcttttt tagattagaa accatatctt ctttattact
40201    atactccatt cagctcaatg accagtatat agaaggtagt tgataaatat ttgttgaatg
40261    aatgaaaaac ttagctgaag ttcaccttttt ccattttcagt ccacagtgat cttttgccttt
40321    ctggcttgat aaagcacttg aagtaagttc tgcattcaca cggcacagca ctctattgtg
40381    tggtcttgat gccttcagtc aggtcgtgcc atcttaattc attaatatgc tactaaaatt
40441    agggggtcaga ttttctactc attgttttat ccaaactctc agcatagatc tggattcact
40501    tgtcttaaag ccagtgtaac agaaatatta gcttggggga gaagagtcat tttccccaga
40561    gtggtctttt cccccataagc cctctataaa aatgaccta ctgtcacgat tctgttctta
40621    gaacatgaca tgaaatccgg ggtcttagtt tctgagtgtt gggagcaagc catcaccttc
40681    gggagagcag atttgcttgt agaagtcttg aacttcatat aaacatcgtt catttcaggc
40741    atactgtcaa aaatctaaac agtcctaaat taggagctta ttataagtta ttacagattt
40801    cctcctgttg cttccagatt attgtgttaa aaggatctgg taaataccag atcttttagta
```

-continued

```
40861  tgatgactaa tgtcctgcca aaataagggg ggaaaaaacc cctttcaaag ttattctgga
40921  aacgcaggtg gctctgtcca gtagtacaga tctgcagccc cccaccacce caccccgcc
40981  cttaccctc ttagacagct tgttacttcc aatccttgga aagagctctt ttaagattgg
41041  gagttacttt cacaattgct tagactaaga agacaaagcc tgttgtcttg ctaacaattg
41101  ctctgtgtgg tcaatctttg gtggtcagca aaattatccc caaatgccag aattcaaacg
41161  agtaactcag gcattgaact ttaaaataga tgtttaattc ttcaatagga actcttaaca
41221  cctgtcagat gcttggaatg ggatgaggca gaaagtagac ggcagtgtac aaaatgcaaa
41281  aaaaaaaaaa aaaaaattgc atttcgctga acatgggactc cacatttcca tttcagccaa
41341  agtggacact cacagtcttg actcaatttt aattagtgga aaaatagtga aagaaaacga
41401  aagaagcatt agtttttttt taaagagcct taattatgcc agatgtctta acgttttgat
41461  tctaatgagc attttccaga cttaagctac ttctatttgc agtgtgctct ctggataaca
41521  ttccctctct ccacatacac accactacca catgtctcta ggaattaaat tactatcacc
41581  ctccacgagg aactccactc aatacctaag ctactttgc tctggagatt ccctcaagga
41641  atctcaattg agcttaactt tgaaaacatt tacaaggtct tatacccaca taagataaag
41701  cagtgtactg agtggatatg caatacaatg aaataacttt taaatttact gtttttgagc
41761  atcattatct tctaaatttt gtccccctcc tccctcaaat tcatatgttg aagccctaaa
41821  cccaaatgtg actgtatttg gagagagggt ctgtaagaag gtaataaagg ttaagagagg
41881  tcataagggt agagccttta tccaatggga ctggtgtcct tataagaaga agaagagata
41941  ctggagagct cgctctctct ccaggcacac agagaggaaa ggcatgtga gaacacaaca
42001  agaagacagc catcttcaag ccaggaggag aagccttgcc agaaacccac cccaacagca
42061  ccttgatctt ggacttctag tctccagaat ggtgataaaa ttacattctg ttatttaagc
42121  cacccagtct gtgatattct gttattatga tagcccaagc agactgataa gtgcttacta
42181  ttgcttgctg atccccaagt gcttcgttta cattatctca tttaatcttc acaacaaccc
42241  tatgaggtag acactattat tattcgcatt ttaaatatga gtaaactgag gcttagaaag
42301  gatgacaact ttccgagagt cacacacagt gtcagagccc tctgattcca gatggatact
42361  atattatgta aattaaaata agttaaaata tctttaaggt atgtcaaggc ttaaaattgt
42421  ggctggtgtg tgtcatttat tcttcccatt catattcctg gatttttttt gtcagtggta
42481  ccaaattaaa cctaacttga gttaatccca atctaagtta acacacgtaa tgaaaccata
42541  atgctcacat ttgatcaata tacaccaggg aatggttacc ttatcatttt tctcatacta
42601  tttgccttta aaggttggca taatctgttc ttgagtataa agttgtaggt ggatttgaat
42661  cttttttatta agcaatgctg tcaagtactg cagttgaagc tgcaaatcgt ggttcatctg
42721  gtgagaaaca tactctggat tctaagaagc ctgctccttc cccagtgcat ataatttaat
42781  gggaggaaca agacaatcaa gaaaaatgtc ttgaaatatc tattttatt tagtgcacca
42841  tttatttgcc cagagcacta atgggatatg tagaaggtat atatggacag cctatggaaa
42901  atagaaaactt tgaggatgta aatccattgc caggacactg aaatgatggc aaatacacac
42961  ctggagttaa acaaatactg gtttcattca cagcactgcc acttatttct gctgcagtct
43021  agacaagtta ctcaaccctg ctctacctca ggttcaatat gtataaaata ggaataacat
43081  atcaacctcc aaaggttatg gaattaaat gaaattatgt ctatagaaag ctcagcatct
43141  tgtctggtgt attagtcatg gatcttcaga gaaacagaac caataagatg tatgtaaaga
43201  gagagggaga cagaaatatt tattatgcgg aattggctca catgactatg gaggctagga
43261  agtcctatct gccgtctgca agttgggagac ccaagaaagc aggtggtggt gtttgtgggtg
43321  taattcagtc cgaatctgaa ggcctgggag ctgggggggag ctgtggtata agtctcagtt
43381  caagcggagg agcagctcaa acagtaaggc aggggtggaaa ggagcacatt cctctttttt
43441  ccatttttg ttctattcca atcctcagtc cattggatga tgtccaccta catgggtgag
43501  ggcaatcac tatactgagt ccactgattc aaatactaat cttatccagg aacaccctca
43561  tggacatatt cagaaatat gtttaatctg ggcacttgt gtcccattca aattgacaca
43621  cattcaattt attagccatt gttattgaca tcttccacag cggtgagttt ttcttccgta
43681  acatatttat ctagccactc aacatcctgg caaaactcct ttttggctca ttggtatcat
43741  caaagcagat gctttaggca cattcaaggt aacttccagc cctcagaaga tataatatga
43801  aagaagaaga aacagagctc aaagtagaaa aaaaattatt ttcaaaatg aagaactatt
43861  atttccagc tcccaggaga cttccaaca ataacagca aacagtagaa gatgattatg
43921  cattacagaa gagacagcta ttttataaaa gatttaaac aatgtacaac aaacaccact
43981  gggcccacca gcacaacaca gacagggata caagccagtg tggagttggt ggcaatgccc
44041  taggaattcc gcagaatcac tggagtgagt ttgaatccca gttacataga cctaggcatt
44101  aaattagcat cagctaaagg cctaagaaaa gtcagactta aacaacagaa attgatcaag
44161  gagcaaaacac atgcataccg tgacactcag tgtggctact gttgttcaac agagcccagg
44221  tttctctgac atcaaatcat tgccttgatg acctcagtac gagaggacag gacaagttaa
44281  aacctctaaa ggataagatc agagaagcct aactacgact taggctatca ggcagtgaca
44341  gttaacagtt gccaaaactg tttcctgttt atggcacaaa gttgggtaaa gtaagttgtt
44401  cagccaggac tgtaattttc taagccccc tgcaccttag caatgctgta agcctgagtt
44461  ctagccaatg ggataggaga agtgatgggt gccacatcca gactcagctc atagagcttc
44521  ccaaacttttc tccactactc tatcttcctc cagccaccaa acagagataa tcatagtgac
44581  cttggaagct aaatgctgaa gactgcagag cctccaccag cctgcatccc tgaatgactg
44641  gtacatcccc tccttcccac gcccccttaa atgactcaag acattttaca ggtaagaaat
44701  aaacatgggc cgggcgtggt ggctcacgcc agtaatccta acactttggg aggccgaggc
44761  aggcggatca cgaggtcagg agatcaagac catcccggct aacacggtga aaccccgtct
44821  ctactaaaaa tacaaaaaat tagctgggtg tggtggcacg cacctgtagt cccagctact
44881  tgggacgctg aagcaggaga atcgcttgaa accgggaggc agacgttgca gtgagctgag
44941  atcgcaccac tgcactccag cctggtgaca gagagagact ccatctcaaa aaaaaaaaa
45001  aagaaactta tattgtgtgt aaggccttat gcatttttagt acctacttag aacagttagc
45061  attgccctca ctaatacaac tagcattatc ctaactagta aagttataaa tattcatcac
45121  atgaatattg ctagagaaag aggggcccagg aacttgaagc atgttttctg ttctgttttc
45181  tttttctact tttttcctact ctgatgtgta ctgggcatat atcagaaatg gttttttgagt
45241  gttgaatgaa tgaatacctg acctgactga cctatgacaa ataatctaac ttcttttttgc
45301  cttcagtacc taaagccata attaacatcg caatgtttgc cacttattg aaatgtaatg
45361  aggattaata aaatatctga catgccattc tgagttcctt tgggtaagaa atacaataaa
45421  ttaagtacag aataagtaca atcagtatag gaaattaagt ataaattaag tacaggataa
45481  gtacaatgtg tacccattaa acacaaatcc agtagaagtc aggttatata aaatgtaaag
45541  ttctctagaa tccaataatc tcaaatcact acgataatat aaacaagtga gagtgagtag
```

-continued

```
45601  tattatctag tatattaatc aggtaaaata acttcacttc tccttaaaag atgccttaat
45661  aactaagaag agtcattaac taattactca caaataattt ctcttataga aatgtgaacc
45721  tctggtttta ttgttagctg gacatacata aattgatgtg atctttctgt taaaggtggt
45781  ggcacctaac aagtactgtt atgggtgtta gtctgagatg gacaggaaat tcagtcaccg
45841  atatatttaa aagactcacc gaaaaggagg taccactgat agggtttcca gctttcagtg
45901  ctgattgtga aaatgagaaa tatatttctg aacatacttt ttttctttac tttttattta
45961  agatatgggg tctcactatg tcacccagac tgagtgcagt ggctattcac aggcataatt
46021  ccacatttga ttagcatggg agttttgacc tgctctgttt ccatcctggg ctgcttcacc
46081  cctctttagg aaacttatag tcctctgttc cagggaagtc atcatactga tgccatactt
46141  agtgtggata ccctattggc ataggtgcagt acagcccaga attcctgggc tcaaacaaca
46201  ctcccgcctc agcctccaga gtggctgggg ctgcaggcat gtgccaccac acccagatga
46261  aaataatttt aactaatttg attttacatt aatatctgtt aagggtgacc ttacattata
46321  tatgatccag gtcccttaaa ggaagacaaa cacatgatgc ctgtctgaag gcttaagtta
46381  gccagaattg gtgggtgaat tatttttcac ctgatgatct ggactgaagg aaatgcccac
46441  cactggaact ttggttaagt ttaacaccat gttattcaag atgcatccct cccatgtcta
46501  caatctcttc acaatactat gattcattca ttcattcatt cacaaaatac ctactgagca
46561  cctgggctag aagctggaga tttgaaaatg cccaagatac agtccttgtt tcacacagc
46621  cacagcctaa ttttaaaaaa cacacaatat atacaataca gctgtattag atatctaaat
46681  gcattccaaa ctccatcttt gtgtcataga ctgttatgca ataggaacta aaaagaaata
46741  ttccatgttt caccatctat gctgcaaata taatctaagt ttctaaggtt tatgagttca
46801  cctcaactat ttattgttct gtttcaacct agccagccag cataacacca caggcttttt
46861  ttgtgatgca gaaattttag atgcccaaat taagaggatt ccatcttgag ttgaccaaaa
46921  ttcttatcat tctcataaat gaaaaacctt atttacatga cttttagcct ttgatttgcc
46981  cactctacta cagtgttaga agcccaatgt ctccttctag ttttccttta cgtattcctg
47041  cttgggccag aaaacattag tagggatata gaggtgatgt agtaagtggt agccatttgg
47101  ccaggaaaac tttggaacaa aaatcttata gtacagcctt ctttgaataa cacctgtgcc
47161  cccagggaaa atgggtatt attatgagca gaaaaaaaaa agccatccta ccacttggga
47221  ggaattgtta gcaggcaagt gatcatgtaa tacacagcaa ttgtggattg taagggcaag
47281  attccagacc atgataacaag ccggctgtc tgcccaaggt taatgggta atatccttgc
47341  ttactccagc tcagagtcaa attaacttta taaactctga gtataggttc tgtcttttgt
47401  ctatagaagt taagatttaa tattctgaag gggaccagat gatttagtgt ttcatggagc
47461  gtttgtccct cttttcaaca gactgcaaac acatcccctt ttccaagacg ctctctgaa
47521  aaaagaccca gacaggtgag attctttgcc aacagccttt tttactttgt ttgggaaatc
47581  tgtcagacat tgtgtgaaga gaatacctgg actcgttaca gctgtgcttc actgaggact
47641  actgtgcatc atccgattta aattttcgct gaagctctct ctacaaactg ccaaaatggt
47701  ttcaatact gtaaaaggaa agccgtttaa atgagtttgg ttttataggg taggagagaa
47761  gaagaatcca tcatgtatca aaggagtgaa ttgattgatt gcattttac ttttcaatta
47821  atcgttttgg cagcctgaaa gagaaggtca gaagatctgt ccccagttga atgctattgt
47881  tgtcagagcg aagcgtgcca ctttcagtga ctgctatgct gtatttaaca tctggttgtt
47941  tggaagcaca atgattattt cctgggagta gcaattttca actactactt ttgtatgata
48001  tttacaaaat atcccttgct ctgtgggagat actgactgag acaacagtgg cgctccaggg
48061  taagtcttag acagaagcag ctccagagaa gcaagtgcac tgacagattg ccactgccct
48121  gggattcaga aatgttccgt gctcatcttc tcagatcact gccttcgtgt ttactggtga
48181  aagcacctgc tgctgaaaaa tgctaagtca gcagcccaaa gttgtgggaa ttttatacct
48241  atttcacaca cttaccaaac acacttctag gccaggctct cacacctgca atcctaacac
48301  ttttgaaggc ctaagtggga agtttgcttg agcccaggag aaccccatct ctacaaaaaa
48361  ataaaaaata aaatatctgg gcatggtagc ttgcgcctgt agtcctaact actcaggagt
48421  ctgaggtgga aggatggctt gagcccagga ggttgaggca gcagtgagcc atgattacgc
48481  actgcactcc agcctgggtg acagagcaag accctctcta aaaactagaa tagaataaaa
48541  taaaataaaa taaacacttc taatatgaga tatgttacgc ctgtaacatg aaatgtaaat
48601  caaaagatag cctgaggaac caagcacttg aactggtatt ggtaccagat ttgccatcca
48661  cagatggtaa atatcagatt ttgatatat aggaaaatct gctaaatcat tggtgtgtgc
48721  cattctccct gctagagagc tcagaggcta gtcatgaagg cagatgtata gtaaacacat
48781  gattttgcca ctgtctgcca aaagttagta atgccacctg ggcatgatga acttgtttga
48841  ggacgctttc attttggctg cacatccttg aggatcgtc taagcaacct taaactccgg
48901  agcaatattt catcaatcca ggatgaaatt cagttgtgat gatggctgca taactctatc
48961  aacttacttt taaaatactg aatcgtacac ttaaaatgga agaagcttat tgtatgtaaa
49021  atatgcccca taaacattaa caatgttttgt aataagcaat aaatattgtt aaataaacaa
49081  aatataaata aatagccaat gtaatttcct cagatatttt gacaactgct ttgaattaac
49141  ttcctgccca acacatatat ttatattatg aatatatatg ccattaatgt ggcttctcaa
49201  cttgtcataa gaaatgattt gtcagtatcc aatttgggcc aggcacggta cctcacacct
49261  gtaatcccca cacttggaa gtctgagcca ggcagatcac tcgaggtcag gagttcgaga
49321  ccagcctggc caacatggtg aaaccccgtc tctactaaaa ataaaaaaat tagccgggca
49381  tggtggtgga ttcctgcaat cccagctact cgggaggctg agacaggaga atcacaggag
49441  aaacccagga ggcagaggtt gcagtgagcc aagattgctc cactgcactg cagcctgggt
49501  gacagagcca gaatccatct caaaaaatat atagatagat agatagatag acagatagat
49561  agatagatag atagatagat agatagatag atagatagat agatatatag atatcctcag
49621  ctatttttgac atatgtatat atacacacat atatatatcc tatttttac atataattaa
49681  ctatttttaa atcaagataa acatttgttt gctcttatgt ccaactgaac acagaataca
49741  ttttaaaacc aaaaatacat tttagatcta gacagtatat caataaggat gaatatttcc
49801  tgatcaatca ttgggaaaga atgaaaataa gaataacttt ataatgatc acagaaagaa
49861  tgtcataacc ataccccttaa gaataattgt ctgatattct gataaaatta tatacacaag
49921  tttctctcat aggaagatag tacttaatgc tttaagaatt aaattcttca tatattat
49981  ggctattttc ctatcgttgg tgccttactt agagtggggg gaaaagcctt gattcatttt
50041  agcataacta ctaattttt cactgaaaga taactatcct tcttccttta atgtaacttc
50101  tattttcact ggtttgaata atgaccataa atctttaat agataccttta caaaagccag
50161  ttatcattct tcaagctct atgatccttg ccagtgtatc taaaactggt tcagactcaa
50221  aagtaacttc ccacagaaaa ttgctgcttt tcttgaggtt tagggaatga atctactctt
50281  aaatactatt taatctgtaa tgtaaggaag ccactctctt tctaggcaat taaagggaga
```

-continued

```
50341  caaatggtga acatctagaa ccgtccattt gtatctaatt attcttttta ttaataaaa
50401  gttcaacaga aatgctttca aaggcttgag acgacaaaat catttattcc tactatttgg
50461  tgttgttctt atgcacttaa ttttatgcac aatggtccca taattattct gaggggggag
50521  gataactgct aatttccata atttccaatt attatttgat cctcacagta attctttaag
50581  ccaggtatat tattattatt aattattaga gatagagtct ctatcaccca ggctggagtg
50641  cagtggtgtg atcatagctc cactgtacct cctgggtaca aactatcctc ctgcctcagc
50701  cttccaacta gctaggactg cagacatgtg ccactacgct cagctaaatt tttttcttaa
50761  agacaaggtc tcactatgtt gcccaggcct ggtcctgaac tccctggcct caagcaatcc
50821  tccctcctg gactgccaaa gtgctgggat tacaggtatg agccaccaca cccggcctta
50881  agcagggcat attattatat cctttcaata gtttgagaaa ctgaatctta atgaggttaa
50941  atatcttggc caagtttatt aggccagtga gtagcaggga cagaattcaa acccaggact
51001  gattctaaag tcagagttaa ctgcttgcca gtcgagtaag aaaagctgaa aaccaaagaa
51061  tctgacacaa aactctggtc tgggggaagc tttccaaagg acagaatcag accaacccca
51121  agtttgtgtt gactctgaag aattgagtta ccctgaggcc tagatgtaaa tattatgcca
51181  gaagatactg gctcgtggga aaagctgccc caaggactta ctggaaggag tactctccag
51241  ggagaagacg taggtttgcg aatttcagcc taagacagaa tctggttatg gctaacaaaa
51301  gttgtgacct gtcacttatg gaaaattata aattgatatt tgcttctaac cactttagct
51361  gggttacttt aataagacca ttatgatgct cacagatggc cagttgcctc actgatcatc
51421  tcaaatgcaa agagtggctc atacaatttg gaaaggacaa agaccaagct gaacagtaag
51481  ttttggctgg aaacacccta aacattttct aggagcgctt tcttcctgct ggcagaagaa
51541  aacaaatcta cttggttatt ataagatgtt tcattttctt cttttaccc ccaaagaaaa
51601  atatgctttc ctgagaaatc tgaaattata aggtgctctt ttagatattg ccacataatt
51661  tacacttctg gcaaagattc tccccgcagc cacttgggat gcattctcat tcagcacact
51721  ggcactgtta tgtactttg ataaaggtct tattcactgg aatgaccatg gtaacccact
51781  gtccttcgat tgtccccact ggactttttg ttgggtggct tgaattgtta agtgattgga
51841  tgaccctgtt cccacaaag cccgttaggt gggagatgaag cacagatgag tccatttaag
51901  ggctcatcaa ggtctggcaa gactggagct gggtagctct ccttgcctttg gccaggacct
51961  ccaaagcttt ctgtttccac attgaaactt ggccaatctt gtcagctcag tgacaatgaa
52021  aaaaaaatg aaacttggtt aataggatta tatgatttgg ggagtagaat gttgttacag
52081  atgatttatt ttgaaagctg atttcactct agcgaaaaca agctcaaccc attacaccag
52141  agactgtggt gccaaacaca atcatttcca gtttgaaaga tgtgattgct ttttaatgtg
52200  gaaatttcac aaggttacaa aaaggaaaaa aattaaactc cttttcatata acaaagtcac
52261  tttggaatat gggttgcaat gcactgacaa tgtccagaca cccttaccac ctcttaccac
52321  atcacaagtc agaaaggtgg atcagtttga tttacaccat ttcttggttg tgttttctc
52381  atgcctttga aatagcctaa tagttttttca ccaaataaa tagtaatata tgttcaatac
52441  tggaagtatg catggtcagg caaggacagg agagatagag gagataatcc aggtaaagaa
52501  acctcctctg caggcttgtg cttgcatgtg tgtgtatgca tatgtgtttg aattgtcctc
52561  caccaaaatg acctcatttg ctttctcagg tttgaccaga ccagtagcct gttttttag
52621  ttggttccag tttgtacaac ctgggttcac taggttctgt accaccttct tcctccccaa
52681  tcccataccct ttgagagact ttgataagag taaagaccca tcaaaaaaat ttttaaagtg
52741  atcatagaat atggctgaga ttatcaaaat ggtgacagtt aggttttggt tctgccgtat
52801  ttcatcagat cttaaaactc tttgctagtc tgtaatccag agtgaaattc ttagaaaaga
52861  atcagtggca gaaagtgttt ctactggcaa aaatcaccaa attgagaaag atcaaaaatt
52921  taagctgttt tgaagagaat tggatatttt tcatttctgc atccttaaat taggccttca
52981  tccatagctg tggatgatga ttctagggggg ttgagggggga aatacggcaa tgacagtgta
53041  gcagcatttt tcagaacctg ggataaaaat gacacataca ccatgaaacc tttttgtcct
53101  tccagtaatt gttttgttt gttttgtttt tttgcctgtg aatttgaat acatgtcatc
53161  ctgttctttt gtgactgaca ggaagaaagc aggtgaagaa actctatgat tgcagggctc
53221  cttgcagaag cttggccgac aaaattatta ttgcatctgc tggacccagc acaaaaggac
53281  agaagtccaa gtaaaattaa aggatccagg aaactggaaa ggaaaagtgc ttgcctttt
53341  taaggtgaaa tttgagcaaa atgagttggg aatcagaaaa ataagcaaaa cgagattaga
53401  acatccagtt ttcagtttaa gccattccta gttagctcct gggtgttcac acttactcca
53461  ccatgccattg agcactcaga ccaacccaga actcctagat caccccaagtc taatgtagtg
53521  agtatacatt ttcttctct ttccttttta gattattcct ttctgttca ttgtcacttc
53581  agttatcata ttggaatatt gaccctgatt attatgcttc ttagcatcaa ttcacaaaag
53641  aagaagacag gcactataaa atagaatttg ggatcatata gatcgatgtc actggtgcct
53701  agagaaaagg caacatttat tgagtggcta cattgttcca aacattgcat ctacttatct
53761  catttaatcc tcacaaaaac ttgagacaga tattattatc atactttgtg ttgggaggaa
53821  attgagatgc agaaattta atagcccaca gattcatctg atttatagcc cctgctcatc
53881  ccattaggcc gttctgcctc ccaacttcat ttgaagtagc aaaagcctat tgattctact
53941  agctgaggga tgggcttatt taatgatatg agcctagtta ttttgccttt taagatctca
54001  gggcccttga ttatgtgact ttgagagaag agtttggaga tctgcagatg aaaggaaagt
54061  gaaacattac attcagtagt cagttagata atgataaact gttattggca atgtaggttg
54121  gtccagcaag taaggctttg agaccaataa taataaaaat atcatcttac atttatatta
54181  tgtgcacagg tctttgtgct ctttcatata tatcttcaca tttaatcctc caacaaccct
54241  gtaactaatc aagcagaga ttattatccc atttgatagg agaagaaact atgagttaga
54301  gcggtttaag caatttgttt gtgatcacat ggataagcaa aaaagagtct aaacccagct
54361  ccactttct atctcttaag ccagttctca tttctctatg gtagaatgtg agctttatat
54421  ccaacttagc actggcgtcc taaggaaact ttgccacctc tatcatcctt ctattgtgct
54481  gcttatcata ctgtatttaa gttactgggt cactcaccctt catatccatc aacttcaagc
54541  tccttgaaat gagggacttt ttttctttct tattgaaaaa aaaacatttt attaagttt
54601  ctaaattgac cagagtgcaa attcttaaat cctaccattc aaaactgaca gttgccaaca
54661  gtttgatatt tttttctgt ctttcatctc tgtattctta gtacctagca taatgcctgg
54721  catagagtgg atgtctaatg aatgttgtt acatttaact gtggggatcca taattatggg
54781  aatgaattag aaaattggtt acctaataca gaaataaatt tggtatttta tttctttttat
54841  tcctaaagtt gtcatatctg agatgtttct gaaacattta tccatttt actattttat
54901  ggtaagatga caatggtaat cataagaagg ttttggaaaa tgcatctctc tgctatgtgt
54961  ttcttttaaag gcgaactata catgcccccta tgacaatatc cccacaatga atgccatact
55021  aggtatggat tgatggtttc ttcagttttg ttttgtttg ttttaatga ttccttcttg
```

-continued

```
55081   aatttcagtg gttgctaaga ctgcacatct acacaggaat agaaaactac atgaaaccag
55141   actctaagct cagagggcaa gcatgcacac gcaccagaaa tcatgctatt ccaatccaaa
55201   tgaactaaat ccttccgtaa cgtgtggtca aggagttaag ttctaaagga aaatgcaaat
55261   agcctaaagt ggaaaccata tacgtctgcc tccttcagtc tctaaaccta tgacagaact
55321   ctgtggagaa aggtggcagc aaagcatctt aatgttctct taatacttca ccaagtaatg
55381   atagcctcac caagtgcttc gaaggaacta gacagtaagg gccaaagttt gggtttggaa
55441   aagagaggaa gcaaactgac tctgtggttt gttatgagat cctgggagga gctttgagtg
55501   ttacaaagaa tctttccttt tctaacctat ccagcctcct cctactccct catgggtttt
55561   cttcttttt catagaagct tggcaggctg gttaagaaag gataacggga gaaaatgacc
55621   cctcggctca ggtatccttt ggcctatgac tatgggccca atagtagatt gtgagactag
55681   gtcttttca ttgagtctgt cttactgaga ggaaaaactg ctttgtgtga tgactttatg
55741   gcaaatgcta gcaacagctc tgccctgcat actgaaagag agacatttct gaccgcagct
55801   catgaaccac acttatttac tctggcacat gcccactatt tgttcatagg ctttctgtct
55861   ctactaaatg cgttccaatt ttggaggcta aatcattgcc agtagtttcc aggacattcc
55921   gctaggctaa gcaaaattgc cctaagcggt agtcagaaac cactggagta gtattgtaaa
55981   tacagactat ttgcagaaaa tgaaagatac cgaacatctt atcttttt gtgctgcaga
56041   aatccatgag ttgtattttg cagaaagcca tgcaaggcac tagcaagaaa caagaggagg
56101   gtacgaggac tttcatcccc actagagctc agaaattgtg ctcaaaacca ctttgaaagt
56161   tgggcacagc ctaaaacagt tataagggca tactatggcc gtgttcagga ggcatgctag
56221   agattaggta cagcctaacc aatagtagct ttttgctcag tatggatttt taaatgatct
56281   gaaaacagtg gagcaataat aagaagaaaa taaatggtgg tcctcatggg catctttata
56341   accattctg tattcagtga cagccgtccc ctcccaatgt cagtcatcac cttggactta
56401   aatgatggct taatgggtca tgttgaacca cgctgagtct gagatctagg ataaffgaga
56461   aattctccat ttgtaataaa acctcccagc actattgagc tgtgtattcc atatcttgtt
56521   tcaggcaggg actaagaaaa ggagatatta catgatattg cttcctgtg catagctctt
56581   tcacatgttt cctattaaat ttgtttccaa ccaagcggag attttattta cacattggct
56641   ttaataataa ataagtgtgt gcattataaa ttcagcaact ttggtatcaa ctcgccgata
56701   tgatcatgtt tgtgtttgga aaaggggaagg aagttcactc tgaaagcaaa tgatctatca
56761   aaaggaataa ttttttttgg aggtggctaa gcagattctt gcaagtactt acatattgca
56821   taataccct tgagacttat tgaaataaat cttcttcatc ctaagggcaa agcaaaatta
56881   agttgaaata aaccacaatt aaaactccat gcattgagtt aggagggaga aggaagccta
56941   tacatatctc tatccatgtg tattctgtta acatttaaga cattttaact ttgggtagtg
57001   gacagcatga atgggggacta ggtaggaaca aggccaccac atcaaactga tagtggggta
57061   gaagaaacat ttgacacctc tcgccttctc tgccctctgt ctgtgtttaa ttttgctaaa
57121   tcattcccgt ctggagattg tatattttaa tctgcctctc caagcaacac agaggtacgg
57181   tgtcaggaag cttgatctca gaggcaggca aagagatgca aaagctataa agaccccaag
57241   gcccaagaaa gacagaaaag gaacagggcg gggttgtgcc taaaatggca ttagcctaaa
57301   attggcatat ggagtaactg ggaagatggc actgggagat gtaacattct ctcatggtaa
57361   atttaggact ttatctgtgt ttgtgttttt aaaagttaat atcccttga aaggtctaaa
57421   gatgacttcc tgggaaatat aaactacct gaaattttac tggagaagac attccatagc
57481   aaccaacttc aaagtgagct agatttgtcc atcagagata caaaggtaat agaaaagggg
57541   ggaaaactga aatgtgacaa aaactaaaat atgtgttgct tgtgtgacca tgcattgaaa
57601   catcatgaca cgatagccca tatcaatagt cagtttaaga gaaaaaaata tcgccctgtc
57661   tgcatatcct aacacagctc ccaaataagt cacttagatc tgtttgggga caactttgaa
57721   ttcacatgtt ctaggtattg gtttaggta tcatgtccat atatagaaaa tggacatgat
57781   aatagtttct acctatagat taaatatgag gcccaaatga gaaccaagca aataacgtgc
57841   taagcatggt acttggaaca gactagctac tcaaaaatta taacaattat tatctagaaa
57901   tcttgcatga tgtgagaatt tctttaatgt agtgcgataa tgataactaa tagcttcctc
57961   cccagaaaag aacagccttg acccctaattt ataattattt tgtttatttc tcatatttat
58021   attttatttc tcatatatat tttcccctgc tcaggttttat tgagaactct atgaatttag
58081   cctcattgca gcattgctca ccactgtaat aatcccctaa cagtattagc attgtgattt
58141   tcatgaaaac aaaacagcaaa tatggtgtgg gctcacacac agatctgcat tgcaactctg
58201   aatggggaaa aaaacccttc tgaatggcat ttcttgatgt tttaatcaat atgaccattt
58261   aaaaagatga ttaaactatc tatttatgct ttttgccaat aaagcagatg ctgattataa
58321   cagttctgta acctcatcac tttcctacaa aaatccttgc ttagttgcat gtgtctagta
58381   gcaatgccat tcttccttaa aacttaacaa ttatgactct aggttgtttt gtttaagcat
58441   ctttccatat taattattat ttagtagtta taggagcagt agagtagtta gctcaaatga
58501   gagaacaatt agtaaatgaa gaccagagat ttgtgcagtg ggtgtgtgta tgtgcatgtg
58561   tgcacatgtg tatgcttaga tggcactgga aatttttatgc cctgtgtgca tttatgcatg
58621   tgaaagacac acatttcat acaaaaaacca cataattatt aagaatcaac aatggtgctc
58681   ttgattctca ctagaaatcc tgtaagtcac atgggaagtt ttcctaagag tttaaggtta
58741   aatcagagtc ctgtctagtc aataactcaa tgaatatgtt ctggctaggc tatgaagata
58801   ttcaaaaaat attggattag tagaacaaaa atgaaacata aacagtgtca aatcaaaact
58861   gctggggcat tttttaaaag ttctttggct tgagtcatta tgtaatcaga aataaagcat
58921   tgttgctgtt ttcaagaga cagttggaga gcagagtgca gactgcatca gcaacacatc
58981   aacacttaaa acaggcatgg attgtgagat tacatattac aagtatgaat cagctgcaca
59041   tactctgaa tcatttgcct ttctgatctt ttaggaataa gctgtagtca aaccacgggc
59101   tgaggccagg agtgcctggg tgaaggtgca tatacactat atatatatac actatgcacc
59161   ctcacccagg cactcctggc ctcagcccat ggcgccaacc cccagggagg agaaaggtgt
59221   gtacagtccc tagtcttcct gttgacggag cagtcaggca cattctcagg ctgtcttgct
59281   ccttgcagc acctcctctg tcagctgcga tgcacctgg ctatgcgaaa cagatactcc
59341   gactctccca aactccacag ttgggccttc cttactcaga acaggtagtt gtctacgtgc
59401   atgattttga ggatgtttta aaatgttct tgcccccaaa atattactcc caccgatttg
59461   aaacataagt cctggaattt caccactgaa aaattcacaa ctttaagtta aaacactgct
59521   gttgtgaaag ccactcttga agtataaagc ccctaccctc cacccctgca ttaggaggaa
59581   caatgtatta aatcgttttt accttttctg ctcttattct aattagatta tcagatcact
59641   tccttttccc ttggaaggca gaaataaata tccaatggga atagggcatg atacaggtag
59701   aatctgataa gaaatttggc aaacatgaga agtggacaag gtccacagcg tatcagctca
59761   ggtaagggcc acaacgaagg gactctgggt aaccagatta caaaattaca cctctgggtt
```

-continued

```
59821  gggtaagtaa gtggggaaag gggaggagtg ggagaaggag taggagagag gaagaacact
59881  tccaaaatag gtaaatgttg ccaaagagcc acttcccagc atttcctaag gctggccctg
59941  ctagggggta aaccttccag caaaatacat cctaaaaaat gtcaccttc cccagtgaac
60001  acatatccca cccccactct ctcctctgcc tagttccat acagaaggct tacagttgct
60061  gtggcagcct ctaaattttt ccacgaacca ctcatggaac aaaagtattt acggaaccta
60121  gagttcttca accaaataat catatgacag atttcccaat tctgcacact aagccttggc
60181  cttggcacat caataaatcc ctttcatgtt gttagctgga agacagtgag taagtctctt
60241  gagaattaca gagacgtgca caggctactc agagtacccc tgccaaaaga agatgtagtg
60301  cattatgggt agttcttgtc cctagttag gaataggtca ttatttttaa tcagggaata
60361  cattttttcta tcttatgaaa tcttcaccct cttttggcag gcctttagtt ttttaagaaa
60421  gctgcatata ttttaatat ataatatata tgacctatta agatgatccc agtacgattg
60481  gtttcctgga agactagaag cctggtctat cactccaccc tctccaacca cctgatgcca
60541  ttacttccaa gtcatggaac ttccctatgc actcaagaac tgcagggttc tttgggcaat
60601  ttctcaggct gtgtttcata aacaggccca gaaactcctg gaatggagc tgtctcaatt
60661  catatgaaag aagcctctcc agagttcttt atacatctcc taggagaggc aggggaggta
60721  ggatgaaggg agtggagttg atgcctaaga taggaaaaga cataattatt aggagaaatt
60781  tccttagct tttcaaccca gttccctaag ttaagaaggg attaggagt ccagttttcc
60841  tgatactttc ttagtattaa taaaagcatg gaatttgttt aaattaacac tagaggagta
60901  tcattgatat ttcagcatct gtcagtgtct tataatgaag ctatgtatac caataataat
60961  ttttaatgta ctttcattt aactagagga ggaggaaaaa gagggagaag aagaaaaaca
61021  cactgaagct actctgtttc attcaattta attttcaag caagctacaa acaaggatga
61081  agtcattatg catctattat ctcaaacatt caataatgttt tactaagtat attatttatt
61141  ctcacagcaa ctgtttcagg aatgcaaaaa ccagcagaat tatctatagt tcacagatga
61201  gttacaaaat aattagataa aaacaattta gtttcctcac tagttgtttt gtcttcataa
61261  ttccacatta tttaaaagac tttcttttt tacatcgagt tgattgggtg cttcagtaca
61321  ataaggacac agccttagat gaaaaaaata gtggtcaatt ttccaaaatt aaataatgaa
61381  aaaatggtgg tgctgctact accatcagcc aagaatatag ttgtagaaat atcttatcag
61441  aaatatcatt ctactcatca actcaagaaa acctttcttg tgaaccatac agattaaata
61501  gttttaacag agattatgtc taagaaggcc acccaaactc acctttcaat tactcattcc
61561  cttgtagcaa ctttagagac attaagtatc ttaggccaca aatacatatg ttacattgaa
61621  attgagtaca tttgagttt ctatcctctg ggctaaaatt agtagtcaat cacagactct
61681  ttcttcgaga taatgttacc aaggaaaaaa tgtctcttca agattcttgt ggattagata
61741  gatgaaattc tccctataca aggctagtgc ctctgaacaa ttttgatcct gacccagtaa
61801  aaataatctc tacatttggt cttggaatc tgaggaggaa aactaaaaca actggtcatt
61861  actgaagggg gcttcaataa ttactttaat gggagagagt gattttatgt gaaggtcttc
61921  gtgacaactc aggaagaaac aagcaaaaga aaaactgttt tcacagcttg tgacaaacca
61981  ataccaataa ataagaatga caccttgatt gtttatccca gggactctaa tacttaggtt
62041  gaccatataa tttatcgtcc aaaccaagat tcatcagaca gtgaacaggg ttgcaattaa
62101  caattatgct ggaaaaacag gtgtaaacca ggacagttca ggcatgcagg gcttacagtt
62161  accttagtaa tactggaaag ggggattgat tatagaagaa cactgagata gggcaggttt
62221  ctaattaatg ttgaatatga aggggacatc cataaggatt ttaatacatg ctcattttaa
62281  cagtagcagt tagtgacatc ccagttatgc cctcttttta ctgatgatga aattgatgag
62341  cttttatcttg tcaaatggta gattatctta tatctcaggc atattggaag ggacatgggt
62401  tcttttttta accctggaga tcagttatta gcataatcat gccccttatga cctgaacatg
62461  aatgccctt ccttagagaa taacctactt acctggaaga aaggagtttt caatcaatct
62521  ttcagaactt acaatgtatt aaaggtgatg ttcatcacag attatcttgg gggaataaga
62581  gaccatcgtt aggatggagc ttggcacaca gtaggtacac aataaaatgtg tgttgacaga
62641  gactcagcag aataaataat ttttttaaaa gaaatcatat atttgttttt attcaactt
62701  tcctaaacag ttgaatataa gagagaaaat acacattaga gtcaacaaat tgcctgtctg
62761  tagaaatcac agcaaacaaa ctgctcataca gaacttacag aagagatagt atctctcggt
62821  agaacaagct taaaagatga aacagccttt cttttctttt gatttatttg ttattatgaa
62881  aaataggatt aagcatattt aattgaagta tctctcccctt ccttgatagg accatcatct
62941  tggagaagaa atttgatgtt ggtgttgaat aaagttcacc aatgatttgg ccatgaaata
63001  agagatgag gagttcctga aagcctgtgt agaaagactt acagaagaaa taagaaactg
63061  aagtaaagga aacaggaaat aataaaaaga aaggataggg aagatgttac atttaggga
63121  agctgggtga agagtagaag aaacttctat atactctttt tgcaaatact tgtaagtcta
63181  ctattatttc aaaataaaaa gttagaacaa attttttaa aagacatgag aaaattgaga
63241  tggagaaata aactgtctta agagcaattc catataattt gaataggcta aaggaagctt
63301  tagtgaactt ctcaccattc tttattcaat attcagggaa cattttttg agcactttct
63361  ttgtaaccgt cattcttcta aatgttaaag atgtagtaaa caaaaaattt ctgttcttat
63421  aggtcttata ttccagttca tatttataat agacaactaa taggtagata tataatgtgt
63481  cagatgatgg taaaaataaa gcagggtaaa ggggtaccgt gaaatgggtg agtgctgttc
63541  tagataggat attcatggaa ggtttctgat aagtaacat ttgggctgaa tgaagggaga
63601  gaactgagcc acatgaatac ttgagaaaag agtattccac acctatggca agtataaagg
63661  ccctgaggta ggagcatgcc tggtatgttc aaaaaacagc aaggaaatca aggtggcatg
63721  aaaacagcaa ggaggagaga atggggggctg accagagaga cgtagagtga atacaggaag
63781  catgtaggcc ttgaaggcta tggtgaagac tttggatgtc actctgagta agatgggagc
63841  cattggaggg tttttgagtaa aacaatggca taaactgatt tgtatttttt aaagaaccac
63901  tttggctgcc atcagtgaac agatttagg gggaaaagat ggaagcaagg gagctgataa
63961  gaggctattg cactaatcta ggtgagtgat aatcaggctt agaccagggc tttagtggtg
64021  gaggtagtga aagcagttag aacaaagtag agcttcaatt aagttgtcat ttagcaaata
64081  tgaaaggtta gtgcaggcag gtgggtccac ttgttttgga catgttaagt ttagatgcct
64141  gttagaaagc taaatagtgg tgtcaagaag acaccaagtc cactttttgga ggccgagggg
64201  ggtagatcac ctgaggttca agaccagcct ggctaacatg gtgaaacccc atctctacta
64261  aaattacaaa aattaggccag gcgtggaggc agatgcctgt aatcccagct actcaggagg
64321  ctgagacagg agaattgctt gaacccggga ggcagaagtt gcagtgagcc aagatcatgc
64381  cactgcactc tagcctgggc aacaaagagc gaaactctgt ctcagaaaaa aaaaaaaaaa
64441  aaaagaacag aagaaggaga caccaagtcc atagtttagg tacaagctgg agtttgcaca
64501  taaaaaaact tggaagacat cagcatggag atggtattca aagccaaagg ctagatgagc
```

-continued

| | |
|---|---|
| 64561 | tcactgagag aatgggtttg aataaagaag gcaggtggct cgagaactga gcagtcccca |
| 64621 | cttttcaagg tgaaagagga taaagaagaa actcaggagt agtctgtgag gcagaagaag |
| 64681 | atccaagaaa gagaagtgtc cagaagacca aaaaaaagta ttgcaaggag aaagtgattg |
| 64741 | gctgtgacca acaagttggg aggtaaagat ggagactgaa aactggccac tggatttagc |
| 64801 | aagtaagtac cataaatgac ctcaacacaa gagttcagag acagcggtta gggctgaaag |
| 64861 | cctgagagga ataggtttaa ggatgaatgg gaggggagaa agtatcttta caaaagtaaa |
| 64921 | gtcaacgttg tcaaggggaa ttgctgtaaa ggaaaacaga gaaatggtgt ggtatgtgaa |
| 64981 | ggggatgtgg agttgaggaa gttctcttgg attttgttct ttgagactgg aaatacaact |
| 65041 | tatttgtaga taggaatcat ccagaaagca aataaatctt cctgaaatag gtcaggagtt |
| 65101 | ttatttaacc aagttgaagt gtgtaaagta ggaatcagga agattttagt tgcattattc |
| 65161 | ttgattaatt aaaaagggaa gtggctgaga gaggaactac cagtagtatt accatgattt |
| 65221 | ccatggtcat gaccttagct gggccctatt gataaaggtg aatgcatgag agtaaagata |
| 65281 | aaggaataga aacttcacaa agcttcagag aaaaggtcaa agaaagagatc tgaaatgaat |
| 65341 | ccatgagata tagcaaacag caaaataaag ctagacagaa atgctggaga attttcttga |
| 65401 | taggtgtaca gaaatcaagt gcaattattt gggtttgaga tgtatgagtt atttattata |
| 65461 | aattgctatg tgccttgtgt aaaacaaaat cagacaatat agaactacat aggataaaaa |
| 65521 | acggaaagta tgtgtgcgca cacgcacgtg cacacacaca cacgtgcaca cacacacact |
| 65581 | ttcttttttcc ctagggggaa ccactgttaa caatttggtg catctcctta tagatgtgta |
| 65641 | tatgtgtgtg tatatccatg catatatgta tgtatgtata attacattac aaaaatatca |
| 65701 | tatactattt acactattcc gcaccttgct ttttatacct aaaatatgtc ttttgtattt |
| 65761 | ttccatctca gtaaagatag ctctactttc ttctttatta aaaaaatgaa taggcaatac |
| 65821 | atgaacatga tacactatat aaaagggaca acagagatag tcttccaatt tctgagtcag |
| 65881 | tcagtttctc cccagagaca accactatta ccagttcctt aaatgtcctt cctcagttag |
| 65941 | gcaatgcata gaaacatata tgtatgtatt tatacaaatg gtagcacacc atacacattg |
| 66001 | ttctgtgctt tgcttttttaa attttaactg tgtatcgtgg ataccactcc atagatgaag |
| 66061 | ctgcctcatt cttttaaatg gcaatataat actgcactct attgtcttta tttaattaaa |
| 66121 | tcctgtatct gaatgtttct aattttcac aatgagctca atgcaaccat actgagcaat |
| 66181 | aatgaagaac ttattcaaca agaagaaaga aaaaaaacaa aattaaaaaa aaagaccaaa |
| 66241 | agaaatcatt tgagactgta aagaattgtg aattaagacc aaatgaggcc aggcacgatg |
| 66301 | gctcacacct gtaatcccag cactttggga ggccgaggta ggcgaatcac ttgaggtcag |
| 66361 | gagtttgagt ctggccaaca tggtgaaact ccatctctac taaaaataca aaaattagcc |
| 66421 | aggagtggtg gcaggaagct gtaatcccag ctatttggga agctgaggca acagaatcac |
| 66481 | ttgaaccagg gaggcgaagt ttgcagtgaa tggagatcac accactgcac tccagcctgg |
| 66541 | gtgacaaact aagactatct caaaggaaaa aaaaaaaaaa aaactaatgt cactaaaatg |
| 66601 | atccatttac tgggaaaact ccaaaacaaa aaacaatagt gaaattttcc ttctatataa |
| 66661 | aatacattat taactgaatt ggctagaaag acaatgtctt gtggcggcta gtcttaggca |
| 66721 | tggaagatgt cagttctgtg accactgggt aggtgagtaa aattgaatca ttcaattctc |
| 66781 | ttttgcttcac ttccccattt ggaagaggaa taattgtgtt caatgtctct acctgctctg |
| 66841 | aagacatgca ggaaaaaaca gaaacatgaa cctgcacata gcagaaaaatt ctcaagtaag |
| 66901 | atcctctcgg gtaataatgt tagaatgact ctggccaagt tatgtcttaa agagagcagc |
| 66961 | tgaatttaga ggcagagaca tgtgtgtatc agaatcaact gggaagagtt ttcaaactac |
| 67021 | tccttgtctt gctccctccc cgcatcccag ttgagaacca taatgactga agaaaacttc |
| 67081 | cggtggctgg tgccataagt gataggacat aagcatttgg gttctaaaaa aggggggagat |
| 67141 | gcacacagtg gtgatgaagg tcatgagttt cagtttcagg gatgcctggg tttgagcatt |
| 67201 | ggctttactc cttattgact atatgatctt gaactattta tttaaacttt ggaaaatctt |
| 67261 | catttcctca tctgtgaagc acctgccaca tagttagtac tcaatagtta cggcattggt |
| 67321 | tccttggtaa ctctgacctt aactgtccac tttgaactac agatttaagg aaatatctgc |
| 67381 | tctcatatgg gtttatcaat taattctccc ataacagttt aatagatgta ggatctgtaa |
| 67441 | aaacatatat gcataaatac ataattttaa agctggacat ggctctttaa tcataaagtt |
| 67501 | taccctcaat aatgcctcat ttttatgaatg tagaaactga ggctctgaaa ggcatgagac |
| 67561 | ttgtccaagg tgatagagct gataggcatg agtcaggact agagctgaat cttccatctt |
| 67621 | ctagtctagc atcttcttgt cacttcttgc ctctctaaaa ccacacattt aataagataa |
| 67681 | aatatacttg cttttaaaaag ctaatgatgt gaatattatt tcctttctat ttcaggggtc |
| 67741 | attatatagg acaagaaaaa tcctgtgaag tgatcctcat ccagctaata aaattaacta |
| 67801 | tacaagaagg tatagaaaac ccctccctat cattgcagag gtggcatcca aagacccaag |
| 67861 | aaaggagtca gcaatagcct aggatccagg actcagagag agacccatat tgggaaaagg |
| 67921 | tgctgaataa ggggtagagt ttttatattc cttacccagc cccaaattaa cttccccagg |
| 67981 | ctagtcctct gtttcaagct tctatgcctc ccttgaggag tcacaagatt tccaaaagct |
| 68041 | ccatgttttt ttcacatggc tgtttcttcc tcgaattctt tattcctgcc cacctgacta |
| 68101 | atatggacat tagtgtatct gcaataaatt tatactacaa ttctgccatc ctaggcaaac |
| 68161 | atggaggtga ccagacccgc aatgaattca ggaagcggaa tgtggttagt gactaatacc |
| 68221 | aaggaatcat aaatgcaatt caactgataa cagttaggtc tgcgcctcta aaacaggac |
| 68281 | caaaggatct tctgggctcc ctcaacaaag ctgggcgcca acactgactg aatagctatc |
| 68341 | cttgggtctg actcacccga cccagtggag tggaggggaa ggtcacagaa ctggaagcac |
| 68401 | atccagtcca gttctggaca cctgcctgtc tgcccacgaa tgaccactgt ggaatctaag |
| 68461 | gcaagcagac agctcccaaa actcaccctg gagtctgcct ccgtgcatgg cccagcaacc |
| 68521 | acagcagtct ccactccatc cctggccacc atcagaaagg catctgttac ctcctgcctg |
| 68581 | gccttcagtt ctgtggttgc tagtataacc caacggccat aaatttcaaa ctctgctaaa |
| 68641 | tgttgaccta cttctaactc tgactgcaac acttccccctt tgggataacg gtcttactcc |
| 68701 | tgagtactct ctgctaaatg agtgccacct tgtctctttc ctctgcatca ttataattaa |
| 68761 | taagcaacaa tatcatcccct catgattatg ttcttattag atgttaactg gccttagcat |
| 68821 | cattatctca ttaaacctt ccacctaaat tactttatca gcttccctcc taaggaggtc |
| 68881 | tggtactgtc tgtctgaaag gaatctccta cacaaacaca agaaaccaaa aaggatgatc |
| 68941 | actggtattt agtcctgctc caaatactaa tattttaaa aaattaatgt tatttctact |
| 69001 | actaacaata accttacatt gctataaatc ttcttatcca aagtatttaa agctataccc |
| 69061 | ataagttttt tagcttcctc tcattttttat ggggaaaaaa tgtaaaagaa tgcattctat |
| 69121 | aatatttcta actgttaaaa cttcctccct tatcattacc cattctatt tggaaaaact |
| 69181 | atttccagtt ctttcattaa gatgatgaat ttcaaaattt tatagaaaag gctgtaaaat |
| 69241 | aggtttgctg gtttacttca gttgttctag gtgcaatctt ttcttcaact ttcctgataa |

-continued

```
69301   tgcttagctt ttctttcctt taatagcatt cattttatac attaacctttt tattaaaaag
69361   tagatgaaaa ctattctgct cataaatgaa gaacatagac tagtacgttt ctctagaaat
69421   gctttcattc ctgaggacta atgactttta ttgcttcctc tgttgtcctc acaatttcat
69481   gttaaccatg aactctttta atcttttcct tctttattac taagttctgc acattctcca
69541   aagtttggga agatatgcca tcgagagtcc aaacttgccc ttttacagcc attaatcatg
69601   ttttgtttcc caccctagtc atctcttccc ttccttgcca tcccaaatcc cttaactatc
69661   taccatcatt catcctcact ttcccaagta atttgctatt ttttaatatc ttattatctc
69721   atattcctca ttacccactt atccttcaaa ctctattgtt catttaattt tctcagaaat
69781   tatacagtct tatttggctt gcagcatctt tctccccatt cttgcacacc tacctcacct
69841   tcccactttc caacttcctt tttgtttcca aaggtgcaga tcatgatttg aaatgatgga
69901   aataaatctt aatctccttc cacttactta attttaaaaa tccaatgatc attcccagag
69961   ggaaacctag gtttgtaatt ctcaagcctt gccacagaag caatcaaata cactaggtct
70021   cttttttattt aatcatggat aatacaagga aacgctttct aaaatgaaat attgcacagt
70081   tggttggtgt taatctgaga tgcgccgacc attcttttttc tcctttggga gtgaagccta
70141   gtatggtcag ccaaggacac atttgtgtct tatgaatcta tgtcacataa gccttttttc
70201   ttagggatct aaataaaccg ctaaatacaa atcctgctgt catcaagctt tctgttagtg
70261   tccagcctct tttcttagaa gagcataatc ttagctttaa aaattttttg tttatatttt
70321   gttttttcaac cttcacaggc tttgaggctg ttttcccttt ctcttgatct ttctttgctc
70381   ctcctgaaat ctcaggcgaa ttaattttag caaacactgc aggcatgcag tcttcccttt
70441   attttctcta tttcaggatc cttcctcacc taatccttct ccagttcctt ccttcctatt
70501   tcaagtgcag gacagggatg aactcccatc tttggacagc cccatctttta tatcatcctt
70561   cactttcctc tcatcatttc atttcactcc atacacacac tactttcgtt cctgaccatg
70621   tttggccact tgtgtggctg ctgaagttct ggcagcctgc cttcctggcc atgagtacag
70681   ctacttggtt ccttcagtgc cccccaggtg ctgccaaggc aaaggcatca tgatcattga
70741   ctttatcagt gataacacca aggcaatgga agtaaacata catagggaca gcctcatttc
70801   atgcttaaag gaagaactgg gcaatttcc ccaactcaac tatctcccat tgaacttctc
70861   tgaagaatag tgttcctttt caaagcttat tgattttccc attccattac aggcatataa
70921   aggcctttata tgggaatgag attagtaaat tgtaactact gaaacctagc atgcatctcc
70981   atatgattat gaccttactc tctttctaca ctggccaaag gtatagatgc ttgtgcagtg
71041   ggaaatcctg ctcattgaat gactatgagt acgtttctt gaaaagaaca gagttttcct
71101   gagttaatcc cttttttaat aatccaaatt atctactctt tttttctaaa atgtgacccc
71161   tttcccccctc tgtattctat tacgattcac cacgatttct cctgagggta caatagagtc
71221   taattttctt cattattcaa tttggatcct gttaagagag acagacattc actgcaaga
71281   agaacattta aattttggca aataagttca ttagtattca gaaagctttg caccccctcat
71341   atttaataaa cctttccatt acagagtaag aaatcctgca aaatagtcaa acaaattagc
71401   aatggggcca ccaagagagt acattcaacc tggattcaaa gatgtctcag tttattagtt
71461   ttctgtcaat cattaaaaca agaaagatga aacatgcaat tagatacaag gagacagaac
71521   tcctaattct ttcatcctag ctgaagcaga agagtttaa ttgcttggaa aaataagatt
71581   ttcgttttct ctcaagaggg aagaggaagc aaatataaat tgccttagag tctatggctg
71641   gaggtacaat gctccaaacc atgcaaatga gaggtggaaa gacaagtcca tcatctgtat
71701   gttttgtctt tacaatggcc aatatccaga tatttagaaa tgtgagataa ttggcagaat
71761   attccttttt tcattagaat gtttagagtc acatagagatt actgattctc ttcttcttaa
71821   tgagagtgac actgcactaa aatacttgaa tatgttgtca gttattccag agccaatttt
71881   ccatttatgt gagttatcag tgcccttttgt ttctcttcta agtcctacca gctactctat
71941   cttaggagcc ttacactgtt tataacatat ttaccagagg gaaagtaagg acaaggagag
72001   gagataaaat actaatcaat ccatttagta atgatgaaca tctacaaaat tgaagacgag
72061   aaaattaaaa ctcttggcca tggagaggta tagacgttaa ctgcaggtgt ctgcctgttc
72121   cttgacctca actcagaagt aaaattaaga gttaagagta attaattcta ccatttaagc
72181   cagaaattga aatctctaat actatttcct aggataaaat tgtgaaacca aatagtgtgt
72241   atcagcaatt ctgaatttga aattccatat attgattttt ccataaaata tttctgcac
72301   tcagagatat acatcaaata gatctgctaa tgtaggaaaa aacaaagata caaatttgct
72361   tatataggat tcacaatagg gtaagaatta ctagcagcat cttttttgttt gattaggctt
72421   tttccttttcc ttttttaaaga ggtcaccagc catagggatg tatgaatcac agtatatgtg
72481   aaaacgtcta tttgctgaga ggtactctgt aagattggaa atagtccttc ctaccaggga
72541   gggatggctt acagagtata aagtagtcag tggccttcac tgtctggagg tccttctaca
72601   gatttatcct aagaaataaa agattgtttc ttccttatat ctgaagatag atcttttcac
72661   aatgactcta gggctgaata attatcttt tttttttttt ttcaagacag ggtctcccta
72721   tgtcacccag gctggagtaa tggcatgatc tcggctcact gcagcctcga cctcacaggc
72781   tcaagcaatc ctcccatctc agcctcctgt cataggccac cacacgcagc taatttgtgt
72841   attttttttgt agagctgggg tttttgccatg ttcccctaggc tacacttgaa ttcctgggct
72901   caagcaatct gctgcctcgg cctcccaaag tgctgtgatt acaagtgtgc agcaccatgc
72961   ctggccctgc ataattatct gatgtgtatc tcaaggcatg ctaaaagttg cttgagtaga
73021   atggggcatc tgtctgtagt tggttaccct gggacatggg cacattcccc tgggatatcg
73081   ttgattcttt ccaaagagaa agacagcaga tgaaagaaat tagggttttg tctcctggag
73141   actgggaaag tctcaggttt accttgtatc tccaaaccta gcacacacct ggtacacggc
73201   aatgcatcat gctcaataga aatgtgatga agggaaggag agggagaaag gtagcgggga
73261   aaaaaggagg ggataaagct cccatatgct ctacagtgta tattcctaca accttcctaa
73321   ctccaaaggg gagaagcaga ctcactgtat cctaaaacat tgataaaaca cccacttcag
73381   aaaaaagtaa taacaatcaa gtaactattg aagatctatt tgacctaaca gcatagaaac
73441   agaagaatta cacactggcc agctgtagcg taggcctga tcttaatgtt ttagagctgg
73501   agaggcctgg agtcactcaa gaggcatcca aatggaatgt gaaatgactt acccacagtc
73561   acatagcttg ttagtattag aacacaaact aaaacccagg tctcaaaatt cccagcccag
73621   catttttcac gctgcagttt cctatataga acagaagcaa tagctgttct tgaatcctat
73681   cccttcctgt ttcctaaccc aagtcacttc atatgtcctt ccgcagaggc cctgctaacc
73741   ttaagccctt tccctggtac cacagaactt tgtacaactt gctggggga aacagcccat
73801   ggtcatacgc catttataga atgcaggctt ataganaacatg gtcaatagga atgattaagg
73861   aaataggaat tacccctaata attggaacac tggctcaatt atatctttgt ggccatttgt
73921   tagtgtagc cactgttctt catacctaag gggaagctac agtgtaagct ccaagggggc
73981   aggaaccatg tctgtctagc ccctaagtct ctacagtgtc cagtaggtac ttaactatta
```

```
74041  gttgtatttt taaacatgac caccagttcc atatttcatg attccaagca ggttccatca
74101  tggctttatc tacaaataac cagcaatgtc atcctttagc caaatatttt tgaagcatcc
74161  agctctacct tgtgtctcca ataatctaat gaactcaaca cagagtctga ccaccaggcc
74221  cataggcaaa gagttcaagt tccatttgac ttgaactact ctgtgagcaa tgaccctcac
74281  ccccaagtga acgaagactc cctaagggct cacattatag aaatggaaga tagatagtct
74341  gccagtgtct ttattatcaa agccctggag tgcagagaag agacatgtag ggtaatgaat
74401  tggtgtctcc ctcagaccac tacttgttca atctttatta gaggaaaggc tgacctctgt
74461  atgggcaaga accaagcagg aagatcatgg gagcactcag cctaccctct gtggtcataa
74521  acaatctagc tagagtccct gttttatata tcctagtaag aaaaacagaa accctgaagt
74581  caaacagcat attcctctat attctgatta tgccctactt tctaccccta aggaatttaa
74641  caaatcatta cttccaaccc cacacagaat cctccctgag agaagagctg gtaaatatat
74701  tttccatgga tgtgttagcc tactattgac atgttagtgc ccttatagtt tagtcctcca
74761  agcaattgtc cagttgtttt gtgtttaatc tgaccctgct gacagtcatt actcaaaatg
74821  aagaaggcaa tctagagaga aactgtagct gatgctcctc ttctctcagt gggtggacag
74881  cccatccata aagtcttctt gatgatggtg tccaggagcc aggatccaag gagctcaaca
74941  acagcagtgg gaagaattac aggaaaaggt catgctcctc caagggagtg ggttttcctt
75001  tgtctcagca actgtaaaat tataaacaaa agattaaaaa gctaaatcac tgctcaagta
75061  aggatcttgg taaatgcatg gtttactcaa agcctgatga cggattcatt ggcatctaaa
75121  tgaagtctgt ggttttccag acaatggggc agagactaca gaaacacaca aattatgcct
75181  aaggattctc tgttccttcg ttaattttgt tgtaccaaag aaaaaggaaa aactataatt
75241  gcaactaaat acaagtaaat gcaagtaaat ctgcatgcat aaagcatgta gaatacatgg
75301  gctaggaagg gatatactag gggaaaagga gagagagcac aaagaatcaa gagcaaagaa
75361  attgcttctt cccccacgat attgcacagc actgacctga atggtacagc aattatgcga
75421  cctaagtgag agttcaataa ataacaatat ctgggggcaa actgagagtt aagctcccat
75481  gaaaaggtag aagcatagta accaaagcct tagccagtcc ctgggcaatc aatatgattg
75541  ataccccagag tctttaacag aatcagatag gatgataata atctcaccca aagtggttt
75601  aaatgaagca tcactagttt agggaatttc taccaaaaac atcaaaagtg atggtgatag
75661  cgccattatc agagtactgg caaaaccacc aaatcaatgg ctgtcttcgg ctgccatccn
75721  tacttagggg ggcccctctg tccccttcct caggaaccag gagcccagca tccatatgcc
75781  atcatccacc cactctaatt tctttaatgc aacagatagt agctaaacag aaagtcttcc
75841  aatggctaga attgggtatt tcatactagg gtatgaataa ctggttaatt tgactttatc
75901  agcaccataa gacagtgcaa aaaaaaaaa aaaaagaaa gaaagaaata acaattggtg
75961  actttcacac tcctacgagg tatctgcaat ttataaatgg agcttgtgta cataaaactc
76021  ttagttactg taatatgaaa aaaaaataga gagaaggaag ggacaagtga ataaggaaag
76081  agcagggcct tcccatgctt cttgtttaat gtcaccacca tcccacacca accatcaaac
76141  ctccgaacat gggcttaggc aacttggcct ccaatgatac taaacagctg ctaaccccag
76201  tcttagaaga caaatccgtc ctcagagcac acagaagagc tgggtccttt agaaccgatg
76261  actggattta tagagaagcc tcctacagat atgagtgatc atgtctgcat tgctggtgtc
76321  taccctagtc caaatctttc actttacaaa gaagcaaagt gaaaggtgag tggcttgcac
76381  agtgtcctgt agagactaac taaagggtag aaccaggact gagcccaggt ctcccaagac
76441  ccagtccaca gccctatcca ggtaaatccc catgagcata acacactgtg ctccagacac
76501  aggcagaaga tcatattcct caaactctag agtagtattt gggtagtatc tgggtagcaa
76561  tttccccttc ctggacagca atttgattca gtgggtccgg gttgaggcac agttatctac
76621  atgttaacaa gctccatggg gtcttccagg tatagaaacc acccctacac ttggtcccaa
76681  ctctacctac cagcactgca cagagggctg agaggtccct atgaagggac tgctatgggg
76741  acatcctctg gaacccatac atcaaagggc tcctgaccac tgggtcacaa gtcagagccc
76801  tgaaaacaaa caccagccct gaaatctcaa acaagaatg cttagaatgg gacagaaagg
76861  tctcctctta gacctgttga cctagtggc tttggtcctg gcaatatcca agtgatgcct
76921  tcaagcctct tgtgtaacca atctcccaat atgtgctgag ccctactttt gtacaagact
76981  gtgcagggg gctagatgg gcaaagaaaa gtaagcccta gttgcaaaaa ctctaccaag
77041  aagatcagac acgtacactg aaaaagaacc cacgttacag agcagtgttg ttgaggatga
77101  aacaaaacac agatccatat ctgtgtcata taagcttgct cgatgtaact caacaatttc
77161  caaatccact tcctggcaga accatctttc ctggttcctc aaccccccacc ctggggattc
77221  tgattcagta agcctgagga agagcccaga atgtgtcttt tttgccagct gtgaggtaaa
77281  tctaaggtag gcagtccata ggtggacatt tgagattctc acagtgtgtt gaggtcagg
77341  ctgcaaagaa tttaagggaa tctatcttgg ttccttcttt atattaatgg tttgctgctc
77401  ctcaaaattc ttaacttact cacattggcc cctagaatct aagtctgttt ggttttgttc
77461  ctcttaggtc agtcatggtc tatgctgtct tcctacttga aacttcctac ttagggcctc
77521  cttcatgttc ccagcagaaa tctgtttttct ggaaaagggt gcagctttac tcctcaggaa
77581  aacacacagg aaaaaaaaaa gcccatgtcc agccatgtat catatgattc aatttatacc
77641  atttatattg aatgtctaga ataggcaaat ccatacagat agaaaataga ttagtggttg
77701  tagagggctg agggaagtgg aatgggggaac aactgctaat gggtatggag tttcctttg
77761  gaggtgatga agacattctg gaattagccg taatgactgc acaacttttct gactatactg
77821  aaaaaccact ggattgtatg cttcaagagg gtgaatttta tggtatatga attatatctc
77881  aattttttgaa aagcccatgc ataggtaaca cataaaacat acaggtgggt cacctggctc
77941  cctgggccct cacaactact gggtgatgac ccctgggcaa gaggcagggc agccaatgac
78001  aataactacc attcacttgt acttattatg tggcagacag acattcatta cacacagtac
78061  atggttggct cagtacatgg ttatctcaga taagacatca ttaccaaaga tgtggatatt
78121  attatgatga tattgttatc actaacattt taaaatatga caacacgaag ccatagtgaa
78181  gttaaataac ttgaccagtc cacagctagt aagtggcaaa actgatagct agggagatgt
78241  ggcttaatag gcaccaaaag acccctgccc caaaccttgc cccaaaccat gtccctcatg
78301  gatctgtcat tcttatcatt agattgcgg aaagtagaat aataataatg gtggcaataa
78361  tgttgctgag atgtattgag cgctttccag aaatcatcct cgatttatag atgtgaaaac
78421  taaggcagag aatgttaag taaattgccc caaaccacac agctaataag tgatgggagcc
78481  agaacttaaa cacagaccct agtgctaagc tgctcagtca gagatccaac tcagatgtct
78541  gcaggagcag gacaatgata gtgtcaagtg ggccccatat agcatacctt gaaatacaaa
78601  gcagtattga ctcatctttg attcatctat agacatgtgg tacaattttc tcctaatact
78661  aggggaaaaa acaaagcaca agatcagtga taaatggcaa atgatgcttt gcctcaatgt
78721  tgaggatgca aacacgagtg cagaaactat ggcaaattgg agagagagcc acttcaccca
```

```
78781  acagggcttc cccattccac tgtaaccctc cacctctggg tgggtgtgca gtacagtgtt
78841  gccatatttt ctgagataaa gccagaaaga cagatcttta cagaaaatct ttttcatttt
78901  taaaagatag taaagaattc tgcagactac attggtctgt agcagaacac tcttgacttc
78961  aacacatagt aaattgcctc ctcaagcagt tctatgtgac tgggatttag aatttggggt
79021  gaaaagtgac agggtgagtc aagaacagtg aggaggagcc agggtctgaa gactcttgac
79081  gcacacctaa ggaagcagaa cttttattttc taggctaggg aaagccagag ctttgctgtt
79141  ctgttttaag aagggaaagg gaccagatca caaagacacc tctaacgatg tgaaggtaga
79201  ataaccagga aagatagcca aggcagtgag accaactggg aggtaactgt aattatcagc
79261  cccaaactaa ggtagtagca atggaggcaa gagcatgtac tcaagtcaac aactaatagc
79321  aaagatcttc cctgatagac aatagatgtg attgtatcaa aaggggggcac acatatactc
79381  tattagatag ctatactggt agtcccttga tttttttttt taaaaaaaac actatcataa
79441  ggaagaggga gacattagca aatgtgagga agagcactat gagagaaata gagaagggtt
79501  acaggataca acttgttaga ggctgggttt ggcatatgaa agggaaagaa aatgttcttg
79561  gctggagaag agacagctct aaaactgcct aggaaaacaa aagtgaatga gggaaataaa
79621  gaaacacat aaagagttca ggtattaaga aattaagaag aaatatggaa agccggcagg
79681  gaaaaaaaca atcaaccaat gaagaacagt gaaggtccct aatgtccaga tttaatgcag
79741  atgagagaaa ccagtgaagg cattttaaaa agatgttgta atgaaggcac caagaagatt
79801  gctttaacag agactgaact caagaataga gaccacaatg gaggcattta taaggagtag
79861  aaggaaaaga agaccaaaat atgggaaagg attttagtga ttggaaactc acaggcaaag
79921  atgagtctta gagatgtcag aaaggaaaat atgacagat tctggaatat tctcagagtg
79981  aaaataaggt ctaatctgta aaatatacaa agttctctct ccacaagtgc ttaagaagca
80041  gccctgagga gtgccaaaga taacaccaaa gctgcattcc gagggcatga ggaggagaaa
80101  gcagttacca gcaagtccct gaagggaagg gagcaaggat tttagccctc accaggcttg
80161  gtttcattgc ttgtaacatc atccaaatca gaataaagcg ttcaacagaa tggactttc
80221  cagaagtaac cttgtgatgg ctcagagcat tctgggagag ctgcaatagt caagaagact
80281  gaagcaaaaa ggaaaagcct ctgccacaca cagtgcagag atagaggacc aacaataatg
80341  gcaacaaaat atcatattga aaagcattaa gttgtacact aaaagggaag aaatataagg
80401  aggtaggagg aggtaacatc attgacaaca atgtgaaagg gctgtcattt agaagtatgt
80461  catgttatgt ctggtatctt acatacagta ttccatctaa gcctcacatt agatatgcaa
80521  agttactctg ttttgcagaa aaaaaaatgt agaggctatg taagttggt tatttgctaa
80581  aagtcactta gataataagt tttagaggca aggcttgttg gagtctcaaa cttatgcatt
80641  tttctactat accacactgt tggactatgg accatcttcc aatcagatta ctgcaaaagc
80701  cttcctaact gatatttcac ccttacaat tctccttca ctatgtaact caagtaatct
80761  ttctaaaatg cgaatttcat catggtgctt ccctgctcaa atccagtcaa aaaattcctt
80821  ttgatcttaa gatggagtcc aaaccactta gcattccta caaggccctt caggatctgt
80881  ccctactcac cttcccagcc ttatcacaag ctcctctcat tgcagctgac aatgcaatga
80941  ctcttaatat attaaagtcc ccggaatgca ccctgctcat tctcacctcc aggtctttgc
81001  acactttgtc tcttttgcct gaagcactct tcctgacctc ctaaactctc ccctcagtca
81061  gtcaatgcaa cagcttctct tctctcataa aatttaacac actttattga aatcctctcc
81121  accagttctg aggtccccac acctcctaac tgggaactaa catgaggaaag atcctgtttc
81181  tatcttgttc acattcacac ccacctagta gtgccctgac atatcatagg tgttaaacac
81241  atatcttttg aaatggatta ataaattgga tgcagtgggg ctgtcactgg ttactaagtt
81301  aaactatggg tagaggcaaa gggcataact aacaccaaag cctctacttt taatgtctgc
81361  aatttactgt ctatagctga agattctttt cttaggcatc tcgaaaaatt caacatttag
81421  gctgggcctc ctctggctca cacctgtaat gccagcactt tgggaggcca aggcgggcag
81481  ataacttgaa gccaggagtt cgagaccagc ctggctaaca tagcaaaacc ttgtatctac
81541  taaacataca aaaattagcc gggcatggtg gtgtacacct gtaatcccag ctactcggaa
81601  ggctgaggca tgagaatacc tttaacctag gaggcagagg tggcactgag cagagatcat
81661  gccactgcac tccagccagg tgaaacagca agactctgtc tcaaaaataa taataataat
81721  aataataata atctacattt aacagagcat atactctatg cacttcctgt gctcagagct
81781  atgagtaatt ctagggacaa gactcagttc ttgccctaaa caagcttgca gtcagtgga
81841  gtagccttca tattccagtg tgttacaatt cacattctct ttaaacttt ttagaattta
81901  gttgacaagg gatccttgac agtctgttaa gcattgggta actgccaact gactgatcac
81961  tagctccaac aagactacaa ggggcttgag attcgagact gaatcttctt catcattatc
82021  atcccagtgc ccagcatagt ggctggtata taaaaacagg tttaaaataa tcaactgaat
82081  gaatgaaaga atagacaaat gaacaagcaa acaagccaag tcttggaata aagctttggg
82141  atctgggtca gagtctcagc aggaattatt ctccatcatt caacagataa atgactcagc
82201  aacaaatact ctagggaaaa tcagcccatt cgatataaac acacacagag acacacacac
82261  acactgcaga gccacaggag tacgggagca ggacaaaaga gggccagggt aggattttgg
82321  atggttttcc agtgccagct caggttcctc ctgtgacttt aggttcagaa gggagacact
82381  atggggcagg cacacacaca tagagcagtg acatggcttc atctgacccc tacaaactca
82441  aatctgctta ttgagacaca ccatagcgat aaatcaatgg aaaaacaggt agatacatca
82501  atatagtgct catcacatgt tttcaaaact tattaagaaa accttaattt cacatggtat
82561  ttaaatgta tgttaataat caccaacaca aataaatacc ctactgaaat atctgaatag
82621  ttgctatatc tttcaaaatt aaaaccaaat atcagaacaa aaatagctac ctaaatagca
82681  acctttcac acatacacac actcctgaaa tttacctgct gccaacttgt tatttaaata
82741  aacattctg ctacacttta ccaccaaata gtaccttgta gtcagtttaa aaaaccttta
82801  tcaaagtaag agtatggtat tattttgaca ccagacagtc ctttgctttt gtgtgggaatc
82861  actgtgttgc ctgaacagtg tatgatttcg ttttttgtgca gacaatcagc aggtcattag
82921  tgtaccatac aaatcgccct ggactcagga tggagccctg gggaactgaa gctgtaatag
82981  actggaggga agatatggtg ttgctgacag ttacctctga tggcagttaa aaggtatgat
83041  tgcaaccaca tgacagctta atacaacaga tccctgaatt gttcacatgg caaattctga
83101  ttaatggtgt caataatcat tataaatttt taaagttttg tagaggactc cattatatcc
83161  tactatcaga atacaagacc aaccagatcc cttatgaaat aaccatgttt tatcattatt
83221  ttactgccat tggttttaca tgttggtgaa cgtgaattta ttcacatatg gaaggtggtg
83281  gggggcaggg gtctactgca tatttacatg gttcatgaag aaatttttgc ataagaaagt
83341  gaatgtaaga taaattgaaa ctcagtatat gaaccagaat ttgccacttt cacacacaca
83401  cacacacaca catatgcatg catacacaca gagatacaca cacaggataa ggtcaatttc
83461  actgtatcca catctggcaa tgatgtgggc atagtgaaaa gatttcaggt tccctccaga
```

-continued

```
83521   aagcccttag gttacaagaa aaatcatcct acatctaata aacccatctt agatatatct
83581   cccatatggt aaagccctgt tttgctttat tctaacaaat ttgtccttgg attcctctca
83641   cagctgttgc tgctattgtt tatgatgtat tgagccctgg cagtggagtg atgcactgtg
83701   tacaacagag tcaagattcc cacatcactg ggctgtgtga gcattaaatg atctcacctg
83761   tgaagagtcc agagccaccca gtatatttag gggcctgaca tgtaataact gctcaaaaaa
83821   tggtgccaaa aaaatttttt taactaaaat attctaggca cttagtctca agaagaaaaa
83881   acagagtagg tttctaaacc agattaccac caaggtaata aggatgctaa aacaaacaaa
83941   caaataaata atccttcctc acaatttccc cctcactatt ttccaccaca gtttggtttg
84001   acttgagaaa cactggagcc tgtatgtgcc cagcactggg ctagcactgg aggcatggag
84061   atgactatgg ccaccccca gctgtgggtg gctgcccctc tgctggagac atgaaacacc
84121   tgaaattctt tgaaagctga gtcttttgcc accacaacag tatttagaaa atttattata
84181   caaattcaca taaatgatat aatcctataa aggaagatat ttgctcctgt aacacttact
84241   atttaggtca gctgactttt tcatattctg gtagactcct ccttaatgta tagctgccat
84301   acatacagga atcatctttt tattttgcaa tgagttacct agcataagtg aatgattcaa
84361   atgtgctaaa aatcagtaga ctaaattaat gctgattaaa agagcctatg atagcaagcc
84421   tatagatata attcttgtct ataaaatata tcatagctat taccaaagaa attaatctaa
84481   aacttaaaat taccaatact agctagatgt caataaaatat tactaatato aacagataat
84541   tctaatcctt ttggtctatc tgcatgggta atcttcaggc atgtagcctg cagatttcct
84601   caatactttg agttgttcaa tatcattact aatgtttgga ggtccccac cccaaggatt
84661   tcccttttcca tttctatcaa gtttcagcag atcctttct gaagtttaag taagacaagc
84721   ggcttgcctg ttccatatca atttgacttg gaatttagaa gctaaccctt cctcctcttc
84781   ctcttcattt tccttacttt actagcctca tctcccttgt tttacttttct tctcaagttc
84841   ttttttttcca tgctttaagt attaatttaa aagctcccct ttcctatgct ctaagaaaaa
84901   agaatagcag aaggaacaga agacaggttt agaagggtga tcaaacatga agaaacaaga
84961   attttgaagc tcctacgcct ttgaagctcc tactccttta aagctcagct tctctctccg
85021   caatggccaa aaacagatgg acattctaga aagactaaaa gaaagaagat gctaggtagg
85081   aggagacaga atgttgaagg gaggaactca tctcaagttc ttccttcttc taatctcttc
85141   tttccacaac tcatatgcag tggcctttat gctcctagtg gaattgaacc cattgaaagt
85201   tcagtataag gctgggtgca gtggctcatg cttataatcc cagcactttg ggaggccaag
85261   gcaggtggat cactgaggt caggagttca agaccaccct ggccaatgtg gcgaaacccc
85321   gtctccacta aaaatacaaa aattagccag gcatggtggt gcatgcttgt aatcccagct
85381   acttgggagc ttgaggcagg agaatcgctt gaacccagga ggcagaggtt gtagtgagcc
85441   gagatcacac cagttgcagc ctgggcaata gagcaagact ctgtctgaaa gaaaagaaaa
85501   agaaaaagaa gagttcagag taggtaaaag ggacaaatgg catgaagtaa aattccactc
85561   acacacacac aaaaaaattc cccagggtgc ctctagataa attgctcaag tgttgttctc
85621   cacccctctc ccaggccaac acacaacact aggccacctc acacctgaac ttctggttga
85681   gccagaagag cactgaaagt ctgagggcag ggccagaagc ccagcagagc cccaggcagt
85741   gggcccagcc atcacctcg cagggctggg actacatttg ccccccaaac aaccctcaga
85801   aagttgggta ggaggagcag tggggaaggt caaaggcaac ttgggttggc accaacgagg
85861   cctcactcac cttccaccag gctccaaccc tggctatctc agatggtgca agagtcttct
85921   aactctgtct tccaacttcc agttaaacca gaagctggac attcaaggga gggggccagga
85981   atgtggccag ccaggtacag ggacattact gccacacttc ccatcatggc ccacaagtga
86041   gatccaggcc acacaggtgt acttgttgga cagaaacatt ctgagattct attttaaaag
86101   tcttctattc cagatattaa acaatcatga ctgccatttg ctggccgctt actatatatg
86161   gcctggactc accacgaaat aggtcattta attctaacaa caaccctata cagtagatac
86221   agtaattacc tcccctttag atactagaaa actggagcct agaaggacaa aagaaagtca
86281   attccaacta ataaggaca gattcagaat tccattccag ataaaactga ctacaaaacc
86341   cacattttta accatcatat gtagaaaacc aaccttctac actttcaaa gtactcctcc
86401   tggatgggcc ttcagagcac tttgacccttg ttttgttaca ggaacagaat tcaatagcaa
86461   gatggcaaat agttttcctc tatttgtcaa tgtgcctgag gccagaagta gattctagaa
86521   atcagataaa caagtggcag agatagccag gtgcggtggc tcacgcctgt aatcccagca
86581   cttttgggagg ctgaggcggg tggatcacct gaggtcgtga gttcgagacc agcctgacca
86641   atatggtgaa accccatctc tatgaaatac aaaaaattag ctgggtgtgg tggtgcatgc
86701   ctgtgaaccc agctactcag gaggctgagg cagaagaatc acttgaaccc aggaggcaga
86761   ggttgcagtg agccaagatt gcaccattgc actcctgaac aacaagagtg aaactctatc
86821   tcaaaaaaaa aaaaaaaaaa aaaaaaaaaa acaagtggca gagagaatcc atttacaaaa
86881   cagaatttga gggagttagt gtgtgggagc gtatgttctg ggctcagtct agctcagagc
86941   tgatttgtct caaggttaaa gtatttccct tgccttttgg ggggaaccaa tacatgaaaa
87001   tatatcaacc atgaactttta gtcacagctg taaataaaca gataacatat aaacatgtgt
87061   tcaagaggtc cctaaagcat aagcactttg tccactaagt tctttatttt ccaagtctca
87121   ttttcccaaa agatactgac tgccccaaag gagaggtata ataaagtatt ggaaacgttc
87181   tgggaactta ctgaaaaaaa caatagatgc aacaaatgaa gacaaagtca atactgtctt
87241   tatgttcaat ggccccctagc tcttaaaata agcatacctt tatgatttta cagcagttgc
87301   aatgataaat ggaattgata atttaacata tttataaaat aaacattctg cacagtttt
87361   cccttccac agaggcctta agaatcctca tgattatgac tttgggggca ttaggactat
87421   ttataagcga ttcttgtcag cccaatctgc aattatgatt tccccgcccc ccgcccccagc
87481   ccctgtggac tctgaagagt cccctatttg tagttatcaa gggaactccc acttcccatg
87541   gagagagaat gacagtagga tgttatcact tagcttcccc attctctcaa agtcccccaa
87601   ccgaattttc aggattgctc ttcctttcgt gtactatgag acaatagcag gtgttcccg
87661   cttcacccct ttctattcta cagactcctc caaggaagat ggatgctcct ctagaacaat
87721   gaccacaaga aaacaacaga agcaagaaaa gtcaaagatt ataacctaccc aaatctccat
87781   caaaaacaag actcagaagc ctgcaatcat ataaataggc ctatgagatg actcagcttc
87841   ctaagtaata tgatttaggg agaatcaaag gatatatata tatatatata tattccatta
87901   cttttatgta ttcatttca atcagttatt attgagcact ttctgtgtgg gagttactag
87961   aagatgaaga taaatggtc atggggttgt cagatttaac aaataaaaat cccatttt
88021   atctggcaat tctaaattgt cagcaagaga ccatgcctac cacaaggaac tcacaatcta
88081   gtgccctgtg cattccctaa aatttgaaa tctcattaac accttagcaa aactgattta
88141   tctgattagc ttcaaagtcc ataacctgag gctgggtctc gtgctcacg cctataatcc
88201   cagcacttg ggaggcagag agggtggat cacgaggtca ggagatggag accagcctgg
```

| | |
|---|---|
| 88261 | ctaacatggt gaaaccccgt ctctacaaga aatacaaaaa ccagccaggc gtggtagcat |
| 88321 | gcacctgcag tcccagctac ttgggaggct gaggcaggag aatcgcttga acccgggagg |
| 88381 | cagaggttgc agtgagccga gatcgcacca ctgcactcca gcctgggtga cagagtgaga |
| 88441 | ctccgtctca gaaaaaaaaa aaaaaagaag agaaaagaaa aaaagtccat aacctgggag |
| 88501 | aatgatacac agaagacata agttttgagg gaaagaaaag aattagaaag gtccaaggca |
| 88561 | agcatcagca gaatgtcaca gaaggagtaa caatgattga ccgaggacaa caaaatggcc |
| 88621 | ccatgtccat agttgggtgg tagggctagg gtaaagaaat caaaatgagg caactattgc |
| 88681 | tgagaaactc agcttgtttc acctgcattc caaataggtg acaagttcac aaaaaatgtt |
| 88741 | gtcaaggttg gtaaacattt caattagacc tgagcagaac atctagtgag atctcatgcc |
| 88801 | aacttatggt ttggggtgga aaccatacaa aatgtggtgg ttttataggg tttgaacctg |
| 88861 | aaagcaagca aaatgtggtg gtttgggctg tgttttctt ggagtttttt acatactcag |
| 88921 | gcataaaaat tcacagtcaa gcttgggagg tccaatctga aacaataaag ttttcacact |
| 88981 | atcctttcag caaccacaag gaataggctt ccaaaagaag ttgtagactc ttgtttgaat |
| 89041 | atctttaac tatggttgat agatggacta gttaggccat gtttatgtga caaaactga |
| 89101 | ttttgatgtt tggaaagagg aaagaggtcg tcttttcctg gaccaacatt acctacatg |
| 89161 | gaaaaagaca gcaagacttt tttatgcatg ctctttgtgt taataataaa accagttaat |
| 89221 | gattaggtcc attggcagaa atttcttggt tagcctgctg tgagcaactc catagcttga |
| 89281 | atctaaagtg agagtgggct gaggaaaata tttgttttgt cttgtatgtc agttattaaa |
| 89341 | gccacttcaa atccttcatg gaaatatatg cggcataaat aaatgagaag tgccacaaaa |
| 89401 | gaagtgcaga gatggaaaaa gacattcaca tggcaaactt taccatagcc catgctagta |
| 89461 | atttaccatt tcctaatctt aggattccaa atcccaaatt gtatttgcc cagtgcaaga |
| 89521 | tacaatttct gcccctccac tccttcccit tctttgatct cctttgtctg agcaggcaac |
| 89581 | taaaatcttc atgaaaacat ttgagtgtga ggtagcact gtcttggatg tcaagcagta |
| 89641 | caggttctat aatggcttca gagtgccttg gatgggtaca agaaaacaga cttggatgac |
| 89701 | cctccgcaag ttcttttat aactttctgt gaggttcatt ctctgaatct gcaaccaaat |
| 89761 | caaaatattt actatgttct ttagtttgaa aacctgaata tcccttcatc attaatagaa |
| 89821 | attctaatgt tctcacaatg gtgtaaaatt tcattttttc ttttgtaatt ttgtagtgct |
| 89881 | aaattttaatt ttcaaggggg caagggaaaa ggttataaac ataaattacg gtttacatga |
| 89941 | gcagaacagc aggaatcatt attattatca cttacctcat atatttatta agttattcca |
| 90001 | ggaaaaccta gttaatttac atcttgtgcc tttgaaacat ttgataactc caagttgggg |
| 90061 | aattggctta acttttccti tggtagaaga gagtttacag atctaattaa attagctttg |
| 90121 | caggggggtga ttaatctcct taaggaaata gactgctttc aaacactcca gtaacaactg |
| 90181 | tttctaatga ttaatgaaat aaatacaaag aattctggcc tactaattaa agcagatcca |
| 90241 | attatgagtc ttggccacag aatattaatc cctggcttat gtaaatatgt tatatataat |
| 90301 | agattacaat attttataat tctgacatat catagttttat actggtcttc cctaaaatta |
| 90361 | gcctaagaca gtgagggctt cattgtattt ctgttcaaca gttgtaggcg cccaagatgc |
| 90421 | cagcaaaata catctcaaata gcttttgaa atgtttatga tccctccagt ccctgttaac |
| 90481 | tataatatgt gatgacataa ttggattcat tggaagccca cttggctagg acattgtggt |
| 90541 | agttgaaacc tattagcact caagtaaata atccaaatca ccatccaacg aatatgcata |
| 90601 | aaccatatat tgaatagtac aatcgaatgt ctaaggattg gacaggtaac ccaacatgtt |
| 90661 | tataagttct tcaattaaga tagaaactca ccaaaaatag tttgtcctga aaatgtcaag |
| 90721 | aattcattac agaccccaca atcaaaacctc ttcataaagt tactcaggga gaataacagg |
| 90781 | ttcctttag cactccttcc tttttttttt ttttccttc ttttttgag gtggggatct |
| 90841 | tgctctgtca cccaggctgg agtgcactac agtctcaaac ttctagctca agagatcctc |
| 90901 | tcaagtagct aggactacag atgcacacct ctatgcttgg ataattctta tttatttta |
| 90961 | ttttttttt ttgtagagac aggagtttta ctttgttgtc tgggctggac tcaaactcct |
| 91021 | ggcttcaagc aacctccca ccttaacctc ctaagtttta gcactcttct tgagaaatac |
| 91081 | taactagaga aaactaagga cagaagaatc catccaatta caacttattt ataaatgtaa |
| 91141 | accaaacaga aagaaaaaat tgaatacgta tttttcagt gtacatatac tgagtattta |
| 91201 | ctatccatca ggctcagttg tgagttgaga aatataaata ttatgttgtg cttgctacaa |
| 91261 | cttatagttt aaaaaaggag acagataaat aaagcaacaa ttaccataaa acttgcaaaa |
| 91321 | tgctgtaaaa gaaataagca gaggatacta cggaggcata aaaacaggca cctaattcca |
| 91381 | agcattggag attccccaa ggctaatgtc acttgagctg agctggagag gtgagaagtc |
| 91441 | agccaggtgg gcaatgacca aaggagggct ttccagaata aggggatagc atatgcagaa |
| 91501 | gtagaaacta aaaggacttg ttaaacatta cattaacgct aatattaagc attaactagt |
| 91561 | attctttgat catttacttt tcacaaagca acttggtaag cattttacag gcatttgtct |
| 91621 | catttaattc taccattacc atttaaacca gttctattat tattccaatt gtactgaaag |
| 91681 | aaacaggttt agagaagtaa aataacttat tgaagatttt tcaacagtct gactctaaag |
| 91741 | ccccccaccg ccactagact ctaactgcct ccccacgcat gccacagtgg tgcttgtctg |
| 91801 | tcctctgtag gcaatgaaaa gccacacaaa aaatttttagg tgaatctcct aaaagtaagc |
| 91861 | acaacatttt tttaatgtga aaatgactcc cttttttggg tcatttaaaa aatccttttgg |
| 91921 | ttcaatacct tgattatgtc cttgttaaat ttgatttcta tcttgttcag aaaaaggaatc |
| 91981 | atgacttaag aaggacctat tgtgcatgtg aatcacaacc cccataatga agagagaggt |
| 92041 | gaaaatgatg ctgtttccaa taagtagggga tgggaagtgt catgtgtcac tctgatatgc |
| 92101 | gatacagaaa tcaacatgag ttgtcacacc atgcatacag ggtaggactt atcatttata |
| 92161 | cctactctta tggaggcagg gtcagatttc taaatctaaa tactttaaat tcagaatact |
| 92221 | tctccagcaa tctttgcttt ttaattgatg gtcttaaag ggcaagattt gcttagaacc |
| 92281 | atgtttaaga gagaagagtg gaactatagt gatctaaaat gatctaattt tctagaaaat |
| 92341 | tactactttc tccaagctgt ataaactta attaagaaga caaggaggtc tattctctct |
| 92401 | tcttacacac ataccacata ccaggctctt gggatactga taaaaggaag acagtggact |
| 92461 | gaaaagatta aaattttaa caaaactcta aatataatta agatggaatg tttactgcca |
| 92521 | tctttaagga ccaaaaagta accaacattt gttgctcctc tggaaagaaa atatctttca |
| 92581 | cttcaaaata tgggtaaagt cagcttataa agtaatctgt agaaagaaat taagtcacaa |
| 92641 | gtaagacaaa acaaaaatca gctcatatga gcacaataca ttttttcagct aaatatcacc |
| 92701 | aaaataagca ttcctgggac acttaatgcg atgctttgtg catctgtatc caataacatg |
| 92761 | ttctcaacat ctcctaaagg gatattttgg tagcttccac tacatattct ctagaacctg |
| 92821 | actttaatgg tagcagattt agaagaacag ataaaaaaaa aaaaaaaaga aggccactaa |
| 92881 | ggtgagagca cacactgaat atgaaaatat cctccacaat tcacagtaca taatctatgg |
| 92941 | ccacaaaagg tttctcttcc cctactttct attcatgtgg ctctctttca cctgctttct |

-continued

```
93001   ctccttgccc tctttctccc taaactttct tttcccactt gagttctcct accaaaccag
93061   ttctaaaatc acttcaaaag gacatatttg aagcaaagaa gtttaatgta ctttgtccta
93121   catgtaaaag catttgggta gccttggtgt cagtgtgatt tcggctgtca tcaagactgg
93181   cccactgagg ttaaatgaaa atcaacttca ataggaataa tgtgaaagag aatagcattt
93241   ttaacaaatt cagatatctt catgtgttcc tcccaatcta caaattttga agaaagctgg
93301   gtggcagcta caacttcgta agtagcctcc tgtgatatgt tgatgttacc acagcaaatt
93361   gggaaatgag gggaaggatg tgtgtttagc acaaatgctt atgatcatgt gcacatcact
93421   tgtgttgaga atgtagctca gctatattaa ctagactaac tgattaacta tatttatata
93481   tatgggatat gggctgaaaa gcactataaa atttatctgc atgtgtatat gcaagcagag
93541   agaaatgctg tattatctgt ataaatatca ggtagcataa aataaaatac ccctgcagtt
93601   gtttgtttag ggacacattt ggattgagtg agcattataa caatcatctc tttcagaggc
93661   acaaaaacat cacacttttt agtttaata aagtctagtt tttggcagtt cttttatcac
93721   acctgtcatc tcctaagctt tgcttagcca aagcactcag acttgaattt ttgaaattgt
93781   caataaaggc tttctaatct ttaagtctta aattatctaa gcagattaac taccattatt
93841   ctatgcttac aggactccag ggtaaaagac agcagagaaa atacaacttt ttttttttt
93901   tttaggcaat taagtccctg tggaggttgt gtttggggca tgtatttgga atatggtcca
93961   atgtgtttat gtaaataacc aaatagacat ggtgagtaca ttaattccag tatctagatt
94021   tataagacag ctctaagaag cttaattgtc ccactttaa attacaagtt attcttagtt
94081   catattggca attctccagt ttgcaagcaa tgaatgtcct gaagccaagg gagatatctt
94141   gaaggaaaaa aataaataaa aagaaaaaaa gaaagctcat tttcacagca gcgcctatct
94201   ctgtggtgac ctgatttctg ctatgatctc ctttctgaga tcaaagcagg attaatgtga
94261   ttctttactg tttgcattgc acatctcaaa gctctggaga cttaagaaat aagtacaaat
94321   gcagcccttg aacagagggg aaactgaact tgagtgggt gggttaatag cacgaaatag
94381   cacgagggac agctaactat gaaaagttat ttgggatttg gaaggcaata cagaatttag
94441   agtattttgt aagcactgtt gctttctctt ttctcatttt ctgggggcagt ctttcggttg
94501   gttgatgagg ccagcactga atgtcatctt attaatagtc tccataatga cctttttagct
94561   catttggaat gttttgcagc tgctagtatg catgaaaagg gaagggaagc tgctgcatg
94621   ttttcacaag aaagcactt cacattgcta caaccaggca tttataagga ggatttaaaa
94681   gacgggaaaa tcttttaaaa tatcaaaatg ttgagctttt gtgttccac tgcatgttac
94741   attactggat actggaactc ctaaagggtg agtgtttcgg cagccttca gaattgcttg
94801   ctcttttgtt gaagaaaagg caagtcccat attcctggga tctcagaagg cgaaaagaaa
94861   atcgcttta ttcttaatgc ttagtgtaca cactacttgg gaagggagaa gctcacctcc
94921   tccaaaaacg tgactgtgat tttacctgca ttacctagaa gagggcacgc cacagtgtag
94981   cccaatttgc aattttattt ggactcagta ctctatggga gaacaggatc gcggggctgg
95041   gggtgaaggt tttctcagcc tggaatgtga caccacggtt tccactctcg gcttatacaa
95101   ttccacccaa agctcaactt ttccacaact ctgcaagcct agccacacaa agacatccat
95161   acaacaagaa gtcccaacac ctgcagccca ttcaaccagc tgagccctgc ttttcacag
95221   ggtacagaat ttctcggaca acttcttcat gttccctctt ccaagttctt ttaggttagc
95281   actcgccctg tcttttctct caccatttcc tccccttcc tctcctgccc tggctggagg
95341   ccacactcta aacctgtcct cgctactcgg ccaaagccca ggaggtgacc tgagatgaag
95401   gtagtgcagg gtagaacagg gagagagttc tctacacgac cgcacaccag gggaccgggg
95461   gtccttgctg cgtaaccct gcctggcac ccaaagaaat tccacctact ttttcttaac
95521   gtcccttata ccagtcccgc gtggagccag aagatgcggg gagcttggag tcaggctctt
95581   tctagggagt tgggaagggg gtcccacgtg ctggagcgcc ggcagccgca acccagcacc
95641   tacaccttcg cctctgccgt cctggccggcg ccggcctccc actgcccacc ccaagctcct
95701   acctgaaggg gaaattcacc cgaagaacct tgtgagttgc ctcaactgga aaaggagttg
95761   ggtccagaac acaattctca gggccaagaa taggggagac agaatctcag tacctaaata
95821   ctctatgctc gccccctaac tgttttcacc acaacaaaca agcaaattgg actttcttgg
95881   gccgttcct tgcattattt agcttcatct gacggtgtca actgttttct cattattatg
95941   ctgaatttct taacaaggaa attttcagct gaactaagat tgtttggaat ccataacaag
96001   gattgttcgg aatctgtaac taggaattgt ggctgtctgg aagaagtcgc ctgaacattc
96061   tattggagaa gttcggaaca tcaataacaa ctcaccctct gcctttctct ttctaatttt
96121   atactattat tgtctgtgca gccctggttt gcccagccgt gtccctatcac ggggaaacag
96181   tcatgtagct aaaatcatag tagtgaggga cccatgattc gtttaaaaaa tgtgaagttt
96241   taaaatgttg gattttttg aagcttgaac tactatctga aatctcgaat acaattagtc
96301   gttgcgtctt aaaggccttt atatcattga aaatttccta acagcctgta taactttgaa
96361   acaaaacgtt agtgttataa ttcaataaaa gttatttat tattaaaaca cagtgagggc
96421   ctcgtaagtt ttatagcttc tgtcaagaca ttgctaatgt gtgtatgtgc gtgtgtacat
96481   atatatgtac acacatatat atgtacacac acacacacac acacatatat atacatatac
96541   atatatatgt caaggaagaa gcaaacccag attttagggt tggatcttta tttaatatgt
96601   aatatctatg aggtatccaa gtccagaaat caactccacca gttctgtaca ggattctgta
96661   tggagatcaa atctgggatt tctaaagtta agaattcagg cctgggaaat ggattagatt
96721   agatctacct gagcttattt taaaaagaaa gagagggagg gagagagaga gagacaggga
96781   gagaaaagag agacagacag acagaatata catatacata tatagaga gagagagaga
96841   gagagaaata gagtatgtgt gttataggct gttttttta agatctcatt tttaaatgtc
96901   ctgttttgga tgtgatccct tgagttcaat acatgatctt tttcaacttg caaagaatct
96961   aagttttgag gaagggaagc acaggccttca gcctctattt catatttta aagtcacagc
97021   acaccaactc ttatatttcc taacttagaa acaaaactta aaaggtaaat ttggaaaatt
97081   aacttaaaag agacacataa tagaggataa cttatctata tctatctgta tatctatata
97141   tctttacaga aataaatgtt tttaaattag taaagatcta agggtaatta aattatatag
97201   tatcctgaaa tacataacat gggaggaggg ccttaaaaat tattccatct agcaatactt
97261   gtatatacac aactagtaag aagtccataa ctatcaatag ccagcagtgc ttgcaaatta
97321   tattgaattg aaacgctact gaaagagttt atctttcatt gtagtttgga attgtgtgaa
97381   ggtatgttat gtacatgatc tatgtatata taattcttat acttatata tatttagaca
97441   tgcacttctt tttaaatgtt tatgtggtta gtcactttaa gagcatcaaa ataaattgtg
97501   cgttggctta cactatctcc cagatattca caaacactga tgaacaaaaa tctttatata
97561   ggaaatgaag agctacccat ttaaagaaaa gaatggaaag gggaactcga tttattctca
97621   tttgtttatc gccagatttc cccccacccc cctgcaaatt catttgaata gcttcaagc
97681   cggaaaatgg aaatgtggct cctgccctct atttcagcgg cagcagcagc gtcctggcaa
```

-continued

```
97741   cagcgcaatt ttctatcatc aaggataaat ggcatcgaac agaacattct gataaaaaaa
97801   aaaaaaaaga aagaaaaaga aagaaagaaa gaaaaaaagc ttcagcccaa ggagcccatg
97861   attgctggcc ttcctgtctg tcatcccttt acaaaatcct ctccgcaaac ctgagcggca
97921   tgctgtcaga gctaataacg tcttctgaag gggctggggg gcgggggggag cacagtcttc
97981   cctgcacaat gttcccattt attaaatcga gtgcttattt taaaattgca aatatctttg
98041   tttggttcac tgaaaattaa aaccaagatg taggaagcta catgatgcga caattattcg
98101   tgtcatatca gagaatcaaa cccctatctc tcccttctcc tggttaaggc tggatgaggg
98161   ggaagggggga gtttgggggt attcgggaca ggaggtttct ggtggaaaaa tacaaatcgg
98221   ttcgccctgc aggtaagctg agagtaactg aaagccggag cagcgatgcc tgtttctacc
98281   aggaagaaag agctaactgt gattccagga gcgcgtgtgg gcgcggtcct cgccgcgacg
98341   ccgcgcgcgg gtcaggctca actgcgaacc ttgccaccga gcttccccgc gggaggcttc
98401   gaatataacc ttgcctattt ctcgcctact gagatttctt tccagaaaag gacattctcc
98461   tgctccgagg agatggatcc ctgaggtccc catgcccgca cagggtgtcc tggaggagtt
98521   tagaggacac tcctgggggcc cttccctgtg tagtacgctt attcccgagg tgggggctga
98581   gaatcgaaga gcagcgcccc ccacactggg attgggggtg gtcgaggggc tacagatgcc
98641   cgcattgggc ttcttagcgg cctaggctga tgcctggagg taggggggat tgggtttggc
98701   tggcgactag cttaatgcc catcgagttc ctgggacacc caagttcagc acttctgcat
98761   gaaaccgaaa cggccaggga ggggcggagt gggccgaggc tgagggagcg gcggtgttga
98821   cgccctcttc ccacccagga tcgatcgatc ggtagggaat tttttatctt tgggaaggag
98881   aggtgaggaa gcggacctaa aacgagggga aaattcgaat ttaatatcct gtataggagg
98941   tcaaaagaaa aaaaatgatg gcgaggaatg cagagggccc taaatggacc ctaagatgaa
99001   gtacgggtgg tggctggaga gctgggactg gaaggtgggg ctggggggaga cgggtaagca
99061   gcttgctttg gtgaggagct cccacgctga gaacggtggg aggagggaat gatggggaaa
99121   cctttgttta atgaggaaac ctaattattg cgcatctgga agtcttagtc cctactacca
99181   gacgaaggcg ggtacctgag ggatgcagtg cgcatgcccg agccgtcgga tttgcatgat
99241   aaggctcgca cgtgagccaa ctccggcgca gcccaggctg tgccgcggcc ggccgccaat
99301   ggaatcttgc tcctactgcg cctccaggtc acattgacat ctcggtttcc ccacaatagg
99361   cctttaaaac ccactttaaa aataaaaaag tgttttagta ttgattctcg cctagacacg
99421   gaagatgtct gtaggaaact gacacggttt agaactacaa ctactattact acaagcaagg
99481   gttaaagtat tcagaattta agaaaaagtt agaaggccgg agagaggggg ctgtttaaag
99541   agctctggcg ggaagtcaag gaatcctggg actgctgcct tcggagccct gaggctaggg
99601   ccaaagctga atctctctga gccttacctg tcacatgaaa atcacaccta cttcattaac
99661   cagaggagcc tcaaaagcag aaacattacc tgtgcaggcc tggcttgaga aagcaaccca
99721   aactgagaaa gcaacccaaa cccacccttt ctccacctca tccccagcca cacctggtgg
99781   ccagggagat ggaaactaga acacctgtat tccatctctc tcccttccc agacaccaaa
99841   gtggtctgtg gggtgagggc catgtgttag ctccctcctc tgtgaaatgc tgctaatttt
99901   agaagggcag aaaagagaaa ggtagagaag tggcatgaat caccaccatg gctaggcctc
99961   ttgtctccac ccatgctctg aggctggaaa gatgagattc tctggggcta tagaaagggt
100021  gggccagctg ggaactatta cccatcctgc cccttctgca caccaaggct gctccctgcc
100081  cttcctgaag caccattctg actgttacca accaaccacc ttgtattctt ctcactatat
100141  attcctgcca gaattgctgc ctacacatgg gcctccagcg tccctaagag tgctcatacc
100201  ctgtgacaag aaaaccattt gttcttactg aaataaaaca tgtgggggatt gtcatttgca
100261  gttcctctcc ccttttgtgt aattcacaag tctctgatgt aggattaggc ttcaaatgca
100321  tttggtcaag tacatacatt ttagtactca gcttaaacaa tgtcatgctt aaaagcacct
100381  cagcaatgcc tctgtttgtc tctaggtctt tgtcaccctc caggcctatg attataacat
100441  ggcttttttgt ttcttttttg agaatgtgaa ccagagcccc accccagccc tccaaaatgc
100501  aagacactaa aaagtgacct caaggtctta cctgctcatc taaatcaat attatttgac
100561  caatgagtat tatgtcacat atcgtgtaag catatagctt ccaatagcca cgtctatttt
100621  caaataagga gataccctacc gaaccttcag aaatgccagc tggtagtttc tgtatagaac
100681  aacaaacttt ctcacaatag tgttttcgga ttgtctttga aaaaggtaag cttttctctaa
100741  actggcccca taaatcaaa agagtgttgg cttcaattat ataaggctgc aaaatgagat
100801  agccatgttg tctaaaatac ttcttgaaca ctttggattt cagaacactt tttcttataa
100861  tagacttctc tttgtgcttt aaggaatagg ataatggtgt gtttgaaagg aaatatagac
100921  cataaaaaag tccattagcc aatcaataat tgtcacaatc ctcaattaaa gcaaaattat
100981  cttttccttgt cctataagtg gctggaataa acaaagaaat ttttcttctt gaccatttta
101041  ggtaaaattg aacgaacata agtctcaaat tcatgtcctg gtctcttcct aaggcaggtt
101101  tcagatcatc cataaggcta actttgatga caactctctg tcatctctga agaaggaaag
101161  atcagcaggc tgggggggtct agagagggac actgcagtgt gggctctgga cagtgaccag
101221  gaacccatca ttggccacaa cttcaggctc tggagctgct gttcacaggc atcttcaact
101281  cccacctaga ctgccctgca aagtctcttt gtctcacatt tgtgctgact tcccattggc
101341  tccttctcat tccccactgt cacggctggc cctcagcacc ctatgccagc aaggctagtt
101401  gattaaaaaa ctatatacat atattcacac actgagctgg gagcatttcc ttccatgta
101461  gcaaagcccc tctgatttaa gactggtcaa attaatagga aacagcaaag gaggttaaag
101521  agggaaatta ttgaggacaa tgactgcaga catgcagtct acagtgcaga gtctgcctt
101581  tcctgaggat tcagagctgt gcccacaaat cagatgggcg gaacaatccc ccatcccacc
101641  ccccatgttt ggggtcatta gaattagagg tagcttcagg ggattccctt tcctctagca
101701  tgggtcagcc aggaggcaag aaggaggcta ggaggctggg gaccctcatc agtcccacta
101761  agcctccaga aggtatcttt tccatctgcc cctacttgct cccccagtgg gtcccgcgtg
101821  cctagccccc acaccccccgc cttgcgggag ttattttaat gacactaaat gtgctccagg
101881  aagctttccc ctctctcct ctctctccct ctccccctcc ctccctccct ctctctctct
101941  ctctctctct ctctgtctct cttcctctcc tactctctcc ctctctctcc tgggatctct
102001  ctctctctct ctctctgtct ctcttcctct cctactctct ccctctctct cctgggagct
102061  aacccaagcc tgtgcaccgg agggcagctg acagctgagc gtggcggggg cggggttggg
102121  ggtggggagg tggcggctgt tccaagcgca ggattctgga gtccaccggc gcttgggcag
102181  gtagcaagca gagctagctg cacgttgccc cggccggcgt tttcaaacaa cttgaattac
102241  aggctacatc ttgaatatga attagccttc cgcactggtg tgaattcgct ttgaaactca
102301  acttgtcaag tatggtttta attaaacatc ttccggcctc gaaagattac atgttttgta
102361  aaatatattc tagcatgaaa tttacttcca cgatctgaaa ttagttttt ggtaaatgtt
102421  ttcataaaaa agaaatacga ggtgtgtgtg tgtgtgtgtg tgtgtgtgtg tgtgtcagag
```

-continued

```
102481  agagagaaga gaagggggt atgaagtagt ttatattcac tgccttcctt taaaacgtcc
102541  taccagctgg acttggagcc tgacaggtcc cgggtcccag gtcccaggca gccccggccg
102601  gggcagggcc aagaccgcgt gcccaggaca agtaagtaac tcaaacccga cccgccaagc
102661  gtggcccaag ctgcttttgc agttggggac aattgagcgg acacacaagt taatcccgca
102721  ctgatttgtt tcggatccat ctgcaggacg cctgatgcct ccccttggc tgctgcagcg
102781  gacacctgcc tccctcccca tcccagactg ctctgcttgt cccatgaaag cagagaaaag
102841  aaaccatagg gtgcggaacg gacctcagta gtattcaaga caacacttca ccgtgaaatg
102901  taaagttctc ctttaagaat tcctgcctaa tattgagaac aacagccatg tcaattgata
102961  gccgttctaa cagacagtcc gaactgctcc aaaccactct aaaagcttgc cttgatggag
103021  aaggggcctc tggggcctct ctatcacctg cctggggcc tctatttccc aagtagcct
103081  caaagaaaaa agaccctatg ctcccgcgta gggtaggaa aagtgcctgc tatgatgggt
103141  cttctattc aatacagaat taagagtgg gtccctgtgg aattctcttc ctaactactc
103201  tctgaggaac cagccaattc tgacgggatt tgctggattc gagcaaaact tggcgcacat
103261  gggtggggt gtgatgggga gcaggaggga gggggcgca tctcctttct tccagataat
103321  tgggacccag caaagaagga gggtggagc ggtagggaga gttatttgcg gtcatcaact
103381  gaaataggca aaaccaataa cgcaccctcgc tttcgcct gttactcca tccccattca
103441  gtgattggca aagcaggccc tgaaggcaaa ggcaataatt gctccgcgct ctccttacta
103501  gggaaatgtg taggcatttg aagtgtacta aaaataaacg aaggagcgag aaaatgaaaa
103561  ggggacagag tgacaatttg cggcaattaa agcgtctgcg cgctgttgcc ggaggaacag
103621  ggacccacag cggttttgt tttcccaggc ttgatgatgt gactaactcg ttagagaatt
103681  tgcgtcctag gttgtgtgtg tgtgtgtact tgcgtgtgtg tgtgtacacg cgcgtgagca
103741  ttcagcaacc caggagccca cagcaatggc cggatccgtg ggggaggaga gagcctagaa
103801  ccctaaaaac tcctttggcc tccagaaaga ccccggtgca gctctctacc ctaaccccta
103861  agccctctc aagtgagagc ctctcagtta gtactcagtt gccacgtctc gcaggaactt
103921  tggagcaagt tttcagctcc caggtgtcca acctttaaaa ggaaaagcat aataatacta
103981  accttctt cacgaccacg cgaaacgcaa aggatgtgga gtgggagg gaggaaaaaa
104041  aaaggggcgg ccagccaaat caaagcttgg gagacatttt gacagtgcgc ttgaaataat
104101  gctcttaatt tttggaaggt tttcaagaag gggtgggg gcacgtggga gaaccacaac
104161  tttctcctgt ctgtcactca agcggccaga gagggctcca acctccagct cccgcggcaa
104221  cacacagtgg gaaattgctt caagatacag tggggctcta ttcttctct accctgccc
104281  cgccttccc gagcagtgaa cttcacagag agggtggtaa gggagggtta tcctgggtgt
104341  caaaaatctg tgcatagcct gagatcagaa gagttaaccc caggccctag acccagccca
104401  gcggccaaac tggcacccg tgctgatcag cccccgcatc cccatatctg catcccccata
104461  tctacctccc cagtcggggg tggtgaggtt tggggagggg gggcgacact accatatgca
104521  tccaccacct aagtccagcc caggctggct tcaatgaaag ctggcaaatc cggcgaatct
104581  cgcagaaatt ttcttcgaac ttaattcaat tttaaagtgg attttacta ttaaaaacgc
104641  tgccgagcaa cacattgaat taatctgact gtacggtttt aattacagtg agggtttctc
104701  tacaaatctg tacaagacag tggctggttc ttgaggatc tctgcctcct gaattccatt
104761  atcgggcccc tggttcctg cagacggcag ctcgtgggag ccagctgcgg tgcgagcgtt
104821  cagtcgccct ctgcttctgc cgggcctcct ggctcctgtc cctcctccct tccttcatcc
104881  cagcccatg gagagcccag gattcctgcc tgtcatttga gactgctgaa ctgatatcct
104941  gaaacgctac ccttgctttt taaactcttg ggccccagac ttttgagccc cctgagcatc
105001  gttcttaaag tggctcgttt tgtctgggag ggtgacctct tgtgtagtgt ttttgaagg
105061  gttctcctgc ttcgacttag cagctgttag agtgggcagc gtgatgccca gtctgtctga
105121  gggaaagca ggttaggaaa tgggaggag aaaggggtag aagactagtg aagagcttgg
105181  tttgggggag tctaggcccc ccacctccag ccctacccc accccatct ccactctcctg
105241  gcccctagagg aaatatacat ggcgtagatc tgcaggtaac aggctgctt ttatcagctc
105301  tcattttgtt cattgttgt gcaattagca ttgtaggggca atggtaccta gcaaacagga
105361  ccaggtagaa aacttaaaca caaaggaag ccgactcata ctcaaactct tttgtccact
105421  ctcttatatt ctttttctaa ctctcttttct atgtcccctg ctttgtccc attctctcct
105481  tccctccgca caagtatgt gcgagtaaag acagtgaatc caaatatgaa ccagcaaaat
105541  ggacgcaacc tctcaatgtg tatttaaaga attggaggct ttgagctctg tcggggaagg
105601  gccccactca gcagagtgca agggatgagg agcatttgg ctctctgcac aaaatttgta
105661  aaacctgcca ggaaaaaaaaa aaaccagtaa ttattccatt cccagggtag tgggaaggg
105721  gctctctttc tccagatgc gtgtgtgtgt gtgtgcgcgc gcgcgcgcgc gctttaaagg
105781  agtctctttt ctgaacaaga aaaagagag aaagaaaag agagagaatg aatgggcaca
105841  gttggaagaa tggaatgtga aaaaacaaaa acaaccttag cttctaaggg cattcaaatt
105901  tgttgccctc taaaaaagtt ttactaaaaa gctaataaat tacatttcca tttattggga
105961  tattcccaaa taaaggagat aaggagtatt tatgaacagg tatgagtata aaagtcacca
106021  gttcatatat atcacaagag tagacagata cagaacaaac tcaccctctc tctttctcat
106081  gaaaaacggt tttcatttat ttttctgtta taacaagagg accaacatga tagcaagggg
106141  atgttttcat cccaggtttt cctgaagagt tgtcccaagc agggctgtcc tttaatgtta
106201  ggcattttct gtgacctgc tattgttact gctgatgaag cgatgaagga attaaacaga
106261  agatgcttgg aggcatttag gaagacagct atattaactc cttattatgc ctaaaaatag
106321  tctactgttt cctgttgata cttgttccct accactataa ggctgtattt atcctccaat
106381  ggtcaggggt ccctgctttc caaagactgg cttgcttaaa gctgactct aacacccct
106441  cccttctccc tttgctctga tatatttccc atcagggcaa atatggagag ctcaaccta
106501  gcatagccta cagattgaaa agacagacat cagcatttaa cttgttttat tctaagtgtt
106561  taaacattgt tgagtccttt ttttcctggg cttagagaaa gaggagtgtt tttgtattag
106621  gagtggggtc ctatgcttgt taaaagagaa aaaagagaga ggattgagg ggagagggca
106681  gacaagcaga ccgacctctg tatacaatcc taaaattagg gaaggtagaa acatgcgctg
106741  cttttcccct aaatcaattc tgggcacagc acatcagctc cctctattaa gaaagccttg
106801  ggtgctcaca cacttgggaa tggagtcatg gagaaggcaa atgatgttta gtttgagaag
106861  ctggttagct ttgttttcat aattccactg gactccaagt ttgaaaatgc ctggagcagg
106921  agcctgtagg ttgggacatg catagttaac attctccaaa ttggacagtc ttgaaaaact
106981  ctgtgaagcc ccctgtggga gccagtgtca tgtcagagtt ttctaactgg ctattcttgg
107041  gacctatgac tagagagatg aggaaaatgt tatccccaaa cttaagtgag actctttcta
107101  aacatggggt aaactgaggc cacttttta ctggatttgg gggcatctaa gagagaaggg
107161  tgttaatatg gacaatacag cttatcacca cagacaagaa caccaatgtt tccttgtata
```

-continued

```
107221  gactgatact tttgcaactc ctgaagatgc catcactggc aagaggcagc tcccatgtgc
107281  cccagagctt tcactgttgt ctgtgtgttg ggggagggga gaaagtcgtg cgggttacca
107341  ggatatcagg caccctttcc ttacatacat acacaaacag agttttacag tatattgaat
107401  gaggaaaaga ctagcaagtt ttttttttct tcaccaatgt ctcccgttga gaaggggcta
107461  tgtaagtcaa tactgagtaa tttctttgaa ttcaaaggct atttatccag gtctaatttc
107521  tttagaatta aagtgataac tgagctcaac ttagcaacca aacccatcca ggtcctgcct
107581  ggtttgaatg tacttctaca gcccgtgagg ctgcaaaacc acttcgggca ccccaaagca
107641  tttccaggcc tacatgcgtg agcaaacacc ggtccagacc aggaacagca ggagattctt
107701  tgacccaaga gcccattcct ccaacagtgg cctccggcag acccgggagg tctgtgttg
107761  gcaatacaca agcatttctc tctaaataac attgacactc gcaatacaaa ttccaacatc
107821  tcaacaccct aaaaagcaaa aagcagctta ggcctcaaat cctgcctagt gaatatgacc
107881  ctcacttact acaagcccta aaagagcctt agggctccta ctccagattg cagggtttac
107941  ttttattttg aatgataaag acttcgaggg ccttgcccgc cctcctcctc ccaccccgcaa
108001  gggttggccc gcgttcccct gcgggcgaga caaagaagca ggagccagga cccggctggc
108061  gcctaacccg gcgccggggc cttgagcccc tgaggtgtgc gcctcctgc aaggcccaa
108121  agaacccgag ttttgcccc ttgctgaagg gttggaagtg cgggctggac tagtgcaaac
108181  aagagtgact ccaaccgcct tacttcagct cattaccgtc acccatgaaa acggaatgaa
108241  ggactgggaa gccaatctgc cgcgttcaat tggagagaaa tgactgtcgg aagaggccct
108301  gcggtaaata gcctctgagc cgcgaactct atgcgccgtg gccggtggca gaggccacac
108361  ctggcagcca ctcgtggcgc gccaccttgg catgttgtgt gcgggtcaca ctatctccag
108421  ttttccattc tcgatactgg caggaaagtc tgatagtcag gcctgaagtt tagattccat
108481  cccgcaagcg cagagatatc acaccaagtg ggacctctcg ctcgttccac ttcccagccc
108541  ctgactgtct ctgagctcag actgggtcgc ccagcaggtt tcagcaggac ctttaccatg
108601  caccacaact accacctcag tcagctgct tcactggaac agagtgcaag gattttagcc
108661  actaactatt aggggaaggt tgagagcccct gaagctacaa cccggacaat cccagccttc
108721  ccggcttcct cagcaatcaa acaaatgaga aaaaaaaatc cccttgcaag tagaggcagc
108781  tgcactctgg atacagtgct caattgcagg gaccttccga ggccctgcca cgacatactc
108841  taattggggt gcagccagag ttgcaggaag ctggcgagga aagcggtgca cctgtgagca
108901  taaagcgaaa aacatagaca agcacagggt gagggtgtag ggggtgaaac gccttcacgg
108961  tgttaacaac aagctgcagg gtataaagca ataaaactgc cacgtctacc tgctggtatt
109021  gaggacatta caaacagtct cggcgcgcag cccgcgtgta ccgagagcgc actagggttg
109081  gggagtgggaa ggtgggtgg gaaatcttct cttttcctga cattccccttc tgtcccccac
109141  cccccacatc tccccttac ttagcccacc tttcttttc catgaagctt ttctgttgtt
109201  gttttaattc attgccgatt tgtaaacgtg tagatcgtgt tactggttcg cgtgttaaag
109261  tgcacctctt gttaaaaggt gggggaacagg gcacgccact taaaaatgaa ttcagagtta
109321  ctgaaccggc tccccagact caagaactta agcgcaacgg gctgggaaaa ggaggggagg
109381  aggagcgcaa acgccgctga cctgggaact cggaggaaac tcgcgggcag cgagcttcag
109441  gtcttctgat acattgaagg aaagaaagaa agacaggaaaa agaaaaaac aaactgtcct
109501  ggagatagct agacatccag ggctgggagc tgggaaaatc aattggcata agccgctgcc
109561  ggcgggcttc gcgcaacgta aaaaataaag tccaagctgc tccatctgca gccaccctt
109621  tctggagtta aaggggcaag cggcaccttt tctctatttc tcagttttcct tcggtcctgt
109681  aacttatgga gtccagaaga agtaggatat acagaagtcc tcagtagttt tcccaaaggg
109741  agacactgtc tccttcccgc aacctccaga cactgcagta cagggttgtt agatattaga
109801  tagtacgttt ctccgtgtgg gcaaaggctc gcggcttagg tctctaagca gatcgaaagt
109861  cggggtccag accgagagga tcttcaggtc tcgtccaccc aatctcaagc ctctggaagg
109921  gcgggctgcc ggcgacctcc tccagtcccg ggacccggaa cccgggaccc tggacgccgg
109981  tgcgggcggg cctgccctcc tctgtgcctg gcccccagtc tggcccctcct acctgttgac
110041  caggcctgaa ccacgcaccg gggctccgct gtctctgctt ggctgcctta acctgcgtgg
110101  gtctggagac cggagggaga aaggctagat ccgcagccttt gggctgctcc gaacttaatg
110161  tcttttcccca gtccatcttt gaaagagaag tggttctacc acctggatgt gcggatataa
110221  atcccccttgc aaataataaa tggattaata ataacaaggt atgaagttct ttataagaa
110281  aaaaaggaga gaattgaaac taaatgcggc agttagacaa ccattttgat aagaggataa
110341  ttgaggcgac actggtgtat aattagagga taatttatgc tatatccact tttattccac
110401  ctcccaaat aaacccagtc cataatcatt acaggcaaat tgttctgaat tttatagcag
110461  caatttgaac aaagtactgc agttaatcat gggagatttt tgtgtattcc tgattagaac
110521  tctaattgcc tccttccaga agtaaaaat aactgtaaaa cgactctatt tttatcatta
110581  acaatgttga cataaaaata aaatcaattg gaattgtaat cgagagacaa atttaggacg
110641  aaggcacttt tacttgggta gtttatattg taatcaagat ttgccaaacc actaaccgca
110701  tgtatcattt gcatatattt gaaagcatta cagtagcttc tgttttcaat aggaaaaaat
110761  gcattactgt cagtcctcca acgattcgtt tcagaacac gctgctgcgt tctgaaaga
110821  aaaaaaagac gcccccccccc cccacaacct tttgtacaat atataagaaa tacggcctga
110881  aacggcaggg accgagccag aacagggtct gattttttct tttctgtacc acccccagt
110941  ggggtggagc ccaggtgtga gggttcgtct tccttctgtg gtttcaataa aatacgtcta
111001  gaaaatcca cggtgacaag gagctcccac aagagtgtag taggaccaga gtggcaggga
111061  cgtcaagaaa ggggggcctg gatttaatgc gggggtgggg tcactgcttc taagcacagg
111121  caacctacaa gggtgcaaag ggattgaaag agagcagccc ccagttggct gtttcaaggc
111181  tgagatattg gcaactgggg ctccgggatt tggggcacga gctgcggcgg gaagcatcgg
111241  cggccggccg ggcagaggcg cctccctccc caacggcccc gggcgccaca cagccgcc
111301  cccggctgca gctccggctg ggattggaac tgcggaaggt aggcgaagaa ctctgcaagt
111361  cgcgcacacg ccagtagaag ccgtgcgcct gtgacgtcag gggggcgactg accaatgggg
111421  aggcactgcc ctttgggagac aaaccattcg actcgtggcg tctgcatcaa gtctgaaagc
111481  agacgcgcaa ctttcgcaga atcccaccta aaatctctgc cttaaactgc accagccccc
111541  aaaaaatcca agggggggaaa gcaggcgggg ggagagcaga ttcccccctc cccctctcct
111601  ctcccatccc tcctccttcc tcctcccttt gagttaacaa ggcccgctc actatatctc
111661  ttttatattaa atatatatat atattagaga agagcgaggg agagggagaa ccacctccac
111721  ccccctcttt aaattctttt tttttttttt ttttttttt gcaaggatcc aaagagctaa
111781  ggtggctgca gaggggagag cggcgcgagc caagtggggg aggggtggagg aaacccggga
111841  gaaggctttc tccagccccc aaagttttg atgatgacca tgactacgat ggctgacggc
111901  ttggaaggcc aggactcgtc caaatccgcc ttcatggagt tcgggcagca gcagcagcag
```

-continued

```
111961  cagcagcaac agcagcagca gcagcagcag caacagcaac agccgccgcc gccgccgccg
112021  ccgccgccgc agccgcactc gcagcagagc tccccggcca tggcaggcgc gcactaccct
112081  ctgcactgcc tgcactcggc ggcggccggcg gcagcggccg gctcgcacca ccaccaccac
112141  caccagcacc accaccacgg ctcgccctac gcgtcgggcg gagggaactc ctacaaccac
112201  cgctcgctcg ccgcctaccc ctacatgagc cactcgcaga cagcccctta cctccagtcc
112261  taccacaaca gcagcgcagc cgcccagacg cgagggggacg acacaggtga gaggccgctg
112321  gggcagctcg cttctcccgc ctcccgactg cccctaccc cgcccgcccg ctcacttcct
112381  cgacgcccgg gcctccgccg gcccctccc ccaggcggcc ccgcgcgccc ttggccgggc
112441  cccgtgcgcg cccgctcgcc tggcgcctgc ctgccggcct ctcccagccg ggcccttcc
112501  cgccgccgcg gaccctcagc ttccgacgcg cagttcgggc tgagtcccgg gcccggcgca
112561  ggcttcgttc gacgagttag tccacactgc gctctccagc ctcctgggtc tgtgcgccct
112621  tttccttgct ccttccctcc aggctgtaac ccacgtttga cccggctggg gacatttctg
112681  ggccggaact ggggagcgtg ttttgcttcc cagcccacgc tgggcaggca gtggcctact
112741  ttgcgtgggg cgccccgtgc tcctcagtga ctcggaggga agctggcctg gctttcgctc
112801  tggttaaact agtaacagtc aggctctttc cagtgggctt taaagtgtcc ctcaccttca
112861  tccctgaccg ggccccctat ctagcttttc gctacagtgt tggctgctcc tttgttcgtg
112921  gaggggaagc aaagaacctc gggctgatgg ttctcagcac ccgagggga caaagttgcc
112981  gtgagaggcg cagcctgctc gtgggctggt ctgagctgtt ggttgtgttt tgtttgagga
113041  tttggtcctc ctcaggagag tcatttcaaa acatgccgag gatgcttgat gcactgagct
113101  tggagctggt gacatcaagt caactggccg cgtaaacacc tgggtggctc aagcacagct
113161  tcaggtactg ttaagccggg cacagggcc ccgctccgcc cggacagctg ccgccttgct
113221  gcgctgcgca ccccagagag cctccggcac cgcctccgct gcggcaaagc gggctgtttg
113281  tctgagggcc tctggcgctc ccttggccca gacgctgcac attgttcggg ccagggactg
113341  ggtcaaggag attacgcaga cgctgggagc acacgggcag agtggaccaa gagaggtcgg
113401  ggcatcatag ggattttcg aggtaaccct tattgggctt tggggagact cgttgcatgc
113461  cacgccagga gcagggagat ggcagcagta gcctcccggg tgaccgctcc tctgtattat
113521  ttgcttacag atcaacaaaa aactacagtg attgaaaacg gggaaatcag gttcaatgga
113581  aaagggaaaa agattcggaa gcctcggacc atttattcca gcctgcagct ccaggcttta
113641  aaccatcgct ttcagcagac acagtatctg gcccttccag agagagccga actggcagct
113701  tccttaggac tgacacaaac acaggtaatt cccgagaagc ccaagtatcc ctgaaatgct
113761  ggtaccgctt gcagatcggg cagggagcac atcaggagga attgttggcc tagtcaacca
113821  aggatggaag gagcttaatg acaaatgcct tttgctccag ttatgcactt tcctgggaca
113881  acacagtttg gaatgaatga cctggtattg aatactggat tggatttgca catcctccca
113941  accctcggcg accccacccc agcctagaat cctttgtga ccaaactcat aattcaattg
114001  agtgttattc cagagcagaa caacatgaaa gagaacaaac atttaggaga aaaggtgta
114061  caagccagga ggcagaataa ggttcaactt ttttaaggat ccttttgtag gccctgggaa
114121  ctaataaggt tttcaaccca ttgacacaga aagaaaactt gtgaaatgaa ctaagaaaaa
114181  acaaagtagg catagggttcc aatgaggttt agtaaaggct ccaaagtgca atctatttat
114241  cctaggagtg tcaaggtggg ttttctgaa gatttcccta agcacggtgg ttaagtcatc
114301  tgggtgacag actgatgtgg tctgagctgc ctccctggag cacaggactt gggtgcagtg
114361  gcagagttgg agatcaaaga gaaatgttac caaaattgta acaggtgaag ccacagttaa
114421  gtacagttac tgaagttctc ccatcctact aatttgaaag ccatagaagg catttcagat
114481  ttcacaagaa ggagcttagg tgagtatatt aggaccctgg tcaaaaagcc aggctgcaat
114541  cacctgcagt ttttgttgat taatttacct acatggagta agtaggcctc atctgatgta
114601  ggtaatcttc agcaagggga cctcaggttt tatgagactg ttgctgcaga ctgattgtgt
114661  gttgacttaa gacagttgtt cctaagctc ttttcaatt tagcctgttt tctctttcca
114721  tattgctatt cataatattt gggtttgat atgaagggat tccggctatt cagtgacttg
114781  tatgcgtctt gaaaaagtag attcttatgg ctagggaatt ttaaaggtaa aggaagctgc
114841  accataaaat ttccttcttc aaataaagta gatctgaaat gttggcctag atatgctccc
114901  atcccagatt cccgattcac gtttaatttt cagaagccct ttgacttta attactatac
114961  taacaatcat gtgatgatcc ttgaccacag tttgactagg caacatacaa aatagggaat
115021  gaaggagctg cagtccttaa tccctgcaag gttatgggga tatatttatg tctggagaaa
115081  gatgcttcat gtataatcta tggcatatgc aatatatgca tagatatatt caaggcattt
115141  agttataaat gtacaggctt taattcttc agtcatttgc tccttgtacc tttatagaga
115201  taacagcttt tgggtatctc tatgcatgta cacggagaaa atgactgtgt aaaatagtta
115261  ttttacatag actaaattta cattactaaa tttatgtaa aatgacaaga ctttcagagg
115321  aggtgcattc aattgaatgg ctttgatttg aaagggctgc ttttaaaaat cctttaggct
115381  ttggacctgg tcatctcatt cagctttttc ttatttatac tgttgttta aacctacgct
115441  agcacgcaat tctagaatta caataacttt aggtatccag gcaagatacc tagtatgttg
115501  taggaagtgg gactgtaaga ggctagaaag aggtggaagg aggcggggac ttggcttgta
115561  ggcgttggcg gtggttgttt ttgttttttt gttttttttgc tttttaata ttgcttctaa
115621  atccctgagt gacgttagag gcactggttt gatgtttatg ggcctaatga ttgctgcatt
115681  tcttgcaggt gaagatatgg tttcagaaca aacgctctaa gtttaagaaa ctgctgaagc
115741  agggcagtaa tcctcatgag agcgacccc tccagggctc ggcggccctg tcgccacgct
115801  cgccagcgct gcctccagtc tgggacgttt ctgcctcggc caagggtgtc agtatgcccc
115861  ccaacagcta catgcctggc tattctcact tccacaccag gacacgatgc
115921  agagaccaca gatgatgtga gttgcccaag ggaacaccct agggaaacgt ctgaacaagg
115981  aaaagaggat ccgggacctg cttgtatctg cgaaaaggag ccaaaggagc aggcttagga
116041  gagctcataa gtgtggcaag aagccgacta ggctcattct ctctcccctct ctctctctct
116101  ccctctcctt tctttttact tcttccttc ctccattcct tcttttttc ctttccttt
116161  ctactttct tttcttttttg cctttcacct ttttctcat ttaccttctc tcttgagcaa
116221  cgtcagtaat tgatcttgca tctcagagag agagaaagag catgtgtgag agagaaactg
116281  gtttctatgc cagcactcct gaaacccctt actgtaagga tattttctct tacccttgg
116341  gatccaggct ctgagtctct tctcttgg agtatccatc aaaatgactt ttttaaaaa
116401  cagattttcc cccaaccaga agaatctgca caaacttggc agcgttttta cttgtttaat
116461  gagttaaga cattacatgg tgaaagagaa gcattttgga ctcctgcatt tttattacc
116521  attcccagac tgacgagaaa aagaaaattc ctcacataac agcccttctc taaagaaaaa
116581  ggaaaagtg gctgtaagat tagaacattg ctacaaaggg aatgctgcat gttttatcaa
116641  aatgcaatga ccaggaatga tggttgatta aaaaaaaaca aaacaaaaac cactctttcc
```

-continued

```
116701  ccaccccacc cccccaaacc ctgaactgga atcaggaaag acggaggaaa caatcaaaat
116761  caccattcta ttgctttgac acctttacta ggtgaattgg tggcattcac aaagctaata
116821  gggacgttta tatcaagaaa catttctgta tatattgttg aattttagtt gtacatatac
116881  tttgtatgtt tttgtcttct ttcatatatg gagtaaaagc cacaaaacgc tgagtgtctt
116941  gtatatttct ctctctgtgt gtctctgtcc ctctctttcc tccctcctcc ctcacttccc
117001  ttcccccat taaattttct atcacccttta aaaaaattcc tatttcctaa tatgggaagt
117061  catatgtata tatatgaaca tcaagtgcct gcaaagatgt cagtttgcac actagccttt
117121  gtcttaggta gtttaacatt aaccatggat gttctttcaa ctttctttac atattacgtt
117181  tttattgtaa tttctacaca tttacctatg ttttaaacat tagaatgacc tatcctcaag
117241  ttaacttcta gacatcacag tagtttctag tgctgaaact gagtattctc ctttcccttt
117301  tcccagccaa aataatacag ccatatttgt ctttgtttgg atgcagtttt ttaaaatata
117361  ggaaagaaaa aaatagagag tagagtgcac aattatgcct acttaatgtt taaaaccat
117421  tgccagctag ctaggtagga aaatgcacta tgctggatga aatacatcct tccgatcttg
117481  gggaaagcac agaaataatg aaaatgaaaa gtcctttcgt catacaagca ggaagcccca
117541  tactgcgaga attaatggct acagacctgg gcatccttca aattatgaac cttgaaacca
117601  ctgagccatt tatcagaagt caatagagat actcagagtg ctccatataa tgcagcgac
117661  atacagtcgt gcaaaaggac agtcactata attagacaca aagcaaagac tacttaccaa
117721  tatacccgtt ccttttttg ttgagcaact tccacgctca gtcagtcttc agaatggttt
117781  aaaaccgatc agtcttgtca ttttctagca ttcgcattgt tacattagga aaaatgtttt
117841  cttttcttt ttccccttc ctactgtgaa actttgggtt cgtagctccc caggatcaat
117901  tctgaacaaa gcctccagct gcagtgccat ccaatttgaa gcagacattg gggacaattt
117961  aaggttttta tccacaagaa ggttttttc cattctctta aatgcagcca taattagagt
118021  aattttcat gtagcccgct gattacagcg ttttaccgt caaagataat tacctgtaat
118081  ttcttccac ttaatact aaaaagccat ctttatttag attcaggaac aggaaagcg
118141  aaacaaaaga gggaaattat tctgttattc atacacaaat tgcagagacg taggacctaa
118201  aattgaaaat taaccaaaat tataatgctg aaaagaatgg aagaggctgc agaagtacag
118261  ctggtagtgg ggctttgctg aattattcaa attacgttag ggagaatgct accatacatc
118321  gaaaccaaca ctaattttc gttaaaaaaa attcaccaga tgcatgccaa accactgtga
118381  gtgcataaca ttctgaaacc cggcaaatgc atgttgacat attcgaggtg ttgtcatgat
118441  gcatttgtat ctatctcttt atctcttaac aggagtttaa ttaaacaaga aattctgcca
118501  agtagtcccc cccacccccag actgccctttg gaactgggct ttctctggat cctctgaacc
118561  ttaagggtta atatttttac tctttagaat gtattgaccc tatggtaagc ggattcccga
118621  gggagggatt ggtaggaggg gcgtgggcga aaggcatcgc ccagtggtgg tgcctacgac
118681  gcctccccac gttcggactt ctccagaggt tgcagagttc gagctgtgga gcctagttct
118741  gaccgtattt cctatttaaa aagagataaa gtgggggaga gagagaacaa tagctggggg
118801  tggggtagag gaggggagggg atgaagagaa cgatttctct ttggcaccaa taaacatctc
118861  attatcttt gacacaactt agtcaaaagg ttctgccgc cggagaaagg cctttttgca
118921  ctggaatgga aaaccaaaga tttctcaggc acttaacatc tctagttgct tacaatgtct
118981  acacggtcag gaaacagagt catctataga tagaacagca ccgcttcttg ctggagactt
119041  ccttggtgcg tccctaaatc tgggtttct agctccctag cttggttctg cgtctcagcc
119101  aatcatgccc ctccaacccc aaggtcgcag cgtttgttct cggagggcag taactccaag
119161  atccgcatag cctccccctc cccccgccc caacacacca gcttgaggca aagacctga
119221  aaagcagcct tgaaggggtt cagaggccag ttattccgga aaccttcccc caagtggagg
119281  aaagatgtcg aaggggcttc accgtccaga gattcatcag actacacctg cctttgcaaa
119341  tgtccgcata cctgtggttc taaaggagcc ccgtcgcgag ctccgtttga tatcttgtcg
119401  cctcaaaatc taaaatcatg gccacgtgta aagacctctc tggatttacc taggattagc
119461  tgtgaataat aatttcaaa tagattttag cttggaatct ccagcagagt ctctccacac
119521  cttatagaaa catggtactt ttcgcaggct ccagtcacaa gctgcaccaa atacatcaac
119581  aacatagaaa acaagaaga caatcgaat acttaaggat cccattctca ctcgaatcct
119641  ttcactcaac agaacaacaa cccttttac tgttagaggg gataaaaggt cagcatagag
119701  aaatctataa agcaaagttg tagcccatga taaattacaa cggcaacatg tatctggaa
119761  agtgtgagaa gagaaataag aactgttcct tgaagtatgc aagaaataaa aacttaccct
119821  cagtgaatat ctcttaagca atgatcaggg tttagaaatc tatactgaac caaagcacag
119881  gagaatattt ttctgagtct cagggcagaa gctctttctc tatattcttg gttgagtgag
119941  cacatccagg tgtgaaattg tttgcacacc ccagccacctc ttatattgcc agcaaaatta
120001  gctgttatta ctgtcactgt ttagtgatgg ttagcgtggt acaaaaaaaa aaaaaaaaaa
120061  aaaaaaaact gctgtaatca agacctggcg catctttgca aattacagat aattgtaaac
120121  gtccagatta tgataatagc atcctaatcc agcctgcaat ataattatta cagagtgtta
120181  catctgaaac tgtccagtag ggctaattca gccattattt agaccctatt tttgcactgc
120241  aaatggggttg ctgagctgaa aatgtacgat tgtaatttca cagggcactc aatgagtaat
120301  ggtataggaa gaggaaaata caaaagtgaa atgtgaacag tagcgatcaa atcaaaccct
120361  gaaggacaaa agactgtttg attcatatgg aaaaagaaga gcgagaatta agaaaatagc
120421  aaatcagtgg tctgaagcat ttcatgtcca aatcttcaat agtgcagggc tgatgtgttt
120481  gcaagggctg ctgcatctgc tgcttgtctg gagtctaaaa taattttct ttttctttct
120541  ttttccaac cccctgtctt ttttcccc ttctctctcc agaaacattt tcctgttta
120601  aaaatgtgtc cctccccaa agcaaagaac atttgtcagt ttcaccattg ttccacaaa
120661  atcgcctgag agtgtgcctg tcacttgttt atgaacattt tcttaaatga atttgctgtc
120721  tctcttgtta tccaagcaaa atgcccttgg gcacttgtgt ttctgccctc tgtcttcatt
120781  ctctttcagc aggaactaag tcatagaatc ctaaaggata ttagcagaaa acgtattaat
120841  tgctgctaat taaatatagc cggctgggaa gctgtcttct ccagttggct tggctggcta
120901  ttggttttaa tcctatcatt aacttttatt aattaacatt ccccccccc catataaacc
120961  agtccagctg ctgcttttgc tacctgtcac caatgtgcta aaatgagcaa ggtcaatctt
121021  attaaaatat aggaggacca aagaaggagg gagttagagc aagagaggga gagttagagc
121081  aagagaggct ggagacaggc tggggacta tgctggtccc agagtcaaag agctctaggg
121141  gttcaagctg ttttcttccag gaggatgaac cctgccctgg tggagggttc tggagtctag
121201  ttctggttcc tggtggggac ctcctagtca aagataccta aagccccattt atccccagga
121261  gctcaattt cccaccatga atacagagaa tttcctaggc atcttttcta gcctctgggc
121321  caatgtgtgt cgactctccc tcctcccacc acttcacaga cccgggagct gcccaaccag
121381  ggccaccctg caggatggca agcaggttttc ctagctcttg tgaatttaag ggcaataatg
```

-continued

```
121441    aaatgtcccc tgtttagtga cccctgttta tagatgaaag ttgagtccat atcctgctct
121501    tcctccgccc ctcttccctg accttgcaaa tggcaagtgg cagaaatagt cctggataac
121561    aataagcttc cattggcagg tttctgtctt cttggttagc gagagaaaaa aaaagccttt
121621    aaaataaatc atagcttggg aactgtttac caccccttcac cctcacccac ttcttaaaaa
121681    aaaaaaaaac actagactgc atggtgaaga tcccacagag aatccttacc gaagctagga
121741    gagagggagg gtatgtgtgt agaatgatgt tataaagcca ttttttccc ttcctgtggt
121801    gaaaggtcgt aatgtgtggt atttcacggt tttatataaa tcttggttta ggatgtggaa
121861    cagactcaat aatacatgtg cttttggcaa agagactcct tcggatccca taaatcagaa
121921    gtaaataaga agtccaagtg aacaaaagag caggaacatt taattgatgc aaagcaggac
121981    tctcatctgc tttaaagaga ggtcatgta aattccctca gttcctatct tcacggttag
122041    agcccgacct ataaaacagg ttattacatt acagccggca gccttggatg attgaaagga
122101    aaggctcccc accccaaaca cacacacaca cacacacaca cacacacacg caatagatac
122161    aatgtatact ttctgccctg aggaatctaa agcctgtcag atgcaacaga aaacgctggg
122221    ggttggcgcg gggggggaaga dacagggctg cgtagaaaat atttaaccaa tcccacatgt
122281    gccaccgcta tttgggctat ttttaaggcc cagagttcgc tgcgactggg ctgaggttga
122341    aaaaaaccaa gcactgtgtg caaagaccgc gggcaacctg ggagcgcgag ccgaggccga
122401    gagcaagccg cagcgccccc tccccaagct ctggagcggc gggagcctcc accggctact
122461    gtgggagggg gtgcttaagg gtggaggagc tgggtgaccg caggccggatc cgccggcgtg
122521    gcgagcttcc cagaggtgcc cgagggcgtc tgccctctgg gtgtgcctcc gggagggcta
122581    gagagctcta ggttggcaag atcccagtga ccattgggag gcgcgcgatc caaggggttg
122641    cagggatggg gcgagagaga ggggcggttg ggtagcctaa aggtccctct cccagaatac
122701    aaggaagcgc taagaaggag gatgtggggg cagtgttcca gcaggcatcc caggctcttc
122761    cggctggaga gctcaggaga ctgagcggtg tcaaggctgg agtgagctat agggtgcgct
122821    ggggaggaggt gagcgcagcc tggctttggc gcgctgtggg tgactcccag gacggcgcgg
122881    ccaggacgcc gcgagccgtg gggcgtccgg tgggatcaaa ggaaccagag gaggccagcc
122941    gacgcgtctg ggattgtggg ataaggggcg ggagagagga gattgacatg ggcggggaga
123001    tcctggcctg gcctgtgtca ccggagggg ttgtgtgcgt ttgtgtcttt gtgcggatca
123061    acgctctcgg gcctgaggcc gtgccctggg tggatccgag tgtgagtgga caggctcccg
123121    ggtgggtgcc cagacgggag ggagagcgag cgagcgagat caagggcagc gaggtctgcg
123181    ggttcctctg tgtgtgtgtc tcaggccctg tggctcagca ctgagccgc ctggcaccca
123241    caggaatgcg gcttctctcg gatccccagg ccgccccttg tcccacaagg aggtggccgc
123301    caggaaaaag gggggaaaag gggcagaaat ccgcctagct caaccccgagc ctcaaacaaa
123361    ggccaattta tctgatctct tacaggatgg cccaggaggt ggtctgggca ccgaagaatc
123421    gcgctggccc tgaccgcatg ccccagcctt cctgggtt gtgaggagct ctgaaggtgg
123481    gggtgaggtg ttgtaagtaa ggggtgggga gtatgaagac gcccactgaa aagaacatta
123541    atcttagaaa ggacttgatt cgtcttggga gcatatact gagagctagg caagtggaaa
123601    ccggaagggg caggcagagg ggtcacccag tgcgatgtca agagtggggc cggctggtcc
123661    gggaatatgc tggggagtgg agcacgttta tattcgacgt aggaaaaca atggagagga
123721    agagaaggtg gaagggaggg caagggagag aaacatcaca tagatatttt tagactttgc
123781    tgaagatctg ttattttttac atccttgggc tcgggacggc agggagttaa attccccctga
123841    gagaatcccc atggggccag ggaaagcccg ctgcagactg gtttaccaga atatttttgt
123901    ccacggctcc cagaccaagc taaaaaataa aaaccgcacg agagaaaagg cctttgcgag
123961    tggaagaagt gaggttggca caagggaagg aatcctgaaa ccaagtctgt gtccgcgcgg
124021    cgttggtctg ggccaccctcg caatgaggct ttagtgatct taacgacaag cagcctcaaa
124081    gctagggtgg aggagtggtc atttagaaag agcttccctc tttctctaga agaatccgaa
124141    ccctcccctc cctcagctcg gccgcgcccg gtgaataggg atgaggaagg gatccccctt
124201    cttttccacc agtaatgggg ctggggagtt gataggggaca gctggaaaaa tatctgccct
124261    cttttgtgtgc acaaaggaaa acagtatgtt ccaagcacat tcttgccact cacaggcagc
124321    cagtaggtga gaaatattgg aggtgtgcag tgggtgcgcc ctcaccccca accttcccaa
124381    acacgcaccc cttggcaggg agaggcgtcc gcgcagggga aagccaggcg ctggcacacc
124441    gcgggcgcgg gtttctccca gtcggagtcg ccagaaataa agcgctagct ctcggtgtaa
124501    tggaaactcc cgaatcctt acaagcaaag aaagaaaagc aggaagtgga tatcttcatc
124561    tcttcccaa tccccctatt ctctgtgagc gcagaaaaca aaatgggggca ccctttgcgt
124621    tcccgcccc ccccccgccc ccgcaaacc ttccattgc cccctcttcc ccgcacccag
124681    tgctccttcc gagaaagtac ggctggagcc gactggggag acggaaatat tgagtcgcgg
124741    ccgctggggg tgccggagga ggggtgcaca ggccaggctg ccgggcgtag ttctgcctcg
124801    gagccaggct gcgggatatg tctaaagagc ggtcaaaata ctgattcctc caagaagcaa
124861    gctgttccac actggcgggc ctggtaactc ttctagaaaa aaagtaaagg aagagaac
124921    gaaaaaaata aaggaggtgg aaggaggta ggggagaaag aggaggagga ggcaggcaga
124981    gagacagaga aaatgagaga gaaagagaga gagagaggag agagagacga gacagagaga
125041    gaaacatgta ggtaaggtaa attcccctca aggcacatag cgtgcctttt caggtctagt
125101    ctcccaaccc tggaagagcc ttctgagaaa tcctcagtga caggatataa tttttttatgc
125161    tctaatctac ccccacttta agaaggctct tttgtcacat ttattgctgc tgacttccta
125221    gctgtaaaat atttcacatg catcttgtaa tttccaaccc aacattttcc ttcgtatcct
125281    aaggaaagag agtctgcccc actgaaggac ggccagacag aaagcacct acaattcagg
125341    cctgggtctt taggtgcagt gcatagctct ggtcatgctg ttggtatcta catgcaggag
125401    tgcaagaaga aggaagggac acagggcaca gctgcagcaa gtccttcctc tctgtcccaa
125461    agaaggcttc ccaaaggaga aatcctagta aacagattct attttgcatc atttagaacc
125521    tgtttgccac tgttttatgt aaaagcaaaa cagaggaagc tccttcctga aaaaaggaag
125581    gcgggaaggg aaatattaag agtattatct cacacaaaat gaaatcaaca cggcgccaca
125641    atgctttcat tccttccttt ccccaaccct gaagttccct cttccaata tctgcaatgt
125701    tttcatctct cgaaagagc cgatacattt ataatcatac tccaaagagt ccaaggtct
125761    atcatttgcc atgctccaaa cattttagat ttttaaaaaa tgtaataggt gtgaggctag
125821    atttcttttt cattttctca tctctggaaa ctcccctttga agggtaattt gtctaattgc
125881    tctggcacta cacagaggct gatgggtggg ggccttctc caagataatt gctttgagct
125941    tagaattcag aggggttatt gagggattt c tgttgccttc taactcacat acagggtgag
126001    agggatgtat ttttattttca gcattacttt ctacctgaaa caattatgag atatggcagt
126061    actataaaca tgccatatat attatatata tatatgcaca cacacacaca aagtatagca
126121    ttgaacatat atacatatac agtctgcatg catagagccc cgacttctgt tttcttttt
```

| | |
|---|---|
| 126181 | gccttgttgg atctctgcag agcttgtcct tctttagttg ccttcaataa aacttcacta |
| 126241 | gccagttatc agaggggcag aatgaagtat ttttcagaaa cattccgctt ttcatggtcg |
| 126301 | aaataatttt atttatccag aatatacagt ttaattcctc tatctacact tatttacatg |
| 126361 | gctaaaataa cattgaaaaa agtctttga aaagttgagg tcatagattt caaggcacca |
| 126421 | ttgaaagtgt ccacagttgc gcaaaaaaag tcctctgtaa aaaaggggg ggtcttttga |
| 126481 | aatgcaataa cttacatgca aaaaaagct ttacacatga atcttttca gttttccgaa |
| 126541 | cttccccata tgaattcctt tctttatgat tttctagaac agcaaaacac agtagtccca |
| 126601 | aaaaagagag taagagagag cagcccatct aatagagtgt cccggaggcc agcgccagcg |
| 126661 | ggtgctgtaa ggagcccggc ggcggcaggt gggaattgat tgagctggct gcacttgtgt |
| 126721 | accaggatgc agagttctcc aggtagctgg acgctgggga ctggttggag gtcggagggt |
| 126781 | gggcatgagg gtggtggctg agcgagcggg acgagccctg gggctcccac accgctggag |
| 126841 | actgcggcga gttcacgcc attgggtcgc tggagctggg actgtgctcc gggggcatct |
| 126901 | ccccgtttt catgatcttc ttgatcttgg atcttttgtt ctgaaaccag attttcacct |
| 126961 | gagttgggga acaaaggcac acgttaccgg gacactcaga ggtcgcccgc gccttccccg |
| 127021 | gggcggcgac tggaggcatc ttcggacctc tgggcggccc agccctgcct ggcgtctccc |
| 127081 | cgccgcttgc ggcctaccgc caagaagcta tgccttaggc aaaccatgga gctctggccc |
| 127141 | cagagggcgc cctgccggc tcggggcgcc ccgccagc gaggccacga ccccaaggct |
| 127201 | tgtctttgt ttgggctggg ggtgggggac gccagcgcgg cgggtgtgcg cccgagtgtc |
| 127261 | ctcggcggcg gcgcgccctcg tgtaagcctg cgcaggacgc gcggaacgcg gcgaaggtct |
| 127321 | ccaaaacaat cgcgcgagcc cggcggggaa ggggcgtggg gcgggctacg cgcgcctgtg |
| 127381 | gtcagaaaaa ggagcgagct cccaacctcc cgtcctactc ccttcactcg ctctgcagct |
| 127441 | cagagaggcc agaatctgac tgcagctctt ggcggcgact cgaacattct ttatgcttcc |
| 127501 | gtaggcccca gctgggttgg aggagtaaaa ggaatgggac aatccaggaa gactctcac |
| 127561 | gtacaatagc gcccccccacc tcgcgaccct tcggtggccg tggcctgaag ctcccgtagg |
| 127621 | ctcagggcac gacccttcag tttctccgct ccaggcgacg ttctcagcct tttcttagcc |
| 127681 | tgagaccacc gcgagaacac caggccttgc tcaccccga ggaggctcta cattgttaag |
| 127741 | aaaaccagat agctgctctg ggctgcctag gccgccctag aaataaccct ccgcttgctt |
| 127801 | tcaacccgcg aaattggccc cacagctccg gaggcccgct acgggggttggg ggcggggggc |
| 127861 | gcggttagtg ggaggtatct ccagaccgct gatgaatacc atccccaccg tctcaaggcc |
| 127921 | tgactcaccg agttaaagca taggggctga tgtctttggg tctgttagtt tctcacgggt |
| 127981 | actgtcaaaa cagctccagt cccatcgaga ctgaaccgcg cgacccaacc agacgtgcag |
| 128041 | ctcaggcagg tctagtgcat ggcagcgccg tatttaccctg tgttttgtgtc aatcccagcg |
| 128101 | aggcggccag ctcggcgcgt tccggcaagg cgaggtactg agtcttctga aaccttctct |
| 128161 | gtaatgcggc cagctgaaag ctggaataaa tagtcctggg ttacgaact ttctttggtt |
| 128221 | tgccattcac cattctcacc tcgggctcgg tcacttcttt ctctaaataa tcaaaacaga |
| 128281 | ctcagttaaa gcttgtcacc agacaatgcc ccttttgcgg aagggcctca aatagagtcc |
| 128341 | tagagttttct taccactcag tcttcattct ttgcccatat caccaccacc tttgcttttc |
| 128401 | aggaccgcga taaatatgca cctaccccaa atatggaaaa gcgggatagc ctctgattaa |
| 128461 | ttcctactct gttcattcag atagtttgtg caaagcgctt cctacaacac tgctttctcc |
| 128521 | ttggcatctg ggattcagct cttgcggtcg ttgcttcttc tcccggactt gttttacgc |
| 128581 | ccaccctgtg ctcctccgcg tttccgcccc tccccaggct tcaagaacac cagccccctcc |
| 128641 | ccaggcttca aggaggtggc cctgggccgt gacccctactt ctgtcggcgt ctgttcgggc |
| 128701 | gcccgcagaa gccagactct tgggcaggga agacgctaac cgaggtctcc aaagttcaaa |
| 128761 | gacccacaag caaactgctc cttcacttca gcagcaagcg gtcggggccg ccgcagacag |
| 128821 | agggtcgatt atgcaacccc cataatctcg ctgcagatct gcgagggcac agatgtgtct |
| 128881 | ggtttctttt acaaatagac ttaatatgtt cttggcaaaa aaaaaaaaaa aaaaaagaaa |
| 128941 | tcttccactt atgcacggaa tacagagaga gtgaaagaaa cgtagacacc tcaacccggg |
| 129001 | gctctctttt aaagttcagc aagagtcaca cactgagaag gaaccggtgg tggggtgttt |
| 129061 | tcgtaggaaa ggggcggcag gtcaggatga gattctcact gtcatgagta tgggtttggg |
| 129121 | cgggaggggg agggattgcc aaacgcgtgt tgtacaaacc tgccctgggg ctacaactcc |
| 129181 | ccttcctcaa aactaccacc cctctggaac tgacggagaa cctctccagg gtgtgtgtgt |
| 129241 | gtgtgtgtgt gtgtgtgtgt gtgtgtgtca agttccaggg agaagtgtgg aggatgaggg |
| 129301 | ctgtggtctc aattctgcca gagtagggga tgctaatatt agcaggatta ttaatgtgct |
| 129361 | ggtgggaaga gatcaaacct taccaataaa acctctccgc cgagcctcat gcctttctct |
| 129421 | taccgcccaa gctcactaac cctcttaaac tctcaagta agtttcaaag cggacgaaaa |
| 129481 | aggaggacgg aaagacaaat tgtgggcgcc tatggagaca gaaaaaaaaa tctatcctac |
| 129541 | aacgtgaccc ctcagcaacc ctcctccacc tttaaatgc ttttttgttt tggaaatgcc |
| 129601 | tggataaacc gcaaaactct cggcgcgctc ttctctggct ggctacaact ccttaacccc |
| 129661 | cccaccccca cccagccgtgc tcagggcacc cgcaccgtgc tagcttgtgg cggctctcaa |
| 129721 | actaatcctg actgagtttt tgaggcagcc ttctattccc actcgcacca acccagcacg |
| 129781 | cttaccaaaa ttcccaagta accttctctt tgttacgcaa acgccaggag ctgcttgatt |
| 129841 | cttttcttctc tccaccccta tccccttccc agcctagccg gcttcctggc cgggcaagct |
| 129901 | gggaattcag cgactgaagg gccttggaag gtgccggagg ggagagacgc tagttcgaac |
| 129961 | ctccacaggg ctctcctact aaaaatccct aaaatgctgg cccgagaaac tctctttgtt |
| 130021 | ggagggtctg agtcctactc ccttctgccg cgtgcgcccc cactgccgtg aaccgctgtg |
| 130081 | accccccaatc taccacccca tctcgcgccc ccagcgtcct agtcgccctg tatctgccca |
| 130141 | gccttccccc tgtccatgta cctggctggt tggtggcgct tgggacgcgg ttgtaggcgc |
| 130201 | cgccgtactg gtggtaggag ctagcgtagc tatagtcggc ataagctttg gctgggtagc |
| 130261 | tcccggcgga gccgttcacg ccgtgatact gatactggta gggttgaga gctttgccat |
| 130321 | aggaagccga ggtaggagag cagtagccgt gcggggctcc ccccgtaggg ctgtagtagt |
| 130381 | cagaatcggt agctgaagac tcgggcaaaa ttggcgattc ctgagacgga tggtgcatag |
| 130441 | ctgcggacgt ctggaacgga gcttggaagt cgccggatcg gatgctgggg acccttctgt |
| 130501 | caaacactcc tgtcatcgct cacgggcggc ggcagcggct gtccttgctg ttgtggcggc |
| 130561 | ggcagctgcc ctagttggct gtggggctgc tctggtctaa gcagacatgg ctgtgggagc |
| 130621 | gagggaggag gaggaagagg aggaggagag aaggaggagg cggcggccgc ggcgaggagg |
| 130681 | agactgggag tcgtgaagtc tcgtctccg gccggctgac tgctggctga ggcgcagcac |
| 130741 | agccttggtt aaatcccttaa ttgcgcgctt acgcacacgcg gggtggatct ggttctattg |
| 130801 | gccagggcct cgggagcaac agtaacaccc taactcgtcc aactagtttt agcacaacaa |
| 130801 | agcattgctt aaaagggggg tgggggtac tgagggggtg tgtgtgtttg tgtgtgtgcg |

-continued

```
130921  cgcccgcgcg cttgtgtgtg tttttgcttg ttgtggagtg gggaggggtc ttagtctatc
130981  tgtttttagt aaattccaaa gacatcgcag aagccacagc acaaggctct gtgatgtctg
131041  gggacaatgt gttccaatca gaagcctcaa aagtgcacat gttttgggaa tgaggtgggc
131101  gaccatcttt ccttgcttcc cactaccccg ccccccgtggg ctgcaccaaa ggcgagtgta
131161  gaattaaaca ctgatactga aatagggagt caaggtgcag ggagtgggga gcgggggat
131221  gtaggatgga ggcaagaagg aagggaaaca gcatttttt ttttttagt ggagtgttgg
131281  gaagcaagtt gtaacttaca tgttttgaaa atttgctctt tggggaaaga ggcaacttcc
131341  tttgcaggag atgagtatct cccggacgcg ggctggacag gaatgcccaa gaaggcacaa
131401  tgtccattaa gccggtgaat ggcagggaga gttcctgcag cccaaagtcc ttataatgac
131461  ttttaaaaat tactgtctta aacacatata acttaaggaa gcccaaatcc tcgttgctgg
131521  cttgcaaaaa gagccaaaca gctccacttc tgtttaatat tttcatctat tttcaagaca
131581  ttggaataaa ggctctttaa ctatgttcag tggccaaaga ctcccgcaaa ggtgaatgga
131641  tccatgtata acctgccata cctccaggaa agaatgggaa agtctcggaa gtggggaagg
131701  agacaaggat caaagccttt gcaaagtcag atgatgctca ttgatttccc cctcctggct
131761  ccatgaatgt ggcccagtct ctccattcc cagacccggg tttctgtacc ctctccctt
131821  tatttcctgc tgcaaagaca tcctacttag ctcgtatgca agggaagaaa ggattcaaga
131881  atcattcagt tgatacacga gatctaaact ttgctcttca ggaggtgcta tccttgttct
131941  agtcgtgatt cagctgggag tttagaaatt cagcataaaa gtctctccca atccccattg
132001  ttactccct caaataggca actccgcgga ctagatcctg atttggggcc ttcctacatc
132061  ttcctttacg gggtccaaga ccggcaatct gggagttcca caggctatct agggttatct
132121  ggcctccct ccgttttccc tcctaccgaa gaagaaagcc tctgtgttag ttgtgtctag
132181  tattagttta gccttacttg gagtgtggag ccactcggcc taaaacaggc cgacgggtag
132241  aggtagggtg tctggaactc agagcaagat acagcccgc tcaggaactc caaagcagag
132301  ctgccgtgcg tgcaccaact ccctgccttt gcggtctgga ctgcaccaga aaaacacagc
132361  tattgtcgca cttcctttcg ggggaaactt cagcaccggg agactggccg ccagcagcat
132421  tctccttctc ccactggccc gagtcacgag ctttgggcct gggctgccgc gggcttctct
132481  gagatagact tcggggtaaa cagagctgca gctgccagcc agccctgact tgacgctgtc
132541  gattaccgac aggctgttaa ccgtctagat gtaggctgtg aggagctaaa gaacaggagg
132601  gaaacatggg tctgcggtcc tgggctctgc tctggagaag ttatcggcgc ccatcgagtc
132661  acctgataca cactgccatt taattacaga aatcgcttcc tcagatcaat gccaaggaca
132721  gttcaaagca cctcccggca aagacaagtg ggcagggagc caggcctccc ttcctctggt
132781  cccctatctt cgacactttt ggttaaatag agatttgagt taccacatgg ttatactgaa
132841  cagggtgttc ctagcaatgc ccttacacct tgctgagatg gcagattcta accaggatgg
132901  gattggaagc tgcagaattg gggcaaaatt tagaagttcg ggatccgatt gaaaataatg
132961  ttacaatgtc aaattagttc tagacctgc taaatttcac cccccaaaa ccccgcagtc
133021  aaaatggaca ttctttccca catttcataa aagcaaaaa ggagtgggcc gggaggaaag
133081  aatttaactt ctttgtttcg gttcctaaag cgttagaacg ttggccctca cgcagacttg
133141  agccattctg ctgctgggtg agaccaaatc tggatgtgtc tctacaggtc cagagcctca
133201  actttcttga ttttgttcct cttticaagg ttgacccac tccccactcc accccttcct
133261  taaaggcagc cgggagggag aggaagcact aagttaaaag cagcggagag tctgttcaca
133321  gtacagtttt atttaatttc acaatatagg cattgtagct ctgtgcactg ccggctgctc
133381  tgcgggcctg tctgcggctt cggaccacg ctcaggacat acaccggcca gtatcccggc
133441  tctcggagca gcaaactttt gctggtgttg tgagggagtt ctcacactag ggcctccagc
133501  tttgtcctaa ggccagcggg ctggacgcta ttgcctctca aaatccaccg acaaatccag
133561  ccgtgggagaa acagccccac ggcatcaaac tcttccagca gtgcgcttcc cgctgagaca
133621  cgtaggaaga atgtaagtaa tttcatcttt tagtagctga aatctgcaaa gggagggaag
133681  gggaagtagc gggagggaag ccctaagata agtgcaagtc tttaccacga gcgccaccca
133741  gtgtcctcga gcaacattgc gcaaatggca aacccccaagc tcagtcactg gccagacacc
133801  aactggtcct tagtgttaga gttcacttcc aggtggcttt cttctctgt acttccaata
133861  catctttctc tcaattccca tgcccttct ttccttctt gtacattcat acttttcctt
133921  cctctccca ccggctcacc ttttctggg tcaccttttt cttggtgccc cctgtcctat
133981  ccctcaattc ttaggtgtaa ggcgctcctt cagtgtccc acctggggtg actggaaggc
134041  atcaaggatg actctccttt cctagccttt tattattatt attattatta ttattatcat
134101  tattattatt attattattt ggacagagtc ttgctttgtt gctcaggctg gagtgcagtg
134161  gcatgatctt ggctcactgc aacctctgcc tcctgggttc aagcgattct cttgcctcag
134221  cctcctgagt agctgggatt acaggcatct gccaccacgc ccggctaatt tttgtacttt
134281  tagtagaggc aggtttcgc catgttggtc aggctggtct cgaactcctg acctcaagga
134341  atccacacaa cttggcctcc cagagggcta gcattacaga tgtgagccac cgccccccggc
134401  cgccttcct agacatttgt gaagaagcag gccctcctttt agttagatga ggtgcttggg
134461  aagctttcgg tcattcacta ctatgggctg aaaagagtgc cactgagtgt gcagggagag
134521  agccgcagaa ggggggtgggg tagcagaaaa tcttaataac agcatttact caacttctc
134581  catgtagcct atctggagat ctgtttactc atagaagtgc caacagtaga acaccttttc
134641  ttttgggctt gaaactcaga aaattcagtg cagttgaaaa tatttaattt acgaacttaa
134701  gatattttta atatggaaac tttcatttat ataaaacatt gtacacatca attggatgtt
134761  cataattcag gtaaataaag gaccccttaa tatgatgcta gcattgtata ggcatacttg
134821  gtataaaaag cactttgact ttatcagtag aatactcatt cttttaaagt ccagttttgg
134881  gggtgaggtt tattttctt ttatttgca ctgcttttatc cattatcttt ttttatctgt
134941  ccagtgaaaa atgctctgag caattcactc ttatcatgat ccatttagag tactttcat
135001  cccagaaatc tcaaacacaa caaaactggt taagtcaaac attttgtgga ggtagacctg
135061  agtaatcatt ttattacaat ggagctgcag ttatctttga gctggggcac taaggccgtt
135121  taataactta aggtaacagc tctgaaatat tcaatttgat atttgtatag aaaaagcaca
135181  tttcttggaa ctagggtggg atgaaaagat aggagttatg attgcaaaag tagcaaaggc
135241  tttcaaaaat agcacaagtt gttggtcact ggttttggca atgcaactga atggcctttg
135301  tctcccaata gagggctagg cacactgact tggatctagc atcagaggt ggttcatctg
135361  agttaggaaa actatttaat tcccccatgta ggttcaaact tcttcccatg tgtttatgag
135421  gctgaactaa ctaggcccaa gctaaaatgt ttaggagccc atttaaatca acagtgagct
135481  tatctaggga gagagaagag gggaaagtggg tgtgaagggt aacaggataa atagaaaaaa
135541  ggtttcctcc catgctgaaa ttaattataa tatccccttg ccctcaagaa aaatgtgttt
135601  ggagttaaag agcatcccca acaaagtaaa tctcaaagga ttcactagta ggcaattata
```

-continued

```
135661  taaatattct gaataaatta aaaatcccca gagggaaaaa ctattttcca cttaattcca
135721  acctaataag atttttggtt tatttccaaa tgatagggca gatcatagac ttctacacgt
135781  tttgttttta taattaagac attaaaatat gtttattcat ttaacttaaa cataactagc
135841  taggaaaacg ccttaagtat ccactcaaat ctattctcta tgagacaaat ttaatatacc
135901  acagctgaaa acacttcaag ttcatctaac taggaagtaa atgggattat attattatat
135961  gtctttgcaa actgaaattg aggcatattc ttcatcctaa attcggattt catcttcttg
136021  aaaggaaggt ttggctgtgg tactatttac aaaacccttta ttcttcttaa agatatacaa
136081  atattccaaa ttctaaaaat acccccttgtg gagttaaaag aaaagtaatt gacagacagg
136141  aattcagagc aatgatccac ctcttgcaag gaaatagcaa gagtgaagct tcagtcatct
136201  ttaataacat cctaattcca agatctattt agaattttaa agttcattga tcctaagcca
136261  ctgtatttta tgatctgaca atattgtatg cagagatgca gaaaaccaat tctgaagcca
136321  aagccagatt attcaaacac tgtgagctgc gtaaaacttg gcccacaacg tacatgcaca
136381  agggcagatg gtataattt ataggcattt ttaccatctg ccctaattat atcattttaa
136441  tagattaaaa caaacagaaa gaaaatacaa aaccttttctc tacagctgtg tttactacct
136501  ttaccttta taaagaaaaa aattcttaaa caggcaaccc cagcctgaga taagaggttt
136561  ccctgctgtg ttacacagca caatcagtcg aagctgcagt gcccacctgg acttgcatcc
136621  ctctgtgctc ctgcagaata aaattaaggc aacagaaagg aaaagtcaat agctttccaa
136681  gtgaagtgta gctgacagca atggagtcac ttttaaaaat tgtgggcaga aaagatacgt
136741  tatttgcagc aagaagctta gtaatactca atgtatatag cccatgggca gttaagcaaa
136801  attttacttt ttcaacatta agtcttcagt tttattttat tttactgttt caacatagca
136861  ggctcttgga tggtacatgt agcaaagtat aataaacata taccttagta taatttattg
136921  ctgcatcctg attttataatt ttgggcatat aactgcatgt gtccagtagt ttgtgtgcat
136981  tcccctgttg atgcatgcgt ttcagttggt tacttagcga atcaaggaac actgtagttg
137041  ttgctccaac ttttggacag accctcacttt gcagacaacc tactatgcgt ctgcatgcac
137101  cactattagt ctaaaatgag gtttagggat gtctggaatt tttcttacaa gttccaggaa
137161  tccttggagt tagagaagga aaagatactt atgacactcg ggatgttagc aaggtatata
137221  ccagcattgc attaataat ttcttagaat aaaaaaagca aaattggaaa tcaacaaatc
137281  agataaacaa aaactatagg caagaaaaac tgtcttcata catgaaaaaa ttcagaatgt
137341  accattattc cctacagttc tctgttgcct tcttttgttat ttgagtctct agctgcttca
137401  tgggtacact gttacagcct ttttacacat gccattcaag agattcagac acatttaggg
137461  ttatgttata gagtaactgt gctaggttgc tagcagttaa cctgcatagc aaacttggag
137521  aggataggaa gaatgtttta gcatcaggat aaatagatga accaaagagg atatcatatt
137581  tgctaaagtg ataatacttt taatggaatt attcctgaag cctgttaatt tggcacaaaa
137641  atagggcgga aagtatctaa taattaaaat tgcctggtaa gtcttcctaa cttataagaa
137701  taatggaaga gattagaaga gaaataggcc aaagaacaga aagcaaaatg atagaaatag
137761  atctactttg cactctgaat taaaataatc actggggaac attcaggaaa aagtacttgt
137821  ccaccccgagg actgtcttt agggaacact tctcagagaa gttggaatga aagtcacttc
137881  ttttgtgactc ccttttacta gggtcattaa aattcaacat ggccttaaaa atcacagttt
137941  aggaaaaatg ttctgtaaat gtttcgagta cgttattggg ctccattcct cttcagagtc
138001  ttatggcgag tatttggcat gtcttgcaaa ttttatagac ctttaaatgg ttttcccaa
138061  agggatttca catataattc acttatactt tcacagtgcc ttgaagcaa gctatgtctg
138121  cctgttttgg gtggtcctca acttttatat atttgccttt catttaactt gaacttgctc
138181  atattccata ttggcattcc tacctcaccc tttattggtg ggtttgagtg gtgatgtggt
138241  ggcactgcct gccagctact gctgttggga gtaaagtgcc tgcctggcct ttgaacagtg
138301  ccaagtttgt attccctctg tctcacacta tgcctaggaa tatctgggca tggaatttcc
138361  agctcaatgc agggctgcca tctcccccctc tcttgcctaa tccctcccat caccatcctt
138421  gcaattgtca ctttctccat gggcatggag gctaaccact gggcttgcct agcctcctgc
138481  tccagtccct gcagatcagc gtgctcctga aatgagaga tgcctggctc agtgctccca
138541  tgtctatgaa agacaaatgg ccacctcatc tgctctccag ggattgggcc agaggagata
138601  acactgataa aacttgcaat taggaatttt atatttggtt agcgctttga taatggatat
138661  ccactttcaa atacatttgt tttgaatgaa aggtattcct tgaataccta attgacagat
138721  taatttactg aggcccaaat aatccactt tataataata attccttgca tttgcttaga
138781  gttttaaact tttttttaat tccagaaagt tctcgtataa ttgattgttt actctcacaa
138841  tattcttgag aggcaagtaa ggcaggaaga aacctgattt cccaacttc tatttgacat
138901  acactatgta aattgtgttg ttacctaaga gtagttaaaa tttcccatgg tcaaaatgct
138961  ctctgtatgc acatacaaaa agagttggtc atggactgaa gtaaacttat tactgttta
139021  atattaaaca acaataacaa caacaacaat tcaggccagg cgaggtgggg catgcctgta
139081  atcatagcac tttggaaggc caaagtggga agatcacttg agctcaagag tttgagacca
139141  gcctgggcaa tgtagtgaca cctctacaaa aaattttaaaa attcccaaa catggtgaca
139201  tgtacctgtg gtcccagcta cttgggaggc tgaggtggga agttcacttg agcccaggag
139261  gttgaggctg cagtgagcca tgatcatgcc actgcactcc agcctgggtg acaaagtgag
139321  accctgtctc aaaaaaaaca aaaaaaaatc tcaaaaccaa tgataggcat ttactgtatg
139381  ctaaatgctt tgtgcgtatt atttcattta atctttacag cagcctgtaa ggaggtgcca
139441  ttattatcca ttttatatag atgaatgtga ggcagacaga ttaagaaaga aatttaaggc
139501  caggcacggt ggctcatgcc tgtaatccca cacttgggg aggctgaggc gggaaaatca
139561  caaagtcagg agatcgagac catcctagct aacacggtga aaccccgtct ctactaaaaa
139621  tacaaaaata aaaataaaaa taaaaaaatt agccgggcat ggtggtgggc gcctgtagtc
139681  ccagctactt gggaggctga gtcaggagac tggcgtaaac ccgggaggca gaggttgcag
139741  ttagccaaga tcgcaccact gcactccagc ctgggcgaca gagcaagact ccgtctctaa
139801  aaaaaaaaag aaagaagaa aagaaaaaaa aaagaaattt aactattatc ctgtggctaa
139861  taagttatt gcataggagt tctctaaaaa ccagaaatcc tatccctgt ggaaaacaaa
139921  agcatagaat tgaggcttta aataccagaa taacgtttct gttgctactc tcctttttt
139981  gtgtgttctt agacctaaag acacatacaa taagctgtgg ctgtttagt tgtagttgtt
140041  tggttttgtt ttgagaggtg acagcgtgct ggcagccctt gcagccatcg cttgctctcg
140101  gtgcctcctc ggccttggtg cccattctgg ccgcgcttga ggagcccttc agcccgctgc
140161  tgcaccgtgg gagcccttct ctgggctggc cgaggctgga gccggctccc tcggcttgtg
140221  gggaggtgtg gagggagagg cacggggtgg aaccgggct gtgcgcgggg cttgcaggcc
140281  agctagagtt ccaggtgggc ctgggctcgg cggtcccgca ctcgagcgg ttgggggtc
140341  ctgctggccc acggcagtgc ggggcttagc acccaggcca gcagctgtgg agggtgcgct
```

-continued

```
140401  tggtcctcca gcagtgctgg cccaccagca ctgcgctgga tttctcaccg ggccttagct
140461  gcctccccac agggcagggc tcgggacctg cagcccgcca tgcctgattc tccccccccg
140521  ccccgggacc ctggggtcct gcatggcctg agcctcccca atgagcgcag ccccctgctc
140581  cacggagcca ggtcccatag actgcccaag ggctgaggag tgcgggcaca ccacacagga
140641  ctggtgggca gctccatctg cggccccagt gagagatcca ctgggtgagg ccagctgggc
140701  tcctgagtct agtggggact tggagaacct ttgtgtctag ctaagggatt gtgagtgcac
140761  caattggcac tctgtgtctg tctcaagttt tgtgaacaca ccaatcagca ccctgtgtct
140821  agctcagggt ttgtggatgc accaatcagc actctgtatc tagctaatct ggtggggact
140881  tggagaatct ttatgtctag ctaagggatt gtgaatacat caatcagcac tctgtatcta
140941  gctcatggtt tgtaaacaca ccaatcagca ccctgtgtct agctcggggt ttgtggatgc
141001  accaatcagc actctgtatc tagctaatct ggtggggact tggagaatct ttatgtctag
141061  ctaagggatt gtgaatgcac caatcagcac tctgtgtca gctcaaggtt tgtaaatgca
141121  ccaatcagcg ctctgtgtct agctaatctg gtggggacct ggagaatctt tatgtctagc
141181  taagggattg tgaatgcacc aatcagcact ctgtatctag ctcaaggttt gtaaaggcac
141241  cagtcagcac tctgtgtcta gctcaggctt tgtaaataca ccaattgaca cactgtatct
141301  agctaatcta gtgggggtgg agaacttttg tgtctagctc agggattgta aacgcaccaa
141361  tcagcaccct gtcaaaatag acgaatcaac tctctgtaaa acagaccaat tggctctctg
141421  taaagtggac caatcagcag gatgtgggtg gggccagata agagaataaa agcaggctgc
141481  ctgagccaac agtgacagcc ggctggggtc tcttttccaca ttgggaagct atgttcttca
141541  cctttttgcaa taaatcttgc tgctgctcac tctttgggtc cacactgcct ttctgagctt
141601  taacactgc cacgaaggtc tgcagcttca ttcctgagcc ggcgagacca cgaacccacc
141661  agaaggaaaa aactccaaac acatgtgaac gtcagaagga acaaactccg gacacgctgc
141721  ctttaagaac tgtaacactc accatgggg tcagcggctt cattcttgaa gtcagtgaga
141781  ccaataaccc aattctggac actgcgtgtg tgtgtgtgtg tgtgtgtgtg tgtgtgtgtg
141841  tttgcgtttt tttttttgtt tttttttgt ttttgaggtg gagtctcact ctgtcaccca
141901  ggctgcagtg cagtggcacg atctcagttg actgcaacct ctgcctaccg ggttcatgtc
141961  attctcccac ctcagcctcc ggagtagctg ggactacagg tgccagccac tacgcccagc
142021  taattttgtt tttgtatgtt tagtagagac agggttttcac cgtgttagtc aggatggtct
142081  gtatctcctg acctcgtgat ccgcttgcct tggcctccca aagtgctggg attacaggct
142141  tgagccacca tgcccggcaa tgatagtttg tttatatcaa cagtttcgtt tccctttaat
142201  cagtttcact tttctttaga atccaattgt tgggtattag tatccacatc tgaggaaatt
142261  gaatggaaat atactgtaaa tctgaggtag ggcgtttttt agtgttggaa caaggaaaat
142321  tcagggaaaa gtttctctta atagctgttt tataactgat gttaaatgtc gatgagcaat
142381  tggtccctgg aaacaactga tgacaaacac acataaaact aagcagcaga tcttgtccca
142441  ccgtttgccc ccattcttta tttctcttg tttttcacat acgtgtctca cacatctatc
142501  tacagactat tctggcaaaa tgttcacact gtttctttaa caaagttacg tatagaatga
142561  ccatataact tatccaaact gagacttttt tgtttttttg gagacgggt tttgctcttg
142621  ttgcccaggc tggagtacaa tggcaggatc tcggctccct gcaacttctg cctcctcagt
142681  tcaagtgatt cttctgcctc agcctcccga gtagctggga ttacacgcat gcgccaccac
142741  acctggctaa ttttgtagtt ttagtagaga cggggttttct ccatgttggt caggctgatc
142801  tcaaactccc gaccgcaggt gatccgaccg cctcggcccc ccaagtgctg ggattacagg
142861  catgagccac cgcacctggc ccaaactggg acatttttga aagtgaaaag gggttgataa
142921  ttactgggac aataggagta aattggaata gtcctggcta aaccttgatt ttgtggcata
142981  tttctcatac actccaaagt ccttcgggag gccatcttgg aaagtcctgt ccagtagcct
143041  ggcatcatgg aaacttgcct ggttagcaaa gcttagtttt tttttagttg ccttggggtt
143101  gacttacata gccatcctc agtaggttag ggatggtccg gaccaccacc tgtacatatg
143161  caggttgtgc aatacatgag tgtgcaatgg tgaagggagg tggagggtgg aatccagccc
143221  acactatact tgcccagcca aataccccaag tgagggactg catctgcact gagaaaggag
143281  catctatttc ccactcacac aaagttccc cagggaatgg tagactctct gagtacaaca
143341  aagttcactt cctatctaa cattttccta attgtcact ctatatccct tacttcattt
143401  tgattattat cttttaata gttttggcag aaattgtgcc tctataattt ttaaaacact
143461  taatctgaat gcctcacata atagaaaact ttagagaatt gaaacctgag gcttccaaat
143521  gcacaaaagt ataagtatac taaaagattt ttttctttc ttttctttc ttttttga
143581  gacagagttc tgccatgttg cccaggctgg tctggaattc ctgggggctca aagggtccac
143641  ctgcctcggc ctcccaaaat gttggattac aggtgtgagc cactgtgcct gatctgtttc
143701  ctttcatct cagaacttcc taaggttttt cgaaatcttg tatatagaga agataaatgc
143761  ttctgcctac agtgaccatg cattaacgca ctgtatttct tttcttacat gaggtgtgcc
143821  atgtataaca aagatttccc ttactgccta ggttccctca aagagtgaaa cttggaggac
143881  tattatttt cacaaaactt tttaaacgta ctcctgcccct tgcaagagaa atgactatct
143941  ggtacaatta acgttggacc atagaccccaa agaacagtga atatttcaaa cacaaattgc
144001  ttttgagaat catagtccta ttctgggctt gaagacattc atgtaggaaa ttaacagaaa
144061  attttaataa agactctttg gataaagaaa attagatgag gaatgccagt ttgtcttta
144121  agttgcttga gcagatctgt cataacagac attgccccag attgtggaac cctttccttc
144181  ttacatcttt taatggtagt agaacttaca ataccataat ttcctttcat ttttgacagt
144241  gttatactat cttttttagat ttacactgac agcatttcat cttgacatca ttagatcatc
144301  tcacctgact tttgcatggt gcacatcatt acattatgat ggtgctatac aattaccagt
144361  gaaatgaata gggtattaac atgattactg aaaaaacgtt agcacataca gatatagcat
144421  tctgtaattg aaagcatatt atagctatta attggtctgc ccaacactcc tgggatccag
144481  tgaaacttcc tttttttttt tttttttt tttttttt accaagttgg ataatgaaag
144541  ggagtgactt agacaatatt acagaactag gcagtggctg aactttctt aacttccttg
144601  atgttttaaa gcctaagaaa gttgggtgtg aagatttata gtaactaatc actgtcttga
144661  aagggcagac aagtgagaaa attccacaag aataccactt tttctagttt ccatttcagg
144721  actatcatgg caattattga gaatcaattc ttctaggttt tgtgagagtt ttgggagaca
144781  agtaatctgg aattatttaa agtgtccacc ttaaatggaa ttgatttggt ctgagaaaaa
144841  tcacataact tttaaaagtt aatcattaat caggaaatgt tgtgatcaaa ggttgataca
144901  gaacaactt tagaactata gaaatctga ttattgaaaa gcctctatac tttcttcgta
144961  tatttttcta aaatattgat aatgccttac caatgacatc ctagacttga gagactcagt
145021  gttgtctttg aggagaggat gaactgactc cttttctaa atcatataat tcatcctgag
145081  ttccaattttt aaggtgacta aataaaattaa ttgtatgaat tagttaaaat tttgcaaact
```

-continued

```
145141  ttttgagctt cactttgttt tctcatttct tctcatttgt atgaagtgaa tatgtatcat
145201  aaagattatc atgagggtaa aatgagataa cagatataaa actctcagct taatgcttgg
145261  gcacagtaga cactcaataa agtggagcag ttcctataat tcaggagacc ttgactggtc
145321  tgggaactag agcagaaact ttggcggctt gaaagtggta gttcttaggg gacatttctt
145381  cactcttggc ccttcttctg ctacgtttac actgcctgga gaagtcacag ggatcatgat
145441  tttccttgaa tgttttctgc catgactcag cagtaaaaca gcagtatcag tggatggagc
145501  tggtagatgg atcagaatca gcttatctga ctttaactaa tattgtttta tcgaattttc
145561  ccccacccac ctgcaaaagg aagaaaccaa atgagaggaa tacaaatttt cactgtaatt
145621  gaatcaaatc ataacacctg gaattacgca tatgtctatc ttgattggcc tatttacagc
145681  catatatatt ttgtggcaaa ctagtgtgtt taagaaatgg gcttttgagg tcaggaatat
145741  tgcatcattt atattttaag cacaattttc agtcttttcct tagaccttgg aatttactct
145801  tttctcttca ctcccagcct gactaccact cagttcatct catcccccat attgcaatag
145861  cctccaactg gtctttgcac cttcaggctc tccaagctcc actccagtca cctatcacaa
145921  tgatcgctat tccctatagg tcaagtctaa acttcacatc gtggcacaaa agtcttccag
145981  aatctgctcc aaccctaaca atctagtata tctccatctt ttttagcttc caaatccatc
146041  tcatttcttc agccaagttg attttctccc tgttgcctga tcatatcgaa cactttcca
146101  ggtctacctc gttgactgtt cattctctta cctatctctg cgttcagtgt cgaaaacaga
146161  agtcattcta aatgttttag gcagcaagga attgaatgcc agggactggg tgcttacaaa
146221  gtgtcagaag ggttggagga agggtctaag ctgggcctct aatgacaact cctggagcac
146281  caggaagggt gctaccagaa agactgaatt cagaacccac tgctgtagca ataaccccag
146341  gatcagaagc tgctgccatt actgctgcta taattgcctc ccaacgaaag gagctggggg
146401  aaaacgaaaa acaaaaaaac actggaatgt gattggggag aaaacacaaa aatttatatt
146461  tccatacct gtcactatca ataaaagcaa aaaggtgtgt gaaatggcc tctcacttct
146521  gttttctaca tgggatacaa agccatttac tctgcactgc aaaatcctag ttgcaaagaa
146581  gtcttggtgt acatgaaggc aactagaagt gaggtggatg aacattaaga gagacttctt
146641  ccttcccctc tgttaccaaa atcttgtata tccatttcaa ggatcagttc aaatattgta
146701  tcctccagga aacagcaagc aatgtcaatg gtagatcttt atgcttccta atcaccctta
146761  acccacattg cagagatggt caatatgcag tttacttagc catccctgc cttcctacac
146821  ctctagtggt catcccactt gaatttcaag attaaagcac aagatttact cagcctggaa
146881  ttggcctcag aatccttctt accacaatac tcaagtcagc cttaatcaac tgatgggaga
146941  tgatgcttca gataagccct gtttgcaagc cctgaagtct attattcagg catctagaca
147001  gcttttgatt aaatatatta gatagcaatt ctgacttgat cgttccctaa cctcaaagca
147061  tgatggtctg aaataaggat actggtggat ttgtgtgttg caggggggcgg gaagtaaata
147121  gtcctgaatc atagattta gatctggaaa tggcttcaag aaataccttg gtacagctct
147181  ttgtctgtag gcaggaaagc ttttatatct gagtttaaaa atgaataaac tgagggccag
147241  agaaattaag taactttctg agtttacaca gatatattt gttatctgat aacagcatat
147301  tacacttcaa gatggaatta ctaatgaatc tacttctctc atctttgtg cttctttatt
147361  attgataatt catcacagtc tataaaatac aaatttagta actgagtttt tctccttttc
147421  attatcttcg tttctaccag gaaataatca caaatggcaa caaaacaaaa caaaaaaata
147481  cctagcataa gagtacaggt tgtagaatac tgtttattac catgttcaac cttgagaaaa
147541  attgcaaaat aggtgaaatt tatctaaatt gacttctgtc tttaagtatg tcttttttcc
147601  ttcctgtagg ttcctaagac ttttatgaat atttaaggtt tcccacaggc tctttatccc
147661  tggagaactg tcttatacct agagcttttt catttacata ttttctattc atcagggcac
147721  tcatcaccctt tatgagctac taacctaaaa ctgatgaagt aacaagagtt ttgtgtacct
147781  ttgccttgcc ataatctata tcttactgac ttctcctgat aaaaaattgc caccaactta
147841  gtgccataaa ataacacaat ttattatctt acagttctgt aggtcacaag tctggtgtgg
147901  gcctcaccag cccaaaatca aggtgctggc aggctgtgct ccttctggag gctttaaggg
147961  ggaattattt cctgcttgtg gggttgttga aaaatttgat tccttgtagt tgtagagctg
148021  aggtcctggt ttccttgctg tctgtcagct gaatgctgat cccaggttct acaagctgct
148081  atgttcccta gctcatggtt cgcttcctcc accttttaag tctgcaatgt tgaatggaga
148141  ccttctcaca tcacagttct ctgagctact cttcctcctt taagggctca tatgatgaga
148201  ttaatccaac tcaaataatt caggataatc atctcacctc caggttgtaa ccttacttat
148261  tcacatctgc acagtccctt ttgccatatt tgctaactt atttacagaa ctaggacatt
148321  gacacctttg ggaggccgta ttctgcctac cacaccttggc ttccatagca taatcacatc
148381  ttgatccagt ttccctcttt atttattgcc ttccttcctt ctttcctttt atccttctta
148441  acacacgatt gagcatctac tataatgata agtacttaca taagtgtgat gaatacaaag
148501  atgacaacag catgaccct ttgtcatctt tgttactcaa gttactgtct ggttgctctt
148561  ctcttactct tctgattgct tctttttttgt gtaatatctt tcttctaccc caaggcagaa
148621  tttggaatct gtcacatgga gcctgtcagt gtcctatcct gaataactca tttagtgcta
148681  agattgcctg catatgaatc tatttataca catatctcag attctacttc tctttttcag
148741  acctctctcc tgaattccac ttatacacct tcaggtggac attttaaattt actccataat
148801  cacctccaac tcagttagga tggaacttat cattatgctt cagacttctt tctttcttta
148861  agaagctcaa aaattctcct agtcacaaag gtagaaaact tttcaatgag tcttaactgc
148921  ccctcgtct tattttgta acagggatgc tatttgggggg aggggggggtat taaacttata
148981  tatttatctt tggtaatacc taattactag ttgtcccaca gctctcatat ccagagccaa
149041  gtagggtcaa cttctgtcat agagtttttcg ccatagaaca agaaagattt accttctgcc
149101  tctgatgggg aggctgtgga aatctgccct agagtagaag agagataaga cgtggcagac
149161  ttcaagttga gacaaaggtc aaaggaagat gcaattcatt ctgggagtat gaggaagaga
149221  aggagcaaat cagtagcagg aaggcaagtg gtcagattct ccttttgcact aacgttctgg
149281  agtgaaatta ggaacaaggg ggaaactaca aacagagtgt tttgcccttg agtcagagct
149341  ggctagaagc tcaccaaact tgcttttttcc tgaaagacac ccagactaca ttcttagat
149401  tctcttgcag tcagttggca gccacatgac taagttccag ccaatagaat gtggcaaaac
149461  tgatggactc attactttca tctgggtcat taaaaccctc tgtgtgatcc tcctgaatct
149521  ttcaagcca atggaaaacc ctcaggtcct ccggcaaggg ctcttcacct ttttgaatca
149581  ttatggatcc ttgcagcagt ccggtgggagc ctatgaactc ttttagaac agtgttttta
149641  aatgtatgaa ataaaagcca aagattaca attaaaacag attattttga aacacagtta
149701  acaaagtatc ttaaaatgca aatctgtgat acggtaatgt gtgttcttct ttattaatgc
149761  attaaattac aagatctagt ggcaagtata ataactacca tgtttcaac atgctgatga
149821  tataaagaga tagccttgat acctgaagtg tgaaaaaaa tctgtgattt atttcaatga
```

-continued

```
149881  caaagttgca ggcttagcag acatctttca gttaacaaag gtcacaggac ttgcccagcc
149941  acctttgcgg cttagactag tatgtgaatc tgagacccca tctcctttat tgcctttgga
150001  tcacataaat cctcccagc cttgcctcgt attcgcagat gttatcctgg ggtgcagcag
150061  gatgaagggg gagaatctca gagtttgagc cataaacctg aaatagaccg aattacttaa
150121  aagggggaac tatttaaagc tgaagagaat gaataatgt caccaggcaa atttaacctt
150181  tctgactctt cagtggggtg gggtggaact taactgtgaa attttgatca acaggagaca
150241  ctaaaggagc cggatatgat gtagggaaaa cttctgccac ttaaaaatga gagaaagcct
150301  ggcttttgtg cccccacct tccacatggg aaaagtagag aaagaagga aagtgatgta
150361  gaggaagaag caaagtagga gaggcatagg tcatagcttc caactctggg ctgaaatttg
150421  cagatatagg gatgtgggct gggttgagaa gaaagaggct tttgctgtga ttctaattgg
150481  aatgcggagg ccatgcaaag tagcctcttt cgaacctgga gggtccagaa aggtagagat
150541  gttggtaaga atggttaagg agagggctat tgttactctt cctcagttcc catgtgatgt
150601  gcaggcactc agaaattct gcatgcttca tgggacaatg tgaagaatag ctgattgggg
150661  agctggtagt cttgtttagg gactgttgta gggaagggt aggtgacaat actcacgtga
150721  aactactcac agaactcatt tttttcaagg gcaggaaaaa aataacagac acttaataga
150781  ggattacagc aatggctata gtcatgatgg aacagagtca gcaagagaag accactgcgt
150841  gtgaatcagt aaagagaata acctgcaagt tcctcaggca tccctcagca gacctgagtg
150901  caaaggatc agggacctgc ccagccacac ctcagcagag agcagctagg acttagatga
150961  ctattcacag ctccaactcc atcattgcca tgatatcaca tgaacctgaa cctctctgac
151021  aatgagaggc caccatggag aggagcagtg gaagagagag agaatctgaa ggaagcagtt
151081  ttcaaaagag atagagttat tgctaagtga ttttataaca gaaagactaa gacacttaaa
151141  tgtttaagct ttcttgaccc cagattcata cttagggtaa tggggtctca tgaggaagat
151201  gattggttat gaaaataaag aaacaggatt tttttccta tatgcataat ttgtacattt
151261  gaagccctct tacatttctc ctttggtggt aagagagctt gcaaaaaatg gcccaaattc
151321  tccattgctc tctgtatcga cttgtatca taaagttgca gctctccca tgaaaaagtt
151381  gagtctactt tttgaatcca gacaggactt gtgactttct ttggccaaaa gaacacagca
151441  gaaatcatga tgcactggtt tgaagcccat gcctcaggag gtctttcatt gctttcctgg
151501  acttctactg tcagcatgag agccagctct ggccagcatg ctgcagaaga gagaccttat
151561  gaggaggact caggccatct caaatgaggt catcctagac cagccagcct ccagctgacc
151621  taacagatgg ctcatgggtg agcccagctt agatcagcca agcctgtccc agatgaacag
151681  aatcttccag ccaactcaca gattcattaa gccactaaat tttcatttaa gccactacat
151741  tttggggtgg tttgttatgc accaagagct aactgataaa cctacagaag taataatata
151801  tcctattgcc tcttctcttt ctgtcatatg tcacaataac cactttatct tcttacctt
151861  caggcttttt cctctccaaa ccaccttgca gccctgaggt agaccaagcc ttctgcatgc
151921  ttctttcttt tcccttaagc cctgagggtc aaaataacaa tagtacttga caccaagtca
151981  ctcactgatt ttatttcctg gaatacagtt ccttccttt gctataaccc ccagtatttg
152041  atcttcctca gtcactgcag tagctgccac cctgaagctc tcctgggaac accttcccaa
152101  ctgaggccca ggatgcagat tgctggtctg gcatgctttc tgtaccactc tctacccatc
152161  ctgtcctgga ggggattttt atctacgctt atttggaggg tcttttcagt ggctatctct
152221  caaccttggg tcatccagcc ttctcatggt tatagtgctc taaggtcttc aaaaggatgc
152281  ttgtatttt aatctcttag ctccaatgat caagaaagaa caagaagaaa ggactggata
152341  tacagtggaa tatatttaac cttaacagga atgaaattcc tataatgctg caacatggat
152401  gaacctcgaa aacattgtgc taagtgaaac aagccagaca caaaagacca catattgtat
152461  gatttcactt atatgaagta ctgctatggt ttgaatgttt gtcccctcca aaactcatgt
152521  tgaaatttaa tccccaatag gtggtattga gaggtggagt cttttaagag gtgattggat
152581  catggggact ctgccctcat aaagagatta gtccattcat ggattaagga attaatgagt
152641  tataatggca gtgagactgg tggctttata agaagaggaa gagagacctg agctggcaca
152701  ctcaatccac ttaccatgta atgtactact ccacctcagg acttagcaga gagtccccac
152761  cagtaagaag gcccttacta gatgtagtcc ctcaaccttg gatttctcag cctccataac
152821  tgtagaaata aattcctttt tttttttt tttttttt tttctgagac agagtctcac
152881  tctgtcgcac aggctggagt gcggtggcgc catctccgct cactgcaagc tccgcctccc
152941  aggttcacgc aattctcctg ccacagcctc tgagtagct gggactacag gtgcccgcca
153001  ccacgcccgg ctaattttt ttgtattttt agtagagacg gggtttcacc atgttagcca
153061  ggatggtctc catctcctga cctcgtgatc caccgcctc ggcctcccaa agtgctggga
153121  ttacaggcgt gggccaccac gcccggcccc ttttcttta aaattaccca gcttcaggta
153181  ttctgttata agcaacagaa aatggactaa gacaggtacc tggaatagtc aaatacacca
153241  agacagaagg tagaacagtg attcctagga gttggggaa gggaggagta gggagttttt
153301  taatgtgtat aaagttcagt atgggatgat ggaaaagttc gacagctgca tagtagtgat
153361  ggctgcacaa taatgtgaat gtacttaaag ccgctgaact ttacacttaa tagttaaaat
153421  ggcaaatttt atgttacata tattttacta aataaaaatg taaaataaaa agaaccacaa
153481  tgggggttcca ctttatatgc attagaattg ctataataaa aaattttaat gaaggtggga
153541  caaagaggtt ttcagcacaa tcttcgaact ctccaaaact tggcatgtgt ctctaacctc
153601  actcctagaa tccttgagac tttactttcc ttctgagctt gagagtctta ctctgtgttt
153661  tgatgcgagt cctctgtctt atttcaggct tttccatctc ttaagtcctt ctatctttta
153721  aggtctagtt caaatcccat ttgctatatg aaaacctctc tgatcaccac cctaatcttt
153781  ctgtcctttg agctatcctt gatcttattg tttgtgccat tatttatccc ttttcataaa
153841  tagtttaata ttatttaaaa tgtttttaaa agtttttaaa tatattttta aatttcttt
153901  aaaattttg tggttacata atagtgtata tatttattgg atatatgagg tgttttgata
153961  caggcatgca atgtgaaata agcacatcat ggagaatggg gcatccatcc cctcaagcat
154021  ttatctcttg agttacaaat agtccagtga cattccttat tttaaaatat ataattaaga
154081  tattattggc cagggatgat ggctcacgcc tataatctca gcactttggg aggccgaggc
154141  aggtggatca cttgaggtca ggaatttgag accagtctgg ccaatacggt gaaaccctgt
154201  ttctactaaa aatacaaaaa ttcccaggt gtggtggtcc acacctgtag tctaagctac
154261  tcaggaggct gaggcaggag aattgcttga acctgggaag cagaggttgc agtgagccga
154321  gatcgcacca ctgcactcca gcctgagtga caaagcaaga ctctgtctca aaaaaaaaa
154381  agaagttatt attgactata gtcaccctga tgtgctatta aatagtaggt cttattcacc
154441  gaatagttct ttatgtattt gcacattgat acccatatca acatctattt attgggtgct
154501  agattctctc aatccaacta atcaatacat accttaaaaa ataagagacg gaattttttg
154561  tctcttgggt tctcttatag tagctaataat agaactctgc acatattgtt tgctcagtaa
```

-continued

```
154621  ttgttgatcc atcatttaat tctatgttgt tctggccaac atagccttga cagggctttt
154681  ctgaggaaaa tgcctaatca agtgtttctc aacctgattt tcttcattgt atccccctga
154741  cccaggaaac tttacagact ttttttttt gctaatcatc tcccctatga aattttacta
154801  ctacagatag gcagtctgtc tgtacagaat ttctatacag ccatacacaa aaagagcaag
154861  aatttttccc ccaagaacca atcccccgca cacctgaagg gaatattatc cccattgaga
154921  atgcatgtct taacccttca tgaccttcag caaggcagtg gggaagatgt ttgggtggtt
154981  ctccaggcat ttcaggctcc tcaaagcaca gcaccataga ggtctttctg ttccacctcc
155041  ctgagtacct aaaaaccctg ctttttcttt gtttctttc tttctttt ttttctccg
155101  tgattattgc ttttggtggt agttttctgc attcacaggt gaggacagaa actgaaaata
155161  ccctctctaa aatgtactac tttctctaca tctcacagtt gttgggttat taacttattt
155221  gcttattttg ggggagggga ataagcatct gtaatcgaca caggaaatat acaacgttgc
155281  cgcttctctt taggtgcata gcaccacttg aaaaggacag agcacagtat ataggatgga
155341  agactgccac tagggcatat ggtgctttgt ttgaaataga aaaaggtgcc ccttccttca
155401  ggtcccacag ccctagcagt gtgcacagtc agcctgcact tgagctccct tgtctgggta
155461  actttatgga gggaaccacc tgcacacctt caaacagtaa cacctgacta aacaaacata
155521  caaatatggg aattcatatg tttaaaacat attttaaaat atatttaaaa catactttaa
155581  atactgtgaa acagttatgc cctgtgtagc cacaagctcc ttttcccatc ttattgactg
155641  cagggttttgg atttgggaaa gacagaatac ttctctttgc ttggacatgg tgtgcaactg
155701  gcataggtcc catgttggag tgtgggagca tccggagaga gagcatttct aaagtgaatg
155761  ccagacaagt cgtcatgtag cacacatatc tctcgggaca cttttcccgg aatttcatt
155821  gcgtttttcc ctctctaatc tgggcttccc atctgaacgt ttaaatttta ggtcagatta
155881  aaacattcca tcaaacttca ataattgtta atttgaaaat acattttcat aaaactaaac
155941  acaaacgttt tttttctttt cccagttact agtaatcaaa aagttctgtt ttataaagct
156001  taagttgga atttccacca aatatctgat tttctactgt tgccatattt tcacttcaag
156061  tagaaataac tatctatatt accaatatca ttgcatcaca taaattagga aaaatttgta
156121  tggcttctga tagaataaag taatactagc agtttatttt tgattgctct gaagtatcct
156181  ataaatgact taacaaactc cctaaagtat tactaacatg attcttaatg gaaaatatgt
156241  aaatgtctct gtggataagc atttgtaactt aaaaatatag acttcaaaat accagtgggt
156301  aaacatctta aaatatgtatc aggttttttca gattgcttaa gcttttttaa ggcttgttgt
156361  tatagaagaa ttgatgaaga taactgaaga ttatgagctt aatttgagat tcataaatat
156421  ctgatttata tttcaggaaa tacaggaaaa ttctttttctt ttctcatcag tatctaaagt
156481  tcttaaaaag ttatccacat tgcagggagg caagatggcc gaataggaac agcaagggtc
156541  tatagctccc aaagagacaa acgcagaagg caggtgattt ctgcacttcc aactgaggta
156601  cccgattcat ctcactggga ctgttagac agtggggtgca gcacatggaa ggcgagcaga
156661  ggcagggtgg gccatcgcct cacctgggaa gcacaaggaa tcggggaact ccctccgcta
156721  gccaagggaa gccatgaggg actgtgccat gaaggacggt gctatccggc ccagatacta
156781  tgcttttccc atggtcttca caacctgcag accagaagat tccctcgggt gcctacacca
156841  ccagagcccct ggatttcaag cacaaagctg ggaggtcatt tcagcagaca ccaagctagc
156901  agcaggagtt ttttcgttc cccagtggta cctggaacta cagcgagaca gaactgctca
156961  ctcccctgta aagggggctg aatccaggga gccaaatggt cttgctcagt ggatcccacc
157021  cccatgaagc ccagcaagct aagatccact ggcttgaaat tcttgtggcc agcacagcag
157081  tctgaagttg acctgggggtg ctcgagcttg gtggggagaa gggtgtccac cattactgag
157141  gcttaagtag gcggttttcc cctcacagtg gaaacaaagc cgcagggagg ttcaaactgg
157201  gtgtggaacc caccacagca ctccaaagcc gctgtagaca gactgcctct ctagattcct
157261  cctctctggg cagggcatct ctgaaagaaa ggcagcagcc ctactcaggg gcttagagat
157321  aaaactccca tctccctgga acagagcacc tggggggaagg ggcagctgtg ggcccaccttt
157381  cagcaaactt aaacgtttct gcctgctagc actgaagaga gcagtggatc tcctagcaca
157441  gactgcctcc tcaagtgggt ccctgacccc ccatgcctcc tgactgggag acacctccca
157501  gcaggggtcg acagacacct catcacggaa agctccagct ggcatctggt gcatgccctt
157561  ctgggataaa gcttccagag gaaggagcag gcagcaatca ttgctgttct gcacctcctg
157621  ctggtcatac cccaggaaac aggggtctgga gtggaactcc agcaaactcc agcagacctg
157681  cagcagaggg gcctgactgt tagaaggaaa actaacaaac agaaagcaat agcatcaaca
157741  tcaacaaaaa ggacgcccac gcaaaa4ccc catcagaagg tcatcaaaaa ccaaaggtag
157801  ataaatccac gaagatgagg aaaaaccagc acaaaaagtc tgaaaattcc aaaaaccaga
157861  acaactcttc tcctccgaag gatcacaact actcgccggc aagggaacaa aactggatgg
157921  agaatgagtt tgcaaaattg acagaagtag gtttcagaag gtgggtgata acaaactcct
157981  ccccgctaaa ggagcatgtt ctagcccaat gcaaggaagc taagaacctt tataaatggt
158041  tacaggaact gctaactaga ataaccagtt tagacaagac cataaatgac ctgatggagc
158101  taaaaaacac agcacaagaa ctttgtgaag catatacaag tatcaatagc tgaatcgatc
158161  aagcagatga aaggatatca gagattgaag agcaacttaa tgaaataaag catgaagaca
158221  agattagaga aaaaaaatga aaaggaatga aaaaagcctc caagaaatat gagagtatgt
158281  gaaaagacta aacctatgtt gattggtgta cctgaaagtg acggggagaa tggaaccaag
158341  ttggaaaaca cacttcagga tattatccag gagaacttcc ccaacctaga aaacaggac
158401  aacattcaaa ttcaggaaat acagagaaca ccacaaagat actcctcaag aagagcatcc
158461  caagacacat aattgtcaga ttcacttaga ttgaaatgaa ggaaaaaatg ttaagggcag
158521  ccagagagaa aggtcaggtt acccgcaaag ggaagcccat cagactaaca gcagatctct
158581  ctgaagaagc cctacaagcc agaagagagt gggggtcaac attcaacatt cttaaagaaa
158641  agaattttca acccagaatt tcatattcag ccaaactaag cttcctaagt gaaggagaaa
158701  taacacccctt tacagacaag cagatgctga gggatttttg tcaccaccag gcctgtgtta
158761  caagagctcc tgaaggaagc actacatatg gaaaggaaaa accggtagca gccactacaa
158821  aaacatacca aaatgtaaag acctttgacc caatgaagaa actgcatcaa ctaatagaca
158881  aaataaccag ctagcatcat aatgacagga tcaaattcac acataacaat attaaccta
158941  aatgtaaatg ggctaaatgc ttcaattaaa agacagactg gcaaattgga taaagagtca
159001  agacccatca gtgtgcggta ttcaggagac ccatccacgt gcagacacac ataggctcaa
159061  aataaagaga tagaggaata tttatcaagc aaatgaagg caaaaaaaaa aaaaagcagg
159121  gattgaaatc ctagtctctg ataaaacaga ctttaaagca acaaaggtca taaaagacaa
159181  agaagggcat tacataatgc taaagtgatc aatgcaacaa gaagagctaa ctatcctaaa
159241  tatacattca cccaatatac gagcactcag attcataaaa cgagttctta gagacctaca
159301  aagagactta tactcccaaa caataatagt gggagacttt aacaccccac tgtcaatatt
```

-continued

```
159361  agacagatca acaagacaga aaattaacaa ggacattcag gacttgaact cagctcttga
159421  ccaagcagac ctaatagaca gaactctcca ccccaaatca acagaatata cattcttctc
159481  aacctcacat agtacttatt ctaaaattgg ccgcaaaatt agaagtaaaa cactcctgag
159541  caaatgcaaa agaatggaaa taacgaacag tctctcagac aacagtgcaa tcaaattaga
159601  actcaggatt aagaaactca ctcaaaacca catagctaca tggaaactga acaacttact
159661  gctgaatgac tacgaggtaa agcgtaagag ggaagtttag taggctgggt gcagtggctc
159721  atgcctgtaa tcccagcact ttgggaggcc aaggcagcca gatcacaagg tcaggagatc
159781  gagaccatct tggccaacat ggtgaaacac catctctact aaaaatacaa tatttagctg
159841  ggtatggtgg catgcacttg tagtcccagc tacccaggag gctgaggccg gagaattgct
159901  tgaacccgag aggtggaggg tgcagtgagc cacgatcatg ccactgcact ctagcctggg
159961  caacagaatg agactctgaa aaagaaaaaa aaaaagagg gaaatttata gtactaaatg
160021  tccacatcag aaagctagaa agatctcaaa tcgacaccct cacatcacaa ttaaaggaac
160081  tagagaagca agagcaaaca aattcaaaag ctagcagaat acaagaaata actaaaatga
160141  gagcagaact gaaaaatata aagacacaaa aaacccatta acaaaatcaa tgaatccagg
160201  ggctggtgtt ttgaaaagat taacaaaatg gatagaccac tagcaagact aataaaagag
160261  aaaagagaga agaatcaaat agcacaaata aaaaatgata aaggggatat caccactggt
160321  cacacagaaa tacaaattac catcagagaa tactataaac acttctacgt gaataaacta
160381  gaaaatctag aagaaattga taaattctga gacacataca ccctcccaag actaaaccag
160441  gaagaagtca aatccctgaa tagaccaata acaaattctg aaattgaggc agtaatagct
160501  taccaaccaa aaaagcccca ggagcagatg gattcacagc caaattctgc cagaggtaca
160561  aacaggagtt ggtaccattc cttctgaaac tattccaaac aatagaaaaa gagggaatcc
160621  tccctaactc attttatgag gctagcatca ttctgatacc aaaacctggc agagacccaa
160681  caaaaaagaa aatttcagac caatatccct gatgaacatt gatgcaaaaa tcctcaatca
160741  aatattggca aaccaaatcc agcagcacat taaaaagcta atccaccacg atcaagttgg
160801  cttcatccct gggatgcaag gctggctcaa catatgtgat aatcaataaa cgtaatccat
160861  cacataaaca gaaccaatga caaaaaccac atgattatct caatagatgc agaaaagacc
160921  tttgataatg ttcaacaccc ctacatgcta aaaacactca ataaactagg tgttgatgga
160981  acatatctca aaataataag agctatttat gacaaactca cagccaatat cactactgaaa
161041  gggcaaaagc tgaaagtatt cccttgaaa accagcacaa gacaagggtg acctctctta
161101  cctctcctat tcaacatagt gttaacaaat gatactgatc agggcaatca ggcaagagaa
161161  agaaataaag catattcaat taggaagcga gaaagtcaaa ttgtctctgt ttgcagatga
161221  catgattgca tatttagaaa accccatcct ctcagcccca aaactcctta agctgataag
161281  caacttcagc aaagtctcag gatacaaaat caatgtgcaa aaatcacagg cattcccata
161341  caccaataac agacaaacag agagccaaat catgagtgaa ttcccattca gaattgctat
161401  aaagagaata aaatacctag gaatccaaca tcaaagggat gtgaaggacc tcttcaagga
161461  gaactacaaa ctactgctca aggaaataag agaggacaca aacaaatgga aaaacattct
161521  atgctcatag ataggaagaa tcaatattgt gaaaatggct atactgccca aagtaattta
161581  tagattcagt gctattccca tcaagctacc actgactttc ttcacagaat tggaaaaaac
161641  tactctaagc tt
```

SEQUENCE LISTING

The patent contains a lengthy "Sequence Listing" section. A copy of the "Sequence Listing" is available in electronic form from the USPTO web site (http://seqdata.uspto.gov/sequence.html?DocID=6605432B1). An electronic copy of the "Sequence Listing" will also be available from the USPTO upon request and payment of the fee set forth in 37 CFR 1.19(b)(3).

What is claimed is:

1. A process for detecting the presence or absence of methylation of CpG dinucleotide rich regions of nucleic acid sequences within a genomic DNA sample, the process comprising:
   a) contacting the genomic DNA sample with an enzyme that is not methylation-sensitive, but which cleaves the nucleic acid sequences into fragments in which CpG islands are preserved and which have ends corresponding to the cleavage motif of the non methylation sensitive enzyme;
   b) ligating the fragments, via the ends corresponding to the cleavage motif of the non methylation sensitive enzyme, to linker primers to form ligated linker primer products;
   c) contacting the ligated linker primer products with a methylation-sensitive enzyme which digests the ligated linker primer products having unmethylated CpG dinucleotide sequences but not methylated CpG dinucleotide sequences to form a digestion product comprising methylated CpG island loci, and wherein fragments cleaved by the methylation-sensitive enzyme are rendered non-amplifiable by the linker primers;
   d) amplifying the digestion product to form amplicons of the methylated CpG island loci;
   e) labeling the amplicons;
   f) contacting the labeled amplicons with a screening array comprising a plurality of nucleic acid fragments affixed to a solid support; and
   g) determining the presence or absence of labeled amplicons bound to the plurality of nucleic acid fragments affixed to the solid support of the screening array to thereby detect the presence or absence of methylation of CpG dinucleotide rich regions.

2. The process of claim 1 wherein the plurality of nucleic acid fragments affixed to the solid support of the screening array are derived from a CpG dinucleotide rich genomic library.

3. The process of claim 2 wherein the plurality of nucleic acid fragments affixed to the solid support of the screening array are CpG dinucleotide rich fragments which comprise a sequence of at least about 200 nucleotides of which at least about 50% are guanine and cytosine.

4. The process of claim 3 wherein the plurality of nucleic acid fragments comprise at least 20 nucleic acid fragments affixed to the solid support of the screening array.

5. The process of claim 3 wherein the plurality of nucleic acid fragments affixed to the solid support of the screening array each contain a promoter and a first exon of a gene.

6. The process of claim 5 wherein the plurality of nucleic acid fragments affixed to the solid support of the screening array each comprise a nucleic acid sequence which is expressed in an organism.

7. The process of claim 6 wherein the plurality of nucleic acid fragments comprise at least 20 nucleic acid fragments affixed to the solid support of the screening array.

8. The process of claim 7 wherein the plurality of nucleic acid fragments comprise at least 100 nucleic acid fragments affixed to the solid support of the screening array.

9. The process of claim 8 wherein the plurality of nucleic acid fragments comprise at least 500 nucleic acid fragments affixed to the solid support of the screening array.

10. The process of claim 1 wherein the solid support of the screening array comprises nylon, glass or silicon.

11. The process of claim 1 wherein the label is selected from the group consisting of radioisotopes and fluorescent labels.

12. The process of claim 1 wherein the enzyme is selected from the group consisting of MseI, Tsp509I, NlaIII and BfaI and the methylation sensitive enzyme is selected from the group consisting of BstU I, SmaI, SacII, EagI, MspI, HpaII, HhaI and BssHII.

13. The process of claim 12 wherein the enzyme is MseI and the methylation sensitive enzyme is BstU I.

14. The process of claim 1, further comprising comparing, between or among two or more mammalian genomic DNA samples, by assessing the presence or absence in each of methylation of one or more CpG dinucleotide-rich regions of a nucleic acid, wherein said process is used for determining differential methylation at the one or more CpG dinucleotide-rich regions of a nucleic acid.

15. The process of claim 14, wherein at least one of the mammalian genomic DNA samples comprises genomic DNA from a tissue selected from the group consisting of breast cancer tissue, prostate cancer tissue, colon cancer tissue, lung cancer tissue, liver cancer tissue and ovarian cancer tissue.

16. The process of claim 15, wherein the tissue is that of breast cancer.

17. The process of claim 1 wherein the nucleic acid sequence comprises a nucleic acid sequence isolated from a cancer cell.

18. The process of claim 17 wherein the cancer cell is selected from the group consisting of a breast cancer cell, a prostate cancer cell, a colon cancer cell, a liver cancer cell and an ovarian cancer cell.

19. The process of claim 18 wherein the cancer cell is a breast cancer cell.

20. The process of claim 19, wherein the plurality of nucleic acid fragments affixed on the solid support of the screening array comprise a combination of CpG island fragments, said combination comprising at least 20 sequences each having at least a 15 to 20 nucleotide contiguous portion of a sequence selected from the group consisting of SEQ ID NO:7, SEQ ID NO:15, SEQ ID NO:16, SEQ ID NO:17, SEQ ID NO:22, SEQ ID NO:23, and SEQ ID NO:25.

21. The process of claim 19, wherein the plurality of nucleic acid fragments affixed on the solid support of the screening array comprise a combination of CpG island fragments, said combination comprising at least 20 sequences each having at least a 15 to 20 nucleotide contiguous portion of a sequence selected from the group consisting of SEQ ID NO:7, SEQ ID NO:15, SEQ ID NO:16, SEQ ID NO:17, SEQ ID NO:22, SEQ ID NO:23, SEQ ID NO:25, SEQ ID NO:31, SEQ ID NO:36 and SEQ ID NO:38.

22. The process of claim 1 wherein the nucleic acid sequence comprises a nucleic acid sequence isolated from a non-cancerous cell.

* * * * *

UNITED STATES PATENT AND TRADEMARK OFFICE
CERTIFICATE OF CORRECTION

PATENT NO.     : 6,605,432 B1                                                  Page 1 of 1
DATED          : August 12, 2003
INVENTOR(S)    : Tim Hui-Ming Huang It is certified that error appears in the above-identified patent and that said Letters Patent is hereby corrected as shown below:

Column 29, line 19, through Column 360, line 42 are deleted.

Signed and Sealed this

Sixteenth Day of September, 2003

JAMES E. ROGAN
*Director of the United States Patent and Trademark Office*